US012161625B2

(12) United States Patent
Du et al.

(10) Patent No.: US 12,161,625 B2
(45) Date of Patent: *Dec. 10, 2024

(54) SUBSTITUTED PYRROLIZINE COMPOUNDS AND USES THEREOF

(71) Applicant: Gilead Sciences, Inc., Foster City, CA (US)

(72) Inventors: Jinfa Du, Redwood City, CA (US); Joshua A. Kaplan, Foster City, CA (US); Thorsten A. Kirschberg, San Carlos, CA (US); Tetsuya Kobayashi, Pleasanton, CA (US); Scott E. Lazerwith, Burlingame, CA (US); Rick Andrew Lee, Livermore, CA (US); Jonathan William Medley, San Mateo, CA (US); Michael L. Mitchell, Castro Valley, CA (US); Philip Anthony Morganelli, Oakland, CA (US); Hyung-Jung Pyun, Fremont, CA (US); Sophia L. Shevick, San Diego, CA (US); Neil H. Squires, San Francisco, CA (US); William J. Watkins, Saratoga, CA (US)

(73) Assignee: Gilead Sciences, Inc., Foster City, CA (US)

(\*) Notice: Subject to any disclaimer, the term of this patent is extended or adjusted under 35 U.S.C. 154(b) by 0 days.

This patent is subject to a terminal disclaimer.

(21) Appl. No.: 18/059,806

(22) Filed: Nov. 29, 2022

(65) Prior Publication Data
US 2023/0270719 A1 Aug. 31, 2023

Related U.S. Application Data

(60) Continuation of application No. 17/089,030, filed on Nov. 4, 2020, now abandoned, which is a division of application No. 16/403,247, filed on May 3, 2019, now Pat. No. 10,874,640, which is a division of application No. 15/686,499, filed on Aug. 25, 2017, now Pat. No. 10,328,053.

(60) Provisional application No. 62/380,063, filed on Aug. 26, 2016, provisional application No. 62/416,020, filed on Nov. 1, 2016.

(51) Int. Cl.
| | |
|---|---|
| A61K 31/403 | (2006.01) |
| A61K 31/03 | (2006.01) |
| A61K 31/16 | (2006.01) |
| A61K 31/38 | (2006.01) |
| A61K 31/4192 | (2006.01) |
| A61P 31/20 | (2006.01) |
| C07D 487/04 | (2006.01) |
| C07D 519/00 | (2006.01) |

(52) U.S. Cl.
CPC .......... *A61K 31/403* (2013.01); *A61K 31/03* (2013.01); *A61K 31/16* (2013.01); *A61K 31/38* (2013.01); *A61K 31/4192* (2013.01); *A61P 31/20* (2018.01); *C07D 487/04* (2013.01); *C07D 519/00* (2013.01)

(58) Field of Classification Search
CPC ........ A61K 31/03; A61K 31/16; A61K 31/38; A61K 31/403; A61K 31/4192; C07D 487/04; C07D 519/00; A61P 31/20
See application file for complete search history.

(56) References Cited

U.S. PATENT DOCUMENTS

| | | | |
|---|---|---|---|
| 5,733,912 | A | 3/1998 | Wasicak et al. |
| 6,232,320 | B1 | 5/2001 | Stewart et al. |
| 8,629,274 | B2 | 1/2014 | Hartman et al. |
| 8,653,115 | B2 | 2/2014 | Nan et al. |
| 9,181,288 | B2 | 11/2015 | Hartman et al. |
| 10,328,053 | B2 | 6/2019 | Du et al. |
| 10,836,769 | B2 | 11/2020 | Gutierrez et al. |
| 10,874,640 | B2 | 12/2020 | Du et al. |
| 11,420,974 | B2 | 8/2022 | Gutierrez et al. |
| 2005/0054850 | A1 | 3/2005 | Wu et al. |
| 2005/0137187 | A1 | 6/2005 | Souers et al. |
| 2005/0137243 | A1 | 6/2005 | Souers et al. |
| 2005/0187279 | A1 | 8/2005 | Souers et al. |
| 2005/0222236 | A1 | 10/2005 | Tsantrizos |
| 2005/0277638 | A1 | 12/2005 | Souers et al. |
| 2005/0288233 | A1 | 12/2005 | Venkatraman et al. |
| 2006/0100204 | A1 | 5/2006 | Cogan et al. |
| 2006/0122146 | A1 | 6/2006 | Chun |
| 2007/0135461 | A1 | 6/2007 | Rodgers et al. |
| 2009/0209533 | A1 | 8/2009 | Zablocki et al. |
| 2009/0326019 | A1 | 12/2009 | Or et al. |
| 2010/0113549 | A1 | 5/2010 | Block et al. |

(Continued)

FOREIGN PATENT DOCUMENTS

| | | |
|---|---|---|
| AU | 2012204508 A1 | 4/2013 |
| EP | 0274867 A2 | 7/1988 |

(Continued)

OTHER PUBLICATIONS

International Search Report and Written Opinion for PCT International Application No. PCT/US2019/019428 mailed on Apr. 23, 2019, 20 pages.
Abbas et al. (Feb. 2010) "Novel Substituted and Fused Pyrrolizine Derivatives: Synthesis, Anti-Inflammatory and Ulcerogenecity Studies", European Journal of Medicinal Chemistry, 45(2):482-491.
"JVirHep Supplement Sheet", Journal of Vascular and Interventional Radiology, 8 pages.

(Continued)

*Primary Examiner* — Kara R McMillian
(74) *Attorney, Agent, or Firm* — Mintz, Levin, Cohn, Ferris, Glovsky and Popeo, P.C.

(57) ABSTRACT

This application relates generally to certain substituted pyrrolizine compounds, and pharmaceutical compositions which inhibit HBV replication, and methods of making and using them.

23 Claims, No Drawings

(56) References Cited

U.S. PATENT DOCUMENTS

| | | | |
|---|---|---|---|
| 2012/0184572 A1 | 7/2012 | Song et al. | |
| 2014/0178337 A1 | 6/2014 | Hartman et al. | |
| 2014/0194386 A1 | 7/2014 | Burns et al. | |
| 2014/0275167 A1 | 9/2014 | Hartman | |
| 2015/0132258 A1 | 5/2015 | Hartman | |
| 2015/0197533 A1 | 7/2015 | Hartman et al. | |
| 2015/0216938 A1 | 8/2015 | Hartman | |
| 2015/0225355 A1 | 8/2015 | Hartman | |
| 2015/0259324 A1 | 9/2015 | Hartman et al. | |
| 2015/0274652 A1 | 10/2015 | Hartman | |
| 2015/0307443 A1 | 10/2015 | Xu et al. | |
| 2015/0315159 A1 | 11/2015 | Hartman | |
| 2017/0355701 A1 | 12/2017 | Qiu et al. | |
| 2018/0001207 A1 | 1/2018 | Wei et al. | |
| 2018/0370976 A1 | 12/2018 | Ding et al. | |
| 2019/0292187 A1 | 9/2019 | Gutierrez et al. | |
| 2021/0147429 A1 | 5/2021 | Gutierrez et al. | |
| 2021/0251957 A1 | 8/2021 | Du et al. | |
| 2023/0148157 A1* | 5/2023 | Gutierrez | A61P 31/20 514/343 |

FOREIGN PATENT DOCUMENTS

| | | |
|---|---|---|
| EP | 0498723 A1 | 8/1992 |
| EP | 1217000 A1 | 6/2002 |
| EP | 1479676 A1 | 11/2004 |
| EP | 1867647 A1 | 12/2007 |
| EP | 1867648 A1 | 12/2007 |
| EP | 1932845 A1 | 6/2008 |
| EP | 3381918 A1 | 10/2018 |
| JP | 2014133739 A | 7/2014 |
| KR | 20150025531 A | 3/2015 |
| WO | 9748697 A1 | 12/1997 |
| WO | 9918951 A1 | 4/1999 |
| WO | 9962908 A2 | 12/1999 |
| WO | 0075145 A1 | 12/2000 |
| WO | 0109097 A1 | 2/2001 |
| WO | 0114336 A1 | 3/2001 |
| WO | 0198301 A1 | 12/2001 |
| WO | 0220016 A1 | 3/2002 |
| WO | 0222586 A1 | 3/2002 |
| WO | 02066034 A1 | 8/2002 |
| WO | 02066035 A2 | 8/2002 |
| WO | 02070491 A1 | 9/2002 |
| WO | 02083628 A1 | 10/2002 |
| WO | 02096426 A1 | 12/2002 |
| WO | 03007888 A2 | 1/2003 |
| WO | 03053941 A2 | 7/2003 |
| WO | 03068221 A1 | 8/2003 |
| WO | 03084948 A1 | 10/2003 |
| WO | 03091202 A1 | 11/2003 |
| WO | 2004024705 A1 | 3/2004 |
| WO | 2004024727 A2 | 3/2004 |
| WO | 2004026873 A1 | 4/2004 |
| WO | 2004035581 A1 | 4/2004 |
| WO | 2004050613 A2 | 6/2004 |
| WO | 2004082606 A2 | 9/2004 |
| WO | 2005023761 A2 | 3/2005 |
| WO | 2005033072 A2 | 4/2005 |
| WO | 2005039506 A2 | 5/2005 |
| WO | 2005040133 A1 | 5/2005 |
| WO | 2005090333 A1 | 9/2005 |
| WO | 2005099824 A1 | 10/2005 |
| WO | 2005102381 A1 | 11/2005 |
| WO | 2006077401 A1 | 7/2006 |
| WO | 2006085111 A1 | 8/2006 |
| WO | 2006091862 A2 | 8/2006 |
| WO | 2007019098 A2 | 2/2007 |
| WO | 2007031791 A1 | 3/2007 |
| WO | 2007058990 A2 | 5/2007 |
| WO | 2007085136 A1 | 8/2007 |
| WO | 2007119889 A1 | 10/2007 |
| WO | 2007144202 A1 | 12/2007 |
| WO | 2007144203 A1 | 12/2007 |
| WO | 2007144204 A1 | 12/2007 |
| WO | 2007147336 A1 | 12/2007 |
| WO | 2008025822 A1 | 3/2008 |
| WO | 2008071456 A2 | 6/2008 |
| WO | 2008091349 A1 | 7/2008 |
| WO | 2008091681 A2 | 7/2008 |
| WO | 2008115369 A2 | 9/2008 |
| WO | 2008119792 A1 | 10/2008 |
| WO | 2008124848 A1 | 10/2008 |
| WO | 2009014910 A2 | 1/2009 |
| WO | 2009019295 A2 | 2/2009 |
| WO | 2009033281 A1 | 3/2009 |
| WO | 2009034433 A2 | 3/2009 |
| WO | 2009055437 A2 | 4/2009 |
| WO | 2009074260 A1 | 6/2009 |
| WO | 2009094668 A1 | 7/2009 |
| WO | 2009105782 A1 | 8/2009 |
| WO | 2009126691 A1 | 10/2009 |
| WO | 2009133834 A1 | 11/2009 |
| WO | 2009146539 A1 | 12/2009 |
| WO | 2010008739 A2 | 1/2010 |
| WO | 2010010191 A1 | 1/2010 |
| WO | 2010012761 A1 | 2/2010 |
| WO | 2010022300 A1 | 2/2010 |
| WO | 2010029299 A1 | 3/2010 |
| WO | 2010034740 A1 | 4/2010 |
| WO | 2010045542 A2 | 4/2010 |
| WO | 2010053998 A1 | 5/2010 |
| WO | 2010068287 A2 | 6/2010 |
| WO | 2010092181 A1 | 8/2010 |
| WO | 2010099938 A1 | 9/2010 |
| WO | 2010112124 A1 | 10/2010 |
| WO | 2010115491 A2 | 10/2010 |
| WO | 2011003418 A1 | 1/2011 |
| WO | 2011035231 A1 | 3/2011 |
| WO | 2011048611 A1 | 4/2011 |
| WO | 2011084970 A1 | 7/2011 |
| WO | 2011087051 A1 | 7/2011 |
| WO | 2011113606 A1 | 9/2011 |
| WO | 2011133707 A2 | 10/2011 |
| WO | 2011133722 A2 | 10/2011 |
| WO | 2011143645 A1 | 11/2011 |
| WO | 2011145669 A1 | 11/2011 |
| WO | 2011146401 A1 | 11/2011 |
| WO | 2012014114 A1 | 2/2012 |
| WO | 2012016186 A1 | 2/2012 |
| WO | 2012020567 A1 | 2/2012 |
| WO | 2012028243 A1 | 3/2012 |
| WO | 2012038942 A1 | 3/2012 |
| WO | 2012050868 A1 | 4/2012 |
| WO | 2012058645 A1 | 5/2012 |
| WO | 2012112743 A1 | 8/2012 |
| WO | 2012116135 A2 | 8/2012 |
| WO | 2012123938 A1 | 9/2012 |
| WO | 2012129562 A2 | 9/2012 |
| WO | 2012158672 A2 | 11/2012 |
| WO | 2012158844 A1 | 11/2012 |
| WO | 2012159047 A1 | 11/2012 |
| WO | 2012169649 A1 | 12/2012 |
| WO | 2013006394 A1 | 1/2013 |
| WO | 2013017189 A1 | 2/2013 |
| WO | 2013042139 A1 | 3/2013 |
| WO | 2013059278 A2 | 4/2013 |
| WO | 2013085877 A1 | 6/2013 |
| WO | 2013087162 A1 | 6/2013 |
| WO | 2013096744 A1 | 6/2013 |
| WO | 2013113841 A1 | 8/2013 |
| WO | 2013144228 A1 | 10/2013 |
| WO | 2013161871 A1 | 10/2013 |
| WO | 2014031872 A2 | 2/2014 |
| WO | 2014033167 A1 | 3/2014 |
| WO | 2014033170 A1 | 3/2014 |
| WO | 2014033176 A1 | 3/2014 |
| WO | 2014039595 A1 | 3/2014 |
| WO | 2014045305 A1 | 3/2014 |
| WO | 2014096965 A2 | 6/2014 |
| WO | 2014102818 A1 | 7/2014 |
| WO | 2014106019 A2 | 7/2014 |
| WO | 2014118133 A1 | 8/2014 |

(56) References Cited

FOREIGN PATENT DOCUMENTS

| | | |
|---|---|---|
| WO | 2014128486 A1 | 8/2014 |
| WO | 2014131847 A1 | 9/2014 |
| WO | 2014151958 A1 | 9/2014 |
| WO | 2014161888 A1 | 10/2014 |
| WO | 2014179144 A1 | 11/2014 |
| WO | 2014184350 A1 | 11/2014 |
| WO | 2014184365 A1 | 11/2014 |
| WO | 2014206344 A1 | 12/2014 |
| WO | 2015002894 A1 | 1/2015 |
| WO | 2015011281 A1 | 1/2015 |
| WO | 2015026935 A2 | 2/2015 |
| WO | 2015051230 A1 | 4/2015 |
| WO | 2015057945 A1 | 4/2015 |
| WO | 2015058140 A1 | 4/2015 |
| WO | 2015059212 A1 | 4/2015 |
| WO | 2015085238 A1 | 6/2015 |
| WO | 2015118057 A1 | 8/2015 |
| WO | 2015148854 A1 | 10/2015 |
| WO | 2015180631 A1 | 12/2015 |
| WO | 2016008011 A1 | 1/2016 |
| WO | 2016023511 A1 | 2/2016 |
| WO | 2016110821 A1 | 7/2016 |
| WO | 2016113273 A1 | 7/2016 |
| WO | 2016128908 A1 | 8/2016 |
| WO | 2016189129 A1 | 12/2016 |
| WO | 2016201370 A1 | 12/2016 |
| WO | 2016201440 A1 | 12/2016 |
| WO | 2017001655 A1 | 1/2017 |
| WO | 2017012379 A1 | 1/2017 |
| WO | 2017015451 A1 | 1/2017 |
| WO | 2017040963 A1 | 3/2017 |
| WO | 2017046605 A1 | 3/2017 |
| WO | 2017076346 A1 | 5/2017 |
| WO | 2017083304 A1 | 5/2017 |
| WO | 2017114512 A1 | 7/2017 |
| WO | 2017156255 A1 | 9/2017 |
| WO | 2017161028 A1 | 9/2017 |
| WO | 2017161524 A1 | 9/2017 |
| WO | 2017162007 A1 | 9/2017 |
| WO | 2017173274 A1 | 10/2017 |
| WO | 2017193063 A1 | 11/2017 |
| WO | 2017209265 A1 | 12/2017 |
| WO | 2018039531 A1 | 3/2018 |
| WO | 2019165374 A1 | 8/2019 |

OTHER PUBLICATIONS

Campagna et al. (Jun. 2013) "Sulfamoylbenzamide Derivatives Inhibit the Assembly of Hepatitis B Virus Nucleocapsids", Journal of Virology, 87(12):6931-6942.

Chang et al. (2015) "Prevention of Hepatitis B", Cold Spring Harbor Perspectives in Medicine, 5:12 pages.

Cho et al. (2014) "2-Amino-N-(2-6-dichloropyridin-3-yl) Acetamide Derivatives as a Novel Class of HBV Capsid Assembly Inhibitor", Journal of Viral Hepatitis, 21:843-852.

Cho et al. (2012) "Structure-Based Design And Biochemical Evaluation Of Sulfanilamide Derivatives As Hepatitis B Virus Capsid Assembly Inhibitors", Journal of Enzyme Inhibition and Medicinal Chemistry, 10 pages.

Gane et al. (2014) "Phase 1a Safety and Pharmacokinetics of NVR 3-778, a potential First-In-Class HBV Core Inhibitor", Novira Therapeutics Post AASLD LB-19, 1 page.

Katen et al. (2013) "Assembly-Directed Antivirals Differentially Bind Quasi equivalent Pockets to Modify Hepatitis B Virus Capsid Tertiary and Quaternary Structure", Structure Article, pp. 1406-1416.

Ray et al. (Jan. 2016) "Tenofovir alafenamide: A Novel prodrug of Tenofovir for the Treatment of Human Immunodeficiency Virus", Antiviral Research, 125:63-70.

International Preliminary Report on Patentability for PCT International Application No. PCT/US2017/048565 mailed on Mar. 7, 2019, 8 pages.

Wenxi, et al. (2014) "Research Progress of Non-nucleoside Small Molecule Inhibitors Against Hepatitis B Virus", Chemical and Biological Engineering, 31(11):5-11.

\* cited by examiner

SUBSTITUTED PYRROLIZINE COMPOUNDS AND USES THEREOF

PRIORITY CLAIM

This application is a continuation of U.S. application Ser. No. 17/089,030, filed Nov. 4, 2020, which is a divisional of U.S. application Ser. No. 16/403,247, filed May 3, 2019, which is a divisional of U.S. application Ser. No. 15/686,499, filed Aug. 25, 2017, which claims priority to U.S. Provisional Application Nos. 62/380,063, filed Aug. 26, 2016, and 62/416,020, filed Nov. 1, 2016, all of which are incorporated herein in their entireties for all purposes.

FIELD

This application relates generally to certain substituted pyrrolizine compounds, and pharmaceutical compositions which inhibit HBV replication, and methods of making and using them.

BACKGROUND

The hepatitis B virus (HBV) is an enveloped, partially double-stranded DNA virus. HBV is an infectious disease that affects the liver. Initial symptoms of infection may include vomiting, jaundice, lethargy, dark urine, and abdominal pain. Chronic HBV infection can result in cirrhosis and liver cancer. Currently available therapies can inhibit replication of the virus and minimize liver damage; however, there are no currently available therapies that can reliably clear an HBV infection.

In view of the continued prevalence of HBV infection, there is a need for new therapeutic options, including new inhibitors of HBV replication. Additionally, compounds capable of inhibiting HBV replication while having low predicted metabolic clearance are of particular interest.

SUMMARY

The present disclosure provides a compound of Formula (I):

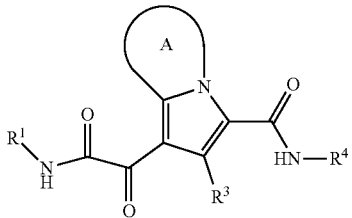

Formula I or a pharmaceutically acceptable salt thereof, $R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$;

each $R^{1A}$ is independently halogen, —OH, —CN, $C_{1-2}$ haloalkyl, —C(O)NR$^X$R$^Y$, $C_{6-10}$ aryl optionally substituted with 1 to 3 $R^{1D}$, or a 5 to 8 membered heteroaryl having 1 to 3 heteroatoms selected from N, O, and S, optionally substituted with 1 to 3 $R^{1D}$, provided no more than 1 $R^{1A}$ is $C_{6-10}$ aryl optionally substituted with 1 to 3 $R^{1D}$ or 5 to 8 membered heteroaryl having 1 to 3 heteroatoms selected from N, O, and S optionally substituted with 1 to 3 RID;

each $R^{1B}$ is independently —CN, halogen, $C_{1-6}$ alkyl optionally substituted with 1 to 3 —OH or —NR$^a$R$^b$, $C_{2-4}$ alkynyl, $C_{1-4}$ alkoxy, $C_{1-2}$ haloalkyl, $C_{3-6}$ cycloalkyl, —C(O)NR$^X$R$^Y$, or a 5 to 8 membered heteroaryl having 1 to 3 heteroatoms selected from N, O, and S optionally substituted with 1 to 3 $R^{1D}$, provided no more than 1 $R^{1B}$ is $C_3$-6 cycloalkyl or 5 to 8 membered heteroaryl having 1 to 3 heteroatoms selected from N, O, and S optionally substituted with 1 to 3 $R^{1D}$;

each $R^{1C}$ is independently $C_{1-6}$ alkyl, oxo, $C_{1-4}$ haloalkyl, —C(O)H, —C(O)$C_{1-4}$ alkyl, —C(O)O$C_{1-4}$ alkyl, or a 5 to 12 membered heteroaryl having 1 to 3 heteroatoms selected from N, O, and S optionally substituted with 1 to 3 $R^{1D}$, provided no more than 1 $R^{1C}$ is a 5 to 12 membered heteroaryl having 1 to 3 heteroatoms selected from N, O, and S optionally substituted with 1 to 3 $R^{1D}$;

each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;

each $R^Y$ is independently —H or $C_{1-6}$ alkyl optionally substituted with 1 to 3 $R^Z$;

or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$;

wherein each $R^Z$ is independently halogen, methyl, ethyl, oxo, —OH, —S(O)$_2$C$_{1-3}$alkyl, or 3 to 8 membered monocyclic or bicyclic heterocyclyl having 1 to 3 heteroatoms selected from N, O, and S;

each $R^a$ is —H, $C_{1-3}$alkyl, or a 3 to 8 membered monocyclic or bicyclic heterocyclyl having 1 to 3 heteroatoms selected from N, O, and S, optionally substituted with 1 to 3 $R^Z$;

each $R^b$ is —H or $C_{1-3}$alkyl; or $R^a$ and $R^b$ taken together form a 3 to 8 membered monocyclic or bicyclic heterocycle optionally substituted with 1 to 3 $R^Z$;

the moiety

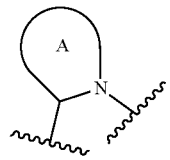

is a pyrrolidine or a 5-7 membered bicyclic heterocycle having one nitrogen, optionally substituted with 1 to 6 $R^2$ groups;

wherein each $R^2$ is independently halogen, $C_{1-3}$alkyl, —OH, or —O$C_{1-3}$ alkyl;

$R^3$ is —H, halogen, or $C_{1-4}$ alkyl;

$R^4$ is $C_{6-10}$ aryl optionally substituted with 1 to 5 $R^{4A}$, or 5 to 12 membered heteroaryl having 1 to 3 heteroatoms selected from N, O, and S, optionally substituted with 1 to 4 $R^{4B}$; and each $R^{1D}$, $R^{4A}$, and $R^{4B}$ are independently —CN, halogen, $C_{1-4}$ alkyl, —$OC_{1-4}$alkyl, —$OC_{1-4}$ haloalkyl, or $C_{1-4}$ haloalkyl.

In certain embodiments, the present disclosure provides a pharmaceutical composition comprising a compound of the present disclosure, or a pharmaceutically acceptable salt thereof, and a pharmaceutically acceptable excipient. In certain embodiments, the pharmaceutical composition comprises one or more additional therapeutic agents.

In certain embodiments, a method of inhibiting HBV replication is provided, comprising administering a compound of the present disclosure, or a pharmaceutically acceptable salt thereof, to an individual (e.g. a human).

In certain embodiments, a method of treating or preventing a HBV infection is provided, comprising administering to an individual (e.g. a human) in need thereof a therapeutically effective amount of a compound of the present disclosure, or a pharmaceutically acceptable salt thereof. In certain embodiments, the method of treating or preventing a HBV infection comprises administering one or more additional therapeutic agents.

In certain embodiments, a compound of the present disclosure, or a pharmaceutically acceptable salt thereof, for use in medical therapy is provided.

In certain embodiments, the use of a compound of the present disclosure, or a pharmaceutically acceptable salt thereof, for treating or preventing a HBV infection, is provided.

In certain embodiments, the use of a compound of the present disclosure, or a pharmaceutically acceptable salt thereof, for the manufacture of a medicament for treating or preventing a HBV infection, is provided.

Kits comprising the compounds, or pharmaceutically acceptable salts thereof, or pharmaceutical compositions of the foregoing are also provided. Articles of manufacture comprising a unit dose of the compounds, or pharmaceutically acceptable salts thereof, of the foregoing are also provided. Methods of preparing compounds of the present disclosure are also provided.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

I. DEFINITIONS

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or ($C_u$-$C_v$) indicates that the following group has from u to v carbon atoms, where u and v are integers. For example, "$C_{1-6}$alkyl" indicates that the alkyl group has from 1 to 6 carbon atoms.

"Alkyl" is a linear or branched saturated monovalent hydrocarbon. For example, an alkyl group can have 1 to 10 carbon atoms (i.e., ($C_{1-10}$)alkyl) or 1 to 8 carbon atoms (i.e., ($C_{1-8}$)alkyl) or 1 to 6 carbon atoms (i.e., ($C_{1-6}$ alkyl) or 1 to 4 carbon atoms (i.e., ($C_{1-4}$)alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"Alkoxy" refers to the group —O-alkyl, where alkyl is as defined above. For example, $C_{1-4}$alkoxy refers to an —O-alkyl group having 1 to 4 carbons.

"Alkynyl" is a linear or branched monovalent hydrocarbon radical with at least one carbon-carbon triple bond. For example, an alkynyl group can have 2 to 8 carbon atoms (i.e., $C_{2-8}$ alkyne,) or 2 to 6 carbon atoms (i.e., $C_{2-6}$ alkynyl) or 2 to 4 carbon atoms (i.e., $C_{2-4}$ alkynyl). Examples of alkynyl groups include, but are not limited to, acetylenyl (—C≡CH), propargyl (—$CH_2$C≡CH), and —$CH_2$—C≡C—$CH_3$.

The term "halo" or "halogen" as used herein refers to fluoro (—F), chloro (—Cl), bromo (—Br) and iodo (—I).

The term "haloalkyl" as used herein refers to an alkyl as defined herein, wherein one or more hydrogen atoms of the alkyl are independently replaced by a halo substituent, which may be the same or different. For example, $C_{1-4}$haloalkyl is a $C_{1-4}$alkyl wherein one or more of the hydrogen atoms of the $C_{1-4}$alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1, 2, 3, 4-tetrahydronaphthyl. Non-limiting examples of aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, and triazolyl.

The term "cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocyles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 5 to about 20 annular atoms, for example from 3 to 12 annular atoms, for example from 5 to 10 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

The term "oxo" as used herein refers to =O.

A "compound of the present disclosure" includes compounds disclosed herein, for example a compound of the present disclosure includes compounds of Formula (I), (II), (III), (IIIa), or (IV), including the compounds of Examples 1 to 32. Also, compounds of Examples 1-49 are included. Further, compounds of Examples 1 to 152 are included.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing HBV infection" refers to administering to a subject who does not have a detectable HBV infection an anti-HBV therapeutic substance. It is understood that the subject for anti-HBV preventative therapy may be an individual at risk of contracting the HBV virus. It is also understood that prevention does not require a 100% success rate. In some instances, prevention may be understood as a reduction of the risk of infection, but not a complete elimination the occurrence of an infection.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

As used herein, "co-administration" includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastererically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present disclosure includes tautomers of any said compounds.

A "solvate" is formed by the interaction of a solvent and a compound. Solvates of salts of the compounds described herein are also provided. Hydrates of the compounds described herein are also provided.

A "prodrug" is a biologically inactive derivative of a drug that upon administration to the human body is converted to the biologically active parent drug according to some chemical or enzymatic pathway.

II. COMPOUNDS

The present disclosure provides a compound of Formula (I):

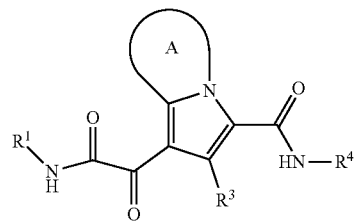

Formula I or a pharmaceutically acceptable salt thereof, wherein:

$R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$.

each $R^{1A}$ is independently halogen, —OH, —CN, $C_{1-2}$ haloalkyl, —C(O)$NR^XR^Y$, $C_{6-10}$ aryl optionally substituted with 1 to 3 $R^{1D}$, or a 5 to 8 membered heteroaryl having 1 to 3 heteroatoms selected from N, O, and S, optionally substituted with 1 to 3 $R^{1D}$, provided no more than 1 $R^{1A}$ is $C_{6-10}$ aryl optionally substituted with 1 to 3 $R^{1D}$ or 5 to 8 membered heteroaryl having 1 to 3 heteroatoms selected from N, O, and S optionally substituted with 1 to 3 $R^{1D}$;

each $R^{1B}$ is independently —CN, halogen, $C_{1-6}$ alkyl optionally substituted with 1 to 3 —OH or —$NR^aR^b$, $C_{2-4}$ alkynyl, $C_{1-4}$ alkoxy, $C_{1-2}$ haloalkyl, $C_{3-6}$ cycloalkyl, —C(O)$NR^XR^Y$, or a 5 to 8 membered heteroaryl having 1 to 3 heteroatoms selected from N, O, and S optionally substituted with 1 to 3 $R^{1D}$, provided no more than 1 $R^{1B}$ is $C_{3-6}$ cycloalkyl or 5 to 8 membered heteroaryl having 1 to 3 heteroatoms selected from N, O, and S optionally substituted with 1 to 3 $R^{1D}$;

each $R^{1C}$ is independently $C_{1-6}$ alkyl, oxo, $C_{1-4}$ haloalkyl, —C(O)H, —C(O)$C_{1-4}$ alkyl, —C(O)O$C_{1-4}$ alkyl, or a 5 to 12 membered heteroaryl having 1 to 3 heteroatoms selected from N, O, and S optionally substituted with 1 to 3 $R^{1D}$, provided no more than 1 $R^{1C}$ is a 5 to 12 membered heteroaryl having 1 to 3 heteroatoms selected from N, O, and S optionally substituted with 1 to 3 $R^{1D}$;

each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;

each $R^Y$ is independently —H or $C_{1-6}$ alkyl optionally substituted with 1 to 3 $R^Z$ or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$ wherein each $R^Z$ is independently halogen, methyl, ethyl, oxo, —OH, —S(O)$_2$C$_{1-3}$alkyl, or 3 to 8 membered monocyclic or bicyclic heterocyclyl having 1 to 3 heteroatoms selected from N, O, and S;

each $R^a$ is —H, $C_{1-3}$alkyl, or a 3 to 8 membered monocyclic or bicyclic heterocyclyl having 1 to 3 heteroatoms selected from N, O, and S, optionally substituted with 1 to 3 $R^Z$;

each $R^b$ is —H or $C_{1-3}$alkyl; or $R^a$ and $R^b$ taken together form a 3 to 8 membered monocyclic or bicyclic heterocycle optionally substituted with 1 to 3 $R^Z$;

the moiety

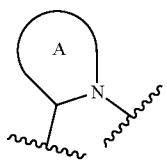

is a pyrrolidine or a 5-7 membered bicyclic heterocycle having one nitrogen, optionally substituted with 1 to 6 $R^2$ groups;

wherein each $R^2$ is independently halogen, $C_{1-3}$alkyl, —OH, or —OC$_{1-3}$ alkyl;

$R^3$ is —H, halogen, or $C_{1-4}$ alkyl;

$R^4$ is $C_{6-10}$ aryl optionally substituted with 1 to 5 $R^{4A}$, or 5 to 12 membered heteroaryl having 1 to 3 heteroatoms selected from N, O, and S, optionally substituted with 1 to 4 $R^{4B}$; and each $R^{1D}$, $R^{4A}$, and $R^{4B}$ are independently —CN, halogen, $C_{1-4}$ alkyl, —OC$_{1-4}$alkyl, —OC$_{1-4}$ haloalkyl, or $C_{1-4}$ haloalkyl.

In certain embodiments of a compound of Formula (I), (II), (III), (IIIa) or (IV), $R^4$ is phenyl optionally substituted with 1 to 5 $R^{4A}$ or pyridinyl optionally substituted with 1 to 4 $R^{4B}$. In certain embodiments of a compound of Formula (I), (II), (III), (IIIa) or (IV), $R^4$ is phenyl optionally substituted with 1 to 3 $R^{4A}$. In certain embodiments of a compound of Formula (I), (II), (III), (IIIa) or (IV), $R^4$ is pyridinyl, optionally substituted with 1 to 4 $R^{4B}$. In certain embodiments of a compound of Formula (I), (II), (III), (IIIa) or (IV), each $R^{1D}$, $R^{4A}$, and $R^{4B}$ are independently —CN, halogen, $C_{1-4}$ alkyl, or $C_{1-4}$ haloalkyl. In certain embodiments of a compound of Formula (I), (II), (III), (IIIa) or (IV), each $R^{4A}$ is independently Cl, F, —CF$_3$, —CHF$_2$, —CH$_3$, —OCF$_3$, —OCF$_2$H, or —CN. In certain embodiments of a compound of Formula (I), (II), (III), (IIIa) or (IV), each $R^{4A}$ is independently Cl, F, —CF$_3$, —CHF$_2$, —CH$_3$, or —CN. In certain embodiments of a compound of Formula (I), (II), (III), (IIIa) or (IV), each $R^{4B}$ is independently Cl, F, —CF$_3$, —CHF$_2$, —CH$_3$, —OCF$_3$, —OCF$_2$H, or —CN. In certain embodiments of a compound of Formula (I), (II), (III), (IIIa) or (IV), each $R^{4B}$ is independently Cl, F, —CF$_3$, —CHF$_2$, —CH$_3$, or —CN.

In certain embodiments of a compound of Formula (I), (II), (III), (IIIa) or (IV), $R^4$ is pyridinyl, optionally substituted with 1 to 3 groups selected from F, Cl, CF$_3$, and CHF$_2$. In certain embodiments of a compound of Formula (I), (II), (III), (IIIa) or (IV), $R^4$ is pyridin-4-yl, optionally substituted with 1 to 3 groups selected from F, Cl, CF$_3$, and CHF$_2$.

In certain embodiments of a compound of Formula (I) or (II), $R^3$ is —Cl or —CH$_3$. In certain embodiments of a compound of Formula (I) or (II), $R^3$ is —CH$_3$.

In certain embodiments of a compound of Formula (I), the moiety

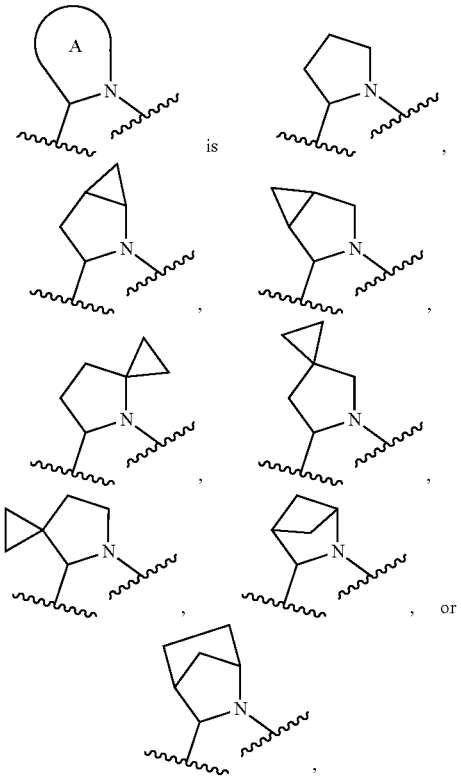

each of which is optionally substituted with 1 to 6 $R^2$.

In certain embodiments of a compound of Formula (I), the moiety

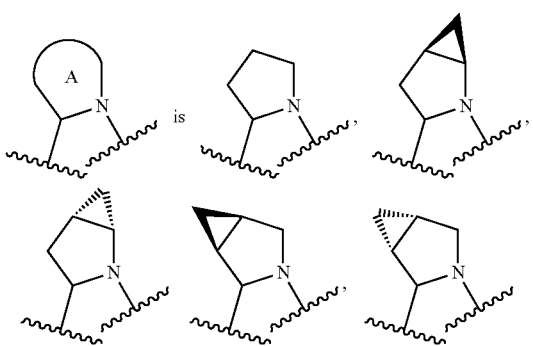

-continued

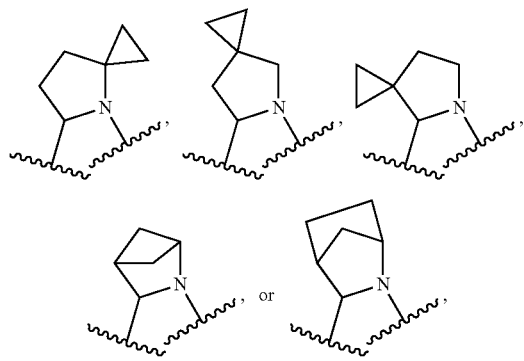

each of which is optionally substituted with 1 to 6 $R^2$.

In certain embodiments of a compound of Formula (I), the moiety

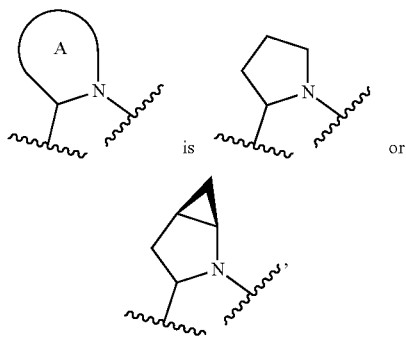

each of which is optionally substituted with 1 to 6 $R^2$.

In certain embodiments of a compound of Formula (I), the moiety

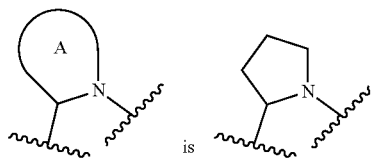

which is optionally substituted with 1 to 6 $R^2$.

In certain embodiments of a compound of Formula (I), the moiety

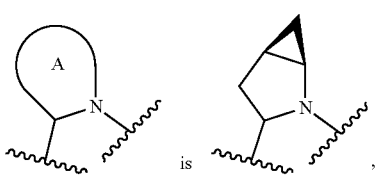

which is optionally substituted with 1 to 6 $R^2$.

In certain embodiments of a compound of Formula (I), the moiety

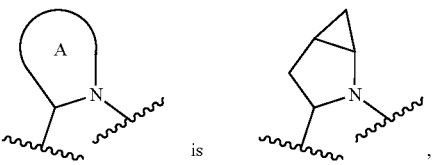

which is optionally substituted with 1 to 6 $R^2$.

For the avoidance of doubt, when the moiety

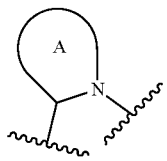

is a pyrrolidine or a 5-7 membered bicyclic heterocycle having one nitrogen, the one nitrogen refers to the nitrogen depicted in the structure

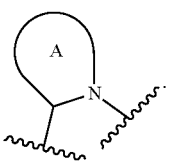

In certain embodiments of a compound of Formula (I), each $R^2$ is independently $C_{1-3}$ alkyl, —OH, or —$OC_{1-3}$ alkyl.

In certain embodiments of a compound of Formula (I), each $R^2$ is independently $R^2$ is —$CH_3$ or OH.

In certain embodiments of a compound of Formula (I), the compound is a compound of Formula (II)

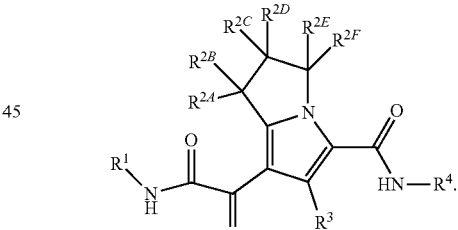

Formula II

In certain embodiments of a compound of Formula (I), is a compound of Formula (II) wherein:

$R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$;

each $R^{1A}$ is independently halogen, —OH, —CN, $C_{1-2}$ haloalkyl, —$C(O)NR^XR^Y$, $C_{6-10}$ aryl optionally substituted with 1 to 3 $R^{1D}$, or a 5 to 12 membered heteroaryl having 1 to 3 heteroatoms selected from N, O, and S, optionally substituted with 1 to 3 $R^{1D}$, provided no more than 1 $R^{1A}$ is $C_{6-10}$ aryl optionally substituted with 1 to 3 $R^{1D}$ or 5 to 12 membered heteroaryl having 1 to 3 heteroatoms selected from N, O, and S optionally substituted with 1 to 3 $R^{1D}$;

each $R^{1B}$ is independently —CN, halogen, $C_{1-6}$ alkyl optionally substituted with 1 to 3 —OH or —$NR^aR^b$, $C_{1-4}$ alkoxy, $C_{1-2}$ haloalkyl, $C_{3-6}$ cycloalkyl, —C(O)$NR^XR^Y$, or a 5 to 8 membered heteroaryl having 1 to 3 heteroatoms selected from N, O, and S optionally substituted with 1 to 3 $R^{1D}$, provided no more than 1 $R^{1B}$ is $C_{3-6}$ cycloalkyl, or 5 to 8 membered heteroaryl having 1 to 3 heteroatoms selected from N, O, and S optionally substituted with 1 to 3 $R^{1D}$;

each $R^{1C}$ is independently $C_{1-6}$ alkyl, oxo, $C_{1-4}$ haloalkyl, —C(O)H, —C(O)$C_{1-4}$ alkyl or —C(O)O$C_{1-4}$ alkyl;

each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;

each $R^Y$ is independently —H or $C_{1-6}$ alkyl optionally substituted with 1 to 3 $R^Z$ or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$ wherein each $R^Z$ is independently halogen, methyl, ethyl, oxo, —OH, —S(O)$_2C_{1-3}$alkyl, or 3 to 8 membered monocyclic or bicyclic heterocyclyl having 1 to 3 heteroatoms selected from N, O, and S;

each $R^a$ is —H, $C_{1-3}$alkyl, or a 3 to 8 membered monocyclic or bicyclic heterocyclyl having 1 to 3 heteroatoms selected from N, O, and S, optionally substituted with 1 to 3 $R^Z$;

each $R^b$ is —H or $C_{1-3}$alkyl; or $R^a$ and $R^b$ taken together form a 3 to 8 membered monocyclic or bicyclic heterocyclyl optionally substituted with 1 to 3 $R^Z$;

each of $R^{2A}$, $R^{2B}$, $R^{2C}$, $R^{2D}$, $R^{2E}$, and $R^{2F}$ are independently —H, halogen, $C_{1-3}$alkyl, —OH, or —O$C_{1-3}$ alkyl, or $R^{2C}$ or $R^{2D}$ may be taken together with $R^{2E}$ or $R^{2F}$ to form a cyclopropyl group;

$R^3$ is halogen or methyl;

$R^4$ is phenyl optionally substituted with 1 to 5 $R^{4A}$, or pyridinyl, optionally substituted with 1 to 4 $R^{4B}$; and each $R^{1D}$, $R^{4A}$, and $R^{4B}$ are independently —CN, halogen, $C_{1-4}$ alkyl, —O$C_{1-4}$alkyl, —O$C_{1-4}$ haloalkyl, or $C_{1-4}$ haloalkyl.

In certain embodiments of a compound of Formula (I) or (II), $R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$;

each $R^{1A}$ is independently halogen, —OH, —CN, $C_{1-2}$ haloalkyl, —C(O)$NR^XR^Y$, $C_{6-10}$ aryl optionally substituted with 1 to 3 $R^{1D}$, or a 5 to 12 membered heteroaryl having 1 to 3 heteroatoms selected from N, O, and S, optionally substituted with 1 to 3 $R^{1D}$, provided no more than 1 $R^{1A}$ is $C_{6-10}$ aryl optionally substituted with 1 to 3 $R^{1D}$ or 5 to 12 membered heteroaryl having 1 to 3 heteroatoms selected from N, O, and S optionally substituted with 1 to 3 $R^{1D}$;

each $R^{1B}$ is independently halogen, $C_{1-6}$ alkyl optionally substituted with 1 to 3 —OH or —$NR^aR^b$, $C_{1-4}$ alkoxy, $C_{1-2}$ haloalkyl, —C(O)$NR^XR^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$;

each $R^{1C}$ is independently $C_{1-6}$ alkyl, oxo, $C_{1-4}$ haloalkyl, —C(O)H, —C(O)$C_{1-4}$ alkyl or —C(O)O$C_{1-4}$ alkyl;

each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;

each $R^Y$ is independently —H or $C_{1-6}$ alkyl optionally substituted with 1 to 3 $R^Z$;

or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$ wherein each $R^Z$ is independently halogen, methyl, ethyl, oxo, —OH, —S(O)$_2C_{1-3}$alkyl, or 3 to 8 membered monocyclic or bicyclic heterocyclyl having 1 to 3 heteroatoms selected from N, O, and S;

each $R^a$ is —H, $C_{1-3}$alkyl, or a 3 to 8 membered monocyclic or bicyclic heterocyclyl having 1 to 3 heteroatoms selected from N, O, and S, optionally substituted with 1 to 3 $R^Z$;

each $R^b$ is —H or $C_{1-3}$alkyl; or $R^a$ and $R^b$ taken together form a 3 to 8 membered monocyclic or bicyclic heterocyclyl optionally substituted with 1 to 3 $R^Z$;

each of $R^{2A}$, $R^{2B}$, $R^{2C}$, $R^{2D}$, $R^{2E}$, and $R^{2F}$ are independently —H, halogen, $C_{1-3}$alkyl, —OH, or —O$C_{1-3}$ alkyl, or $R^{2C}$ or $R^{2D}$ may be taken together with $R^{2E}$ or $R^{2F}$ to form a cyclopropyl group;

$R^3$ is halogen or methyl;

$R^4$ is phenyl optionally substituted with 1 to 5 $R^{4A}$, or pyridinyl, optionally substituted with 1 to 4 $R^{4B}$; and each $R^{1D}$, $R^{4A}$, and $R^{4B}$ are independently —CN, halogen, $C_{1-4}$ alkyl, —O$C_{1-4}$alkyl, —O$C_{1-4}$ haloalkyl, or $C_{1-4}$ haloalkyl.

In certain embodiments of a compound of Formula (I) or (II), the compound is a compound of Formula (III)

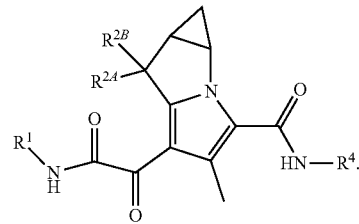

Formula III wherein $R^1$, $R^{2A}$, $R^{2B}$, and $R^4$, are as defined herein for (I), (II), (III), (IIIa), or (IV), or any combination thereof.

In certain embodiments of a compound of Formula (I), (II), or (III), the compound is a compound of Formula (IIIa)

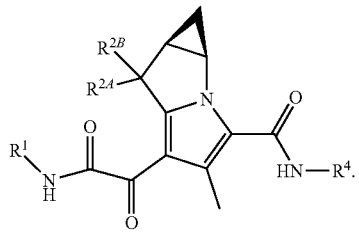

Formula IIIa wherein $R^1$, $R^{2A}$, $R^{2B}$, and $R^4$, are as defined herein for Formula (I), (II), (III), (IIIa), or (IV), or any combination thereof.

In certain embodiments of a compound of Formula (I) or (II), the compound is a compound of Formula (IV):

Formula IV

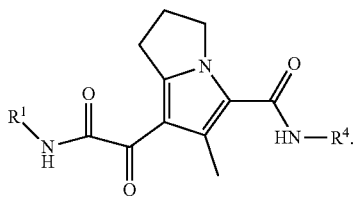

wherein $R^1$ and $R^4$, are as defined herein for are as defined herein for Formula (I), (II), (III), (IIIa), or (IV), or any combination thereof.

In certain embodiments of a compound of Formula (I), (II), (III), (IIIa), or (IV), $R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$.

In certain embodiments of a compound of Formula (I), (II), (III), (IIIa), or (IV), $R^1$ is $C_{1-6}$ alkyl optionally substituted with 1 to 3 $R^{1A}$. In certain embodiments of a compound of Formula (I), (II), (III), (IIIa), or (IV), $R^1$ is $C_{1-6}$ alkyl optionally substituted with 1 to 3 $C_{1-2}$haloalkyl. In certain embodiments of a compound of Formula (I), (II), (III), (IIIa), or (IV), $R^1$ is methyl, ethyl, propyl, butyl, or pentyl, optionally substituted with 1 to 3 $R^{1A}$. In certain embodiments of a compound of Formula (I), (II), (III), (IIIa), or (IV), $R^1$ is ethyl or butyl optionally substituted with $C_{1-2}$haloalkyl.

In certain embodiments of a compound of Formula (I), (II), (III), (IIIa), or (IV), $R^1$ is

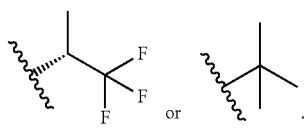

In certain embodiments of a compound of Formula (I), (II), (III), (IIIa), or (IV), $R^1$ is ethyl, propyl, or butyl optionally substituted with 1 to 3 $R^{1A}$, wherein each $R^{1A}$ is independently $C_{1-2}$haloalkyl, —OH, —C(O)NH$_2$, —C(O)NH(C$_{1-3}$alkyl), or —C(O)N(C$_{1-3}$alkyl)$_2$.

In certain embodiments of a compound of Formula (I), (II), (III), (IIIa), or (IV), $R^1$ is

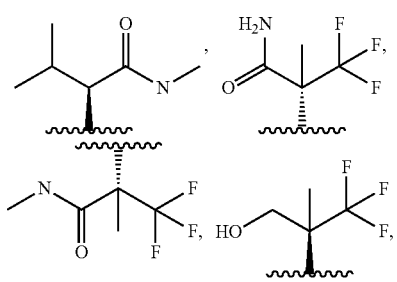

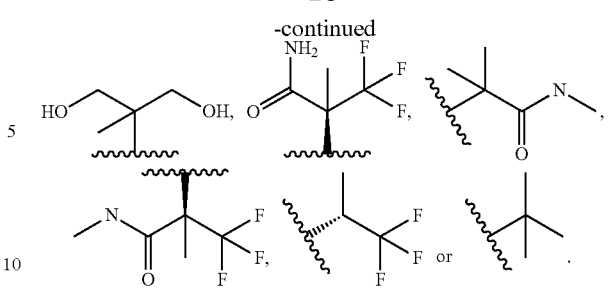

In certain embodiments of a compound of Formula (I), (II), (III), (IIIa), or (IV), $R^1$ is $C_{3-8}$ cycloalkyl optionally substituted with 1 to 4 $R^{1B}$. In certain embodiments of a compound of Formula (I), (II), (III), (IIIa), or (IV), $R^1$ is cyclopropyl or cyclobutyl, optionally substituted with 1 to 3 $R^{1B}$. In certain embodiments of a compound of Formula (I), (II), (III), (IIIa), or (IV), each $R^{1B}$ is independently halogen, $C_{1-3}$alkyl substituted with —NR$^a$R$^b$, —C(O)NR$^X$R$^Y$, or 5 to 8 membered heteroaryl having 1 to 3 heteroatoms selected from N, O, and S optionally substituted with 1 to 3 $R^{1D}$. In certain embodiments of a compound of Formula (I), (II), (III), (IIIa), or (IV), each $R^{1B}$ is independently fluoro, —CH$_2$NR$^a$R$^b$, triazolyl, thiadiazolyl, or —C(O)NR$^X$R$^Y$. In certain embodiments of a compound of Formula (I), (II), (III), (IIIa), or (IV), each $R^{1B}$ is independently fluoro, —CH$_2$NR$^a$R$^b$, or —C(O)NR$^X$R$^Y$. In certain embodiments of a compound of Formula (I), (II), (III), (IIIa), or (IV), one or two $R^{1B}$ is independently halo and one $R^{1B}$ is —C(O)NR$^X$R$^Y$. In certain embodiments of a compound of Formula (I), (II), (III), (IIIa), or (IV), wherein $R^a$ is methyl or a 4 to 7 membered monocyclic or bicyclic heterocyclyl having 1 to 3 heteroatoms selected from N, O, and S optionally substituted with 1 to 3 $R^{1Z}$, $R^b$ is —H, or $R^a$ and $R^b$ are taken together to form a 4 to 7 membered monocyclic or bicyclic heterocyclyl having 1 to 3 heteroatoms selected from N, O, and S optionally substituted with 1 to 3 $R^{1Z}$, $R^X$ is methyl or a 4 to 7 membered monocyclic or bicyclic heterocyclyl having 1 to 3 heteroatoms selected from N, O, and S optionally substituted with 1 to 3 $R^{1Z}$, $R^Y$ is —H, or $R^X$ and $R^Y$ are taken together to form a 4 to 7 membered monocyclic or bicyclic heterocyclyl having 1 to 3 heteroatoms selected from N, O, and S optionally substituted with 1 to 3 $R^{1Z}$. In certain embodiments of a compound of Formula (I), (II), (III), (IIIa), or (IV), 1 or 2 $R^{1B}$ is optionally fluoro and one $R^{1B}$ is —CH$_2$NR$^a$R$^b$, where $R^a$ is thietanyl substituted with 1 to 3 oxo or methyl groups or 2-oxa-6-azaspiro[3.3]heptanyl and $R^b$ is —H or $R^a$ and $R^b$ are taken together to form 2-oxa-6-azaspiro[3.3]heptanyl. In certain embodiments of a compound of Formula (I), (II), (III), (IIIa), or (IV), 1 or 2 $R^{1B}$ is optionally fluoro and one $R^{1B}$ is —C(O)NR$^X$R$^Y$ wherein $R^X$ is methyl or thietanyl optionally substituted with 1 to 3 methyl or oxo groups, $R^Y$ is —H, or $R^X$ and $R^Y$ are taken together to form 2-oxa-6-azaspiro[3.3]heptanyl, 2-thia-6-azaspiro[3.3]heptan-6-yl, azetidinyl, 2,6-diazaspiro[3.3]heptanyl, 6-oxa-1-azaspiro[3.3]heptan-1-yl, each of which is optionally substituted with 1 to 3 groups that are independently fluoro, oxo, methyl, or —S(O)$_2$CH$_3$.

In certain embodiments of a compound of Formula (I), (II), (III), (IIIa), or (IV), $R^1$ is

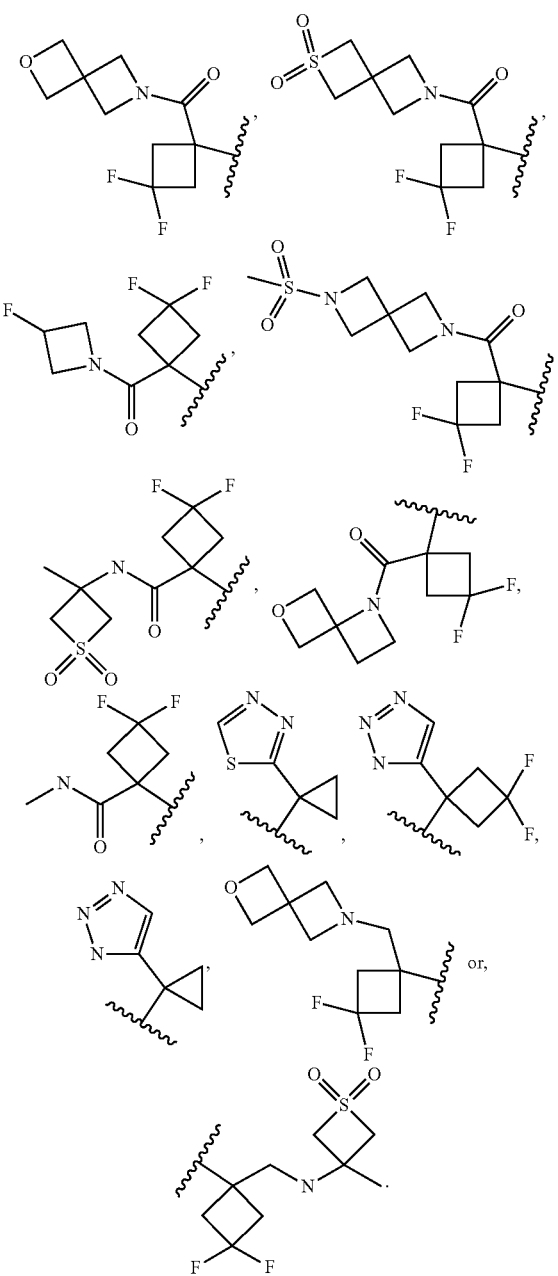

In certain embodiments of a compound of Formula (I), (II), (III), (IIIa), or (IV), $R^1$ is $C_{3-5}$ cycloalkyl optionally substituted with 1 to 4 $R^{1B}$, wherein each $R^B$ is independently halogen, ethynyl, —CN, $C_{1-3}$alkyl substituted with —OH, or —NR$^a$R$^b$, —C(O)NR$^X$R$^Y$, phenyl optionally substituted with 1 to 3 $R^{1D}$, or 5 to 8 membered heteroaryl having 1 to 3 heteroatoms selected from N, O, and S optionally substituted with 1 to 3 $R^{1D}$ In certain embodiments of a compound of Formula (I), (II), (III), (IIIa), or (IV), $R^1$ is cyclopropyl, bicyclo[1.1.1]pentanyl, cyclobutyl optionally substituted with 1 to 3 $R^{1B}$ wherein each $R^{1B}$ is independently halogen, ethynyl, —CN, $C_{1-3}$alkyl substituted with —OH or —NR$^a$R$^b$, —C(O)NR$^X$R$^Y$, phenyl optionally substituted with 1 to 3 $R^{1D}$, or 5 membered heteroaryl having 1 to 3 heteroatoms selected from N, O, and S optionally substituted with 1 to 3 $R^{1D}$ In certain embodiments of a compound of Formula (I), (II), (III), (IIIa), or (IV), $R^1$ is cyclopropyl or cyclobutyl, optionally substituted with 1 or 2 fluoro and one of tetrazolyl optionally substituted with $C_{1-3}$alkyl, oxadiazolyl optionally substituted with $C_{1-3}$alkyl, triazolyl optionally substituted with $C_{1-3}$alkyl, or thiadiazolyl.

In certain embodiments of a compound of Formula (I), (II), (III), (IIIa), or (IV), $R^1$ is

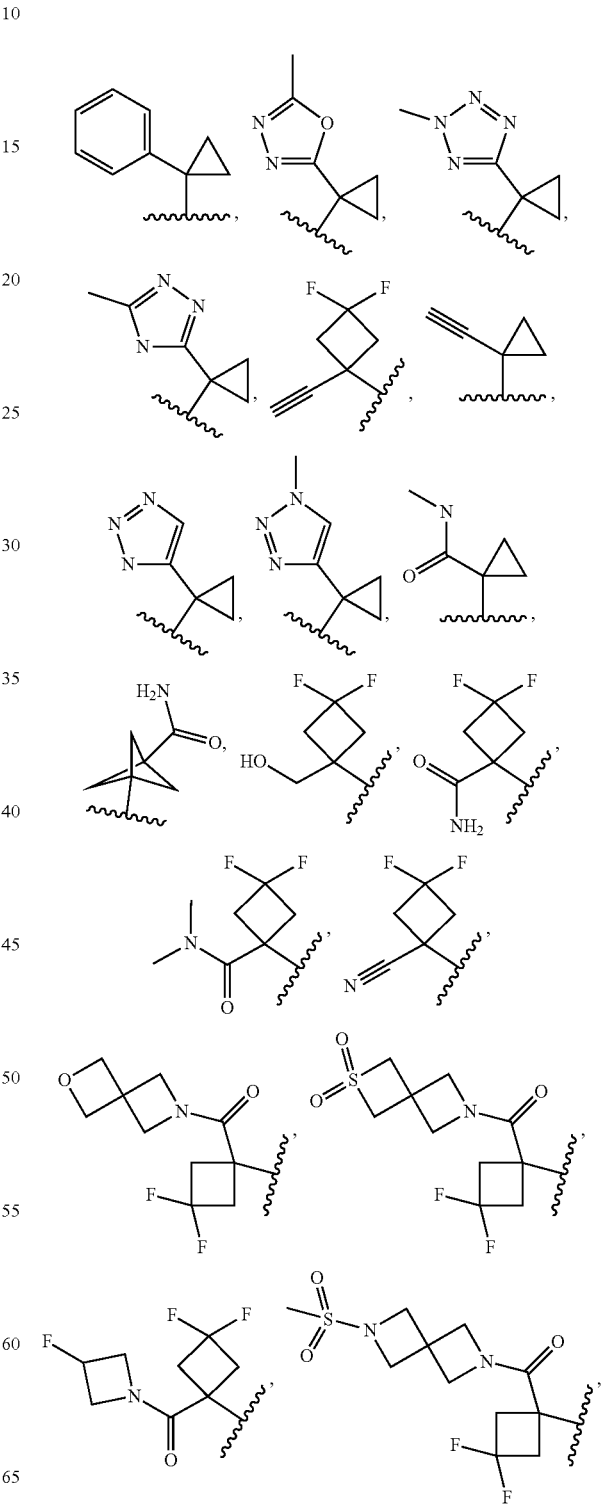

-continued

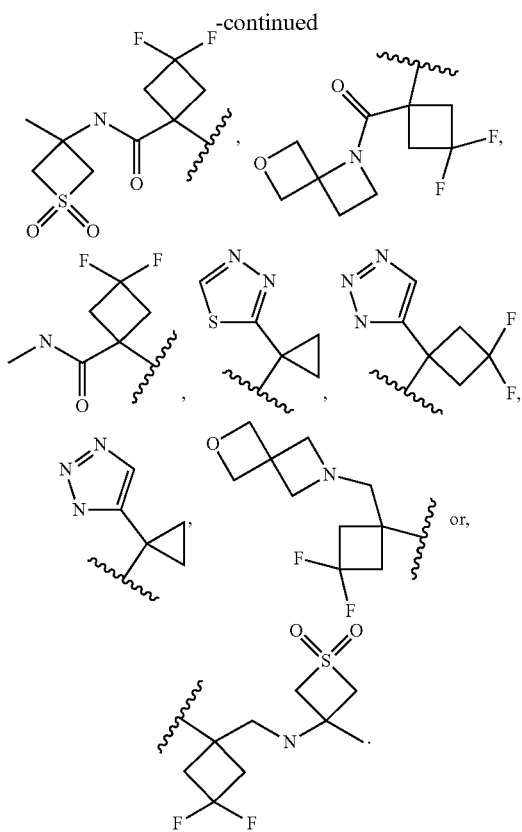

In certain embodiments of a compound of Formula (I), (II), (III), (IIIa), or (IV), $R^1$ is

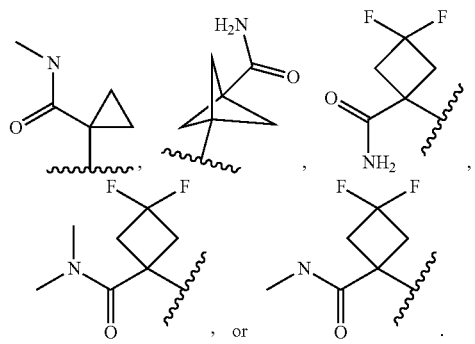

In certain embodiments of a compound of Formula (I), (II), (III), (IIIa), or (IV), $R^1$ is

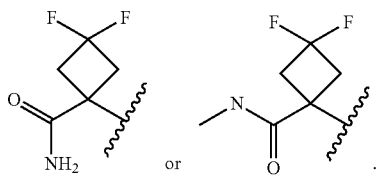 [SMILES: *C1(C(N)=O)CC(F)(F)C1 ; *C1(C(=O)NC)CC(F)(F)C1]

In certain embodiments of a compound of Formula (I), (II), (III), (IIIa), or (IV), $R^1$ is a 3 to 8 membered monocyclic or bicyclic heterocyclyl having 1 to 3 heteroatoms selected from N, O, and S, optionally substituted with 1 to 3 $R^{1C}$. In certain embodiments of a compound of Formula (I), (II), (III), (IIIa), or (IV), $R^1$ is a 3 to 5 membered monocyclic heterocyclyl having 1 to 3 heteroatoms selected from N, O, and S, optionally substituted with 1 to 3 $R^{1C}$. In certain embodiments of a compound of Formula (I), (II), (III), (IIIa), or (IV), $R^1$ is oxetanyl or thietanyl optionally substituted with 1 to 3 $R^{1C}$. In certain embodiments of a compound of Formula (I), (II), (III), (IIIa), or (IV), each $R^{1C}$ is independently $C_{1-3}$alkyl, —$CF_3$, or oxo.

In certain embodiments of a compound of Formula (I), (II), (III), (IIIa), or (IV), $R^1$ is:

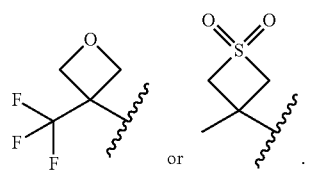

In certain embodiments of a compound of Formula (I), (II), (III), (IIIa), or (IV), $R^1$ is

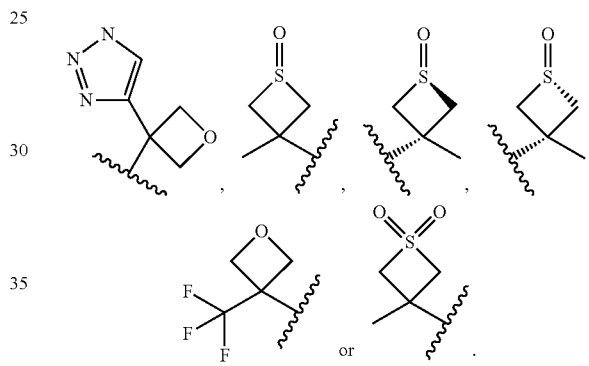

In certain embodiments of a compound of Formula (I), (II), or (III), the compound is a compound of Formula (IIIa)

Formula IIIa

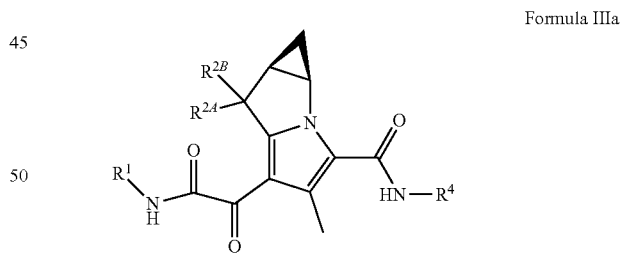

wherein:
$R^1$ is $C_{1-6}$ alkyl optionally substituted with 1 to 3 $R^A$, $C_{3-8}$ cycloalkyl optionally substituted with 1 to 4 $R^{1B}$, or $R^1$ is a 3 to 8 membered monocyclic or bicyclic heterocyclyl having 1 to 3 heteroatoms selected from N, O, and S, optionally substituted with 1 to 3 $R^{1C}$;
each $R^{1A}$ is independently $C_{1-2}$haloalkyl;
each $R^{1B}$ is independently halogen, $C_{1-6}$ alkyl optionally substituted with one $NR^aR^b$, $C_{1-2}$ haloalkyl —C(O)$NR^XR^Y$, or 5 to 8 membered heteroaryl having 1 to 3 heteroatoms selected from N, O, and S optionally substituted with 1 to 3 $R^{1D}$ provided no more than 1 $R^{1B}$ is $C_{3-6}$ cycloalkyl or 5 to 8 membered heteroaryl having 1 to 3 heteroatoms selected from N, O, and S optionally substituted with 1 to 3 $R^{1D}$;
  each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;
  each $R^Y$ is independently —H or $C_{1-6}$ alkyl optionally substituted with 1 to 3 $R^Z$
    or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$;
  wherein each $R^Z$ is independently halogen, methyl, ethyl, oxo, —OH, —S(O)$_2$C$_{1-3}$alkyl, or 3 to 8 membered monocyclic or bicyclic heterocyclyl having 1 to 3 heteroatoms selected from N, O, and S;
  each $R^{1C}$ is independently $C_{1-6}$ alkyl, oxo, $C_{1-4}$ haloalkyl;
  each $R^a$ is —H, $C_{1-3}$alkyl, or a 3 to 8 membered monocyclic or bicyclic heterocyclyl having 1 to 3 heteroatoms selected from N, O, and S, optionally substituted with 1 to 3 $R^Z$;
  each $R^b$ is —H or $C_{1-3}$alkyl; or
  $R^a$ and $R^b$ taken together form a 3 to 8 membered monocyclic or bicyclic heterocycle optionally substituted with 1 to 3 $R^Z$
  $R^{2A}$ and $R^{2B}$ are each —H;
  $R^4$ is phenyl optionally substituted with 1 to 5 $R^{4A}$ or pyridinyl optionally substituted with 1 to 4 $R^{4B}$, wherein each $R^{4A}$ is independently Cl, F, —CF$_3$, —CHF$_2$, —CH$_3$, —OCF$_3$, —OCF$_2$H, or —CN and each $R^{4B}$ is independently Cl, F, —CF$_3$, —CHF$_2$, —CH$_3$, —OCF$_3$, —OCF$_2$H, or —CN; and
each $R^{1D}$ is independently —CN, halogen, $C_{1-4}$ alkyl, or $C_{1-4}$ haloalkyl.
  In certain embodiments of a compound of Formula (III) or (IIIa), $R^1$ is $C_{3-8}$ cycloalkyl optionally substituted with 1 to 4 $R^{1B}$, one or two $R^{1B}$ is optionally halogen and one $R^{1B}$ is —C(O)NR$^X$R$^Y$, $R^X$ is $C_{1-6}$ alkyl, $R^Y$ is —H, or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$; wherein each $R^Z$ is independently halogen, methyl, ethyl, oxo, —OH, —S(O)$_2$C$_{1-3}$alkyl, $R^{2A}$ and $R^{2B}$ are —H; $R^4$ is phenyl optionally substituted with 1 to 5 $R^{4A}$, or pyridinyl, optionally substituted with 1 to 4 $R^{4B}$; and each $R^{4A}$ and $R^{4B}$ are independently —CN, halogen, $C_{14}$ alkyl, or $C_{1-4}$ haloalkyl. In certain embodiments of a compound of Formula (III) or (IIIa), $R^1$ is $C_{3-8}$ cycloalkyl optionally substituted with 1 to 4 $R^{1B}$, one or two $R^{1B}$ is optionally halogen and one $R^{1B}$ is —C(O)NR$^X$R$^Y$, $R^X$ is $C_{1-6}$ alkyl, $R^Y$ is —H, or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$; wherein each $R^Z$ is independently halogen, methyl, ethyl, oxo, —OH, —S(O)$_2$C$_{1-3}$alkyl, $R^{2A}$ and $R^{2B}$ are —H; $R^4$ is phenyl optionally substituted with 1 to 5 $R^{4A}$, or pyridinyl, optionally substituted with 1 to 4 $R^{4B}$; and each $R^{4A}$ and $R^{4B}$ are independently —CN, halogen, $C_{1-4}$ alkyl, —OC$_{1-4}$alkyl, —OC$_{1-4}$ haloalkyl, or $C_{1-4}$ haloalkyl.
  In certain embodiments of a compound of Formula (III) or (IIIa), $R^1$ is cyclobutyl optionally substituted with 1 to 3 $R^{1B}$, one or two $R^{1B}$ is optionally fluoro and one $R^{1B}$ is —C(O)NR$^X$R$^Y$, $R^X$ is $C_{1-6}$ alkyl, $R^Y$ is —H, $R^{2A}$ and $R^{2B}$ are —H; $R^4$ is phenyl optionally substituted with 1 to 5 $R^{4A}$ which are independently Cl, F, —CF$_3$, —CHF$_2$, —CH$_3$, or —CN. In certain embodiments of a compound of Formula (III) or (IIIa), $R^1$ is cyclobutyl optionally substituted with 1 to 3 $R^{1B}$, one or two $R^{1B}$ is optionally fluoro and one $R^{1B}$ is —C(O)NR$^X$R$^Y$, $R^X$ is $C_{1-6}$ alkyl, $R^Y$ is —H, $R^{2A}$ and $R^{2B}$ are —H; $R^4$ is phenyl optionally substituted with 1 to 5 $R^{4A}$ which are independently Cl, F, —CF$_3$, —CHF$_2$, —CH$_3$, —OCF$_3$, —OCF$_2$H, or —CN.
  In certain embodiments of a compound of Formula (I) or (II), the compound is a compound of Formula (IV):

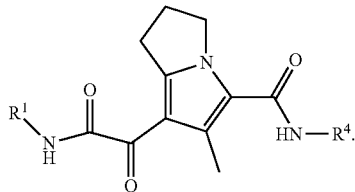

Formula IV wherein:
  $R^1$ is $C_{1-6}$ alkyl optionally substituted with 1 to 3 $R^{1A}$, $C_{3-8}$ cycloalkyl optionally substituted with 1 to 4 $R^{1B}$, or $R^1$ is a 3 to 8 membered monocyclic or bicyclic heterocyclyl having 1 to 3 heteroatoms selected from N, O, and S, optionally substituted with 1 to 3 $R^{1C}$;
  each $R^{1A}$ is independently $C_{1-2}$haloalkyl;
  each $R^{1B}$ is independently halogen, $C_{1-6}$ alkyl optionally substituted with one NR$^a$R$^b$, $C_{1-2}$ haloalkyl —C(O)NR$^X$R$^Y$, or 5 to 8 membered heteroaryl having 1 to 3 heteroatoms selected from N, O, and S optionally substituted with 1 to 3 $R^{1D}$ provided no more than 1 $R^{1B}$ is 5 to 8 membered heteroaryl having 1 to 3 heteroatoms selected from N, O, and S optionally substituted with 1 to 3 $R^{1D}$;
  each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;
  each $R^Y$ is independently —H or $C_{1-6}$ alkyl optionally substituted with 1 to 3 $R^Z$
    or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$
  wherein each $R^Z$ is independently halogen, methyl, ethyl, oxo, —OH, —S(O)$_2$C$_{1-3}$alkyl, or 3 to 8 membered monocyclic or bicyclic heterocyclyl having 1 to 3 heteroatoms selected from N, O, and S;
  each $R^{1C}$ is independently $C_{1-6}$ alkyl, oxo, $C_{1-4}$ haloalkyl;
  each $R^a$ is —H, $C_{1-3}$alkyl, or a 3 to 8 membered monocyclic or bicyclic heterocyclyl having 1 to 3 heteroatoms selected from N, O, and S, optionally substituted with 1 to 3 $R^Z$;
  each $R^b$ is —H or $C_{1-3}$alkyl; or
  $R^a$ and $R^b$ taken together form a 3 to 8 membered monocyclic or bicyclic heterocycle optionally substituted with 1 to 3 $R^Z$;
  $R^4$ is phenyl optionally substituted with 1 to 5 $R^{4A}$ or pyridinyl optionally substituted with 1 to 4 $R^{4B}$, wherein each $R^{4A}$ is independently Cl, F, —CF$_3$, —CHF$_2$, —CH$_3$, or —CN and each $R^{4B}$ is independently Cl, F, —CF$_3$, —CHF$_2$, —CH$_3$, or —CN; and
  each $R^{1D}$ is independently —CN, halogen, $C_{14}$ alkyl, or $C_{1-4}$ haloalkyl.

In certain embodiments of a compound of Formula (I), (II), (III), (IIIa) or (VI), $R^1$ is $C_{1-6}$ alkyl optionally substituted with 1 to 3 $R^{1A}$, $C_{3-8}$ cycloalkyl optionally substituted with 1 to 4 $R^{1B}$, or $R^1$ is a 3 to 8 membered monocyclic or bicyclic heterocyclyl having 1 to 3 heteroatoms selected from N, O, and S, optionally substituted with 1 to 3 $R^{1C}$; each $R^{1A}$ is independently $C_{1-2}$haloalkyl; each $R^{1B}$ is independently halogen, $C_{1-6}$ alkyl optionally substituted with one $NR^aR^b$, —C(O)$NR^XR^Y$, or 5 to 8 membered heteroaryl having 1 to 3 heteroatoms selected from N, O, and S optionally substituted with 1 to 3 $R^{1D}$ provided no more than 1 $R^{1B}$ is 5 to 8 membered heteroaryl having 1 to 3 heteroatoms selected from N, O, and S; each $R^X$ is independently, $C_{1-6}$ alkyl optionally substituted with 1 to 3 $R^Z$ or 3 to 8 membered monocyclic or bicyclic heterocyclyl having 1 to 3 heteroatoms selected from N, O, and S, optionally substituted with 1 to 3 $R^Z$; each $R^1$ is independently —H; or $R^X$ and $R^1$ are taken together to form a 3 to 8 membered monocyclic or bicyclic heterocyclyl having 1 to 3 heteroatoms selected from N, O, and S, optionally substituted with 1 to 3 $R^Z$ wherein each $R^Z$ is independently halogen, methyl, ethyl, oxo, —OH, or —S(O)$_2C_{1-3}$alkyl, each $R^{1C}$ is independently $C_{1-6}$ alkyl, oxo, or $C_{1-4}$ haloalkyl; $R^a$ and $R^b$ taken together form a 3 to 8 membered monocyclic or bicyclic heterocycle optionally substituted with 1 to 3 $R^Z$; $R^4$ is phenyl optionally substituted with 1 to 5 $R^{4A}$ or pyridinyl optionally substituted with 1 to 4 $R^{4B}$, and each $R^{1D}$, $R^{4A}$, and $R^{4B}$ are independently —CN, halogen, $C_{1-4}$ alkyl, —OC$_{1-4}$alkyl, —OC$_{1-4}$ haloalkyl, or $C_{1-4}$ haloalkyl.

In certain embodiments of a compound of Formula (I), (II), (III), (IIIa) or (VI), $R^1$ is $C_{1-4}$ alkyl optionally substituted with 1 to 3 $R^{1A}$, cyclopropyl or cyclobutyl optionally substituted with 1 to 3 $R^{1B}$, or oxetanyl or thietanyl optionally substituted with 1 to 3 $R^{1C}$; each $R^{1A}$ is independently $C_{1-2}$haloalkyl; one or two $R^{1B}$ is optionally halogen and one $R^{1B}$ is $C_{1-3}$ alkyl optionally substituted with one $NR^aR^b$, —C(O)$NR^XR^Y$, triazolyl optionally substituted with 1 to 3 $R^{1D}$ or thiadiazolyl optionally substituted with 1 to 3 $R^{1D}$; each $R^X$ is independently $C_{1-3}$ alkyl or thietanyl optionally substituted with 1 to 3 $R^Z$; each $R^Y$ is independently —H; or $R^X$ and $R^Y$ are taken together to form a 4 to 7 membered monocyclic or bicyclic heterocyclyl having 1 to 3 heteroatoms selected from N, O, and S, optionally substituted with 1 to 3 $R^Z$ wherein each $R^Z$ is independently halogen, methyl, ethyl, oxo, —OH, or —S(O)$_2C_{1-3}$alkyl, each $R^{1C}$ is independently $C_{1-3}$ alkyl, oxo, or $C_{1-3}$ haloalkyl; $R^a$ and $R^b$ taken together form a 3 to 8 membered monocyclic or bicyclic heterocycle optionally substituted with 1 to 3 $R^Z$; $R^4$ is phenyl optionally substituted with 1 to 5 —Cl, F, —CF$_3$, —CHF$_2$, —CH$_3$, or —CN; and each $R^{1D}$ is independently —CN, halogen, $C_{1-4}$ alkyl, or $C_{1-4}$ haloalkyl.

In certain embodiments of a compound of Formula (I), (II), (III), (IIIa), or (IV), $R^1$ is cyclopropyl or cyclobutyl, optionally substituted with 1 or 2 halogen and —C(O)$NR^XR^Y$ or —CH$_2NR^aR^b$ wherein $R^X$ and $R^Y$ are taken together to form a 4 to 7 membered monocyclic or bicyclic heterocycle having 1 to 3 heteroatoms selected from N, O, and S optionally substituted with 1 to 3 $R^{1Z}$ and $R^a$ and $R^b$ are taken together to form a 4 to 7 membered monocyclic or bicyclic heterocycle having 1 to 3 heteroatoms selected from N, O, and S optionally substituted with 1 to 3 $R^{1Z}$. In certain embodiments of a compound of Formula (I), (II), (III), (IIIa), or (IV), $R^X$ and $R^Y$ are taken together to for 2-oxa-6-azaspiro[3.3]heptanyl, 2-thia-6-azaspiro[3.3]heptan-6-yl, azetidinyl, 2,6-diazaspiro[3.3]heptanyl, or 6-oxa-1-azaspiro[3.3]heptan-1-yl each of which is optionally substituted with 1 to 3 groups that are independently fluoro, oxo, methyl, or —S(O)$_2$CH$_3$. In certain embodiments of a compound of Formula (I), (II), (III), (IIIa), or (IV), $R^a$ and $R^b$ are taken together to form 2-oxa-6-azaspiro[3.3]heptanyl.

In certain embodiments of a compound of Formula (I), (II), (III), (IIIa), or (IV), $R^1$ is cyclopropyl or cyclobutyl, optionally substituted with 1 or 2 halogens and a 5 to 8 membered heteroaryl having 1 to 3 heteroatoms selected from N, O, and S optionally substituted with 1 to 3 $R^{1D}$. In certain embodiments of a compound of Formula (I), (II), (III), (IIIa), or (IV), $R^1$ is cyclopropyl or cyclobutyl, optionally substituted with 1 or 2 halogen and a 5 membered heteroaryl having 1 to 3 heteroatoms selected from N, O, and S optionally substituted with 1 to 3 $R^{1D}$. In certain embodiments of a compound of Formula (I), (II), (III), (IIIa), or (IV), $R^1$ is cyclopropyl or cyclobutyl, optionally substituted with 1 or 2 halogen and triazolyl or thiadiazolyl. In certain embodiments of a compound of Formula (I), (II), (III), (IIIa), or (IV), $R^1$ is cyclopropyl or cyclobutyl, optionally substituted with 1 or 2 halogen and triazolyl. In certain embodiments of a compound of Formula (I), (II), (III), (IIIa), or (IV), $R^1$ is cyclopropyl or cyclobutyl, optionally substituted with 1 or 2 fluoro and triazolyl or thiadiazolyl. In certain embodiments of a compound of Formula (I), (II), (III), (IIIa), or (IV), $R^1$ is cyclopropyl or cyclobutyl, optionally substituted with 1 or 2 fluoro and triazolyl.

In certain embodiments of a compound of Formula (I), (II), (III), (IIIa), or (IV), $R^1$ is cyclopropyl or cyclobutyl, optionally substituted with 1 or 2 halogens and a 5 to 8 membered heteroaryl having 1 to 3 heteroatoms selected from N, O, and S optionally substituted with 1 to 3 $R^{1D}$; $R^4$ is phenyl optionally substituted with 1 to 5 $R^{4A}$ or pyridinyl optionally substituted with 1 to 4 $R^{4B}$, wherein each $R^{4A}$ is independently —CN, halogen, $C_{1-4}$ alkyl, —OC$_{1-4}$alkyl, —OC$_{1-4}$ haloalkyl, or $C_{1-4}$ haloalkyl and each $R^{4B}$ is independently —CN, halogen, $C_{1-4}$ alkyl, —OC$_{1-4}$alkyl, —OC$_{1-4}$ haloalkyl, or $C_{1-4}$ haloalkyl, and each $R^{1D}$ is independently —CN, halogen, $C_{1-4}$ alkyl, or $C_{1-4}$ haloalkyl. In certain embodiments of a compound of Formula (I), (II), (III), (IIIa), or (IV), $R^1$ is cyclopropyl or cyclobutyl, optionally substituted with 1 or 2 halogens and a 5 membered heteroaryl having 1 to 3 heteroatoms selected from N, O, and S optionally substituted with 1 to 3 $R^{1D}$; $R^4$ is phenyl optionally substituted with 1 to 3 $R^{4A}$ wherein each $R^{4A}$ is independently —CN, halogen, $C_{1-4}$ alkyl, —OC$_{1-4}$alkyl, —OC$_{1-4}$ haloalkyl, or $C_{1-4}$ haloalkyl, and each $R^{1D}$ is independently —CN, halogen, $C_{1-4}$ alkyl, or $C_{1-4}$ haloalkyl. In certain embodiments of a compound of Formula (I), (II), (III), (IIIa), or (IV), $R^1$ is cyclopropyl or cyclobutyl, optionally substituted with 1 or 2 fluoro and a triazolyl; and $R^4$ is phenyl optionally substituted with 1 to 3 $R^{4A}$ wherein each $R^{4A}$ is independently —CN, halogen, $C_{1-4}$ alkyl, —OC$_{1-4}$ alkyl, —OC$_{1-4}$ haloalkyl, or $C_{1-4}$ haloalkyl.

In certain embodiments of a compound of Formula (I), (II), (III), (IIIa), or (IV), $R^1$ is cyclopropyl or cyclobutyl, optionally substituted with 1 or 2 halogens and a 5 to 8 membered heteroaryl having 1 to 3 heteroatoms selected from N, O, and S optionally substituted with 1 to 3 $R^{1D}$; $R^4$ is phenyl optionally substituted with 1 to 5 $R^{4A}$ or pyridinyl optionally substituted with 1 to 4 $R^{4B}$, wherein each $R^{4A}$ is independently Cl, F, —CF$_3$, —CHF$_2$, —CH$_3$, or —CN and each $R^{4B}$ is independently Cl, F, —CF$_3$, —CHF$_2$, —CH$_3$, or —CN; each $R^{1D}$ is independently —CN, halogen, $C_{1-4}$ alkyl, or $C_{1-4}$ haloalkyl. In certain embodiments of a compound of Formula (I), (II), (III), (IIIa), or (IV), $R^1$ is cyclopropyl or cyclobutyl, optionally substituted with 1 or 2 halogens and a 5 membered heteroaryl having 1 to 3 heteroatoms selected from N, O, and S optionally substituted with 1 to 3 $R^{1D}$; $R^4$ is phenyl optionally substituted with 1 to 3 $R^{4A}$ wherein each $R^{4A}$ is independently Cl, F, —$CF_3$, —$CHF_2$, —$CH_3$, or —CN and each $R^{1D}$ is independently —CN, halogen, $C_{1-4}$ alkyl, or $C_{1-4}$ haloalkyl. In certain embodiments of a compound of Formula (I), (II), (III), (IIIa), or (IV), $R^1$ is cyclopropyl or cyclobutyl, optionally substituted with 1 or 2 fluoro and a triazolyl; and $R^4$ is phenyl optionally substituted with 1 to 3 $R^{4A}$ wherein each $R^{4A}$ is independently Cl, F, —$CF_3$, —$CHF_2$, —$CH_3$, or —CN.

In certain embodiments of a compound of Formula (I), (II), (III), (IIIa), or (IV), $R^1$ is cyclopropyl or cyclobutyl, optionally substituted with 1 or 2 halogens and a —C(O)$NR^XR^Y$. In certain embodiments of a compound of Formula (I), (II), (III), (IIIa), or (IV), $R^1$ is cyclopropyl or cyclobutyl, optionally substituted with 1 or 2 halogen and —C(O)$NR^XR^Y$, wherein $R^X$ is —H or $C_{1-6}$ alkyl optionally substituted with 1 to 3 $R^Z$ and $R^Y$ is —H or $C_{1-6}$ alkyl optionally substituted with 1 to 3 $R^Z$. In certain embodiments of a compound of Formula (I), (II), (III), (IIIa), or (IV), $R^1$ is cyclopropyl or cyclobutyl, optionally substituted with 1 or 2 halogen and —C(O)$NR^XR^Y$, wherein $R^X$ is $C_{1-3}$ alkyl and $R^Y$ is —H. In certain embodiments of a compound of Formula (I), (II), (III), (IIIa), or (IV), $R^1$ is cyclopropyl or cyclobutyl, optionally substituted with 1 or 2 halogen and —C(O)$NHCH_3$. In certain embodiments of a compound of Formula (I), (II), (III), (IIIa), or (IV), $R^1$ is cyclobutyl substituted with 1 or 2 halogen and —C(O)$NR^XR^Y$, wherein $R^X$ is $C_{1-3}$ alkyl and $R^1$ is —H.

In certain embodiments of a compound of Formula (I), (II), (III), (IIIa), or (IV), $R^1$ is cyclopropyl or cyclobutyl, optionally substituted with 1 or 2 halogens a —C(O)$NR^XR^Y$; $R^4$ is phenyl optionally substituted with 1 to 5 $R^{4A}$ or pyridinyl optionally substituted with 1 to 4 $R^{4B}$, wherein each $R^{4A}$ is independently —CN, halogen, $C_{1-4}$ alkyl, —$OC_{1-4}$alkyl, —$OC_{1-4}$ haloalkyl, or $C_{1-4}$ haloalkyl and each $R^{4B}$ is independently —CN, halogen, $C_{1-4}$ alkyl, —$OC_{1-4}$alkyl, —$OC_{1-4}$ haloalkyl, or $C_{1-4}$ haloalkyl, and each $R^{1D}$ is independently —CN, halogen, $C_{1-4}$ alkyl, or $C_{1-4}$ haloalkyl. In certain embodiments of a compound of Formula (I), (II), (III), (IIIa), or (IV), $R^1$ is cyclopropyl or cyclobutyl optionally substituted with 1 or 2 halogens and —C(O)$NR^XR^Y$, wherein $R^X$ is —H or $C_{1-6}$ alkyl optionally substituted with 1 to 3 $R^Z$ and $R^Y$ is —H or $C_{1-6}$ alkyl optionally substituted with 1 to 3 $R^Z$; $R^4$ is phenyl optionally substituted with 1 to 3 $R^{4A}$ wherein each $R^{4A}$ is independently —CN, halogen, $C_{1-4}$ alkyl, —$OC_{1-4}$alkyl, —$OC_{14}$ haloalkyl, or $C_{1-4}$ haloalkyl, and each $R^{1D}$ is independently —CN, halogen, $C_{1-4}$ alkyl, or $C_{1-4}$ haloalkyl. In certain embodiments of a compound of Formula (I), (II), (III), (IIIa), or (IV), $R^1$ is cyclopropyl or cyclobutyl, optionally substituted with 1 or 2 fluoro and —C(O)$NR^XR^Y$, wherein $R^X$ is $C_{1-3}$ alkyl and $R^1$ is —H; and $R^4$ is phenyl optionally substituted with 1 to 3 $R^{4A}$ wherein each $R^{4A}$ is independently —CN, halogen, $C_{1-4}$ alkyl, —$OC_{1-4}$alkyl, —$OC_{1-4}$ haloalkyl, or $C_{1-4}$ haloalkyl. In certain embodiments of a compound of Formula (I), (II), (III), (IIIa), or (IV), $R^1$ is cyclobutyl substituted with 1 or 2 fluoro and —C(O)$NHCH_3$ and $R^4$ is phenyl optionally substituted with 1 to 3 $R^{4A}$ wherein each $R^{4A}$ is independently —CN, halogen, $C_{1-4}$ alkyl, —$OC_{1-4}$alkyl, —$OC_{1-4}$ haloalkyl, or $C_{1-4}$ haloalkyl.

In certain embodiments, the compound of Formula (I), (II), (III), (IIIa), or (IV), is

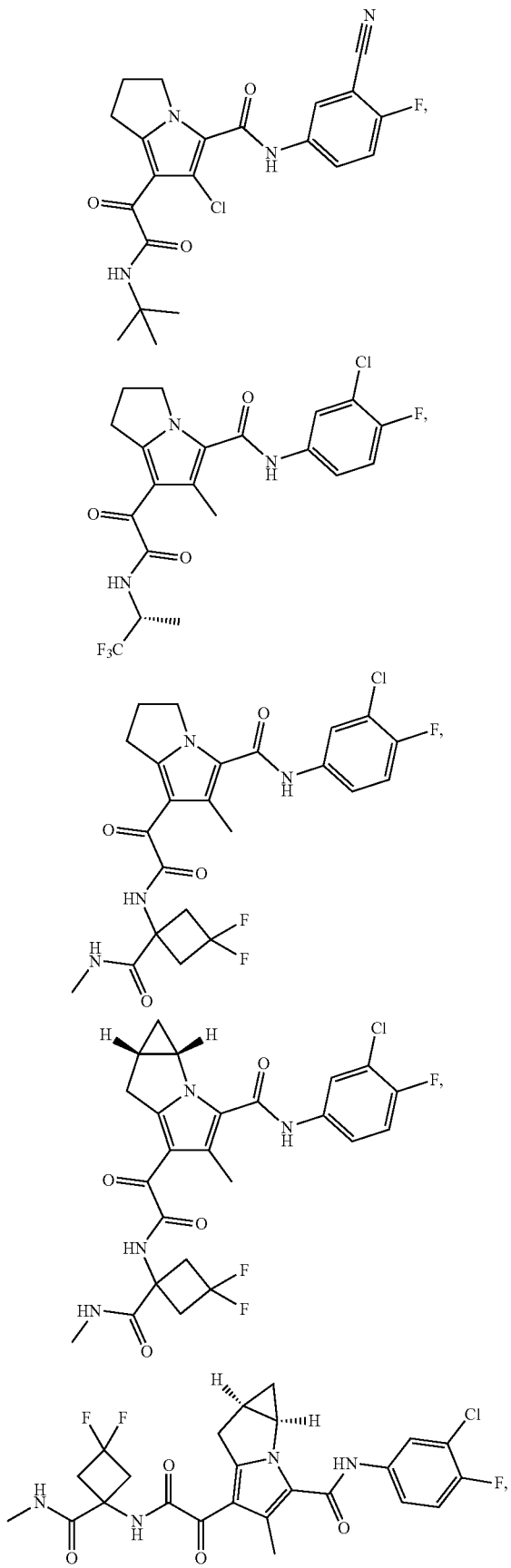

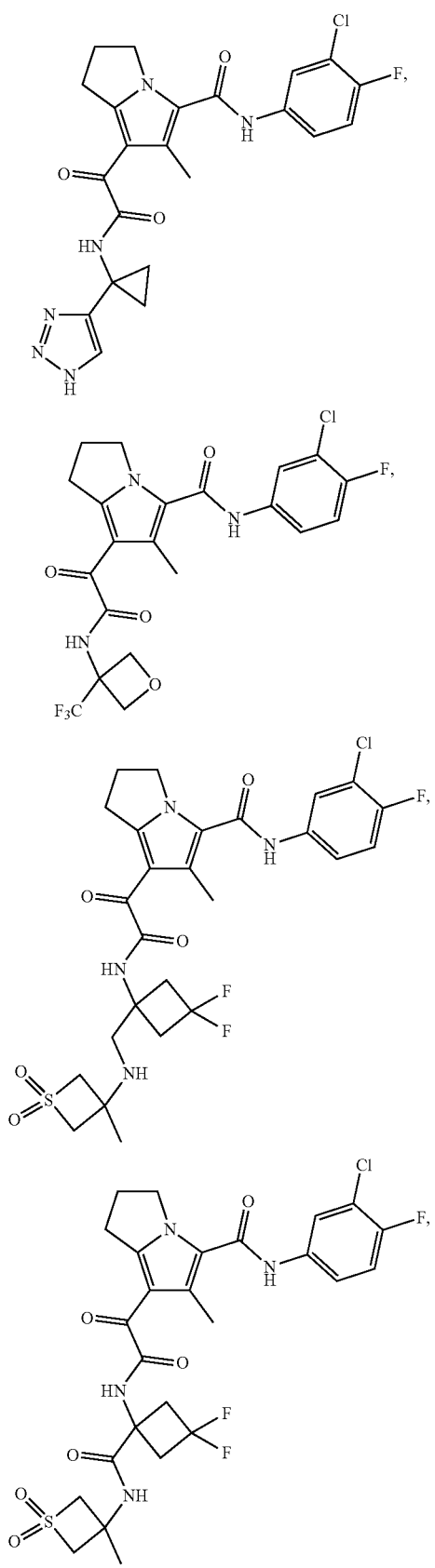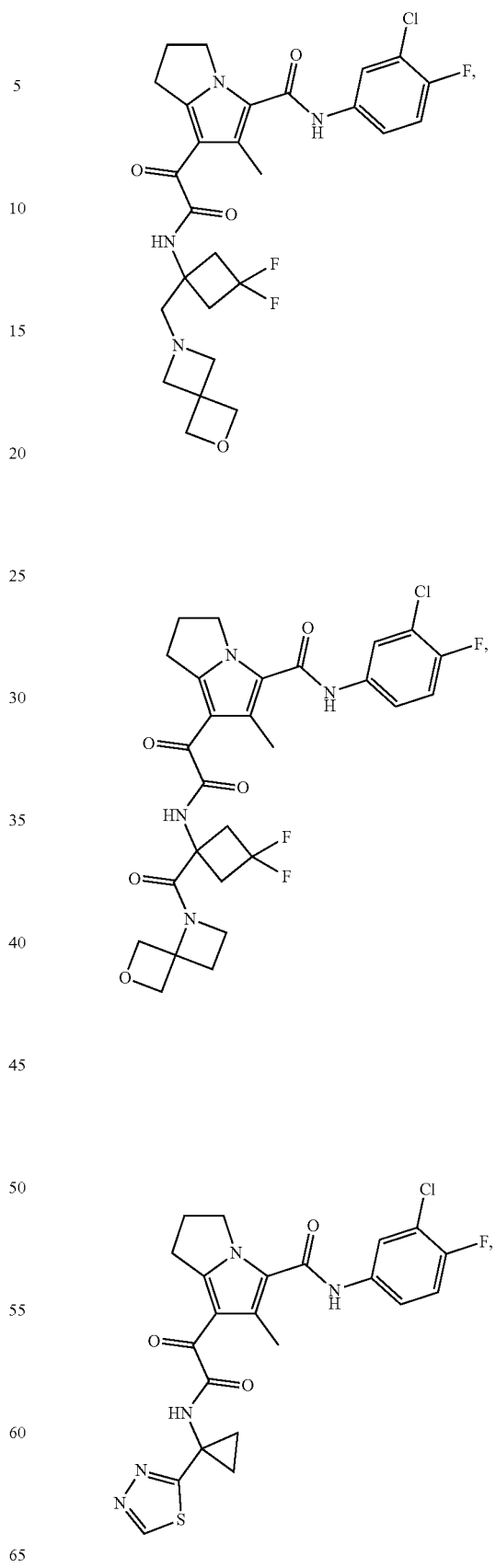

31
-continued
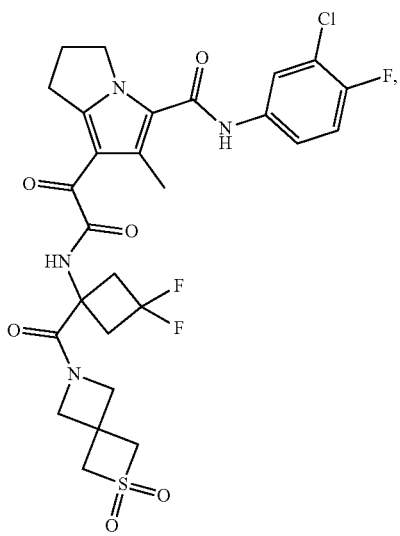
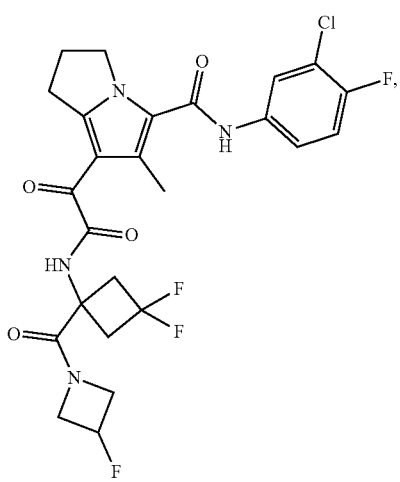
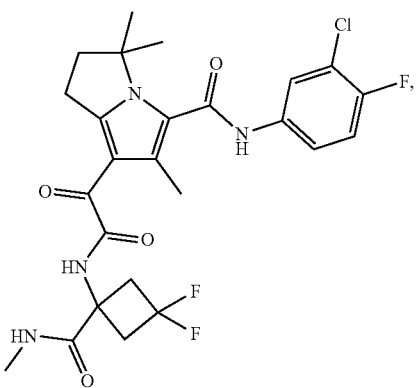
32
-continued
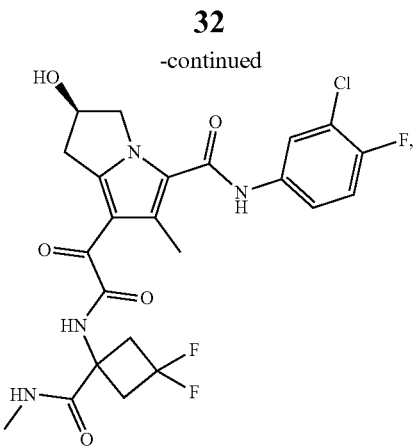
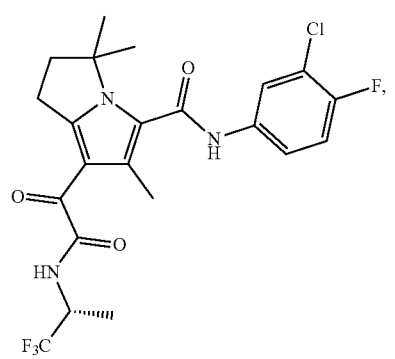
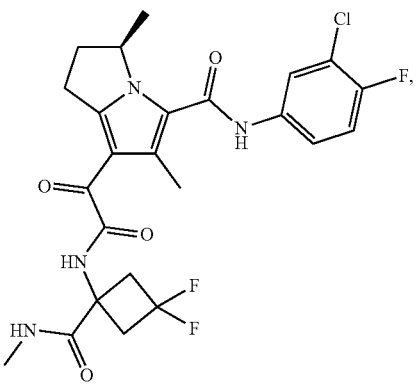
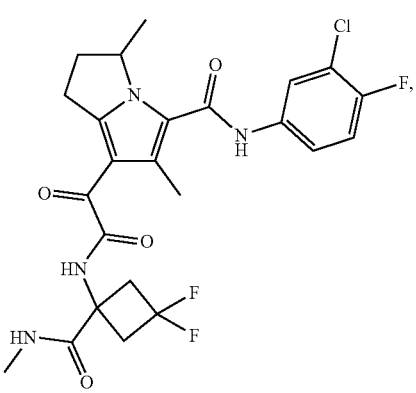

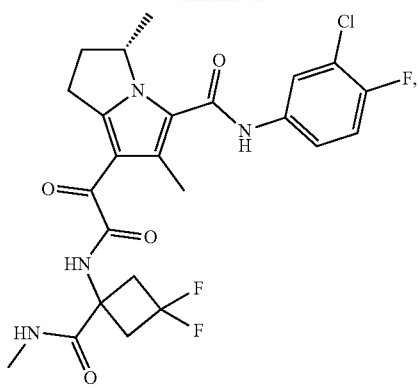
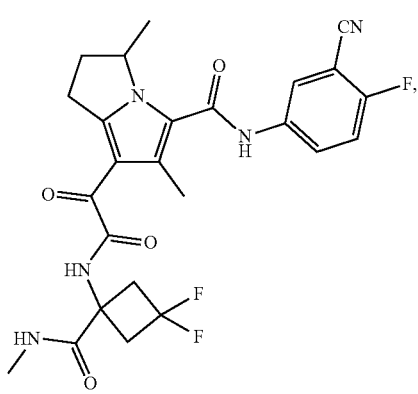
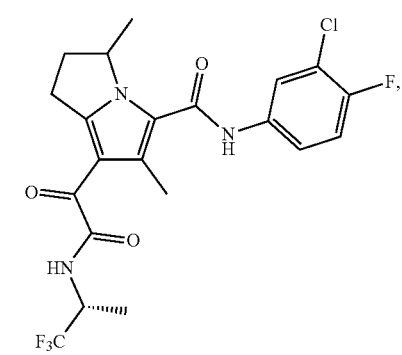
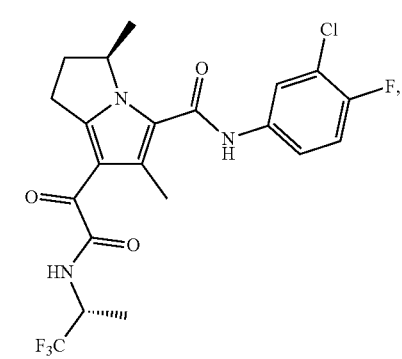
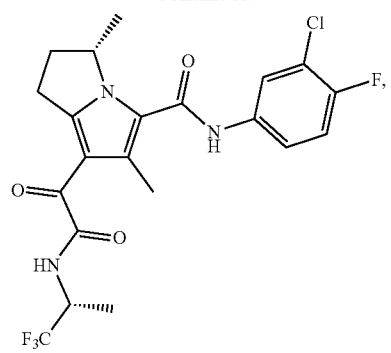
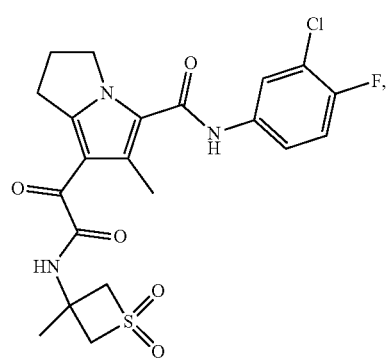
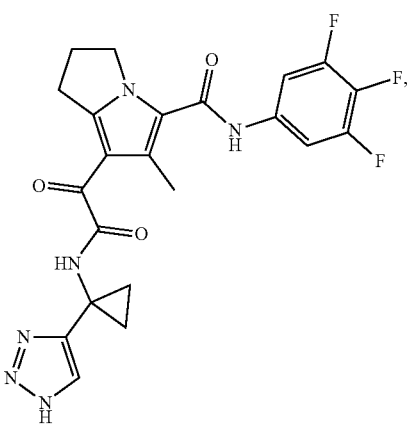
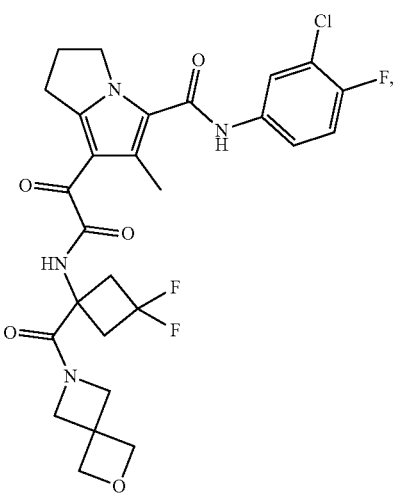

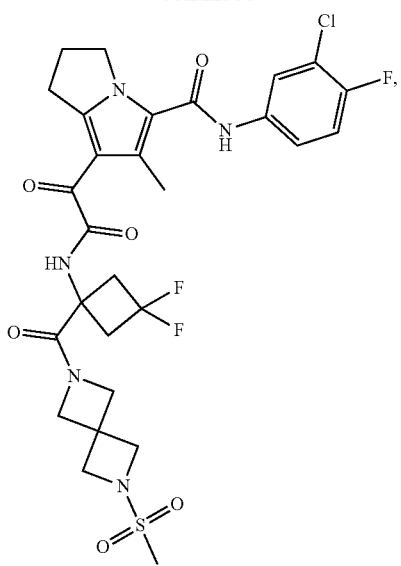
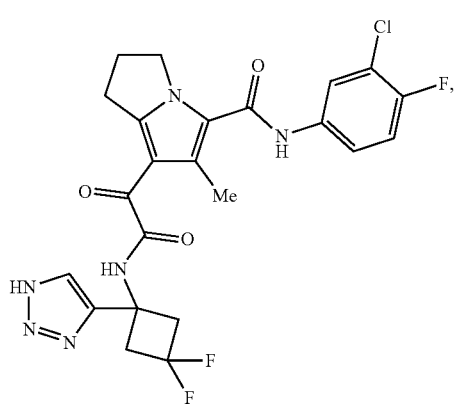
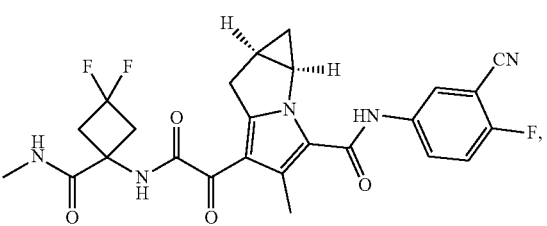
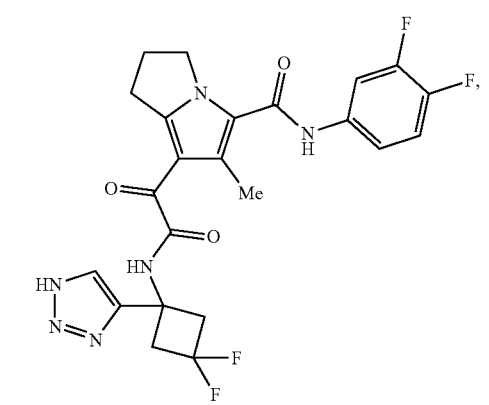
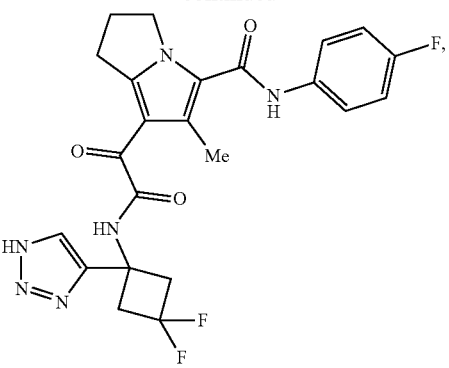
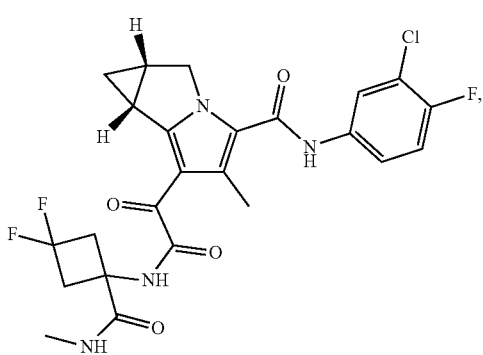
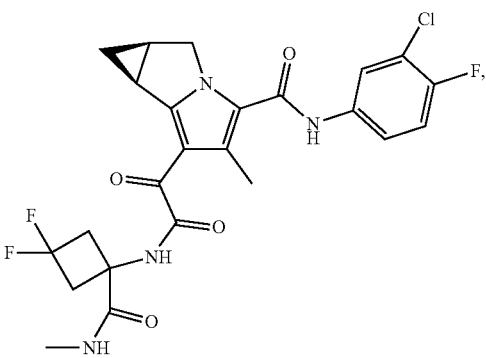
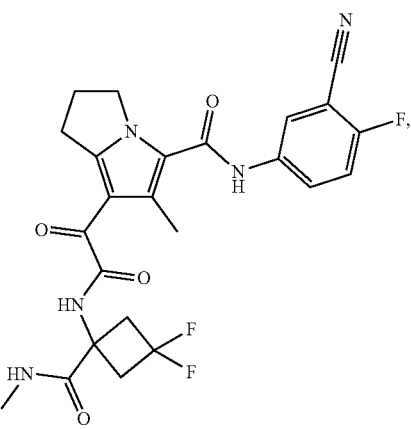

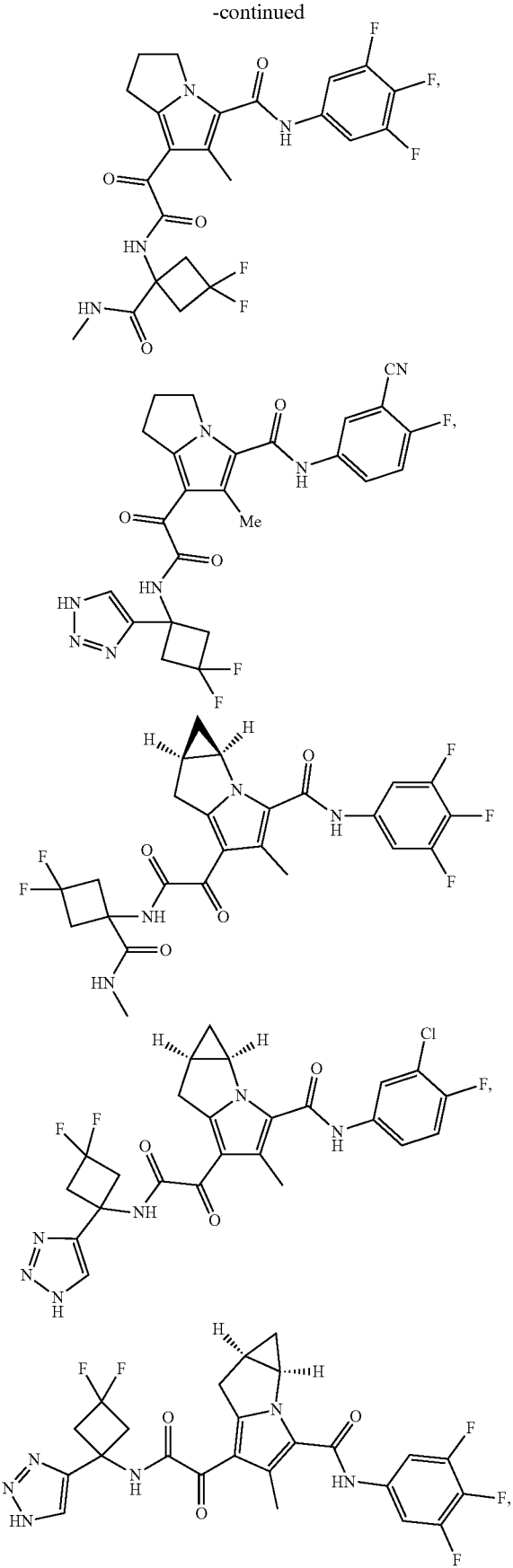
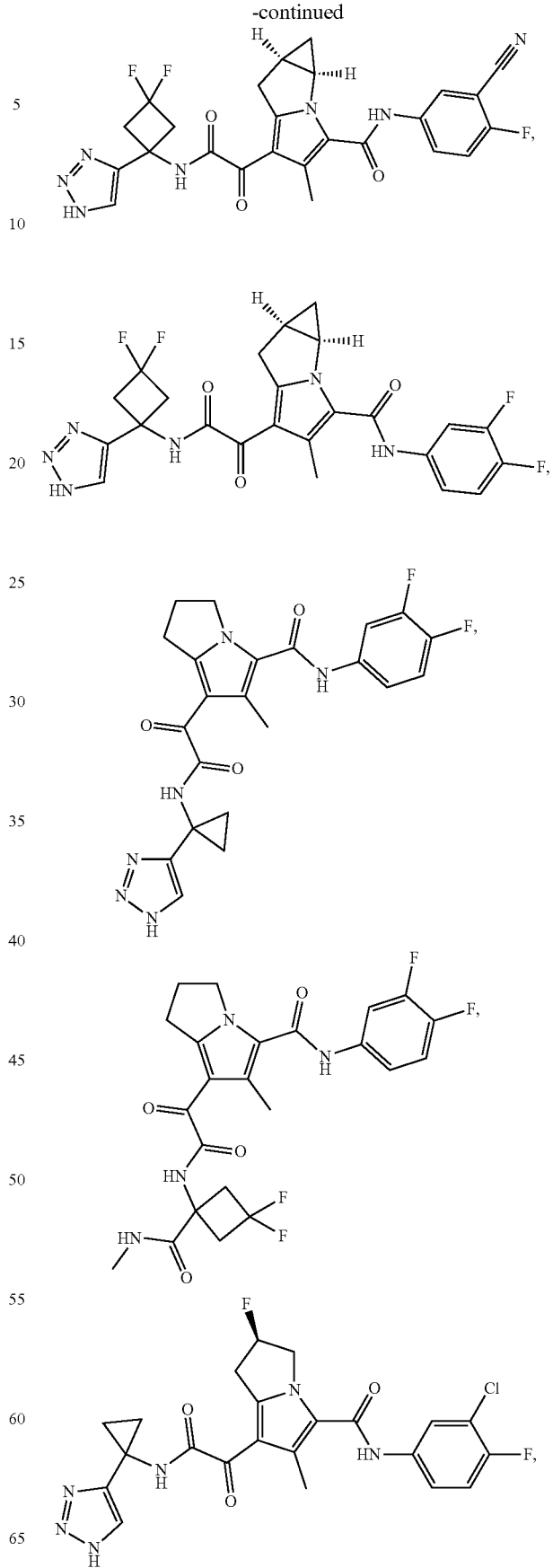

-continued
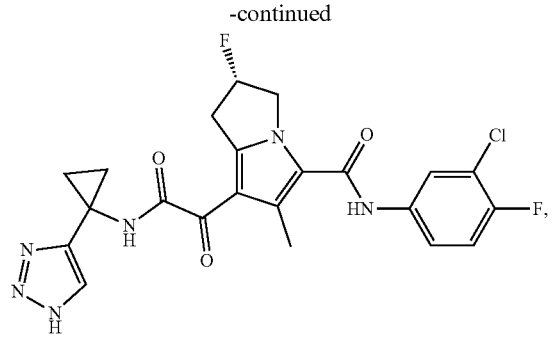
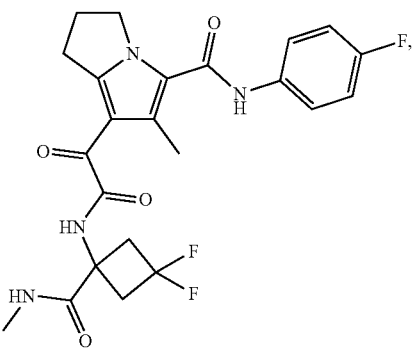
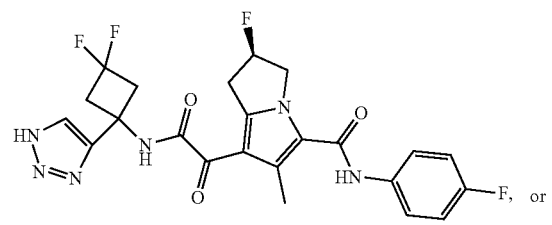
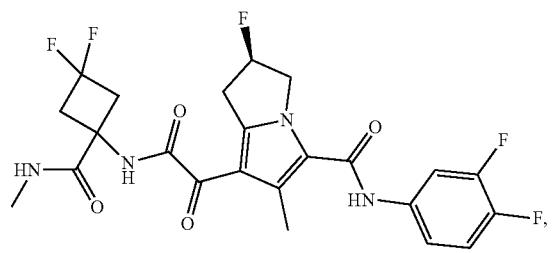
or a pharmaceutically acceptable salt thereof.
In certain embodiments, the compound of Formula (I), (II), (III), (IIIa), or (IV), is
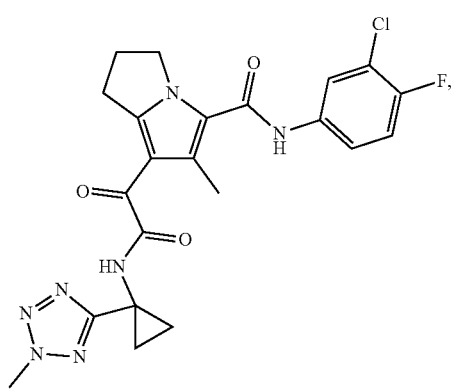
-continued
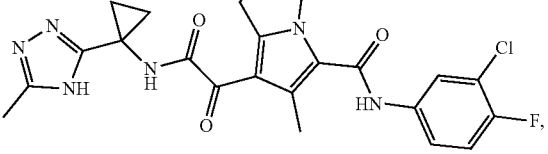
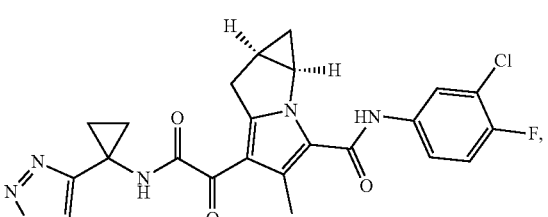
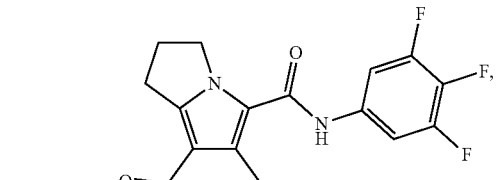
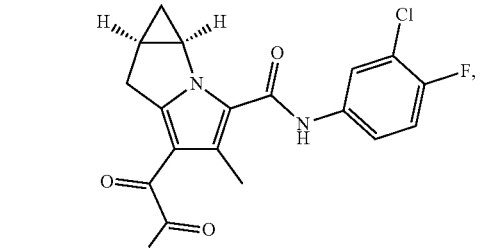
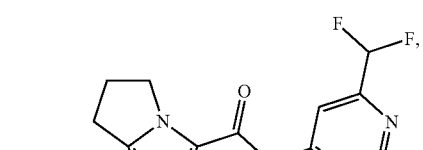
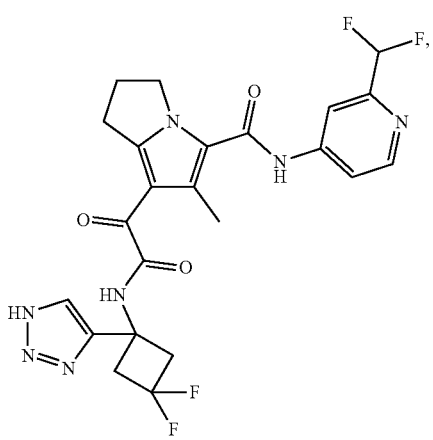

-continued
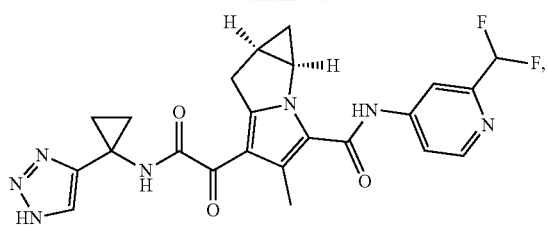
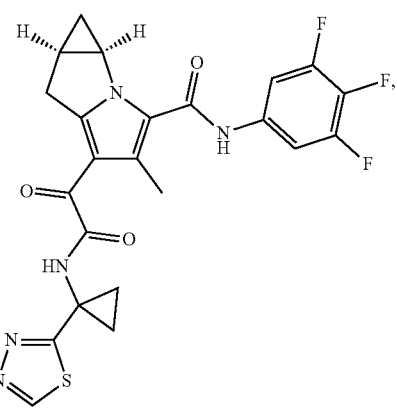
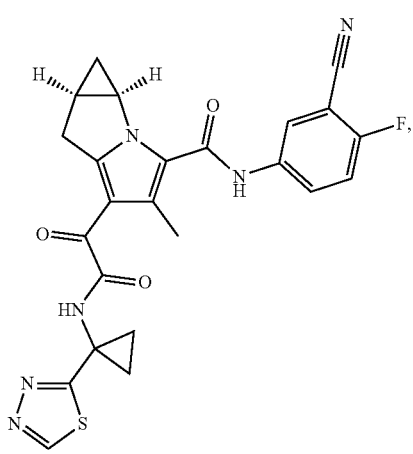
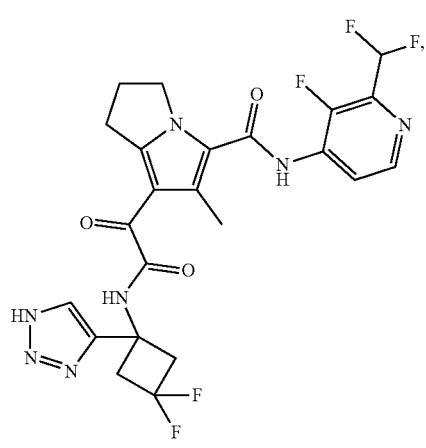
-continued
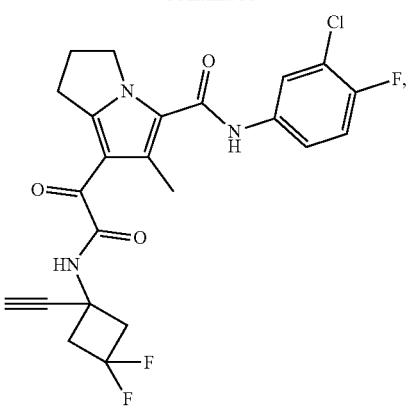
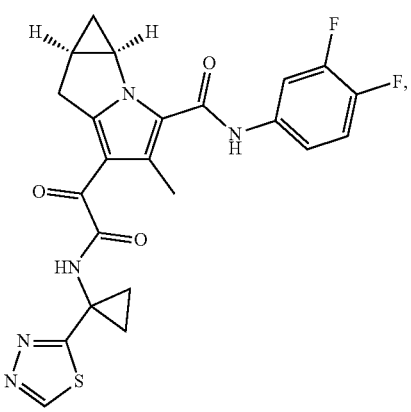
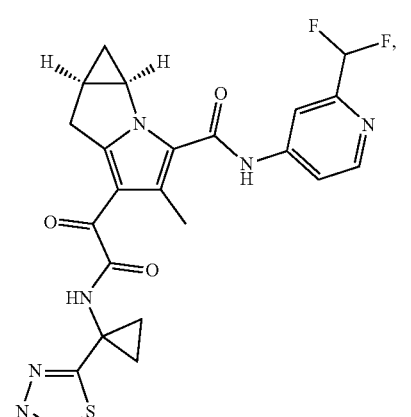
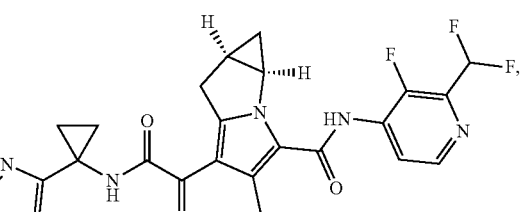

43
-continued
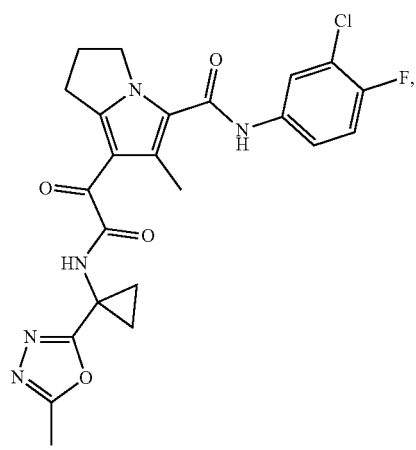
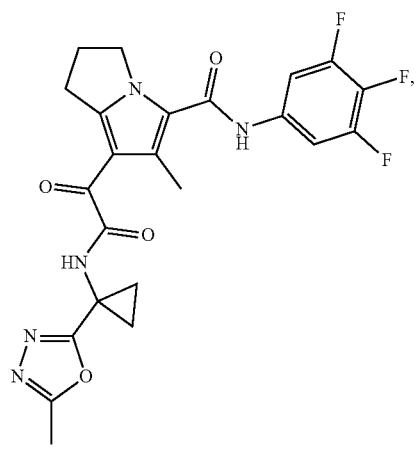
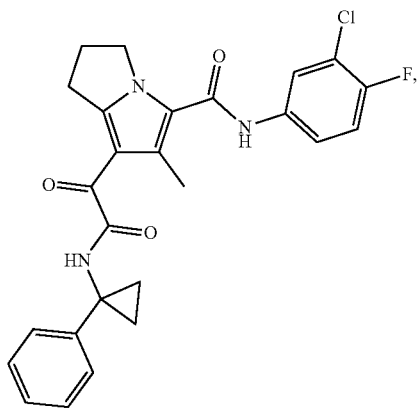
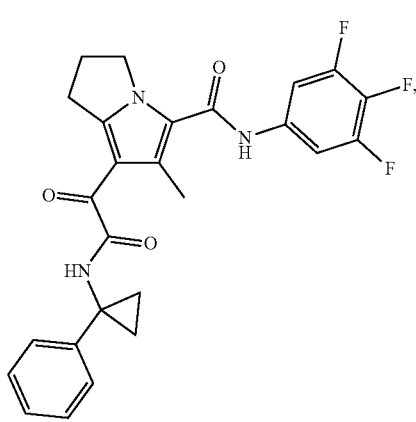
44
-continued
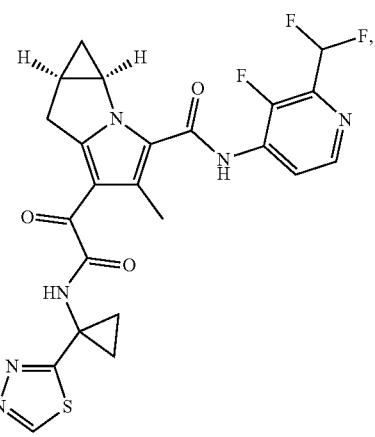
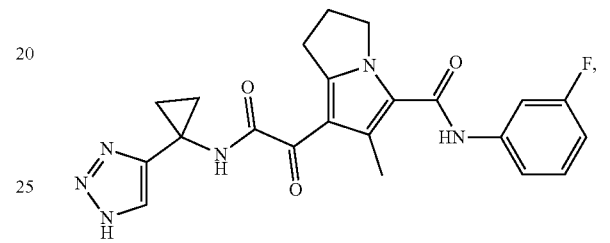
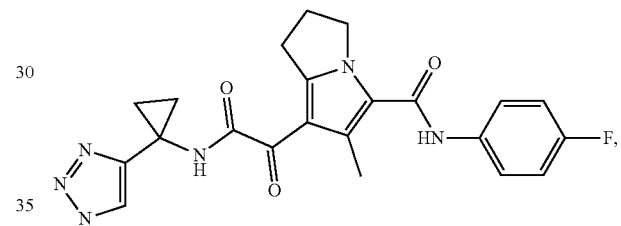
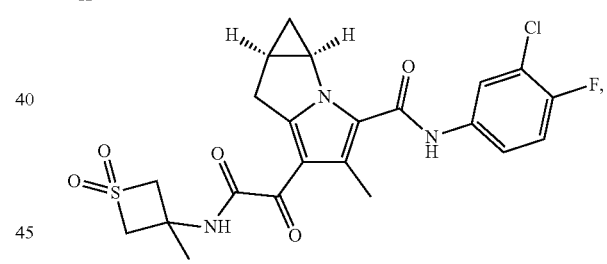
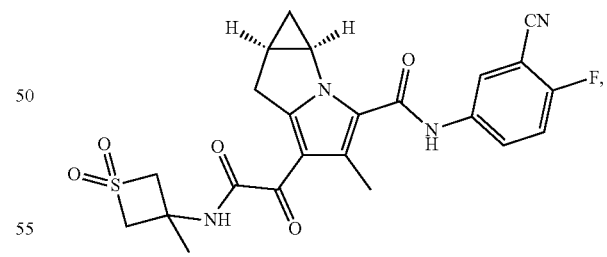
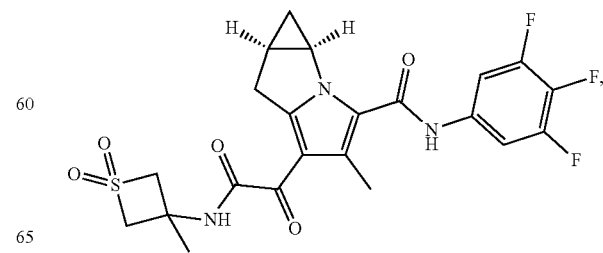

-continued

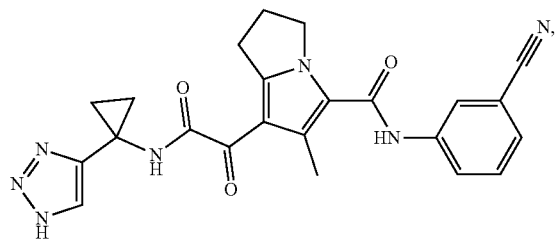
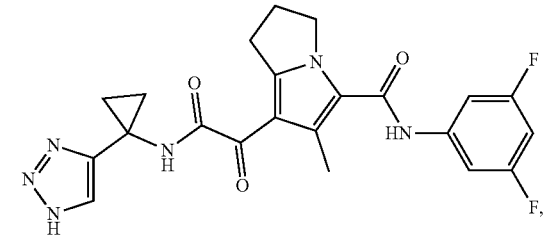
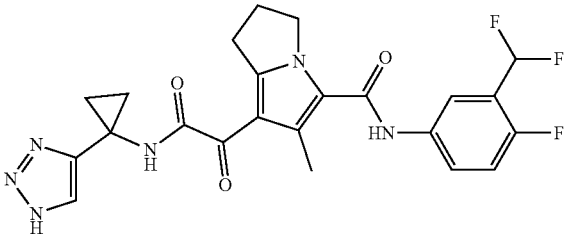
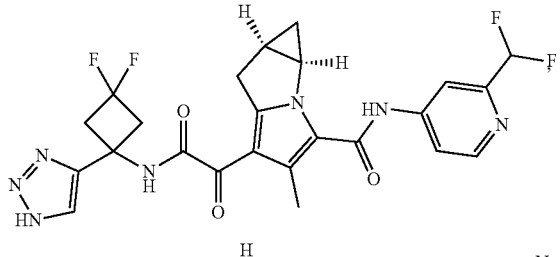
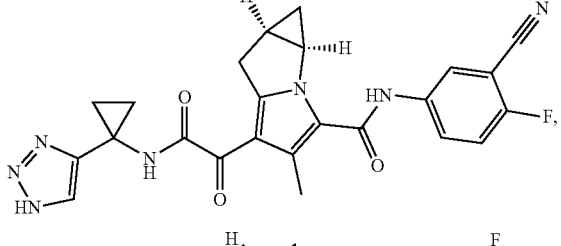
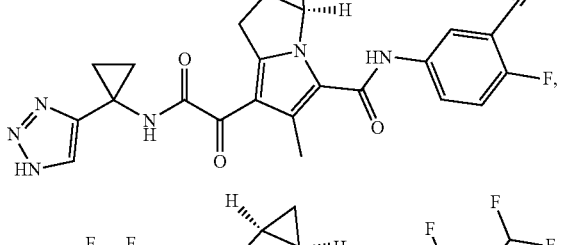
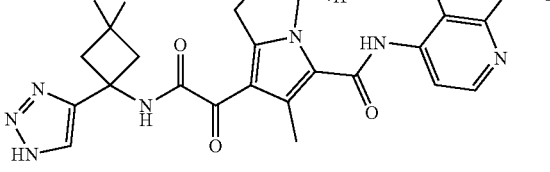
-continued
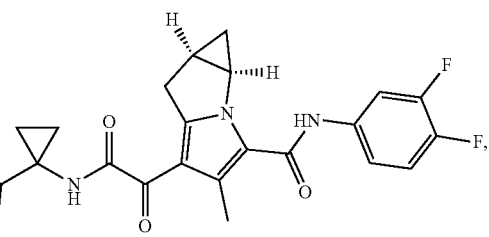
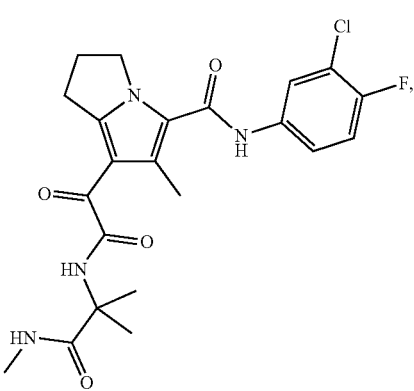
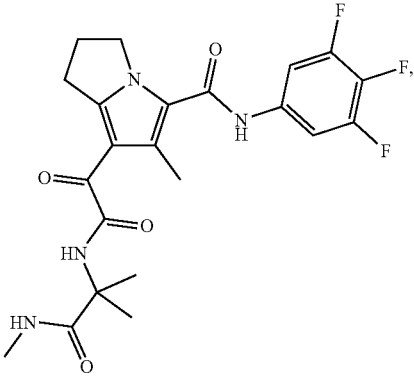
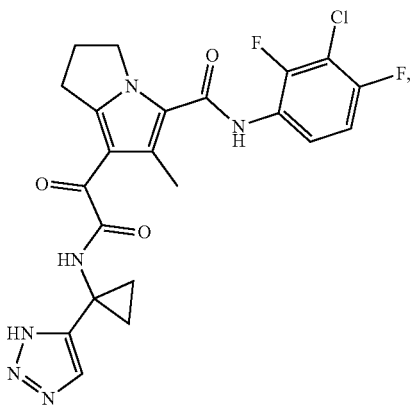

47
-continued
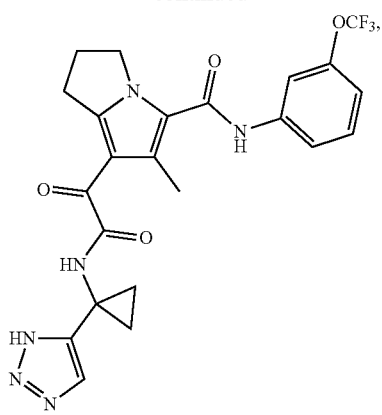
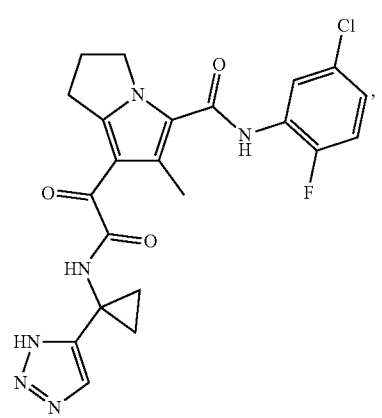
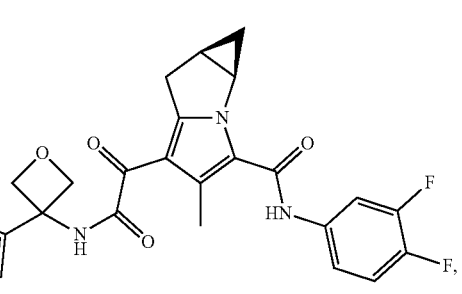
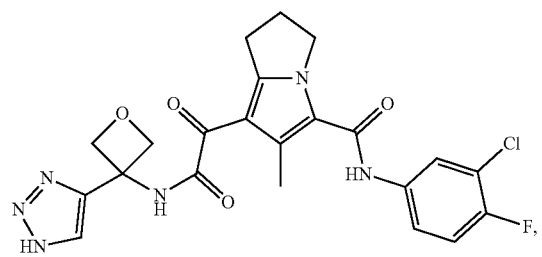
48
-continued
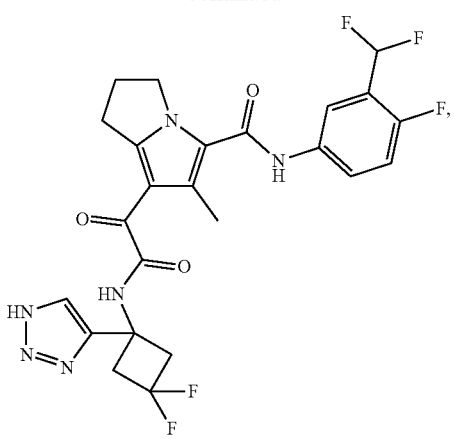
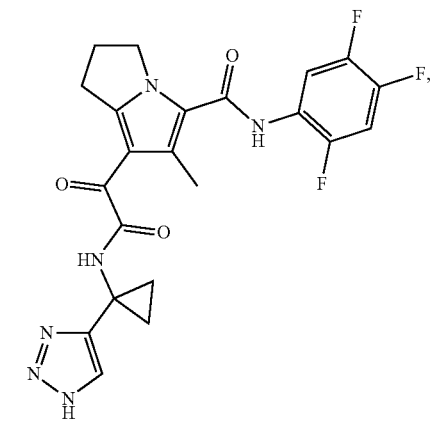
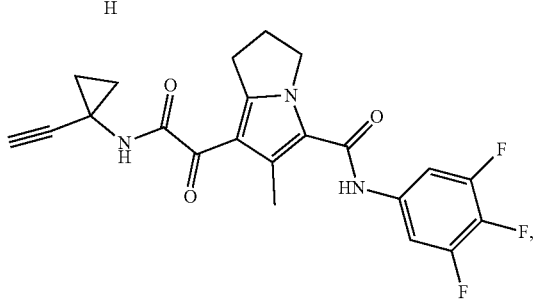

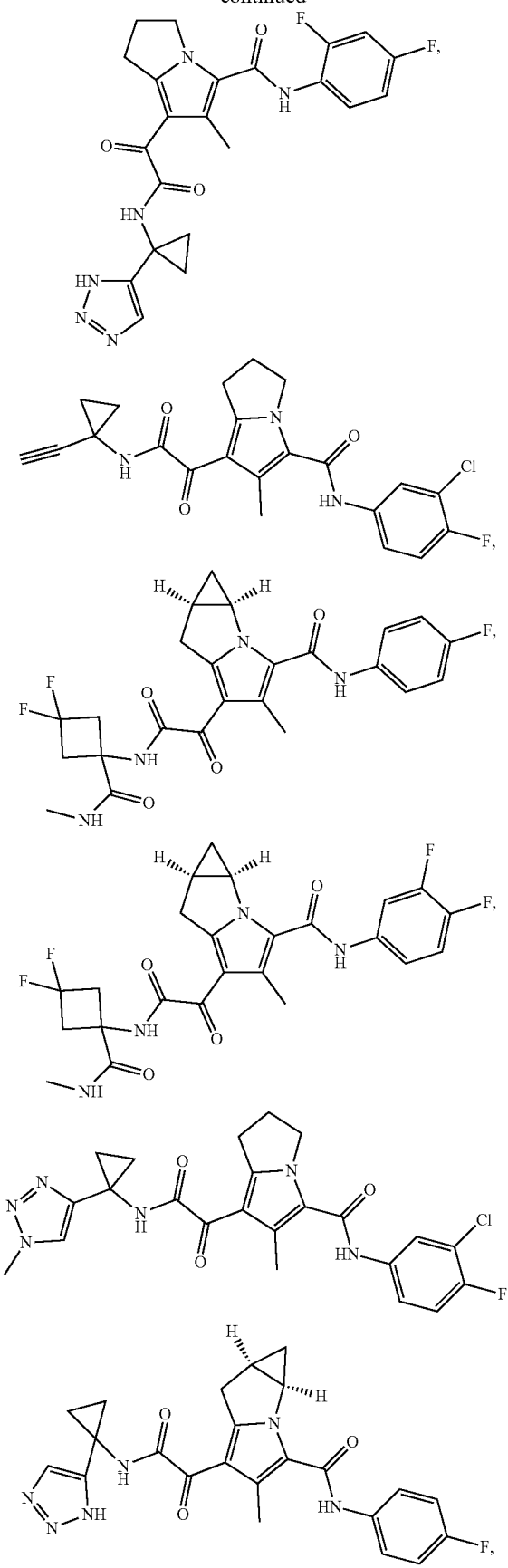

51
-continued
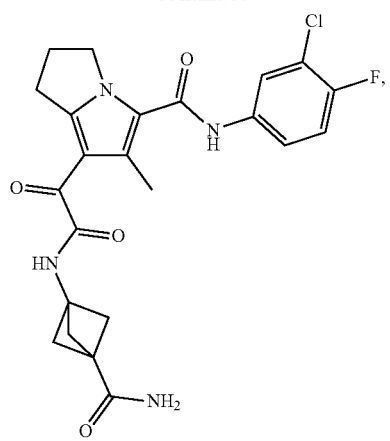
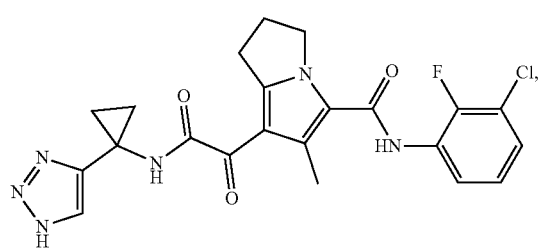
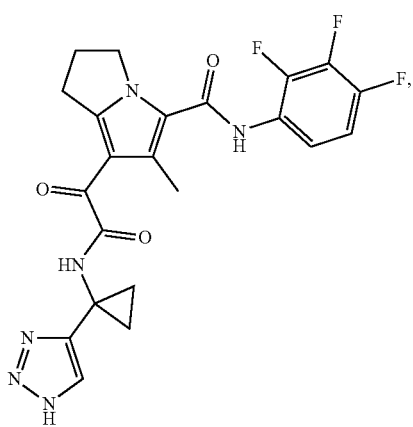
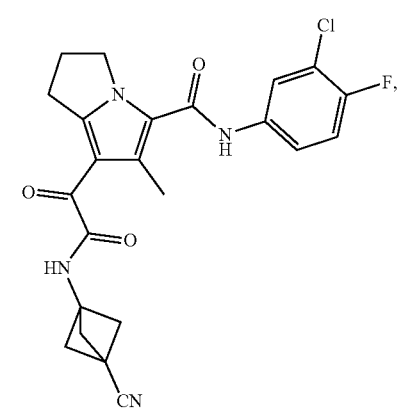
52
-continued
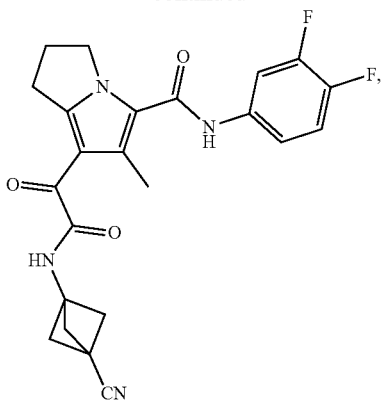
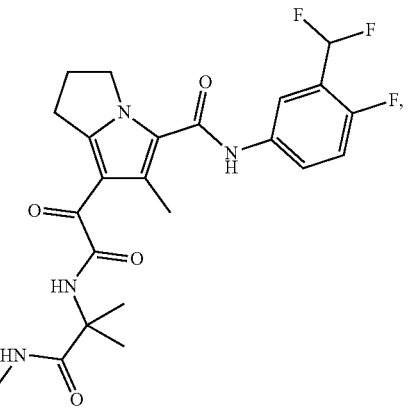
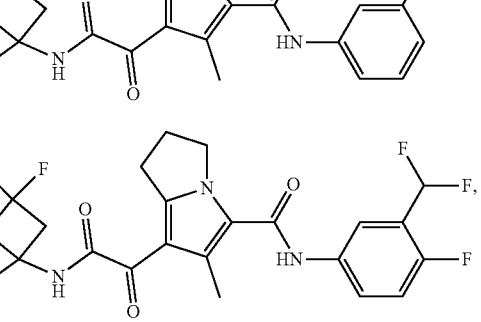
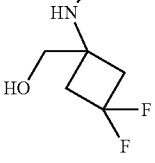

53
-continued
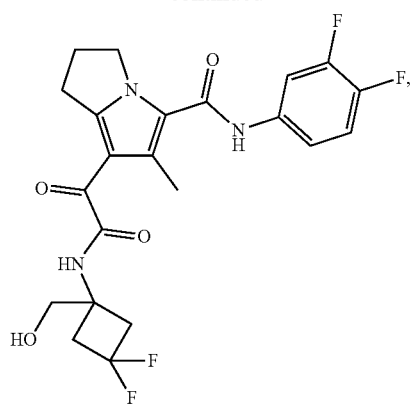
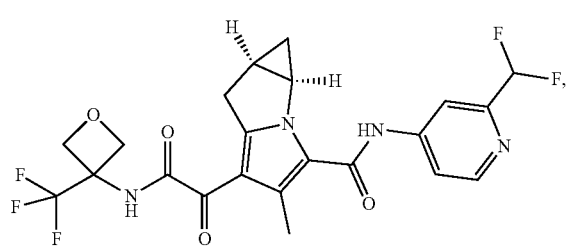
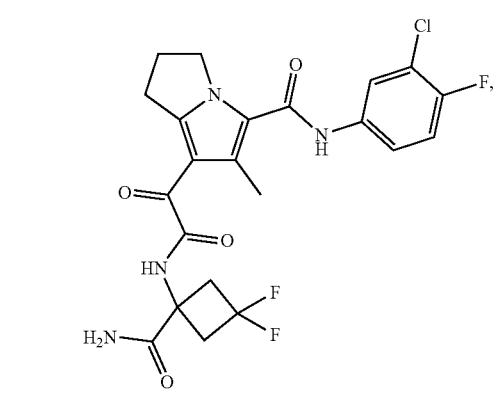
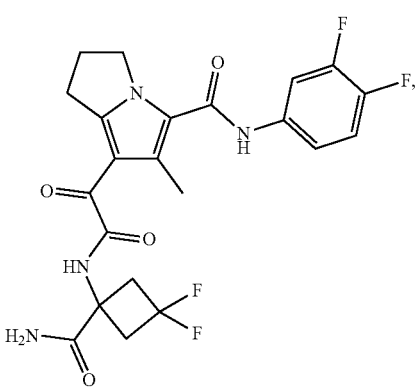
54
-continued
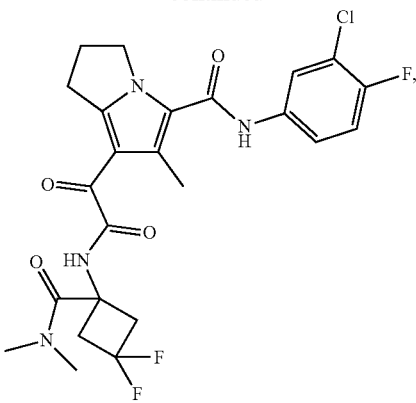
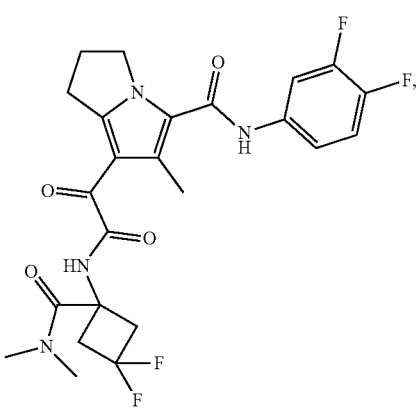
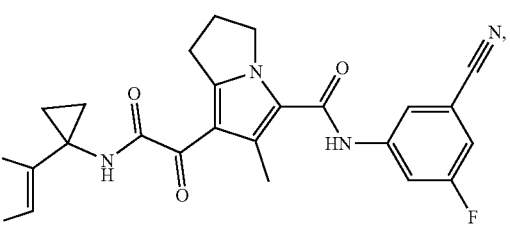
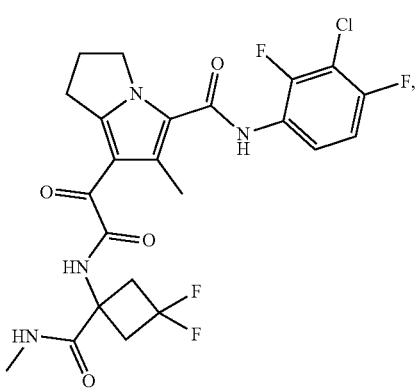

55
-continued
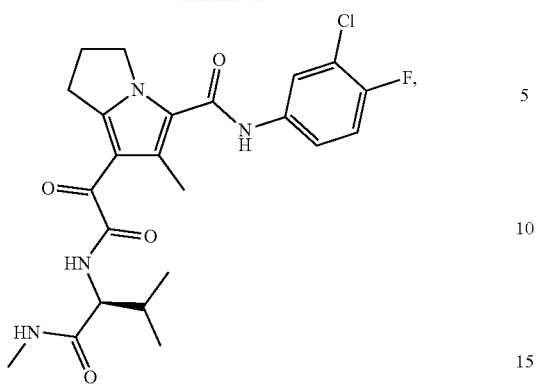
56
-continued
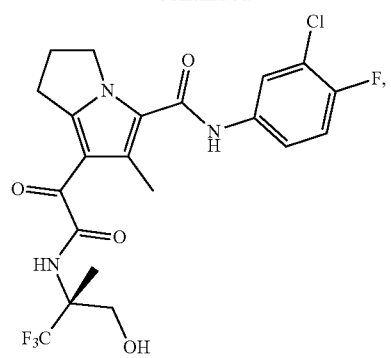
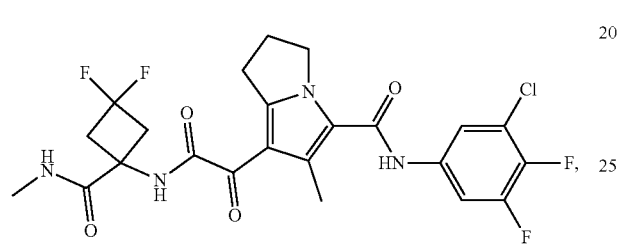
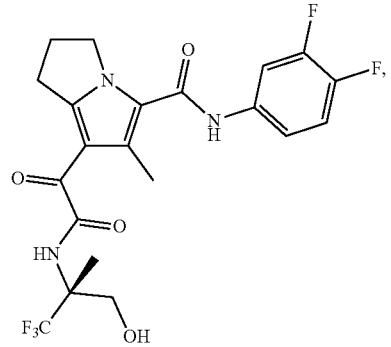
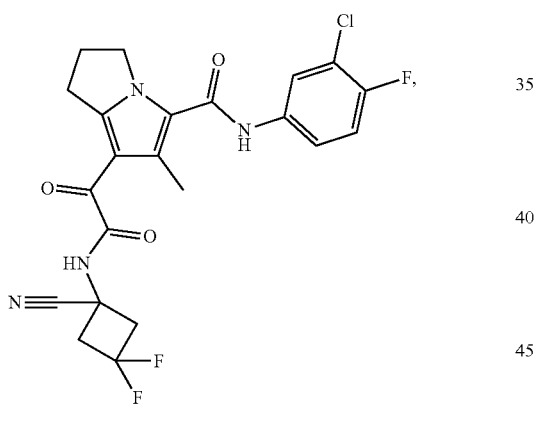
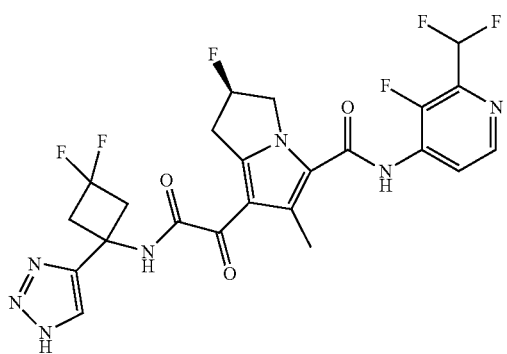
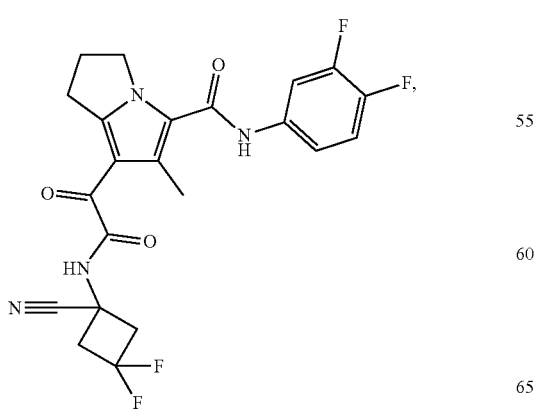
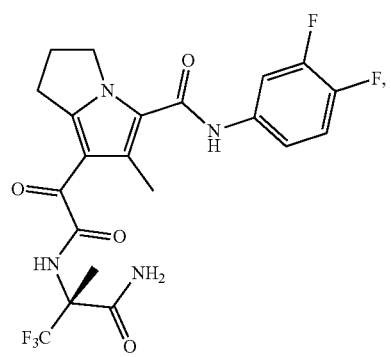

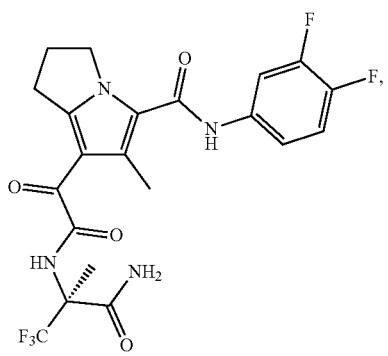
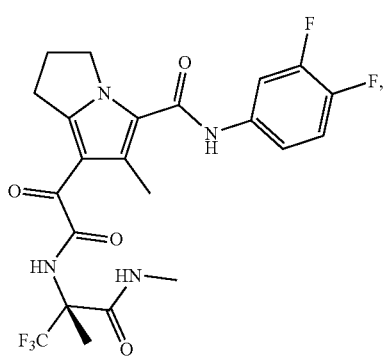
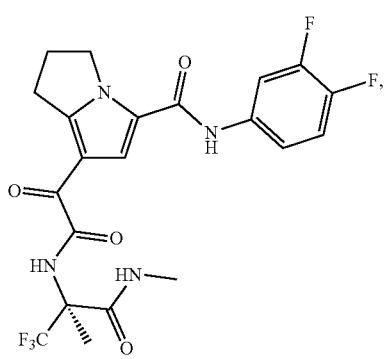
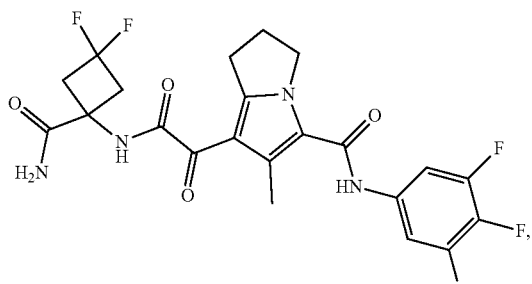
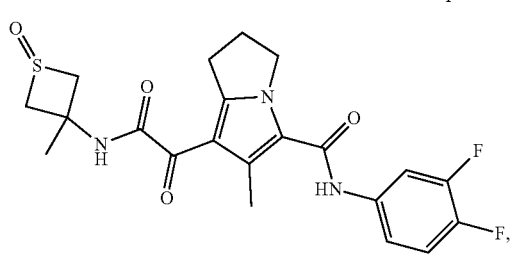
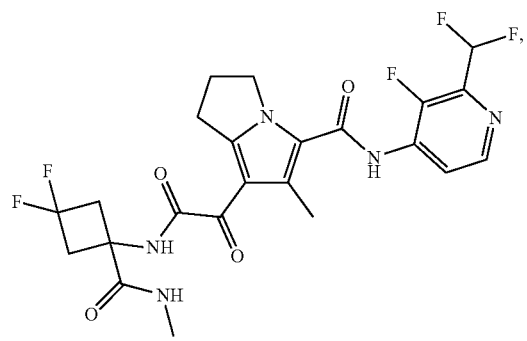 [SMILES: CNC(=O)C1(NC(=O)C(=O)c2c(C)c(C(=O)Nc3ccnc(C(F)F)c3F)n3c2CCC3)CC(F)(F)C1]
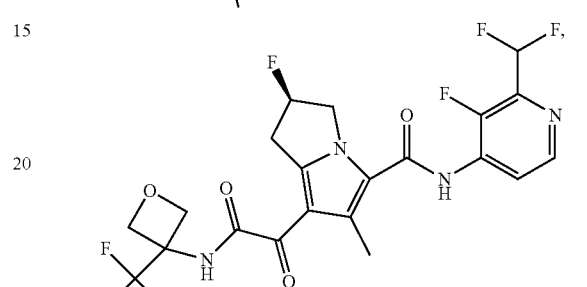
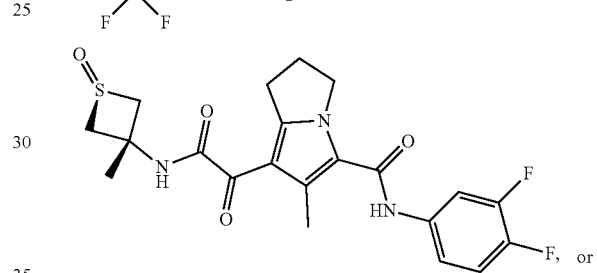
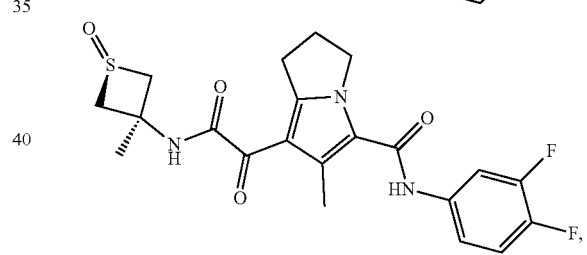
or a pharmaceutically acceptable salt thereof.
In certain embodiments, the compound of Formula (I), (II), (III), (IIIa), or (IV), is
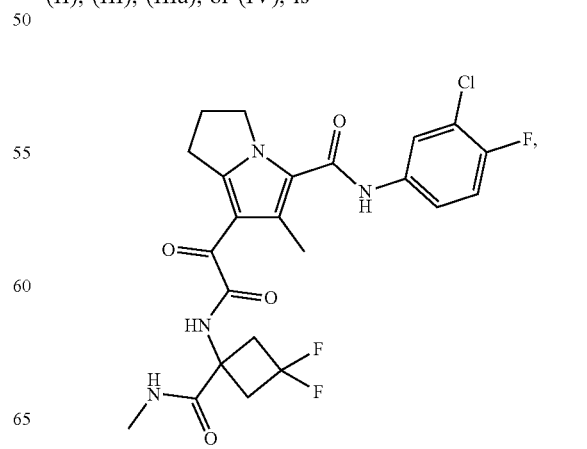

59
-continued
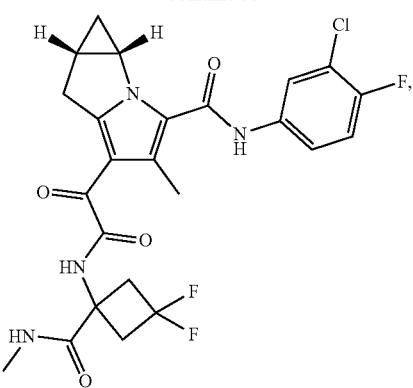
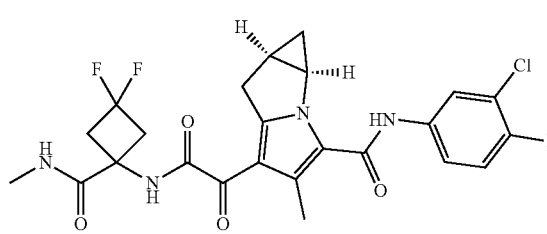
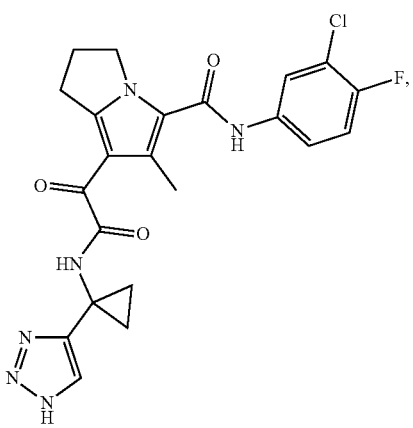
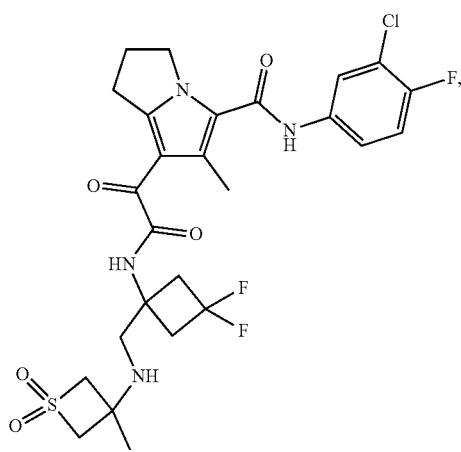
60
-continued
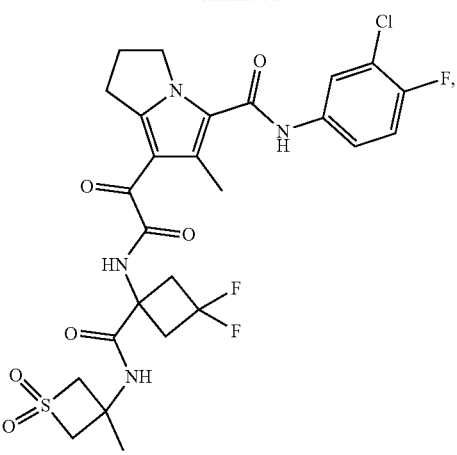
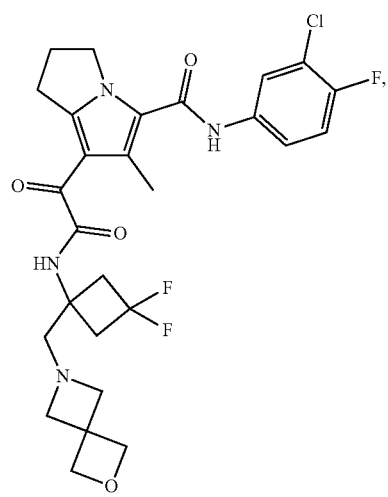
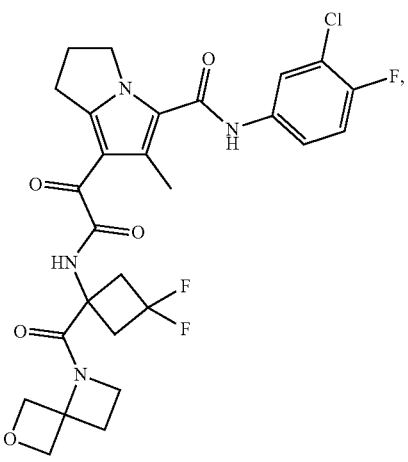

-continued
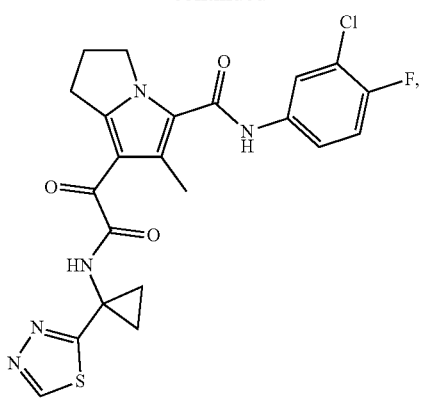
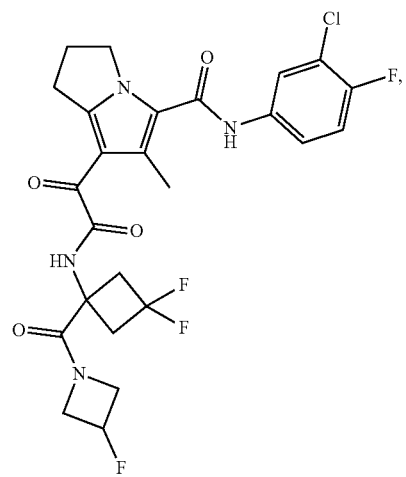
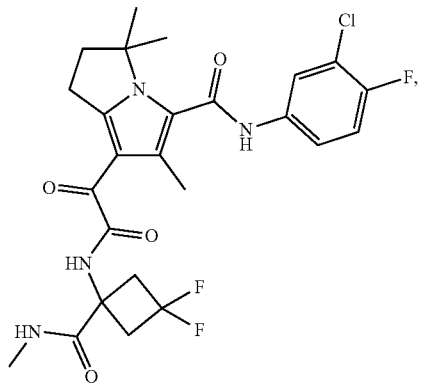
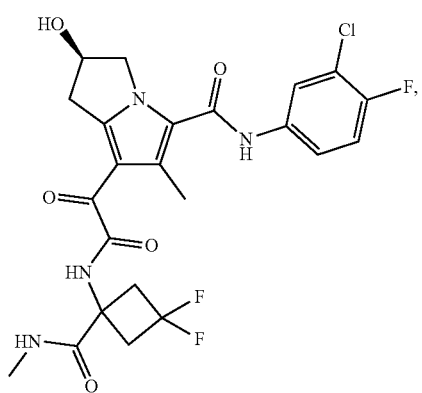
-continued
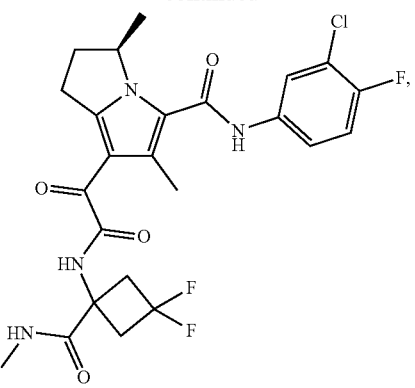
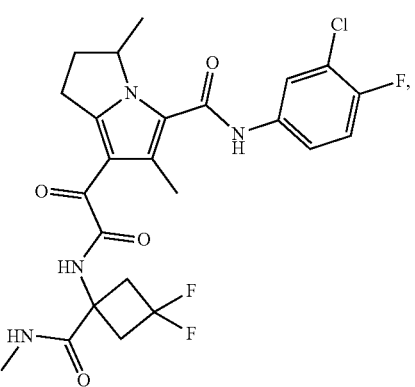
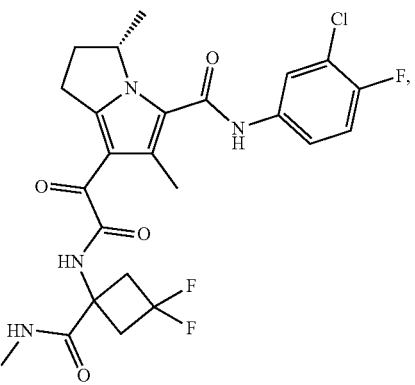

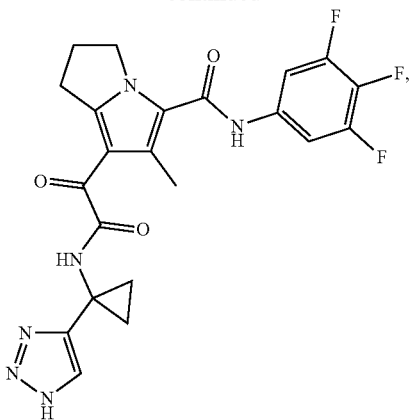
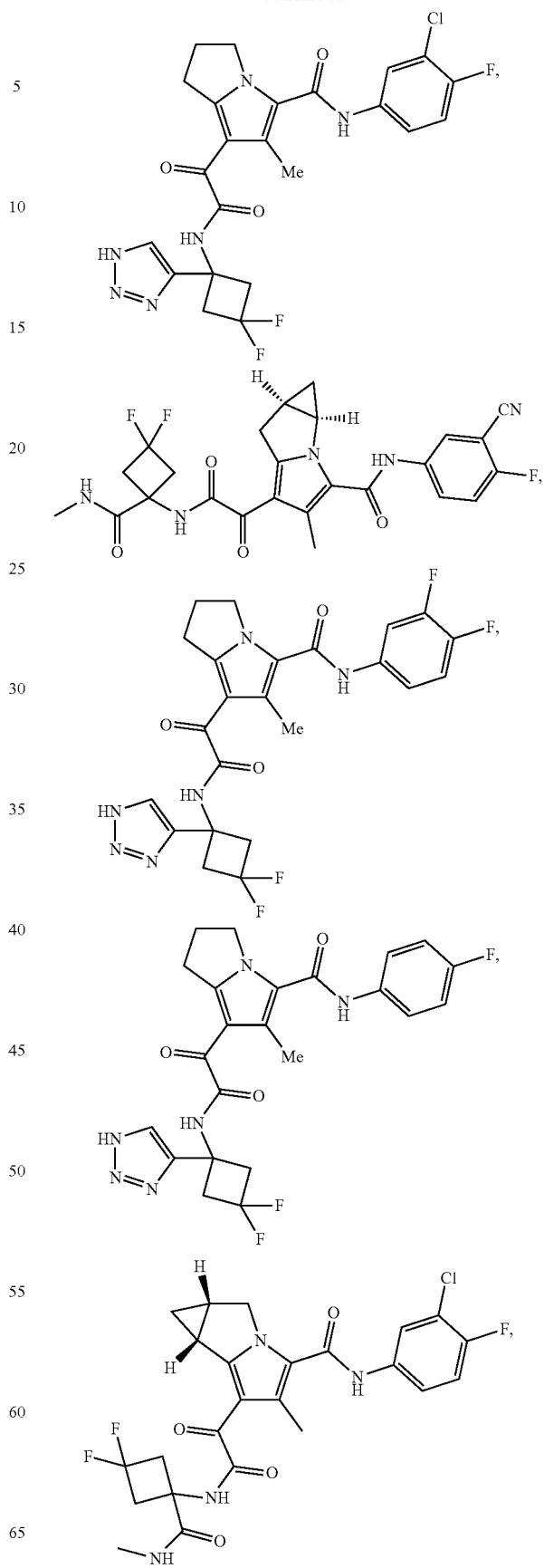

65
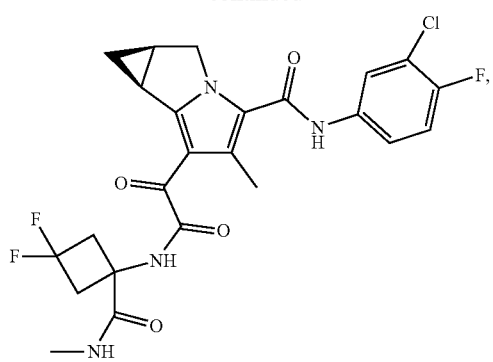
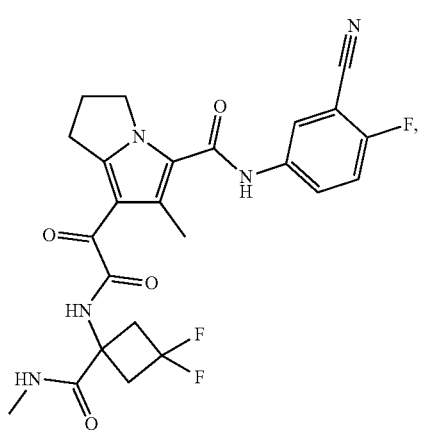
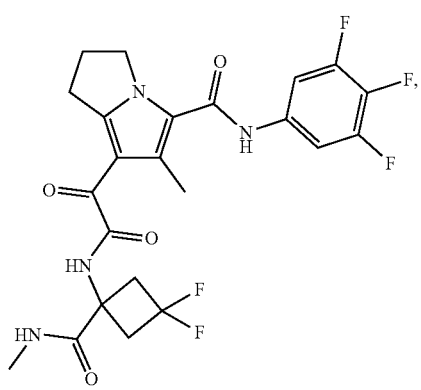
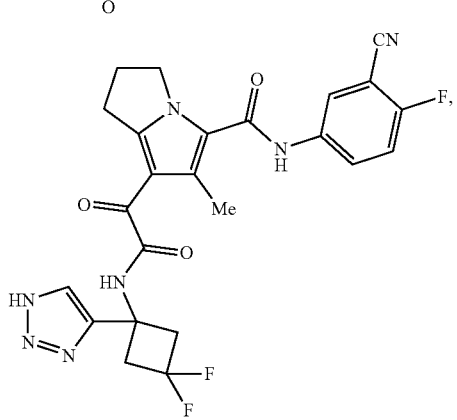
66
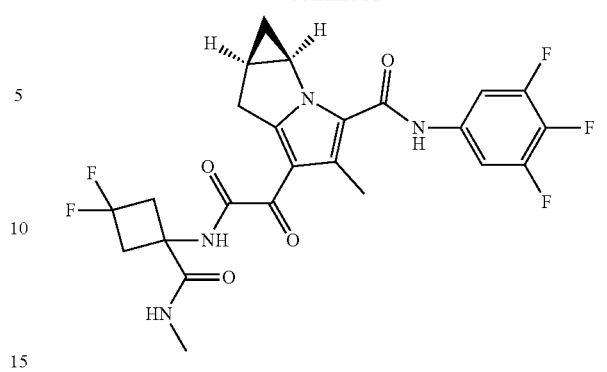
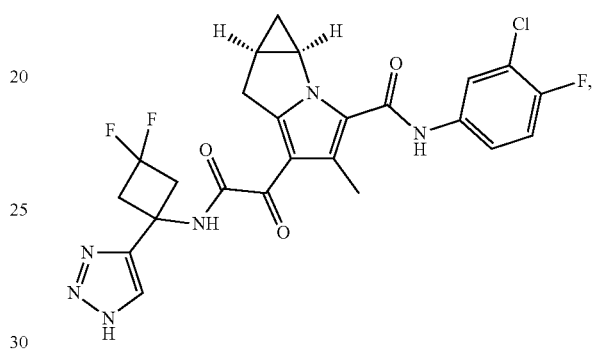
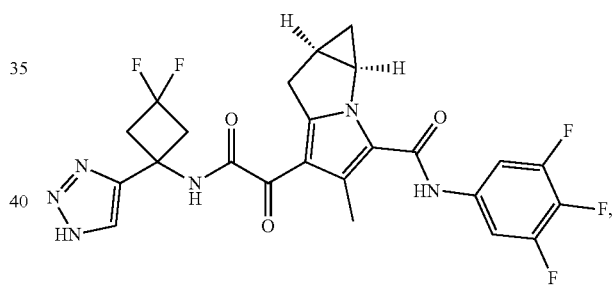
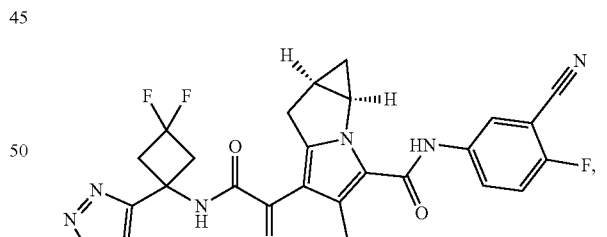
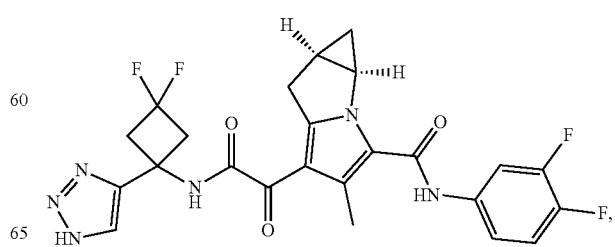

67
-continued
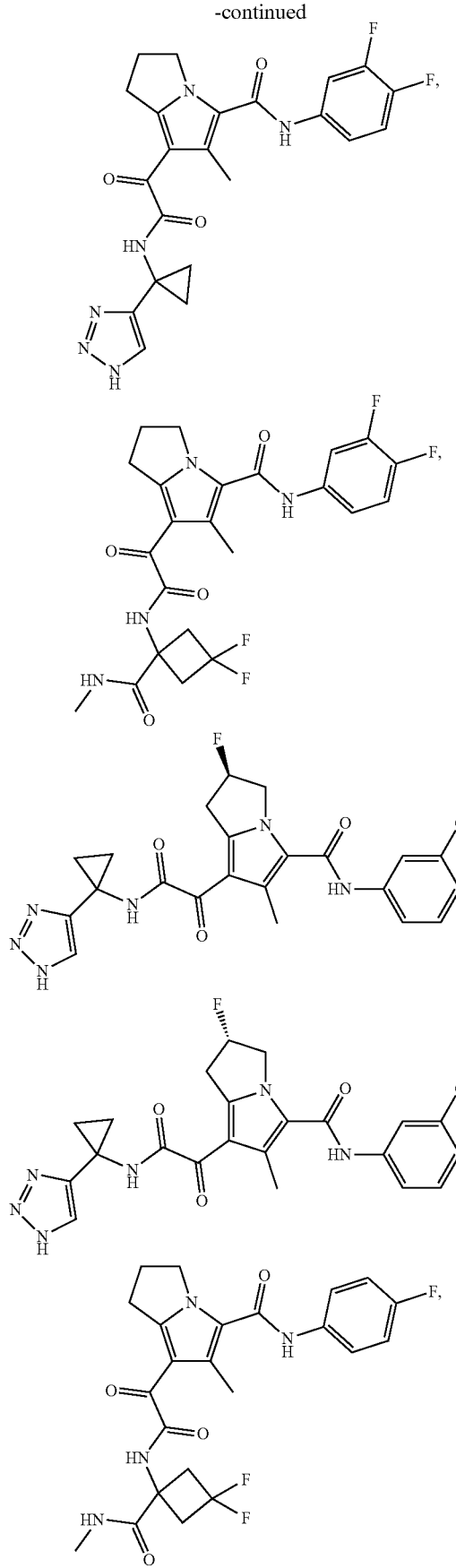
68
-continued
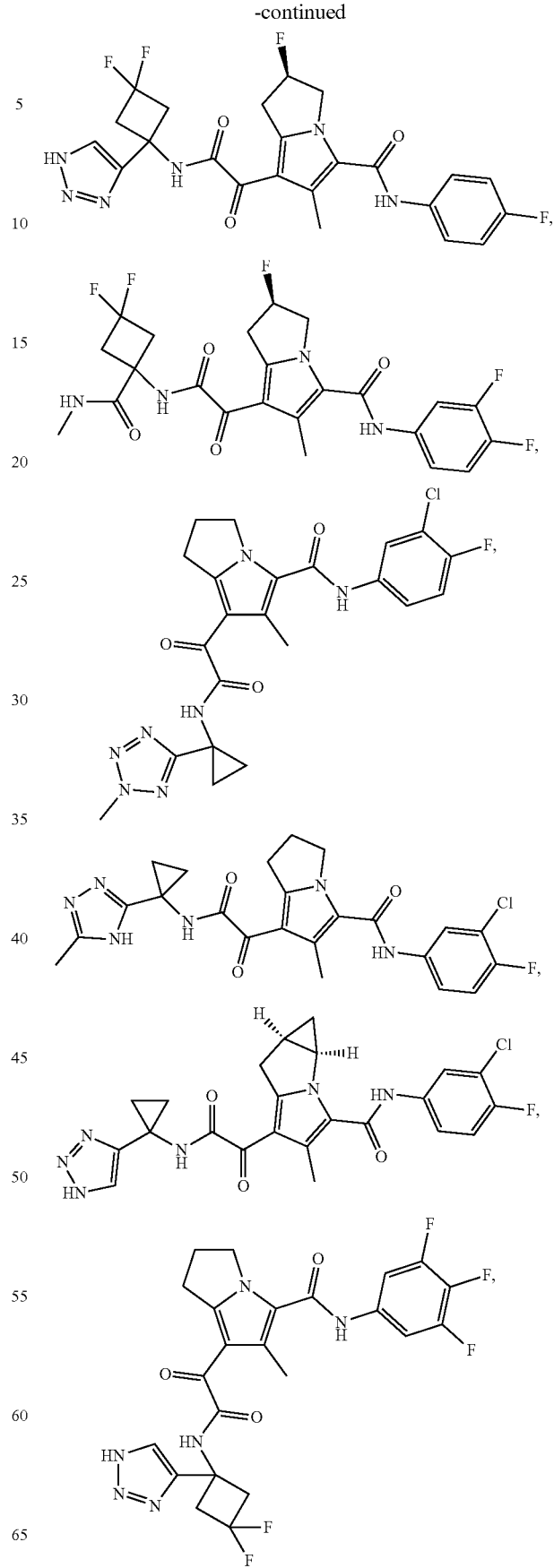

69
-continued
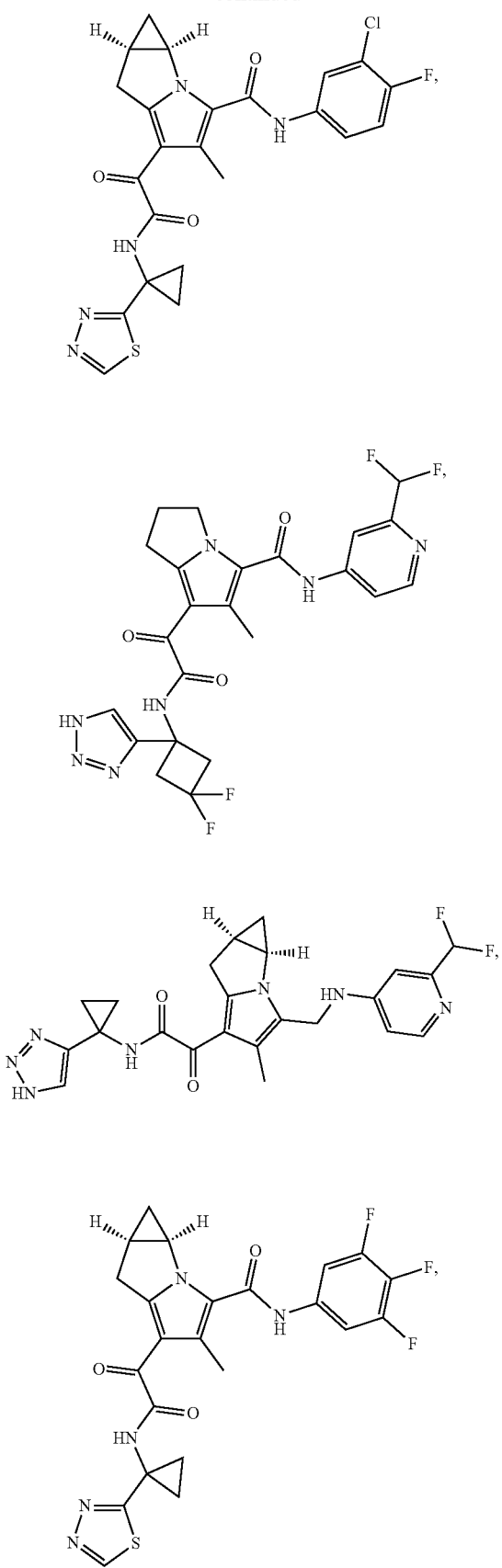
70
-continued
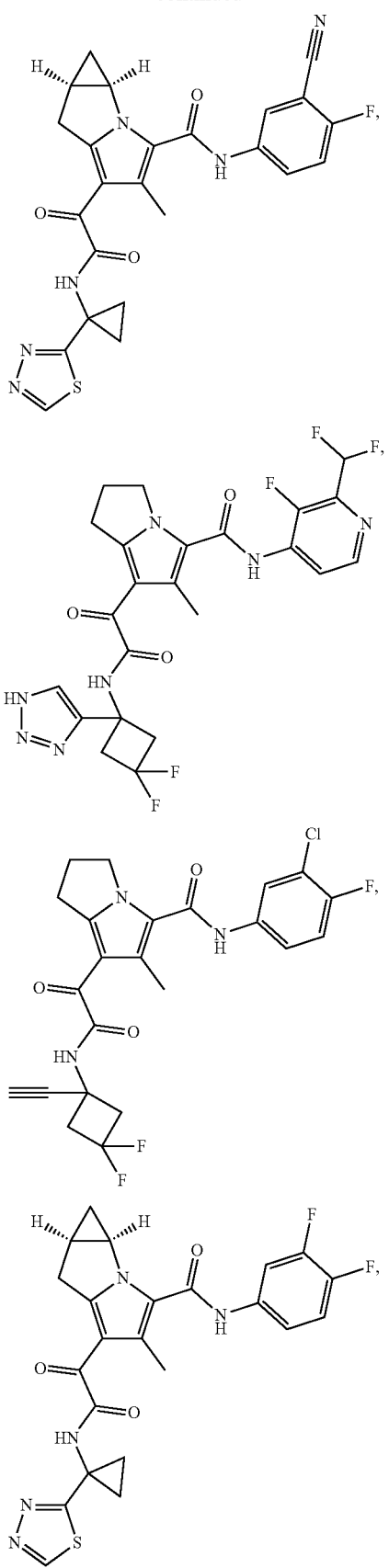

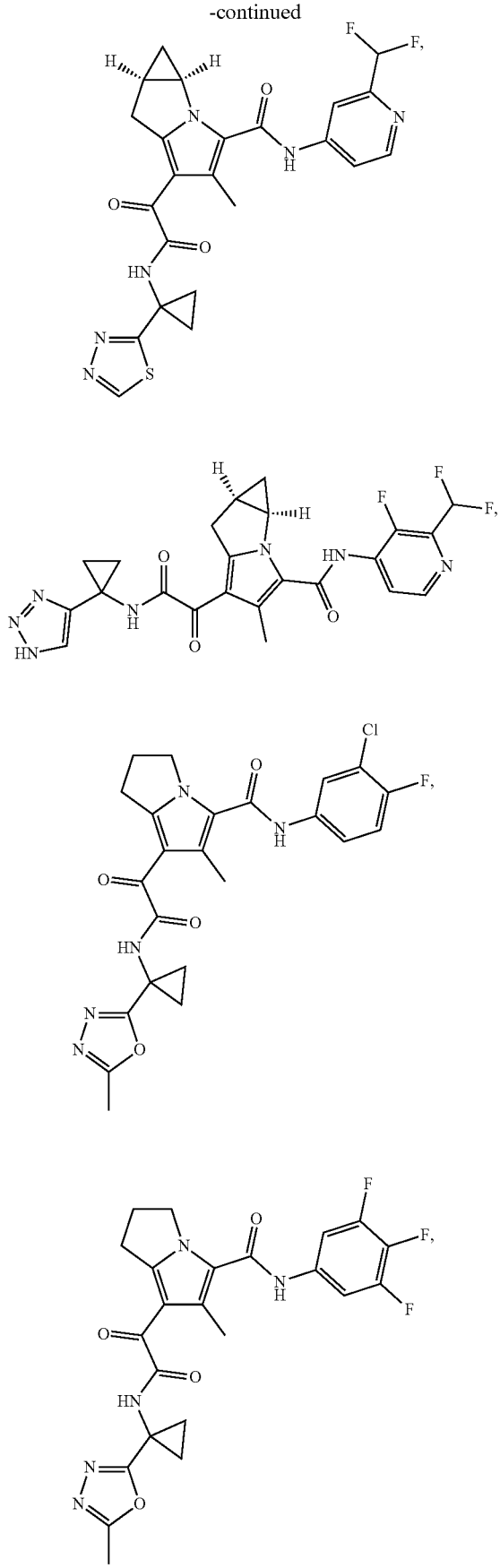
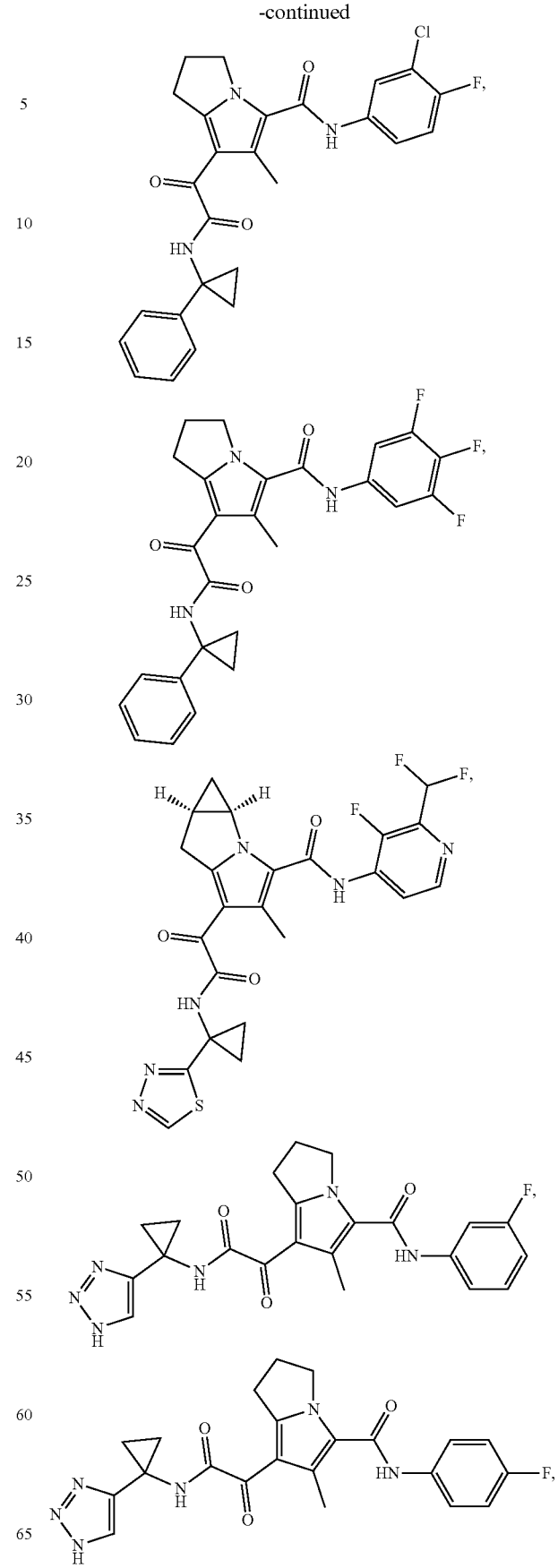

-continued
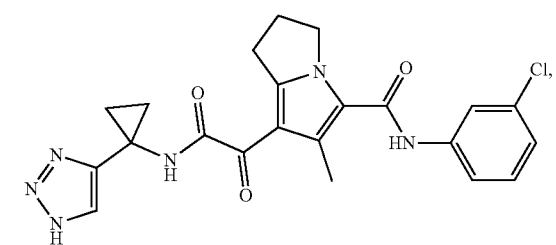
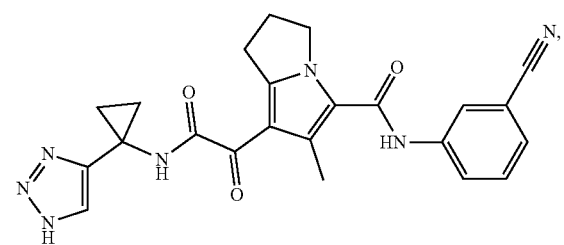
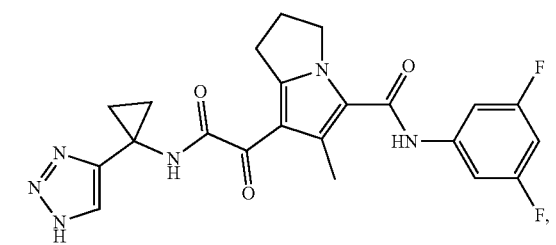
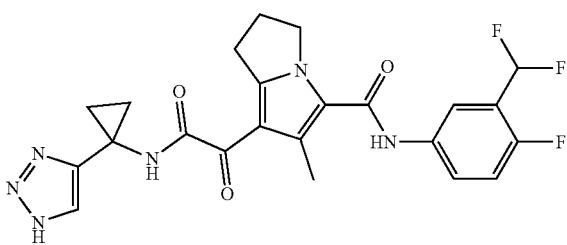
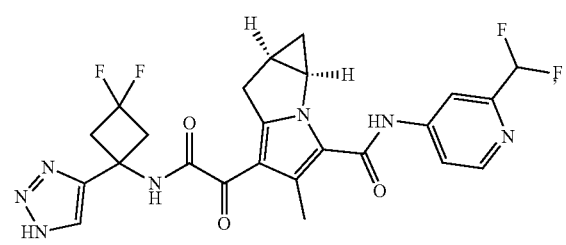
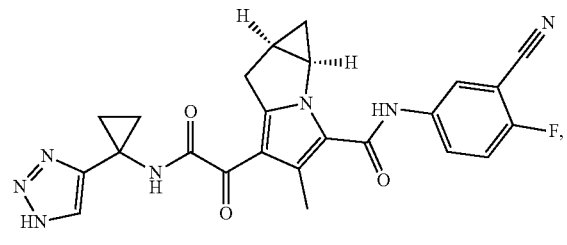
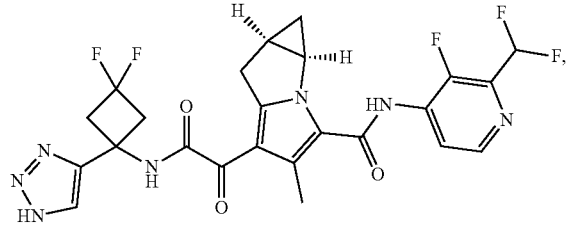

75
-continued
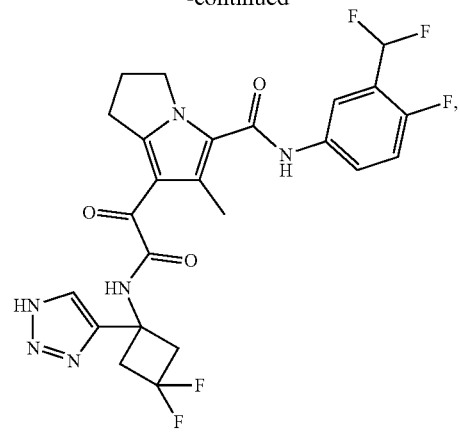
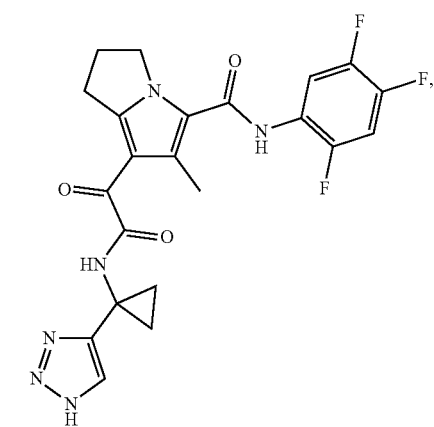
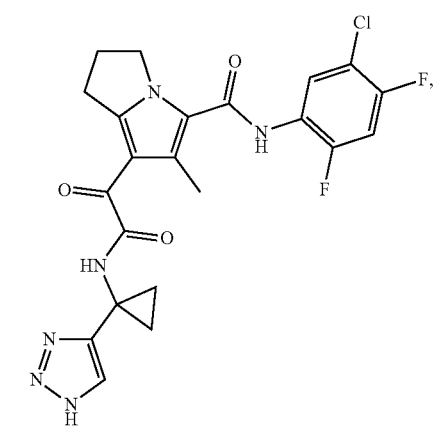
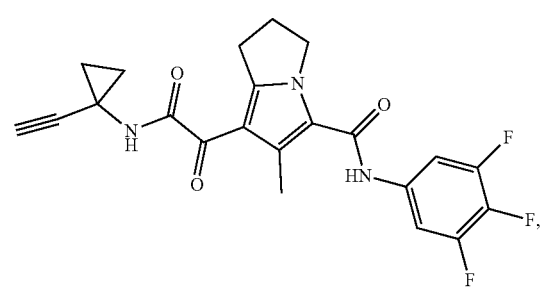
76
-continued
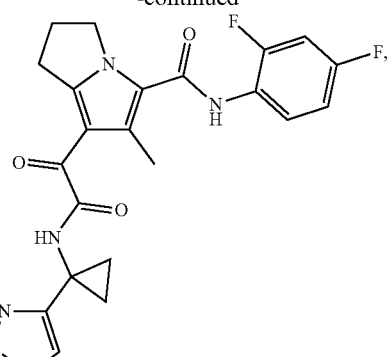
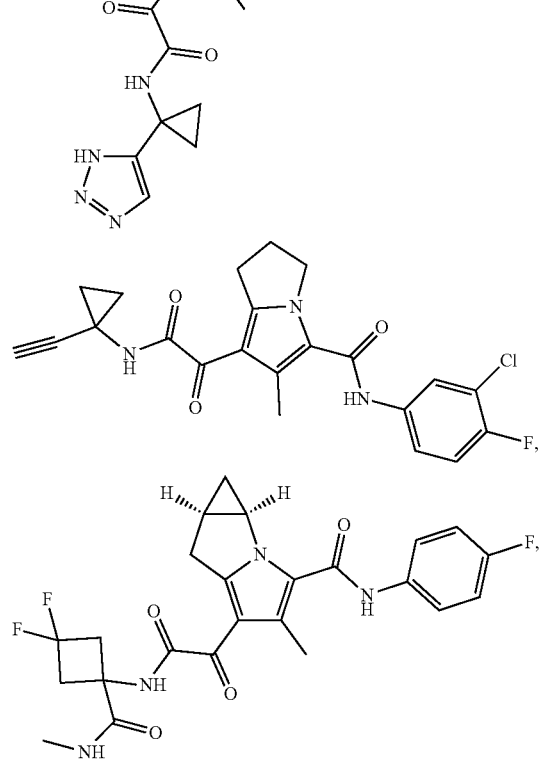
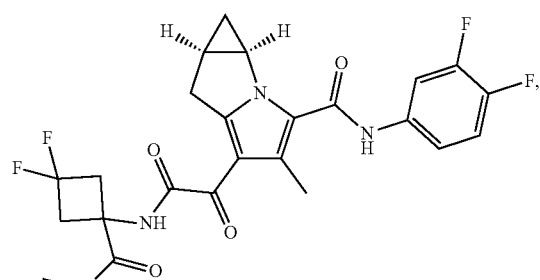
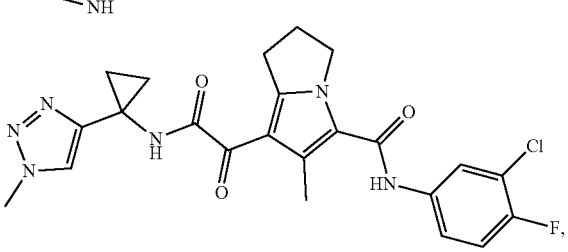
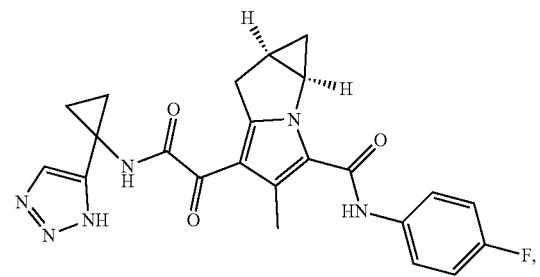

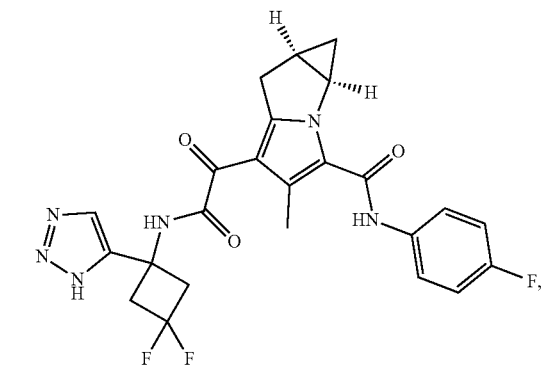
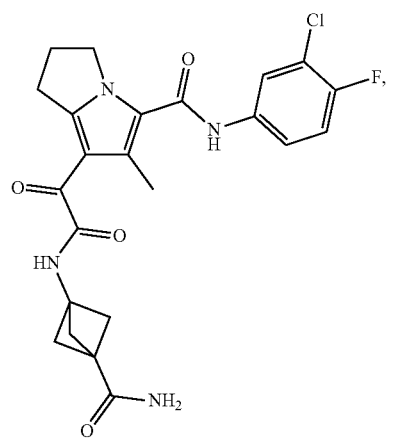
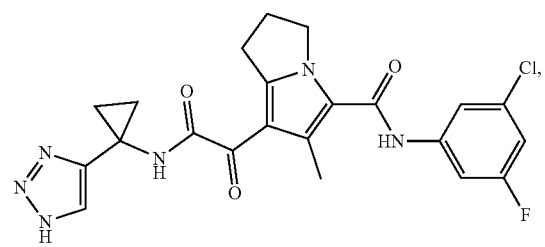
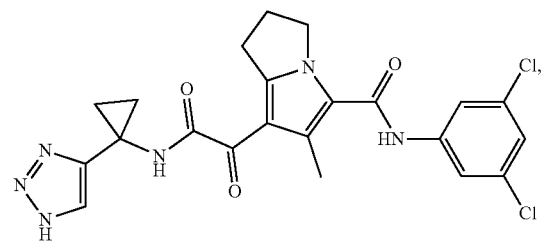
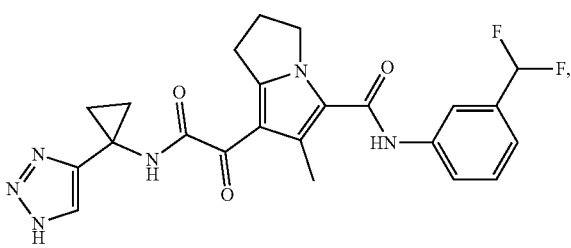
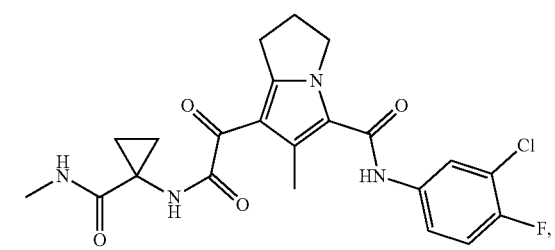
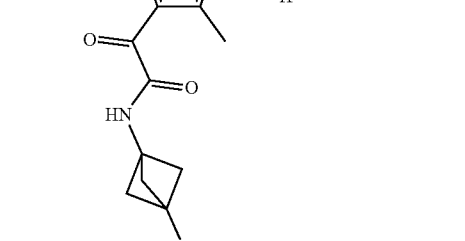

79
-continued
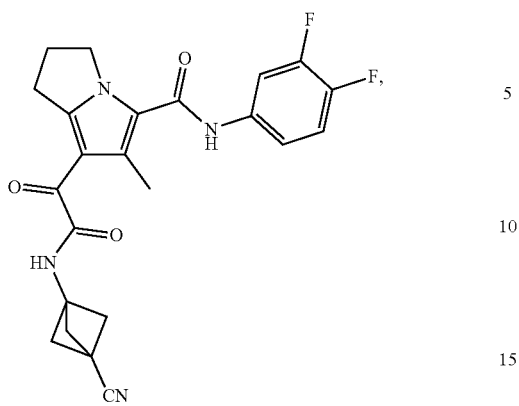
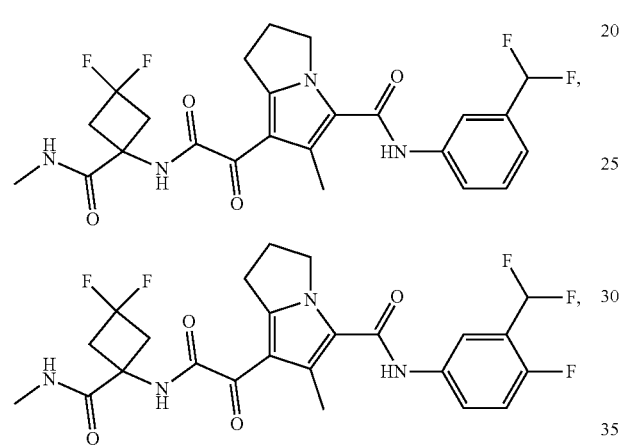
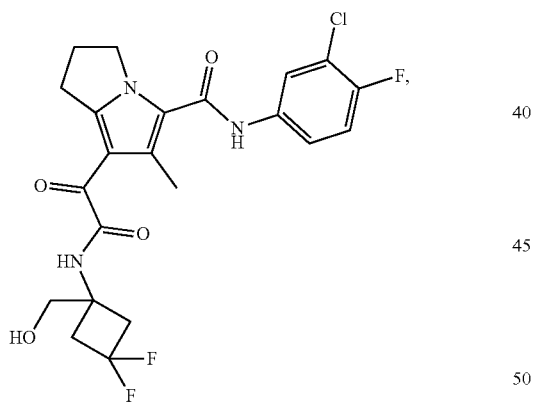
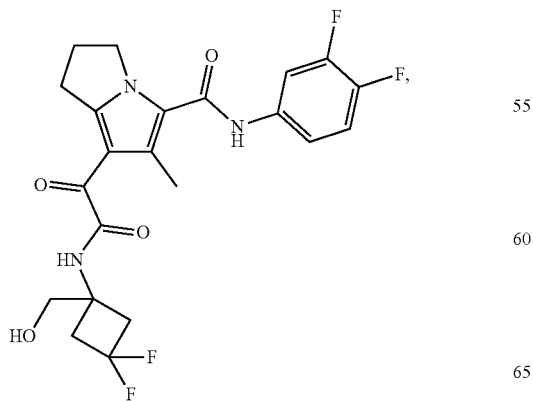
80
-continued
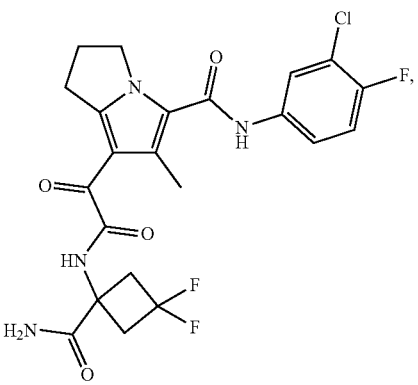
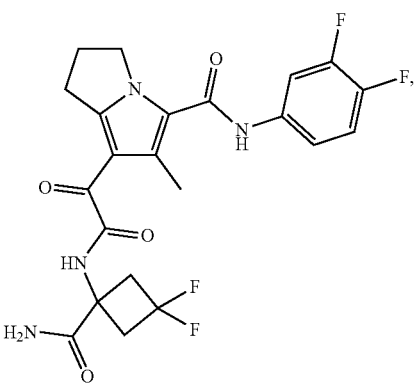
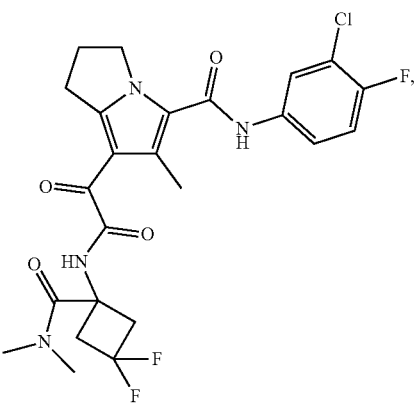
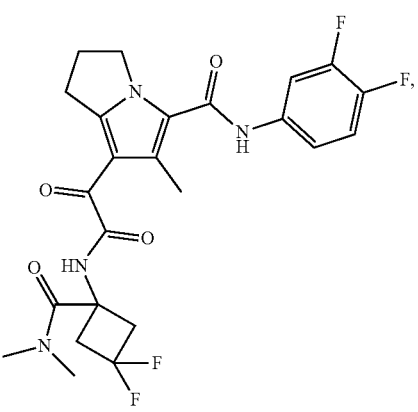

-continued
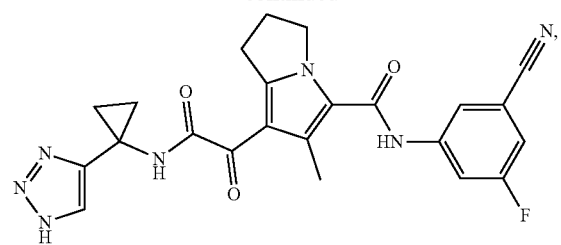
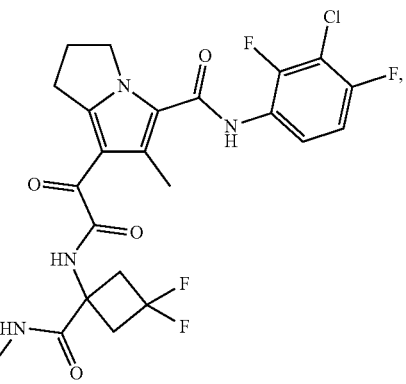
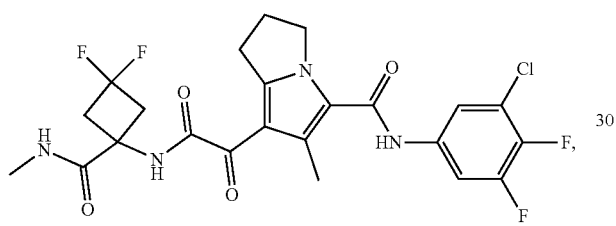
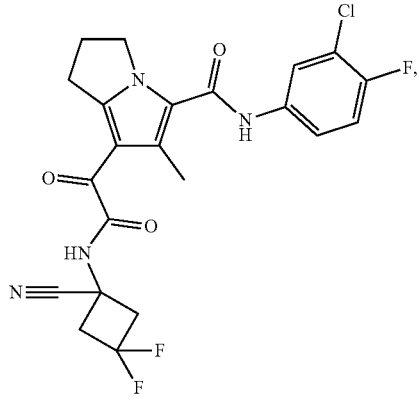
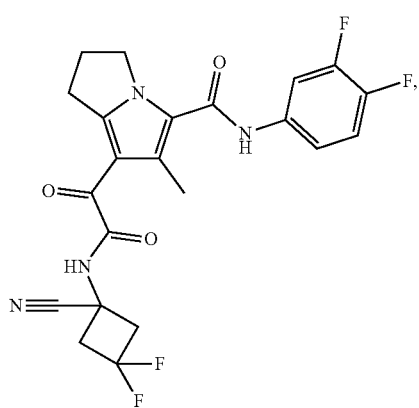
-continued
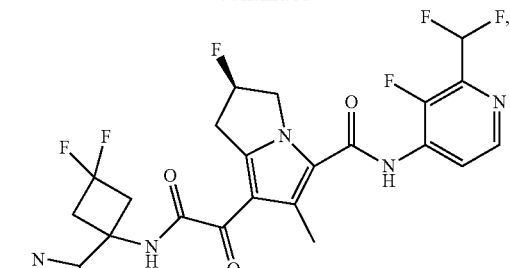
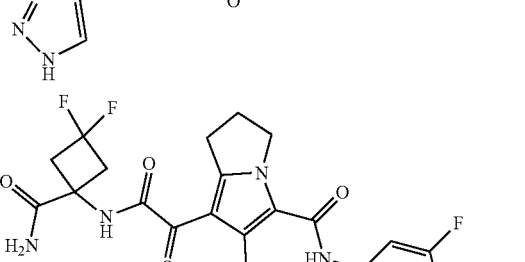
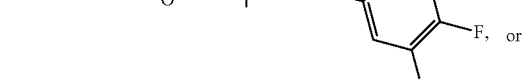, or
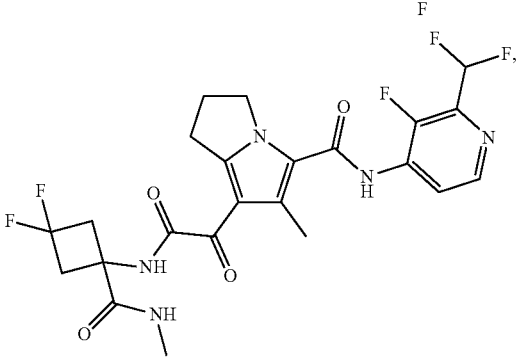
or a pharmaceutically acceptable salt thereof.
In certain embodiments, the compound of Formula (I), (II), (III), (IIIa), or (IV), is
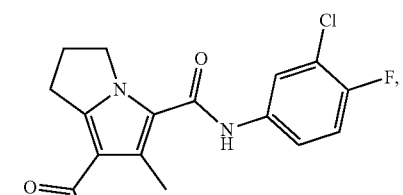
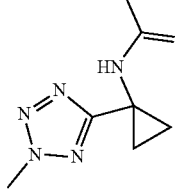
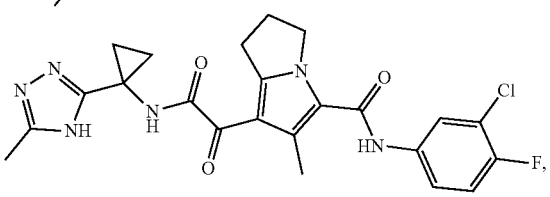

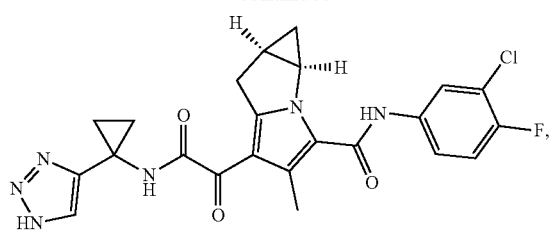
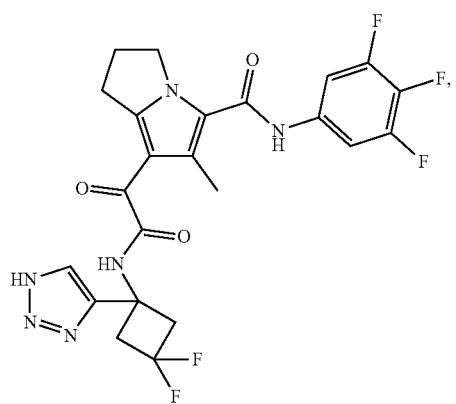
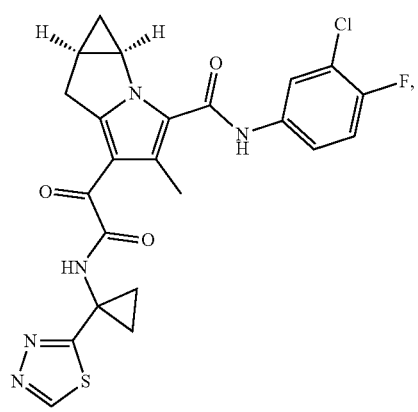
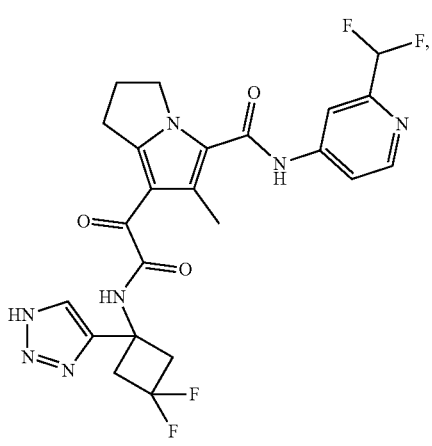
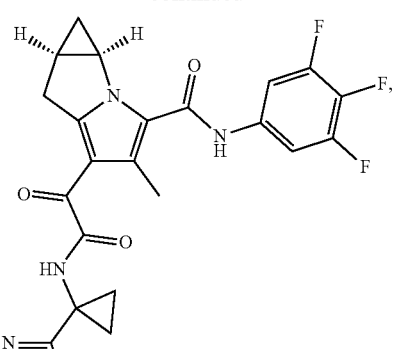
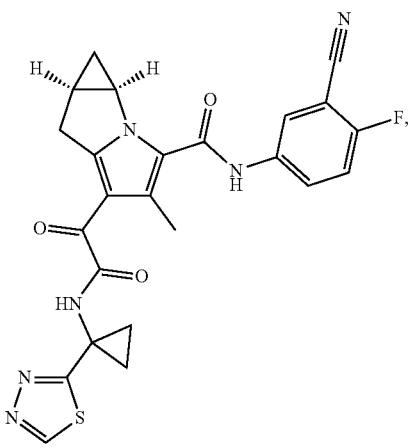
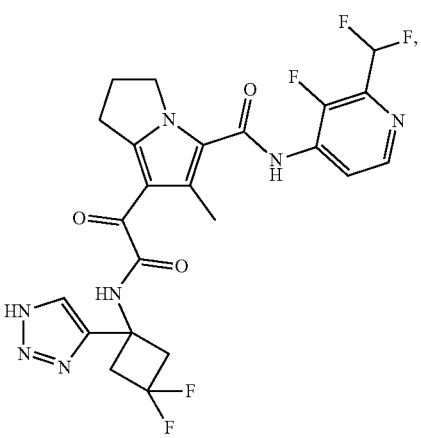
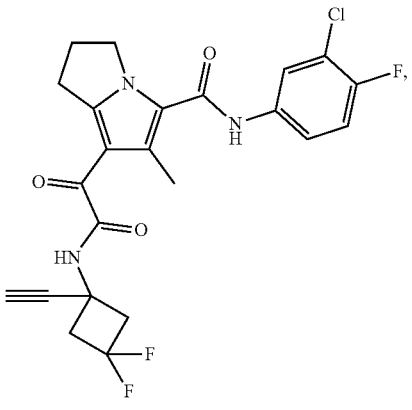

85
-continued
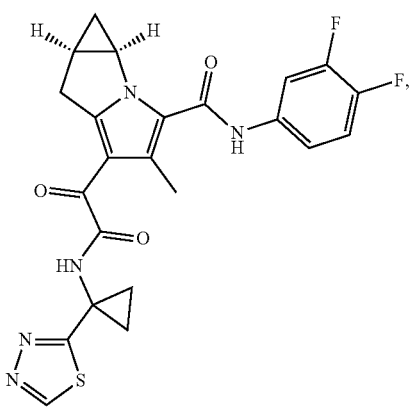
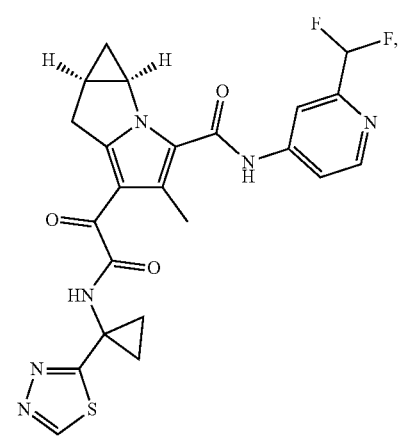
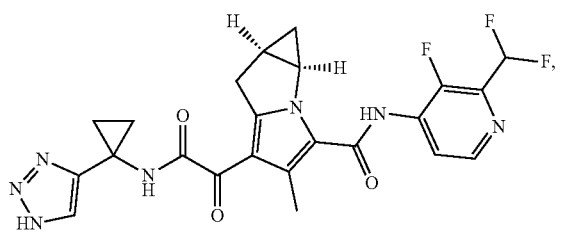
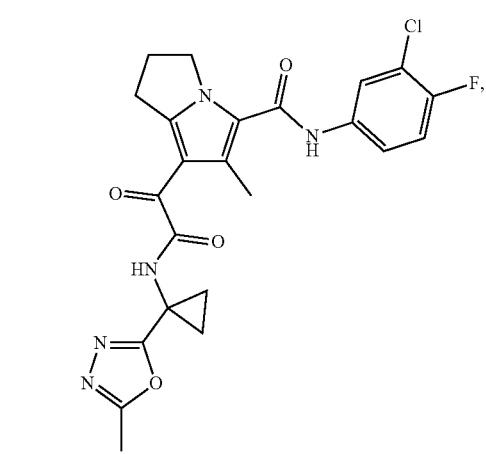
86
-continued
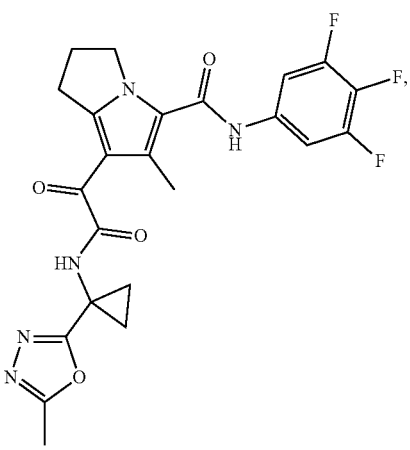
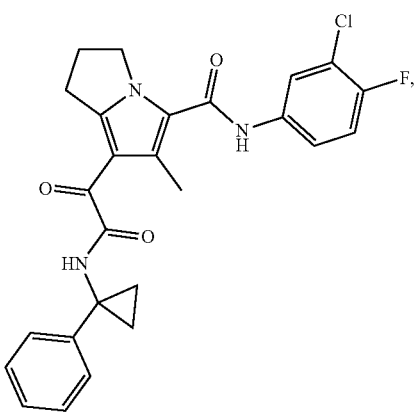
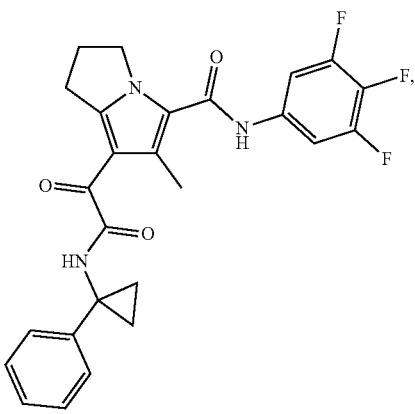
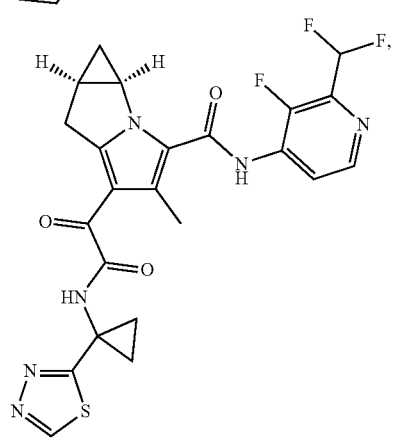

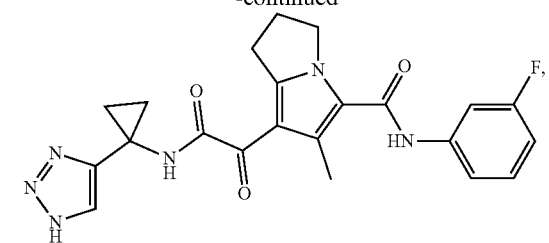
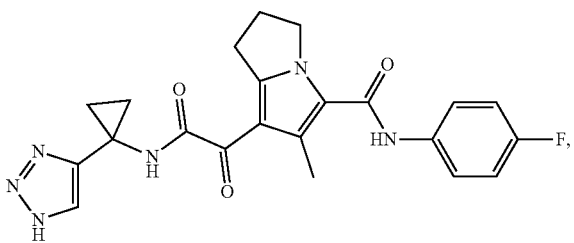
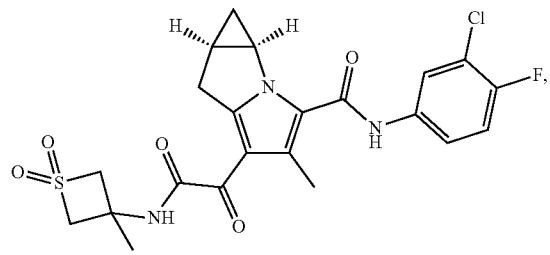
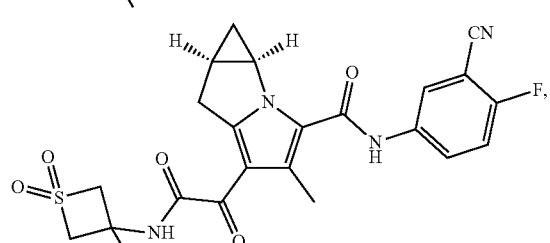
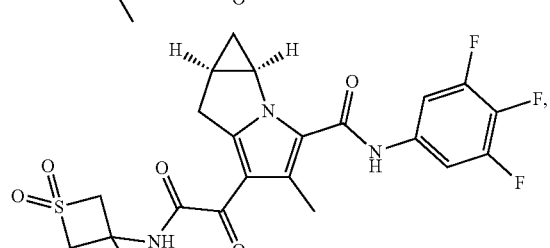
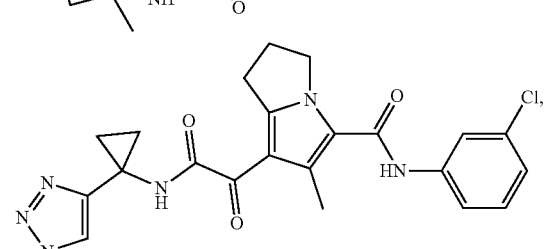
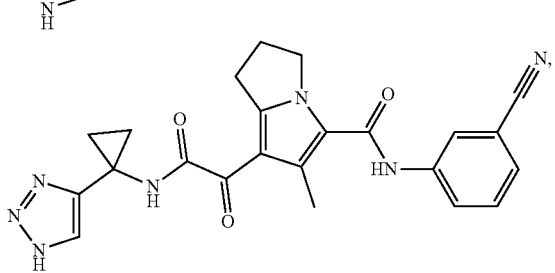
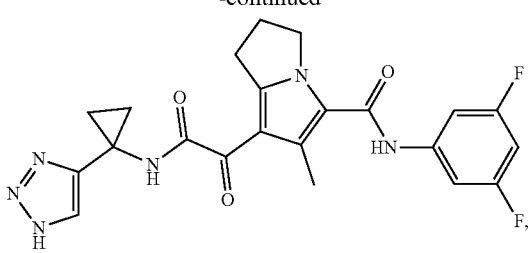
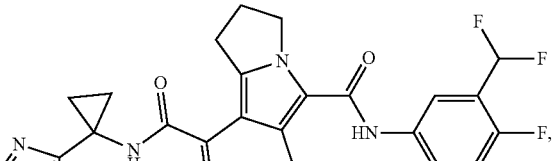
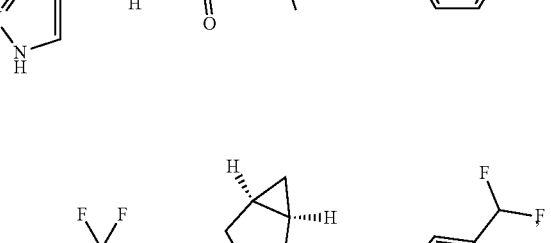
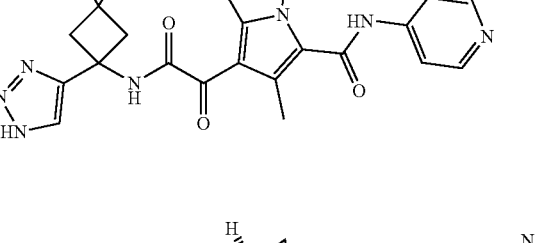
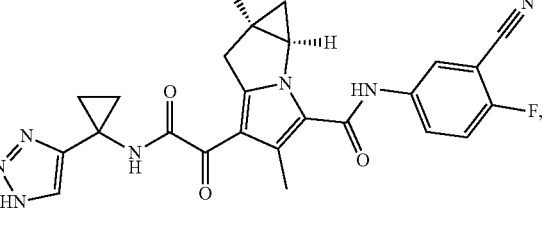
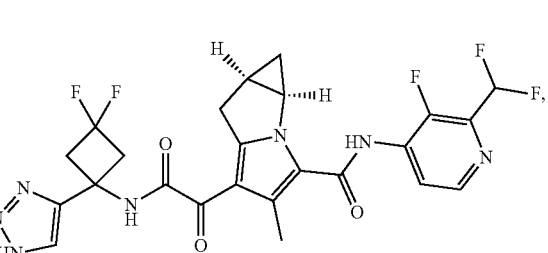
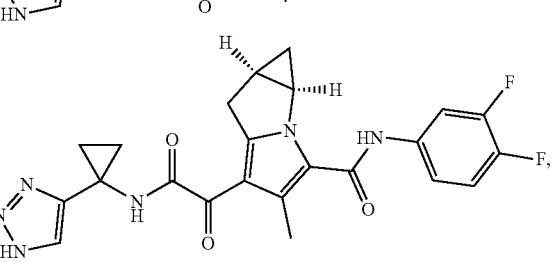

-continued
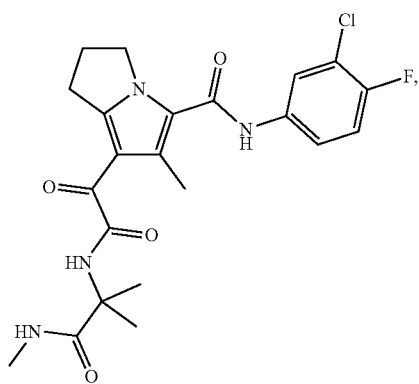
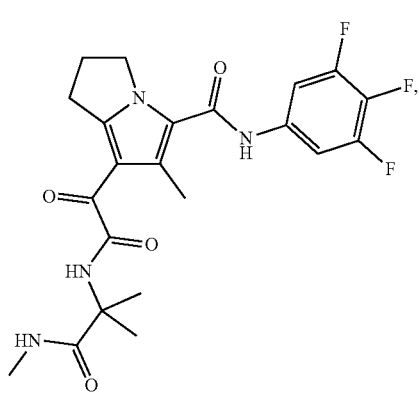
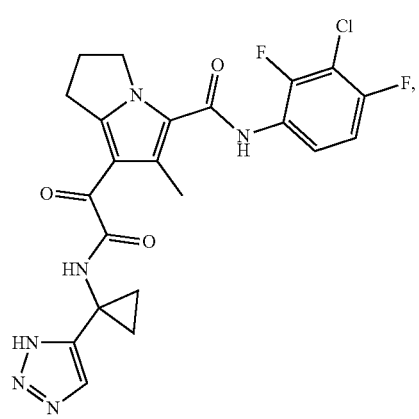
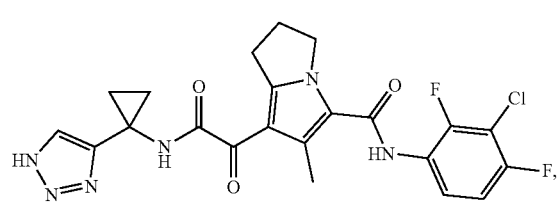
-continued
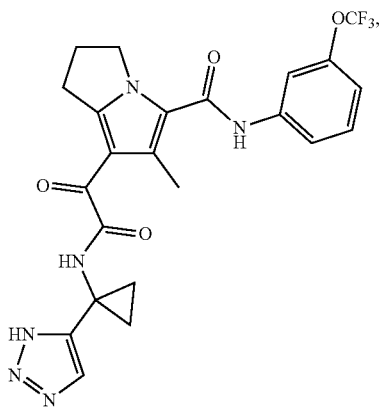
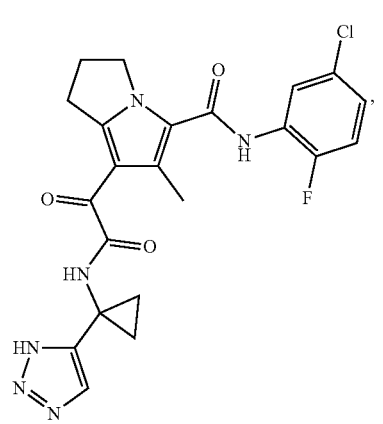
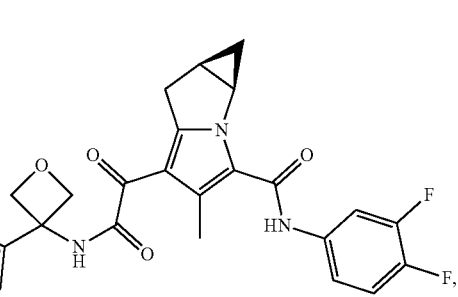
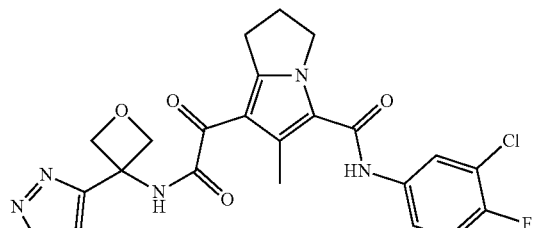

91
-continued
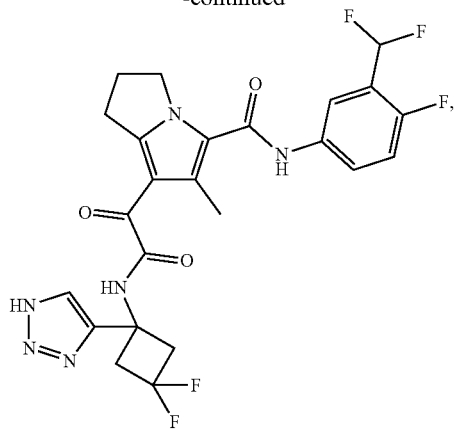
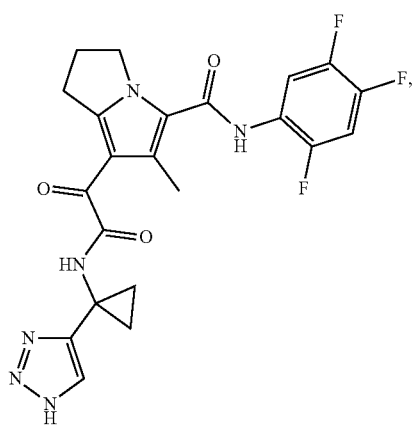
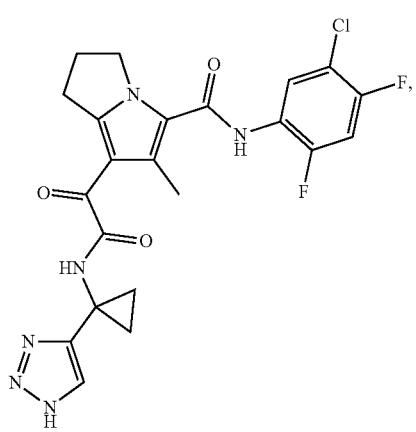
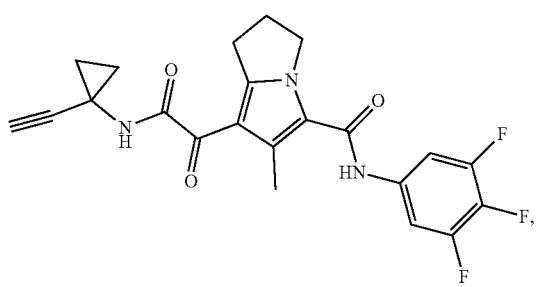
92
-continued
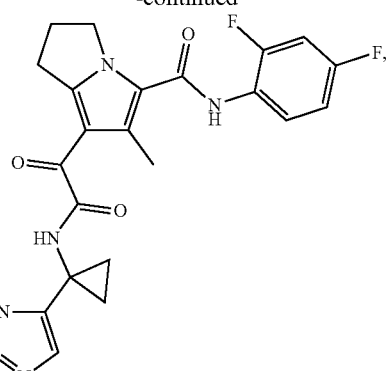
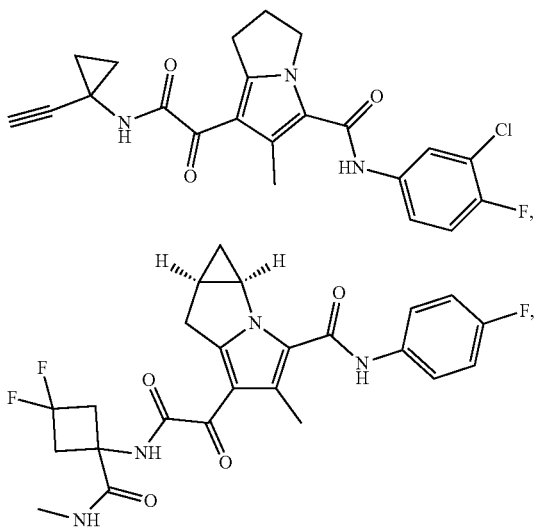
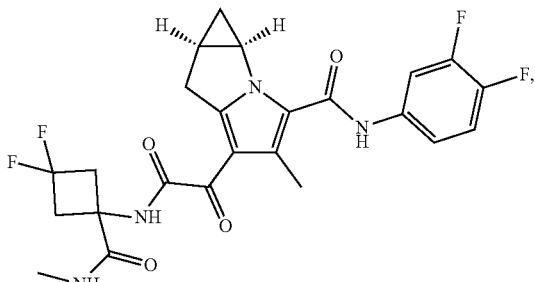
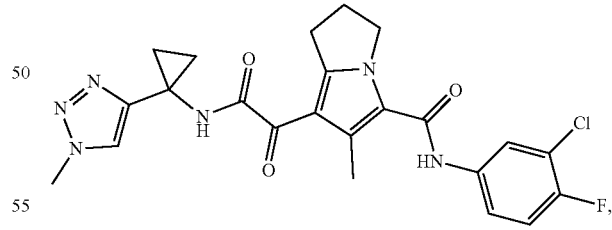
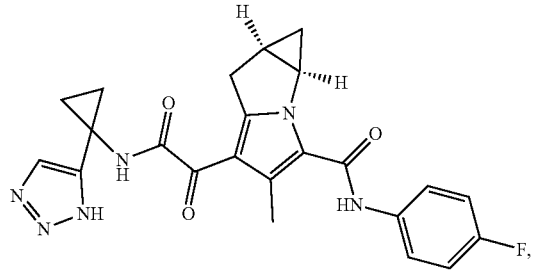

93
-continued
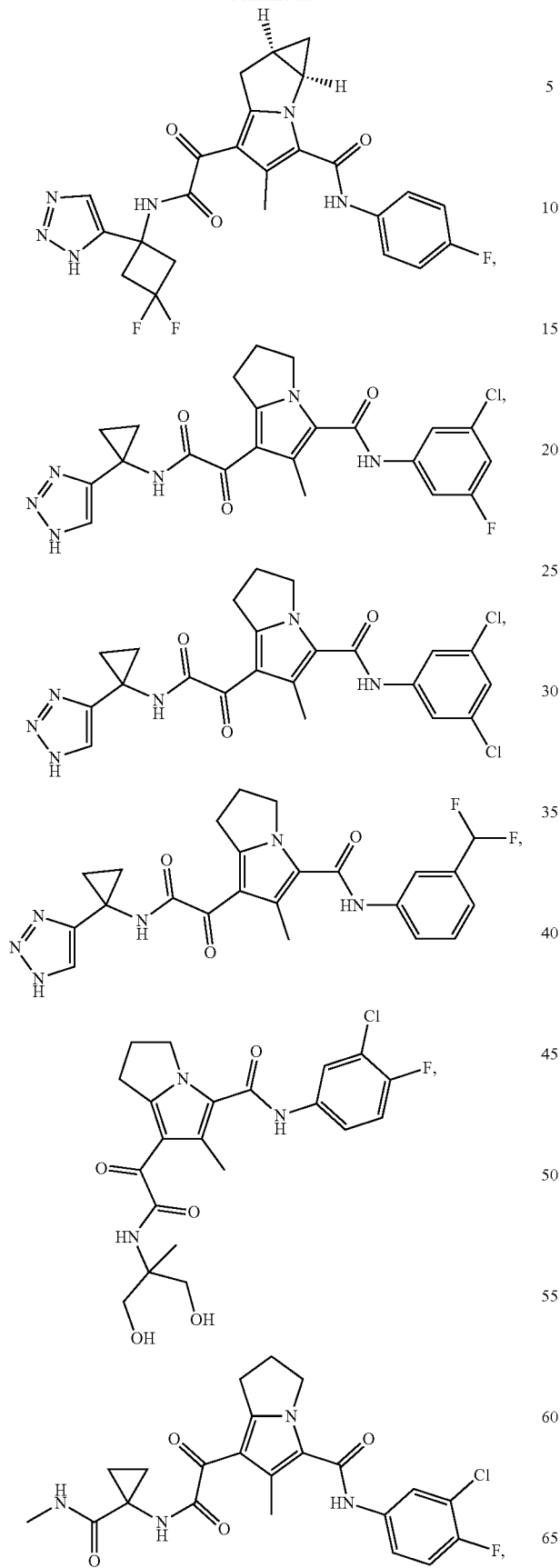
94
-continued
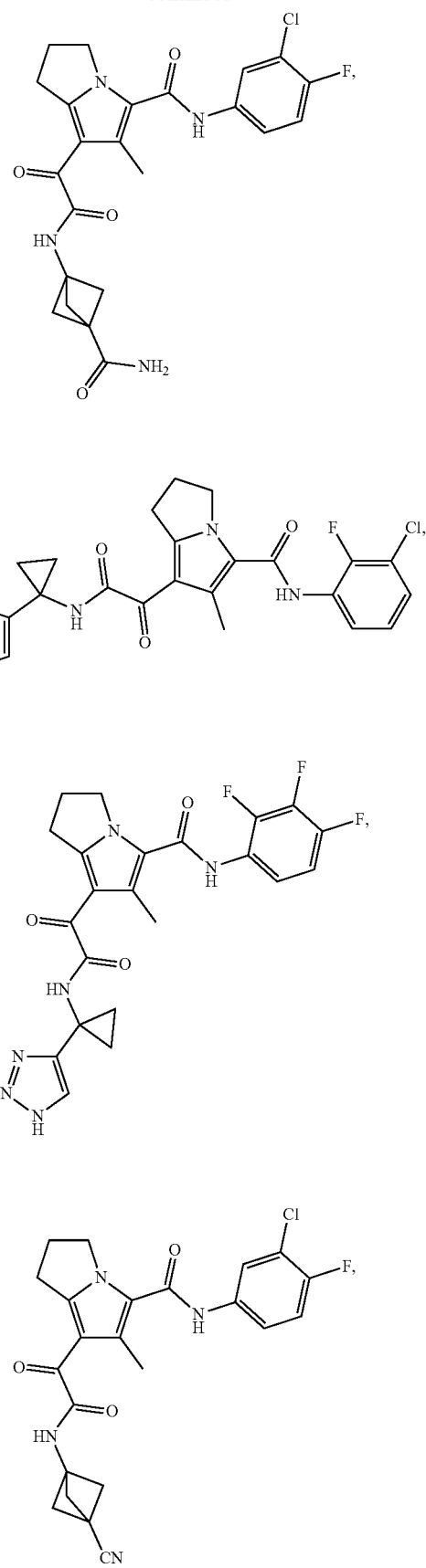

95
-continued
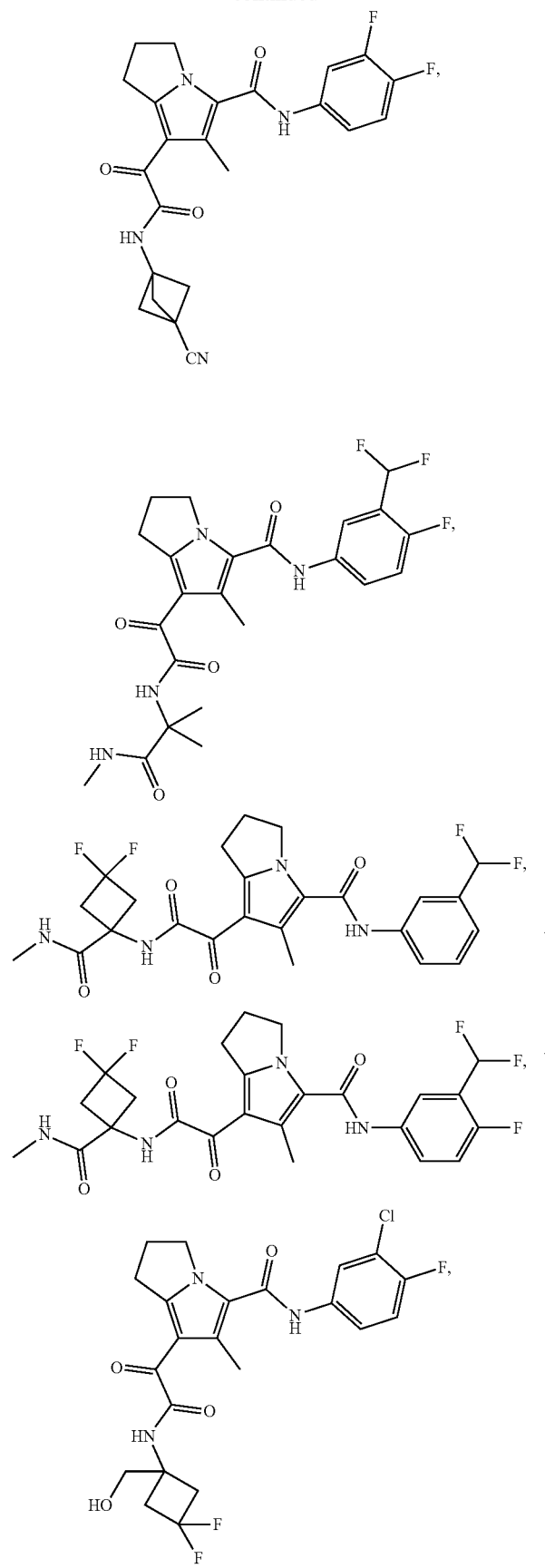
96
-continued
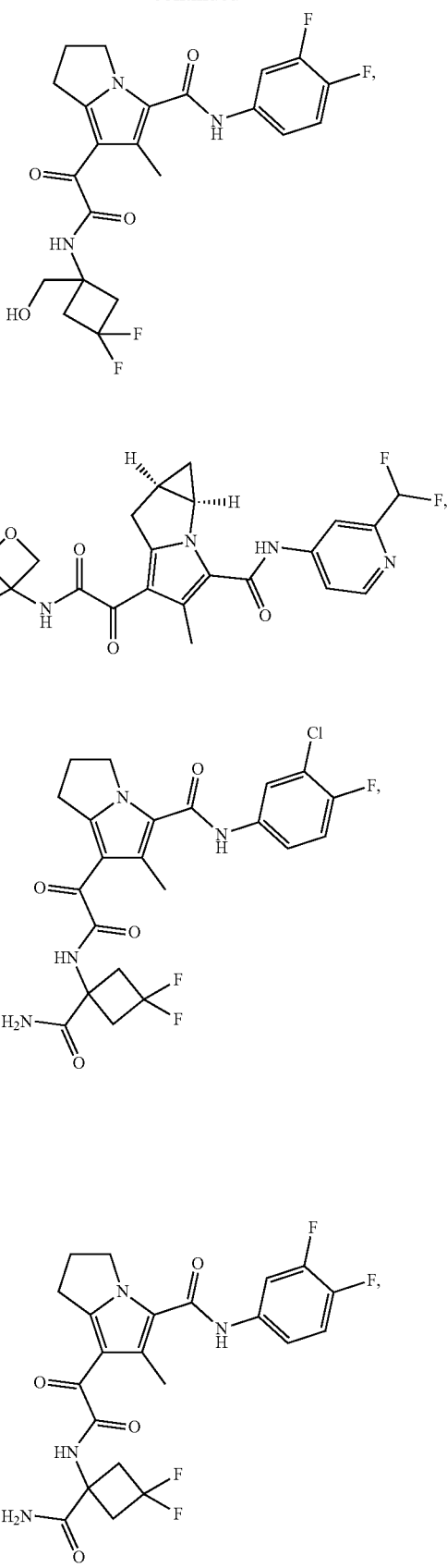

97
-continued
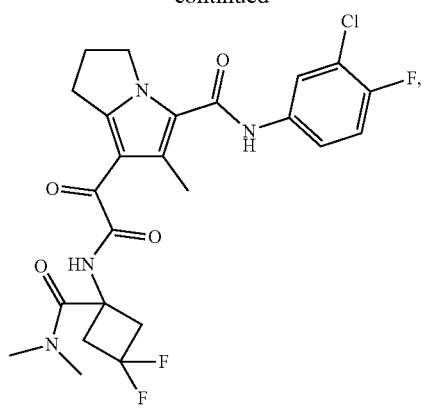
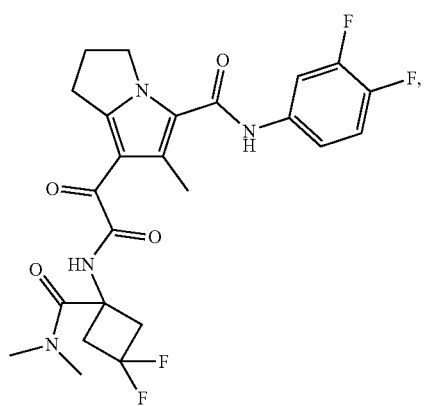
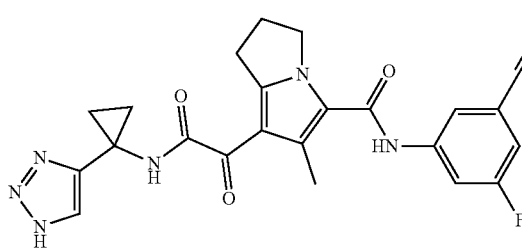
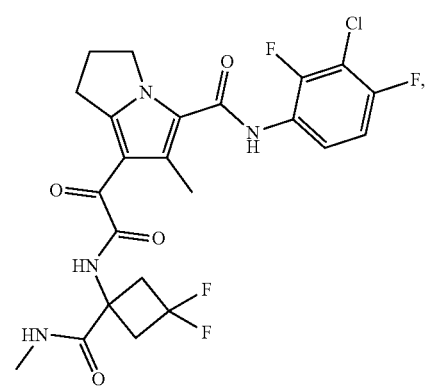
98
-continued
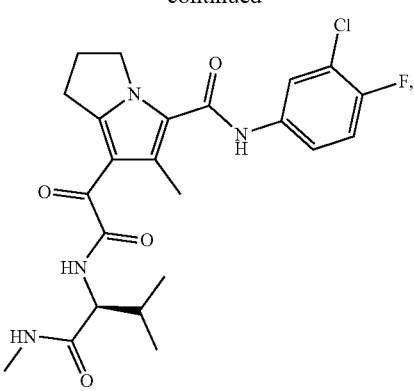
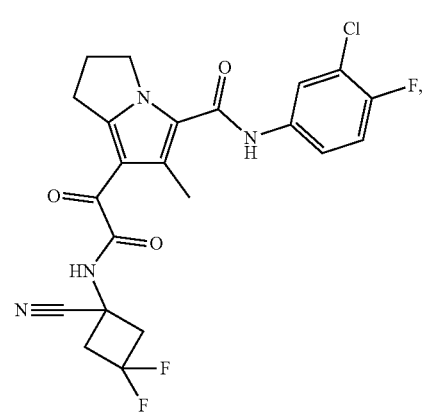
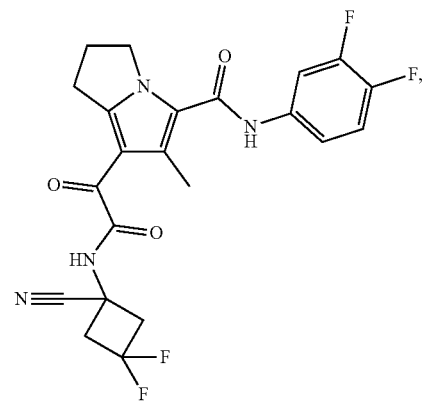

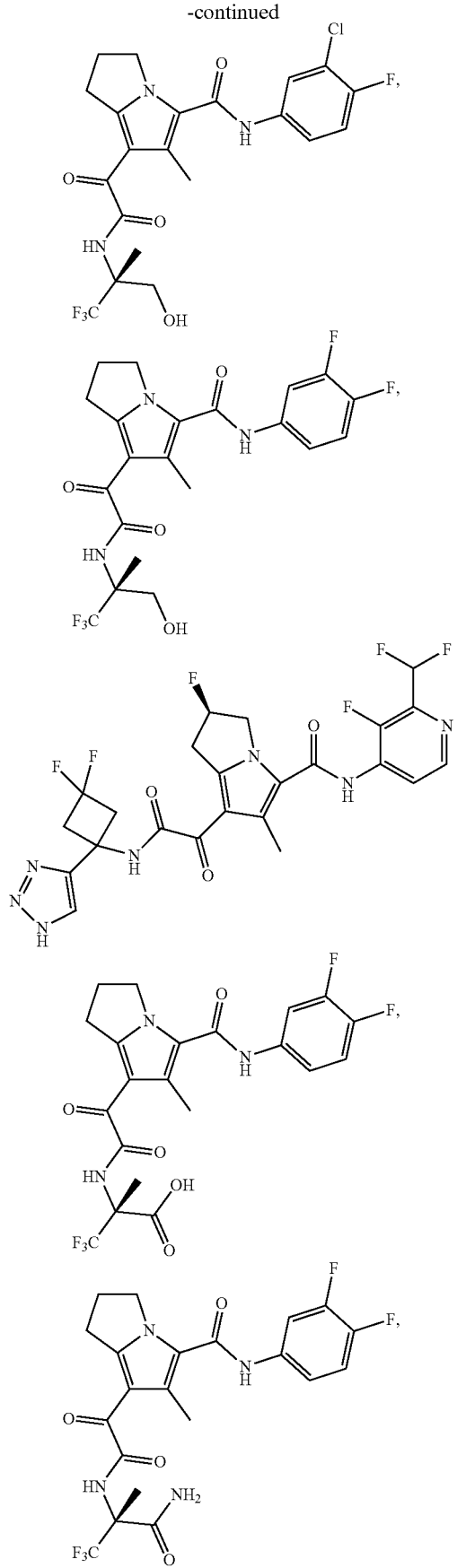

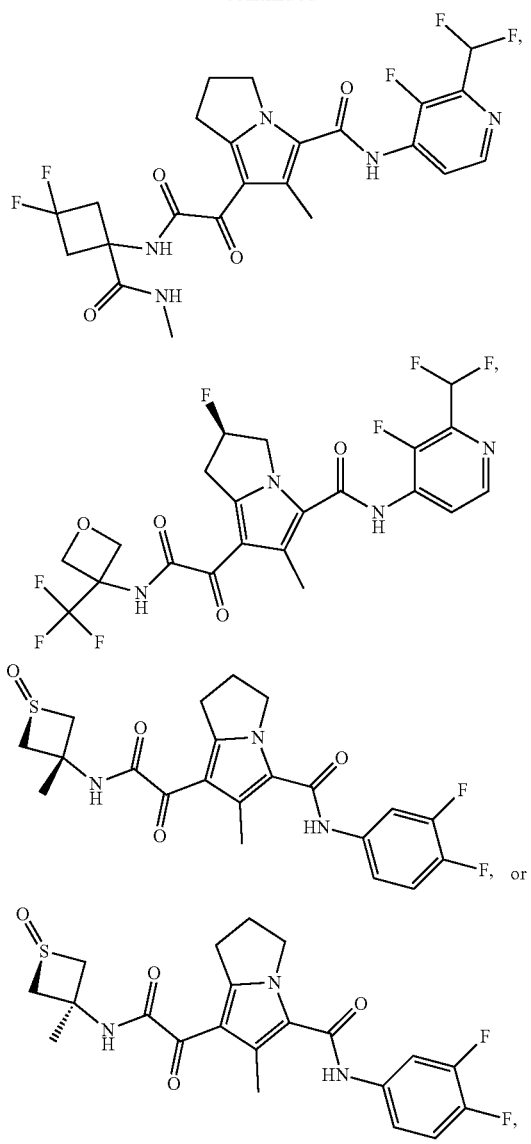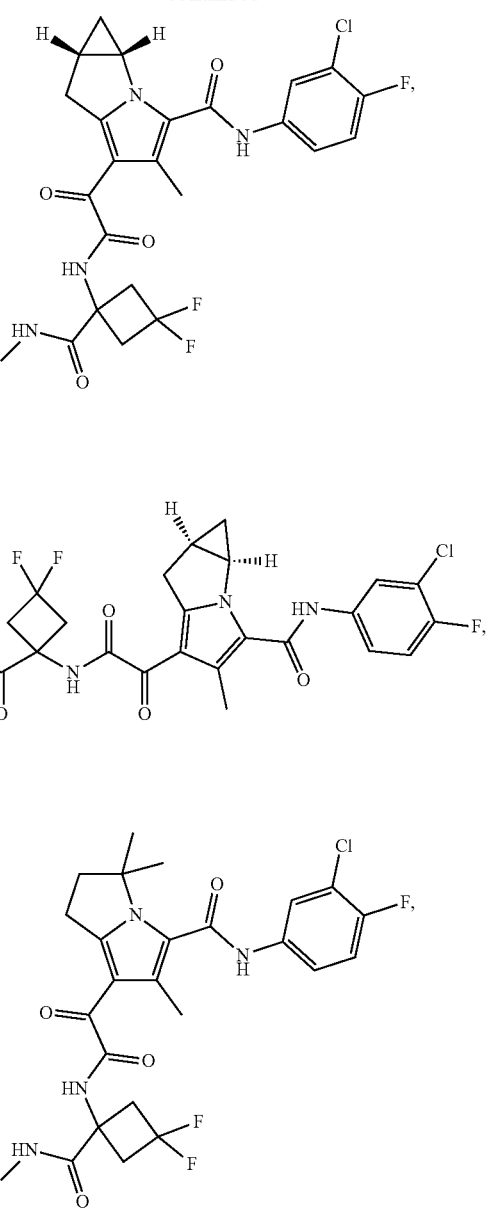
or a pharmaceutically acceptable salt thereof.
In certain embodiments, the compound of Formula (I), (II), (III), (IIIa), or (IV), is
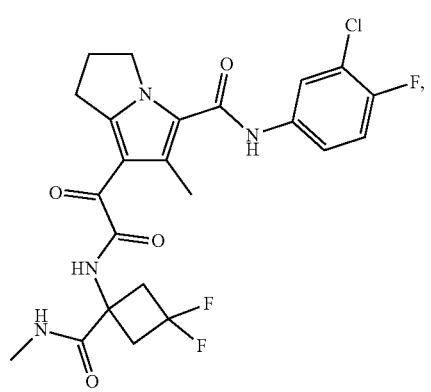

103
-continued
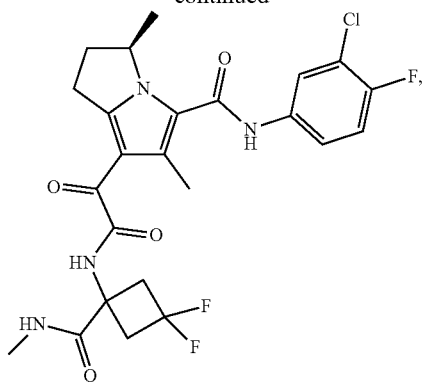
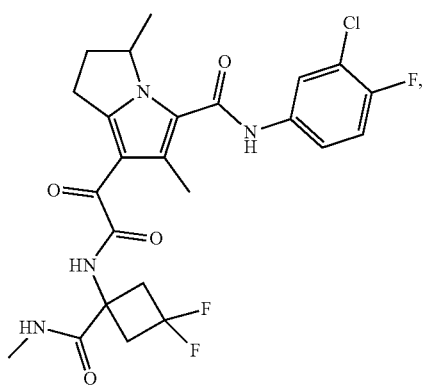
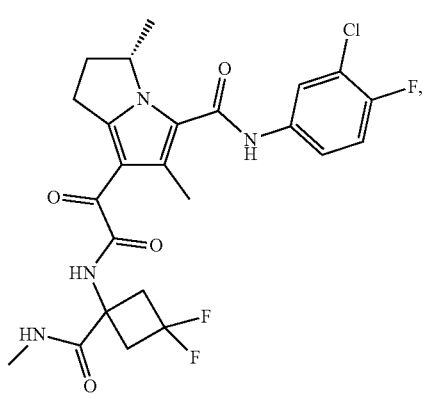
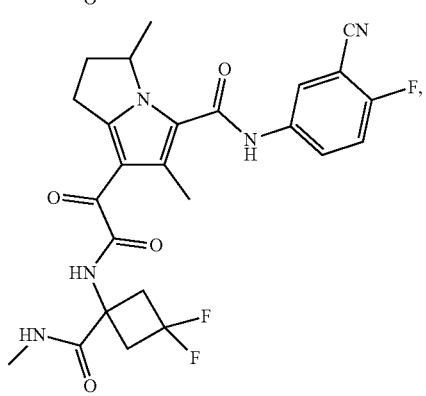
104
-continued
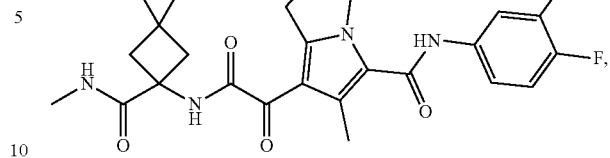
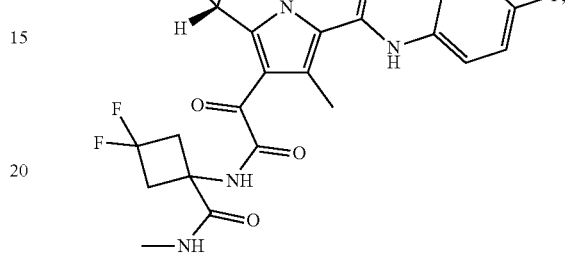
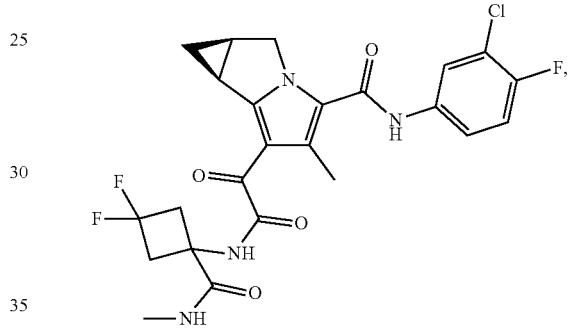
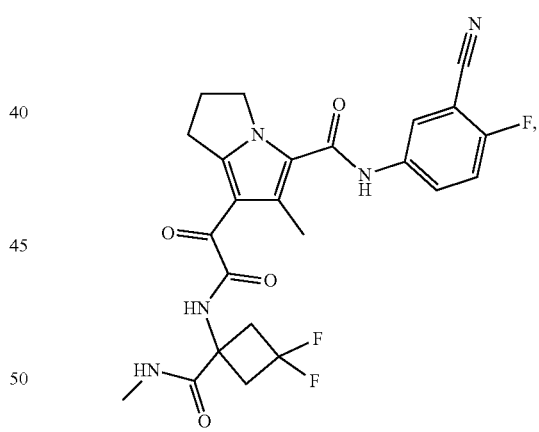
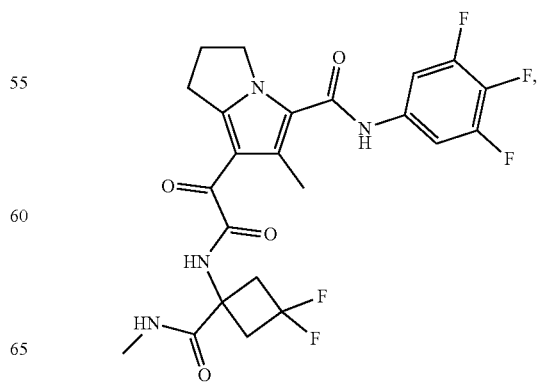

105
-continued
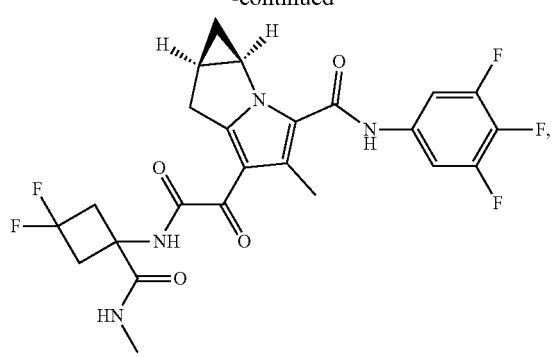
106
-continued
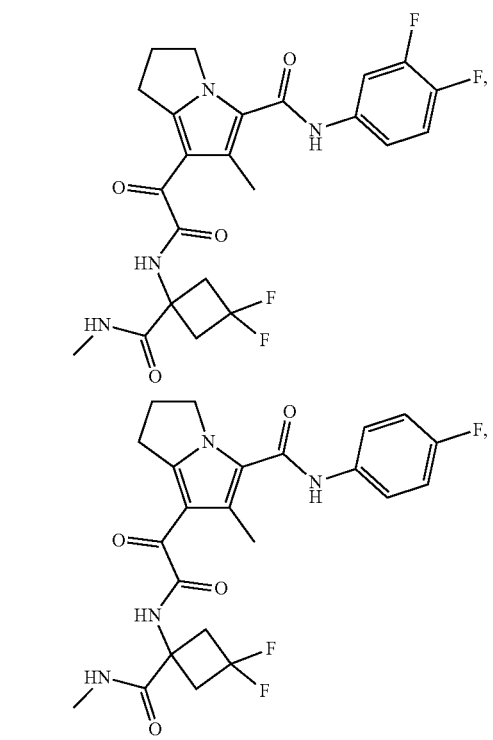

107
-continued
108
-continued
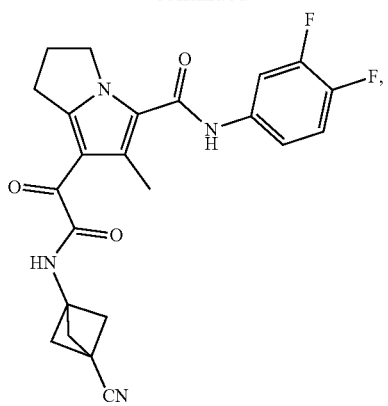
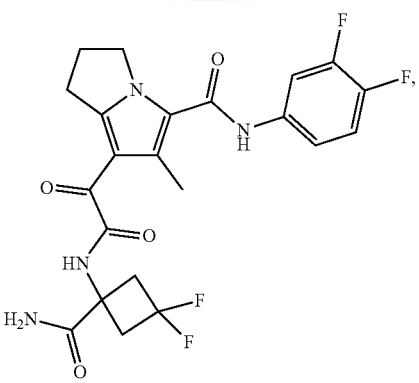

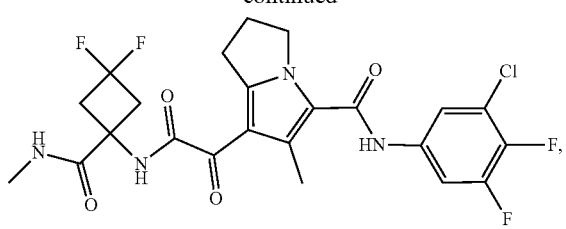
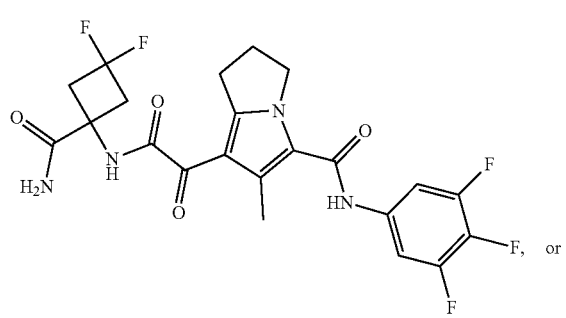
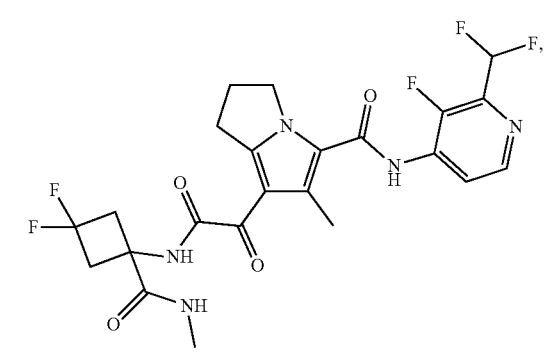
or a pharmaceutically acceptable salt thereof.
In certain embodiments, the compound of Formula (I), (II), or (IV), is
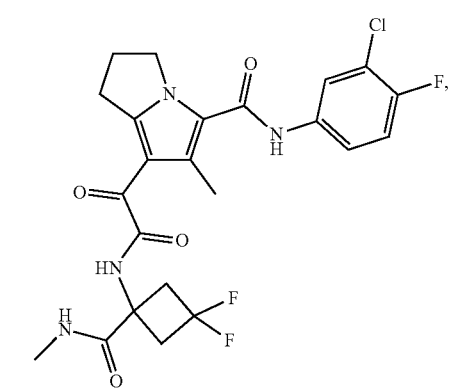
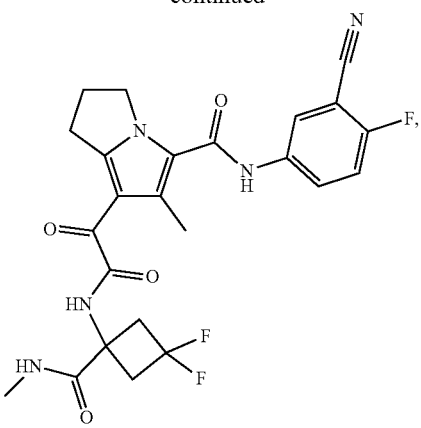
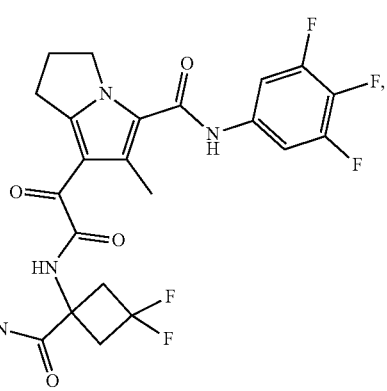
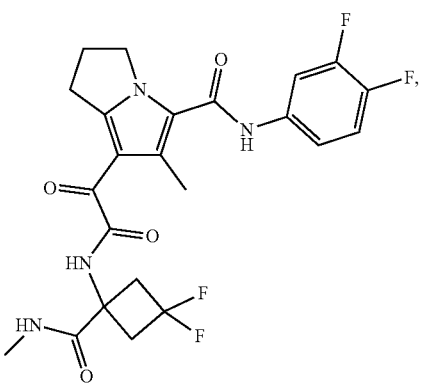
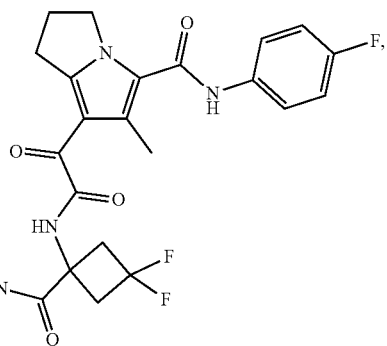

111
-continued
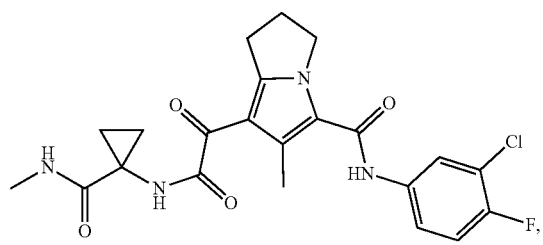
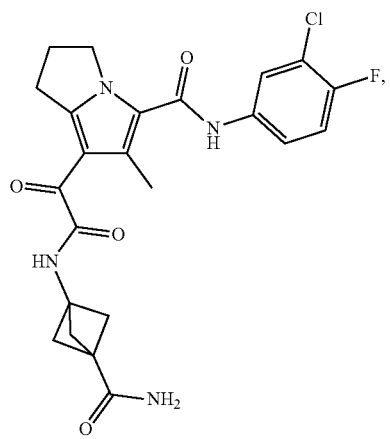
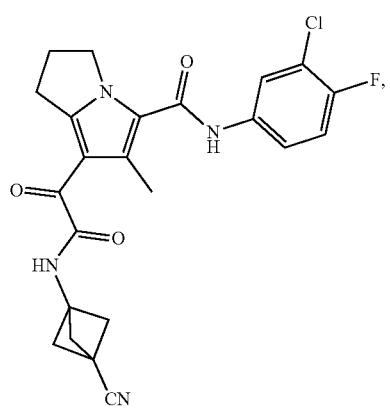
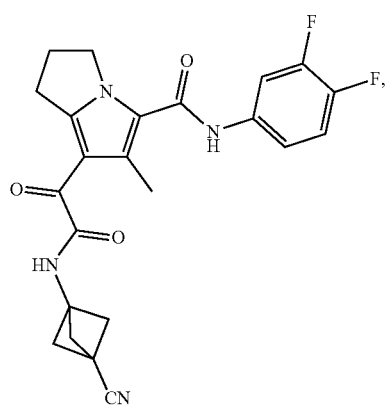
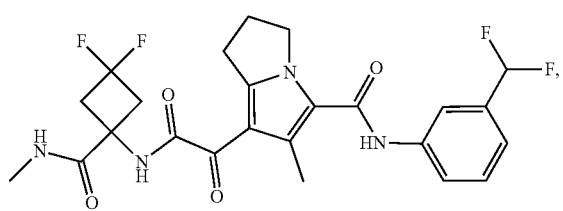
112
-continued
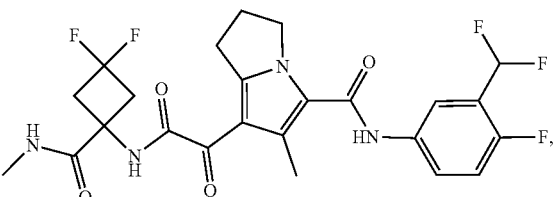
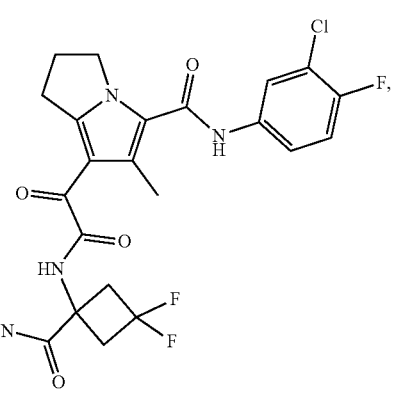
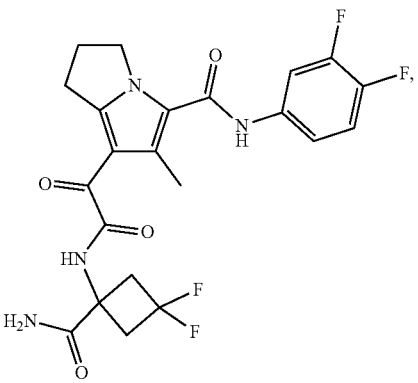
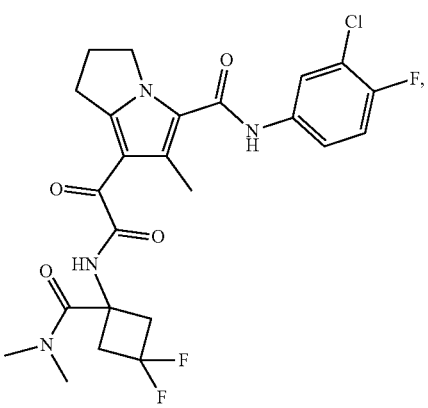

113
-continued
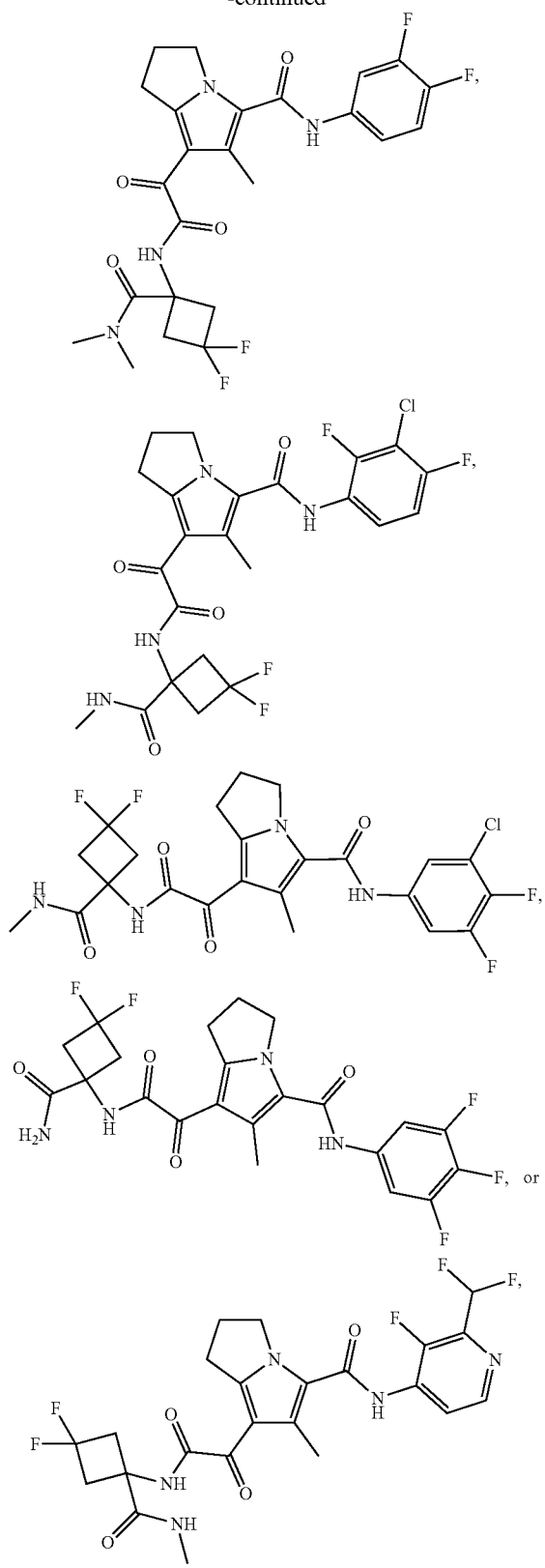
or a pharmaceutically acceptable salt thereof.
In certain embodiments, the compound of Formula (I), (II), or (IV), is
114
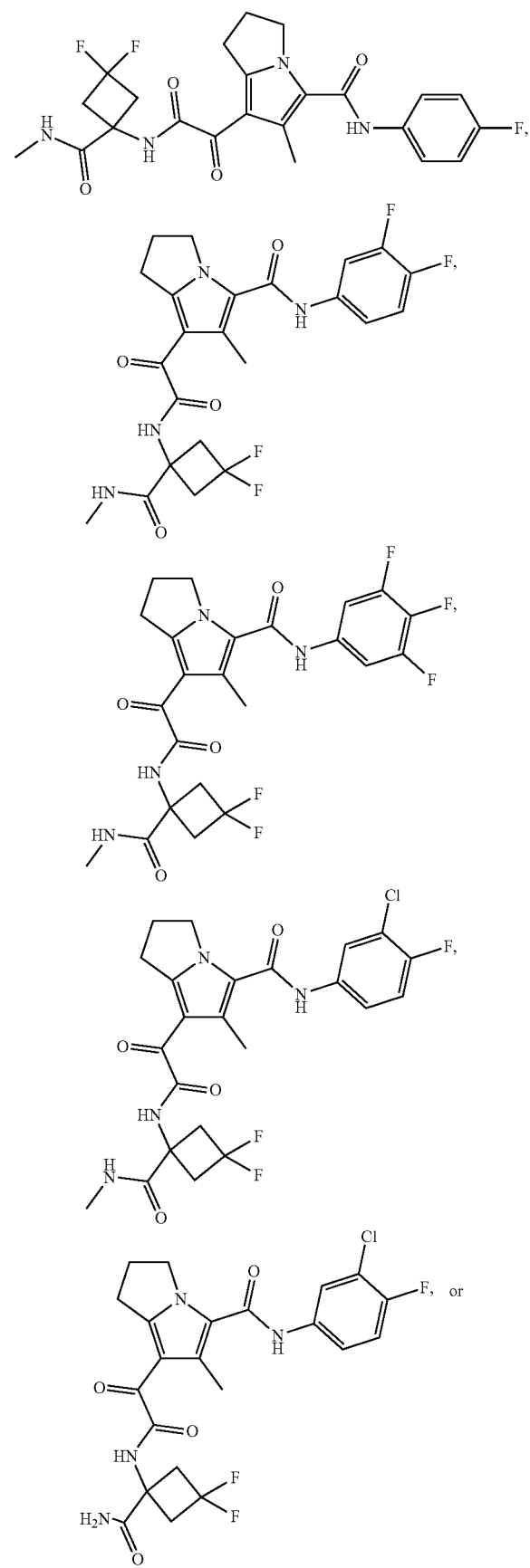

-continued

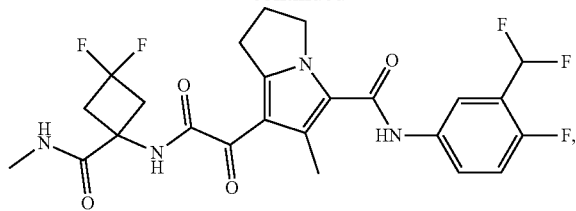 [SMILES: CNC(=O)C1(NC(=O)C(=O)c2c(C)c(C(=O)Nc3ccc(F)c(C(F)F)c3)n3c2CCC3)CC(F)(F)C1]

or a pharmaceutically acceptable salt thereof.

In certain embodiments, the compound of Formula (I), (II), or (IV), is

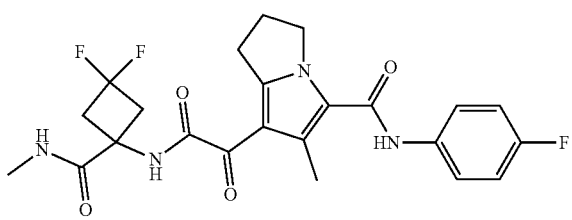 [SMILES: CNC(=O)C1(NC(=O)C(=O)c2c(C)c(C(=O)Nc3ccc(F)cc3)n3c2CCC3)CC(F)(F)C1]

or a pharmaceutically acceptable salt thereof.

In certain embodiments, the compound of Formula (I), (II), or (IV), is

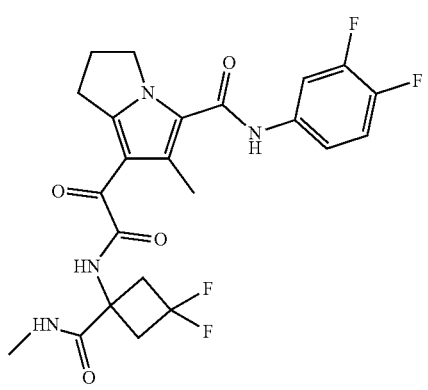 [SMILES: CNC(=O)C1(NC(=O)C(=O)c2c(C)c(C(=O)Nc3ccc(F)c(F)c3)n3c2CCC3)CC(F)(F)C1]

or a pharmaceutically acceptable salt thereof.

In certain embodiments, the compound of Formula (I), (II), or (IV), is

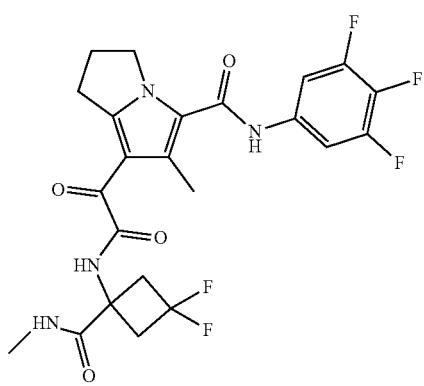 [SMILES: CNC(=O)C1(NC(=O)C(=O)c2c(C)c(C(=O)Nc3cc(F)c(F)c(F)c3)n3c2CCC3)CC(F)(F)C1]

or a pharmaceutically acceptable salt thereof.

In certain embodiments, the compound of Formula (I), (II), or (IV), is

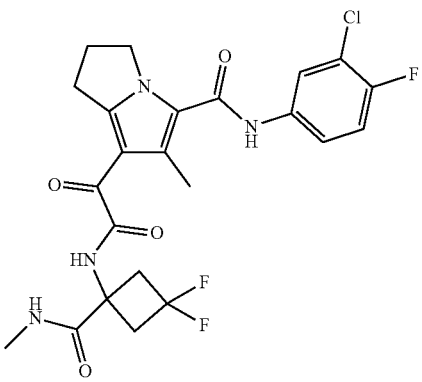 [SMILES: CNC(=O)C1(NC(=O)C(=O)c2c(C)c(C(=O)Nc3ccc(F)c(Cl)c3)n3c2CCC3)CC(F)(F)C1]

or a pharmaceutically acceptable salt thereof.

In certain embodiments, the compound of Formula (I), (II), or (IV), is

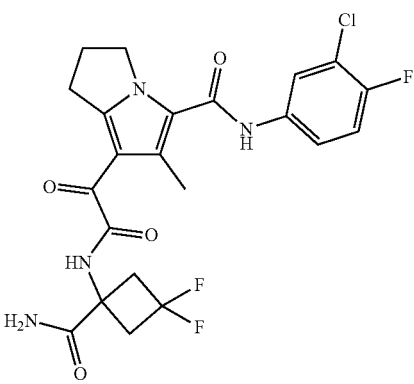 [SMILES: Cc1c(C(=O)C(=O)NC2(C(N)=O)CC(F)(F)C2)c2n(c1C(=O)Nc1ccc(F)c(Cl)c1)CCC2]

or a pharmaceutically acceptable salt thereof.

In certain embodiments, the compound of Formula (I), (II), or (IV), is

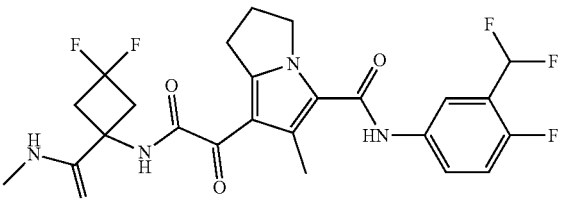

or a pharmaceutically acceptable salt thereof.

It is understood that each of the variables (e.g. $R^1$, $R^2$, $R^3$, $R^4$) may be combined with any other variables for Formula (I), (II), (III), (IIIa) or (IV) (e.g. $R^1$, $R^2$, $R^3$, $R^4$). That is, any of the values for $R^1$ may be combined with any other values for $R^2$, $R^3$, $R^4$, etc., described herein.

III. COMPOSITIONS

In certain embodiments, the present disclosure provides a pharmaceutical composition comprising a compound of the present disclosure (e.g. a compound of Formula (I), (II), (II), (III), (IIIa), or (IV), or a pharmaceutically acceptable salt thereof, and a pharmaceutically acceptable excipient.

In certain embodiments, the pharmaceutical composition comprises one or more additional therapeutic agent, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In certain embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, 21$^{st}$ Edition, Lippincott Williams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

In certain embodiments, a composition comprising a compound of the present disclosure (e.g. a compound of Formula (I), (II), (II), (III), (IIIa), or (IV)), or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

IV. METHODS

In certain embodiments, the present disclosure provides methods for treating a HBV infection, comprising administering to an individual (e.g. a human) infected with hepatitis B virus a therapeutically effective amount a compound of the present disclosure or a pharmaceutically acceptable salt thereof. Typically, the individual is suffering from a chronic hepatitis B infection, although it is within the scope of the present disclosure to treat people who are acutely infected with HBV.

In certain embodiments, a method of inhibiting HBV replication is provided, comprising administering a compound of the present disclosure, or a pharmaceutically acceptable salt thereof, to an individual (e.g. a human).

In certain embodiments, the present disclosure provides a method for reducing the viral load associated with HBV infection infection, wherein the method comprises administering to an individual (e.g. a human) infected with HBV a therapeutically effective amount of a compound of the present disclosure, or a pharmaceutically acceptable salt thereof, wherein the therapeutically effective amount is sufficient to reduce the HBV viral load in the individual.

As described more fully herein, compounds of the present disclosure can be administered with one or more additional therapeutic agent(s) to an individual (e.g. a human) infected with HBV. The additional therapeutic agent(s) can be administered to the infected individual (e.g. a human) at the same time as a compound of the present disclosure or before or after administration of a compound of the present disclosure.

In certain embodiments, a compound of the present disclosure, or a pharmaceutically acceptable salt thereof, for use in treating or preventing a HBV infection is provided. In certain embodiments, a compound of the present disclosure (e.g. a compound of Formula (I)), or a pharmaceutically acceptable salt thereof, for the manufacture of a medicament for treating or preventing a HBV infection is provided. In certain embodiments, a compound of the present As described more fully herein, compounds of the present disclosure can be administered with one or more additional therapeutic agent(s) to an individual (e.g. a human) infected with HBV. Further, in certain embodiments, when used to treat or prevent HBV, a compound of the present disclosure may be administered with one or more (e.g. one, two, three, four or more) additional therapeutic agent(s) selected from the group consisting of HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

V. ADMINISTRATION

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure, may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In certain embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month.

Other therapeutically effective amounts of the compound of the present disclosure are about 20, 25, 30, 35, 40, 45, 50, 55, 60, 65, 70, 75, 80, 85, 90, 95, or about 100 mg per dose.

The frequency of dosage of the compound of the present disclosure are will be determined by the needs of the individual patient and can be, for example, once per day or twice, or more times, per day. Administration of the compound continues for as long as necessary to treat the HBV infection. For example, a compound can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In certain embodiments, when a compound of the present disclosure is combined with one or more additional therapeutic agents as described herein, the components of the composition are administered as a simultaneous or sequential regimen. When administered sequentially, the combination may be administered in two or more administrations.

In certain embodiments, a compound of the present disclosure is combined with one or more additional therapeutic agents in a unitary dosage form for simultaneous administration to a patient, for example as a solid dosage form for oral administration.

In certain embodiments, a compound of the present disclosure is co-administered with one or more additional therapeutic agents.

VI. COMBINATION THERAPY

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments a compound of Formula (I) is formulated as a tablet, which may optionally contain one or more other compounds useful for treating HBV. In certain embodiments, the tablet can contain another active ingredient for treating HBV.

In certain embodiments, such tablets are suitable for once daily dosing.

In the above embodiments, the additional therapeutic agent may be an anti-HBV agent. For example, the additional therapeutic agent may be selected from the group consisting of HBV combination drugs, other drugs for treating HBV, 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, gene modifiers or editors such as CRISPR (including CRISPR Cas9) zinc finger nucleases or synthetic nucleases (TALENs), and combinations thereof.

In certain embodiments, a compound of the present disclosure is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR9 gene stimulator, toll-like receptor (TLR) modulators, Viral ribonucleotide reductase inhibitors, and combinations thereof.

In certain embodiments, a compound of the present disclosure, or a pharmaceutically acceptable salt thereof, is combined with one, two, three, four or more additional therapeutic agents selected from HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, CCC-0975, elvucitabine, ezetimibe, cyclosporin A, gentiopicrin (gentiopicroside), JNJ-56136379, nitazoxanide, birinapant, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682 (Roche), US 2016/0122344 (Roche), WO2015173164, and WO2016023877.

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPER-VAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Interferon Alpha Receptor Ligands

Examples of interferon alpha receptor ligands include interferon alpha-2b (INTRON A©), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1(HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP- 9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRX, IONIS-HBVRX, IONIS-GSK6-LRX, GSK-3389404.

Short Interfering RNAs (siRNA) and ddRNAi.

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience)

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include AT-130, GLS4, NVR-1221, NVR-3778, BAY 41-4109, morphothiadine mesilate, JNJ-379, and DVR-23. Capsid assembly inhibitors such as AB-423.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche).

Retinoic Acid-inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics), US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), and GSK-2879552, RG-6016, ORY-2001.

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

HBV Combination Therapy

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents and a pharmaceutically acceptable excipient are provided.

HBV DNA Polymerase Inhibitor Combination Therapy

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Ax1, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, IDO inhibitors, and hepatitis B virus replication inhibitors.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs©, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs©, DUOBODIES®, BITES©, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

HBV Drug Combination Therapy

In a particular embodiment, a compound disclosed herein, or a pharmaceutically acceptable salt thereof, is combined with an additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®).

In a particular embodiment, a compound disclosed herein, or a pharmaceutically acceptable salt thereof, is combined with one or more additional therapeutic agents, wherein the one or more additional therapeutic agents is selected from tenofovir alafenamide, tenofovir alafenamide fumarate, or tenofovir alafenamide hemifumarate.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Ax1, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, and hepatitis B virus replication inhibitors.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPIVIR-HBV®) and at least a second additional therapeutic agent selected from the group consisting of peginterferon alfa-2b (PEG-INTRON®), MULTIFERON®, interferon alpha 1b (HAPGEN®), interferon alpha-2b (INTRON A®), pegylated interferon alpha-2a (PEGASYS®), interferon alfa-n1 (HUMOFERON®), ribavirin, interferon beta-1a (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (Bio-Generic Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors, and stimulators of NOD2.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs©, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs©, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In certain embodiments, a compound as disclosed herein (e.g., any compound of Formula I) may be combined with one or more (e.g., one, two, three, four, one or two, one to three, or one to four) additional therapeutic agents in any dosage amount of the compound of Formula I (e.g., from 10 mg to 1000 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

VII. KITS

The present disclosure provides a kit comprising a compound of the present disclosure or a pharmaceutically acceptable salt thereof. The kit may further comprise instructions for use, e.g., for use in treating a HBV infection. The instructions for use are generally written instructions, although electronic storage media (e.g., magnetic diskette or optical disk) containing instructions are also acceptable.

The present disclosure also provides a pharmaceutical kit comprising one or more containers comprising a compound of the present disclosure or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also provided are articles of manufacture comprising a unit dosage of a compound of the present disclosure or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

VIII. COMPOUND PREPARATION

The embodiments are also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, 7$^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

The methods of the present invention generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in schemes below, and the particular examples that follow.

General Synthetic Schemes

Schemes 1-2 are provided as further embodiments of the invention and illustrate general methods which were used to prepare certain compounds of the present disclosure and which can be used to prepare additional compounds of the present disclosure. Each of the variables (e.g. $R^1, R^2, R^3, R^4$) can have the values as disclosed herein.

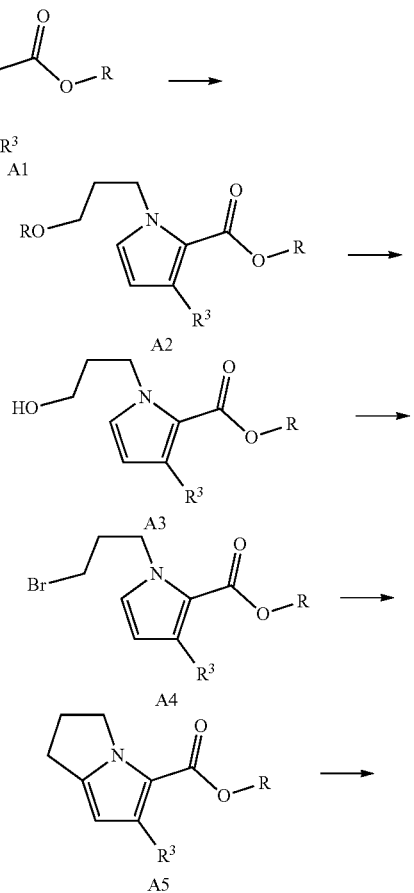

Scheme 1

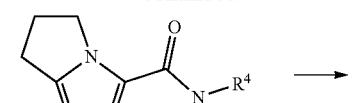

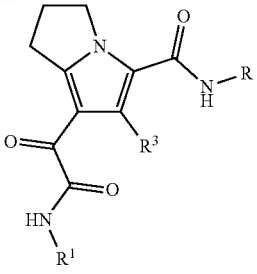

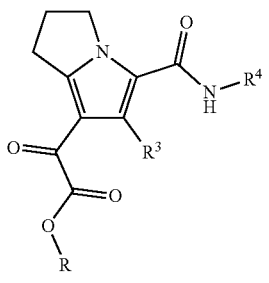

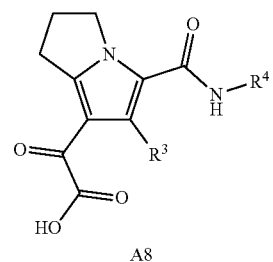

A1 can be converted to A2 by treatment with an appropriate alkyl halide such as (3-bromopropoxy)(tert-butyl)diphenylsilane in the presence of a suitable catalyst such as palladium dichloride bis(acetonitrile. A2 can be converted to A3 through a deprotection with a suitable reagent such as tetrabutylammonium fluoride and further halogenated to A4 with a suitable reagents such as carbon tetrabromide and triphenylphosphine. Cyclization to A5 can be effected with an appropriate radical initiator such as 2,2'-azobis(2-methylpropionitrile) in the presence other reagents such as tributyl tin hydride. Ester hydrolysis with a suitable reagent such as lithium hydroxide followed by amide formation via treatment with an appropriate coupling reagent such as HATU and the appropriate aniline or by conversion to the acid chloride with a reagent such a thionyl chloride or oxalyl chloride followed by treatment with the appropriate aniline gives A6. The aniline may be varied based on the R$^4$ groups disclosed herein. Formation of A7 can be effected by treatment with a suitable reagent such as oxalyl chloride or ethyl 2-chloro-2-oxoacetate and may or may not require the addition of catalyst such as aluminum chloride. Hydrolysis to A8 via a suitable reagent such as lithium hydroxide is followed by preparation of A9 by the coupling of the appropriate amine such as 1,1,1-trifluoropropan-2-amine in the presence of a coupling reagent such as HATU. The amine may be varied for particular R$^1$ groups disclosed herein.

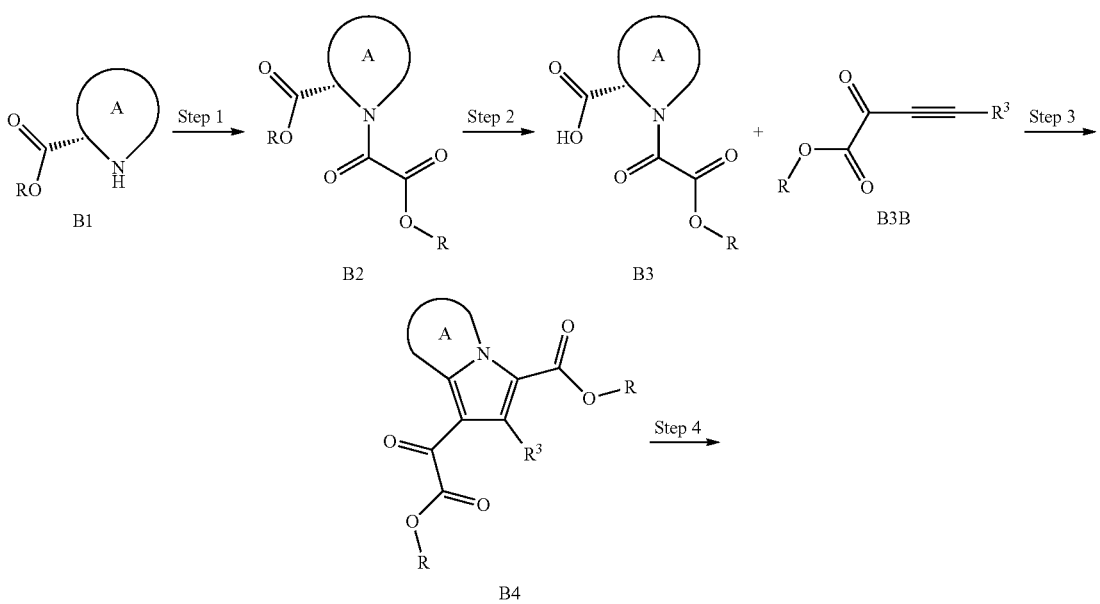

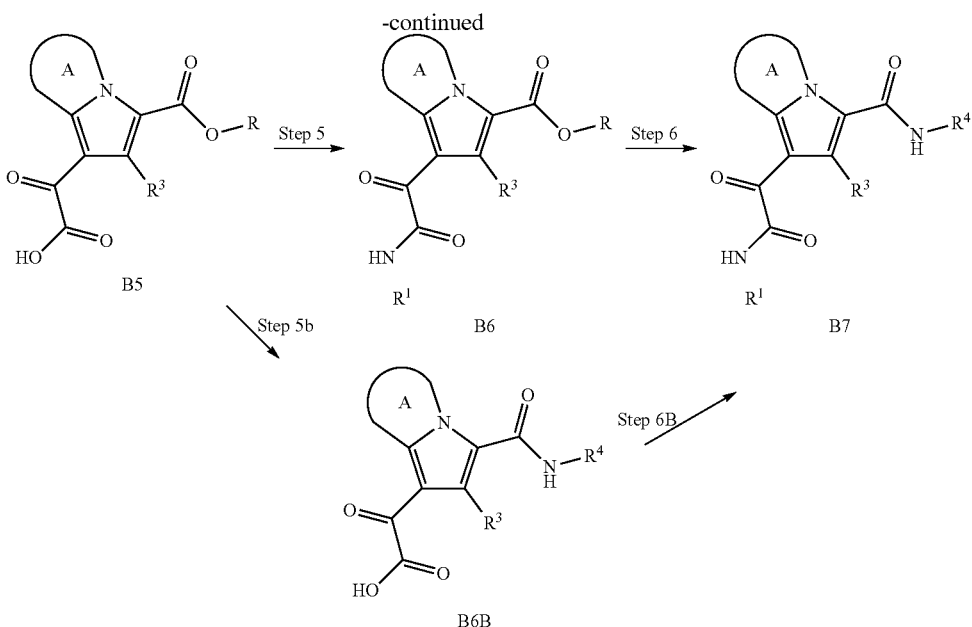

B1 can be converted to B2 by treatment with methyl 2-chloro-2-oxoacetate. Conversion to B3 can be carried out with an appropriate hydroxide reagent such as lithium hydroxide or in some cases with hydrogen gas and a suitable catalyst if the ester is a benzyl ester. B3 can be converted to B4 by treatment with a suitable reagent such as N,N'-diisopropylcarbodiimide and alkyne reagent B3B at elevated temperatures. Alternatively, B3 can be treated with oxalyl chloride, worked up and treated with B3B and a suitable base such as 2,6-di-tert-butylpyridine to give B4. Hydrolysis to B5 can be effected with a suitable reagent such as lithium hydroxide. Conversion to B6 occurs by addition of an appropriate amine (e.g. $R^1$—$NH_2$) and an amide coupling reagent such as HATU. B6 can be converted to desired B7 by treatment with a suitable reagent such as lithium hydroxide at elevated temperatures followed a second amide coupling with an appropriate aniline or heteroaryl amine (e.g $R^4$—NH2) and a coupling reagent such as HATU. Alternatively, B5 can be treated with an aniline or heteroaryl amine in the presence of a reagent such as Lithium bis(trimethylsilyl)amide to give B6B followed by treatment with an appropriate amine and a coupling reagent such as HATU to give desired B7.

REPRESENTATIVE EXAMPLES

Example 1: 7-(2-(tert-Butylamino)-2-oxoacetyl)-6-chloro-N-(3-cyano-4-fluorophenyl)-2,3-dihydro-1H-pyrrolizine-5-carboxamide (1)

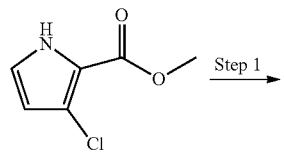

methyl 3-chloro-1H-pyrrole-2-carboxylate

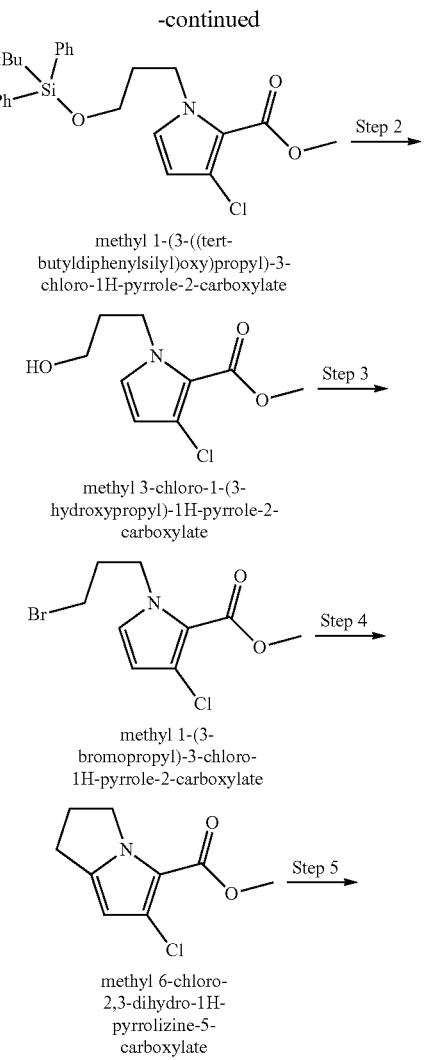

methyl 1-(3-((tert-butyldiphenylsilyl)oxy)propyl)-3-chloro-1H-pyrrole-2-carboxylate methyl 3-chloro-1-(3-hydroxypropyl)-1H-pyrrole-2-carboxylate methyl 1-(3-bromopropyl)-3-chloro-1H-pyrrole-2-carboxylate methyl 6-chloro-2,3-dihydro-1H-pyrrolizine-5-carboxylate

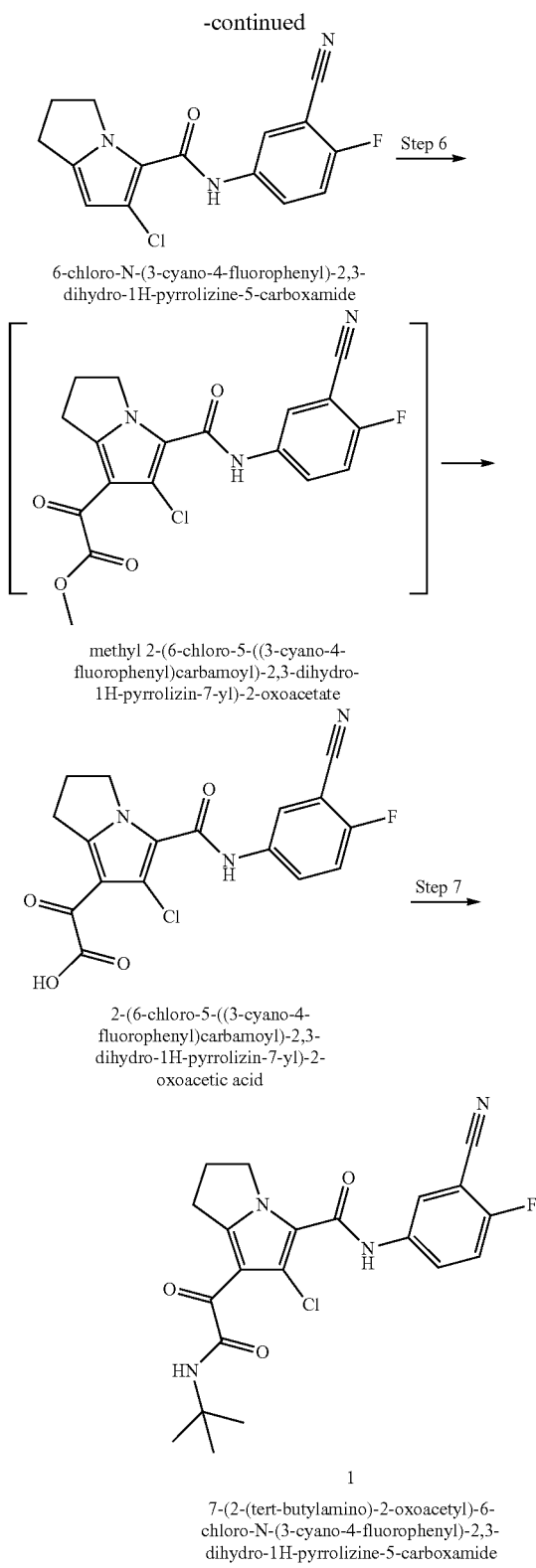

dimethylacetamide (2 mL) was heated at 90° C. for 24 h. Ethyl acetate (100 mL) was added and filtered. The filtrate was washed with water, brine and dried over sodium sulfate. Solvent was removed and the residue was purified by column (0-80% Ethyl acetate in hexane) to give methyl 1-(3-((tert-butyldiphenylsilyl)oxy)propyl)-3-chloro-1H-pyrrole-2-carboxylate.

Step 2 To a solution of methyl 1-(3-((tert-butyldiphenylsilyl)oxy)propyl)-3-chloro-1H-pyrrole-2-carboxylate (0.72 g, 1.60 mmol) in tetrahydrofuran (10 mL) was added portion-wise tetra-n-butylammonium fluoride (1 M in tetrahydrofuran, 1.6 mL, 1.6 mmol) until completion of desilylation as judged by LC/MS. Solvent was removed and the residue was purified by silica gel chromatography (0-80% ethyl acetate in hexanes) to give methyl 3-chloro-1-(3-hydroxypropyl)-1H-pyrrole-2-carboxylate: $^1$H NMR (400 MHz, Chloroform-d) δ 6.80 (d, J=2.8 Hz, 1H), 6.17 (d, J=2.8 Hz, 1H), 4.42 (t, J=6.6 Hz, 2H), 3.88 (s, 3H), 3.61-3.49 (m, 2H), 2.02-1.92 (m, 2H).

Step 3 To a solution of methyl 3-chloro-1-(3-hydroxypropyl)-1H-pyrrole-2-carboxylate (0.3 g, 1.4 mmol) and carbon tetrabromide (0.59 g, 1.79 mmol) in dichloromethane (5 mL) was added triphenylphosphine (0.54 g, 2 mmol) portionwise and the mixture was stirred at ambient temperature for 30 min. The mixture was purified by silica gel chromatography (0-80% ethyl acetate in hexanes) to give methyl 1-(3-bromopropyl)-3-chloro-1H-pyrrole-2-carboxylate: $^1$H NMR (400 MHz, Chloroform-d) δ 6.85 (d, J=2.8 Hz, 1H), 6.16 (d, J=2.8 Hz, 1H), 4.44 (t, J=6.4 Hz, 2H), 3.87 (s, 3H), 3.30 (dd, J=6.4, 5.8 Hz, 2H), 2.33-2.20 (m, 2H).

Step 4 To mixture of methyl 1-(3-bromopropyl)-3-chloro-1H-pyrrole-2-carboxylate (0.175 g, 0.624 mmol), sodium cyanoborohydride (0.059 g, 0.94 mmol) in t-butanol (5 mL) were added tri-n-butyltinhydride (0.02 g, 0.06 mmol) and 2,2'-azobis(2-methylpropionitrile) (0.051 g, 0.31 mmol) and the mixture was stirred at reflux for 7 h. sodium cyanoborohydride and 2,2'-azobis(2-methylpropionitrile) were added independently over hour until HPLC indicated no starting material remained. Ethyl acetate (150 mL) was added and the solution was washed with brine, dried over sodium sulfate. Solvent was removed and the residue was purified by silica gel chromatography (0-80% ethyl acetate in hexanes) to give methyl 6-chloro-2,3-dihydro-1H-pyrrolizine-5-carboxylate: $^1$H NMR (400 MHz, Chloroform-d) δ 5.92 (t, J=0.8 Hz, 1H), 4.31-4.20 (m, 2H), 3.85 (s, 3H), 2.84 (t, J=7.5 Hz, 2H), 2.44 (ddd, J=14.7, 8.0, 6.9 Hz, 2H).

Step 5 To a solution of methyl 6-chloro-2,3-dihydro-1H-pyrrolizine-5-carboxylate (0.030 g, 0.18 mmol) in THF (2 mL), methanol (2 mL), and water (2 mL) added lithium hydroxide hydrate (0.076 g, 1.8 mmol) as solid and the solution was heated at 60° C. for 4 h then ambient temperature overnight. Organic solvent was removed by evaporation and ethyl acetate (50 mL) was added. The mixture was acidified by addition of 1N HCl to pH=1. The organic layer was separated and dried over sodium sulfate. Solvent was removed to give 6-chloro-2,3-dihydro-1H-pyrrolizine-5-carboxylic acid which was used without purification.

To a mixture of 6-chloro-2,3-dihydro-1H-pyrrolizine-5-carboxylic acid (0.015 g, 0.081 mmol) in dichloromethane (5 mL) was added thionyl chloride (0.2 mL) and the solution was heated at 70° C. for 3 h then 80° C. for 2 h. Solvent was removed and the residue was co-evaporated with toluene twice. The residue was dissolved in dichloromethane (5 mL). To the solution was added triethylamine (3 eq) at 0° C. followed by addition of aniline and 4-N,N-dimethylaminopyridine (20 mg). The solution was stirred at ambient temperature for 4 h. Ethyl acetate (100 mL) was added and Step 1 A reaction tube with stirrer was charged with methyl 3-chloro-1H-pyrrole-2-carboxylate (0.32 g, 2.0 mmol), norbornene (0.38 g, 4.0 mmol), potassium bicarbonate (0.60 g, 6.0 mmol), palladium(II) dichloride bis(acetonitrile) (0.052 g, 0.2 mmol) and (3-bromopropoxy)(tert-butyl)diphenylsilane (1.51 g, 4 mmol) in anhydrous the solution was washed with water, brine and dried over sodium sulfate. Solvent was removed and the residue was purified by silica gel chromatography (0-80% ethyl acetate in hexane) to give 6-chloro-N-(3-cyano-4-fluorophenyl)-2,3-dihydro-1H-pyrrolizine-5-carboxamide: $^1$H NMR (400 MHz, Chloroform-d) β 8.58 (s, 1H), 8.05 (dd, J=5.5, 2.8 Hz, 1H), 7.71 (ddd, J=9.1, 4.6, 2.8 Hz, 1H), 7.18 (dd, J=9.1, 8.3 Hz, 1H), 5.97 (s, 1H), 4.40 (dd, J=7.9, 6.5 Hz, 2H), 2.86 (t, J=7.5 Hz, 2H), 2.48 (p, J=7.4 Hz, 2H).

Step 6 6-chloro-N-(3-cyano-4-fluorophenyl)-2,3-dihydro-1H-pyrrolizine-5-carboxamide (5 mg, 0.016 mmol) was dissolved in dichloromethane (5 mL) at 0° C. To the solution was added a solution (0.5 mL) of ethyl 2-chloro-2-oxoacetate (0.5 mL) in dichloromethane (5 mL) dropwise. To the solution was added aluminum chloride (20 mg, 0.18 mmol) at 0° C. and the mixture was stirred at 0° C. for 45 min. Ethyl acetate (150 mL) was added and the aqueous layer was extracted with ethyl acetate (10 mL). The combined organic solution was washed with brine and dried over sodium sulfate. Solvent was removed and the residue was dissolved in ethanol (5 mL). To the solution in ethyl acetate was added 2 N sodium hydroxide (0.5 mL, 1 mmol) and the solution was stirred at 0° C. for 10 min. Organic solvent was removed and the aqueous layer was mixed with ethyl acetate (50 mL). The mixture was acidified by addition of 1N hydrochloric acid to pH=1. The organic solution was washed with brine and dried over sodium sulfate. Solvent was removed to give 2-(6-chloro-5-((3-chloro-4-fluorophenyl)carbamoyl)-2,3-dihydro-1H-pyrrolizin-7-yl)-2-oxoacetic acid which was used for the next reaction without further purification.

Step 7 To a solution of 2-(6-chloro-5-((3-chloro-4-fluorophenyl)carbamoyl)-2,3-dihydro-1H-pyrrolizin-7-yl)-2-oxoacetic acid (6 mg, 0.16 mmol) in N,N-dimethylformamide (5 mL) were added t-butylamine (0.1 mL) and N,N-diisopropylethylamine (0.1 mL). To the solution was added 1-[bis(dimethylamino)methylene]-1H-1,2,3-triazolo[4,5-b]pyridinium 3-oxid hexafluorophosphate (HATU) portionwise and the solution was stirred at 0° C. for 10 min then at ambient temperature for 1 h. Solvent was concentrated to a small volume. Ethyl acetate (150 mL) was added and the solution was washed with brine twice and dried over sodium sulfate. Solvent was removed and the residue was purified by silica gel chromatography (0-80% ethyl acetate in hexanes) to give 7-(2-(tert-butylamino)-2-oxoacetyl)-6-chloro-N-(3-cyano-4-fluorophenyl)-2,3-dihydro-1H-pyrrolizine-5-carboxamide (1).

Example 2: (R)—N-(3-chloro-4-fluorophenyl)-6-methyl-7-(2-oxo-2-((1,1,1-trifluoropropan-2-yl)amino)acetyl)-2,3-dihydro-1H-pyrrolizine-5-carboxamide (2)

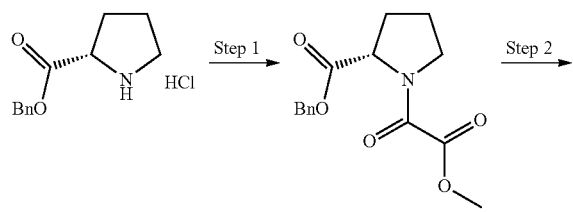

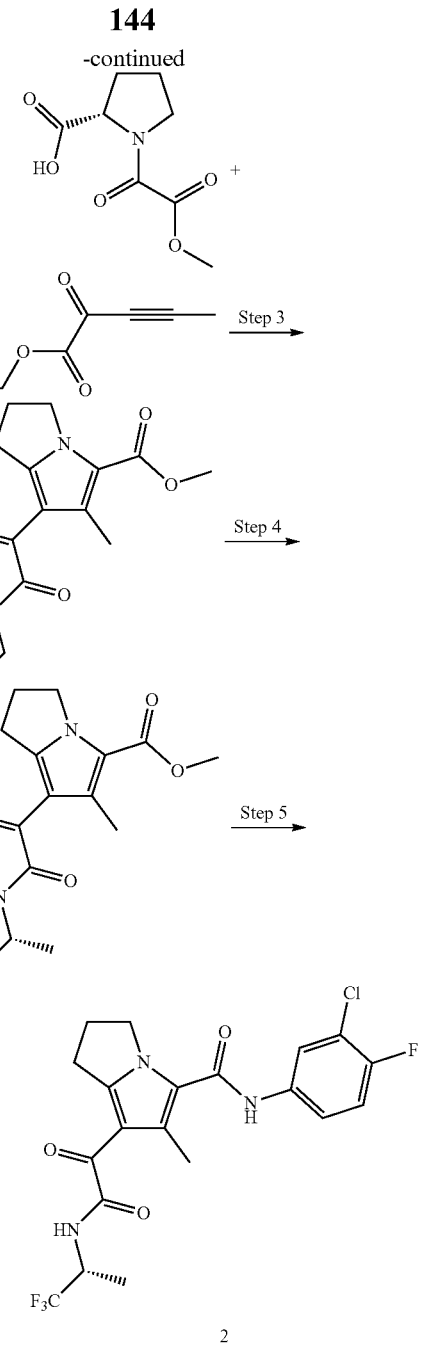

Step 1. To a solution of benzyl L-prolinate hydrochloride (8.83 g, 36.5 mmol) and N-ethyldiisopropylamine (13 mL, 75 mmol) in dichloromethane (150 mL) chilled to 0° C. was added methyl chlorooxoacetate (5.0 mL, 54 mmol) dropwise. The reaction mixture was warmed to ambient temperature and stirred for 1 h, at which point the reaction mixture was quenched by pouring into a cooled aqueous solution of saturated sodium bicarbonate. The aqueous phase was thrice extracted to dichloromethane, the combined organic phases washed with brine, dried over sodium sulfate, filtered, and solvent removed under reduced pressure to provide benzyl (2-methoxy-2-oxoacetyl)-L-prolinate which was carried forward without further purification.

Step 2. A suspension of benzyl (2-methoxy-2-oxoacetyl)-L-prolinate (10.6 g, 36.6 mmol) and 10 wt % palladium on carbon (~50% water, 2.6 g, 1.2 mmol) in ethanol (100 mL)

was stirred under one atmosphere hydrogen for 2 h. Upon completion of reaction the crude mixture was filtered through celite with ethanol rinses and concentrated under reduced pressure to provide (2-methoxy-2-oxoacetyl)-L-proline which was carried forward without further purification.

Step 3. A solution of (2-methoxy-2-oxoacetyl)-L-proline (0.64 g, 3.2 mmol), ethyl 2-oxopent-3-ynoate (475 mg, 3.4 mmol), and N,N'-diisopropylcarbodiimide (0.55 mL, 3.6 mmol) in N-Methyl-2-pyrrolidone (6 mL) was stirred at 140° C. under microwave heating for 45 minutes. The reaction mixture was then poured into a saturated aqueous solution of ammonium chloride and the aqueous phase thrice extracted to ethyl acetate. The combined organic phases were twice washed with a 5% aqueous solution of lithium chloride followed by brine, then dried over sodium sulfate, filtered, and concentrated under reduced pressure. The crude residue was purified by flash chromatography on silica gel (0-50% ethyl acetate in hexanes) to provide methyl 7-(2-ethoxy-2-oxoacetyl)-6-methyl-2,3-dihydro-1H-pyrrolizine-5-carboxylate: $^1$H NMR (400 MHz, Chloroform-d) δ 4.30 (q, J=7.1 Hz, 2H), 4.26-4.18 (m, 2H), 3.79 (s, 3H), 2.92 (t, J=7.6 Hz, 2H), 2.52 (s, 3H), 2.44 (p, J=7.6 Hz, 2H), 1.33 (t, J=7.1 Hz, 3H).

Step 4. To a 0° C. chilled solution of 7-(2-ethoxy-2-oxoacetyl)-6-methyl-2,3-dihydro-1H-pyrrolizine-5-carboxylate (193 mg, 0.69 mmol) in ethanol (2 mL) was added a 4M aqueous solution of sodium hydroxide (0.2 mL, 0.8 mmol). The reaction mixture was stirred at 0° C. for 5 minutes and neutralized by the addition of dilute aqueous hydrogen chloride. The aqueous phase was thrice extracted to ethyl acetate, dried over sodium sulfate, filtered, and concentrated under reduced pressure. One half of the solid obtained was dissolved in N-Methyl-2-pyrrolidone (2 mL) and treated with 1-[Bis(dimethylamino)methylene]-1H-1,2,3-triazolo[4,5-b]pyridinium 3-oxid hexafluorophosphate (160 mg, 0.42 mmol), R-trifluoroisopropylamine (0.04 mL, 0.4 mmol), and N-ethyldiisopropylamine (0.17 mL, 0.98 mmol) and stirred at ambient temperature for 15 minutes. The reaction mixture was diluted with ethyl acetate and washed sequentially with a 5% aqueous solution of lithium chloride, a 5% aqueous solution of sodium bicarbonate, and brine. The organic phase was then dried over sodium sulfate, filtered, concentrated under reduced pressure, and purified by flash chromatography on silica gel (0-20% ethyl acetate in hexanes) to provide methyl (R)-6-methyl-7-(2-oxo-2-((1,1,1-trifluoropropan-2-yl)amino)acetyl)-2,3-dihydro-1H-pyrrolizine-5-carboxylate: $^1$H NMR (400 MHz, Chloroform-d) δ 7.06 (d, J=9.8 Hz, 1H), 4.74-4.59 (m, 1H), 4.30 (t, J=7.4 Hz, 2H), 3.85 (s, 3H), 3.26 (dt, J=16.6, 7.9 Hz, 1H), 3.20-3.08 (m, 1H), 2.60 (s, 3H), 2.46 (qd, J=7.8, 7.3, 3.0 Hz, 2H), 1.41 (d, J=7.0 Hz, 3H)

Step 5. A solution of methyl (R)-6-methyl-7-(2-oxo-2-((1,1,1-trifluoropropan-2-yl)amino)acetyl)-2,3-dihydro-1H-pyrrolizine-5-carboxylate (58 mg, 0.17 mmol) in ethanol (2 mL) was treated with a 4M aqueous solution of sodium hydroxide (0.4 mL, 1.6 mmol) and heated to 60° C. for 2 h then neutralized by the addition of dilute aqueous hydrogen chloride. The aqueous phase was thrice extracted to ethyl acetate, dried over sodium sulfate, filtered, and concentrated under reduced pressure. The solid obtained was dissolved in N-Methyl-2-pyrrolidone (1 mL) and treated with 1-[Bis(dimethylamino)methylene]-1H-1,2,3-triazolo[4,5-b]pyridinium 3-oxid hexafluorophosphate (88 mg, 0.23 mmol), 4-fluoro-3-chloroaniline (67 mg, 0.46 mmol), and N-ethyldiisopropylamine (0.08 mL, 0.43 mmol) and stirred at 80° C. for 2 h. The crude reaction mixture was passed through a syringe filtered and purified by preparative hplc (10-100% acetonitrile in water, 0.1% TFA buffer) to provide (R)—N-(3-chloro-4-fluorophenyl)-6-methyl-7-(2-oxo-2-((1,1,1-trifluoropropan-2-yl)amino)acetyl)-2,3-dihydro-1H-pyrrolizine-5-carboxamide (2).

Synthesis of ethyl 2-oxopent-3-ynoate

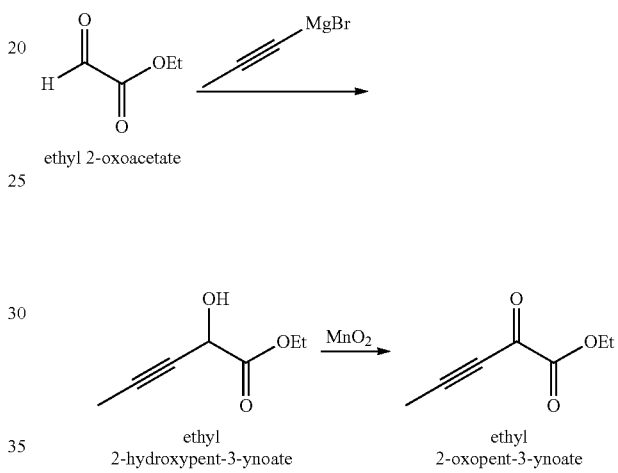

ethyl 2-oxoacetate ethyl 2-hydroxypent-3-ynoate ethyl 2-oxopent-3-ynoate

Step 1. To a solution of ethyl glyoxylate (200 g, 1.96 mol, 1.0 eq) in toluene (1 L) at −40° C. was added a solution of propynylmagnesium bromide (0.5 M in tetrahydrofuran, 4.28 L, 2.14 mol, 1.1 eq) dropwise. The reaction mixture was stirred at −40° C. for 1.5 h, and slowly warmed to 0° C. over 1 h. The reaction was monitored by TLC, quenched by addition of saturated aqueous ammonium chloride solution (1 L). The aqueous layer was extracted with ethyl acetate (2×1 L). The combined organic phases were washed with brine, dried over sodium sulfate, filtered, concentrated under reduced pressure. The residue was purified with flash chromatography on silica (dichloromethane) to afford ethyl 2-hydroxypent-3-ynoate: 1H NMR (400 MHz, CDCl3): δ 4.77 (q, J=2.4 Hz, 1H), 4.35-4.24 (m, 2H), 1.85 (d, J=2.4 Hz, 3H), 1.32 (t, J=7.1 Hz, 3H).

Step 2. To a solution of ethyl 2-hydroxypent-3-ynoate (90.0 g, 634 mmol, 1.0 eq) in dichloromethane (250 mL) was added manganese dioxide (220 g, 2.53 mol, 4.0 eq) was stirred for 5 h at ambient temperature. The reaction mixture was filtered through a pad of Celite, and washed with dichloromethane, and concentrated under reduced pressure (careful to avoid loss of material due to product volatility). The residue was purified with flash chromatography on silica gel (dichloromethane) to afford ethyl 2-oxopent-3-ynoate: 1H NMR (300 MHz, CDCl3): δ 4.35 (q, J=7.1 Hz, 2H), 2.15 (s, 3H), 1.38 (t, J=7.1 Hz, 3H).

Example 3. N-(3-chloro-4-fluorophenyl)-7-(2-((3,3-difluoro-1-(methylcarbamoyl)cyclobutyl)amino)-2-oxoacetyl)-6-methyl-2,3-dihydro-1H-pyrrolizine-5-carboxamide (3)

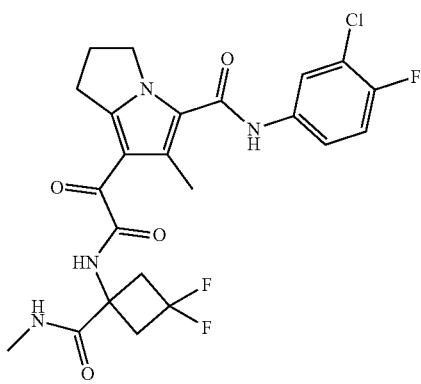

N-(3-chloro-4-fluorophenyl)-7-(2-((3,3-difluoro-1-(methylcarbamoyl)cyclobutyl)amino)-2-oxoacetyl)-6-methyl-2,3-dihydro-1H-pyrrolizine-5-carboxamide (3) was synthesized in a manner similar to Example 2 using 1-amino-3,3-difluoro-N-methylcyclobutane-1-carboxamide hydrochloride in place of R-trifluoroisopropylamine.

Synthesis of 1-amino-3,3-difluoro-N-methylcyclobutane-1-carboxamide hydrochloride

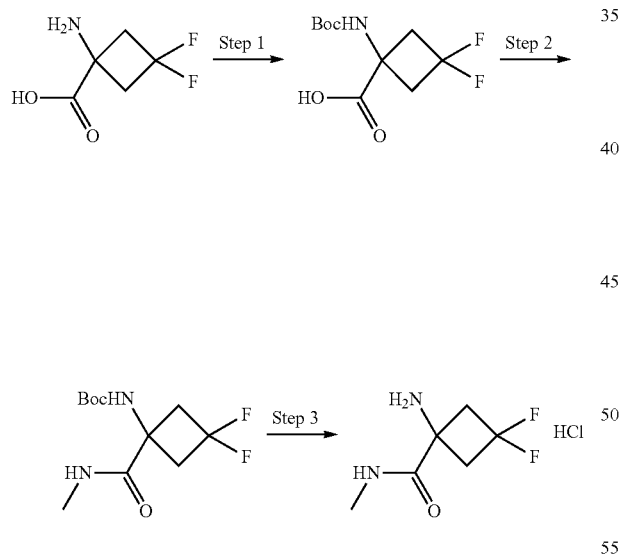

Step 1. To a 0° C. solution of 1-amino-3,3-difluorocyclobutane-1-carboxylic acid (990 mg, 6.55 mmol) in methanol (8 mL) was added a 1M aqueous solution of sodium hydroxide (7 mL, 7 mmol) followed by di-tert-butyl dicarbonate (1.8 g, 8.2 g). The reaction mixture was warmed to ambient temperature was stirred for 14 h, acidified with dilute aqueous hydrogen chloride, and extracted to diethyl ether. The ethereal phase was washed with 1:1 water:brine, dried over sodium sulfate, filtered, and concentrated under reduced pressure to afford 1-((tert-butoxycarbonyl)amino)-3,3-difluorocyclobutane-1-carboxylic acid which was carried forward without further purification.

Step 2. To a 0° C. solution of 1-((tert-butoxycarbonyl)amino)-3,3-difluorocyclobutane-1-carboxylic acid (1.65 g, 6.6 mmol), methanamine hydrochloride (2.28 g, 33.8 mmol), and triethylamine (7.4 mL, 53 mmol) in N,N-dimethylformamide (24 mL) was added 1-[Bis(dimethylamino)methylene]-1H-1,2,3-triazolo[4,5-b]pyridinium 3-oxid hexafluorophosphate (3.75 g, 9.86 mmol). The reaction was warmed to ambient temperature and stirred for 20 h, at which point the reaction mixture was diluted with diethyl ether, washed with a saturate aqueous solution of sodium bicarbonate, a 5% aqueous solution of lithium chloride, and brine. The ethereal phase was then dried over sodium sulfate, filtered, and concentrated under reduced pressure to afford tert-butyl (3,3-difluoro-1-(methylcarbamoyl)cyclobutyl)carbamate which was carried forward without further purification.

Step 3. Tert-butyl (3,3-difluoro-1-(methylcarbamoyl)cyclobutyl)carbamate (1.3 g, 4.92 mmol) was dissolved in a 4M solution of hydrogen chloride in dioxane (20 mL, 80 mmol) and stirred at 90° C. for 90 minutes. Solvent was removed under reduced pressure, twice azeotroping with toluene, and the resultant material dried under high vacuum to afford 1-amino-3,3-difluoro-N-methylcyclobutane-1-carboxamide hydrochloride: $^1$H NMR (400 MHz, DMSO-d6) δ 8.86 (s, 3H), 8.44 (s, 1H), 3.27 (dd, J=13.3, 7.5 Hz, 2H), 3.05 (q, J=14.3 Hz, 2H), 2.69 (d, J=4.5 Hz, 3H).

Example 4 (1aS,6aS)-N-(3-chloro-4-fluorophenyl)-5-(2-((3,3-difluoro-1 (methylcarbamoyl)cyclobutyl)amino)-2-oxoacetyl)-4-methyl-1,1a,6,6a-tetrahydrocyclopropa[b]pyrrolizine-3-carboxamide (4)

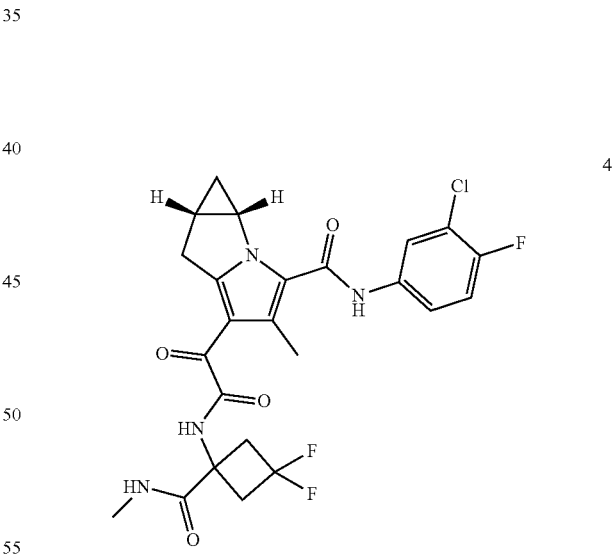

(1aS,6aS)-N-(3-chloro-4-fluorophenyl)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxamide (4) was synthesized in a manner similar to Example 3 using benzyl (1S,3S,5S)-2-azabicyclo[3.1.0]hexane-3-carboxylate in place of benzyl L-prolinate hydrochloride.

149

Example 5 (1aR,6aR)-N-(3-chloro-4-fluorophenyl)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxamide (5)

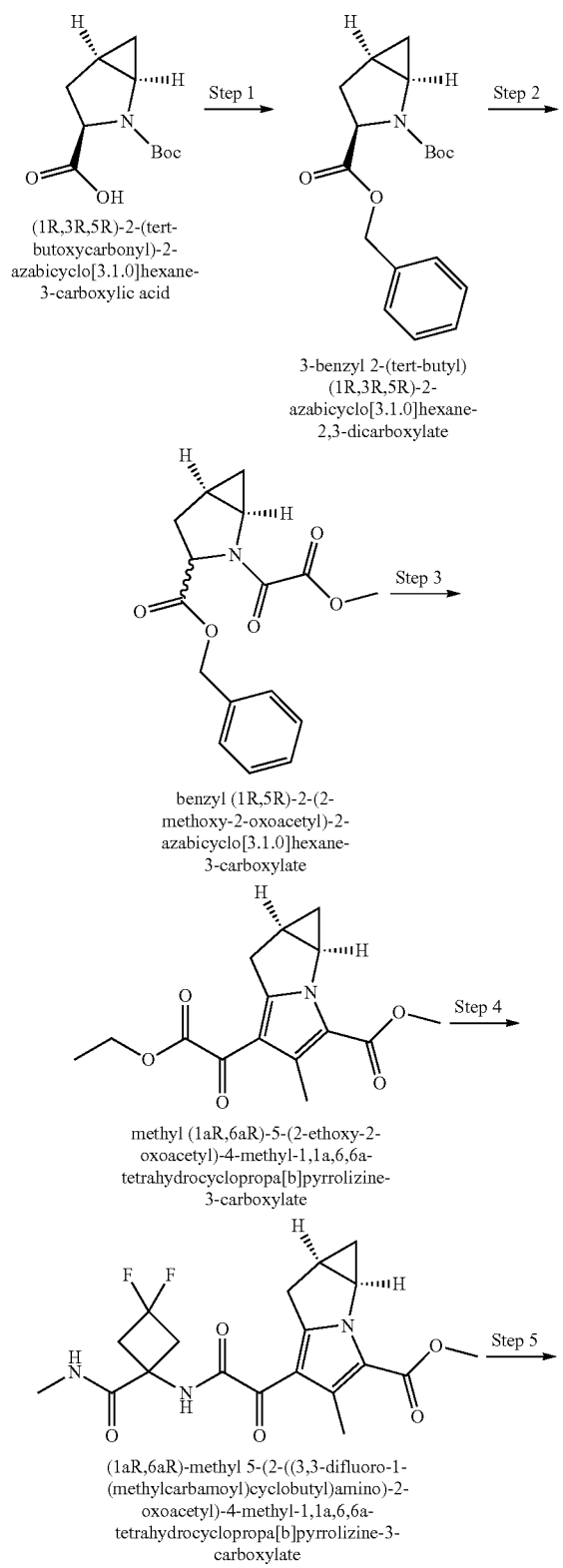

150

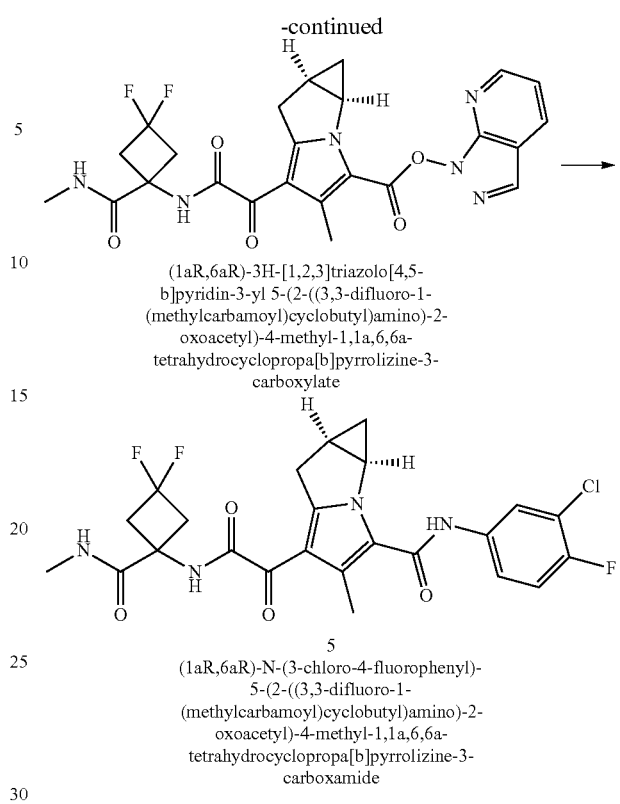

(1aR,6aR)-3H-[1,2,3]triazolo[4,5-b]pyridin-3-yl 5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylate 5
(1aR,6aR)-N-(3-chloro-4-fluorophenyl)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxamide Step 1. A suspension of (1R,3R,5R)-2-(tert-butoxycarbonyl)-2-azabicyclo[3.1.0]hexane-3-carboxylic acid (500 mg, 2.20 mmol), 4-(dimethylamino)pyridine (592 mg, 4.85 mmol), and N,N'-dicyclohexylcarbodiimide (918 mg, 4.45 mmol) in dichloromethane (7 mL) was stirred at ambient temperature as benzyl alcohol (0.27 mL, 2.61 mmol) was added. The resulting mixture was stirred at ambient temperature overnight. The reaction mixture was diluted with diethyl ether (30 mL), and stirred at ambient temperature for 30 min before filtering off the solids. After the filtrate was concentrated, the residue was dissolved in diethyl ether again and filtered off the insoluble solids. (repeated 4 times) The residue was purified by silica gel column chromatography eluting 0-25% ethyl acetate in hexanes to give 3-benzyl 2-(tert-butyl) (1R,3R,5R)-2-azabicyclo[3.1.0]hexane-2,3-dicarboxylate: $^1$H NMR (400 MHz, Chloroform-d) δ 7.34 (m, 5H), 5.25-5.03 (m, 2H), 4.68 (dd, J=11.6, 3.0 Hz, 0.4H), 4.55 (dd, J=11.5, 3.3 Hz, 0.6H), 3.55 (td, J=6.3, 2.5 Hz, 0.6H), 3.46 (td, J=6.3, 2.4 Hz, 0.4H), 2.70-2.42 (m, 1H), 2.05 (q, J=2.8, 2.0 Hz, 0.6H), 2.01 (t, J=3.6 Hz, 0.4H), 1.45-1.55 (m, 1H), 1.49 (s, 3.6H), 1.34 (s, 5.4H), 0.90 (td, J=5.5, 5.1, 2.4 Hz, 0.6H), 0.87-0.80 (m, 0.4H), 0.77-0.69 (m, 0.6H), 0.65 (q, J=6.7 Hz, 0.4H): LCMS-ESI+ (m/z): [M-C$_4$H$_8$+H]$^+$ calculated for C$_{14}$H$_{16}$NO$_4$: 262.11; found: 261.81.

Step 2. A solution of 3-benzyl 2-(tert-butyl) (1R,3R,5R)-2-azabicyclo[3.1.0]hexane-2,3-dicarboxylate (564 mg, 1.78 mmol) in dichloromethane (2 mL) was stirred at ambient temperature as trifluoroacetic acid (2 mL) was added. After 1 h, the solution was concentrated and the residue was co-evaporated with toluene (×1) before drying in vacuum for 1 h to get crude benzyl (1R,3R,5R)-2-azabicyclo[3.1.0]hexane-3-carboxylate trifluoroacetic acid salt: LCMS-ESI+ (m/z): [M+H]$^+$ calculated for C$_{13}$H$_{16}$NO$_2$: 218.12; found: 218.05.

A solution of the above crude benzyl (1R,3R,5R)-2-azabicyclo[3.1.0]hexane-3-carboxylate hydrochloride and N,N-diisopropylethylamine (0.78 mL, 4.48 mmol) in dichloromethane (5 mL) was stirred at 0° C. as methyl oxalyl chloride (0.18 mL, 1.96 mmol) was added. After 30 min at 0° C., the resulting solution was washed with water. After the aqueous fraction was extracted with ethyl acetate, and the combined organic fractions were dried over magnesium sulfate. After filtration, solvent was removed and the residue was purified by silica gel column chromatography (0-85% ethyl acetate in hexanes) to give benzyl (1R,5R)-2-(2-methoxy-2-oxoacetyl)-2-azabicyclo[3.1.0]hexane-3-carboxylate: $^1$H NMR (400 MHz, Chloroform-d) δ 7.44-7.28 (m, 5H), 5.34-5.28 (m, 0.5H), 5.20-5.09 (m, 2H), 4.91 (dd, J=11.6, 3.3 Hz, 0.5H), 3.98-3.89 (m, 1H), 3.91 (s, 1.5H), 3.69 (s, 1.5H), 2.77-2.65 (m, 0.5H), 2.65-2.53 (m, 0.5H), 2.34 (dd, J=13.6, 2.6 Hz, 0.5H), 2.09 (dd, J=13.7, 3.3 Hz, 0.5H), 1.72 (dq, J=8.9, 6.0 Hz, 0.5H), 1.61 (dq, J=8.7, 5.7 Hz, 0.5H), 1.01 (ddd, J=6.4, 5.2, 2.6 Hz, 0.5H), 0.92-0.78 (m, 1H), 0.66-0.56 (m, 0.5H). LCMS-ESI+ (m/z): [M+H]$^+$ calculated for $C_{16}H_{18}NO_5$: 304.12; found: 304.01 and 304.03.

Step 3. A mixture of benzyl (1R,5R)-2-(2-methoxy-2-oxoacetyl)-2-azabicyclo[3.1.0]hexane-3-carboxylate (504 mg, 1.66 mmol) and 20% palladium hydroxide on carbon (51 mg) in ethanol (7 mL) was stirred under hydrogen atmosphere at room temperature for 45 min. The reaction mixture was filtered and the solids were washed with ethanol. The filtrate was concentrated and co-evaporated with toluene twice and dried in vacuo to give crude (1R,5R)-2-(2-methoxy-2-oxoacetyl)-2-azabicyclo[3.1.0]hexane-3-carboxylic acid: LCMS-ESI+ (m/z): [M+H]$^+$ calculated for $C_9H_{12}NO_5$: 214.07; found: 213.96.

To a solution of oxalyl chloride (2 mL, 7.11 mmol) and 1% DMF in toluene (1.8 mL) in toluene (10 mL) was added crude (1R,5R)-2-(2-methoxy-2-oxoacetyl)-2-azabicyclo[3.1.0]hexane-3-carboxylic acid (2.32 mmol) in dichloromethane (4 mL) dropwise. The resulting solution was stirred at ambient temperature for 1 h. The solution was concentrated and the residue was co-evaporated with toluene (10 mL). The resulting residue was dried in vacuo for 30 min to give crude methyl 2-((1R,5R)-3-(chlorocarbonyl)-214-azabicyclo[3.1.0]hexan-2-yl)-2-oxoacetate.

After the above crude methyl 2-((1R,5R)-3-(chlorocarbonyl)-214-azabicyclo[3.1.0]hexan-2-yl)-2-oxoacetate was dissolved in acetonitrile (4 mL), 2,6-di-tert-butylpyridine (0.57 mL, 2.54 mmol) followed by ethyl 2-oxopent-3-ynoate (0.47 mL, 3.62 mmol) were added. The resulting solution was stirred at ambient temperature for 2 h. The mixture was concentrated and the residue was purified by silica gel column chromatography eluting with 0-50% ethyl acetate in hexanes to give methyl (1aR,6aR)-5-(2-ethoxy-2-oxoacetyl)-4-methyl-1,1a,6,6a-tetrahydrocyclopropa[b]pyrrolizine-3-carboxylate: $^1$H NMR (400 MHz, Chloroform-d) δ 4.43 (tt, J=6.0, 2.0 Hz, 1H), 4.36 (q, J=7.2 Hz, 2H), 3.89 (s, 3H), 3.23 (dd, J=18.4, 6.8 Hz, 1H), 3.12-2.99 (m, 1H), 2.56 (s, 3H), 2.14-1.99 (m, 1H), 1.39 (t, J=7.2 Hz, 3H), 1.13 (dt, J=8.7, 6.1 Hz, 1H), 0.35 (ddd, J=6.5, 5.1, 2.1 Hz, 1H): LCMS-ESI+ (m/z): [M+H]$^+$ calculated for $C_{15}H_{18}NO_5$: 292.12; found: 291.97.

Step 4. A solution of methyl (1aR,6aR)-5-(2-ethoxy-2-oxoacetyl)-4-methyl-1,1a,6,6a-tetrahydrocyclopropa[b]pyrrolizine-3-carboxylate (322 mg, 1.11 mmol) was stirred in THF (3 mL), MeOH (3 mL) and water (3 mL) and 1 N LiOH (2.2 mL) was added. After 1 h at ambient temperature, the reaction mixture was diluted with water and washed with ether (×1). The aqueous fraction was acidified with 1 N HCl, and the product was extracted with ethyl acetate (×2). The combined extracts were dried with magnesium sulfate and concentrated to give 2-((1aR,6aR)-3-(methoxycarbonyl)-4-methyl-1,1a,6,6a-tetrahydrocyclopropa[b]pyrrolizin-5-yl)-2-oxoacetic acid.

A solution of 2-((1aR,6aR)-3-(methoxycarbonyl)-4-methyl-1,1a,6,6a-tetrahydrocyclopropa[b]pyrrolizin-5-yl)-2-oxoacetic acid (279 mg, 1.06 mmol), 1-[Bis(dimethylamino)methylene]-1H-1,2,3-triazolo[4,5-b]pyridinium 3-oxid hexafluorophosphate (HATU, 605 mg, 1.59 mmol) and 3,3-difluoro-(1-methylaminocarbonyl)-1-cyclobutanamine hydrochloride (255 mg, 1.27 mmol) in DMF (3 mL) was stirred at ambient temperature as N,N-diisopropylethylamine (0.92 mL, 5.28 mmol) was added. After 30 min at rt, the reaction mixture was diluted with ethyl acetate and washed with saturated aqueous ammonium chloride (×2), saturated aqueous sodium bicarbonate (×2), and brine (×1). After the aq. fractions were extracted with ethyl acetate (×1), the organic fractions were combined, dried over magnesium sulfate. After filtration, solvent was removed and the residue was purified by silica gel column chromatography eluting 0-100% ethyl acetate in hexanes to give methyl (1aR,6aR)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylate: $^1$H NMR (400 MHz, Chloroform-d) δ 7.68 (s, 1H), 6.66 (d, J=7.9 Hz, 1H), 4.45 (tt, J=6.0, 2.0 Hz, 1H), 3.89 (s, 3H), 3.55-3.29 (m, 3H), 3.26-3.10 (m, 1H), 3.00-2.83 (m, 2H), 2.82 (d, J=4.8 Hz, 3H), 2.56 (s, 3H), 2.11-1.99 (m, 1H), 1.11 (dt, J=8.6, 6.0 Hz, 1H), 0.30 (ddd, J=6.1, 5.0, 2.1 Hz, 1H): LCMS-ESI+ (m/z): [M+H]$^+$ calculated for $C_{19}H_{22}F_2N_3O_5$: 410.15; found: 410.01.

Step 5. To a solution of methyl (1aR,6aR)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylate (212 mg, 0.52 mmol) in THF (2 mL), MeOH (2 mL) and water (3 mL) was added 1 N LiOH (1.6 mL) at rt. The resulting mixture was stirred at 60° C. bath for 8 h. After the reaction mixture was diluted with water and acidified with 1 N HCl, the product was extracted with ethyl acetate (6×). The combined extracts were dried with magnesium sulfate, concentrated, and dried to give crude (1aR,6aR)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylic acid: LCMS-ESI+ (m/z): [M+H]+ calculated for $C_{18}H_{20}F_2N_3O_5$: 396.14; found: 396.01.

A solution of the above crude (1aR,6aR)-5-(2-((3,3-difluoro-1-methylcarbamoyl)cyclobutyl)amino)-2-oxoacetyl)-4-methyl-1,1a,6,6a-tetrahydrocyclopropa[b]pyrrolizine-3-carboxylic acid and 1-[bis(dimethylamino)methylene]-1H-1,2,3-triazolo[4,5-b]pyridinium 3-oxid hexafluorophosphate (HATU, 296 mg, 0.78 mmol) in dichloromethane (3 mL) was stirred at ambient temperature as N,N-diisopropylethylamine (0.36 mL, 2.07 mmol) was added. After 1.25 h at rt, the reaction mixture was diluted with ethyl acetate (30 mL) and washed with saturated aqueous ammonium chloride (×2), saturated aqueous sodium bicarbonate (×2), and brine (×1). After the aq. fractions were extracted with ethyl acetate (×1), the organic fractions were combined, dried over magnesium sulfate. After filtration, solvent was removed and the residue was co-evaporated with toluene (×1) and dried in vacuum for 20 min give crude 3H-[1,2,3]triazolo[4,5-b]pyridin-3-yl (1aR,6aR)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylate.

Step 6. A solution of the above crude 3H-[1,2,3]triazolo[4,5-b]pyridin-3-yl (1aR,6aR)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylate and 3-chloro-4-fluoroaniline (233 mg, 1.60 mmol) in 2-methyltetrahydrofuran (5 mL) was stirred at ambient temperature as 2,6-lutidine (0.24 mL, 2.06 mmol) was added. The resulting mixture was stirred at 50° C. bath for 20 h followed by 75° C. for 70 h. The reaction mixture was concentrated and the resulting residue was purified by silica gel column chromatography eluting 0-100% ethyl acetate in hexanes to give (1aR,6aR)-N-(3-chloro-4-fluorophenyl)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxamide (5) and impure 3H-[1,2,3]triazolo[4,5-b]pyridin-3-yl (1aR,6aR)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylate.

Example 6 7-(2-((1-(1H-1,2,3-Triazol-4-yl)cyclopropyl)amino)-2-oxoacetyl)-N-(3-chloro-4-fluorophenyl)-6-methyl-2,3-dihydro-1H-pyrrolizine-5-carboxamide (6)

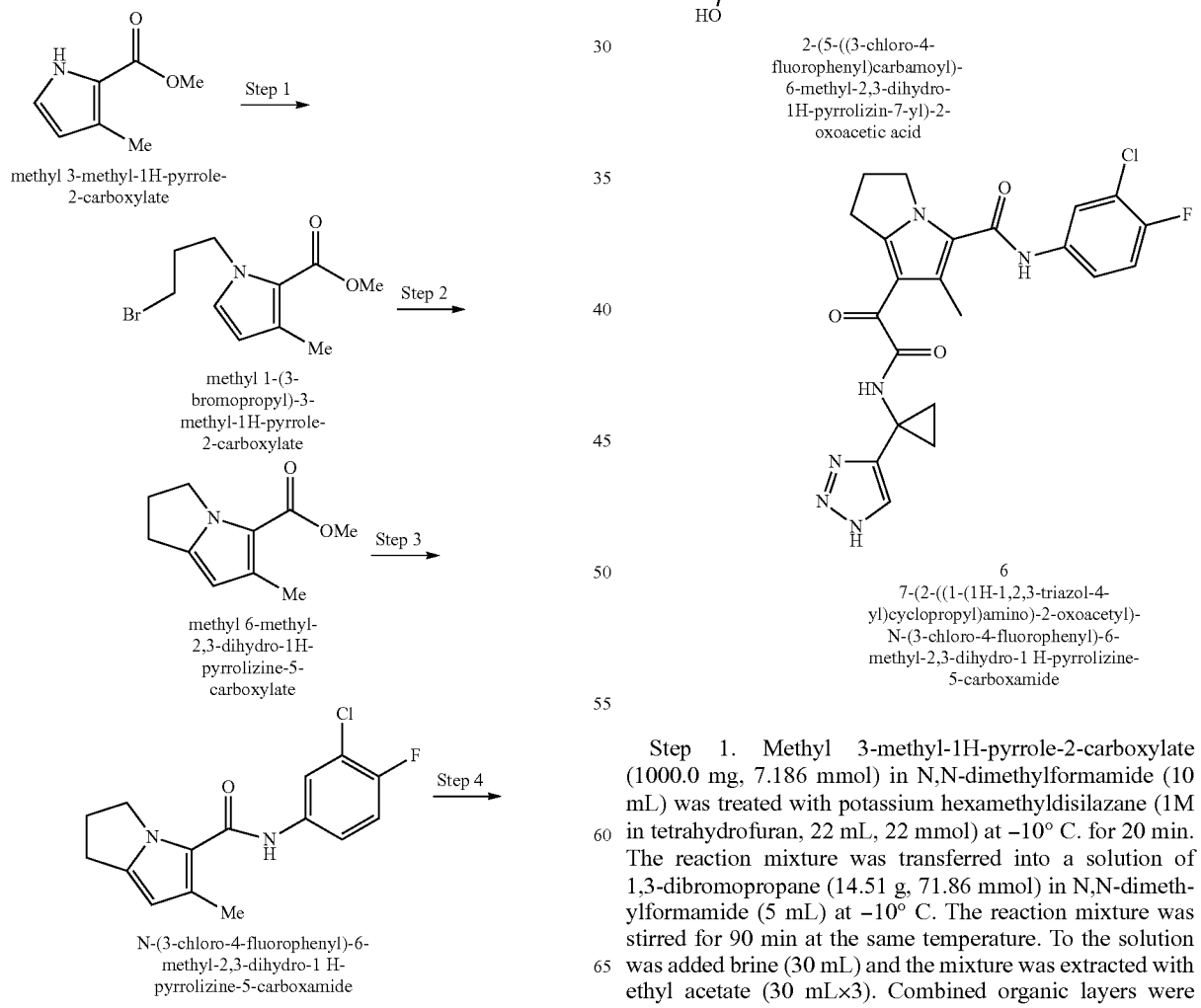

Step 1. Methyl 3-methyl-1H-pyrrole-2-carboxylate (1000.0 mg, 7.186 mmol) in N,N-dimethylformamide (10 mL) was treated with potassium hexamethyldisilazane (1M in tetrahydrofuran, 22 mL, 22 mmol) at −10° C. for 20 min. The reaction mixture was transferred into a solution of 1,3-dibromopropane (14.51 g, 71.86 mmol) in N,N-dimethylformamide (5 mL) at −10° C. The reaction mixture was stirred for 90 min at the same temperature. To the solution was added brine (30 mL) and the mixture was extracted with ethyl acetate (30 mL×3). Combined organic layers were washed with brine and dried over sodium sulfate. After filtration, solvent was removed and the residue was purified a silica gel column chromatography (0-7% ethyl acetate/hexanes) to give methyl 1-(3-bromopropyl)-3-methyl-1H-pyrrole-2-carboxylate LCMS-ESI+ (m/z): [M+H]+ calculated for $C_{10}H_{15}BrNO_2$: 259.0; found: 259.1.

Step 2. Methyl 1-(3-bromopropyl)-3-methyl-1H-pyrrole-2-carboxylate (1450 mg, 5.574 mmol) in toluene (364 mL) was treated with tri-n-butyltinhydride (3233.6 mg, 11.15 mmol) in the presence of 1,1'-(diazene-1,2-diyl)bis(cyclohexane-1-carbonitrile) (408.6 mg, 1.672 mmol, 0.3 equiv.) at 120° C. for 2 h. Toluene was removed under a reduced pressure. To the residue was added aqueous 8% potassium fluoride (100 mL) and diethylether (100 mL) and stirred at ambient temperature for 10 h. After a filtration to remove colorless precipitation, the mixture was extracted with diethylether. The organic layer was washed with brine and dried over sodium sulfate. After a filtration, solvent was removed and the residue was purified by a silica gel chromatography (0-7% ethyl acetate/hexanes) to give methyl 6-methyl-2,3-dihydro-1H-pyrrolizine-5-carboxylate LCMS-ESI+ (m/z): [M+H]+ calculated for $C_{10}H_{14}NO_2$: 180.1; found: 180.1.

Step 3. Methyl 6-methyl-2,3-dihydro-1H-pyrrolizine-5-carboxylate (165.0 mg, 0.921 mmol) and 3-chloro-4-fluoroaniline (268.0 mg, 1.841 mmol) in tetrahydrofuran (6 mL) was treated with lithium hexamethyldisilazane (1M in tetrahydrofuran, 2.76 mL, 2.76 mmol) at ambient temperature for 30 min. To the reaction mixture was added water (30 mL) and the mixture was extracted with ethyl acetate (3×30 mL). The organic layer was washed with brine (30 mL) and dried over sodium sulfate. The solvent was removed under a reduced pressure and the crude mixture was recrystallized from ethyl acetate and hexanes repeatedly to give N-(3-chloro-4-fluorophenyl)-6-methyl-2,3-dihydro-1H-pyrrolizine-5-carboxamide LCMS-ESI+ (m/z): [M+H]+ calculated for $C_{15}H_{15}ClFN_2O$: 293.1; found: 293.1.

Step 4. N-(3-Chloro-4-fluorophenyl)-6-methyl-2,3-dihydro-1H-pyrrolizine-5-carboxamide (189.6 mg, 0.648 mmol) and methyl 2-chloro-2-oxoacetate (238.0 mg, 1.943 mmol) in 1,2-dichloroethane (10 mL) was treated with aluminum chloride (431.8 mg, 3.238 mmol) and stirred at ambient temperature for 16 h. Celite (3 g), water (0.5 mL) and tetrahydrofuran (15 mL) were added and the mixture was stirred at ambient temperature for 30 min. The mixture was filtered through celite (3 g) using ethyl acetate (80 mL). The solvent was removed to give crude methyl 2-(5-((3-chloro-4-fluorophenyl)carbamoyl)-6-methyl-2,3-dihydro-1H-pyrrolizin-7-yl)-2-oxoacetate LCMS-ESI+ (m/z): [M+H]+ calculated for $C_{18}H_{17}ClFN_2O_4$: 379.1; found: 379.1.

Step 5. Methyl 2-(5-((3-chloro-4-fluorophenyl)carbamoyl)-6-methyl-2,3-dihydro-1H-pyrrolizin-7-yl)-2-oxoacetate (245.5 mg, 0.648 mmol) was treated with aqueous 2N-lithium hydroxide (3 mL) in tetrahydrofuran (3 mL) and methanol (6 mL) and stirred at ambient temperature for 1 h. The reaction mixture was acidified with aqueous 1N-hydrochloric acid (7 mL) at 0° C. The mixture was extracted with ethyl acetate (3×30 mL). Combined organic layers were washed with brine (30 mL) and dried over sodium sulfate. The solvent was removed to give crude 2-(5-((3-chloro-4-fluorophenyl)carbamoyl)-6-methyl-2,3-dihydro-1H-pyrrolizin-7-yl)-2-oxoacetic acid LCMS-ESI+ (m/z): [M+H]+ calculated for $C_{17}H_{15}ClFN_2O_4$: 365.1; found: 365.1.

Step 6. 2-(5-((3-Chloro-4-fluorophenyl)carbamoyl)-6-methyl-2,3-dihydro-1H-pyrrolizin-7-yl)-2-oxoacetic acid (100.0 mg, 0.274 mmol) was treated with 1-[bis(dimethylamino)methylene]-1H-1,2,3-triazolo[4,5-b]pyridinium 3-oxid hexafluorophosphate (HATU, 312.7 mg, 0.822 mmol) in the presence of N,N-diisopropylethylamine (212.6 mg, 1.645 mmol) in 1,2-dichloroethane (2 mL) and stirred at ambient temperature for 10 min. The mixture was transferred into another flask charged with 1-(1H-1,2,3-triazol-4-yl)cyclopropan-1-amine dihydrochloric acid (108.1 mg, 0.548 mmol, 2 equiv.) in 1,2-dichloroethane (2 mL). The reaction mixture was stirred at ambient temperature for 30 min. To the mixture was added water (30 mL) and the mixture was extracted with ethyl acetate (3×30 mL). Combined organic layers were washed with brine (30 mL) and dried over sodium sulfate. After a filtration, the organic solvent was removed under reduced pressure to give a crude mixture that was purified by preparative HPLC (Phenomenex Luna C18 column, 5% to 100% gradient acetonitrile in water with 0.1% TFA) to give 7-(2-((1-(1H-1,2,3-triazol-4-yl)cyclopropyl)amino)-2-oxoacetyl)-N-(3-chloro-4-fluorophenyl)-6-methyl-2,3-dihydro-1H-pyrrolizine-5-carboxamide (6).

Synthesis of
1-(1H-1,2,3-triazol-4-yl)cyclopropan-1-amine dihydrochloric acid

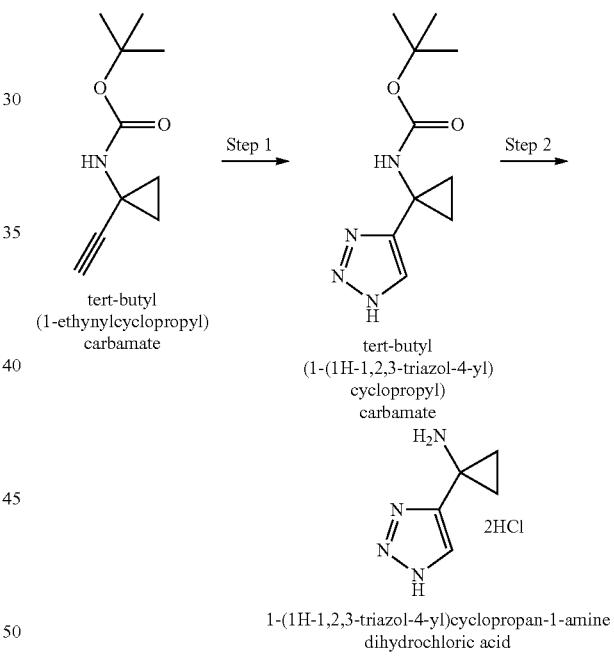

tert-butyl
(1-ethynylcyclopropyl)
carbamate tert-butyl
(1-(1H-1,2,3-triazol-4-yl)
cyclopropyl)
carbamate 1-(1H-1,2,3-triazol-4-yl)cyclopropan-1-amine
dihydrochloric acid Step 1 tert-Butyl (1-ethynylcyclopropyl)carbamate (200.0 mg, 1.104 mmol) was treated with azidotrimethylsilane (508.6 mg, 4.414 mmol, 4 equiv.) in the presence of copper iodide (21.0 mg, 0.11 mmol) in N,N-dimethylformamide (1 mL) and methanol (1 mL) and stirred at 110° C. for 2 h. After cooling, purification by prep HPLC (Phenomenex Luna C18 column, 5% to 100% gradient acetonitrile in water with 0.1% TFA) gave tert-butyl (1-(1H-1,2,3-triazol-4-yl)cyclopropyl)carbamate. LCMS-ESI+ (m/z): [M+H]+ calculated for $C_{10}H_{17}N_4O_2$: 225.1; found: 225.1.

Step 2 tert-Butyl (1-(1H-1,2,3-triazol-4-yl)cyclopropyl)carbamate (243.2 mg, 1.084 mmol) was treated with hydrogen chloride (4N in 1,4-dioxane, 4 mL) in methanol (2 mL) and stirred at 110° C. for 1 h. The organic solvent was removed under a reduced pressure to give 1-(1H-1,2,3- triazol-4-yl)cyclopropan-1-amine dihydrochloric acid. LCMS-ESI+ (m/z): [M+H]+ calculated for $C_5H_9N_4$: 125.1; found: 125.1.

Example 7. N-(3-chloro-4-fluorophenyl)-6-methyl-7-(2-oxo-2-((3-(trifluoromethyl)oxetan-3-yl)amino)acetyl)-2,3-dihydro-1H-pyrrolizine-5-carboxamide (7)

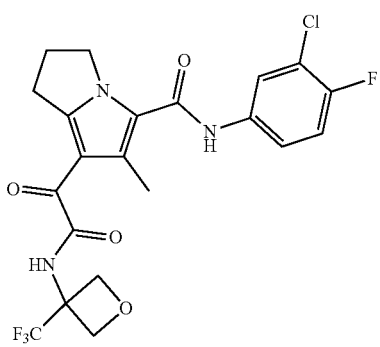

N-(3-chloro-4-fluorophenyl)-6-methyl-7-(2-oxo-2-((3-(trifluoromethyl)oxetan-3-yl)amino)acetyl)-2,3-dihydro-1H-pyrrolizine-5-carboxamide (7) was synthesized in a manner similar to Example 2 using 3-(trifluoromethyl)oxetan-3-amine in place of R-trifluoroisopropylamine.

Example 8 N-(3-chloro-4-fluorophenyl)-7-(2-((3,3-difluoro-1-(((3-methyl-1,1-dioxidothietan-3-yl)amino)methyl)cyclobutyl)amino)-2-oxoacetyl)-6-methyl-2,3-dihydro-1H-pyrrolizine-5-carboxamide (8)

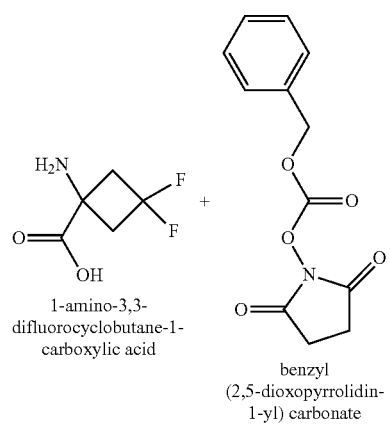

1-amino-3,3-difluorocyclobutane-1-carboxylic acid benzyl (2,5-dioxopyrrolidin-1-yl) carbonate

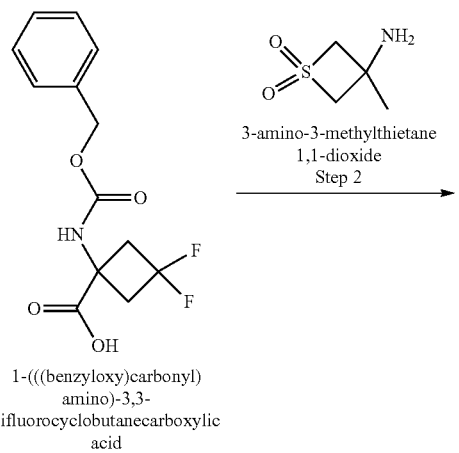

3-amino-3-methylthietane 1,1-dioxide

Step 2

1-(((benzyloxy)carbonyl)amino)-3,3-difluorocyclobutanecarboxylic acid

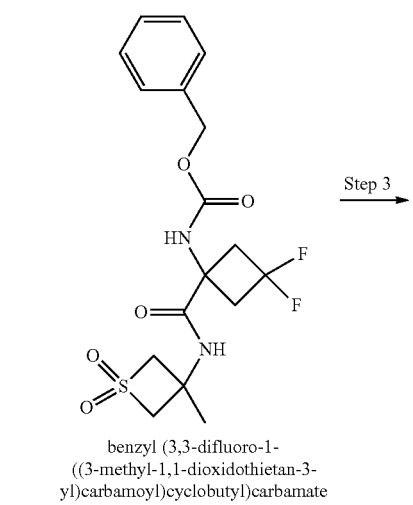

Step 3 benzyl (3,3-difluoro-1-((3-methyl-1,1-dioxidothietan-3-yl)carbamoyl)cyclobutyl)carbamate

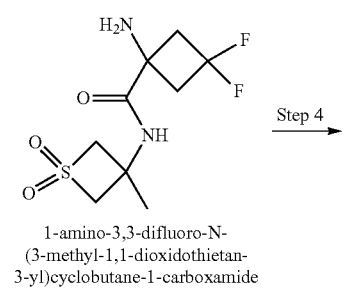

Step 4

1-amino-3,3-difluoro-N-(3-methyl-1,1-dioxidothietan-3-yl)cyclobutane-1-carboxamide

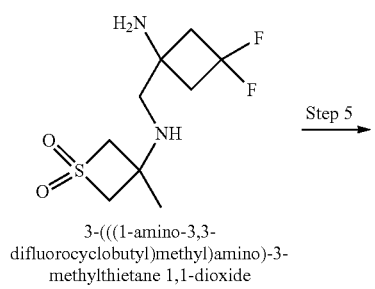

Step 5

3-(((1-amino-3,3-difluorocyclobutyl)methyl)amino)-3-methylthietane 1,1-dioxide

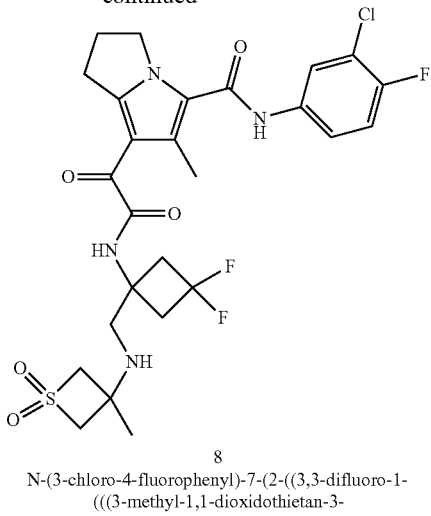

8

N-(3-chloro-4-fluorophenyl)-7-(2-((3,3-difluoro-1-(((3-methyl-1,1-dioxidothietan-3-yl)amino)methyl)cyclobutyl)amino)-2-oxoacetyl)-6-methyl-2,3-dihydro-1H-pyrrolizine-5-carboxamide Step 1 To a suspension of 1-amino-3,3-difluorocyclobutane-1-carboxylic acid (300.0 mg, 1.99 mmol) and benzyl (2,5-dioxopyrrolidin-1-yl) carbonate (593.7 mg, 2.38 mmol, 1.2 equiv.) in acetonitrile (6 mL) at rt, was added diisopropylethylamine (796.8 mg, 5.96 mmol, 3 equiv.) and the solution was stirred at the same temperature for 1 h. The reaction mixture was quenched with sat. sodium chloride aqueous solution (30 mL) and the whole was extracted with ethyl acetate (30 mL×3). Combined organic layer was washed with brine and dried over sodium sulfate. After filtration, solvent was removed to give crude 1-(((benzyloxy)carbonyl)amino)-3,3-difluorocyclobutane-1-carboxylic acid (580 mg). This was used in the subsequent step without further purification: LCMS-ESI+ (m/z): [M+H]$^+$ calculated for $C_{13}H_{13}F_2NNaO_4$: 308.1; found: 308.0.

Step 2 1-(((Benzyloxy)carbonyl)amino)-3,3-difluorocyclobutane-1-carboxylic acid (566.2 mg, 1.985 mmol) and 3-amino-3-methylthietane 1,1-dioxide (268.3 mg, 1.985 mmol, 1 equiv.) were treated with 2-(7-aza-1H-benzotriazole-1-yl)-1,1,3,3-tetramethyluronium hexafluorophosphate (2.80 g, 11.91 mmol, 6 equiv.) in the presence of N,N-diisopropylethylamine (1.54 g, 11.91 mmol, 6 equiv.) in dichloroethane at ambient temperature for 90 min. To the solution was added brine (30 mL) and the whole was extracted with ethyl acetate (30 mL×3). Combined organic layer was washed with brine and dried over sodium sulfate. After filtration, solvent was removed and the residue was purified by preparative reverse phase high performance liquid chromatography (Phenomenex Luna C18 column, 5% to 100% gradient acetonitrile in water with 0.1% TFA) to give benzyl (3,3-difluoro-1-((3-methyl-1,1-dioxidothietan-3-yl)carbamoyl)cyclobutyl)carbamate (356.4 mg). LCMS-ESI+ (m/z): [M+H]$^+$ calculated for $C_{17}H_{21}F_2N_2O_5S$: 403.1; found: 403.1.

Step 3 Benzyl (3,3-difluoro-1-((3-methyl-1,1-dioxidothietan-3-yl)carbamoyl)cyclobutyl)carbamate (218.8 mg, 0.54 mmol) was treated with 10% palladium carbon (210.0 mg) in methanol (10 mL) under a hydrogen atmosphere (1 atm) at ambient temperature for 90 min. The mixture was filtered through Celite (3 g) using methanol (70 mL). Removal of the solvent from the filtrate under a reduced pressure gave the 1-amino-3,3-difluoro-N-(3-methyl-1,1-dioxidothietan-3-yl)cyclobutane-1-carboxamide. LCMS-ESI+ (m/z): [M+H]$^+$ calculated for $C_9H_{15}F_2N_2O_3S$: 269.1; found: 269.0.

Step 4 1-Amino-3,3-difluoro-N-(3-methyl-1,1-dioxidothietan-3-yl)cyclobutane-1-carboxamide (30.0 mg, 0.112 mmol) was treated with diisopropylalminum hydride (1M in tetrahydrofuran, 0.6 mL, 0.60 mmol) at ambient temperature for 15 min. To the reaction mixture were added Celite (3 g), water (0.5 mL) and EtOAc (70 mL) to stir at ambient temperature for 30 min. The mixture was filtered through Celite (3 g) using EtOAc (30 mL). Removal of the solvent gave the crude 3-(((1-amino-3,3-difluorocyclobutyl)methyl)amino)-3-methylthietane 1,1-dioxide (20.9 mg). LCMS-ESI+ (m/z): [M+H]$^+$ calculated for $C_9H_{17}F_2N_2O_2S$: 255.1; found: 255.1.

Step 5 2-(5-((3-Chloro-4-fluorophenyl)carbamoyl)-6-methyl-2,3-dihydro-1H-pyrrolizin-7-yl)-2-oxoacetic acid (15.0 mg, 0.041 mmol) was treated with 1-[bis(dimethylamino)methylene]-1H-1,2,3-triazolo[4,5-b]pyridinium 3-oxid hexafluorophosphate (HATU, 93.8 mg, 0.247 mmol, 6 equiv.) in the presence of diisopropylethylamine (31.9 mg, 0.247 mmol, 6 equiv.) in 1,2-dichloroethane (2 mL) at ambient temperature for 20 min. The mixture was transferred into another flask charged with 3-(((1-amino-3,3-difluorocyclobutyl)methyl)amino)-3-methylthietane 1,1-dioxide (20.9 mg, 0.082 mmol, 2 equiv.). The reaction mixture was stirred at ambient temperature for 30 min. To the mixture was added water (30 mL) and the whole was extracted with ethyl acetate (30 mL×3). Combined organic layer was washed with brine (30 mL) and dried over sodium sulfate. After a filtration, the organic solvent was removed under a reduced pressure to give a crude mixture. The crude mixture was purified by a preparative reverse phase high performance liquid chromatography (Phenomenex Luna C18 column, 5% to 100% gradient acetonitrile in water with 0.1% TFA) to give N-(3-chloro-4-fluorophenyl)-7-(2-((3,3-difluoro-1-(((3-methyl-1,1-dioxidothietan-3-yl)amino)methyl)cyclobutyl)amino)-2-oxoacetyl)-6-methyl-2,3-dihydro-1H-pyrrolizine-5-carboxamide (8).

Example 9. N-(3-chloro-4-fluorophenyl)-7-(2-((3,3-difluoro-1-((3-methyl-1,1-dioxidothietan-3-yl)carbamoyl)cyclobutyl)amino)-2-oxoacetyl)-6-methyl-2,3-dihydro-1H-pyrrolizine-5-carboxamide

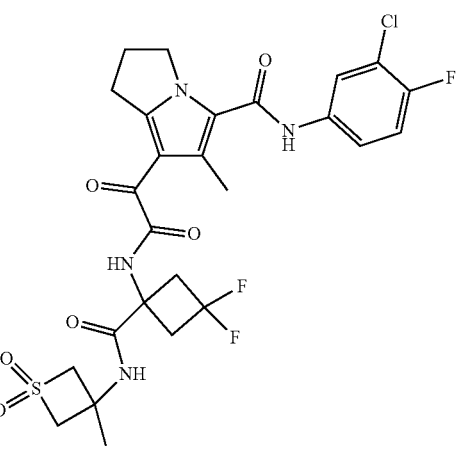

9

N-(3-chloro-4-fluorophenyl)-7-(2-((3,3-difluoro-1-((3-methyl-1,1-dioxidothietan-3-yl)carbamoyl)cyclobutyl)amino)-2-oxoacetyl)-6-methyl-2,3-dihydro-1H-pyrrolizine-5-carboxamide N-(3-chloro-4-fluorophenyl)-7-(2-((3,3-difluoro-1-((3-methyl-1,1-dioxidothietan-3-yl)carbamoyl)cyclobutyl)amino)-2-oxoacetyl)-6-methyl-2,3-dihydro-1H-pyrrolizine-5-carboxamide (9) was synthesized in a manner similar to Example 2 using 1-amino-3,3-difluoro-N-(3-methyl-1,1-dioxidothietan-3-yl)cyclobutane-1-carboxamide in place of 3,3-difluoro-1-(1H-1,2,3-triazol-5-yl)cyclobutan-1-amine.

Example 10 7-(2-((1-((2-oxa-6-azaspiro[3.3]heptan-6-yl)methyl)-3,3-difluorocyclobutyl)amino)-2-oxoacetyl)-N-(3-chloro-4-fluorophenyl)-6-methyl-2,3-dihydro-1H-pyrrolizine-5-carboxamide (10)

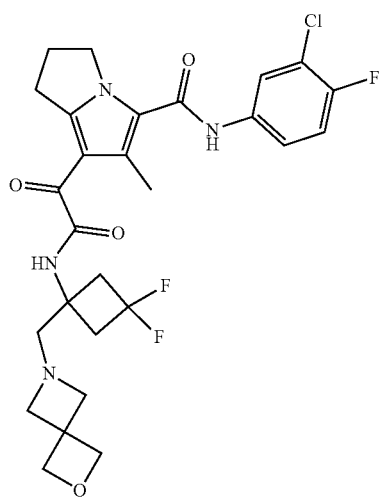

7-(2-((1-((2-oxa-6-azaspiro[3.3]heptan-6-yl)methyl)-3,3-difluorocyclobutyl)amino)-2-oxoacetyl)-N-(3-chloro-4-fluorophenyl)-6-methyl-2,3-dihydro-1H-pyrrolizine-5-carboxamide (10) was synthesized in a manner similar to Example 8 using 2-oxa-6-azaspiro[3.3]heptane in step 2 in place of 3-amino-3-methylthietane 1,1-dioxide.

Example 11 N-(3-chloro-4-fluorophenyl)-7-(2-((3,3-difluoro-1-(6-oxa-1-azaspiro[3.3]heptane-1-carbonyl)cyclobutyl)amino)-2-oxoacetyl)-6-methyl-2,3-dihydro-1H-pyrrolizine-5-carboxamide (11)

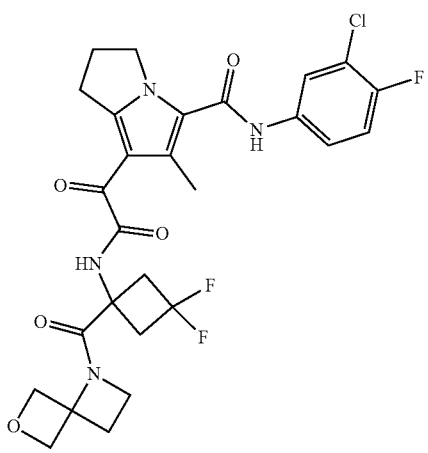

N-(3-chloro-4-fluorophenyl)-7-(2-((3,3-difluoro-1-(6-oxa-1-azaspiro[3.3]heptane-1-carbonyl)cyclobutyl)amino)-2-oxoacetyl)-6-methyl-2,3-dihydro-1H-pyrrolizine-5-carboxamide (11) was synthesized in a manner similar to Example 8 and 9 using 6-oxa-1-azaspiro[3.3]heptane in step 2 in place of 3-amino-3-methylthietane 1,1-dioxide.

Example 12 7-(2-((1-(1,3,4-thiadiazol-2-yl)cyclopropyl)amino)-2-oxoacetyl)-N-(3-chloro-4-fluorophenyl)-6-methyl-2,3-dihydro-1H-pyrrolizine-5-carboxamide (12)

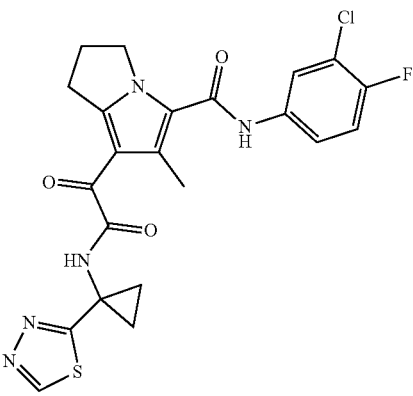

7-(2-((1-(1,3,4-thiadiazol-2-yl)cyclopropyl)amino)-2-oxoacetyl)-N-(3-chloro-4-fluorophenyl)-6-methyl-2,3-dihydro-1H-pyrrolizine-5-carboxamide (12) was synthesized in a manner similar to Example 6 using 1-(1,3,4-thiadiazol-2-yl)cyclopropan-1-amine in place of 1-(1H-1,2,3-triazol-4-yl)cyclopropan-1-amine dihydrochloric acid.

Example 13 N-(3-chloro-4-fluorophenyl)-7-(2-((1-(2,2-dioxido-2-thia-6-azaspiro[3.3]heptane-6-carbonyl)-3,3-difluorocyclobutyl)amino)-2-oxoacetyl)-6-methyl-2,3-dihydro-1H-pyrrolizine-5-carboxamide (13)

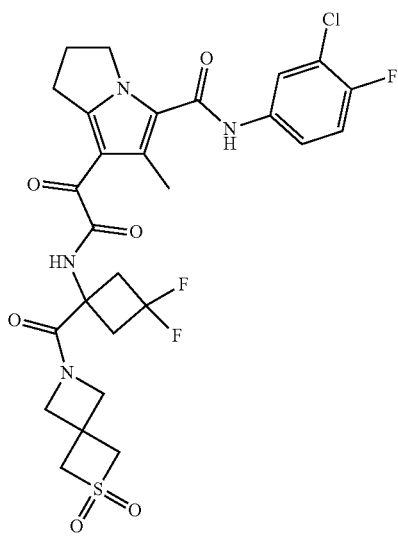

N-(3-chloro-4-fluorophenyl)-7-(2-((1-(2,2-dioxido-2-thia-6-azaspiro[3.3]heptane-6-carbonyl)-3,3-difluorocyclobutyl)amino)-2-oxoacetyl)-6-methyl-2,3-dihydro-1H-pyrrolizine-5-carboxamide (13) was synthesized in a manner similar to Example 8 using 2-thia-6-azaspiro[3.3] heptane 2,2-dioxide in place of 3-amino-3-methylthietane 1,1-dioxide Example 14 N-(3-chloro-4-fluorophenyl)-7-(2-((3,3-difluoro-1-(3-fluoroazetidine-1-carbonyl)cyclobutyl)amino)-2-oxoacetyl)-6-methyl-2,3-dihydro-1H-pyrrolizine-5-carboxamide (14)

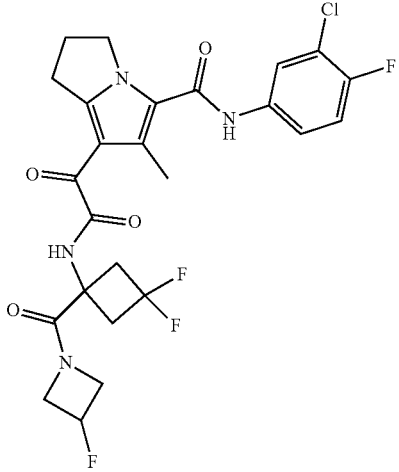

14

N-(3-chloro-4-fluorophenyl)-7-(2-((3,3-difluoro-1-(3-fluoroazetidine-1-carbonyl)cyclobutyl)amino)-2-oxoacetyl)-6-methyl-2,3-dihydro-1H-pyrrolizine-5-carboxamide (14) was synthesized in a manner similar to Example 8 using 3-fluoroazetidine in place of 3-amino-3-methylthietane 1,1-dioxide Example 15 N-(3-chloro-4-fluorophenyl)-7-(2-((3,3-difluoro-1-(methylcarbamoyl)cyclobutyl)amino)-2-oxoacetyl)-3,3,6-trimethyl-2,3-dihydro-1H-pyrrolizine-5-carboxamide (15)

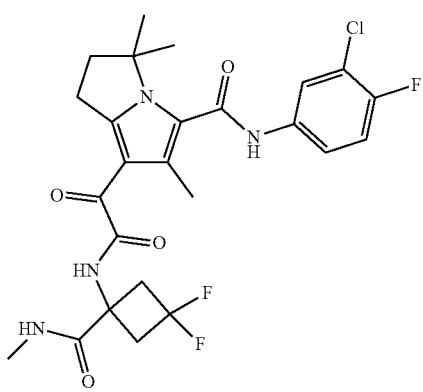

15

N-(3-chloro-4-fluorophenyl)-7-(2-((3,3-difluoro-1-(methylcarbamoyl)cyclobutyl)amino)-2-oxoacetyl)-3,3,6-trimethyl-2,3-dihydro-1H-pyrrolizine-5-carboxamide (15) was synthesized in a manner similar to Example 5 using benzyl (S)-5,5-dimethylpyrrolidine-2-carboxylate in place of benzyl (1R,3S,5R)-2-azabicyclo[3.1.0]hexane-3-carboxylate.

Example 16 (R)—N-(3-chloro-4-fluorophenyl)-7-(2-((3,3-difluoro-1-(methylcarbamoyl)cyclobutyl)amino)-2-oxoacetyl)-2-hydroxy-6-methyl-2,3-dihydro-1H-pyrrolizine-5-carboxamide (16)

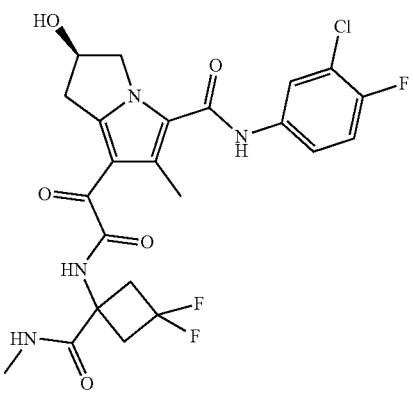

16

(R)—N-(3-chloro-4-fluorophenyl)-7-(2-((3,3-difluoro-1-(methylcarbamoyl)cyclobutyl)amino)-2-oxoacetyl)-2-hydroxy-6-methyl-2,3-dihydro-1H-pyrrolizine-5-carboxamide (16) was synthesized in a manner similar to Example 5 using benzyl (2S,4R)-4-((tert-butyldimethylsilyl)oxy)pyrrolidine-2-carboxylate in place of benzyl (1R,3S,5R)-2-azabicyclo[3.1.0]hexane-3-carboxylate.

Example 17 (R)—N-(3-chloro-4-fluorophenyl)-3,3,6-trimethyl-7-(2-oxo-2-((1,1,1-trifluoropropan-2-yl)amino)acetyl)-2,3-dihydro-1H-pyrrolizine-5-carboxamide (17)

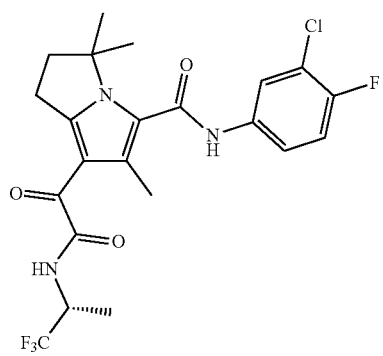

17

(R)—N-(3-chloro-4-fluorophenyl)-3,3,6-trimethyl-7-(2-oxo-2-((1,1,1-trifluoropropan-2-yl)amino)acetyl)-2,3-dihydro-1H-pyrrolizine-5-carboxamide (17) was synthesized in a manner similar to Example 5 using benzyl (S)-5,5-dimethylpyrrolidine-2-carboxylate in place of benzyl (1R,3S,5R)-2-azabicyclo[3.1.0]hexane-3-carboxylate and R-trifluoroisopropylamine in place of 1-amino-3,3-difluoro-N-methylcyclobutane-1-carboxamide hydrochloride.

Example 18 N-(3-chloro-4-fluorophenyl)-7-(2-((3,3-difluoro-1-(methylcarbamoyl)cyclobutyl)amino)-2-oxoacetyl)-3,6-dimethyl-2,3-dihydro-1H-pyrrolizine-5-carboxamide (racemic) (18)

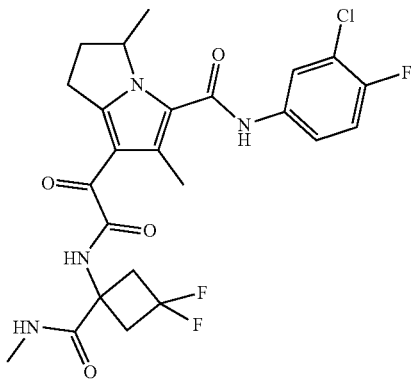

18

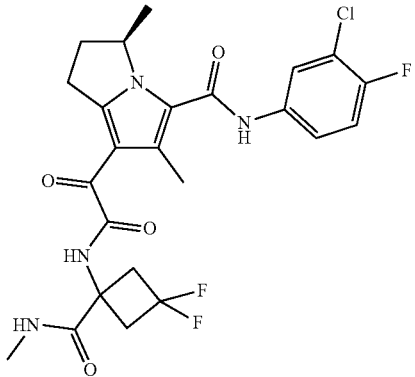

22

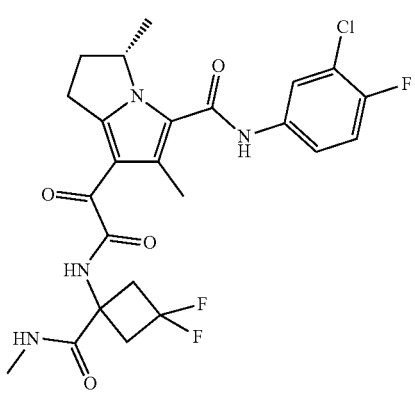

23

Example 22 N-(3-chloro-4-fluorophenyl)-7-(2-((3,3-difluoro-1-(methylcarbamoyl)cyclobutyl)amino)-2-oxoacetyl)-3,6-dimethyl-2,3-dihydro-1H-pyrrolizine-5-carboxamide (single enantiomer) (22)

Example 23 N-(3-chloro-4-fluorophenyl)-7-(2-((3,3-difluoro-1-(methylcarbamoyl)cyclobutyl)amino)-2-oxoacetyl)-3,6-dimethyl-2,3-dihydro-1H-pyrrolizine-5-carboxamide (single enantiomer) (23)

Racecemic N-(3-chloro-4-fluorophenyl)-7-(2-((3,3-difluoro-1-(methylcarbamoyl)cyclobutyl)amino)-2-oxoacetyl)-3, 6-dimethyl-2,3-dihydro-1H-pyrrolizine-5-carboxamide (18) was synthesized in a manner similar to Example 5 using benzyl (2S)-5-methylpyrrolidine-2-carboxylate in place of benzyl (1R,3S,5R)-2-azabicyclo[3.1.0]hexane-3-carboxylate. Single stereoisomers were purified from racemic material via chiral supercritical fluid chromatography (OD-H column 4.6×100 mm, 3.0 ml/min, 30% isopropanol in carbon dioxide). The first eluting compound (0.85 min) was assigned the structure of compound (22) and the second eluting compound (1.29 min) was assigned the structure of compound (23).

Example 19 N-(3-cyano-4-fluorophenyl)-7-(2-((3,3-difluoro-1-(methylcarbamoyl)cyclobutyl)amino)-2-oxoacetyl)-3,6-dimethyl-2,3-dihydro-1H-pyrrolizine-5-carboxamide (19)

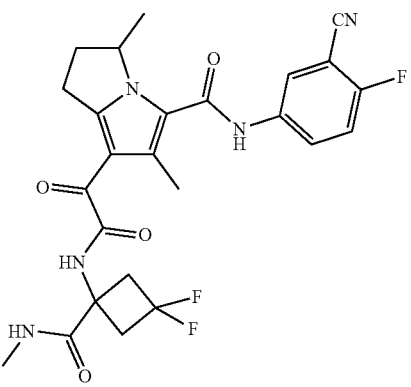

19

N-(3-cyano-4-fluorophenyl)-7-(2-((3,3-difluoro-1-(methylcarbamoyl)cyclobutyl)amino)-2-oxoacetyl)-3, 6-dimethyl-2,3-dihydro-1H-pyrrolizine-5-carboxamide (19) was synthesized in a manner similar to Example 5 using benzyl (2S)-5-methylpyrrolidine-2-carboxylate in place of benzyl (1R,3S,5R)-2-azabicyclo[3.1.0]hexane-3-carboxylate and 3-cyano-4-fluoroaniline in place of 3-chloro-4-fluoroaniline.

Example 20 N-(3-chloro-4-fluorophenyl)-3,6-dimethyl-7-(2-oxo-2-(((R)-1,1,1-trifluoropropan-2-yl)amino)acetyl)-2,3-dihydro-1H-pyrrolizine-5-carboxamide (mixture

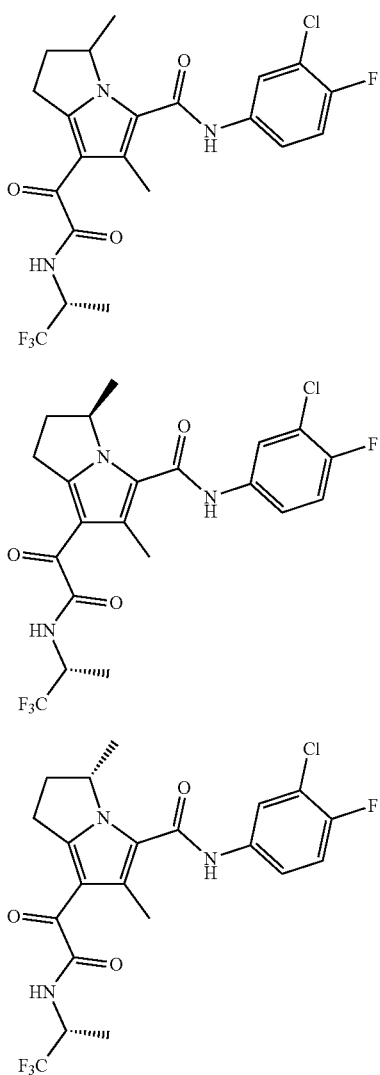

Example 24 N-(3-chloro-4-fluorophenyl)-3,6-dimethyl-7-(2-oxo-2-(((R)-1,1,1-trifluoropropan-2-yl)amino)acetyl)-2,3-dihydro-1H-pyrrolizine-5-carboxamide (single diastereomer) (24)

Example 25 N-(3-chloro-4-fluorophenyl)-3,6-dimethyl-7-(2-oxo-2-(((R)-1,1,1-trifluoropropan-2-yl)amino)acetyl)-2,3-dihydro-1H-pyrrolizine-5-carboxamide (single diastereomer) (25)

A diastereomeric mixture of N-(3-chloro-4-fluorophenyl)-3,6-dimethyl-7-(2-oxo-2-(((R)-1,1,1-trifluoropropan-2-yl)amino)acetyl)-2,3-dihydro-1H-pyrrolizine-5-carboxamide (20) was synthesized in a manner similar to Example 5 using benzyl (2S)-5-methylpyrrolidine-2-carboxylate in place of benzyl (1R,3S,5R)-2-azabicyclo[3.1.0]hexane-3-carboxylate and R-trifluoroisopropylamine in place of 1-amino-3,3-difluoro-N-methylcyclobutane-1-carboxamide hydrochloride. Single stereoisomers were purified from the mixture of diastereomers via chiral supercritical fluid chromatography (ID column, 4.6×150 mm, 3.0 ml/min, 30% isopropanol in carbon dioxide). First peak 1.06 min 24, $2^{nd}$ a peak 1.79 25

Example 21 N-(3-chloro-4-fluorophenyl)-6-methyl-7-(2-((3-methyl-1,1-dioxidothietan-3-yl)amino)-2-oxoacetyl)-2,3-dihydro-1H-pyrrolizine-5-carboxamide (21)

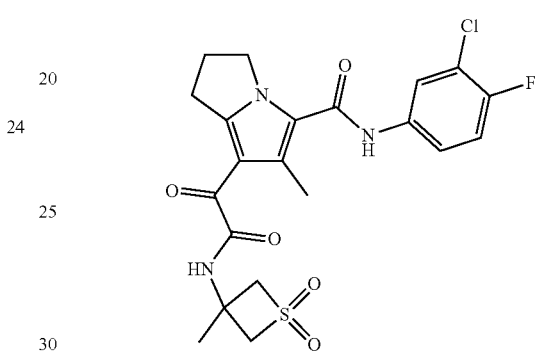

N-(3-chloro-4-fluorophenyl)-6-methyl-7-(2-((3-methyl-1,1-dioxidothietan-3-yl)amino)-2-oxoacetyl)-2,3-dihydro-1H-pyrrolizine-5-carboxamide (21) was synthesized in a manner similar to Example 6 using 3-amino-3-methylthietane 1,1-dioxide in place of 1-(1H-1,2,3-triazol-4-yl)cyclopropan-1-amine dihydrochloric acid.

Example 26 N-(3-chloro-4-fluorophenyl)-7-(2-((3,3-difluoro-1-((3-methyl-1,1-dioxidothietan-3-yl)carbamoyl)cyclobutyl)amino)-2-oxoacetyl)-6-methyl-2,3-dihydro-1H-pyrrolizine-5-carboxamide (26)

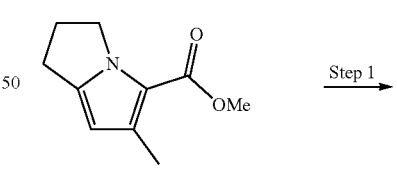

methyl 6-methyl-2,3-dihydro-1H-pyrrolizine-5-carboxylate

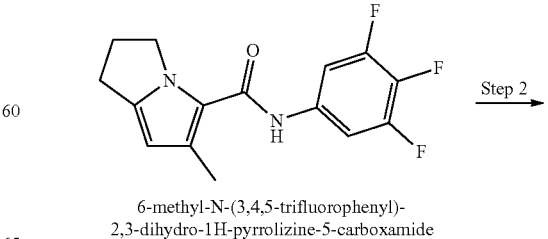

6-methyl-N-(3,4,5-trifluorophenyl)-2,3-dihydro-1H-pyrrolizine-5-carboxamide

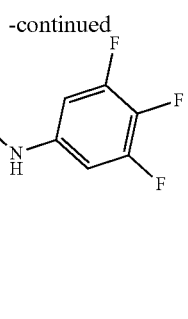

methyl 2-(6-methyl-5-((3,4,5-trifluorophenyl)
carbamoyl)-2,3-dihydro-1H-pyrrolizin-7-yl)-
2-oxoacetate Step 3

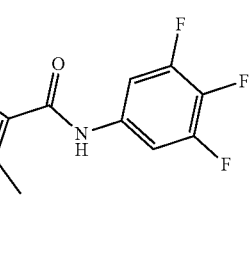

2-(6-methyl-5-((3,4,5-trifluorophenyl)
carbamoyl)-2,3-dihydro-1H-pyrrolizin-7-yl)-
2-oxoacetic acid Step 4

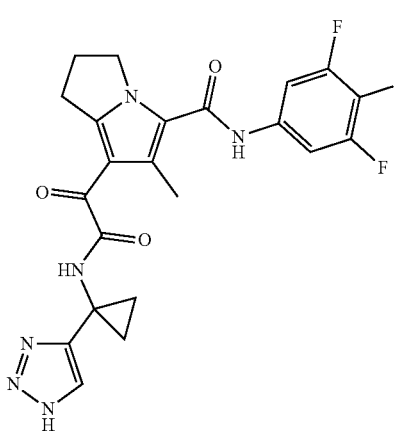

26
7-(2-(((1-(1H-1,2,3-triazol-4-yl)cyclopropyl)
amino)-2-oxoacetyl)-6-methyl-N-(3,4,5-
trifluorophenyl)-2,3-dihydro-1H-
pyrrolizine-5-carboxamide Step 1 Methyl 6-methyl-2,3-dihydro-1H-pyrrolizine-5-carboxylate (52.1 mg, 0.291 mmol) and 3,4,5-trifluoroaniline (85.5 mg, 0.581 mmol, 2 equiv.) in tetrahydrofuran (6 mL) was treated with lithium hexamethyldisilazane (1M in tetrahydrofuran, 0.87 mL, 0.87 mmol, 3 equiv.) at ambient temperature for 30 min. To the reaction mixture was added water (30 mL) and the mixture was extracted with ethyl acetate (30 mL×3). The organic layer was washed with brine (30 mL) and dried over sodium sulfate. The solvent was removed under a reduced pressure and the crude mixture was purified by preparative reverse phase high performance liquid chromatography (Phenomenex Luna C18 column, 5% to 100% gradient acetonitrile in water with 0.1% TFA) to give 6-methyl-N-(3,4,5-trifluorophenyl)-2,3-dihydro-1H-pyrrolizine-5-carboxamide LCMS-ESI+ (m/z): [M+H]$^+$ calculated for $C_{15}H_{14}F_3N_2O$: 295.1; found: 295.1.

Step 2 6-Methyl-N-(3,4,5-trifluorophenyl)-2,3-dihydro-1H-pyrrolizine-5-carboxamide (54.6 mg, 0.186 mmol) was treated with methyl 2-chloro-2-oxoacetate (68.2 mg, 0.557 mmol) in the presence of aluminum chloride (123.7 mg, 0.928 mmol) in 1,2-dichloroethane (2 mL) at ambient temperature for 3.5 h. To the reaction mixture were added Celite (3 g), water (0.5 mL), tetrahydrofuran (15 mL) and EtOAc (80 mL) and stirred at ambient temperature for 30 min. The mixture was filtered through Celite (3 g) using ethyl acetate (30 mL×2). Removal of the solvent followed by purification by preparative reverse phase high performance liquid chromatography (Phenomenex Luna C18 column, 5% to 100% gradient acetonitrile in water with 0.1% TFA) gave methyl 2-(6-methyl-5-((3,4,5-trifluorophenyl)carbamoyl)-2,3-dihydro-1H-pyrrolizin-7-yl)-2-oxoacetate: LCMS-ESI+ (m/z): [M+H]$^+$ calculated for $C_{18}H_{16}F_3N_2O_4$: 381.1; found: 381.1.

Step 3 Methyl 2-(6-methyl-5-((3,4,5-trifluorophenyl)carbamoyl)-2,3-dihydro-1H-pyrrolizin-7-yl)-2-oxoacetate (26.6 mg, 0.070 mmol) was treated with aqueous 2N-lithium hydroxide (1 mL) in methanol (2 mL) and tetrahydrofuran (1 mL) at ambient temperature for 30 min. The mixture was acidified with 1N-hydrochloric acid (4 mL) under ice-water bath cooling. The mixture was extracted with ethyl acetate (30 mL×2) and the combined organic layers were washed with brine (30 mL) and dried over sodium sulfate. After filtration, solvent was removed to give crude 2-(6-methyl-5-((3,4,5-trifluorophenyl)carbamoyl)-2,3-dihydro-1H-pyrrolizin-7-yl)-2-oxoacetic acid: LCMS-ESI+ (m/z): [M+H]$^+$ calculated for $C_{17}H_{14}F_3N_2O_4$: 367.1; found: 367.1.

Step 4 1-(1H-1,2,3-triazol-4-yl)cyclopropan-1-amine dihydrochloric acid (20.5 mg, 0.165 mmol, 2 equiv.) and 2-(6-methyl-5-((3,4,5-trifluorophenyl)carbamoyl)-2,3-dihydro-1H-pyrrolizin-7-yl)-2-oxoacetic acid (30.2 mg, 0.082 mmol) was treated with 2-(7-aza-1H-benzotriazole-1-yl)-1,1,3,3-tetramethyluronium hexafluorophosphate (94.1 mg, 0.247 mmol) in the presence of N,N-diisopropylethylamine (63.9 mg, 0.495 mmol) in 1,2-dichloroethane (2 mL) and stirred for 16 h at ambient temperature. To the solution was added brine (30 mL) and the mixture was extracted with ethyl acetate (30 mL×3). The combined organic layers were washed with brine (30 mL) and dried over sodium sulfate. After filtration, solvent was removed and the residue was purified by preparative reverse phase high performance liquid chromatography (Phenomenex Luna C18 column, 5% to 100% gradient acetonitrile in water with 0.1% TFA) to give 7-(2-(((1-(1H-1,2,3-triazol-4-yl)cyclopropyl)amino)-2-oxoacetyl)-6-methyl-N-(3,4,5-trifluorophenyl)-2,3-dihydro-1H-pyrrolizine-5-carboxamide (26).

Example 27 N-(3-chloro-4-fluorophenyl)-7-(2-((3,3-difluoro-1-(2-oxa-6-azaspiro[3.3]heptane-6-carbonyl)cyclobutyl)amino)-2-oxoacetyl)-6-methyl-2,3-dihydro-1H-pyrrolizine-5-carboxamide (27)

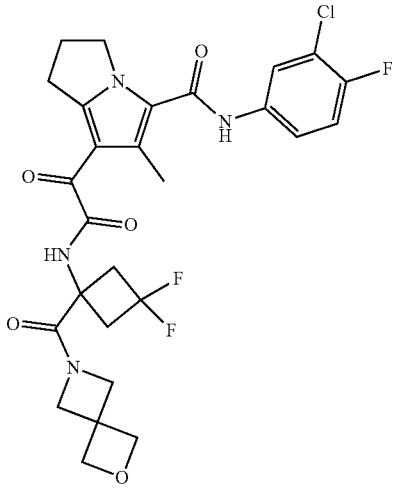

27

N-(3-chloro-4-fluorophenyl)-7-(2-((3,3-difluoro-1-(2-oxa-6-azaspiro[3.3]heptane-6-carbonyl)cyclobutyl)amino)-2-oxoacetyl)-6-methyl-2,3-dihydro-1H-pyrrolizine-5-carboxamide (27) was synthesized in a manner similar to Example 8 using 2-oxa-6-azaspiro[3.3]heptane in place of 3-amino-3-methylthietane 1,1-dioxide.

Example 28 N-(3-chloro-4-fluorophenyl)-7-(2-((3,3-difluoro-1-(6-(methylsulfonyl)-2,6-diazaspiro[3.3]heptane-2-carbonyl)cyclobutyl)amino)-2-oxoacetyl)-6-methyl-2,3-dihydro-1H-pyrrolizine-5-carboxamide (28)

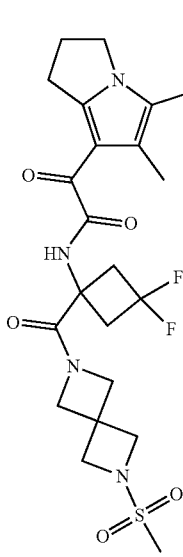

28

N-(3-chloro-4-fluorophenyl)-7-(2-((3,3-difluoro-1-(6-(methylsulfonyl)-2,6-diazaspiro[3.3]heptane-2-carbonyl)cyclobutyl)amino)-2-oxoacetyl)-6-methyl-2,3-dihydro-1H-pyrrolizine-5-carboxamide (28) was synthesized in a manner similar to Example 8 using 2-(methylsulfonyl)-2,6-diazaspiro[3.3]heptane in place of 3-amino-3-methylthietane 1,1-dioxide.

Example 29 N-(3-chloro-4-fluorophenyl)-7-(2-((3,3-difluoro-1-(1H-1,2,3-triazol-4-yl)cyclobutyl)amino)-2-oxoacetyl)-6-methyl-2,3-dihydro-1H-pyrrolizine-5-carboxamide (29)

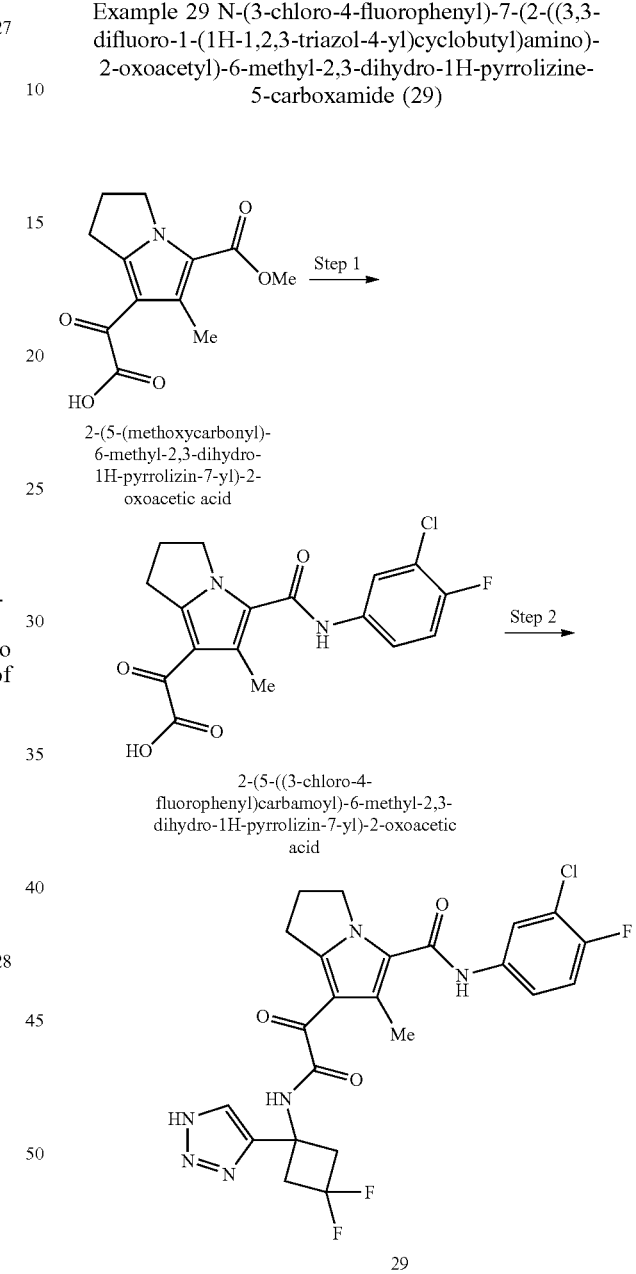

Step 1. Lithium bis(trimethylsilyl)amide solution (1.0 M in tetrahydrofuran, 2.39 mL, 2.4 mmol) was added via syringe over 2 min to a stirred mixture of 2-(5-(methoxycarbonyl)-6-methyl-2,3-dihydro-1H-pyrrolizin-7-yl)-2-oxoacetic acid (150 mg, 0.597 mmol) and 3-chloro-4-fluoroaniline (400 mg, 2.39 mmol) in tetrahydrofuran (5.0 mL) at 0° C. After 10 min, the reaction mixture was warmed to ambient temperature. After 19 h, saturated aqueous ammonium chloride solution (10 mL) and diethyl ether (125 mL) were added sequentially. The organic layer was washed sequentially with aqueous hydrogen chloride solution (0.5

M, 2×100 mL) and brine (50 mL), dried over anhydrous magnesium sulfate, filtered, and concentrated under reduced pressure to give 2-(5-((3-chloro-4-fluorophenyl)carbamoyl)-6-methyl-2,3-dihydro-1H-pyrrolizin-7-yl)-2-oxoacetic acid.

Step 2. 1-((Dimethylamino)(dimethyliminio)methyl)-1H-[1,2,3]triazolo[4,5-b]pyridine 3-oxide hexafluorophosphate (V) (391 mg, 1.03 mmol) was added as a solid to a stirred mixture of 2-(5-((3-chloro-4-fluorophenyl)carbamoyl)-6-methyl-2,3-dihydro-1H-pyrrolizin-7-yl)-2-oxoacetic acid (150 mg, 0.411 mmol), 3,3-difluoro-1-(1H-1,2,3-triazol-4-yl)cyclobutan-1-aminium chloride (95.3 mg, 0.452 mmol), and 4-methylmorpholine (226 µL, 2.06 mmol) in N,N-dimethylformamide (5.0 mL) at ambient temperature. After 17 h, piperidine (500 µL) was added. After 30 min, the reaction mixture was purified by reverse phase preparative HPLC (10-100% acetonitrile in water, 0.1% trifluoroacetic acid) to give N-(3-chloro-4-fluorophenyl)-7-(2-((3,3-difluoro-1-(1H-1,2,3-triazol-4-yl)cyclobutyl)amino)-2-oxoacetyl)-6-methyl-2,3-dihydro-1H-pyrrolizine-5-carboxamide (29).

Synthesis of 3,3-difluoro-1-(1H-1,2,3-triazol-4-yl)cyclobutan-1-aminium chloride

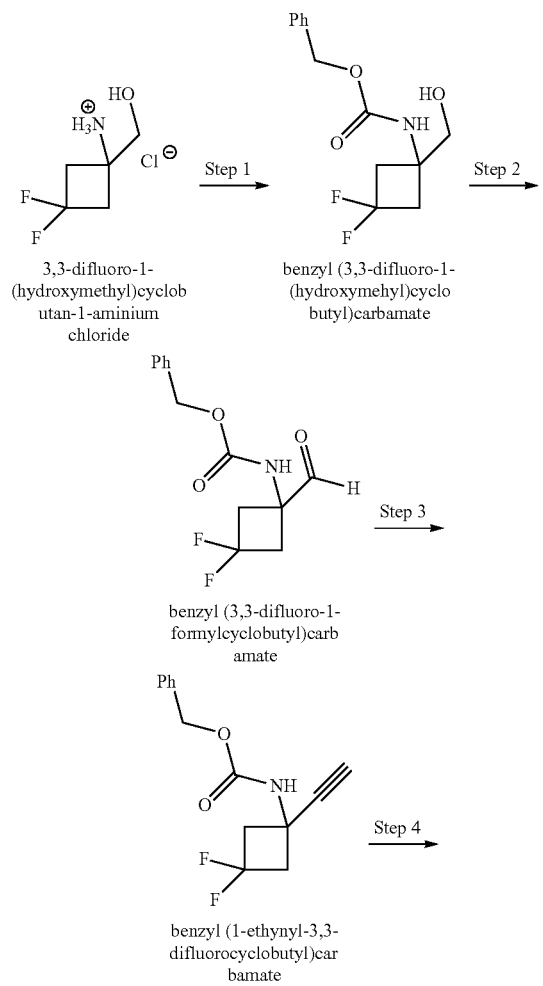

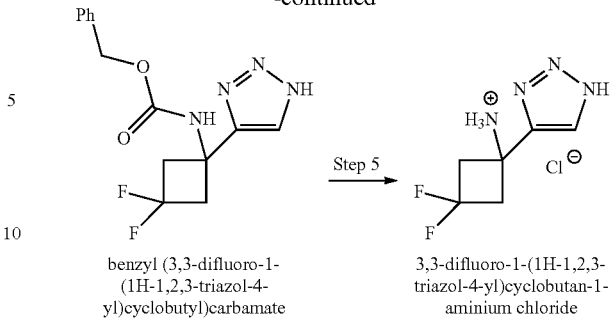

Steps 1-3. Benzyl (2,5-dioxopyrrolidin-1-yl) carbonate (696 mg, 2.79 mmol) was added as a solid to a stirred mixture of 3,3-difluoro-1-(hydroxymethyl)cyclobutan-1-aminium chloride (485 mg, 2.79 mmol) and N-ethyl-N-isopropylpropan-2-amine (1.22 mL, 6.99 mmol) in dichloromethane (20 mL) at ambient temperature. After 19 h, water (5 mL) and diethyl ether (100 mL) were added sequentially. The organic layer was washed with aqueous hydrogen chloride solution (2×70 mL) and water (70 mL), was dried over anhydrous magnesium sulfate, was filtered, and was concentrated under reduced pressure. The residue was dissolved in dichloromethane (20 mL), and the resulting solution was stirred at ambient temperature. Dess-Martin periodinane (1.78 g, 4.19 mmol) was added as a solid. After 4 h, aqueous sodium thiosulfate solution (1.0 M, 25 mL) and diethyl ether (100 mL) were added sequentially. The organic layer was washed with saturated aqueous sodium bicarbonate solution (2×100 mL) and water (100 mL), was dried over anhydrous magnesium sulfate, was filtered, and was concentrated under reduced pressure. The residue was dissolved in methanol (20 mL), potassium carbonate (1.16 g, 8.38 mmol) was added as a solid, and the resulting heterogeneous mixture was stirred at 0° C. Dimethyl (1-diazo-2-oxopropyl)phosphonate (629 µL, 4.19 mmol) was added via syringe. After 5 min, the reaction mixture was warmed to ambient temperature. After 15 h, the reaction mixture was filtered through celite, and the filter cake was extracted with ethyl acetate (80 mL). The filtrate was concentrated under reduced pressure, and the residue was dissolved in diethyl ether (100 mL). The organic layer was washed with water (50 mL), was dried over anhydrous magnesium sulfate, was filtered, and was concentrated under reduced pressure. The residue was purified by flash column chromatography on silica gel (0 to 10% ethyl acetate in hexanes) to give benzyl (1-ethynyl-3,3-difluorocyclobutyl)carbamate.

Step 4. Azidotrimethylsilane (344 µL, 2.59 mmol) was added via syringe to a stirred mixture of benzyl (1-ethynyl-3,3-difluorocyclobutyl)carbamate (491 mg, 1.85 mmol) and copper(I) iodide (17.6 mg, 92.5 µmol) in N,N-dimethylformamide (3.5 mL) and methanol (0.4 mL) at ambient temperature, and the resulting mixture was heated to 100° C. After 6 h, the reaction mixture was cooled to ambient temperature, and diethyl ether (130 mL) was added. The organic layer was washed sequentially with a mixture of brine and water (1:1 v:v, 100 mL) and water (100 mL), was dried over anhydrous magnesium sulfate, was filtered, and was concentrated under reduced pressure. The residue was purified by flash column chromatography on silica gel (0 to 40% ethyl acetate in hexanes) to give benzyl (3,3-difluoro-1-(1H-1,2,3-triazol-4-yl)cyclobutyl)carbamate.

Step 5. A heterogeneous mixture of benzyl (3,3-difluoro-1-(1H-1,2,3-triazol-4-yl)cyclobutyl)carbamate (307 mg, 0.995 mmol) and palladium on activated carbon (10% wt/wt, 248 mg, 23.3 µmol) in ethanol (10 mL) at ambient temperature was placed under 1 atm of hydrogen gas and stirred vigorously. After 1.5 h, the reaction mixture was filtered through celite, and the filter cake was extracted with ethyl acetate (80 mL). Hydrogen chloride solution (4 M in 1,4-dioxane, 0.5 mL) was added via syringe to the filtrate, and the resulting mixture was swirled vigorously for 1 min and then concentrated under reduced pressure to give 3,3-difluoro-1-(1H-1,2,3-triazol-4-yl)cyclobutan-1-aminium chloride.

Example 30 (1aR,6aR)-N-(3-cyano-4-fluorophenyl)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxamide (30)

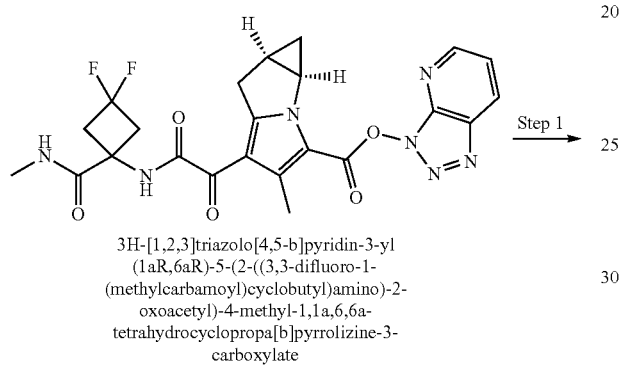

3H-[1,2,3]triazolo[4,5-b]pyridin-3-yl (1aR,6aR)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylate

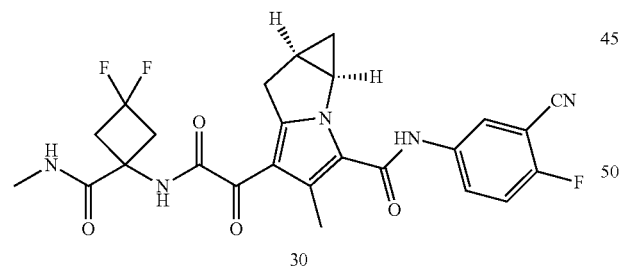

30

Crude 3H-[1,2,3]triazolo[4,5-b]pyridin-3-yl (1aR,6aR)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxylate from Example 5 was purified by silica gel column chromatography eluting with 0-10% methanol in dichloromethane. This material was converted to desired (1aR,6aR)-N-(3-cyano-4-fluorophenyl)-5-(2-((3,3-difluoro-1-(methylcarbamoyl)cyclobutyl)amino)-2-oxoacetyl)-4-methyl-1,1a,6,6a-tetrahydrocyclopropa[b]pyrrolizine-3-carboxamide (30) in a manner similar to Example 5, Step 6 using 5-amino-2-fluorobenzonitrile in place of 3-chloro-4-fluoroaniline.

Example 31 7-(2-((3,3-difluoro-1-(1H-1,2,3-triazol-4-yl)cyclobutyl)amino)-2-oxoacetyl)-N-(3,4-difluorophenyl)-6-methyl-2,3-dihydro-1H-pyrrolizine-5-carboxamide (31)

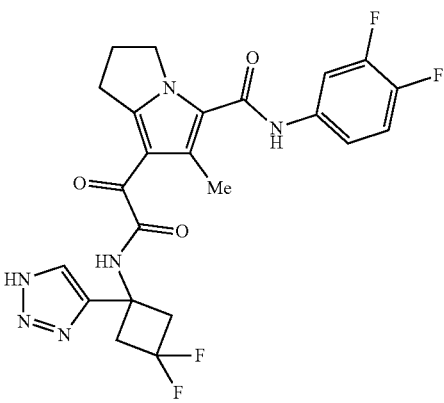

7-(2-((3,3-difluoro-1-(1H-1,2,3-triazol-4-yl)cyclobutyl)amino)-2-oxoacetyl)-N-(3,4-difluorophenyl)-6-methyl-2,3-dihydro-1H-pyrrolizine-5-carboxamide (31) was synthesized in a manner similar to Example 29 using 3,4-difluoroaniline in place of 3-chloro-4-fluoroaniline.

Example 32 7-(2-((3,3-difluoro-1-(1H-1,2,3-triazol-4-yl)cyclobutyl)amino)-2-oxoacetyl)-N-(4-fluorophenyl)-6-methyl-2,3-dihydro-1H-pyrrolizine-5-carboxamide (32)

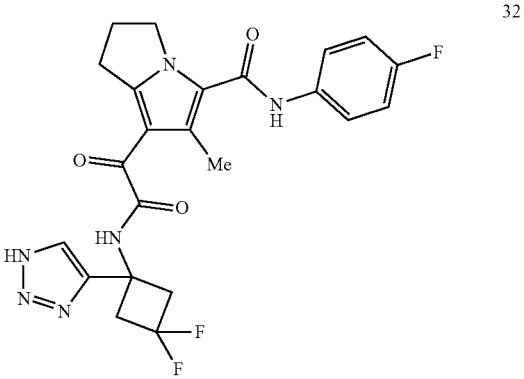 [SMILES: Cc1c(C(=O)C(=O)NC2(c3c[nH]nn3)CC(F)(F)C2)c2n(c1C(=O)Nc1ccc(F)cc1)CCC2]

7-(2-((3,3-difluoro-1-(1H-1,2,3-triazol-4-yl)cyclobutyl)amino)-2-oxoacetyl)-N-(4-fluorophenyl)-6-methyl-2,3-dihydro-1H-pyrrolizine-5-carboxamide (32) was synthesized in a manner similar to Example 29 using 4-fluoroaniline in place of 3-chloro-4-fluoroaniline.

Example 33 (1aS,6bR)-N-(3-chloro-4-fluorophenyl)-6-(2-((3,3-difluoro-1-(methylcarbamoyl)cyclobutyl)amino)-2-oxoacetyl)-5-methyl-1,1a,2,6b-tetrahydrocyclopropa[a]pyrrolizine-4-carboxamide (33)

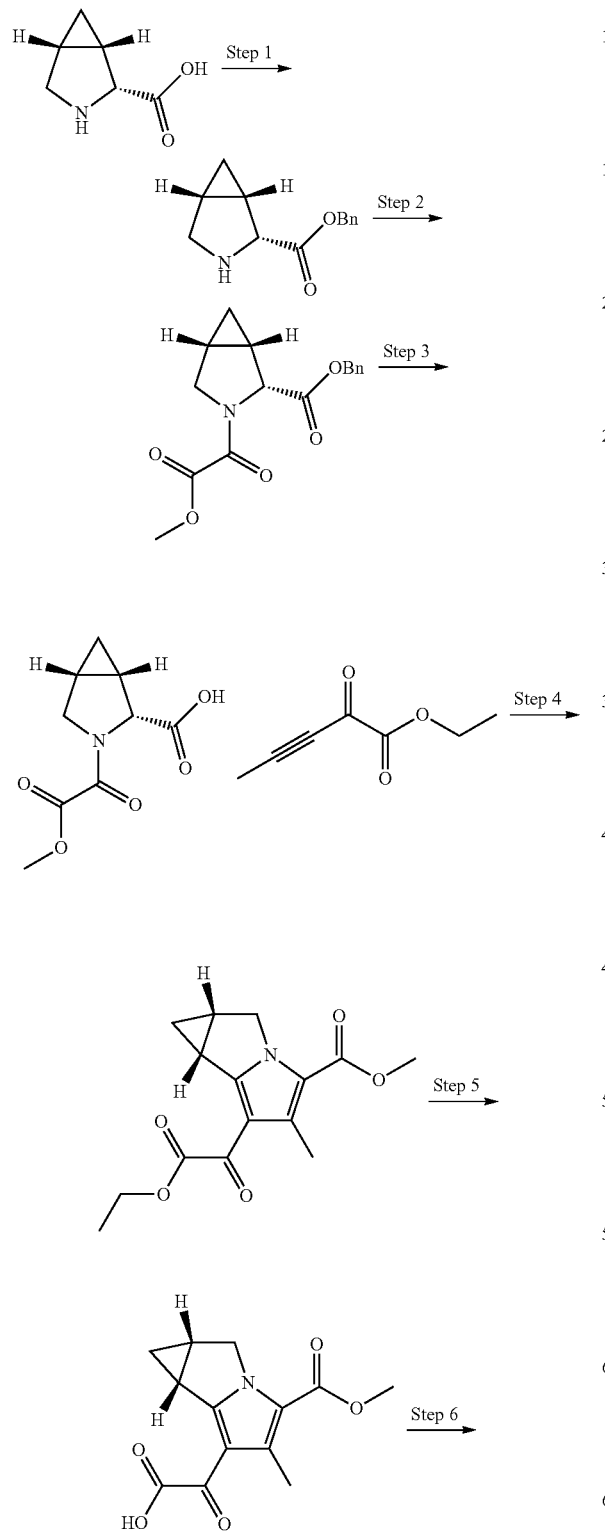

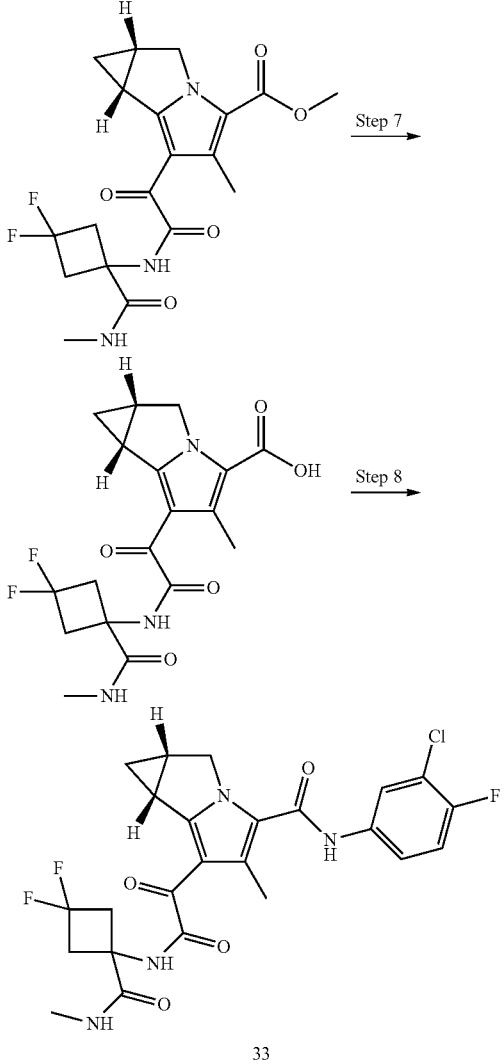

Step 1. To benzyl alcohol (4.2 g, 39 mmol) was thionyl chloride (2.0 g, 17.3 mmol) at 0° C. To this mixture was then added (1S,2R,5R)-3-azabicyclo[3.1.0]hexane-2-carboxylic acid (0.5 g, 3.9 mmol). The reaction was allowed to reach ambient temperature and stirred for 12 h. The reaction was then partitioned with saturated ammonium chloride and ethyl ether. The aqueous was then taken and basified and extracted with ethyl acetate the organic was then dried over magnesium sulfate to give benzyl (1S,2R,5R)-3-azabicyclo[3.1.0]hexane-2-carboxylate. The material was carried forward without further purification. LCMS-ESI+ (m/z): [M+H]$^+$: 218.05.

Step 2. A solution of benzyl (1S,2R,5R)-3-azabicyclo[3.1.0]hexane-2-carboxylate (0.4 g, 1.84 mmol) and N-ethyldiisopropylamine (0.9 mL, 5.5 mmol) in dichloromethane (20 mL) was stirred at 0° C. as methyl chlorooxoacetate (0.25 mL, 2.7 mmol) was added dropwise. The reaction mixture was warmed to ambient temperature and stirred for 1 h, at which point the reaction mixture was quenched by pouring into a cooled aqueous solution of saturated sodium bicarbonate. After the aqueous phase was thrice extracted with dichloromethane, the combined organic phases were washed with brine, dried over sodium sulfate, filtered, and solvent removed under reduced pressure to provide benzyl (1S,2R,5R)-3-(2-methoxy-2-oxoacetyl)-3-azabicyclo[3.1.0]hexane-2-carboxylate which was carried forward without purification. LCMS-ESI+ (m/z): [M+H]+: 303.99.

Step 3. A suspension of Benzyl (1S,2R,5R)-3-(2-methoxy-2-oxoacetyl)-3-azabicyclo[3.1.0]hexane-2-carboxylate (0.44 g, 1.5 mmol) and 10 wt % palladium on carbon (~50% water, 0.15 g, 0.7 mmol) in ethanol (20 mL) was stirred under one atmosphere hydrogen for 2 h. Upon completion of reaction the crude mixture was filtered through celite with ethanol rinses and concentrated under reduced pressure to provide (1S,2R,5R)-3-(2-methoxy-2-oxoacetyl)-3-azabicyclo[3.1.0]hexane-2-carboxylic acid which was carried forward without further purification. LCMS-ESI+ (m/z): [M+H]+: 213.93.

Step 4. To a solution of oxalyl chloride (0.3 mL, 3.6 mmol) and 1% DMF in toluene (0.5 mL) in toluene (10 mL) was added crude (1S,2R,5R)-3-(2-methoxy-2-oxoacetyl)-3-azabicyclo[3.1.0]hexane-2-carboxylic acid (0.7 mmol) in dichloromethane (4 mL) dropwise. The resulting solution was stirred at ambient temperature for 1 h. The solution was concentrated and the residue was co-evaporated with toluene (10 mL). The resulting residue was dried in vacuo for 30 min to give crude methyl 2-((1S,2R,5R)-2-(chlorocarbonyl)-3-azabicyclo[3.1.0]hexan-3-yl)-2-oxoacetate.

After the above crude methyl 2-((1S,2R,5R)-2-(chlorocarbonyl)-3-azabicyclo[3.1.0]hexan-3-yl)-2-oxoacetate was dissolved in acetonitrile (4 mL), 2,6-di-tert-butylpyridine (0.24 mL, 1.0 mmol) followed by ethyl 2-oxopent-3-ynoate (0.2 mL, 1.53 mmol) were added. The resulting solution was stirred at ambient temperature for 2 h. The mixture was concentrated and the residue was purified by silica gel column chromatography eluting with 0-50% ethyl acetate in hexanes to give methyl (1aS,6bR)-6-(2-ethoxy-2-oxoacetyl)-5-methyl-1,1a,2,6b-tetrahydrocyclopropa[a]pyrrolizine-4-carboxylate. LCMS-ESI+ (m/z): [M+H]+: 291.96.

Step 5. Methyl (1aS,6bR)-6-(2-ethoxy-2-oxoacetyl)-5-methyl-1,1a,2,6b-tetrahydrocyclopropa[a]pyrrolizine-4-carboxylate (0.1 g, 0.4 mmol) was dissolved in MeOH (5 mL), this was cooled to 0° C. and 1N NaOH (0.5 mL) was added the reaction was stirred for 30 mins till complete, reaction was condensed down and evaporated twice with toluene to give 2-((1aS,6bR)-4-(methoxycarbonyl)-5-methyl-1,1a,2,6b-tetrahydrocyclopropa[a]pyrrolizin-6-yl)-2-oxoacetic acid which was carried forward without further purification. LCMS-ESI+ (m/z): [M+H]+: 262.05.

Step 6. A solution 2-((1aS,6bR)-4-(methoxycarbonyl)-5-methyl-1,1a,2,6b-tetrahydrocyclopropa[a]pyrrolizin-6-yl)-2-oxoacetic acid (60 mg, 0.228 mmol), 1-[Bis(dimethylamino)methylene]-1H-1,2,3-triazolo[4,5-b]pyridinium 3-oxid hexafluorophosphate (HATU, 129 mg, 0.342 mmol) and 3,3-difluoro-(1-methylaminocarbonyl)-1-cyclobutanamine hydrochloride (37 mg, 0.228 mmol) in DMF (3 mL) was stirred at ambient temperature as N,N-diisopropylethylamine (0.11 mL, 0.68 mmol) was added. After 30 min at rt, the reaction mixture was diluted with ethyl acetate and washed with saturated aqueous ammonium chloride (×2), saturated aqueous sodium bicarbonate (×2), and brine (×1). After the aq. fractions were extracted with ethyl acetate (×1), the organic fractions were combined, dried over magnesium sulfate. After filtration, solvent was removed and the residue was purified by silica gel column chromatography eluting 0-100% ethyl acetate in hexanes to give methyl (1aS,6bR)-6-(2-((3,3-difluoro-1-(methylcarbamoyl)cyclobutyl)amino)-2-oxoacetyl)-5-methyl-1,1a,2,6b-tetrahydrocyclopropa[a]pyrrolizine-4-carboxylate. LCMS-ESI+ (m/z): [M+H]+: 408.22.

Step 7. To a solution (1aS,6bR)-6-(2-((3,3-difluoro-1-(methylcarbamoyl)cyclobutyl)amino)-2-oxoacetyl)-5-methyl-1,1a,2,6b-tetrahydrocyclopropa[a]pyrrolizine-4-carboxylate (102 mg, 0.25 mmol) in THF (2 mL), MeOH (2 mL) and water (3 mL) was added 1 N LiOH (1.6 mL) at rt. The resulting mixture was stirred at 60° C. bath for 8 h. After the reaction mixture was diluted with water and acidified with 1 N HCl, the product was extracted with ethyl acetate (6×). The combined extracts were dried with magnesium sulfate, concentrated, and dried to give crude (1aS,6bR)-6-(2-((3,3-difluoro-1-(methylcarbamoyl)cyclobutyl)amino)-2-oxoacetyl)-5-methyl-1,1a,2,6b-tetrahydrocyclopropa[a]pyrrolizine-4-carboxylic acid: LCMS-ESI+ (m/z): [M+H]+: 394.25.

Step 8. A solution of (1aS,6bR)-6-(2-((3,3-difluoro-1-(methylcarbamoyl)cyclobutyl)amino)-2-oxoacetyl)-5-methyl-1,1a,2,6b-tetrahydrocyclopropa[a]pyrrolizine-4-carboxylic acid (99 mg, 0.25 mmol), 3-chloro-4-fluoro aniline (35 mg, 0.25 mmol) and 1-[bis(dimethylamino)methylene]-1H-1,2,3-triazolo[4,5-b]pyridinium 3-oxid hexafluorophosphate (HATU, 141 mg, 0.38 mmol) in DMF (3 mL) was stirred at ambient temperature as N,N-diisopropylethylamine (0.13 mL, 0.75 mmol) was added. After 1.25 h at rt, the reaction mixture was diluted with ethyl acetate (30 mL) and washed with saturated aqueous ammonium chloride (×2), saturated aqueous sodium bicarbonate (×2), and brine (×1). After the aq. fractions were extracted with ethyl acetate (×1), the organic fractions were combined, dried over magnesium sulfate. To the reaction was added 2,6-lutidine (0.1 mL, 1.0 mmol) this was condensed to a thin film and heated till reaction was complete which was purified via reverse phase HPLC 0-100% acetonitrile in water to give (1aS,6bR)-N-(3-chloro-4-fluorophenyl)-6-(2-((3,3-difluoro-1-(methylcarbamoyl)cyclobutyl)amino)-2-oxoacetyl)-5-methyl-1,1a,2,6b-tetrahydrocyclopropa[a]pyrrolizine-4-carboxamide (33).

Example 34 (1aR,6bS)-N-(3-chloro-4-fluorophenyl)-6-(2-((3,3-difluoro-1-(methylcarbamoyl)cyclobutyl)amino)-2-oxoacetyl)-5-methyl-1,1a,2,6b-tetrahydrocyclopropa[a]pyrrolizine-4-carboxamide (34)

Compound 34 was synthesized in a manner similar to Example 33, using (1R,2S,5S)-3-azabicyclo[3.1.0]hexane-2-carboxylic acid in place of (1S,2R,5R)-3-azabicyclo[3.1.0]hexane-2-carboxylic acid.

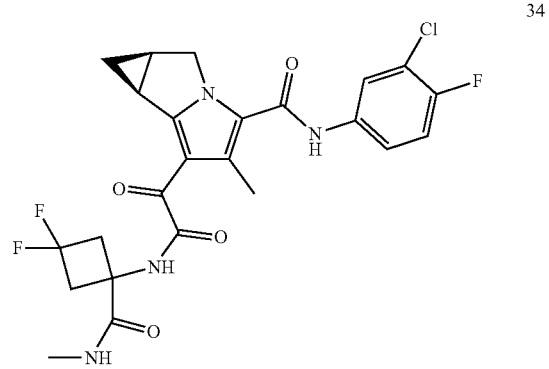 [SMILES: CNC(=O)C1(NC(=O)C(=O)c2c(C)c(C(=O)Nc3ccc(F)c(Cl)c3)n3c2[C@H]2C[C@H]2C3)CC(F)(F)C1]

34

Example 35 N-(3-cyano-4-fluorophenyl)-7-(2-((3,3-difluoro-1-(methylcarbamoyl)cyclobutyl)amino)-2-oxoacetyl)-6-methyl-2,3-dihydro-1H-pyrrolizine-5-carboxamide (35)

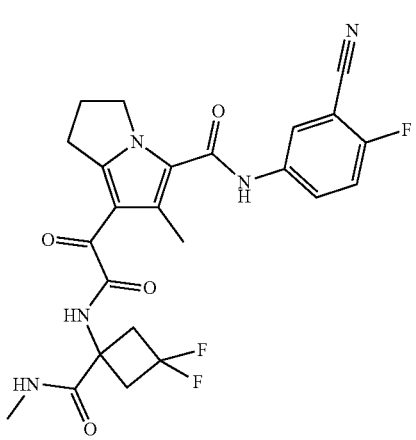

N-(3-cyano-4-fluorophenyl)-7-(2-((3,3-difluoro-1-(methylcarbamoyl)cyclobutyl)amino)-2-oxoacetyl)-6-methyl-2,3-dihydro-1H-pyrrolizine-5-carboxamide (35) was synthesized in a manner similar to Example 3 using 3-cyano-4-fluoroaniline in place of 3-chloro-4-fluoroaniline.

Example 36 7-(2-((3,3-difluoro-1-(methylcarbamoyl)cyclobutyl)amino)-2-oxoacetyl)-6-methyl-N-(3,4,5-trifluorophenyl)-2,3-dihydro-1H-pyrrolizine-5-carboxamide (36)

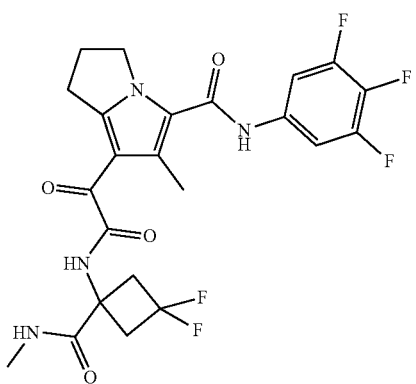

7-(2-((3,3-difluoro-1-(methylcarbamoyl)cyclobutyl)amino)-2-oxoacetyl)-6-methyl-N-(3,4,5-trifluorophenyl)-2,3-dihydro-1H-pyrrolizine-5-carboxamide (36) was synthesized in a manner similar to Example 3 using 3,4,5-trifluoroaniline in place of 3-chloro-4-fluoroaniline.

Example 37 N-(3-cyano-4-fluorophenyl)-7-(2-((3,3-difluoro-1-(1H-1,2,3-triazol-4-yl)cyclobutyl)amino)-2-oxoacetyl)-6-methyl-2,3-dihydro-1H-pyrrolizine-5-carboxamide (37)

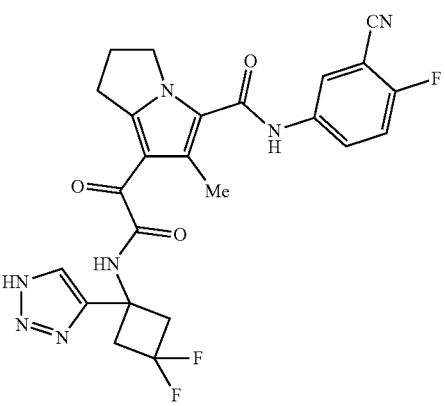

N-(3-Chloro-4-fluorophenyl)-7-(2-((3,3-difluoro-1-(1H-1,2,3-triazol-4-yl)cyclobutyl)amino)-2-oxoacetyl)-6-methyl-2,3-dihydro-1H-pyrrolizine-5-carboxamide (37) was synthesized in a manner similar to Example 29 using 5-amino-2-fluorobenzonitrile in place of 3-chloro-4-fluoroaniline.

Example 38. (1aR,6aR)-5-(2-((3,3-difluoro-1-(methylcarbamoyl)cyclobutyl)amino)-2-oxoacetyl)-4-methyl-N-(3,4,5-trifluorophenyl)-1,1a,6,6a-tetrahydrocyclopropa[b]pyrrolizine-3-carboxamide (38)

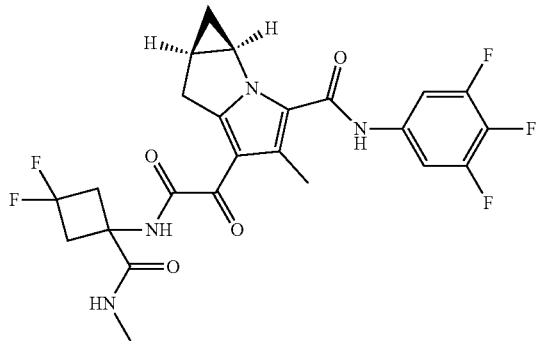

Example 38 was synthesized in a manner similar to Example 5 using 3,4,5 trifluoro aniline in place of 3-chloro-4-fluoro aniline.

Example 39 (1aR,6aR)-N-(3-chloro-4-fluorophenyl)-5-(2-((3,3-difluoro-1-(1H-1,2,3-triazol-4-yl)cyclobutyl)amino)-2-oxoacetyl)-4-methyl-1,1a,6,6a-tetrahydrocyclopropa[b]pyrrolizine-3-carboxamide (39)

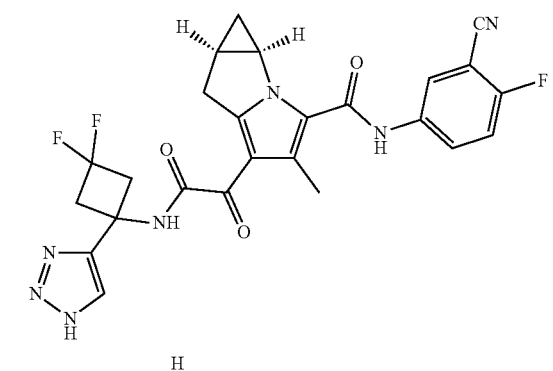

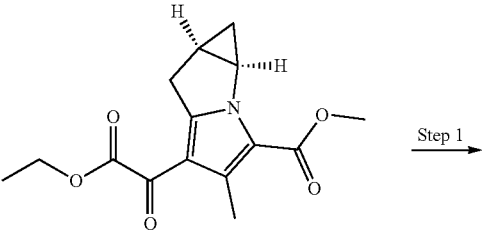

methyl (1aR,6aR)-5-(2-ethoxy-2-oxoacetyl)-4-methyl-1,1a,6,6a-tetrahydrocyclopropa[b]pyrrolizine-3-carboxylate

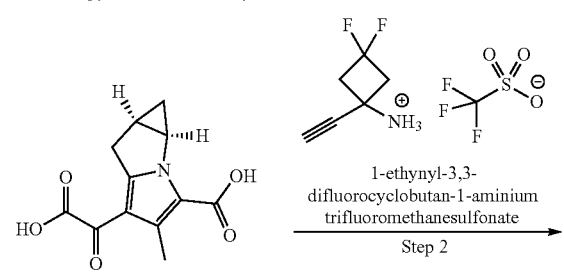

(1aR,6aR)-5-(carboxycarbonyl)-4-methyl-1,1a,6,6a-tetrahydrocyclopropa[b]pyrrolizine-3-carboxylic acid 1-ethynyl-3,3-difluorocyclobutan-1-aminium trifluoromethanesulfonate

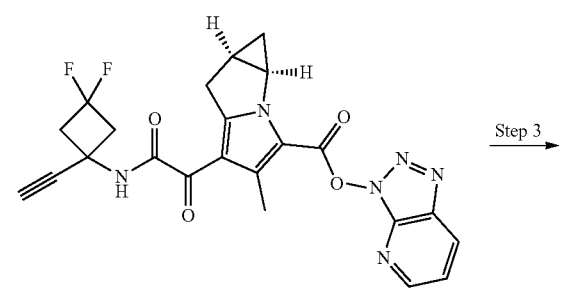

3H-[1,2,3]triazolo[4,5-b]pyridin-3-yl (1aR,6aR)-5-(2-((1-ethynyl-3,3-difluorocyclobutyl)amino)-2-oxoacetyl)-4-methyl-1,1a,6,6a-tetrahydrocyclopropa[b]pyrrolizine-3-carboxylate

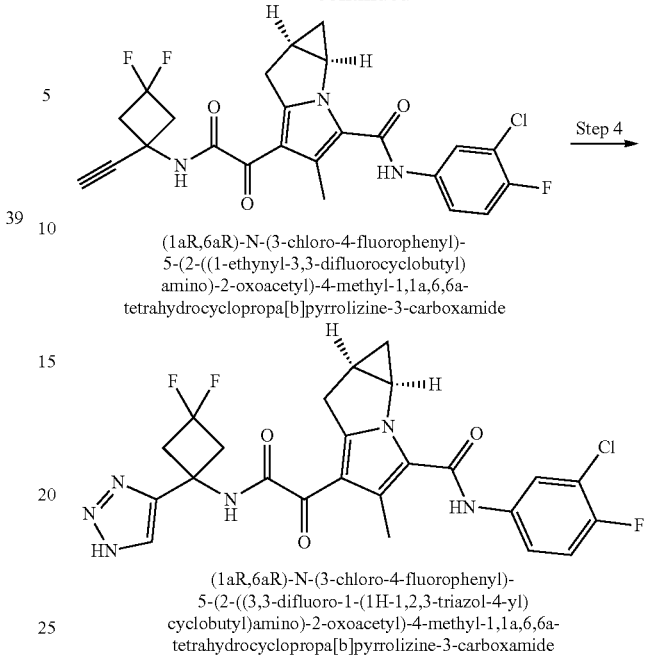

(1aR,6aR)-N-(3-chloro-4-fluorophenyl)-5-(2-((1-ethynyl-3,3-difluorocyclobutyl)amino)-2-oxoacetyl)-4-methyl-1,1a,6,6a-tetrahydrocyclopropa[b]pyrrolizine-3-carboxamide (1aR,6aR)-N-(3-chloro-4-fluorophenyl)-5-(2-((3,3-difluoro-1-(1H-1,2,3-triazol-4-yl)cyclobutyl)amino)-2-oxoacetyl)-4-methyl-1,1a,6,6a-tetrahydrocyclopropa[b]pyrrolizine-3-carboxamide Step 1. To a solution of methyl (1aR,6aR)-5-(2-ethoxy-2-oxoacetyl)-4-methyl-1,1a,6,6a-tetrahydrocyclopropa[b]pyrrolizine-3-carboxylate (2.500 g, 8.58 mmol) in tetrahydrofuran (20 mL), methanol (20 mL), and water (20 mL) was added 1 M lithium hydroxide (25.75 mL). After the resulting mixture was stirred at 65° C. for 8 h, the solution was concentrated to remove organic solvents, and the remained aqueous solution was diluted with water, acidified, and then the product was extracted with ethyl acetate. The extracts were dried over magnesium sulfate. After filtration, solvent was removed to get (1aR,6aR)-5-(carboxycarbonyl)-4-methyl-1,1a,6,6a-tetrahydrocyclopropa[b]pyrrolizine-3-carboxylic acid: LCMS-ESI+ (m/z): [M+H]+ calculated for $C_{12}H_{12}NO_5$: 250.07; found: 249.94.

Step 2. A solution of (1aR,6aR)-5-(carboxycarbonyl)-4-methyl-1,1a,6,6a-tetrahydrocyclopropa[b]pyrrolizine-3-carboxylic acid (230 mg, 0.923 mmol), 1-ethynyl-3,3-difluorocyclobutan-1-aminium trifluoromethanesulfonate, which was prepared from benzyl (1-ethynyl-3,3-difluorocyclobutyl)carbamate (291.4 mg, 1.099 mmol), 1-[bis(dimethylamino)methylene]-1H-1,2,3-triazolo[4,5-b]pyridinium 3-oxide hexafluorophosphate (844.3 mg, 2.221 mmol) in N,N-dimethylformamide (5 mL) was stirred at 0° C. as N,N-diisopropylethylamine (1.6 mL, 9.185 mmol) was added. After 1 h, the reaction mixture was diluted with ethyl acetate (50 mL), washed with 10% aqueous citric acid (×2), saturated sodium bicarbonate (×2), and brine (×1). After the aqueous fractions were extracted with ethyl acetate (×1), the organic fractions were combined, dried over magnesium sulfate. After filtration, solvent was removed and the residue was purified by silica gel column chromatography eluting 0-90% ethyl acetate in hexanes to give 3H-[1,2,3]triazolo[4,5-b]pyridin-3-yl (1aR,6aR)-5-(2-((1-ethynyl-3,3-difluorocyclobutyl)amino)-2-oxoacetyl)-4-methyl-1,1a,6,6a-tetrahydrocyclopropa[b]pyrrolizine-3-carboxylate: 1H NMR (400 MHz, Chloroform-d) δ 8.76 (dd, J=4.5, 1.4 Hz, 1H), 8.46 (dd, J=8.4, 1.4 Hz, 1H), 7.49 (d, J=1.4 Hz, 1H), 7.48-7.45 (m, 1H), 4.48 (t, J=6.0 Hz, 1H), 3.65 (dd, J=19.3, 6.9 Hz, 1H), 3.40 (d, J=19.2 Hz, 1H), 3.20 (h, J=13.5, 12.9

Hz, 4H), 2.76 (s, 3H), 2.53 (s, 1H), 2.14 (p, J=6.2 Hz, 1H), 1.17 (dt, J=8.6, 6.1 Hz, 1H), 0.54-0.39 (m, 1H)): LCMS-ESI+ (m/z): [M+H]+ calculated for $C_{23}H_{19}F_2N_6O_4$: 481.14; found: 480.86.

Step 3. To a solution of 3H-[1,2,3]triazolo[4,5-b]pyridin-3-yl (1aR,6aR)-5-(2-((1-ethynyl-3,3-difluorocyclobutyl)amino)-2-oxoacetyl)-4-methyl-1,1a,6,6a-tetrahydrocyclopropa[b]pyrrolizine-3-carboxylate (46.2 mg, 0.096 mmol) and 3-chloro-4-fluoroaniline (50.3 mg, 0.346 mmol) in dichloromethane (3 mL) was added 2,6-lutidine (0.05 mL, 0.429 mmol) and the resulting mixture was concentrated to an oil. The resulting oil was heated at 100° C. bath for 22 h. The residue was dissolved in dichloromethane and the insoluble material was filtered off. After the concentration of the filtrate, the residue was purified by silica gel column chromatography eluting 0-20% methanol in dichloromethane to give (1aR,6aR)-N-(3-chloro-4-fluorophenyl)-5-(2-((1-ethynyl-3,3-difluorocyclobutyl)amino)-2-oxoacetyl)-4-methyl-1,1a,6,6a-tetrahydrocyclopropa[b]pyrrolizine-3-carboxamide: $^1$H NMR (400 MHz, Acetonitrile-$d_3$) δ 8.26 (s, 1H), 7.89 (dd, J=6.8, 2.6 Hz, 1H), 7.82 (s, 1H), 7.53 (ddd, J=9.0, 4.2, 2.6 Hz, 1H), 7.23 (t, J=9.1 Hz, 1H), 4.30 (tt, J=5.9, 1.9 Hz, 1H), 3.35 (dd, J=18.7, 6.8 Hz, 1H), 3.25-3.05 (m, 5H), 2.79 (s, 1H), 2.49 (s, 3H), 2.12-2.02 (m, 1H), 1.08 (dt, J=8.6, 5.8 Hz, 1H), 0.32-0.19 (m, 1H): $^{19}$F NMR (376 MHz, Acetonitrile-$d_3$) δ −88.61 (dp, J=198.8, 11.1 Hz, 1F), −93.14 (dp, J=198.9, 12.6 Hz, 1F), −123.80 (ddd, J=8.9, 6.8, 4.3 Hz, 1F): LCMS-ESI+ (m/z): [M+H]+ calculated for $C_{24}H_{20}ClF_3N_3O_3$: 490.11; found: 490.17.

Step 4. A solution of (1aR,6aR)-N-(3-chloro-4-fluorophenyl)-5-(2-((1-ethynyl-3,3-difluorocyclobutyl)amino)-2-oxoacetyl)-4-methyl-1,1a,6,6a-tetrahydrocyclopropa[b]pyrrolizine-3-carboxamide (23.8 mg, 0.049 mmol) in N,N-dimethylformamide/methanol (9:1 mixture, 2 mL) was stirred at 0° C. bath while argon gas was bubbled for 30 min. To the solution was added copper iodide (2.00 mg, 0.0105 mmol) under argon atmosphere and argon gas was bubbled further through the resulting mixture for 5 min. After azidotrimethylsilane (15 mg, 0.130 mmol) was added to the mixture, the resulting vial was kept tightly and the mixture was stirred at 100° C. bath for 12 h. The reaction mixture was diluted with ethyl acetate and washed with 5% lithium chloride solution (×2). After the aqueous fractions were extracted with ethyl acetate (×1), the organic fractions were combined and dried over magnesium sulfate. After filtration, solvent was removed and the residue was purified by silica gel column chromatography 0-20% methanol in dichloromethane to give (1aR,6aR)-N-(3-chloro-4-fluorophenyl)-5-(2-((3,3-difluoro-1-(1H-1,2,3-triazol-4-yl)cyclobutyl)amino)-2-oxoacetyl)-4-methyl-1,1a,6,6a-tetrahydrocyclopropa[b]pyrrolizine-3-carboxamide (39).

Synthesis of 1-ethynyl-3,3-difluorocyclobutan-1-aminium chloride

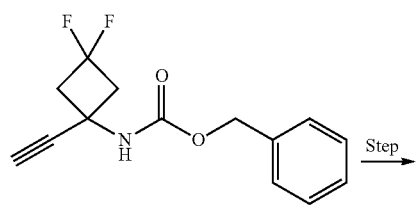

benzyl (1-ethynyl-3,3-difluorocyclobutyl)carbamate

Step →

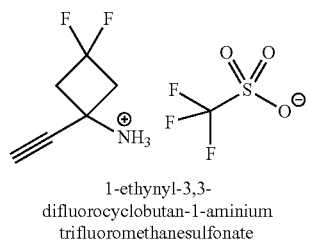

1-ethynyl-3,3-difluorocyclobutan-1-aminium trifluoromethanesulfonate

Step A solution of benzyl (1-ethynyl-3,3-difluorocyclobutyl)carbamate (291.4 mg, 1.099 mmol) and anisole (0.36 mL, 3.312 mmol) in dichloromethane (4 mL) was stirred at 0° C. bath as trifluoromethanesulfonic acid (0.2 mL, 2.260 mmol) was added. After 2 min, the mixture was stirred at room temperature for 2.25 h. The reaction mixture was diluted with water (~40 mL) and washed with a mixture of ether and hexane (1:3, 40 mL×1). The resulting aqueous fraction was concentrated using rotorvap to get crude 1-ethynyl-3,3-difluorocyclobutan-1-aminium trifluoromethanesulfonate: LCMS-ESI+ (m/z): [M+H]+ calculated for $C_6H_8F_2N$: 132.06; found: 131.91.

Example 40 (1aR,6aR)-5-(2-((3,3-difluoro-1-(1H-1,2,3-triazol-4-yl)cyclobutyl)amino)-2-oxoacetyl)-4-methyl-N-(3,4,5-trifluorophenyl)-1,1a,6,6a-tetrahydrocyclopropa[b]pyrrolizine-3-carboxamide (40)

40

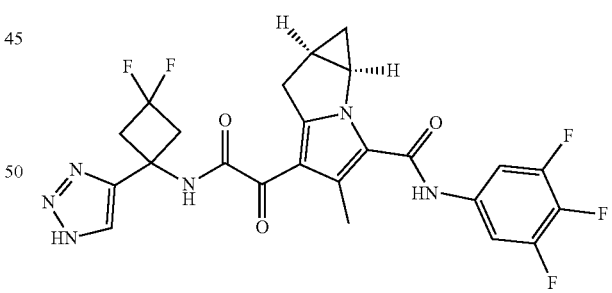

(1aR,6aR)-5-(2-((3,3-difluoro-1-(1H-1,2,3-triazol-4-yl)cyclobutyl)amino)-2-oxoacetyl)-4-methyl-N-(3,4,5-trifluorophenyl)-1,1a,6,6a-tetrahydrocyclopropa[b]pyrrolizine-3-carboxamide (40) was synthesized in a manner similar to Example 39 using 3,4,5-trifluoroaniline in place of 3-chloro-4-fluoroaniline.

Example 41 (1aR,6aR)-N-(3-cyano-4-fluorophenyl)-5-(2-((3,3-difluoro-1-(1H-1,2,3-triazol-4-yl)cyclobutyl)amino)-2-oxoacetyl)-4-methyl-1,1a,6,6a-tetrahydrocyclopropa[b]pyrrolizine-3-carboxamide (41)

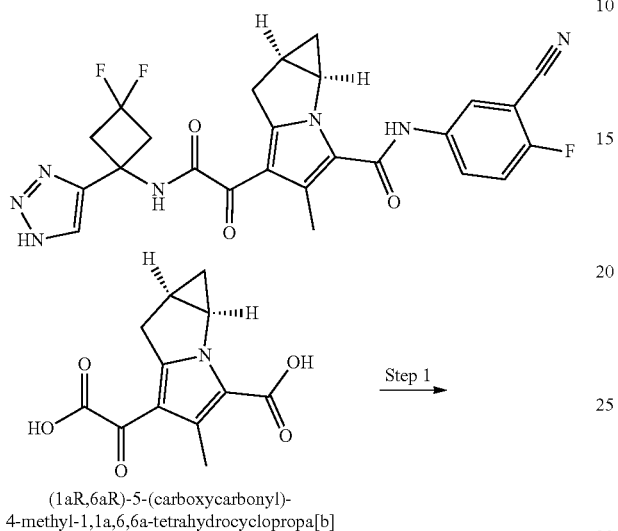

(1aR,6aR)-5-(carboxycarbonyl)-4-methyl-1,1a,6,6a-tetrahydrocyclopropa[b]pyrrolizine-3-carboxylic acid

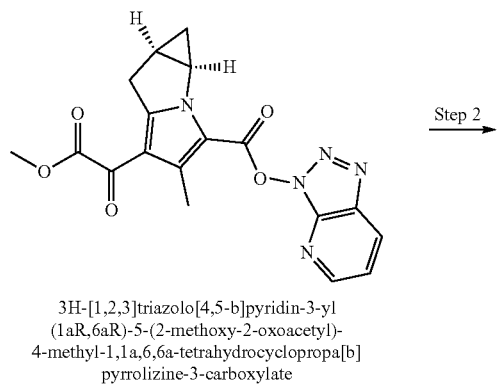

3H-[1,2,3]triazolo[4,5-b]pyridin-3-yl (1aR,6aR)-5-(2-methoxy-2-oxoacetyl)-4-methyl-1,1a,6,6a-tetrahydrocyclopropa[b]pyrrolizine-3-carboxylate

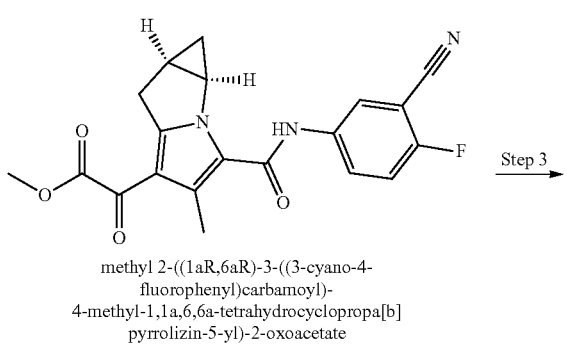

methyl 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetate

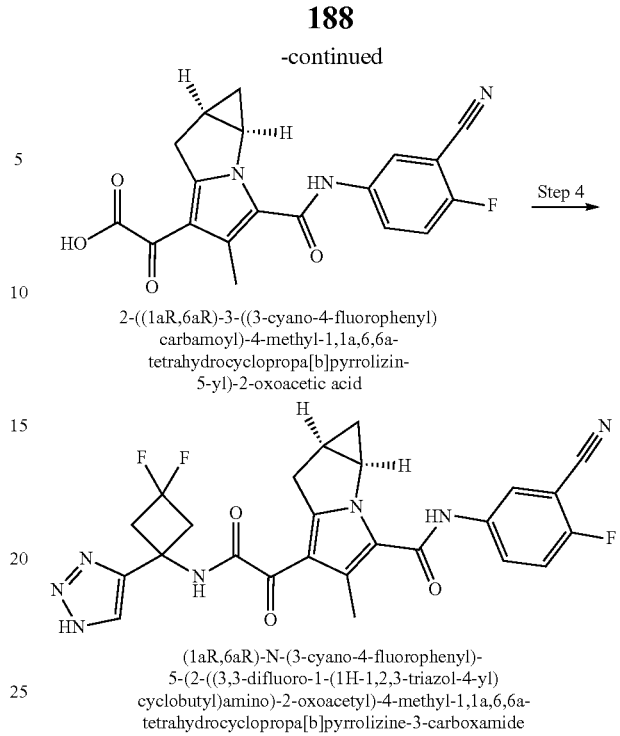

2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetic acid (1aR,6aR)-N-(3-cyano-4-fluorophenyl)-5-(2-((3,3-difluoro-1-(1H-1,2,3-triazol-4-yl)cyclobutyl)amino)-2-oxoacetyl)-4-methyl-1,1a,6,6a-tetrahydrocyclopropa[b]pyrrolizine-3-carboxamide Step 1. A solution of (1aR,6aR)-5-(carboxycarbonyl)-4-methyl-1,1a,6,6a-tetrahydrocyclopropa[b]pyrrolizine-3-carboxylic acid (299.5 mg, 1.202 mmol) in N,N-dimethylformamide (6 mL) and methanol (0.6 mL) was stirred at 0° C. bath as and 1-[bis(dimethylamino)methylene]-1H-1,2,3-triazolo[4,5-b]pyridinium 3-oxide hexafluorophosphate (1150.1 mg, 3.025 mmol) followed by N,N-diisopropylethylamine (1.5 mL, 8.612 mmol) were added. After 2 min, the mixture was stirred at room temperature. After 30 min, the reaction mixture was diluted with ethyl acetate and washed with 5% lithium chloride solution (×2). After the aqueous fractions were extracted with ethyl acetate (×1), the organic fractions were combined, dried over magnesium sulfate. After filtration, solvent was removed and the residue was purified by silica gel column chromatography eluting 0-100% ethyl acetate in hexanes to get 3H-[1,2,3]triazolo[4,5-b]pyridin-3-yl (1aR,6aR)-5-(2-methoxy-2-oxoacetyl)-4-methyl-1,1a,6,6a-tetrahydrocyclopropa[b]pyrrolizine-3-carboxylate: LCMS-ESI+ (m/z): [M+H]$^+$ calculated for $C_{18}H_{16}N_5O_5$: 382.12; found: 381.82.

Step 2. To a solution of 3H-[1,2,3]triazolo[4,5-b]pyridin-3-yl (1aR,6aR)-5-(2-methoxy-2-oxoacetyl)-4-methyl-1,1a,6,6a-tetrahydrocyclopropa[b]pyrrolizine-3-carboxylate (138.7 mg, 0.364 mmol) and 5-amino-2-fluorobenzonitrile (153.8 mg, 1.130 mmol) in dichloromethane (2 mL) was added 2,6-lutidine (0.17 mL, 1.460 mmol) and the resulting solution was concentrated to yield an oil. The resulting oil was heated at 70° C. bath for 20 h. After the residue was triturated with N,N-dimethylformamide and filtered, the filtrate was purified by reverse phase preparative HPLC (10-100% acetonitrile in water, 0.1% trifluoroacetic acid) to get methyl 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetate: $^1$H NMR (400 MHz, Acetonitrile-d$_3$) δ 8.38 (s, 1H), 8.08 (dd, J=5.7, 2.7 Hz, 1H), 7.89 (ddd, J=9.2, 4.8, 2.8 Hz, 1H), 7.33 (t, J=9.0 Hz, 1H), 4.30 (t, J=5.9 Hz, 1H), 3.88 (s, 3H), 3.20 (dd, J=18.2, 6.8 Hz, 1H), 3.06-2.94 (m, 1H), 2.51 (s, 3H), 2.15 (d, J=7.8 Hz, 1H), 1.11 (dt, J=8.7, 6.0 Hz, 1H), 0.39-0.29 (m, 1H): $^{19}$F NMR (376

MHz, Acetonitrile-d₃) δ -115.79—115.91 (m): LCMS-ESI+ (m/z): [M+H]⁺ calculated for $C_{20}H_{17}FN_3O_4$: 382.12; found: 382.14.

Step 3. A solution of methyl 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetate (105.9 mg, 0.278 mmol) in tetrahydrofuran (5 mL), methanol (2 mL) and water (4 mL) was stirred at room temperature as 1 N lithium hydroxide (0.56 mL) was added. After 30 min at room temperature, the reaction mixture was concentrated to remove most of the organic solvent, diluted with water, acidified with 1 N HCl, and the product was extracted with ethyl acetate (×3). The combined extracts were dried over magnesium sulfate. After filtration, solvent was removed to get 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetic acid: LCMS-ESI+ (m/z): [M+H]⁺ calculated for $C_{19}H_{15}FN_3O_4$: 368.10; found: 368.08.

Step 4. A solution of 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetic acid (27.6 mg, 75.14 umol), 3,3-difluoro-1-(1H-1,2,3-triazol-4-yl)cyclobutan-1-amine (14.8 mg, 84.98 umol), and 1-[bis(dimethylamino)methylene]-1H-1,2,3-triazolo[4,5-b]pyridinium 3-oxide hexafluorophosphate (65.80 mg, 173.07 mmol) in N,N-dimethylformamide (1.5 mL) was stirred at room temperature as N,N-diisopropylethylamine (0.1 mL, 574.11 umol) was added. The reaction mixture was diluted with ethyl acetate (30 mL), washed with saturated ammonium chloride (×2), saturated sodium bicarbonate (×2), and brine (×1). After the aqueous fractions were extracted with ethyl acetate (×1), the organic fractions were combined and dried over magnesium sulfate. After filtration, solvent was removed and the residue was purified by reverse phase preparative HPLC (10-100% acetonitrile in water, 0.1% trifluoroacetic acid) to get (1aR,6aR)-N-(3-cyano-4-fluorophenyl)-5-(2-((3,3-difluoro-1-(1H-1,2,3-triazol-4-yl)cyclobutyl)amino)-2-oxoacetyl)-4-methyl-1,1a,6,6a-tetrahydrocyclopropa[b]pyrrolizine-3-carboxamide (41).

Example 42 (1aR,6aR)-5-(2-((3,3-difluoro-1-(1H-1,2,3-triazol-4-yl)cyclobutyl)amino)-2-oxoacetyl)-N-(3,4-difluorophenyl)-4-methyl-1,1a,6,6a-tetrahydrocyclopropa[b]pyrrolizine-3-carboxamide (42)

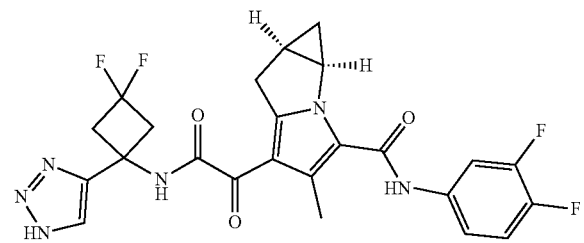

42

(1aR,6aR)-5-(2-((3,3-difluoro-1-(1H-1,2,3-triazol-4-yl)cyclobutyl)amino)-2-oxoacetyl)-N-(3,4-difluorophenyl)-4-methyl-1,1a,6,6a-tetrahydrocyclopropa[b]pyrrolizine-3-carboxamide (42) was synthesized in a manner similar to Example 41 using 3,4-difluoroaniline in place of 3-cyano-4-fluoroaniline.

Example 43 7-(2-((1-(1H-1,2,3-triazol-4-yl)cyclopropyl)amino)-2-oxoacetyl)-N-(3,4-difluorophenyl)-6-methyl-2,3-dihydro-1H-pyrrolizine-5-carboxamide (43)

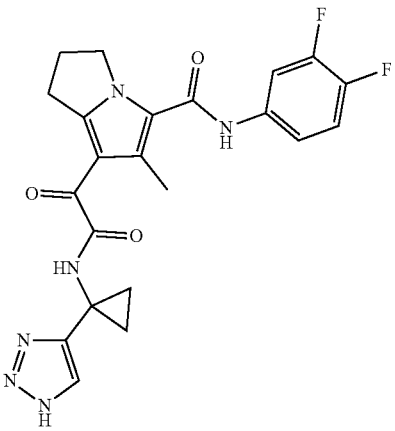

43

7a-(2-((1-(1H-1,2,3-triazol-4-yl)cyclopropyl)amino)-2-oxoacetyl)-N-(3,4-difluorophenyl)-6-methyl-2,3-dihydro-1H-pyrrolizine-5-carboxamide (43) was synthesized in a manner similar to Example 29 using 1-(1H-1,2,3-triazol-4-yl)cyclopropan-1-amine hydrochloride in place of 3,3-difluoro-1-(1H-1,2,3-triazol-4-yl)cyclobutan-1-aminium chloride and 3,4-difluoroaniline in place of 3-chloro-4-fluoroaniline.

Example 44 7-(2-((3,3-difluoro-1-(methylcarbamoyl)cyclobutyl)amino)-2-oxoacetyl)-N-(3,4-difluorophenyl)-6-methyl-2,3-dihydro-1H-pyrrolizine-5-carboxamide (44)

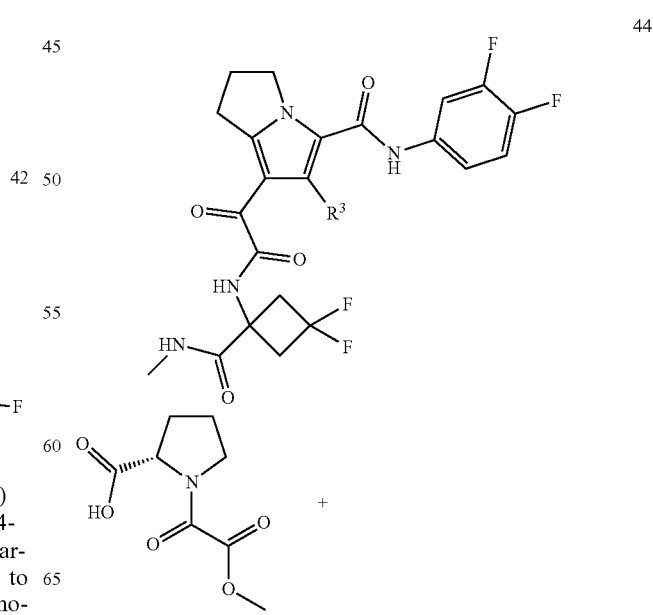

44

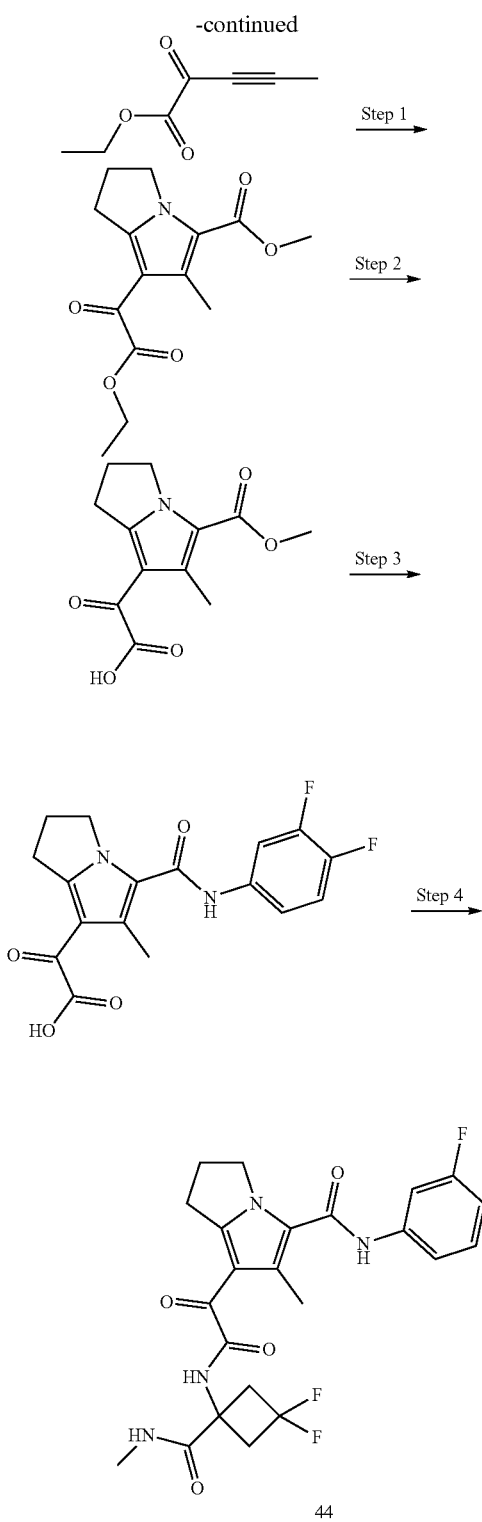

44

Step 1. To a solution of (2-methoxy-2-oxoacetyl)-L-proline (8.75 g, 43.5 mmol) in a 3:1 mixture of toluene:dichloromethane (80 mL) at 0° C. was added oxalyl chloride (7.4 mL, 86 mmol) dropwise, followed by N,N-dimethylformamide (0.1 mL). The reaction solution was allowed to warm to ambient temperature stirred for 2 hours at which point solvent was removed under reduced pressure and the residue redissolved in acetonitrile (80 mL). To this solution was added 2,6-lutidine (15 mL, 129 mmol) followed by ethyl 2-oxopent-3-ynoate (5.1 mL, 39 mmol) and the reaction mixture was allowed to stir overnight. The reaction mixture was then concentrated under reduced pressure, diluted with ethyl acetate, sequentially washed with saturated aqueous solutions of ammonium chloride then sodium chloride, dried over sodium sulfate, filtered, and concentrated under reduced pressure. The residue was purified by silica gel chromatography eluting with 0-60% ethyl acetate in hexanes to afford methyl 7-(2-ethoxy-2-oxoacetyl)-6-methyl-2,3-dihydro-1H-pyrrolizine-5-carboxylate: $^1$H NMR (400 MHz, Chloroform-d) δ 4.36 (q, J=7.1 Hz, 2H), 4.29 (dd, J=8.1, 6.6 Hz, 2H), 3.85 (s, 3H), 3.04-2.92 (m, 2H), 2.59 (s, 3H), 2.52-2.46 (m, 2H), 1.39 (t, J=7.2 Hz, 3H). LCMS-ESI+ (m/z): [M+H]$^+$ calculated for $C_{14}H_{18}NO_5$: 280.12; found: 280.03.

Step 2. To a 0° C. solution of methyl 7-(2-ethoxy-2-oxoacetyl)-6-methyl-2,3-dihydro-1H-pyrrolizine-5-carboxylate (5.54 g, 19.8 mmol) in ethanol (60 mL) was added a 4N aqueous solution of sodium hydroxide (5 mL, 20 mmol). The reaction solution was allowed to stir at 0° C. for 5 minutes, at which point the mixture was acidified by addition of dilute aqueous hydrochloric acid. The mixture was partitioned between water and ethyl acetate, and the aqueous phase thrice extracted to ethyl acetate. The combined organic phases were washed with a saturated aqueous solution of ammonium chloride, dried over sodium sulfate, filtered, and concentrated under reduced pressure to afford 2-(5-(methoxycarbonyl)-6-methyl-2,3-dihydro-1H-pyrrolizin-7-yl)-2-oxoacetic acid which was carried forward without further purification: $^1$H NMR (400 MHz, DMSO-d6) δ 4.21 (t, J=7.3 Hz, 2H), 3.77 (s, 3H), 2.90 (t, J=7.6 Hz, 2H), 2.49 (s, 3H), 2.42 (p, J=7.6 Hz, 2H). LCMS-ESI+ (m/z): [M+H]$^+$ calculated for $C_{12}H_{14}NO_5$: 252.09; found: 252.02.

Step 3. To a solution of 2-(5-(methoxycarbonyl)-6-methyl-2,3-dihydro-1H-pyrrolizin-7-yl)-2-oxoacetic acid (210 mg, 0.84 mmol) and 3,4-difluoroaniline (0.12 mL, 1.2 mmol) in tetrahydrofuran (2.5 mL) was added a 1M solution of lithium hexamethyldisilazide in tetrahydrofuran (2.5 mL, 2.5 mmol). The reaction mixture was allowed to stir for 18 hours and was subsequently quenched with a saturated aqueous solution of ammonium chloride. The aqueous phase was thrice extracted to diethyl ether and the combined organic phases sequentially washed with 1M aqueous hydrochloric acid (twice) then brine, dried over sodium sulfate, filtered, and concentrated under reduced pressure to afford 2-(5-((3,4-difluorophenyl)carbamoyl)-6-methyl-2,3-dihydro-1H-pyrrolizin-7-yl)-2-oxoacetic acid which was carried forward without further purification: LCMS-ESI+ (m/z): [M+H]$^+$ calculated for $C_{17}H_{15}F_2N_2O_4$: 349.10; found: 349.13.

Step 4. To a solution 2-(5-((3,4-difluorophenyl)carbamoyl)-6-methyl-2,3-dihydro-1H-pyrrolizin-7-yl)-2-oxoacetic acid (449 mg, 1.29 mmol), 1-amino-3,3-difluoro-N-methylcyclobutane-1-carboxamide (233 mg, 1.42 mmol), and N-methylmorpholine (0.55 mL, 5 mmol) in dimethylformamide (2 mL) was added 1-[Bis(dimethylamino)methylene]-1H-1,2,3-triazolo[4,5-b]pyridinium-3-oxide hexafluorophosphate (0.81 g, 2.1 mmol) and stirred for 30 minutes. The crude reaction mixture was then passed through a syringe filter and purified by reverse phase preparative HPLC (10-100% acetonitrile in water, 0.1% trifluoroacetic acid) to afford 7-(2-((3,3-difluoro-1-(methylcarbamoyl)cyclobutyl)amino)-2-oxoacetyl)-N-(3,4-difluorophenyl)-6-methyl-2,3-dihydro-1H-pyrrolizine-5-carboxamide (44).

Example 45: (R)-7-(2-((1-(1H-1,2,3-triazol-4-yl)cyclopropyl)amino)-2-oxoacetyl)-N-(3-chloro-4-fluorophenyl)-2-fluoro-6-methyl-2,3-dihydro-1H-pyrrolizine carboxamide (45)

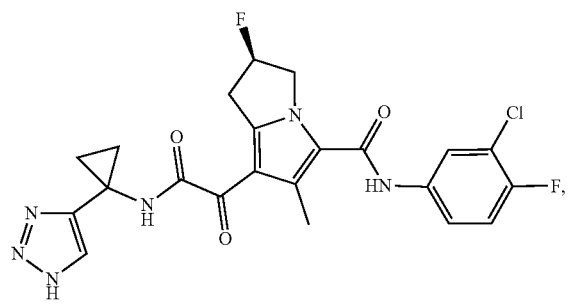

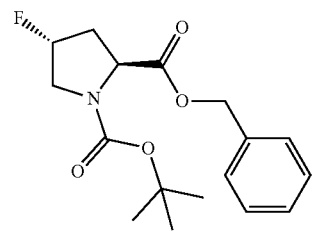

(2S,4R)-1-(tert-butoxycarbonyl)-4-fluoropyrrolidine-2-carboxylic acid

Step 1

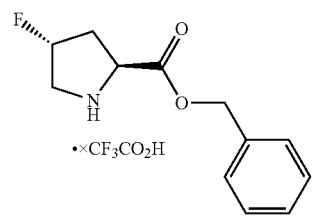

2-benzyl 1-(tert-butyl) (2S,4R)-4-fluoropyrrolidine-1,2-dicarboxylate

Step 2

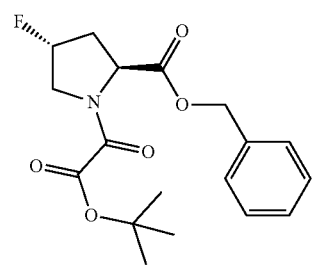

·×CF$_3$CO$_2$H (2S,4R)-2-((benzyloxy)carbonyl)-4-fluoropyrrolidin-1-ium 2,2,2-trifluoroacetate Step 3 benzyl (2S,4R)-1-(2-tert-butoxy)-2-oxoacetyl)-4-fluoropyrrolidine-2-carboxylate

Step 4

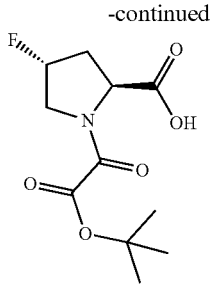

(2S,4R)-1-(2-(tert-butoxy)-2-oxoacetyl)-4-fluoropyrrolidine-2-carboxylic acid

Step 5

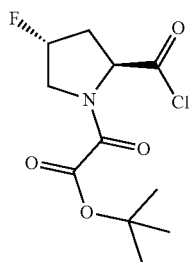

tert-butyl 2-((2S,4R)-2-(chlorocarbonyl)-4-fluoropyrrolidin-1-yl)-2-oxoacetate

Step 6

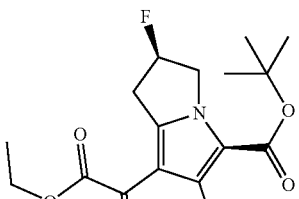

tert-butyl (R)-7-(2-ethoxy-2-oxoacetyl)-2-fluoro-6-methyl-2,3-dihydro-1H-pyrrolizine-5-carboxylate Step 7

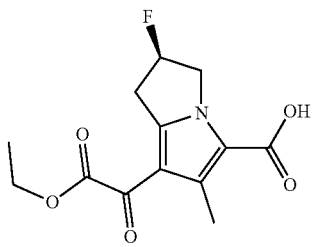

(R)-7-(2-ethoxy-2-oxoacetyl)-2-fluoro-6-methyl-2,3-dihydro-1H-pyrrolizine-5-carboxylic acid Step 8

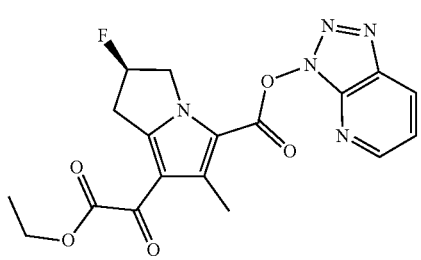

3H-[1,2,3]triazolo[4,5-b]pyridin-3-yl (R)-7-(2-ethoxy-2-oxoacetyl)-2-fluoro-6-methyl-2,3-dihydro-1H-pyrrolizine-5-carboxylate Step 9

-continued

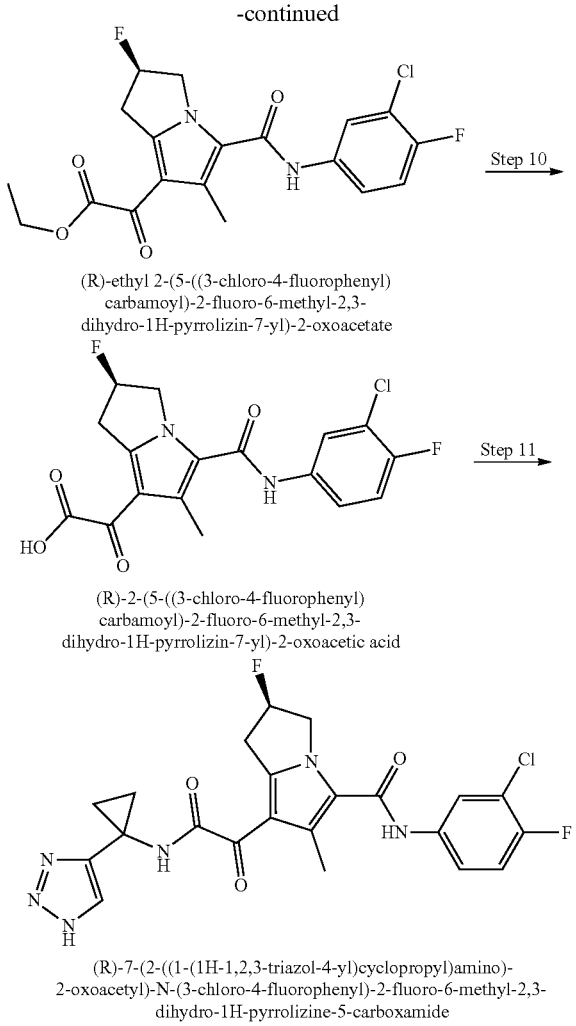

(R)-ethyl 2-(5-((3-chloro-4-fluorophenyl)carbamoyl)-2-fluoro-6-methyl-2,3-dihydro-1H-pyrrolizin-7-yl)-2-oxoacetate (R)-2-(5-((3-chloro-4-fluorophenyl)carbamoyl)-2-fluoro-6-methyl-2,3-dihydro-1H-pyrrolizin-7-yl)-2-oxoacetic acid (R)-7-(2-(((1-(1H-1,2,3-triazol-4-yl)cyclopropyl)amino)-2-oxoacetyl)-N-(3-chloro-4-fluorophenyl)-2-fluoro-6-methyl-2,3-dihydro-1H-pyrrolizine-5-carboxamide Step 1 A mixture of (2S,4R)-1-(tert-butoxycarbonyl)-4-fluoropyrrolidine-2-carboxylic acid (15 g, 66 mmol) and cesium carbonate (32 g, 99 mmol) in N,N-dimethylformamide (100 mL) was stirred at room temperature as benzyl bromide (9.4 mL, 79 mmol) was added via syringe. After being allowed to stir overnight at room temperature, the reaction mixture was diluted with water (~300 mL) and extracted three times with ethyl acetate. The combined extracts were washed once with saturated aqueous sodium chloride solution, dried over anhydrous magnesium sulfate, filtered, and concentrated under reduced pressure. The crude residue was purified via flash chromatography (silica gel) to obtain 2-benzyl 1-(tert-butyl) (2S,4R)-4-fluoropyrrolidine-1,2-dicarboxylate.

Step 2 A solution of 2-benzyl 1-(tert-butyl) (2S,4R)-4-fluoropyrrolidine-1,2-dicarboxylate (6.4 g, 20 mmol) in dichloromethane (35 mL) was stirred at room temperature as trifluoroacetic acid (22 mL) was added. When LC/MS analysis indicated the complete removal of the protecting group, the mixture was concentrated under reduced pressure and (2S,4R)-2-((benzyloxy)carbonyl)-4-fluoropyrrolidin-1-ium trifluoroacetate was carried forward. LCMS-ESI+ (m/z): [M+H]$^+$ calculated for $C_{12}H_{15}FNO_2$: 224.1; found: 224.0.

Step 3 A solution (2S,4R)-2-((benzyloxy)carbonyl)-4-fluoropyrrolidin-1-ium trifluoroacetate (20 mmol assumed) in anhydrous dichloromethane (100 mL) was cooled in an ice-water bath under an atmosphere of argon. N,N-diisopropylethylamine (17 mL, 99 mmol) was added via syringe, followed by tert-butyl oxalyl chloride (3.79 g, 23 mmol). The ice-bath was removed and the mixture was allowed to regain room temperature. The reaction mixture was quenched with water. The aqueous phase was extracted twice with dichloromethane. The combined organic extracts were dried over anhydrous magnesium sulfate, filtered, and concentrated under reduced pressure. The crude residue was purified by flash chromatography (silica gel) to provide benzyl (2S,4R)-1-(2-(tert-butoxy)-2-oxoacetyl)-4-fluoropyrrolidine-2-carboxylate. LCMS-ESI+ (m/z): [M+H]$^+$ calculated for $C_{18}H_{23}FNO_5$: 352.2; found: 351.8.

Step 4 A solution of benzyl (2S,4R)-4-fluoro-1-(2-tert-butoxy-2-oxoacetyl)pyrrolidine-2-carboxylate (6.76 g, 19 mmol) in ethanol (100 mL) was treated with small chunk of dry ice and allowed to stir until the bubbling stopped (to degas the solvent). The reaction mixture then treated with 10% palladium on carbon (wetted with approximately 55% water, 0.55 g, 0.23 mmol). The vessel was stirred under 1 atmosphere of hydrogen for two hours. The mixture was filtered through a pad of Celite diatomaceous earth, and the filtrate was concentrated to give (2S,4R)-1-(2-(tert-butoxy)-2-oxoacetyl)-4-fluoropyrrolidine-2-carboxylic acid. LCMS-ESI+ (m/z): [M+H]$^+$ calculated for $C_{11}H_{17}FNO_5$: 262.1; found: 261.7

Step 5 To a mixture of oxalyl chloride (5.6 mL, 66 mmol) and N,N-dimethylformamide (5 mL of 1% (v/v) N,N-dimethylformamide in toluene) in toluene (60 mL) was added a solution of (2S,4R)-1-(2-(tert-butoxy)-2-oxoacetyl)-4-fluoropyrrolidine-2-carboxylic acid (13 mmol) in dichloromethane (26 mL+15 mL rinsate) dropwise via syringe over 60 minutes. The resulting mixture was stirred at room temperature for 70 minutes, at which time the LC/MS analysis of an aliquot in methanol revealed consumption of the starting acid with concomitant formation of the methyl ester. The mixture was concentrated under reduced pressure, and the putative tert-butyl 2-((2S,4R)-2-(chlorocarbonyl)-4-fluoropyrrolidin-1-yl)-2-oxoacetate was carried forward.

Step 6 Crude tert-butyl 2-((2S,4R)-2-(chlorocarbonyl)-4-fluoropyrrolidin-1-yl)-2-oxoacetate (13 mmol assumed) was dissolved in acetonitrile (50 mL) and treated with 2,6-di-tert-butylpyridine (4.4 mL, 20 mmol) and then dropwise with ethyl 2-oxopent-3-ynoate (1.8 mL, 14 mmol). The resulting solution was stirred at room temperature for 4.5 hours and then refrigerated overnight. The mixture was purified by flash chromatography (silica gel) to provide tert-butyl (R)-7-(2-ethoxy-2-oxoacetyl)-2-fluoro-6-methyl-2,3-dihydro-1H-pyrrolizine-5-carboxylate. LCMS-ESI+ (m/z): [M+H]$^+$ calculated for $C_{17}H_{23}FNO_5$: 340.2; found: 340.0.

Step 7 Tert-butyl (R)-7-(2-ethoxy-2-oxoacetyl)-2-fluoro-6-methyl-2,3-dihydro-1H-pyrrolizine-5-carboxylate (0.99 g, 2.9 mmol) was taken up in DCM (15 mL) and via syringe with TFA (3.3 mL, 43 mmol, 15 eq). After 80 minutes of stirring at room temperature, the mixture was added to approximately 100 mL of saturated aqueous sodium hydrogen carbonate solution. The aqueous phase was extracted once with dichloromethane and then was cooled in an ice-water bath and then acidified to pH 2-3 by the portionwise addition of ca. 20% aqueous sulfuric acid. The resulting suspension was extracted three times with ethyl acetate. The combined extracts were washed once with saturated aqueous sodium chloride solution, dried over anhydrous magnesium sulfate, filtered, and concentrated to dryness under reduced pressure to give (R)-7-(2-ethoxy-2-oxoacetyl)-2-fluoro-6- methyl-2,3-dihydro-1H-pyrrolizine-5-carboxylic acid. LCMS-ESI+ (m/z): [M+H]+ calculated for $C_{13}H_{15}FNO_5$: 284.1; found: 284.0.

Step 8 A solution of (R)-7-(2-ethoxy-2-oxoacetyl)-2-fluoro-6-methyl-2,3-dihydro-1H-pyrrolizine-5-carboxylic acid (0.58 g, 2.1 mmol) in N,N-dimethylformamide (10 mL) was treated successively with N,N-diisopropylethylamine (1.1 mL, 6.2 mmol) and 1-[bis(dimethylamino)methylene]-1H-1,2,3-triazolo[4,5-b]pyridinium 3-oxid hexafluorophosphate (HATU, 0.86 g. 2.3 mmol). After 30 minutes, an additional portion of HATU (0.10 g, 0.26 mmol) was added. Following the passage of 15 minutes, the mixture was partitioned between ethyl acetate and water. The aqueous phase was extracted three times with ethyl acetate. The combined extracts were washed once with saturated aqueous sodium chloride solution, dried over anhydrous magnesium sulfate, filtered, and concentrated under reduced pressure. The crude residue was purified by flash chromatography (silica gel) to provide 3H-[1,2,3]triazolo[4,5-b]pyridin-3-yl (R)-7-(2-ethoxy-2-oxoacetyl)-2-fluoro-6-methyl-2,3-dihydro-1H-pyrrolizine-5-carboxylate. LCMS-ESI+ (m/z): [M+H]+ calculated for $C_{18}H_{17}FN_5O_5$: 402.1; found: 401.9.

Step 9 A suspension of 3-chloro-4-fluoroaniline (0.12 g, 0.79 mmol) and 3H-[1,2,3]triazolo[4,5-b]pyridin-3-yl (R)-7-(2-ethoxy-2-oxoacetyl)-2-fluoro-6-methyl-2,3-dihydro-1H-pyrrolizine-5-carboxylate (0.11 g, 0.26 mmol) in dichloromethane was treated with 2,6-lutidine (0.12 mL, 1.1 mmol). The mixture was concentrated under reduced pressure and then was heated overnight at 80° C. The mixture was purified by flash chromatography (silica gel) to provide ethyl (R)-2-(5-((3-chloro-4-fluorophenyl)carbamoyl)-2-fluoro-6-methyl-2,3-dihydro-1H-pyrrolizin-7-yl)-2-oxoacetate. LCMS-ESI+ (m/z): [M+H]+ calculated for $C_{19}H_{18}ClF_2N_2O_4$: 411.1; found: 411.2.

Step 10 A solution of ethyl (R)-2-(5-((3-chloro-4-fluorophenyl)carbamoyl)-2-fluoro-6-methyl-2,3-dihydro-1H-pyrrolizin-7-yl)-2-oxoacetate (84 mg, 0.20 mmol) in tetrahydrofuran/methanol (1:1, 2 mL) was treated with water (0.5 mL). Additional volumes of tetrahydrofuran (4 mL) and water (1.5 mL) were added. The suspension was heated and sonicated until homogenous and then was transferred to an ice-water bath. Lithium hydroxide monohydrate (13 mg, 0.31 mmol) was added in a single portion. When the reaction was deemed complete by LC/MS analysis, it was acidified with 20% aqueous sulfuric acid. The acidified mixture was extracted three times with ethyl acetate. The combined extracts were washed once with saturated aqueous sodium chloride solution, dried over anhydrous magnesium sulfate, filtered, and concentrated to dryness under reduced pressure to provide (R)-2-(5-((3-chloro-4-fluorophenyl)carbamoyl)-2-fluoro-6-methyl-2,3-dihydro-1H-pyrrolizin-7-yl)-2-oxoacetic acid. LCMS-ESI+ (m/z): [M+H]+ calculated for $C_{17}H_{14}ClF_2N_2O_4$: 383.1; found: 383.1.

Step 11 A mixture of 1-(1H-1,2,3-triazol-4-yl)cyclopropan-1-amine dihydrochloride (70 mg, 0.35 mmol) and (R)-2-(5-((3-chloro-4-fluorophenyl)carbamoyl)-2-fluoro-6-methyl-2,3-dihydro-1H-pyrrolizin-7-yl)-2-oxoacetic acid (78 mg, 0.20 mmol) was taken up in N,N-dimethylformamide (3 mL) and treated successively with N,N-diisopropylethylamine (0.50 mL, 2.9 mmol) and HATU (170 mg, 0.45 mmol). After 40 minutes, additional portions of 1-(1H-1,2,3-triazol-4-yl)cyclopropan-1-amine dihydrochloride (70 mg, 0.35 mmol) and HATU (170 mg, 0.45 mmol) were added. After 48 hours, the mixture was diluted with methanol (3 mL), treated with piperidine (0.3 mL), and concentrated under reduced pressure. The residue was purified by preparative reverse-phase HPLC (5-80% acetonitrile in water, 0.1% TFA buffer) to provide (R)-7-(2-((1-(1H-1,2,3-triazol-4-yl)cyclopropyl)amino)-2-oxoacetyl)-N-(3-chloro-4-fluorophenyl)-2-fluoro-6-methyl-2,3-dihydro-1H-pyrrolizine-5-carboxamide (45).

Example 46 (S)-7-(2-((1-(1H-1,2,3-triazol-4-yl)cyclopropyl)amino)-2-oxoacetyl)-N-(3-chloro-4-fluorophenyl)-2-fluoro-6-methyl-2,3-dihydro-1H-pyrrolizine-5-carboxamide (46)

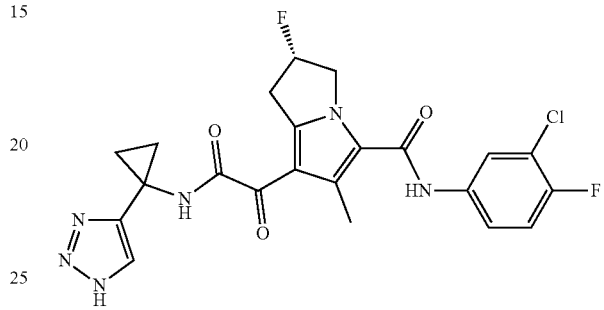

46

(S)-7-(2-((1-(1H-1,2,3-triazol-4-yl)cyclopropyl)amino)-2-oxoacetyl)-N-(3-chloro-4-fluorophenyl)-2-fluoro-6-methyl-2,3-dihydro-1H-pyrrolizine-5-carboxamide (46) was prepared in a manner analogous to Example 45 using (2R,4S)-1-(tert-butoxycarbonyl)-4-fluoropyrrolidine-2-carboxylic acid in place of (2S,4R)-1-(tert-butoxycarbonyl)-4-fluoropyrrolidine-2-carboxylic acid.

Example 47 7-(2-((3,3-difluoro-1-(methylcarbamoyl)cyclobutyl)amino)-2-oxoacetyl)-N-(4-fluorophenyl)-6-methyl-2,3-dihydro-1H-pyrrolizine-5-carboxamide (47)

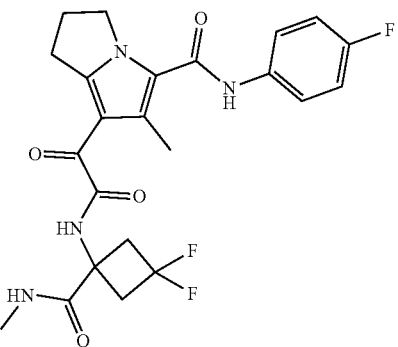

47

7-(2-((3,3-difluoro-1-(methylcarbamoyl)cyclobutyl)amino)-2-oxoacetyl)-N-(4-fluorophenyl)-6-methyl-2,3-dihydro-1H-pyrrolizine-5-carboxamide (47) was synthesized in a manner similar to Example 29 using 4-fluoroaniline in place of 3,4-difluoroaniline and using 1-amino-3,3-difluoro-N-methylcyclobutane-1-carboxamide hydrochloride in place of 3,3-difluoro-1-(1H-1,2,3-triazol-4-yl)cyclobutan-1-aminium chloride.

Example 48: (R)-7-(2-((3,3-difluoro-1-(1H-1,2,3-triazol-4-yl)cyclobutyl)amino)-2-oxoacetyl)-2-fluoro-N-(4-fluorophenyl)-6-methyl-2,3-dihydro-1H-pyrrolizine-5-carboxamide (48)

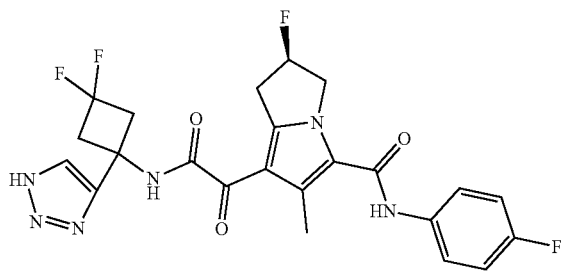

48

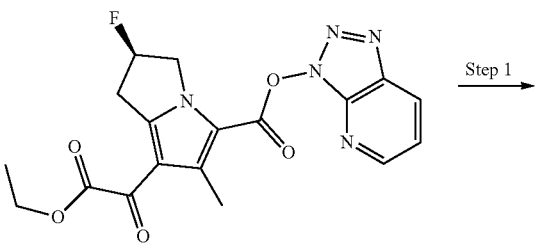

3H-[1,2,3]triazolo[4,5-b]pyridin-3-yl (R)-7-(2-ethoxy-2-oxoacetyl)-2-fluoro-6-methyl-2,3-dihydro-1H-pyrrolizine-5-carboxylate Step 1

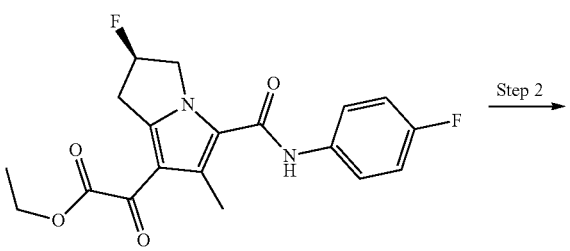

ethyl (R)-2-(2-fluoro-5-((4-fluorophenyl)carbamoyl)-6-methyl-2,3-dihydro-1H-pyrrolizin-7-yl)-2-oxoacetate Step 2

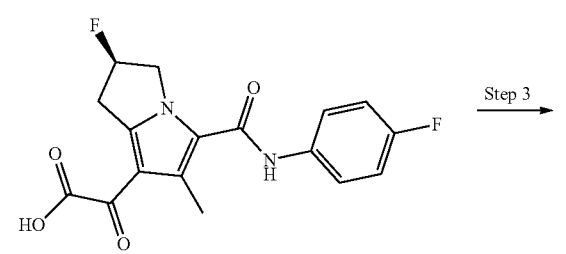

(R)-2-(2-fluoro-5-((4-fluorophenyl)carbamoyl)-6-methyl-2,3-dihydro-1H-pyrrolizin-7-yl)-2-oxoacetic acid Step 3

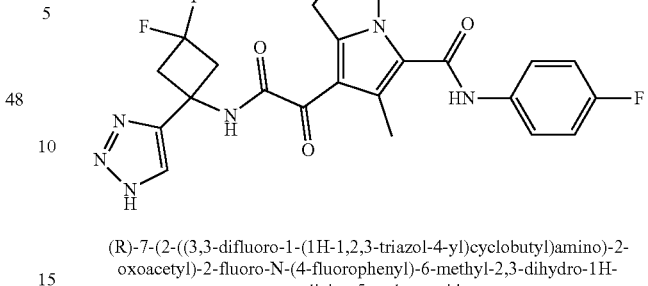

(R)-7-(2-((3,3-difluoro-1-(1H-1,2,3-triazol-4-yl)cyclobutyl)amino)-2-oxoacetyl)-2-fluoro-N-(4-fluorophenyl)-6-methyl-2,3-dihydro-1H-pyrrolizine-5-carboxamide Step 1 A suspension of 4-fluoroaniline (98 mg, 0.88 mmol) and 3H-[1,2,3]triazolo[4,5-b]pyridin-3-yl (R)-7-(2-ethoxy-2-oxoacetyl)-2-fluoro-6-methyl-2,3-dihydro-1H-pyrrolizine-5-carboxylate (0.12 g, 0.29 mmol) in dichloromethane (5 mL) was treated with 2,6-lutidine (0.14 mL, 1.2 mmol). The mixture was concentrated under reduced pressure and then was heated overnight at 80° C. The mixture was purified by flash chromatography (silica gel) to provide ethyl (R)-2-(2-fluoro-5-((4-fluorophenyl)carbamoyl)-6-methyl-2,3-dihydro-1H-pyrrolizin-7-yl)-2-oxoacetate. LCMS-ESI+ (m/z): [M+H]+ calculated for $C_{19}H_{18}F_2N_2O_4$: 377.1; found: 377.2.

Step 2 A solution of ethyl (R)-2-(2-fluoro-5-((4-fluorophenyl)carbamoyl)-6-methyl-2,3-dihydro-1H-pyrrolizin-7-yl)-2-oxoacetate (83 mg, 0.22 mmol) in tetrahydrofuran/water (1:1, 6 mL) was treated with lithium hydroxide monohydrate (11 mg, 0.27 mmol). When the reaction was deemed complete by LC/MS analysis, it was acidified with 20% aqueous sulfuric acid. The acidified mixture was extracted three times with ethyl acetate. The combined extracts were washed once with saturated aqueous sodium chloride solution, dried over anhydrous magnesium sulfate, filtered, and concentrated to dryness under reduced pressure to provide (R)-2-(2-fluoro-5-((4-fluorophenyl)carbamoyl)-6-methyl-2,3-dihydro-1H-pyrrolizin-7-yl)-2-oxoacetic acid. LCMS-ESI+ (m/z): [M+H]+ calculated for $C_{17}H_{15}F_2N_2O_4$: 349.1; found: 349.1.

Step 3 A mixture of 3,3-difluoro-1-(1H-1,2,3-triazol-4-yl)cyclobutan-1-amine (52 mg, 0.30 mmol) and (R)-2-(2-fluoro-5-((4-fluorophenyl)carbamoyl)-6-methyl-2,3-dihydro-1H-pyrrolizin-7-yl)-2-oxoacetic acid (76 mg, 0.22 mmol) was taken up in N,N-dimethylformamide (3 mL) and treated successively with N,N-diisopropylethylamine (0.30 mL, 1.7 mmol) and HATU (0.24 g, 0.64 mmol). After 30 minutes, the mixture was diluted with methanol (~3 mL), treated with 10 drops of piperidine, and concentrated under reduced pressure. The residue was purified by preparative reverse-phase HPLC (10-80% acetonitrile in water, 0.1% TFA buffer) to provide (R)-7-(2-((3,3-difluoro-1-(1H-1,2,3-triazol-4-yl)cyclobutyl)amino)-2-oxoacetyl)-2-fluoro-N-(4-fluorophenyl)-6-methyl-2,3-dihydro-1H-pyrrolizine-5-carboxamide (48).

Example 49: (R)-7-(2-((3,3-difluoro-1-(methylcarbamoyl)cyclobutyl)amino)-2-oxoacetyl)-N-(3,4-difluorophenyl)-2-fluoro-6-methyl-2,3-dihydro-1H-pyrrolizine-5-carboxamide (49)

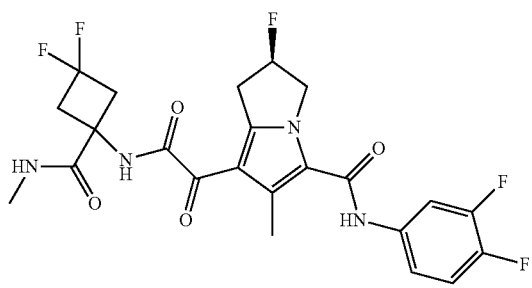

49

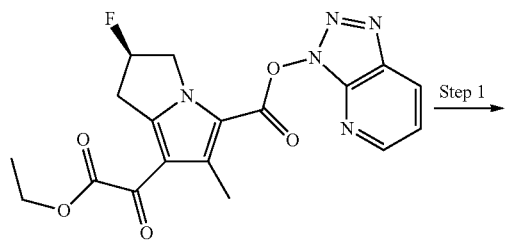

3H-[1,2,3]triazolo[4,5-b]pyridin-3-yl (R)-7-(2-ethoxy-2-oxoacetyl)-2-fluoro-6-methyl-2,3-dihydro-1H-pyrrolizine-5-carboxylate Step 1

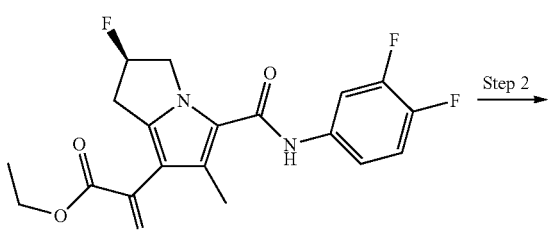

ethyl (R)-2-(5-((3,4-difluorophenyl)carbamoyl)-2-fluoro-6-methyl-2,3-dihydro-1H-pyrrolizin-7-yl)-2-oxoacetate Step 2

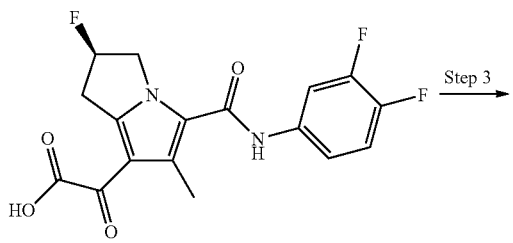

(R)-2-(5-((3,4-difluorophenyl)carbamoyl)-2-fluoro-6-methyl-2,3-dihydro-1H-pyrrolizin-7-yl)-2-oxoacetic acid Step 3

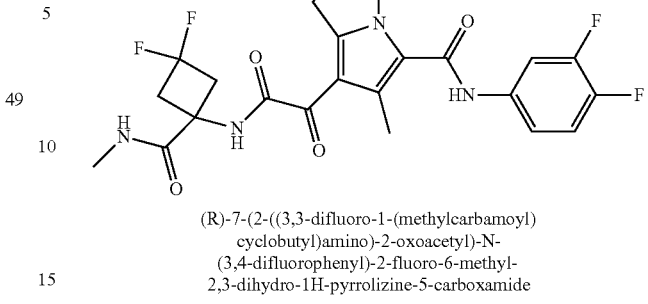

(R)-7-(2-((3,3-difluoro-1-(methylcarbamoyl)cyclobutyl)amino)-2-oxoacetyl)-N-(3,4-difluorophenyl)-2-fluoro-6-methyl-2,3-dihydro-1H-pyrrolizine-5-carboxamide Step 1 A suspension of 3,4-difluoroaniline (0.11 mL, 1.1 mmol) and 3H-[1,2,3]triazolo[4,5-b]pyridin-3-yl (R)-7-(2-ethoxy-2-oxoacetyl)-2-fluoro-6-methyl-2,3-dihydro-1H-pyrrolizine-5-carboxylate (0.14 g, 0.35 mmol) in dichloromethane (5 mL) was treated with 2,6-lutidine (0.16 mL, 1.4 mmol). The mixture was concentrated under reduced pressure and then was heated overnight at 80° C. The mixture was purified by flash chromatography (silica gel) to provide ethyl (R)-2-(5-((3,4-difluorophenyl)carbamoyl)-2-fluoro-6-methyl-2,3-dihydro-1H-pyrrolizin-7-yl)-2-oxoacetate. LCMS-ESI+ (m/z): [M+H]+ calculated for $C_{19}H_{18}F_3N_2O_4$: 395.1; found: 395.2.

Step 2 A solution of ethyl (R)-2-(5-((3,4-difluorophenyl)carbamoyl)-2-fluoro-6-methyl-2,3-dihydro-1H-pyrrolizin-7-yl)-2-oxoacetate (0.14 g, 0.35 mmol) in tetrahydrofuran/water (5:2, 7 mL) was treated with lithium hydroxide monohydrate (30 mg, 0.72 mmol). When the reaction was deemed complete by LC/MS analysis, it was acidified with 20% aqueous sulfuric acid. The acidified mixture was extracted three times with ethyl acetate. The combined extracts were washed once with saturated aqueous sodium chloride solution, dried over anhydrous magnesium sulfate, filtered, and concentrated to dryness under reduced pressure to provide (R)-2-(5-((3,4-difluorophenyl)carbamoyl)-2-fluoro-6-methyl-2,3-dihydro-1H-pyrrolizin-7-yl)-2-oxoacetic acid. LCMS-ESI+ (m/z): [M+H]+ calculated for $C_{17}H_{14}F_3N_2O_4$: 367.1; found: 367.1.

Step 3 A mixture of 1-amino-3,3-difluoro-N-methylcyclobutane-1-carboxamide (100 mg, 0.50 mmol) and (R)-2-(5-((3,4-difluorophenyl)carbamoyl)-2-fluoro-6-methyl-2,3-dihydro-1H-pyrrolizin-7-yl)-2-oxoacetic acid (125 mg, 0.34 mmol) was taken up in N,N-dimethylformamide (3 mL) and treated successively with N,N-diisopropylethylamine (0.30 mL, 1.7 mmol) and HATU (0.26 g, 0.68 mmol). The mixture was partitioned between ethyl acetate and saturated aqueous sodium hydrogen carbonate solution. The aqueous phase was extracted three times with ethyl acetate. The combined organic phases were subsequently washed successively with 10% aqueous hydrochloric acid, water, and a 1:1 mixture of saturated aqueous sodium hydrogen carbonate and sodium chloride solutions. The organics were dried over anhydrous magnesium sulfate, filtered, concentrated, and concentrated. The residue was purified by preparative reverse-phase HPLC (15-90% acetonitrile in water, 0.1% TFA buffer) to provide (R)-7-(2-((3,3-difluoro-1-(methylcarbamoyl)cyclobutyl)amino)-2-oxoacetyl)-N-(3,4-difluorophenyl)-2-fluoro-6-methyl-2,3-dihydro-1H-pyrrolizine-5-carboxamide (49).

1-(2-Methyl-2H-tetrazol-5-yl)cyclopropan-1-amine hydrochloride

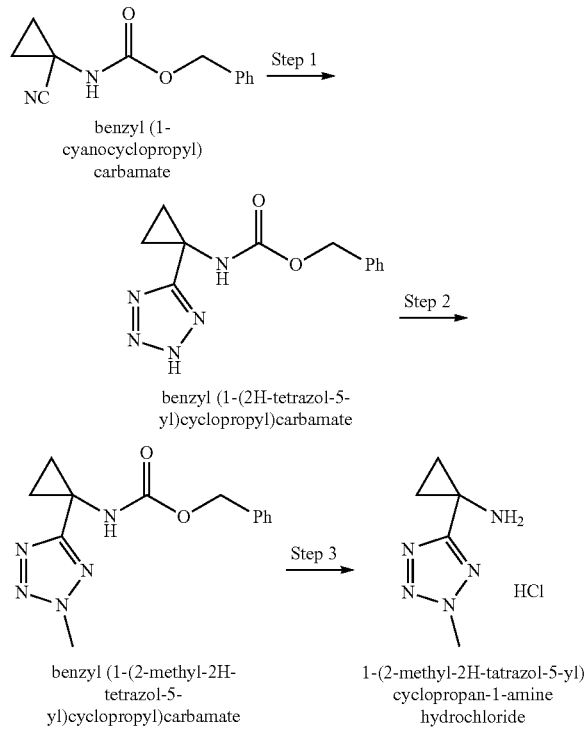

Step 1. A vigorously stirred mixture of benzyl (1-cyanocyclopropyl)carbamate (1.92 g, 8.89 mmol), sodium azide (870 mg, 13 mmol), and ammonium chloride (710 mg, 13 mmol) in N,N-dimethylformamide (20 mL) was heated to 110° C. in a sand bath. After 16 h, the resulting mixture was allowed to cool to ambient temperature and was concentrated under reduced pressure. The residue was purified by was purified by reverse phase preparative HPLC (10-100% acetonitrile in water, 0.1% trifluoroacetic acid) to give benzyl (1-(2H-tetrazol-5-yl)cyclopropyl)carbamate.

Steps 2-3. Diazomethyltrimethylsilane solution (2.0 M in hexanes, 5.1 mL, 10 mmol) was added via syringe over 5 min to a stirred solution of benzyl (1-(2H-tetrazol-5-yl)cyclopropyl)carbamate (2.20 g, 8.49 mmol) in toluene (70 mL) and methanol (20 mL) at ambient temperature. After 20 min, acetic acid was added dropwise via syringe until gas evolution ceased and the yellow color dissipated from the reaction mixture. The residue was dissolved in ethanol (70 mL), palladium on activated carbon (10% wt/wt, 2 g, 2 mmol) was added, and the resulting mixture was stirred vigorously at ambient temperature. After 2 min, the resulting mixture was placed under 1 atm of hydrogen gas. After 90 min, the reaction mixture was filtered through celite, and the filter cake was extracted with ethyl acetate (80 mL). Hydrogen chloride solution (4 M in 1,4-dioxane, 3.0 mL) was added via syringe to the filtrate, and the resulting mixture was swirled vigorously for 1 min and then concentrated under reduced pressure to give 1-(2-methyl-2H-tetrazol-5-yl)cyclopropan-1-amine hydrochloride.

Example 50. N-(3-chloro-4-fluorophenyl)-6-methyl-7-(2-((1-(2-methyl-2H-tetrazol-5-yl)cyclopropyl)amino)-2-oxoacetyl)-2,3-dihydro-1H-pyrrolizine-5-carboxamide

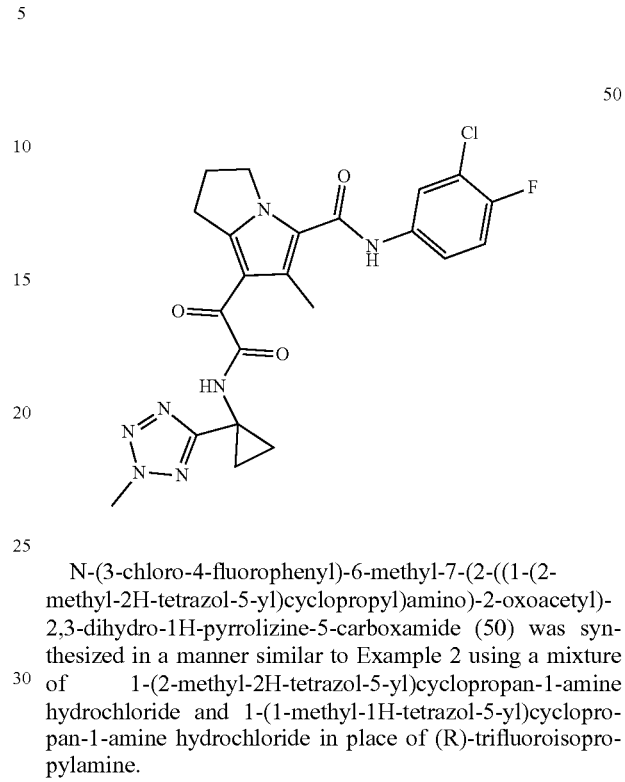

N-(3-chloro-4-fluorophenyl)-6-methyl-7-(2-((1-(2-methyl-2H-tetrazol-5-yl)cyclopropyl)amino)-2-oxoacetyl)-2,3-dihydro-1H-pyrrolizine-5-carboxamide (50) was synthesized in a manner similar to Example 2 using a mixture of 1-(2-methyl-2H-tetrazol-5-yl)cyclopropan-1-amine hydrochloride and 1-(1-methyl-1H-tetrazol-5-yl)cyclopropan-1-amine hydrochloride in place of (R)-trifluoroisopropylamine.

Example 51. N-(3-chloro-4-fluorophenyl)-6-methyl-7-(2-((1-(5-methyl-4H-1,2,4-triazol-3-yl)cyclopropyl)amino)-2-oxoacetyl)-2,3-dihydro-1H-pyrrolizine-5-carboxamide

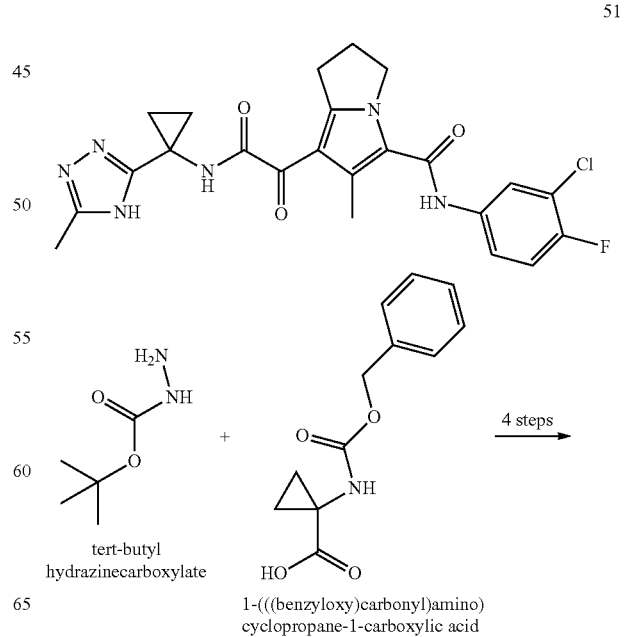

-continued

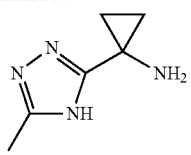

1-(5-methyl-4H-1,2,4-triazol-3-yl)cyclopropan-1-amine 1-(5-methyl-4H-1,2,4-triazol-3-yl)cyclopropan-1-amine was synthesized from tert-butyl hydrazinecarboxylate and 1-(((benzyloxy)carbonyl)amino)cyclopropane-1-carboxylic acid in 4 steps following the procedure describe in WO 2009070485A1.

N-(3-chloro-4-fluorophenyl)-6-methyl-7-(2-((1-(5-methyl-4H-1,2,4-triazol-3-yl)cyclopropyl)amino)-2-oxoacetyl)-2,3-dihydro-1H-pyrrolizine-5-carboxamide (51) was synthesized in a manner similar to Example 6 Step 6 using 1-(5-methyl-4H-1,2,4-triazol-3-yl)cyclopropan-1-amine in place of 1-(1H-1,2,3-triazol-4-yl)cyclopropan-1-amine dihydrochloric acid.

Example 52 (1aR,6aR)-5-(2-((1-(1H-1,2,3-triazol-4-yl)cyclopropyl)amino)-2-oxoacetyl)-N-(3-chloro-4-fluorophenyl)-4-methyl-1,1a,6,6a-tetrahydrocyclopropa [b]pyrrolizine-3-carboxamide

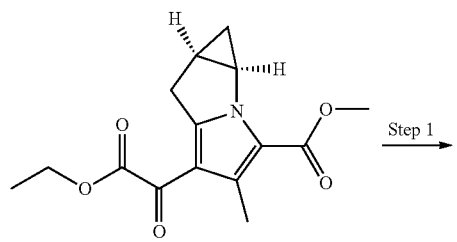

methyl (1aR,6aR)-5-(2-ethoxy-2-oxoacetyl)-4-methyl-1,1a,6,6a-tetrahydrocyclopropa[b]pyrrolizine-3-carboxylate

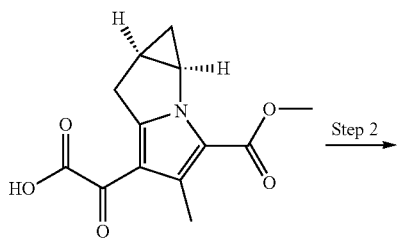

2-((1aR,6aR)-3-(methoxycarbonyl)-4-methyl-1,1a,6,6a-tetrahydrocyclopropa[b]pyrrolizin-5-yl)-2-oxoacetic acid -continued

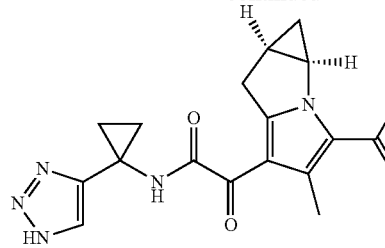

methyl (1aR,6aR)-5-(2-((1-(1H-1,2,3-triazol-4-yl)cyclopropyl)amino)-2-oxoacetyl)-4-methyl-1,1a,6,6a-tetrahydrocyclopropa[b]pyrrolizine-3-carboxylate

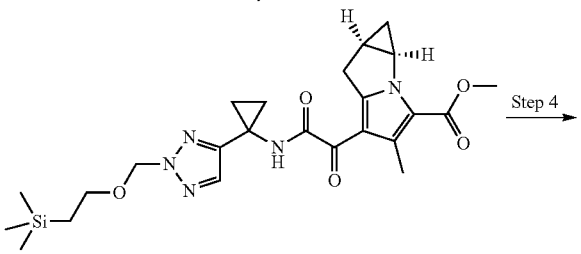

methyl (1aR,6aR)-4-methyl-5-(2-oxo-2-((1-(2-((2-(trimethylsilyl)ethoxy)methyl)-2H-1,2,3-triazol-4-yl)cyclopropyl)amino)acetyl)-1,1a,6,6a-tetrahydrocyclopropa[b]pyrrolizine-3-carboxylate

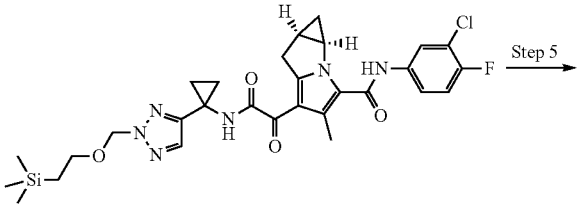

(1aR,6aR)-N-(3-chloro-4-fluorophenyl)-4-methyl-5-(2-oxo-2-((1-(2-((2-(trimethylsilyl)ethoxy)methyl)-2H-1,2,3-triazol-4-yl)cyclopropyl)amino)acetyl)-1,1a,6,6a-tetrahydrocyclopropa[b]pyrrolizine-3-carboxamide

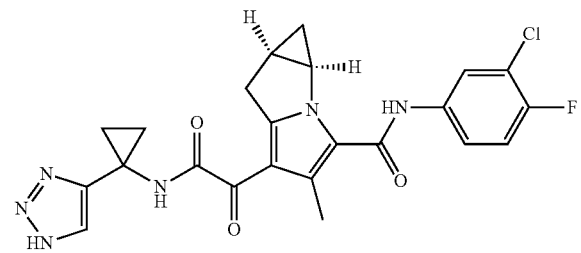

(1aR,6aR)-5-(2-((1-(1H-1,2,3-triazol-4-yl)cyclopropyl)amino)-2-oxoacetyl)-N-(3-chloro-4-fluorophenyl)-4-methyl-1,1a,6,6a-tetrahydrocyclopropa[b]pyrrolizine-3-carboxamide
52

Step 1 and 2 Methyl (1aR,6aR)-5-(2-((1-(1H-1,2,3-triazol-4-yl)cyclopropyl)amino)-2-oxoacetyl)-4-methyl-1,1a,6,6a-tetrahydrocyclopropa[b]pyrrolizine-3-carboxylate was synthesized in a manner similar to Example 54, step 4, using 1-(1H-1,2,3-triazol-5-yl)cyclopropyl)amine hydrochloride in place of 3,3-difluoro-(1-methylaminocarbonyl)-1-cyclobutanamine hydrochloride: $^1$H NMR (400 MHz, Chloroform-d) δ 7.77 (s, 1H), 7.60 (s, 1H), 4.43 (d, J=6.3 Hz, 1H), 3.89 (s, 3H), 3.56-3.39 (m, 1H), 3.23 (d, J=18.9 Hz, 1H), 2.56 (s, 3H), 2.04 (s, 1H), 1.49 (s, 2H), 1.36 (s, 2H), 1.09 (s, 1H), 0.29 (s, 1H). LCMS-ESI+ (m/z): [M+H]+ calculated for $C_{18}H_{20}N_5O_4$: 370.2; found: 370.1.

Step 3 A mixture of methyl (1aR,6aR)-5-(2-((1-(1H-1,2,3-triazol-4-yl)cyclopropyl)amino)-2-oxoacetyl)-4-methyl-1,1a,6,6a-tetrahydrocyclopropa[b]pyrrolizine-3-carboxylate (56.5 mg, 0.153 mmol) and potassium carbonate (42.3 mg, 0.306 mmol) in N,N-dimethylformamide (1.5 mL) was stirred at ambient temperature as 2-(trimethylsilyl)ethoxymethyl chloride (32 uL, 0.184 mmol) was added. The resulting mixture was stirred at ambient temperature for 1.5 h. The reaction mixture was diluted with ethyl acetate and washed with water (×1). After the aq. fractions were extracted with ethyl acetate (×1), the combined organic fractions were dried with magnesium sulfate. After filtration, solvent was removed and the residue was purified by silica gel column chromatography eluting 0-100% ethyl acetate in hexanes to give the pure major isomer of ((2-(trimethylsilyl)ethoxy)methylated methyl (1aR,6aR)-5-(2-((1-(1H-1,2,3-triazol-4-yl)cyclopropyl)amino)-2-oxoacetyl)-4-methyl-1,1a,6,6a-tetrahydrocyclopropa[b]pyrrolizine-3-carboxylate: $^1$H NMR (400 MHz, Chloroform-d) δ 7.68 (s, 1H), 7.51 (s, 1H), 5.56 (s, 2H), 4.43 (ddt, J=6.0, 3.8, 1.8 Hz, 1H), 3.89 (s, 3H), 3.66-3.56 (m, 2H), 3.51 (dd, J=19.0, 6.9 Hz, 1H), 3.24 (dt, J=19.1, 1.2 Hz, 1H), 2.57 (s, 3H), 2.13-1.92 (m, 1H), 1.52-1.45 (m, 2H), 1.36-1.29 (m, 2H), 1.07 (dt, J=8.6, 6.0 Hz, 1H), 0.94-0.86 (m, 2H), 0.28 (ddd, J=6.4, 5.1, 2.0 Hz, 1H), −0.03 (s, 9H). LCMS-ESI+ (m/z): [M+H]+ calculated for $C_{24}H_{34}N_5O_5Si$: 500.2; found: 500.0.

Step 4 A solution of the above pure major isomer of ((2-(trimethylsilyl)ethoxy)methylated methyl (1aR,6aR)-5-(2-((1-(1H-1,2,3-triazol-4-yl)cyclopropyl)amino)-2-oxoacetyl)-4-methyl-1,1a,6,6a-tetrahydrocyclopropa[b]pyrrolizine-3-carboxylate (29.9 mg, 0.060 mmol) in tetrahydrofuran (0.5 mL), methanol (0.5 mL) and water (1 mL) was stirred as 1 N lithium hydroxide (0.185 mL) was added. The mixture was refluxed at 70° C. bath for 6 h. The reaction mixture was diluted with brine, acidified with 1 N hydrochloric acid (~0.19 mL), and transferred to a separatory funnel using brine and ethyl acetate. After two fractions were separated, the aqueous fraction was extracted with ethyl acetate (×1). The combined organic fractions were dried with magnesium sulfate. After filtration, solvent was removed to give crude (1aR,6aR)-4-methyl-5-(2-oxo-2-((1-(2-((2-(trimethylsilyl)ethoxy)methyl)-2H-1,2,3-triazol-4-yl)cyclopropyl)amino)acetyl)-1,1a,6,6a-tetrahydrocyclopropa[b]pyrrolizine-3-carboxylic acid. LCMS-ESI+ (m/z): [M+H]+ calculated for $C_{23}H_{32}N_5O_5Si$: 486.2; found: 486.0.

A solution of the crude (1aR,6aR)-4-methyl-5-(2-oxo-2-((1-(2-((2-(trimethylsilyl)ethoxy)methyl)-2H-1,2,3-triazol-4-yl)cyclopropyl)amino)acetyl)-1,1a,6,6a-tetrahydrocyclopropa[b]pyrrolizine-3-carboxylic acid (0.060 mmol) and 1-[bis(dimethylamino)methylene]-1H-1,2,3-triazolo[4,5-b]pyridinium 3-oxide hexafluorophosphate (35.6 mg, 0.094 mmol) in N,N-dimethylformamide (1.5 mL) was stirred at ambient temperature as N,N-diisopropylethylamine (0.05 mL, 0.287 mmol) was added. After 1 h, the reaction mixture was diluted with ethyl acetate and washed with aqueous ammonium chloride (×2), aqueous sodium bicarbonate (×2), and brine (×1). After the aq. fractions were extracted with ethyl acetate (×1), the organic fractions were combined, dried with magnesium sulfate. After filtration, solvent was removed and the residue was co-evaporated with toluene (×2), dried in vacuum for 30 min to give the crude 3H-[1,2,3]triazolo[4,5-b]pyridin-3-yl (1aR,6aR)-4-methyl-5-(2-oxo-2-((1-(2-((2-(trimethylsilyl)ethoxy)methyl)-2H-1,2,3-triazol-4-yl)cyclopropyl)amino)acetyl)-1,1a,6,6a-tetrahydrocyclopropa[b]pyrrolizine-3-carboxylate. LCMS-ESI+ (n/z): [M+H]+ calculated for $C_{28}H_{34}N_9O_5Si$: 604.3; found: 604.0.

To a solution of the crude 3H-[1,2,3]triazolo[4,5-b]pyridin-3-yl (1aR,6aR)-4-methyl-5-(2-oxo-2-((1-(2-((2-(trimethylsilyl)ethoxy)methyl)-2H-1,2,3-triazol-4-yl)cyclopropyl)amino)acetyl)-1,1a,6,6a-tetrahydrocyclopropa[b]pyrrolizine-3-carboxylate and 3-chloro-4-fluoroaniline (36 mg, 0.247 mmol) in 2-methyltetrahydrofuran (2 mL) was added 2,6-lutidine (0.05 mL, 0.429 mmol) at ambient temperature. The resulting mixture was kept tightly and heated at 80° C. for 111.5 h. After the reaction mixture was concentrated, the residue was purified by by silica gel column chromatography eluting 0-100% ethyl acetate in hexanes to get somewhat impure product. The impure product was further purified by silica gel column chromatography eluting 0-6% methanol in dichloromethane to give (1aR,6aR)-N-(3-chloro-4-fluorophenyl)-4-methyl-5-(2-oxo-2-((1-(2-((2-(trimethylsilyl)ethoxy)methyl)-2H-1,2,3-triazol-4-yl)cyclopropyl)amino)acetyl)-1,1a,6,6a-tetrahydrocyclopropa[b]pyrrolizine-3-carboxamide containing minor impurities: $^1$H NMR (400 MHz, Chloroform-d) δ 7.81 (dd, J=6.5, 2.6 Hz, 1H), 7.69 (s, 1H), 7.51 (s, 1H), 7.43 (s, 1H), 7.38 (ddd, J=8.9, 4.0, 2.8 Hz, 1H), 7.12 (t, J=8.7 Hz, 1H), 5.56 (s, 2H), 4.53-4.41 (m, 1H), 3.67-3.57 (m, 2H), 3.51 (dd, J=19.0, 6.9 Hz, 1H), 3.31-3.16 (m, 1H), 2.61 (s, 3H), 2.06 (p, J=6.0 Hz, 1H), 1.54-1.45 (m, 2H), 1.38-1.30 (m, 2H), 1.25 (s, 1H), 1.10 (dt, J=8.6, 6.0 Hz, 1H), 0.96-0.86 (m, 2H), 0.35-0.26 (m, 1H), −0.03 (s, 9H). $^{19}$F NMR (376 MHz, Chloroform-d) δ −120.73 (ddd, J=8.7, 6.5, 4.1 Hz). LCMS-ESI+ (n/z): [M+H]+ calculated for $C_{29}H_{35}ClFN_6O_4Si$: 613.2; found: 613.0.

Step 5 (1aR,6aR)-N-(3-chloro-4-fluorophenyl)-4-methyl-5-(2-oxo-2-((1-(2-((2-(trimethylsilyl)ethoxy)methyl)-2H-1,2,3-triazol-4-yl)cyclopropyl)amino)acetyl)-1,1a,6,6a-tetrahydrocyclopropa[b]pyrrolizine-3-carboxamide (11.4 mg, 0.019 mmol) was dissolved in dichloromethane (1 mL) and ethanol (0.1 mL) and stirred at rt as trifluoroacetic acid (0.25 mL, 3.265 mmol) was added. The resulting mixture was stirred at ambient temperature for 9 h. After the reaction mixture was concentrated, the residue was dissolved in N,N-dimethylformamide, filtered, and purified by preparative HPLC (column, Gemini 10u C18 110A, AXI/; 250×21.2 mm) eluting 10-90% acetonitrile (0.1% TFA) in water (0.1% TFA). The product containing fractions were combined and freeze-dried to give (1aR,6aR)-5-(2-((1-(1H-1,2,3-triazol-4-yl)cyclopropyl)amino)-2-oxoacetyl)-N-(3-chloro-4-fluorophenyl)-4-methyl-1,1a,6,6a-tetrahydrocyclopropa[b]pyrrolizine-3-carboxamide.

Example 53. 7-(2-((3,3-difluoro-1-(1H-1,2,3-triazol-4-yl)cyclobutyl)amino)-2-oxoacetyl)-6-methyl-N-(3,4,5-trifluorophenyl)-2,3-dihydro-1H-pyrrolizine-5-carboxamide

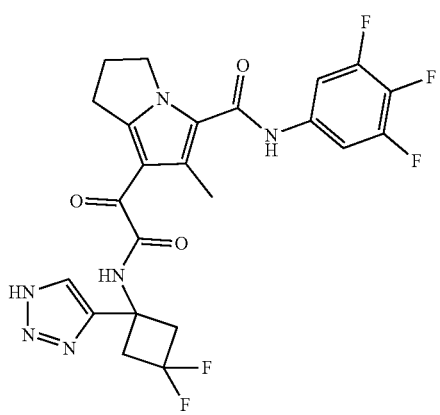

53

7-(2-((3,3-difluoro-1-(1H-1,2,3-triazol-4-yl)cyclobutyl)amino)-2-oxoacetyl)-6-methyl-N-(3,4,5-trifluorophenyl)-2,3-dihydro-1H-pyrrolizine-5-carboxamide (53) was synthesized in a manner similar to Example 29 using 3,4,5-trifluoroaniline in place of 3-chloro-4-fluouroaniline.

Example 54. (1aR,6aR)-5-(2-((1-(1,3,4-thiadiazol-2-yl)cyclopropyl)amino)-2-oxoacetyl)-N-(3-chloro-4-fluorophenyl)-4-methyl-1,1a,6,6a-tetrahydrocyclopropa[b]pyrrolizine-3-carboxamide

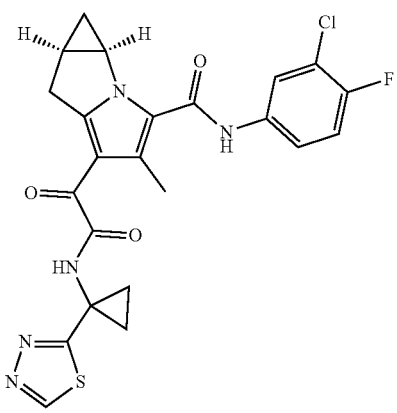

54

(1aR,6aR)-5-(2-((1-(1,3,4-thiadiazol-2-yl)cyclopropyl)amino)-2-oxoacetyl)-N-(3-chloro-4-fluorophenyl)-4-methyl-1,1a,6,6a-tetrahydrocyclopropa[b]pyrrolizine-3-carboxamide (54) was synthesized in a manner similar to Example 5 using 1-(1,3,4-thiadiazol-2-yl)cyclopropan-1-amine hydrogen bromide in place of 3,3-difluoro-(1-methylaminocarbonyl)-1-cyclobutanamine hydrochloride.

Example 55. 7-(2-((3,3-difluoro-1-(1H-1,2,3-triazol-4-yl)cyclobutyl)amino)-2-oxoacetyl)-N-(2-(difluoromethyl)pyridin-4-yl)-6-methyl-2,3-dihydro-1H-pyrrolizine-5-carboxamide

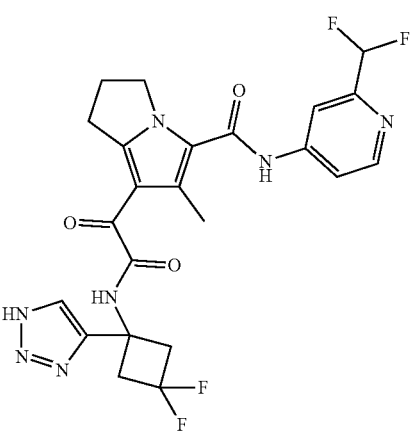

55

7-(2-((3,3-difluoro-1-(1H-1,2,3-triazol-4-yl)cyclobutyl)amino)-2-oxoacetyl)-N-(2-(difluoromethyl)pyridin-4-yl)-6-methyl-2,3-dihydro-1H-pyrrolizine-5-carboxamide (55) was synthesized in a manner similar to Example 29 using 2-(difluoromethyl)pyridin-4-amine in place of 3-chloro-4-fluouroaniline.

Example 56 (1aR,6aR)-5-(2-((1-(1H-1,2,3-triazol-4-yl)cyclopropyl)amino)-2-oxoacetyl)-N-(2-(difluoromethyl)pyridin-4-yl)-4-methyl-1,1a,6,6a-tetrahydrocyclopropa[b]pyrrolizine-3-carboxamide

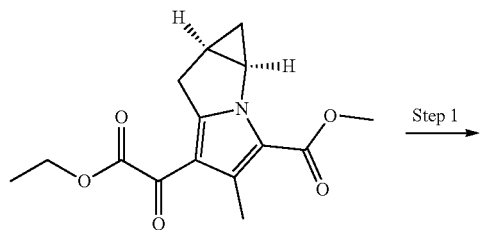

methyl (1aR,6aR)-5-(2-ethoxy-2-oxoacetyl)-4-methyl-1,1a,6,6a-tetrahydrocyclopropa[b]pyrrolizine-3-carboxylate

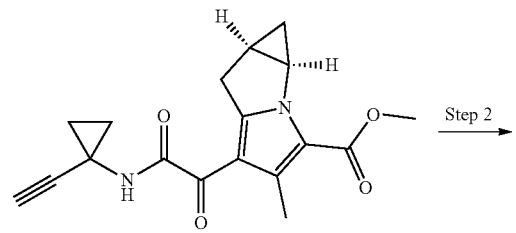

methyl (1aR,6aR)-5-(2-((1-ethynylcyclopropyl)amino)-2-oxoacetyl)-4-methyl-1,1a,6,6a-tetrahydrocyclopropa[b]pyrrolizine-3-carboxylate

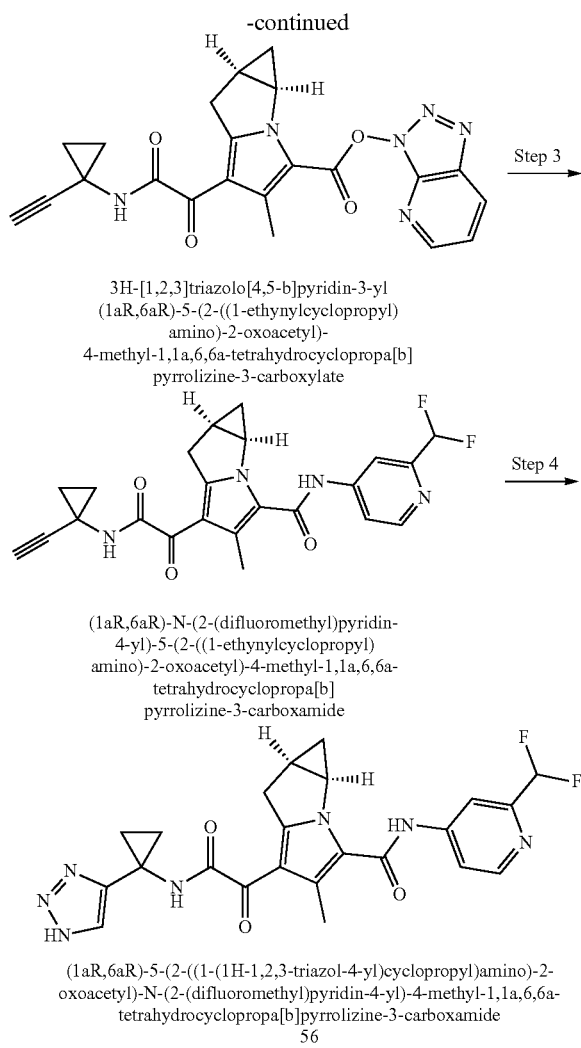

3H-[1,2,3]triazolo[4,5-b]pyridin-3-yl
(1aR,6aR)-5-(2-((1-ethynylcyclopropyl)
amino)-2-oxoacetyl)-
4-methyl-1,1a,6,6a-tetrahydrocyclopropa[b]
pyrrolizine-3-carboxylate (1aR,6aR)-N-(2-(difluoromethyl)pyridin-
4-yl)-5-(2-((1-ethynylcyclopropyl)
amino)-2-oxoacetyl)-4-methyl-1,1a,6,6a-
tetrahydrocyclopropa[b]
pyrrolizine-3-carboxamide (1aR,6aR)-5-(2-((1-(1H-1,2,3-triazol-4-yl)cyclopropyl)amino)-2-
oxoacetyl)-N-(2-(difluoromethyl)pyridin-4-yl)-4-methyl-1,1a,6,6a-
tetrahydrocyclopropa[b]pyrrolizine-3-carboxamide
56

Step 1 and 2 3H-[1,2,3]triazolo[4,5-b]pyridin-3-yl (1aR,6aR)-5-(2-((1-ethynylcyclopropyl)amino)-2-oxoacetyl)-4-methyl-1,1a,6,6a-tetrahydrocyclopropa[b]pyrrolizine-3-carboxylate was synthesized in a manner similar to Example 5, step 4 and 5, using 1-ethynylcyclopropan-1-amine hydrochloride in place of 3,3-difluoro-(1-methylaminocarbonyl)-1-cyclobutanamine hydrochloride: $^1$H NMR (400 MHz, Chloroform-d) δ 8.75 (dd, J=4.5, 1.4 Hz, 1H), 8.46 (dd, J=8.4, 1.4 Hz, 1H), 7.49 (s, 1H), 7.46 (dd, J=8.4, 4.5 Hz, 1H), 4.47 (tt, J=5.9, 1.9 Hz, 1H), 3.68 (dd, J=19.4, 6.9 Hz, 1H), 3.48-3.36 (m, 1H), 2.74 (s, 3H), 2.19 (s, 1H), 2.17-2.08 (m, 1H), 1.42-1.32 (m, 2H), 1.23-1.11 (m, 3H), 0.45 (ddd, J=6.5, 5.2, 2.1 Hz, 1H). LCMS-ESI+ (m/z): [M+H]$^+$ calculated for $C_{22}H_{19}N_6O_4$: 431.2; found: 430.9.

Step 3 To a solution of 3H-[1,2,3]triazolo[4,5-b]pyridin-3-yl (1aR,6aR)-5-(2-((1-ethynylcyclopropyl)amino)-2-oxoacetyl)-4-methyl-1,1a,6,6a-tetrahydrocyclopropa[b]pyrrolizine-3-carboxylate (59.6 mg, 0.138 mmol) and 2-(difluoromethyl)pyridin-4-amine (61.2 mg, 0.425 mmol) in dichloromethane (3 mL) was added 2,6-lutidine (0.07 mL, 0.601 mmol) and the resulting mixture was concentrated to an oil. The resulting oil was heated at 60° C. bath for 4 h, and at 100° C. bath for 17 h. The reaction mixture was was purified by silica gel column chromatography eluting 0-20% methanol in dichloromethane to get (1aR,6aR)-N-(2-(difluoromethyl)pyridin-4-yl)-5-(2-((1-ethynylcyclopropyl)

amino)-2-oxoacetyl)-4-methyl-1,1a,6,6a-tetrahydrocyclopropa[b]pyrrolizine-3-carboxamide: $^1$H NMR (400 MHz, Chloroform-d) δ 8.57 (d, J=5.5 Hz, 1H), 7.83 (d, J=2.1 Hz, 1H), 7.78 (s, 1H), 7.75 (dd, J=5.7, 2.0 Hz, 1H), 7.44 (s, 1H), 6.63 (t, J=55.4 Hz, 1H), 4.48 (dd, J=6.9, 5.0 Hz, 1H), 3.58 (dd, J=19.2, 6.9 Hz, 1H), 3.39-3.22 (m, 1H), 2.61 (s, 3H), 2.18 (s, 1H), 2.15-2.03 (m, 1H), 1.42-1.32 (m, 2H), 1.20-1.06 (m, 3H), 0.32 (ddd, J=6.4, 5.1, 2.1 Hz, 1H). $^{19}$F NMR (376 MHz, Chloroform-d) δ −116.58 (d, J=55.3 Hz). LCMS-ESI+ (m/z): [M+H]$^+$ calculated for $C_{23}H_{21}F_2N_4O_3$: 439.2; found: 439.2.

Step 4 A solution of (1aR,6aR)-N-(2-(difluoromethyl)pyridin-4-yl)-5-(2-((1-ethynylcyclopropyl)amino)-2-oxoacetyl)-4-methyl-1,1a,6,6a-tetrahydrocyclopropa[b]pyrrolizine-3-carboxamide (22.2 mg, 0.051 mmol) in N,N-dimethylformamide/methanol (9:1 mixture, 2 mL) was placed in a thick wall tube containing copper iodide (1.4 mg, 7.351 umol) and azidotrimethylsilane (30 mg, 0.260 mmol) was added to the mixture. The resulting tube was kept tightly and the mixture was stirred at 100° C. bath for 12 h. The reaction mixture was diluted with ethyl acetate and washed with water (×2). After the aq. fractions were extracted with ethyl acetate (×1), the organic fractions were combined, dried with magnesium sulfate. After filtration, solvent was removed and the residue was purified by silica gel column chromatography eluting 0-14% methanol in dichloromethane to get impure product. The impure product was further purified by Preparative HPLC (column, Gemini 10u C18 110A, AXI/; 250×21.2 mm) eluting 10-90% acetonitrile (0.1% TFA) in water (0.1% TFA) to get (1aR,6aR)-5-(2-((1-(1H-1,2,3-triazol-4-yl)cyclopropyl)amino)-2-oxoacetyl)-N-(2-(difluoromethyl)pyridin-4-yl)-4-methyl-1,1a,6,6a-tetrahydrocyclopropa[b]pyrrolizine-3-carboxamide.

Example 57. (1aR,6aR)-5-(2-((1-(1,3,4-thiadiazol-2-yl)cyclopropyl)amino)-2-oxoacetyl)-4-methyl-N-(3,4,5-trifluorophenyl)-1,1a,6,6a-tetrahydrocyclopropa[b]pyrrolizine-3-carboxamide

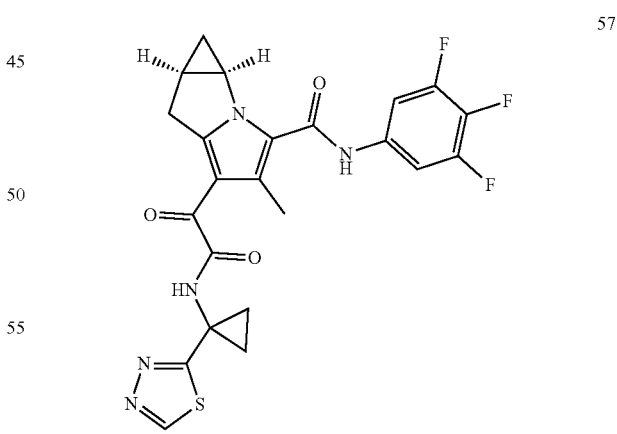

57

(1aR,6aR)-5-(2-((1-(1,3,4-thiadiazol-2-yl)cyclopropyl)amino)-2-oxoacetyl)-4-methyl-N-(3,4,5-trifluorophenyl)-1,1a,6,6a-tetrahydrocyclopropa[b]pyrrolizine-3-carboxamide (57) was synthesized in a manner similar to Example 38 using 1-(1,3,4-thiadiazol-2-yl)cyclopropan-1-amine hydrogen bromide in place of 3,3-difluoro-(1-methylaminocarbonyl)-1-cyclobutanamine hydrochloride.

213

Example 58. (1aR,6aR)-5-(2-((1-(1,3,4-thiadiazol-2-yl)cyclopropyl)amino)-2-oxoacetyl)-N-(3-cyano-4-fluorophenyl)-4-methyl-1,1a,6,6a-tetrahydrocyclopropa[b]pyrrolizine-3-carboxamide (58)

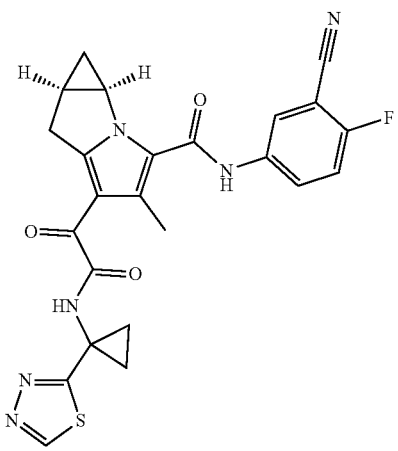

58

(1aR,6aR)-5-(2-((1-(1,3,4-thiadiazol-2-yl)cyclopropyl)amino)-2-oxoacetyl)-N-(3-cyano-4-fluorophenyl)-4-methyl-1,1a,6,6a-tetrahydrocyclopropa[b]pyrrolizine-3-carboxamide (58) was synthesized in a manner similar to Example 30 using 1-(1,3,4-thiadiazol-2-yl)cyclopropan-1-amine hydrogen bromide in place of 3,3-difluoro-(1-methylaminocarbonyl)-1-cyclobutanamine hydrochloride.

Example 59. 7-(2-((3,3-difluoro-1-(1H-1,2,3-triazol-4-yl)cyclobutyl)amino)-2-oxoacetyl)-N-(2-(difluoromethyl)-3-fluoropyridin-4-yl)-6-methyl-2,3-dihydro-1H-pyrrolizine-5-carboxamide

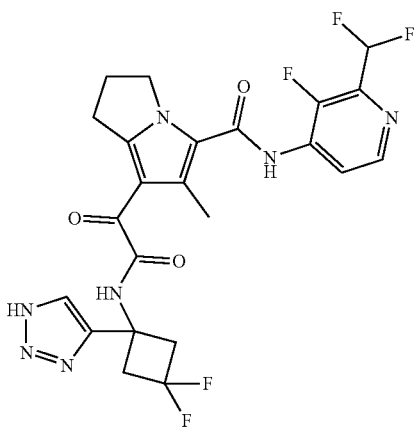

59

7-(2-((3,3-difluoro-1-(1H-1,2,3-triazol-4-yl)cyclobutyl)amino)-2-oxoacetyl)-N-(2-(difluoromethyl)-3-fluoropyridin-4-yl)-6-methyl-2,3-dihydro-1H-pyrrolizine-5-carboxamide (59) was synthesized in a manner similar to Example 29 using 2-(difluoromethyl)-3-fluoropyridin-4-amine in place of 3-chloro-4-fluouroaniline.

214

Example 60. N-(3-chloro-4-fluorophenyl)-7-(2-((1-ethynyl-3,3-difluorocyclobutyl)amino)-2-oxoacetyl)-6-methyl-2,3-dihydro-1H-pyrrolizine-5-carboxamide

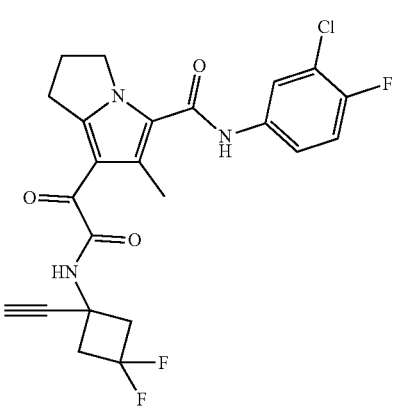

60

N-(3-chloro-4-fluorophenyl)-7-(2-((1-ethynyl-3,3-difluorocyclobutyl)amino)-2-oxoacetyl)-6-methyl-2,3-dihydro-1H-pyrrolizine-5-carboxamide (60) was synthesized in a manner similar to Example 29 using 1-ethynyl-3,3-difluorocyclobutan-1-amine trifluoromethanesulfonate in place of 3,3-difluoro-1-(1H-1,2,3-triazol-4-yl)cyclobutan-1-amine hydrochloride.

Example 61. (1aR,6aR)-5-(2-((1-(1,3,4-thiadiazol-2-yl)cyclopropyl)amino)-2-oxoacetyl)-N-(3,4-difluorophenyl)-4-methyl-1,1a,6,6a-tetrahydrocyclopropa[b]pyrrolizine-3-carboxamide

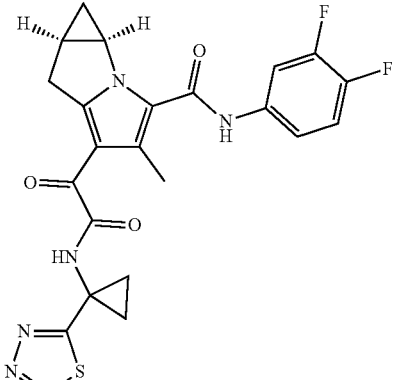

61

(1aR,6aR)-5-(2-((1-(1,3,4-thiadiazol-2-yl)cyclopropyl)amino)-2-oxoacetyl)-N-(3,4-difluorophenyl)-4-methyl-1,1a,6,6a-tetrahydrocyclopropa[b]pyrrolizine-3-carboxamide (61) was synthesized in a manner similar to Example 42 using 1-(1,3,4-thiadiazol-2-yl)cyclopropan-1-amine hydrogen bromide in place of 3,3-difluoro-(1-methylaminocarbonyl)-1-cyclobutanamine hydrochloride.

Example 62. (1aR,6aR)-5-(2-((1-(1,3,4-thiadiazol-2-yl)cyclopropyl)amino)-2-oxoacetyl)-N-(2-(difluoromethyl)pyridin-4-yl)-4-methyl-1,1a,6,6a-tetrahydrocyclopropa[b]pyrrolizine-3-carboxamide

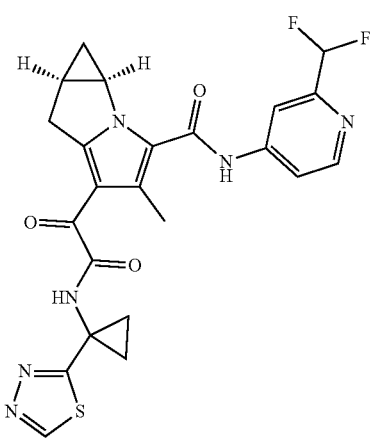

(1aR,6aR)-5-(2-((1-(1,3,4-thiadiazol-2-yl)cyclopropyl)amino)-2-oxoacetyl)-N-(2-(difluoromethyl)pyridin-4-yl)-4-methyl-1,1a,6,6a-tetrahydrocyclopropa[b]pyrrolizine-3-carboxamide (62) was synthesized in a manner similar to Example 56 using 1-(1,3,4-thiadiazol-2-yl)cyclopropan-1-amine hydrogen bromide in place of 3,3-difluoro-(1-methylaminocarbonyl)-1-cyclobutanamine hydrochloride.

Example 63 (1aR,6aR)-5-(2-((1-(1H-1,2,3-triazol-4-yl)cyclopropyl)amino)-2-oxoacetyl)-N-(2-(difluoromethyl)-3-fluoropyridin-4-yl)-4-methyl-1,1a,6,6a-tetrahydrocyclopropa[b]pyrrolizine-3-carboxamide (63)

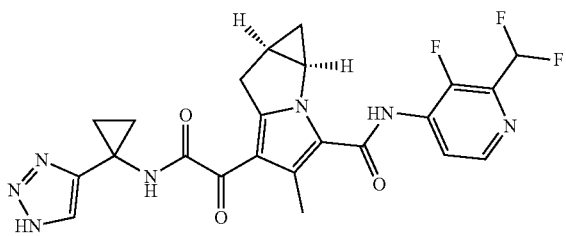

(1aR,6aR)-5-(2-((1-(1H-1,2,3-triazol-4-yl)cyclopropyl)amino)-2-oxoacetyl)-N-(2-(difluoromethyl)-3-fluoropyridin-4-yl)-4-methyl-1,1a,6,6a-tetrahydrocyclopropa[b]pyrrolizine-3-carboxamide (63) was synthesized in a manner similar to Example 56 using 2-(difluoromethyl)-3-fluoropyridin-4-amine in place of 2-(difluoromethyl)pyridin-4-amine.

Example 64. N-(3-chloro-4-fluorophenyl)-6-methyl-7-(2-((1-(5-methyl-1,3,4-oxadiazol-2-yl)cyclopropyl)amino)-2-oxoacetyl)-2,3-dihydro-1H-pyrrolizine-5-carboxamide

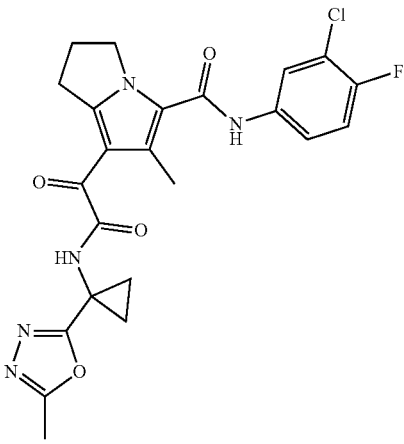

N-(3-chloro-4-fluorophenyl)-6-methyl-7-(2-((1-(5-methyl-1,3,4-oxadiazol-2-yl)cyclopropyl)amino)-2-oxoacetyl)-2,3-dihydro-1H-pyrrolizine-5-carboxamide (64) was synthesized in a manner similar to Example 2 using 1-(5-methyl-1,3,4-oxadiazol-2-yl)cyclopropan-1-amine in place of R-trifluoroisopropylamine.

Example 65. 6-methyl-7-(2-((1-(5-methyl-1,3,4-oxadiazol-2-yl)cyclopropyl)amino)-2-oxoacetyl)-N-(3,4,5-trifluorophenyl)-2,3-dihydro-1H-pyrrolizine-5-carboxamide

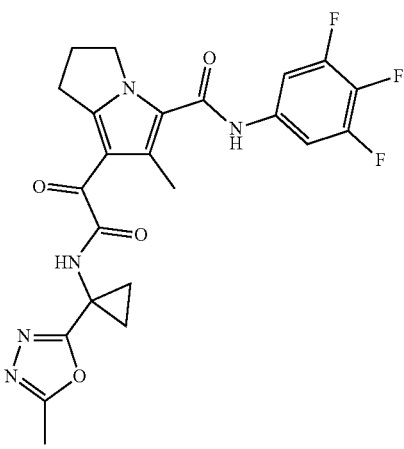

6-methyl-7-(2-((1-(5-methyl-1,3,4-oxadiazol-2-yl)cyclopropyl)amino)-2-oxoacetyl)-N-(3,4,5-trifluorophenyl)-2,3-dihydro-1H-pyrrolizine-5-carboxamide (65) was synthesized in a manner similar to Example 64 using 3,4,5-trifluoroaniline in place of 3-chloro-4-fluoroaniline.

Example 66. N-(3-chloro-4-fluorophenyl)-6-methyl-7-(2-oxo-2-((1-phenylcyclopropyl)amino)acetyl)-2,3-dihydro-1H-pyrrolizine-5-carboxamide

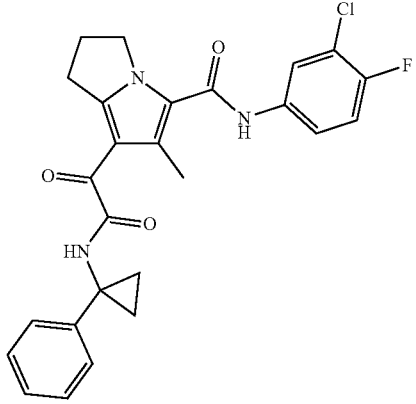

N-(3-chloro-4-fluorophenyl)-6-methyl-7-(2-oxo-2-((1-phenylcyclopropyl)amino)acetyl)-2,3-dihydro-1H-pyrrolizine-5-carboxamide (66) was synthesized in a manner similar to Example 2 using 1-phenylcyclopropan-1-amine in place of R-trifluoroisopropylamine.

Example 67. 6-methyl-7-(2-oxo-2-((1-phenylcyclopropyl)amino)acetyl)-N-(3,4,5-trifluorophenyl)-2,3-dihydro-1H-pyrrolizine-5-carboxamide

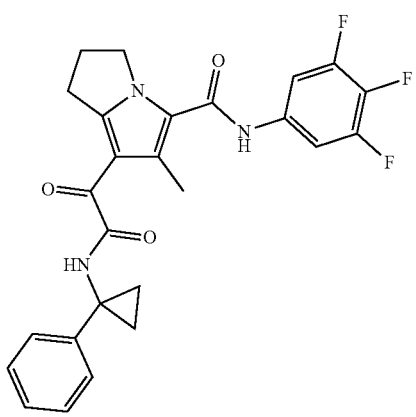

6-methyl-7-(2-oxo-2-((1-phenylcyclopropyl)amino)acetyl)-N-(3,4,5-trifluorophenyl)-2,3-dihydro-1H-pyrrolizine-5-carboxamide (67) was synthesized in a manner similar to Example 66 using 3,4,5-trifluoroaniline in place of 3-chloro-4-fluoroaniline.

Example 68. (1aR,6aR)-5-(2-((1-(1,3,4-thiadiazol-2-yl)cyclopropyl)amino)-2-oxoacetyl)-N-(2-(difluoromethyl)-3-fluoropyridin-4-yl)-4-methyl-1,1a,6,6a-tetrahydrocyclopropa[b]pyrrolizine-3-carboxamide

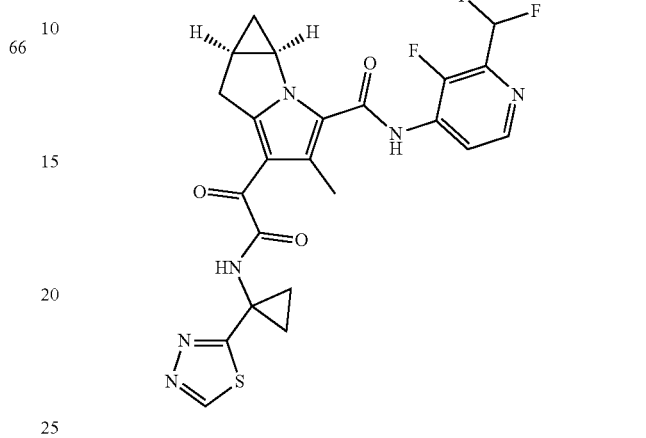

(1aR,6aR)-5-(2-((1-(1,3,4-thiadiazol-2-yl)cyclopropyl)amino)-2-oxoacetyl)-N-(2-(difluoromethyl)-3-fluoropyridin-4-yl)-4-methyl-1,1a,6,6a-tetrahydrocyclopropa[b]pyrrolizine-3-carboxamide (68) was synthesized in a manner similar to Example 63 using 1-(1,3,4-thiadiazol-2-yl)cyclopropan-1-amine hydrogen bromide in place of 3,3-difluoro-(1-methylaminocarbonyl)-1-cyclobutanamine hydrochloride.

Example 69. 7-(2-((1-(1H-1,2,3-triazol-4-yl)cyclopropyl)amino)-2-oxoacetyl)-N-(3-fluorophenyl)-6-methyl-2,3-dihydro-1H-pyrrolizine-5-carboxamide (69)

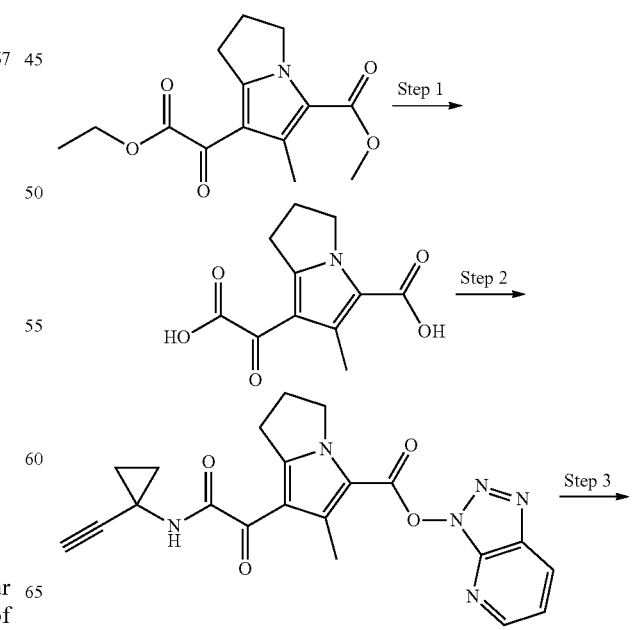

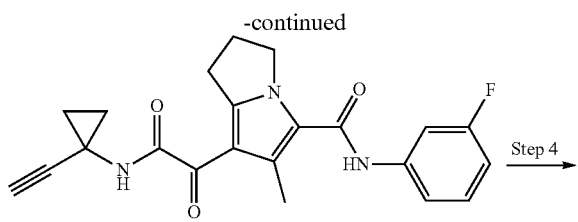

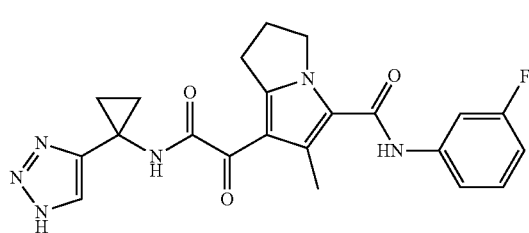

Step 1: Lithium hydroxide (1N, 12.9 mL, 12.9 mmol) was added to a solution of methyl 7-(2-ethoxy-2-oxoacetyl)-6-methyl-2,3-dihydro-1H-pyrrolizine-5-carboxylate (1.2 g, 4.29 mmol) in methanol. The mixture warmed and all material dissolved. The solution was heated at 60° C. for 8 h. The reaction was diluted with water (10 mL) and the majority of the methanol was removed under reduced pressure. The aqueous phase was extracted with ethyl acetate (3×50 mL). The aqueous phase was acidified with hydrochloric acid (1N, 14 mL) and extracted with ethyl acetate (3×50 mL). The combined acidic extracts were washed with brine (50 mL), dried over sodium sulfate. The solvent was removed under reduced pressure. The residue was co-evaporated with ethyl acetate (2×20 mL) and subjected to high vacuum for 2 h, providing 7-(carboxycarbonyl)-6-methyl-2,3-dihydro-1H-pyrrolizine-5-carboxylic acid. $^1$H NMR (400 MHz, DMSO-d6) δ 12.72 (s, 1H), 4.20 (t, J=7.3 Hz, 2H), 2.89 (t, J=7.6 Hz, 2H), 2.49 (s, 3H), 2.40 (p, J=7.5 Hz, 2H).

Step 2: N,N-Diisoprpylethylamine (1.83 mL, 10.5 mmol) was added to a suspension of 7-(carboxycarbonyl)-6-methyl-2,3-dihydro-1H-pyrrolizine-5-carboxylic acid (500 mg, 2.11 mmol) and 1-[Bis(dimethylamino)methylene]-1H-1,2,3-triazolo[4,5-b]pyridinium 3-oxid hexafluorophosphate (1.76 g, 4.64 mmol) in dichloromethane. After 2 min 1-ethynylcyclopropan-1-amine 2,2,2-trifluoroacetate (617 mg, 3.16 mmol) was added. After 30 m the reaction was diluted with ethyl acetate (50 mL) and washed with water (20 mL), saturated ammonium chloride (3×20 mL), saturated sodium bicarbonate (3×20 mL) and brine (20 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing 3H-[1,2,3]triazolo[4,5-b]pyridin-3-yl 7-(2-((1-ethynylcyclopropyl)amino)-6-methyl-2,3-dihydro-1H-pyrrolizine-5-carboxylate. $^1$H NMR (400 MHz, DMSO-d6) δ 9.37 (s, 1H), 9.18 (s, 1H), 8.83 (dd, J=4.5, 1.3 Hz, 1H), 8.73 (dd, J=8.4, 1.4 Hz, 1H), 7.65 (dd, J=8.5, 4.5 Hz, 1H), 4.35 (t, J=7.3 Hz, 2H), 4.19 (s, 1H), 3.08 (s, 1H), 3.07-3.00 (m, 2H), 2.89 (t, J=7.6 Hz, 1H), 2.66 (s, 3H), 2.37 (t, J=7.3 Hz, 1H), 1.21-1.11 (m, 2H), 1.10-0.99 (m, 2H).

Step 3: 2,6-Lutidine (55.5 uL, 0.4785 mmol) 3-fluoroaniline (34.5 uL, 0.358 mmol) and 3H-[1,2,3]triazolo[4,5-b]pyridin-3-yl 7-(2-((1-ethynylcyclopropyl)amino)-2-oxoacetyl)-6-methyl-2,3-dihydro-1H-pyrrolizine-5-carboxylate (50 mg, 0.119 mmol) were dissolved in dichloromethane (3 mL). The majority of the dichloromethane was removed under reduced pressure. The oil was heated neat at 100° C. for 18 h-solid formed. Dichloromethane (3 mL) was added and the mixture was stirred under homogenous. The solid was isolated by filtration and subjected to high vacuum for 30 minutes, providing 7-(2-((1-ethynylcyclopropyl)amino)-2-oxoacetyl)-N-(3-fluorophenyl)-6-methyl-2,3-dihydro-1H-pyrrolizine-5-carboxamide. $^1$H NMR (400 MHz, DMSO-d6) δ 9.97 (s, 1H), 9.21 (s, 1H), 7.65-7.56 (m, 1H), 7.36 (dt, J=22.9, 8.1 Hz, 2H), 6.89 (t, J=8.4 Hz, 1H), 4.13 (t, J=7.3 Hz, 2H), 3.04 (s, 1H), 2.92 (t, J=7.5 Hz, 2H), 2.41 (s, 5H), 1.19-1.11 (m, 2H), 1.07-0.97 (m, 2H).

Step 4: Azidomethyl pivalate (15.2 uL, 0.0995 mmol) was added to a mixture of 7-(2-((1-ethynylcyclopropyl)amino)-2-oxoacetyl)-N-(3-fluorophenyl)-6-methyl-2,3-dihydro-1H-pyrrolizine-5-carboxamide (35.6 mg, 0.0905 mmol) Copper (I)-thiophene-2-carboxylate (3.45 mg, 0.00181 mmol) in methanol 2 mL) and dimethylformamide (1 mL). After 30 min sodium hydroxide (1N, 136 uL, 0.136 mmol) was added. After 15 min the reaction was neutralized with hydrochloric acid (1N, 136 uL, 0.00181 mmol). The volatiles were removed under reduced pressure. The residue was dissolved in N,N-dimethylformamide. The turbid solution was syringe filtered and subjected to preparative HPLC (eluant: 0.1% trifluoroacetic acid in water/0.1% trifluoroacetic acid in acetonitrile). The fractions containing product were combined and subjected to lyophilization providing 7-(2-((1-(1H-1,2,3-triazol-4-yl)cyclopropyl)amino)-2-oxoacetyl)-N-(3-fluorophenyl)-6-methyl-2,3-dihydro-1H-pyrrolizine-5-carboxamide. $^1$H NMR (400 MHz, DMSO-d6) δ 9.98 (s, 1H), 9.36 (s, 1H), 7.65-7.52 (m, 2H), 7.44-7.30 (m, 2H), 6.89 (td, J=8.5, 8.1, 2.2 Hz, 1H), 4.12 (t, J=7.3 Hz, 2H), 2.85 (t, J=7.3 Hz, 2H), 2.41 (s, 3H), 2.40-2.34 (m, 2H), 1.31-1.23 (m, 2H), 1.20 (t, J=3.2 Hz, 2H).

Example 70. 7-(2-((1-(1H-1,2,3-triazol-4-yl)cyclopropyl)amino)-2-oxoacetyl)-N-(4-fluorophenyl)-6-methyl-2,3-dihydro-1H-pyrrolizine-5-carboxamide (70)

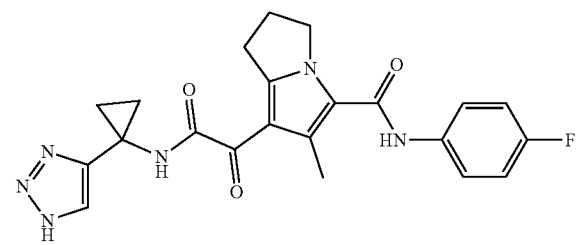 [SMILES: Cc1c(C(=O)C(=O)NC2(c3c[nH]nn3)CC2)c2n(c1C(=O)Nc1ccc(F)cc1)CCC2]

7-(2-((1-(1H-1,2,3-triazol-4-yl)cyclopropyl)amino)-2-oxoacetyl)-N-(4-fluorophenyl)-6-methyl-2,3-dihydro-1H-pyrrolizine-5-carboxamide was synthesized in a manner similar to Example 69 using 4-fluoroaniline in place of 3-fluoroaniline.

Example 71. (1aR,6aR)-N-(3-chloro-4-fluorophenyl)-4-methyl-5-(2-((3-methyl-1,1-dioxidothietan-3-yl)amino)-2-oxoacetyl)-1,1a,6,6a-tetrahydrocyclopropa[b]pyrrolizine-3-carboxamide

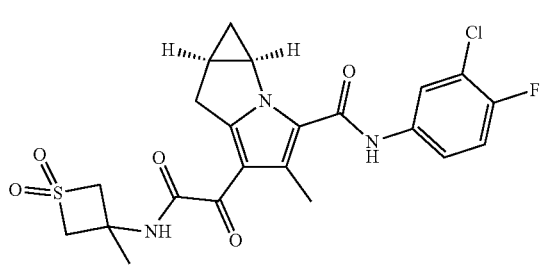

(1aR,6aR)-N-(3-chloro-4-fluorophenyl)-4-methyl-5-(2-((3-methyl-1,1-dioxidothietan-3-yl)amino)-2-oxoacetyl)-1,1a,6,6a-tetrahydrocyclopropa[b]pyrrolizine-3-carboxamide (71) was synthesized in a manner similar to Example 5 using 3-amino-3-methylthietane 1,1-dioxide in place of 3,3-difluoro-(1-methylaminocarbonyl)-1-cyclobutanamine hydrochloride.

Example 72. (1aR,6aR)-N-(3-cyano-4-fluorophenyl)-4-methyl-5-(2-((3-methyl-1,1-dioxidothietan-3-yl)amino)-2-oxoacetyl)-1,1a,6,6a-tetrahydrocyclopropa[b]pyrrolizine-3-carboxamide

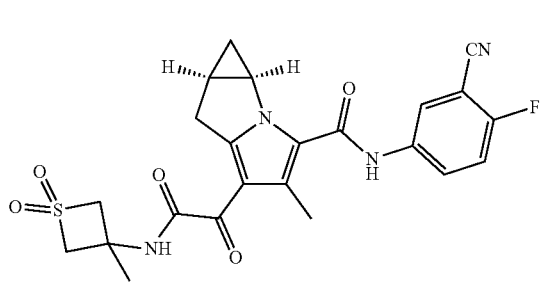

(1aR,6aR)-N-(3-cyano-4-fluorophenyl)-4-methyl-5-(2-((3-methyl-1,1-dioxidothietan-3-yl)amino)-2-oxoacetyl)-1,1a,6,6a-tetrahydrocyclopropa[b]pyrrolizine-3-carboxamide (72) was synthesized in a manner similar to Example 5 using 1-(1,3,4-thiadiazol-2-yl)cyclopropan-1-amine hydrogen bromide in place of 3,3-difluoro-(1-methylaminocarbonyl)-1-cyclobutanamine hydrochloride and 5-amino-2-fluorobenzonitrile in place of 3-chloro-4-fluoroaniline.

Example 73. (1aR,6aR)-4-methyl-5-(2-((3-methyl-1,1-dioxidothietan-3-yl)amino)-2-oxoacetyl)-N-(3,4,5-trifluorophenyl)-1,1a,6,6a-tetrahydrocyclopropa[b]pyrrolizine-3-carboxamide

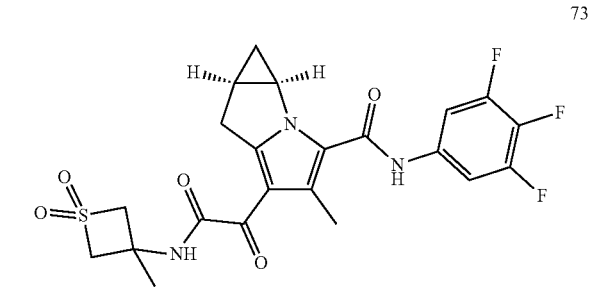 [SMILES: Cc1c(C(=O)C(=O)NC2(C)CS(=O)(=O)C2)c2n(c1C(=O)Nc1cc(F)c(F)c(F)c1)[C@@H]1C[C@@H]1C2]

(1aR,6aR)-4-methyl-5-(2-((3-methyl-1,1-dioxidothietan-3-yl)amino)-2-oxoacetyl)-N-(3,4,5-trifluorophenyl)-1,1a,6,6a-tetrahydrocyclopropa[b]pyrrolizine-3-carboxamide (73) was synthesized in a manner similar to Example 5 using 1-(1,3,4-thiadiazol-2-yl)cyclopropan-1-amine hydrogen bromide in place of 3,3-difluoro-(1-methylaminocarbonyl)-1-cyclobutanamine hydrochloride and 3,4,5-trifluoroaniline in place of 3-chloro-4-fluoroaniline.

Example 74. 7-(2-((1-(1H-1,2,3-triazol-4-yl)cyclopropyl)amino)-2-oxoacetyl)-N-(3-chlorophenyl)-6-methyl-2,3-dihydro-1H-pyrrolizine-5-carboxamide

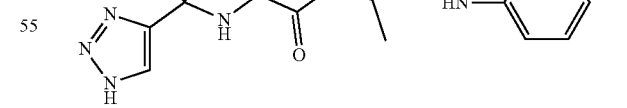

7-(2-((1-(1H-1,2,3-triazol-4-yl)cyclopropyl)amino)-2-oxoacetyl)-N-(3-chlorophenyl)-6-methyl-2,3-dihydro-1H-pyrrolizine-5-carboxamide was synthesized in a manner similar to Example 26 using 3-chloroaniline in place of 3-fluoroaniline.

Example 75. 7-(2-((1-(1H-1,2,3-triazol-4-yl)cyclopropyl)amino)-2-oxoacetyl)-N-(3-cyanophenyl)-6-methyl-2,3-dihydro-1H-pyrrolizine-5-carboxamide

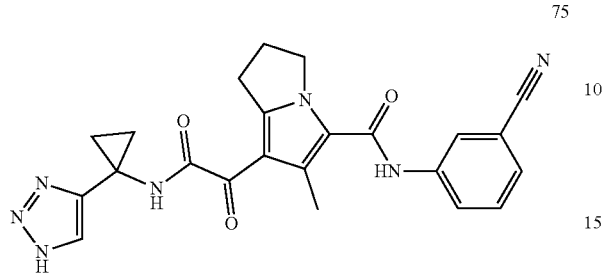

75

7-(2-((1-(1H-1,2,3-triazol-4-yl)cyclopropyl)amino)-2-oxoacetyl)-N-(3-cyanophenyl)-6-methyl-2,3-dihydro-1H-pyrrolizine-5-carboxamide was synthesized in a manner similar to Example 69 using 3-cyanoaniline in place of 3-fluoroaniline.

Example 76. 7-(2-((1-(1H-1,2,3-triazol-4-yl)cyclopropyl)amino)-2-oxoacetyl)-N-(3,5-difluorophenyl)-6-methyl-2,3-dihydro-1H-pyrrolizine-5-carboxamide

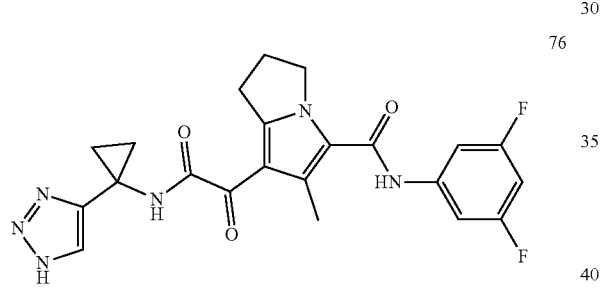

76

7-(2-((1-(1H-1,2,3-triazol-4-yl)cyclopropyl)amino)-2-oxoacetyl)-N-(3,5-difluorophenyl)-6-methyl-2,3-dihydro-1H-pyrrolizine-5-carboxamide was synthesized in a manner similar to Example 69 using 3,5-difluoroaniline in place of 3-fluoroaniline.

Example 77. 7-(2-((1-(1H-1,2,3-triazol-4-yl)cyclopropyl)amino)-2-oxoacetyl)-N-(3-(difluoromethyl)-4-fluorophenyl)-6-methyl-2,3-dihydro-1H-pyrrolizine-5-carboxamide

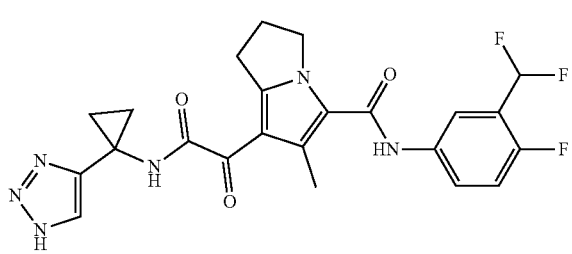

77

7-(2-((1-(1H-1,2,3-triazol-4-yl)cyclopropyl)amino)-2-oxoacetyl)-N-(3-(difluoromethyl)-4-fluorophenyl)-6-methyl-2,3-dihydro-1H-pyrrolizine-5-carboxamide was synthesized in a manner similar to Example 69 using 3-(difluoromethyl)-4-fluoroaniline in place of 3-fluoroaniline.

Example 78. (1aR,6aR)-5-(2-((3,3-difluoro-1-(1H-1,2,3-triazol-4-yl)cyclobutyl)amino)-2-oxoacetyl)-N-(2-(difluoromethyl)pyridin-4-yl)-4-methyl-1,1a,6,6a-tetrahydrocyclopropa[b]pyrrolizine-3-carboxamide

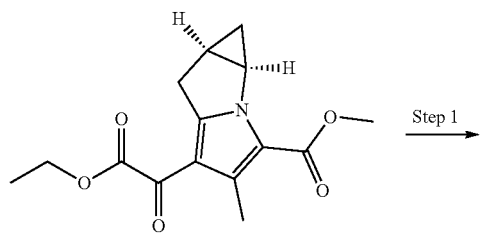

methyl (1aR,6aR)-5-(2-ethoxy-2-oxoacetyl)-4-methyl-1,1a,6,6a-tetrahydrocyclopropa[b]pyrrolizine-3-carboxylate

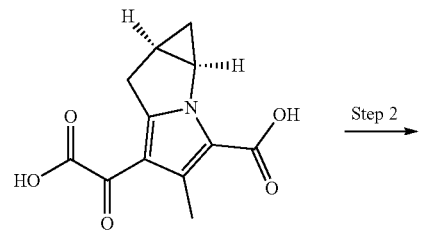

(1aR,6aR)-5-(carboxycarbonyl)-4-methyl-1,1a,6,6a-tetrahydrocyclopropa[b]pyrrolizine-3-carboxylic acid

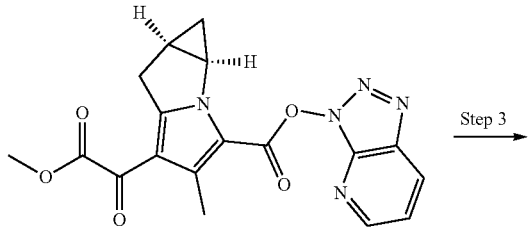

3H-[1,2,3]triazolo[4,5-b]pyridin-3-yl (1aR,6aR)-5-(2-methoxy-2-oxoacetyl)-4-methyl-1,1a,6,6a-tetrahydrocyclopropa[b]pyrrolizine-3-carboxylate

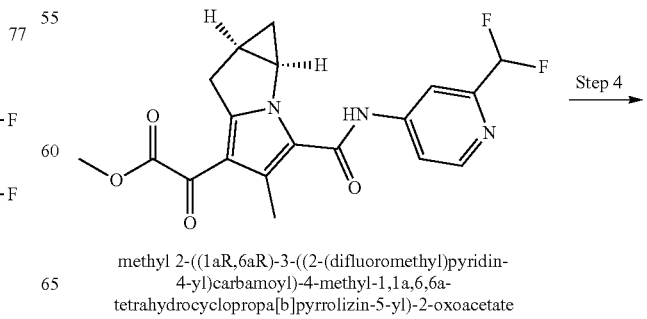

methyl 2-((1aR,6aR)-3-((2-(difluoromethyl)pyridin-4-yl)carbamoyl)-4-methyl-1,1a,6,6a-tetrahydrocyclopropa[b]pyrrolizin-5-yl)-2-oxoacetate

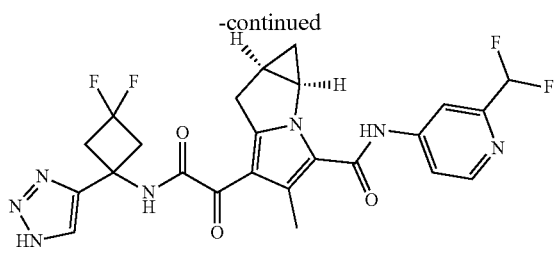

(1aR,6aR)-5-(2-((3,3-difluoro-1-(1H-1,2,3-triazol-4-yl)cyclobutyl)amino)-2-oxoacetyl)-N-(2-(difluoromethyl)pyridin-4-yl)-4-methyl-1,1a,6,6a-tetrahydrocyclopropa[b]pyrrolizine-3-carboxamide
78

Step 1 A solution of methyl (1aR,6aR)-5-(2-ethoxy-2-oxoacetyl)-4-methyl-1,1a,6,6a-tetrahydrocyclopropa[b]pyrrolizine-3-carboxylate (2730 mg, 9.372 mmol) was stirred in tetrahydrofuran (20 mL), methanol (20 mL), and 1 N lithium hydroxide (28 mL) and the resulting solution was stirred at 60° C. for 8 h. After the reaction mixture was concentrated to remove most of the organic solvents, the residual solution was diluted with water (~30 mL) and washed with diethyl ether (×1), acidified with 1 N hydrochloric acid (~28 mL), and the product was extracted with ethyl acetate (×1). The aqueous fraction was saturated with NaCl and extracted with ethyl acetate (×1). After the organic fractions were washed with brine (×1), two organic fractions were combined, dried with magnesium sulfate. After filtration, solvent was removed and dried in vacuum overnight to give (1aR,6aR)-5-(carboxycarbonyl)-4-methyl-1,1a,6,6a-tetrahydrocyclopropa[b]pyrrolizine-3-carboxylic acid. LCMS-ESI+ (m/z): [M+H]$^+$ calculated for $C_{12}H_{12}NO_5$: 250.1; found: 249.9.

Step 2 (1aR,6aR)-5-(carboxycarbonyl)-4-methyl-1,1a,6,6a-tetrahydrocyclopropa[b]pyrrolizine-3-carboxylic acid (201.3 mg, 0.808 mmol) and 1-[bis(dimethylamino)methylene]-1H-1,2,3-triazolo[4,5-b]pyridinium 3-oxide hexafluorophosphate (839.7 mg, 2.209 mmol) were dissolved in N,N-dimethylformamide (4 mL) and methanol (0.4 mL) followed by N,N-diisopropylethylamine (0.98 mL, 5.626 mmol) at ambient temperature. After 30 min, the reaction mixture was diluted with ethyl acetate (~40 mL) and washed with 5% LiCl solution (×2). After the aqueous fractions were extracted with ethyl acetate (×1), the organic fractions were combined, dried with magnesium sulfate. After filtration, solvent was removed and the residue was purified by silica gel column chromatography eluting 0-100% ethyl acetate in hexanes to give 3H-[1,2,3]triazolo[4,5-b]pyridin-3-yl (1aR,6aR)-5-(2-methoxy-2-oxoacetyl)-4-methyl-1,1a,6,6a-tetrahydrocyclopropa[b]pyrrolizine-3-carboxylate: $^1$H NMR (400 MHz, Chloroform-d) δ 8.75 (dd, J=4.5, 1.4 Hz, 1H), 8.46 (dd, J=8.4, 1.4 Hz, 1H), 7.47 (dd, J=8.4, 4.5 Hz, 1H), 4.47 (ddt, J=7.8, 5.9, 1.9 Hz, 1H), 3.93 (s, 3H), 3.34 (dd, J=18.8, 6.9 Hz, 1H), 3.21-3.11 (m, 1H), 2.74 (s, 3H), 2.22-2.12 (m, 1H), 1.20 (dt, J=8.7, 6.1 Hz, 1H), 0.51 (ddd, J=6.7, 5.1, 2.1 Hz, 1H). LCMS-ESI+ (m/z): [M+H]$^+$ calculated for $C_{18}H_{16}N_5O_5$: 382.1; found: 381.8.

Step 3 To a solution of 3H-[1,2,3]triazolo[4,5-b]pyridin-3-yl (1aR,6aR)-5-(2-methoxy-2-oxoacetyl)-4-methyl-1,1a,6,6a-tetrahydrocyclopropa[b]pyrrolizine-3-carboxylate (51.3 mg, 0.135 mmol) and 2-(difluoromethyl)pyridin-4-amine (63.1 mg, 0.438 mmol) in dichloromethane (5 mL) was added 2,6-lutidine (0.07 mL, 0.601 mmol) and the resulting mixture was concentrated to an oil. The resulting oil was heated at 100° C. bath for 21.5 h. The tar was dissolved in dichloromethane and the soluble material was purified by silica gel column chromatography eluting 0-100% ethyl acetate in hexanes followed by another silica gel column chromatography eluting 0-7% methanol in dichloromethane to give methyl 2-((1aR,6aR)-3-((2-(difluoromethyl)pyridin-4-yl)carbamoyl)-4-methyl-1,1a,6,6a-tetrahydrocyclopropa[b]pyrrolizin-5-yl)-2-oxoacetate: $^1$H NMR (400 MHz, Chloroform-d) δ 8.56 (d, J=5.5 Hz, 1H), 7.93-7.80 (m, 2H), 7.73 (dd, J=5.6, 2.3 Hz, 1H), 6.62 (t, J=55.4 Hz, 1H), 4.49 (tt, J=6.0, 1.9 Hz, 1H), 3.90 (s, 3H), 3.23 (dd, J=18.3, 6.8 Hz, 1H), 3.04 (d, J=18.3 Hz, 1H), 2.62 (d, J=3.0 Hz, 3H), 2.21-2.07 (m, 1H), 1.18 (dt, J=8.8, 6.2 Hz, 1H), 0.40 (qd, J=6.1, 4.9, 2.3 Hz, 1H). $^{19}$F NMR (376 MHz, Chloroform-d) δ −116.61 (d, J=55.7 Hz). LCMS-ESI+ (m/z): [M+H]$^+$ calculated for $C_{19}H_{18}N_3O_4$: 390.1; found: 390.1.

Step 4 A solution of methyl 2-((1aR,6aR)-3-((2-(difluoromethyl)pyridin-4-yl)carbamoyl)-4-methyl-1,1a,6,6a-tetrahydrocyclopropa[b]pyrrolizin-5-yl)-2-oxoacetate (18.1 mg, 46.49 umol) in tetrahydrofuran (0.3 mL), methanol (0.3 mL) and water (0.5 mL) was stirred at ambient temperature as 1 N lithium hydroxide (0.1 mL) was added. After 30 min, the reaction mixture was concentrated to remove most of the organic solvent, diluted with water, acidified with 1 N hydrochloric acid, and the product was extracted with ethyl acetate (×2). The combined extracts were dried with magnesium sulfate. After filtration, solvent was removed and dried in vacuum to give crude 2-((1aR,6aR)-3-((2-(difluoromethyl)pyridin-4-yl)carbamoyl)-4-methyl-1,1a,6,6a-tetrahydrocyclopropa[b]pyrrolizin-5-yl)-2-oxoacetic acid. LCMS-ESI+ (m/z): [M+H]$^+$ calculated for $C_{18}H_{16}N_3O_4$: 376.1; found: 376.1.

A solution of the crude 2-((1aR,6aR)-3-((2-(difluoromethyl)pyridin-4-yl)carbamoyl)-4-methyl-1,1a,6,6a-tetrahydrocyclopropa[b]pyrrolizin-5-yl)-2-oxoacetic acid, 3,3-difluoro-1-(1H-1,2,3-triazol-4-yl)cyclobutan-1-amine (12.1 mg, 69.48 umol), and 1-[bis(dimethylamino)methylene]-1H-1,2,3-triazolo[4,5-b]pyridinium 3-oxide hexafluorophosphate (46.80 mg, 123.1 umol) in N,N-dimethylformamide (1 mL) was stirred at ambient temperature as N,N-diisopropylethylamine (0.06 mL, 344.5 umol) was added. After 30 min, the reaction mixture was diluted with ethyl acetate (30 mL), washed with aq. ammonium chloride (×2), aq. sodium bicarbonate (×2), and brine (×1). After the aq. fractions were extracted with ethyl acetate (×1), the organic fractions were combined, dried with magnesium sulfate. After filtration, solvent was removed and the residue was purified by preparative HPLC (column, Gemini 10u C18 110A, AXI/; 250×21.2 mm) eluting 10-90% acetonitrile (0.1% TFA) in water (0.1% TFA) to give (1aR,6aR)-5-(2-((3,3-difluoro-1-(1H-1,2,3-triazol-4-yl)cyclobutyl)amino)-2-oxoacetyl)-N-(2-(difluoromethyl)pyridin-4-yl)-4-methyl-1,1a,6,6a-tetrahydrocyclopropa[b]pyrrolizine-3-carboxamide.

Example 79. (1aR,6aR)-5-(2-((1-(1H-1,2,3-triazol-4-yl)cyclopropyl)amino)-2-oxoacetyl)-N-(3-cyano-4-fluorophenyl)-4-methyl-1,1a,6,6a-tetrahydrocyclopropa[b]pyrrolizine-3-carboxamide

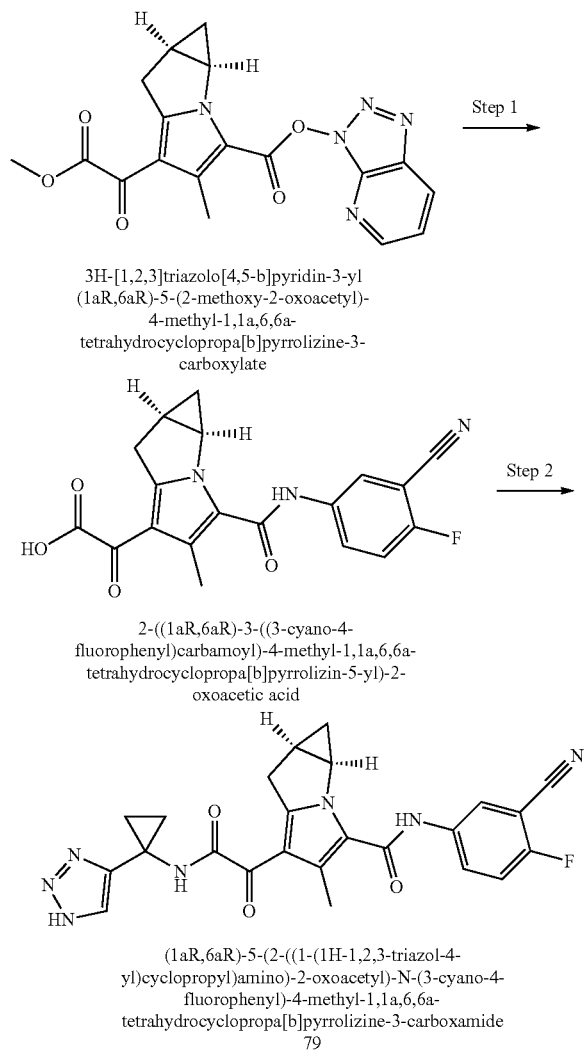

Step 1 To a solution of 3H-[1,2,3]triazolo[4,5-b]pyridin-3-yl (1aR,6aR)-5-(2-methoxy-2-oxoacetyl)-4-methyl-1,1a,6,6a-tetrahydrocyclopropa[b]pyrrolizine-3-carboxylate (138.7 mg, 0.364 mmol) and 5-amino-2-fluorobenzonitrile (153.8 mg, 1.130 mmol) in dichloromethane (2 mL) was added 2,6-lutidine (0.17 mL, 1.460 mmol) and the resulting mixture was concentrated to an oil. The resulting oil was heated at 70° C. bath for 20 h. After the residue was dissolved in N,N-dimethylformamide, the product was purified by preparative HPLC (column, Gemini 10u C18 110A, AXI/; 250×21.2 mm) eluting 10-90% acetonitrile (0.1% TFA) in water (0.1% TFA) to get methyl 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetate: $^1$H NMR (400 MHz, Acetonitrile-$d_3$) δ 8.38 (s, 1H), 8.08 (dd, J=5.7, 2.7 Hz, 1H), 7.89 (ddd, J=9.2, 4.8, 2.8 Hz, 1H), 7.33 (t, J=9.0 Hz, 1H), 4.30 (t, J=5.9 Hz, 1H), 3.88 (s, 3H), 3.20 (dd, J=18.2, 6.8 Hz, 1H), 3.06-2.94 (m, 1H), 2.51 (s, 3H), 2.15 (d, J=7.8 Hz, 1H), 1.11 (dt, J=8.7, 6.0 Hz, 1H), 0.39-0.29 (m, 1H). $^{19}$F NMR (376 MHz, Acetonitrile-$d_3$) δ −115.79−−115.91 (m). LCMS-ESI+ (m/z): [M+H]$^+$ calculated for $C_{20}H_{17}N_3O_4$: 382.1; found: 382.1.

Step 2 A solution of methyl 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetate (105.9 mg, 277.7 umol) in tetrahydrofuran (5 mL), methanol (5 mL) and water (4 mL) was stirred at ambient temperature as 1 N lithium hydroxide (0.56 mL) was added. After 30 min, the reaction mixture was concentrated to remove most of the organic solvent, diluted with water, acidified with 1 N hydrochloric acid, and the product was extracted with ethyl acetate (×3). The combined extracts were dried with magnesium sulfate. After filtration, solvent was removed and dried in vacuum to give crude 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetic acid. LCMS-ESI+ (m/z): [M+H]$^+$ calculated for $C_{19}H_{15}FN_3O_4$: 368.1; found: 368.1.

A solution of the crude 2-((1aR,6aR)-3-((3-cyano-4-fluorophenyl)carbamoyl)-4-methyl-1,1a,6,6a-tetrahydrocyclopropa[b]pyrrolizin-5-yl)-2-oxoacetic acid (18.02 mg, 49.06 umol), 1-(1H-1,2,3-triazol-4-yl)cyclopropan-1-amine (7.49 mg, 60.33 umol), and 1-[bis(dimethylamino)methylene]-1H-1,2,3-triazolo[4,5-b]pyridinium 3-oxide hexafluorophosphate (42.57 mg, 111.97 umol) in N,N-dimethylformamide (1 mL) was stirred at ambient temperature as N,N-diisopropylethylamine (0.07 mL, 401.9 umol) was added. After 30 min, the reaction mixture was diluted with ethyl acetate (30 mL), washed with aq. ammonium chloride (×2), aq. sodium bicarbonate (×2), and brine (×1). After the aq. fractions were extracted with ethyl acetate (×1), the organic fractions were combined, dried with magnesium sulfate. After filtration, solvent was removed and the residue was purified by preparative HPLC (column, Gemini 10u C18 110A, AXI/; 250×21.2 mm) eluting 10-90% acetonitrile (0.1% TFA) in water (0.1% TFA) to give (1aR,6aR)-5-(2-((1-(1H-1,2,3-triazol-4-yl)cyclopropyl)amino)-2-oxoacetyl)-N-(3-cyano-4-fluorophenyl)-4-methyl-1,1a,6,6a-tetrahydrocyclopropa[b]pyrrolizine-3-carboxamide.

Example 80. (1aR,6aR)-5-(2-((3,3-difluoro-1-(1H-1,2,3-triazol-4-yl)cyclobutyl)amino)-2-oxoacetyl)-N-(2-(difluoromethyl)-3-fluoropyridin-4-yl)-4-methyl-1,1a,6,6a-tetrahydrocyclopropa[b]pyrrolizine-3-carboxamide (80)

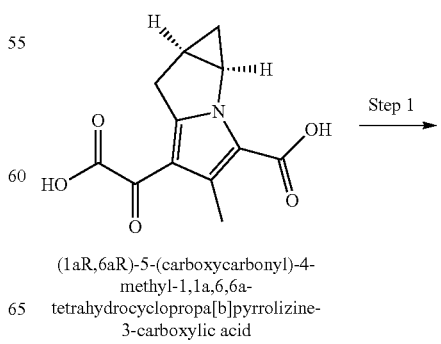

(1aR,6aR)-5-(carboxycarbonyl)-4-methyl-1,1a,6,6a-tetrahydrocyclopropa[b]pyrrolizine-3-carboxylic acid

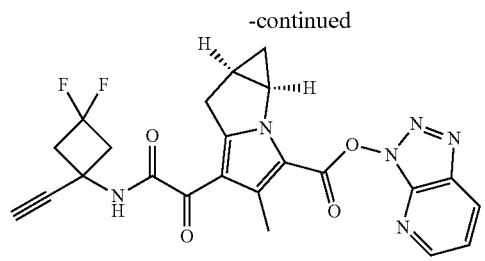

3H-[1,2,3]triazolo[4,5-b]pyridin-3-yl
(1aR,6aR)-5-(2-((-1-ethynyl-3,3-
difluorocyclobutyl)amino)-2-oxoacetyl)-
4-methyl-1,1a,6,6a-
tetrahydrocyclopropa[b]pyrrolizine-3-
carboxylate Step 2

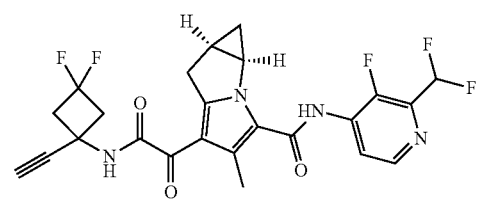

(1aR,6aR)-N-(2-difluoromethyl)-3-
fluoropyridin-4-yl)-5-(2-((1-ethynyl-3,3-
difluorocyclobutyl)amino)-2-oxoacetyl)-
4-methyl-1,1a,6,6a-
tetrahydrocyclopropa[b]pyrrolizine-3-
carboxamide Step 3

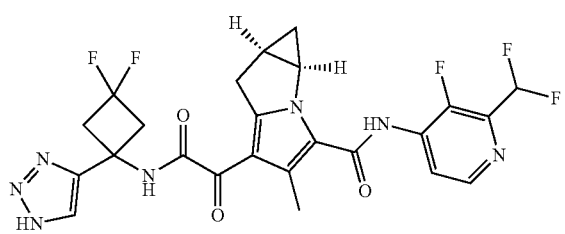

(1aR,6aR)-5-(2-((3,3-difluoro-1-(1H-1,2,3-triazol-
4-yl)cyclobutyl)amino)-2-oxoacetyl)-N-(2-
(difluoromethyl)-3-fluoropyridin-4-yl)-4-methyl-
1,1a,6,6a-tetrahydrocyclopropa[b]pyrrolizine-3-
carboxamide

80

Step 1 A solution of benzyl (1-ethynyl-3,3-difluorocyclobutyl)carbamate (291.4 mg, 1.099 mmol) and anisole (0.36 mL, 3.312 mmol) in dichloromethane (4 mL) was stirred at 0° C. bath as trifluoromethanesulfonic acid (0.2 mL, 2.260 mmol) was added. After 2 min, the mixture was stirred at ambient temperature for 2.25 h. The reaction mixture was diluted with water (~40 mL) and washed with a mixture of ether and hexanes (1:3, 40 mL×1). The resulting aqueous fraction was concentrated using rotorvap and the residue was co-evaporated with toluene (×2), dried in vacuum overnight, to get a 1:2 mixture of 1-ethynyl-3,3-difluorocyclobutan-1-amine and trifluoromethanesulfonic acid.

The mixture obtained above, 1-[bis(dimethylamino)methylene]-1H-1,2,3-triazolo[4,5-b]pyridinium 3-oxide (844.3 mg, 2.221 mmol), and (1aR,6aR)-5-(carboxycarbonyl)-4-methyl-1,1a,6,6a-tetrahydrocyclopropa[b]pyrrolizine-3-carboxylic acid (230 mg, 0.923 mmol) were dissolved in N,N-dimethylformamide (5 mL) and stirred at 0° C. as N,N-diisopropylethylamine (1.6 mL, 9.185 mmol) was added. After 1 h at 0° C., the reaction mixture was diluted with ethyl acetate (50 mL), washed with 10% aq. citric acid (×2), aq. sodium bicarbonate (×2), and brine (×1). After the aq. fractions were extracted with ethyl acetate (×1), the organic fractions were combined, dried with magnesium sulfate. After filtration, solvent was removed and the residue was purified by silica gel column chromatography eluting 0-90% ethyl acetate in hexanes to give 3H-[1,2,3]triazolo[4,5-b]pyridin-3-yl (1aR,6aR)-5-(2-((1-ethynyl-3,3-difluorocyclobutyl)amino)-2-oxoacetyl)-4-methyl-1,1a,6,6a-tetrahydrocyclopropa[b]pyrrolizine-3-carboxylate: $^1$H NMR (400 MHz, Chloroform-d) δ 8.76 (dd, J=4.5, 1.4 Hz, 1H), 8.46 (dd, J=8.4, 1.4 Hz, 1H), 7.49 (d, J=1.4 Hz, 1H), 7.48-7.45 (m, 1H), 4.48 (t, J=6.0 Hz, 1H), 3.65 (dd, J=19.3, 6.9 Hz, 1H), 3.40 (d, J=19.2 Hz, 1H), 3.20 (h, J=13.5, 12.9 Hz, 4H), 2.76 (s, 3H), 2.53 (s, 1H), 2.14 (p, J=6.2 Hz, 1H), 1.17 (dt, J=8.6, 6.1 Hz, 1H), 0.54-0.39 (m, 1H). $^{19}$F NMR (376 MHz, Chloroform-d) δ −88.08−−89.18 (m, 1F), −91.67 (dp, J=200.1, 11.6 Hz, 1F). LCMS-ESI+ (m/z): [M+H]+ calculated for $C_{23}H_{19}F_2N_6O_4$: 481.1; found: 480.9.

Step 2-3 (1aR,6aR)-5-(2-((3,3-difluoro-1-(1H-1,2,3-triazol-4-yl)cyclobutyl)amino)-2-oxoacetyl)-N-(2-(difluoromethyl)-3-fluoropyridin-4-yl)-4-methyl-1,1a,6,6a-tetrahydrocyclopropa[b]pyrrolizine-3-carboxamide was synthesized from 3H-[1,2,3]triazolo[4,5-b]pyridin-3-yl (1aR,6aR)-5-(2-((1-ethynyl-3,3-difluorocyclobutyl)amino)-2-oxoacetyl)-4-methyl-1,1a,6,6a-tetrahydrocyclopropa[b]pyrrolizine-3-carboxylate in a manner similar to Example 56 using 2-(difluoromethyl)-3-fluoropyridin-4-amine in place of 2-(difluoromethyl)pyridin-4-amine.

Example 81 (1aR,6aR)-5-(2-((1-(1H-1,2,3-triazol-4-yl)cyclopropyl)amino)-2-oxoacetyl)-N-(3,4-difluorophenyl)-4-methyl-1,1a,6,6a-tetrahydrocyclopropa[b]pyrrolizine-3-carboxamide

81

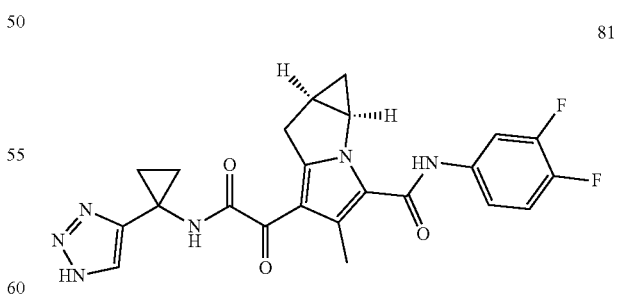

(1aR,6aR)-5-(2-((1-(1H-1,2,3-triazol-4-yl)cyclopropyl)amino)-2-oxoacetyl)-N-(3,4-difluorophenyl)-4-methyl-1,1a,6,6a-tetrahydrocyclopropa[b]pyrrolizine-3-carboxamide (81) was synthesized in a manner similar to Example 79 using 3,4-difluoroaniline in place of 5-amino-2-fluorobenzonitrile.

Example 82. N-(3-chloro-4-fluorophenyl)-6-methyl-7-(2-((2-methyl-1-(methylamino)-1-oxopropan-2-yl)amino)-2-oxoacetyl)-2,3-dihydro-1H-pyrrolizine-5-carboxamide (82)

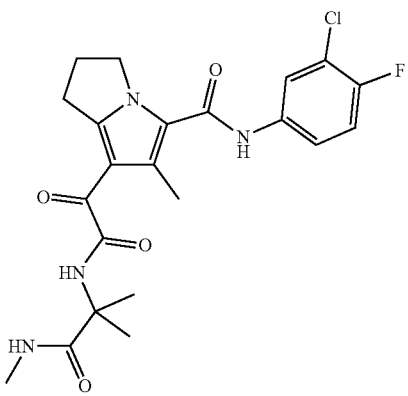

N-(3-chloro-4-fluorophenyl)-6-methyl-7-(2-((2-methyl-1-(methylamino)-1-oxopropan-2-yl)amino)-2-oxoacetyl)-2,3-dihydro-1H-pyrrolizine-5-carboxamide (82) was synthesized in a manner similar to Example 2 using 2-amino-N,2-dimethylpropanamide hydrochloride in place of R-trifluoroisopropylamine.

Example 83. 6-methyl-7-(2-((2-methyl-1-(methylamino)-1-oxopropan-2-yl)amino)-2-oxoacetyl)-N-(3,4,5-trifluorophenyl)-2,3-dihydro-1H-pyrrolizine-5-carboxamide

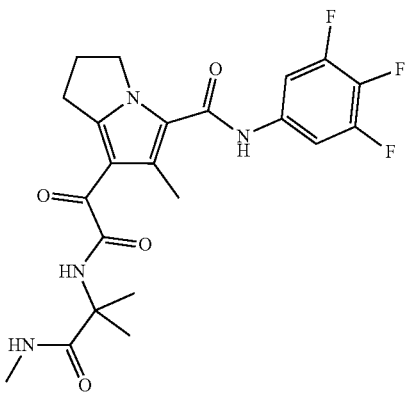

6-methyl-7-(2-((2-methyl-1-(methylamino)-1-oxopropan-2-yl)amino)-2-oxoacetyl)-N-(3,4,5-trifluorophenyl)-2,3-dihydro-1H-pyrrolizine-5-carboxamide (83) was synthesized in a manner similar to Example 82 using 3,4,5-trifluoroaniline in place of 3-chloro-4-fluoroaniline.

Example 84. 7-(2-((1-(1H-1,2,3-triazol-5-yl)cyclopropyl)amino)-2-oxoacetyl)-N-(3-chloro-2,4-difluorophenyl)-6-methyl-2,3-dihydro-1H-pyrrolizine-5-carboxamide

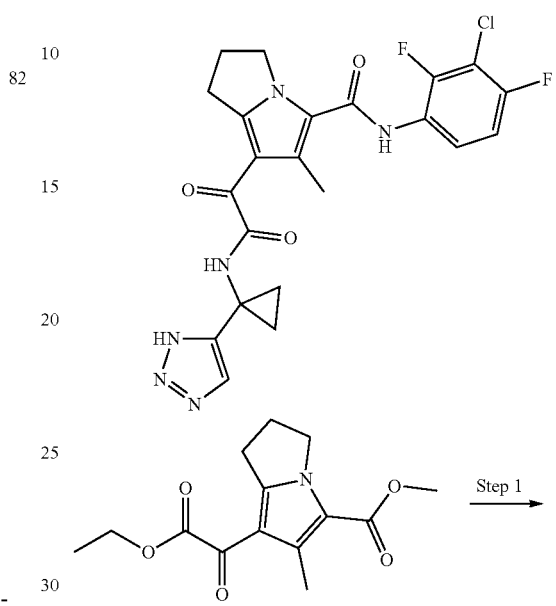

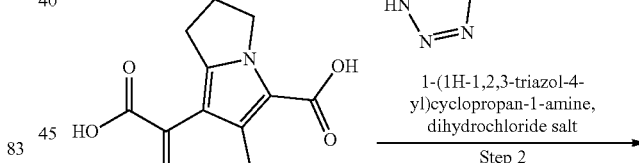

methyl 7-(2-ethoxy-2-oxoacetyl)-6-methyl-2,3-dihydro-1H-pyrrolizine-5-carboxylate

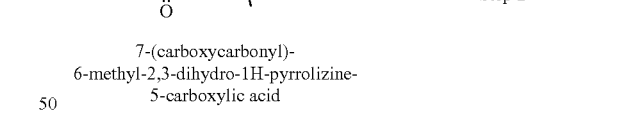

7-(carboxycarbonyl)-6-methyl-2,3-dihydro-1H-pyrrolizine-5-carboxylic acid 1-(1H-1,2,3-triazol-4-yl)cyclopropan-1-amine, dihydrochloride salt

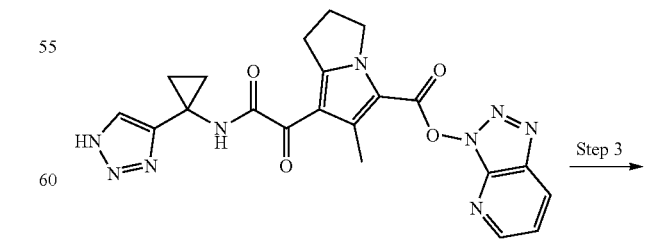

3H-[1,2,3]triazolo[4,5-b]pyridin-3-yl 7-(2-((1-(1H-1,2,3-triazol-4-yl)cyclopropyl)amino)-2-oxoacetyl)-6-methyl-2,3-dihydro-1H-pyrrolizine-5-carboxylate 233
-continued

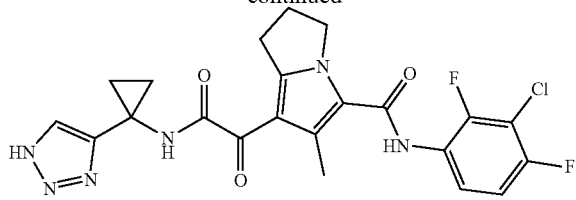

Step 1. To a solution of methyl 7-(2-ethoxy-2-oxoacetyl)-6-methyl-2,3-dihydro-1H-pyrrolizine-5-carboxylate (3.10 g, 11.1 mmol) in methanol (24 mL) was added 1 M lithium hydroxide (33.3 mL). After the resulting mixture was stirred at 65° C. for 3 h, the solution was concentrated to remove organic solvents, and the remained aqueous solution was diluted with water, acidified, and then the product was extracted with ethyl acetate. The extracts were dried over magnesium sulfate. After filtration, solvent was removed to give 7-(carboxycarbonyl)-6-methyl-2,3-dihydro-1H-pyrrolizine-5-carboxylic acid.

Step 2. A solution of 7-(carboxycarbonyl)-6-methyl-2,3-dihydro-1H-pyrrolizine-5-carboxylic acid (107 mg, 0.45 mmol), N,N-diisopropylethylamine (58 mg, 0.45 mmol), 1-[bis(dimethylamino)methylene]-1H-1,2,3-triazolo[4,5-b]pyridinium 3-oxide hexafluorophosphate (360 mg, 0.95 mmol) in dichloromethane (2 mL) was stirred at as 1-(1H-1,2,3-triazol-4-yl)cyclopropan-1-amine dihydrochloride (89 mg, 0.459 mmol) was added as a solution in N,N-dimethylformamide (0.5 mL) was added. After 4 h, the reaction mixture was treated with piperidine (0.2 mL) diluted with ethyl acetate (50 mL), washed with saturated aqueous ammonium chloride, saturated sodium bicarbonate (×2), and brine (×1). After the aqueous fractions were extracted with ethyl acetate (×1), the organic fractions were combined, dried over magnesium sulfate. After filtration, solvent was removed under reduced pressure to afford product which was carried on as crude, 3H-[1,2,3]triazolo[4,5-b]pyridin-3-yl 7-(2-((1-(1H-1,2,3-triazol-4-yl)cyclopropyl)amino)-2-oxoacetyl)-6-methyl-2,3-dihydro-1H-pyrrolizine-5-carboxylate: LCMS-ESI+ (n/z): [M+H]+ calculated for $C_{21}H_{20}N_9O_4$: 462.16; found: 461.9.

Step 3. To a solution of 3H-[1,2,3]triazolo[4,5-b]pyridin-3-yl 7-(2-((1-(1H-1,2,3-triazol-4-yl)cyclopropyl)amino)-2-oxoacetyl)-6-methyl-2,3-dihydro-1H-pyrrolizine-5-carboxylate (104 mg, 0.23 mmol) and 3-chloro-2,4-difluoroaniline (74 mg, 0.45 mmol) in dichloromethane (3 mL) was added 2,6-lutidine (0.1 mL, 0.86 mmol) and the resulting mixture was concentrated to an oil. The resulting oil was heated at 80° C. bath for 3 h. The residue was dissolved in dichloromethane and the insoluble material was filtered off. After the concentration of the filtrate, the residue was purified by reverse phase preparative HPLC (10-100% acetonitrile in water, 0.1% trifluoroacetic acid) to give 7-(2-((1-(1H-1,2,3-triazol-4-yl)cyclopropyl)amino)-2-oxoacetyl)-N-(3-chloro-2,4-difluorophenyl)-6-methyl-2,3-dihydro-1H-pyrrolizine-5-carboxamide.

234
Example 85. 7-(2-((1-(1H-1,2,3-triazol-5-yl)cyclopropyl)amino)-2-oxoacetyl)-6-methyl-N-(3-(trifluoromethoxy)phenyl)-2,3-dihydro-1H-pyrrolizine-5-carboxamide

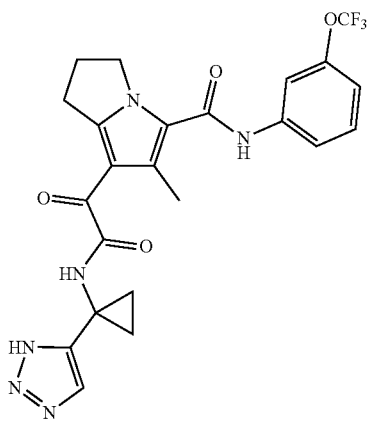

7-(2-((1-(1H-1,2,3-triazol-5-yl)cyclopropyl)amino)-2-oxoacetyl)-6-methyl-N-(3-(trifluoromethoxy)phenyl)-2,3-dihydro-1H-pyrrolizine-5-carboxamide (85) was synthesized in a manner similar to Example 84 using 3-(trifluoromethoxy)aniline in place of 3-chloro-2,4-difluoroaniline.

Example 86. 7-(2-((1-(1H-1,2,3-triazol-5-yl)cyclopropyl)amino)-2-oxoacetyl)-N-(5-chloro-2-fluorophenyl)-6-methyl-2,3-dihydro-1H-pyrrolizine-5-carboxamide

86

7-(2-((1-(1H-1,2,3-triazol-5-yl)cyclopropyl)amino)-2-oxoacetyl)-N-(5-chloro-2-fluorophenyl)-6-methyl-2,3-dihydro-1H-pyrrolizine-5-carboxamide (86) was synthesized in a manner similar to Example 84 using 5-chloro-2-fluoroaniline in place of 3-chloro-2,4-difluoroaniline.

Example 87 (1aR,6aR)-5-(2-((3-(1H-1,2,3-triazol-4-yl)oxetan-3-yl)amino)-2-oxoacetyl)-N-(3,4-difluorophenyl)-4-methyl-1,1a,6,6a-tetrahydrocyclopropa[b]pyrrolizine-3-carboxamide

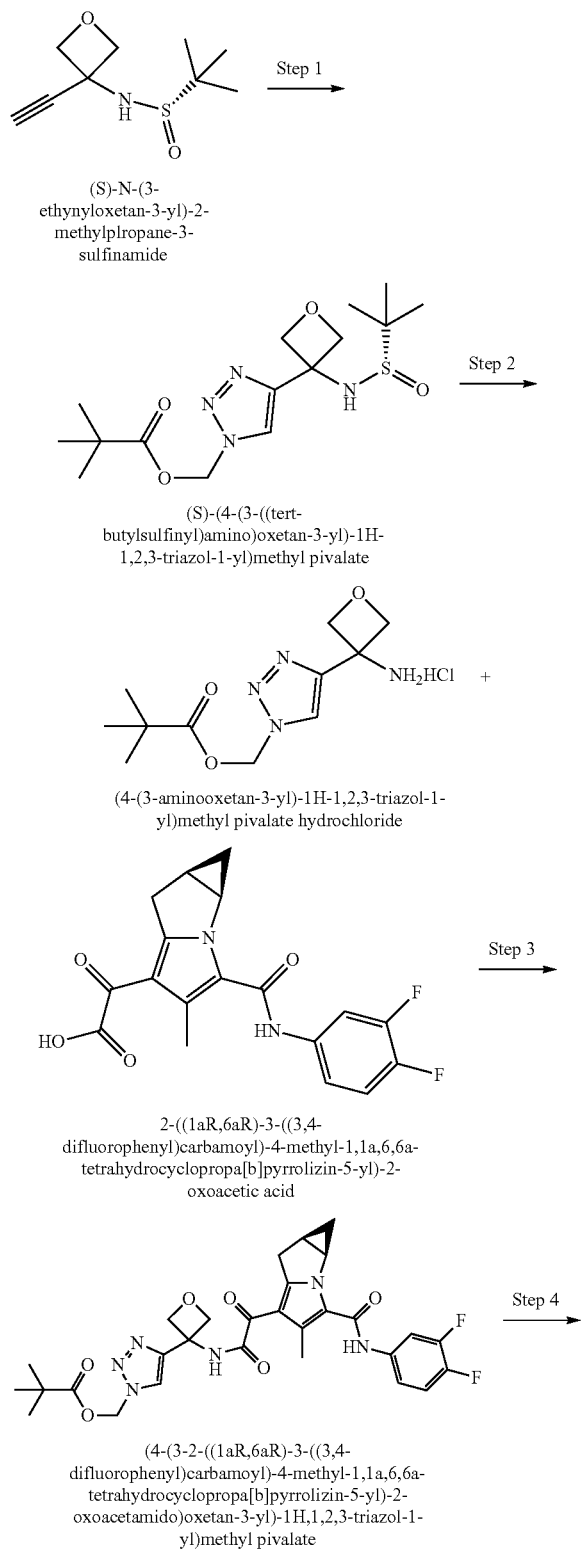

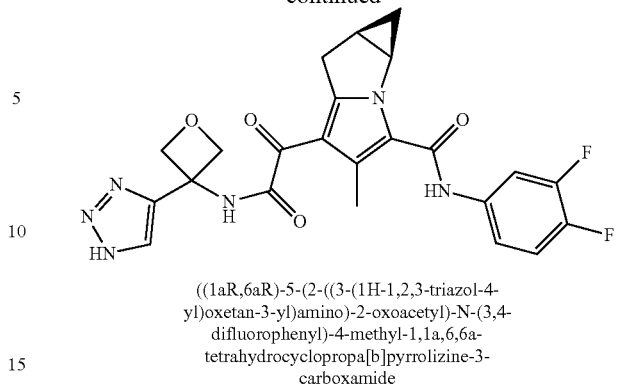

((1aR,6aR)-5-(2-((3-(1H-1,2,3-triazol-4-yl)oxetan-3-yl)amino)-2-oxoacetyl)-N-(3,4-difluorophenyl)-4-methyl-1,1a,6,6a-tetrahydrocyclopropa[b]pyrrolizine-3-carboxamide 87

Step 1 CuTC (15 mg, 0.079 mmol) followed by azidomethyl pivalate (122 µL, 0.795 mmol) were added to a solution of the N-(3-ethynyloxetan-3-yl)-2-methylpropane-2-sulfinamide (160 mg, 0.795 mmol) in THF (2 mL). After 1 h, a green solution formed. The solvent was removed under reduced pressure and the residue was purified by CombiFlash (12 g, Gold, 20-100% EtOAc/Hex) to give (S)-(4-(3-((tert-butylsulfinyl)amino)oxetan-3-yl)-1H-1,2,3-triazol-1-yl)methyl pivolate. $^1$H NMR (400 MHz, Chloroform-d) δ 8.00 (s, 1H), 6.24 (s, 2H), 5.15-5.06 (m, 2H), 4.97 (dd, J=14.6, 6.7 Hz, 2H), 4.37 (s, 1H), 1.28 (s, 9H), 1.20 (s, 9H); LCMS-ESI+: calc'd for $C_{15}H_{27}N_4O_4S$: 359.18 [M+H]+; found: 358.93.

Step 2 To a solution of (4-(3-((tert-butylsulfinyl)amino)oxetan-3-yl)-1H-1,2,3-triazol-1-yl)methyl pivalate (53 mg, 0.148 mmol) in methanol (0.5 mL) at 0° C. was added dropwise, down the side of the flask, HCl in dioxane (4N, 0.22 mL, 0.22 mmol). Reaction mixture was stirred for 1 minute, and then concentrated. Ethyl ether (1 mL) was added to give a white solid and the mixture was concentrated. Ethyl ether (1.5 mL) was added, the resulting white solid was collected by filtration, dried under high vacuum for 5 minutes, then used in next step immediately.

Step 3 The crude (4-(3-aminooxetan-3-yl)-1H-1,2,3-triazol-1-yl)methyl pivalate hydrochloride (14 mg, 0.048 mmol) was dissolved in DMF (0.5 mL) and N,N-Diisopropylethylamine (27 µL, 0.153 mmol) was added, followed by 2-((1aR,6aR)-3-((3,4-difluorophenyl)carbamoyl)-4-methyl-1,1a,6,6a-tetrahydrocyclopropa[b]pyrrolizin-5-yl)-2-oxoacetic acid (10 mg, 0.028 mmol), then HATU (16 mg, 0.042 mmol). Reaction mixture was stirred for 10 minutes, diluted with ethyl acetate and washed with 5% lithium chloride solution, saturated sodium bicarbonate solution, brine. The organic layer was dried ($Na_2SO_4$), filtered, concentrated and purified by CombiFlash (4 g, Gold, 0-100% EtOAc/Hex) to give (4-(3-(2-((1aR,6aR)-3-((3,4-difluorophenyl)carbamoyl)-4-methyl-1,1a,6,6a-tetrahydrocyclopropa[b]pyrrolizin-5-yl)-2-oxoacetamido)oxetan-3-yl)-1H-1,2,3-triazol-1-yl)methyl pivalate: $^1$H NMR (400 MHz, Methanol-d4) δ 8.15 (s, 1H), 7.74 (ddd, J=12.7, 7.3, 2.5 Hz, 1H), 7.37-7.30 (m, 1H), 7.28-7.18 (m, 1H), 6.32 (s, 2H), 5.05 (q, J=3.3, 2.4 Hz, 4H), 4.26 (t, J=5.8 Hz, 1H), 3.21 (dd, J=18.4, 6.7 Hz, 1H), 3.01 (d, J=18.7 Hz, 1H), 2.48 (s, 3H), 2.16-2.06 (m, 1H), 1.18 (s, 9H), 1.08 (dt, J=8.6, 6.0 Hz, 1H), 0.89 (d, J=6.7 Hz, 1H), 0.24 (td, J=5.7, 2.1 Hz, 1H); LCMS-ESI+ (m/z): [M+H]+ calculated for $C_{29}H_{31}F_2N_6O_6$: 597.2; found: 597.2.

Step 4 To a solution of (4-(3-(2-((1aR,6aR)-3-((3,4-difluorophenyl)carbamoyl)-4-methyl-1,1a,6,6a-tetrahydrocyclopropa[b]pyrrolizin-5-yl)-2-oxoacetamido)oxetan-3-yl)-1H-1,2,3-triazol-1-yl)methyl pivalate (9 mg, 0.015 mmol) in methanol (1.5 mL) was added 2M sodium hydroxide (17 μL, 0.034 mmol) and reaction mixture was stirred for 1.5 hours. LCMS showed full conversion. Reaction was quenched with 1N HCl (34 μL, 0.034 mmol), diluted with dichloromethane, adsorbed onto silica gel and purified by CombiFlash (4 g, Gold, 0-100% (20% MeOH/EtOAc)/Hex) to give (1aR, 6aR)-5-(2-((3-(1H-1,2,3-triazol-4-yl)oxetan-3-yl)amino)-2-oxoacetyl)-N-(3,4-difluorophenyl)-4-methyl-1,1a,6,6a-tetrahydrocyclopropa[b]pyrrolizine-3-carboxamide.

Example 88 7-(2-((3-(1H-1,2,3-triazol-4-yl)oxetan-3-yl)amino)-2-oxoacetyl)-N-(3-chloro-4-fluorophenyl)-6-methyl-2,3-dihydro-1H-pyrrolizine-5-carboxamide

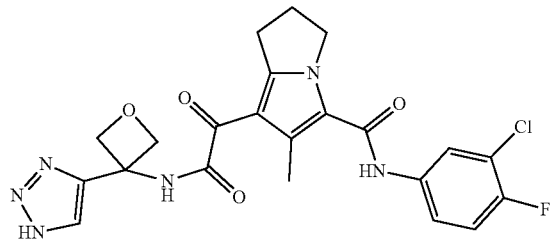

88

7-(2-((3-(1H-1,2,3-triazol-4-yl)oxetan-3-yl)amino)-2-oxoacetyl)-N-(3-chloro-4-fluorophenyl)-6-methyl-2,3-dihydro-1H-pyrrolizine-5-carboxamide (88) was prepared in a similar manner to Example 87 except using 2-(5-((3-chloro-4-fluorophenyl)carbamoyl)-6-methyl-2,3-dihydro-1H-pyrrolizin-7-yl)-2-oxoacetic acid instead of 2-((1aR,6aR)-3-((3,4-difluorophenyl)carbamoyl)-4-methyl-1,1a,6,6a-tetrahydrocyclopropa[b]pyrrolizin-5-yl)-2-oxoacetic acid.

Example 89. 7-(2-((3,3-difluoro-1-(1H-1,2,3-triazol-4-yl)cyclobutyl)amino)-2-oxoacetyl)-N-(3-(difluoromethyl)-4-fluorophenyl)-6-methyl-2,3-dihydro-1H-pyrrolizine-5-carboxamide

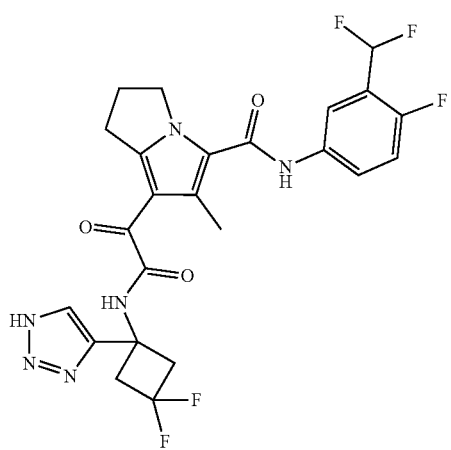

89

7-(2-((3,3-difluoro-1-(1H-1,2,3-triazol-4-yl)cyclobutyl)amino)-2-oxoacetyl)-N-(3-(difluoromethyl)-4-fluorophenyl)-6-methyl-2,3-dihydro-1H-pyrrolizine-5-carboxamide (89) was synthesized in a manner similar to Example 29 using 3-(difluoromethyl)-4-fluoroaniline in place of 3-chloro-4-fluouroaniline.

Example 90. 7-(2-((1-(1H-1,2,3-triazol-4-yl)cyclopropyl)amino)-2-oxoacetyl)-6-methyl-N-(2,4,5-trifluorophenyl)-2,3-dihydro-1H-pyrrolizine-5-carboxamide

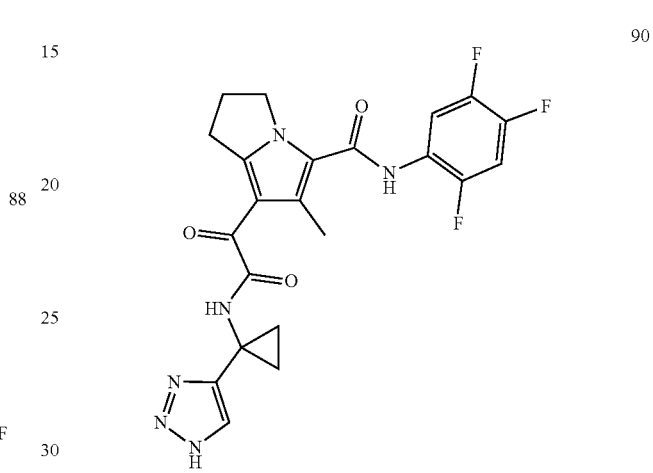

90

7-(2-((1-(1H-1,2,3-triazol-4-yl)cyclopropyl)amino)-2-oxoacetyl)-6-methyl-N-(2,4,5-trifluorophenyl)-2,3-dihydro-1H-pyrrolizine-5-carboxamide (90) was synthesized in a manner similar to Example 29 using 1-(1H-1,2,3-triazol-4-yl)cyclopropan-1-amine dihydrochloric acid in place of 3,3-difluoro-1-(1H-1,2,3-triazol-4-yl)cyclobutan-1-amine and 2,4,5-trifluoroaniline in place of 3-chloro-4-fluoroaniline.

Example 91. 7-(2-((1-(1H-1,2,3-triazol-4-yl)cyclopropyl)amino)-2-oxoacetyl)-N-(5-chloro-2,4-difluorophenyl)-6-methyl-2,3-dihydro-1H-pyrrolizine-5-carboxamide

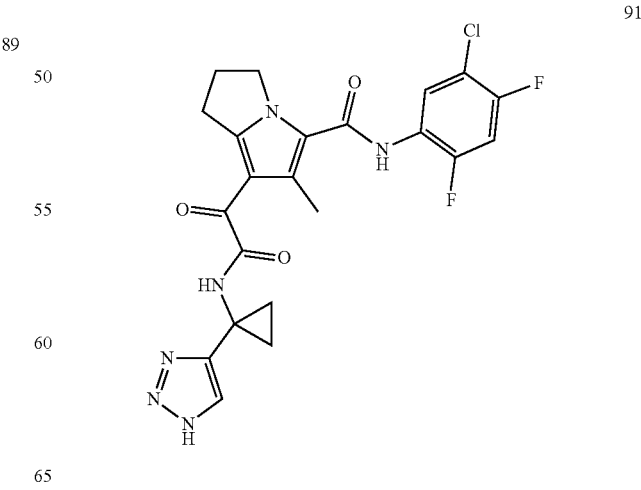

91

7-(2-((1-(1H-1,2,3-triazol-4-yl)cyclopropyl)amino)-2-oxoacetyl)-N-(5-chloro-2,4-difluorophenyl)-6-methyl-2,3- dihydro-1H-pyrrolizine-5-carboxamide (91) was synthesized in a manner similar to Example 90 using 5-chloro-2,4-difluoroaniline in place of 2,4,5-trifluoroaniline.

Example 92. 7-(2-((1-ethynylcyclopropyl)amino)-2-oxoacetyl)-6-methyl-N-(3,4,5-trifluorophenyl)-2,3-dihydro-1H-pyrrolizine-5-carboxamide

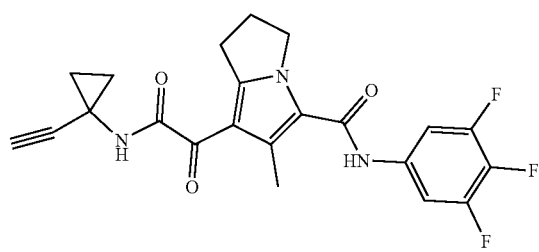

92

7-(2-((1-ethynylcyclopropyl)amino)-2-oxoacetyl)-6-methyl-N-(3,4,5-trifluorophenyl)-2,3-dihydro-1H-pyrrolizine-5-carboxamide (92) was synthesized in a manner similar to Example 26 Step 4 using 1-ethynylcyclopropan-1-amine hydrochloride in place of 1-(1H-1,2,3-triazol-4-yl)cyclopropan-1-amine dihydrochloric acid.

Example 93. 7-(2-((1-(1H-1,2,3-triazol-5-yl)cyclopropyl)amino)-2-oxoacetyl)-N-(2,4-difluorophenyl)-6-methyl-2,3-dihydro-1H-pyrrolizine-5-carboxamide (93)

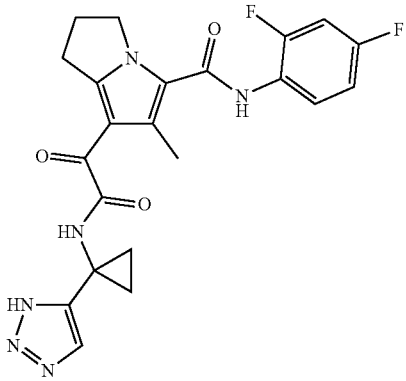

93

7-(2-((1-(1H-1,2,3-triazol-5-yl)cyclopropyl)amino)-2-oxoacetyl)-N-(2,4-difluorophenyl)-6-methyl-2,3-dihydro-1H-pyrrolizine-5-carboxamide (93) was synthesized in a manner similar to Example 84 using 2,4-difluoroaniline in place of 3-chloro-2,4-difluoroaniline.

Example 94. N-(3-chloro-4-fluorophenyl)-7-(2-((1-ethynylcyclopropyl)amino)-2-oxoacetyl)-6-methyl-2,3-dihydro-1H-pyrrolizine-5-carboxamide

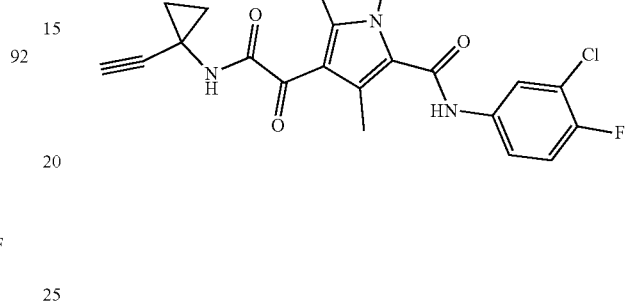

94

N-(3-chloro-4-fluorophenyl)-7-(2-((1-ethynylcyclopropyl)amino)-2-oxoacetyl)-6-methyl-2,3-dihydro-1H-pyrrolizine-5-carboxamide (94) was synthesized in a manner similar to Example 6 Step 6 using 1-ethynylcyclopropan-1-amine hydrochloride in place of 1-(1H-1,2,3-triazol-4-yl)cyclopropan-1-amine dihydrochloric acid.

Example 95. (1aR,6aR)-5-(2-((3,3-difluoro-1-(methylcarbamoyl)cyclobutyl)amino)-2-oxoacetyl)-N-(4-fluorophenyl)-4-methyl-1,1a,6,6a-tetrahydrocyclopropa[b]pyrrolizine-3-carboxamide

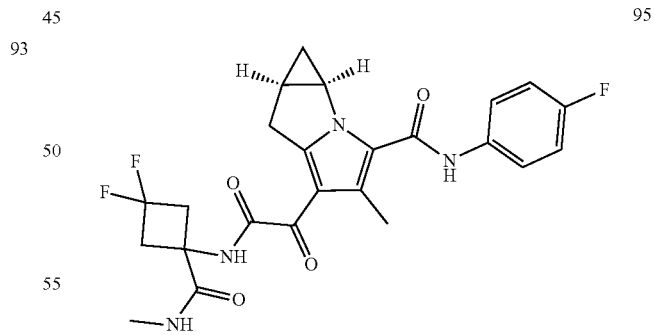

95

(1aR,6aR)-5-(2-((3,3-difluoro-1-(methylcarbamoyl)cyclobutyl)amino)-2-oxoacetyl)-N-(4-fluorophenyl)-4-methyl-1,1a,6,6a-tetrahydrocyclopropa[b]pyrrolizine-3-carboxamide (95) was synthesized in a manner similar to Example 5 using 4-fluoroaniline in place of 3-chloro-4-fluoroaniline.

Example 96. (1aR,6aR)-5-(2-((3,3-difluoro-1-(methylcarbamoyl)cyclobutyl)amino)-2-oxoacetyl)-N-(3,4-difluorophenyl)-4-methyl-1,1a,6,6a-tetrahydrocyclopropa[b]pyrrolizine-3-carboxamide

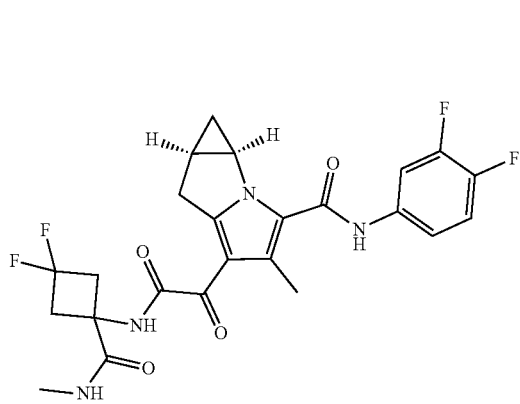

(1aR,6aR)-5-(2-((3,3-difluoro-1-(methylcarbamoyl)cyclobutyl)amino)-2-oxoacetyl)-N-(3,4-difluorophenyl)-4-methyl-1,1a,6,6a-tetrahydrocyclopropa[b]pyrrolizine-3-carboxamide (96) was synthesized in a manner similar to Example 5 using 3,4-difluoroaniline in place of 3-chloro-4-fluoroaniline.

Example 98: N-(3-chloro-4-fluorophenyl)-6-methyl-7-(2-(((1-(1-methyl-1H-1,2,3-triazol-4-yl)cyclopropyl)amino)-2-oxoacetyl)-2,3-dihydro-1H-pyrrolizine-5-carboxamide

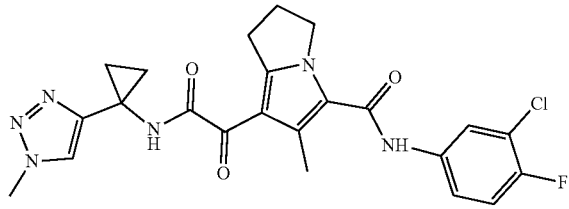

A solution of N-(3-chloro-4-fluorophenyl)-6-methyl-7-(2-oxo-2-((1-(1-(((trimethylsilyl)methyl)-1H-1,2,3-triazol-4-yl)cyclopropyl)amino)acetyl)-2,3-dihydro-1H-pyrrolizine-5-carboxamide (97) (38.0 mg, 0.068 mmol) was treated with tetra n-butylammonium fluoride (53.5 mg, 0.205 mmol) in tetrahydrofuran (2 mL) at rt for 1 h. The reaction mixture was directly injected into preparative reverse-phase HPLC (15-90% acetonitrile in water, 0.1% TFA buffer) to provide N-(3-chloro-4-fluorophenyl)-6-methyl-7-(2-(((1-(1-methyl-1H-1,2,3-triazol-4-yl)cyclopropyl)amino)-2-oxoacetyl)-2,3-dihydro-1H-pyrrolizine-5-carboxamide (98).

Example 99. (1aR,6aR)-5-(2-((1-(1H-1,2,3-triazol-5-yl)cyclopropyl)amino)-2-oxoacetyl)-N-(4-fluorophenyl)-4-methyl-1,1a,6,6a-tetrahydrocyclopropa[b]pyrrolizine-3-carboxamide (99)

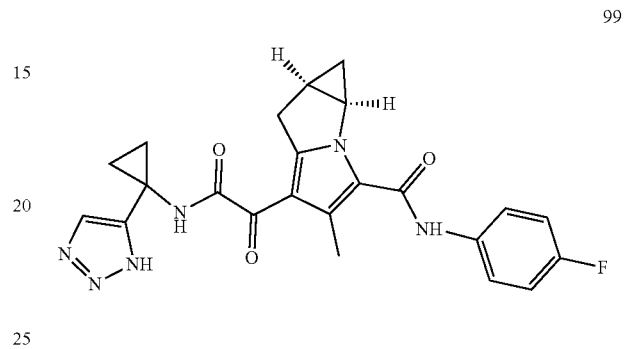

(1aR,6aR)-5-(2-((1-(1H-1,2,3-triazol-5-yl)cyclopropyl)amino)-2-oxoacetyl)-N-(4-fluorophenyl)-4-methyl-1,1a,6,6a-tetrahydrocyclopropa[b]pyrrolizine-3-carboxamide (99) was synthesized in a manner similar to Example 41 using 1-(1H-1,2,3-triazol-5-yl)cyclopropan-1-amine in place of 3,3-difluoro-1-(1H-1,2,3-triazol-4-yl)cyclobutan-1-amine and 4-fluoroaniline in place of 5-amino-2-fluorobenzonitrile.

Example 100. (1aR,6aR)-5-(2-((3,3-difluoro-1-(1H-1,2,3-triazol-5-yl)cyclobutyl)amino)-2-oxoacetyl)-N-(4-fluorophenyl)-4-methyl-1,1a,6,6a-tetrahydrocyclopropa[b]pyrrolizine-3-carboxamide (100)

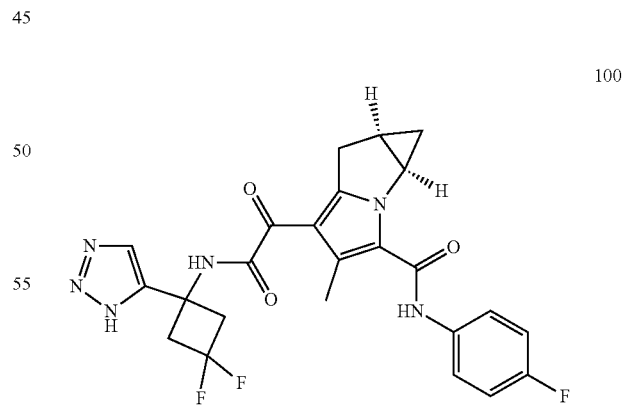

(1aR,6aR)-5-(2-((3,3-difluoro-1-(1H-1,2,3-triazol-5-yl)cyclobutyl)amino)-2-oxoacetyl)-N-(4-fluorophenyl)-4-methyl-1,1a,6,6a-tetrahydrocyclopropa[b]pyrrolizine-3-carboxamide (100) was synthesized in a manner similar to Example 41 using 4-fluoroaniline in place of 5-amino-2-fluorobenzonitrile Example 101. 7-(2-((1-(1H-1,2,3-triazol-4-yl)cyclopropyl)amino)-2-oxoacetyl)-N-(3-chloro-5-fluorophenyl)-6-methyl-2,3-dihydro-1H-pyrrolizine-5-carboxamide

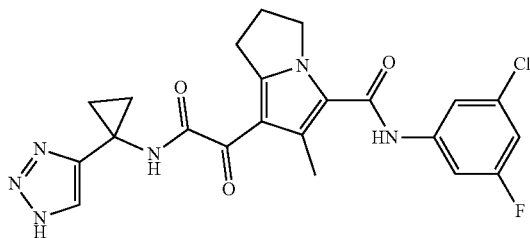

101

7-(2-((1-(1H-1,2,3-triazol-4-yl)cyclopropyl)amino)-2-oxoacetyl)-N-(3-chloro-5-fluorophenyl)-6-methyl-2,3-dihydro-1H-pyrrolizine-5-carboxamide was synthesized in a manner similar to Example 69 using 3-chloro-5-fluoroaniline in place of 3-fluoroaniline.

Example 102. 7-(2-((1-(1H-1,2,3-triazol-4-yl)cyclopropyl)amino)-2-oxoacetyl)-N-(3,5-dichlorophenyl)-6-methyl-2,3-dihydro-1H-pyrrolizine-5-carboxamide

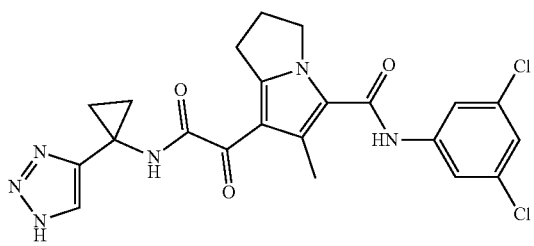

102

7-(2-((1-(1H-1,2,3-triazol-4-yl)cyclopropyl)amino)-2-oxoacetyl)-N-(3,5-dichlorophenyl)-6-methyl-2,3-dihydro-1H-pyrrolizine-5-carboxamide was synthesized in a manner similar to Example 69 using 3,5-dichloroaniline in place of 3-fluoroaniline.

Example 103. 7-(2-((1-(1H-1,2,3-triazol-4-yl)cyclopropyl)amino)-2-oxoacetyl)-N-(3-(difluoromethyl)phenyl)-6-methyl-2,3-dihydro-1H-pyrrolizine-5-carboxamide

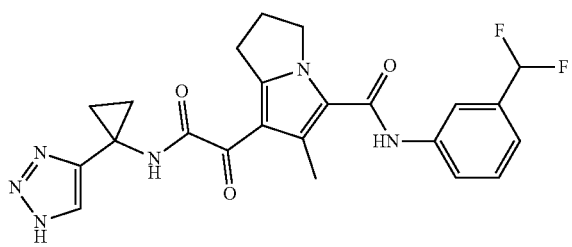

103

7-(2-((1-(1H-1,2,3-triazol-4-yl)cyclopropyl)amino)-2-oxoacetyl)-N-(3-(difluoromethyl)phenyl)-6-methyl-2,3-dihydro-1H-pyrrolizine-5-carboxamide was synthesized in a manner similar to Example 69 using 3-(difluoromethyl) aniline in place of 3-fluoroaniline.

Example 104. N-(3-chloro-4-fluorophenyl)-7-(2-((1,3-dihydroxy-2-methylpropan-2-yl)amino)-2-oxoacetyl)-6-methyl-2,3-dihydro-1H-pyrrolizine-5-carboxamide

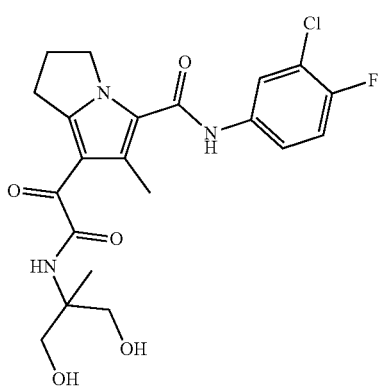

104

N-(3-chloro-4-fluorophenyl)-7-(2-((1,3-dihydroxy-2-methylpropan-2-yl)amino)-2-oxoacetyl)-6-methyl-2,3-dihydro-1H-pyrrolizine-5-carboxamide (104) was synthesized in a manner similar to Example 29 using 2-amino-2-methylpropane-1,3-diol in place of 3,3-difluoro-1-(1H-1,2,3-triazol-4-yl)cyclobutan-1-amine hydrochloride.

Example 105. N-(3-chloro-4-fluorophenyl)-6-methyl-7-(2-((1-(methylcarbamoyl)cyclopropyl)amino)-2-oxoacetyl)-2,3-dihydro-1H-pyrrolizine-5-carboxamide

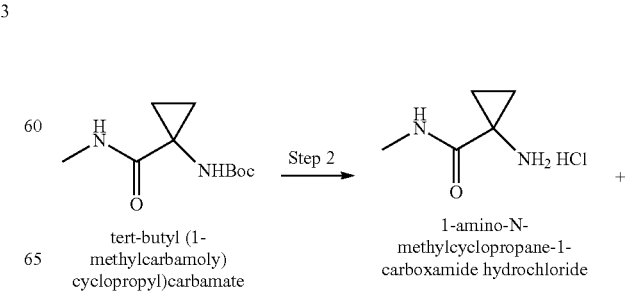

1-((tert-butoxycarbonyl)amino)cyclopropane-1-carboxylic acid tert-butyl (1-methylcarbamoly)cyclopropyl)carbamate 1-amino-N-methylcyclopropane-1-carboxamide hydrochloride

245

-continued

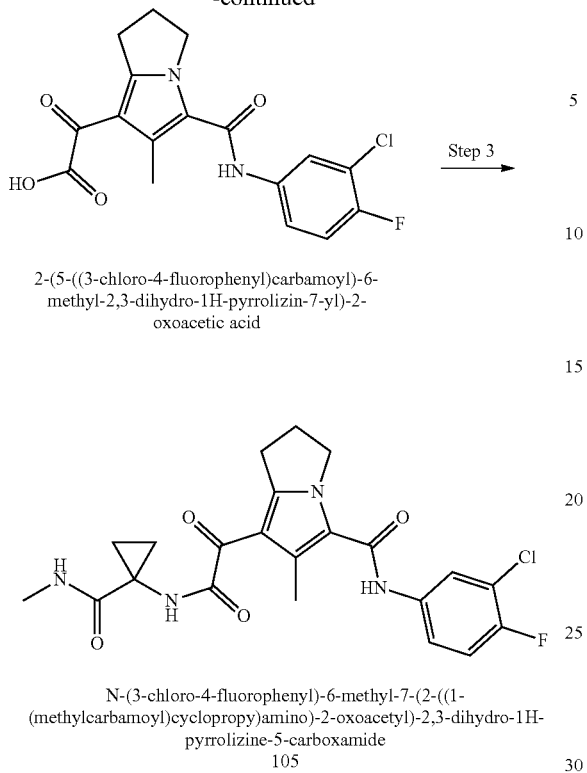

2-(5-((3-chloro-4-fluorophenyl)carbamoyl)-6-
methyl-2,3-dihydro-1H-pyrrolizin-7-yl)-2-
oxoacetic acid N-(3-chloro-4-fluorophenyl)-6-methyl-7-(2-((1-
(methylcarbamoyl)cyclopropy)amino)-2-oxoacetyl)-2,3-dihydro-1H-
pyrrolizine-5-carboxamide
105

Step 1 To a solution of 1-((tert-butoxycarbonyl)amino) cyclopropane-1-carboxylic acid (1.0 g, 4.97 mmol), Methylamine hydrochloride (0.503 g, 7.45 mmol) and N,N-Diisopropylethylamine (3.46 mL, 19.9 mmol) in acetonitrile (50 mL) was added HATU (2.83 g, 7.45 mmol). Reaction mixture was stirred for 30 minutes, concentrated, purified by CombiFlash to give tert-butyl (1-(methylcarbamoyl)cyclopropyl)carbamate. $^1$H NMR (400 MHz, Methanol-d4) δ 2.82 (s, 3H), 2.74 (s, 3H), 1.44 (s, 9H), 1.40 (q, J=4.4 Hz, 2H), 1.01-0.93 (m, 2H).

Step 2 To a solution of tert-butyl (1-(methylcarbamoyl) cyclopropyl)carbamate (94 mg, 0.44 mmol) in 1,-4-dioxane (2 mL) was added 4N hydrogen chloride in 1,4-dioxane (0.5 mL). Reaction mixture turned cloudy after 5 minutes. Reaction mixture was stirred for 1 hour, then stored in freezer overnight. The mixture was filtered and the white solid dried under house vacuum and used in the next step without further purification.

Step 3 To a solution of 2-(5-((3-chloro-4-fluorophenyl) carbamoyl)-6-methyl-2,3-dihydro-1H-pyrrolizin-7-yl)-2-oxoacetic acid (50 mg, 0.137 mmol), 1-amino-N-methylcyclopropane-1-carboxamide hydrochloride (25 mg, 0.164 mmol), and diisopropylethylamine (96 µL, 0.55 mmol) was added HATU (78 mg, 0.206 mmol), Reaction mixture was stirred for 30 minutes, then diluted with ethyl acetate, washed with 1N HCl, water, saturated sodium bicarbonate, 5% lithium chloride solution, brine and dried (Na$_2$SO$_4$), filtered and concentrated. The resulting residue was dissolved in DMF, filtered through a syringe filter and purified by Gilson HPLC (Gemini, 5-100% ACN/H$_2$O+0.1% TFA) and lyophilized to give N-(3-chloro-4-fluorophenyl)-6-methyl-7-(2-((1-(methylcarbamoyl)cyclopropyl)amino)-2-oxoacetyl)-2,3-dihydro-1H-pyrrolizine-5-carboxamide.

246

3-aminobicyclo[1.1.1]pentane-1-carboxamide
hydrochloride

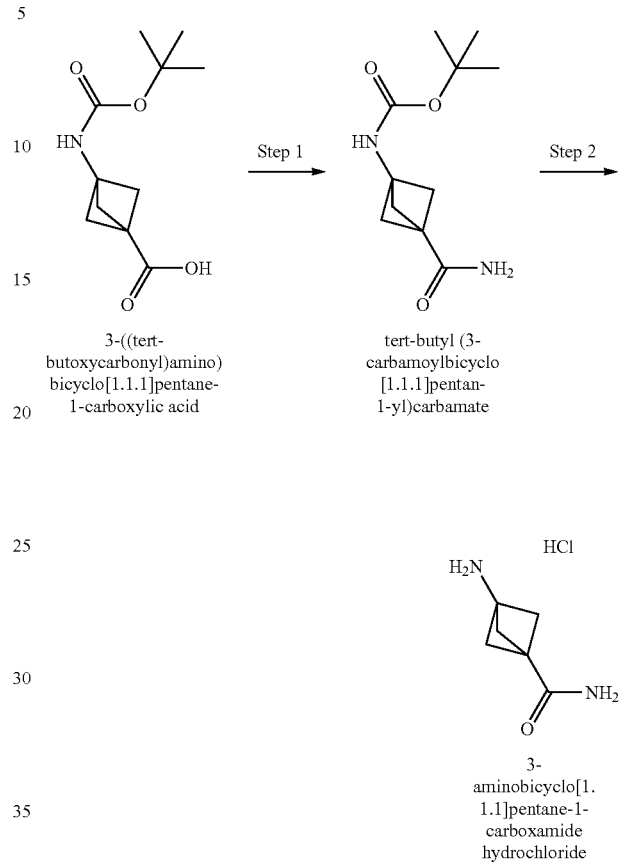

3-((tert-
butoxycarbonyl)amino)
bicyclo[1.1.1]pentane-
1-carboxylic acid tert-butyl (3-
carbamoylbicyclo
[1.1.1]pentan-
1-yl)carbamate 3-
aminobicyclo[1.
1.1]pentane-1-
carboxamide
hydrochloride Step 1. Isobutyl chloroformate (539 µL, 4.16 mmol) was added via syringe to a stirred mixture of N,N-diisopropylethylamine (773 µL, 4.44 mmol) and 3-((tert-butoxycarbonyl)amino)bicyclo[1.1.1]pentane-1-carboxylic acid (630 mg, 2.77 mmol) in tetrahydrofuran (20 mL) at ambient temperature. After 60 min, the resulting mixture was cooled to 0° C. Ammonia solution (0.4 M in tetrahydrofuran, 20.8 mL, 8.32 mmol) and N,N-diisopropylethylamine (773 µL, 4.44 mmol) were added sequentially via syringe. After 15 min, the resulting mixture was warmed to ambient temperature. After 80 min, the reaction mixture was purified by flash column chromatography on silica gel (0 to 15% methanol in dichloromethane) to give tert-butyl (3-carbamoylbicyclo [1.1.1]pentan-1-yl)carbamate.

Step 2. Trifluoroacetic acid (10 mL) was added via syringe to a stirred solution of tert-butyl (3-carbamoylbicyclo[1.1.1]pentan-1-yl)carbamate (1.06 g, 4.67 mmol) in dichloromethane (10 mL) at ambient temperature. After 2 h, the resulting mixture was concentrated under reduced pressure, and the residue was dried azeotropically by concentration under reduced pressure from a mixture of 2-propanol and toluene (1:1 v:v, 2×15 mL). The residue was dried azeotropically by concentration under reduced pressure from hydrogen chloride solution (5.0 M in 2-propanol, 2×5 mL). The residue was dried azeotropically by concentration under reduced pressure from a mixture of 2-propanol and toluene (1:1 v:v, 15 mL) to give 3-aminobicyclo[1.1.1] pentane-1-carboxamide hydrochloride.

Example 106. 7-(2-((3-carbamoylbicyclo[1.1.1]pentan-1-yl)amino)-2-oxoacetyl)-N-(3-chloro-4-fluorophenyl)-6-methyl-2,3-dihydro-1H-pyrrolizine-5-carboxamide

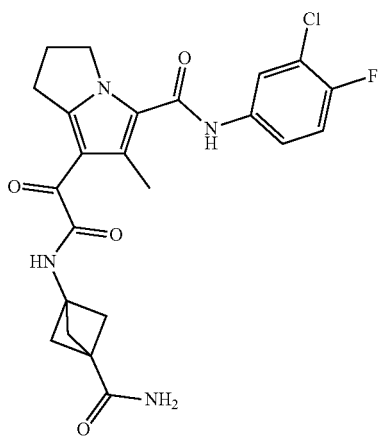

106

7-(2-((3-carbamoylbicyclo[1.1.1]pentan-1-yl)amino)-2-oxoacetyl)-N-(3-chloro-4-fluorophenyl)-6-methyl-2,3-dihydro-1H-pyrrolizine-5-carboxamide (106) was synthesized in a manner similar to Example 29 using 3-aminobicyclo[1.1.1]pentane-1-carboxamide hydrochloride in place of 3,3-difluoro-1-(1H-1,2,3-triazol-4-yl)cyclobutan-1-amine hydrochloride.

3,3-difluoro-1-propionylcyclobutan-1-aminium chloride

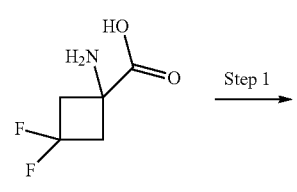

1-amino-3,3-difluorocyclobutane-1-carboxylic acid

Step 1 →

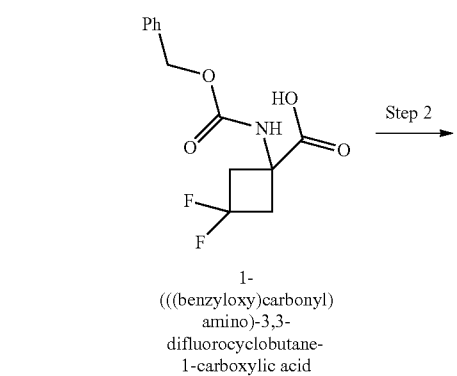

1-(((benzyloxy)carbonyl)amino)-3,3-difluorocyclobutane-1-carboxylic acid

Step 2 →

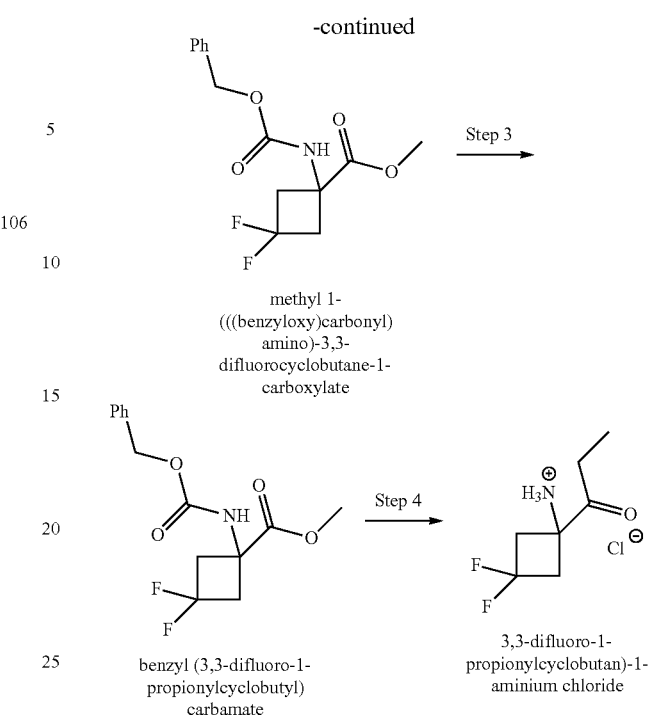

methyl 1-(((benzyloxy)carbonyl)amino)-3,3-difluorocyclobutane-1-carboxylate

Step 3 → benzyl (3,3-difluoro-1-propionylcyclobutyl)carbamate

Step 4 →

3,3-difluoro-1-propionylcyclobutan-1-aminium chloride

Steps 1-2. Benzyl (2,5-dioxopyrrolidin-1-yl) carbonate (3.30 g, 13.2 mmol) was added as a solid to a stirred mixture of 1-amino-3,3-difluorocyclobutane-1-carboxylic acid (2.00 g, 13.2 mmol) and N-ethyl-N-isopropylpropan-2-amine (4.61 mL, 26.5 mmol) in acetonitrile (40 mL) and water (20 mL) at ambient temperature. After 17 h, diethyl ether (500 mL) was added. The organic layer was washed with aqueous hydrogen chloride solution (0.25 M, 2×300 mL) and water (500 mL), was dried over anhydrous magnesium sulfate, was filtered, and was concentrated under reduced pressure. The residue was dissolved in toluene (90 mL) and methanol (27 mL), and the resulting solution was stirred at ambient temperature. Diazomethyltrimethylsilane solution (2.0 M in diethyl ether, 7.94 mL, 16 mmol) was added via syringe over 5 min. After 20 min, acetic acid was added dropwise via syringe until gas evolution ceased and the yellow color dissipated from the reaction mixture. The resulting mixture was concentrated under reduced pressure. The residue was purified by flash column chromatography (0 to 20% ethyl acetate in hexanes) to give methyl 1-(((benzyloxy)carbonyl)amino)-3,3-difluorocyclobutane-1-carboxylate.

Step 3. Ethylmagnesium bromide solution (1.0 M in tetrahydrofuran, 10.0 mL, 10 mmol) was added over 5 min via syringe to a stirred mixture of methyl 1-(((benzyloxy)carbonyl)amino)-3,3-difluorocyclobutane-1-carboxylate (1.00 g, 3.34 mmol) and tetraisopropoxytitanium (989 μL, 3.34 mmol) in tetrahydrofuran (12 mL) at −65° C., and the reaction was allowed to warm to ambient temperature over 18 h. Saturated aqueous ammonium chloride solution (20 mL) and diethyl ether (125 mL) were added. The organic layer was washed sequentially with aqueous hydrogen chloride solution (0.5 M, 50 mL), saturated aqueous sodium bicarbonate solution (50 mL), and brine (25 mL), was dried over anhydrous magnesium sulfate, was filtered, and was concentrated under reduced pressure. The residue was purified by flash column chromatography on silica gel (0 to 20% ethyl acetate in hexanes) to give benzyl (3,3-difluoro-1-propionylcyclobutyl)carbamate.

Step 4. A heterogeneous mixture benzyl (3,3-difluoro-1-propionylcyclobutyl)carbamate (291 mg, 0.979 mmol) and palladium on activated carbon (10% wt/wt, 100 mg, 98 µmol) in ethanol (10 mL) at ambient temperature was placed under 1 atm of hydrogen gas and stirred vigorously. After 110 min, the reaction mixture was filtered through celite, and the filter cake was extracted with ethyl acetate (80 mL). Hydrogen chloride solution (4 M in 1,4-dioxane, 0.30 mL) was added via syringe to the filtrate, and the resulting mixture was swirled vigorously for 1 min and then concentrated under reduced pressure to give 3,3-difluoro-1-propionylcyclobutan-1-aminium chloride.

Example 107. 7-(2-((1-(1H-1,2,3-triazol-4-yl)cyclopropyl)amino)-2-oxoacetyl)-N-(3-chloro-2-fluorophenyl)-6-methyl-2,3-dihydro-1H-pyrrolizine-5-carboxamide

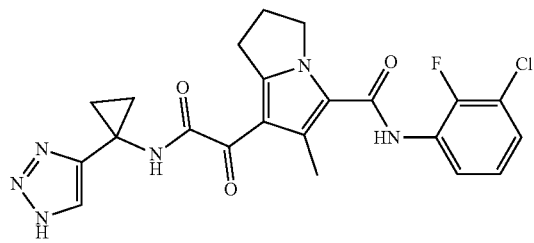

7-(2-((1-(1H-1,2,3-triazol-4-yl)cyclopropyl)amino)-2-oxoacetyl)-N-(3-chloro-2-fluorophenyl)-6-methyl-2,3-dihydro-1H-pyrrolizine-5-carboxamide was synthesized in a manner similar to Example 69 using 3-chloro-2-fluoroaniline in place of 3-fluoroaniline.

Example 111. 7-(2-((1-(1H-1,2,3-triazol-4-yl)cyclopropyl)amino)-2-oxoacetyl)-6-methyl-N-(2,3,4-trifluorophenyl)-2,3-dihydro-1H-pyrrolizine-5-carboxamide (111)

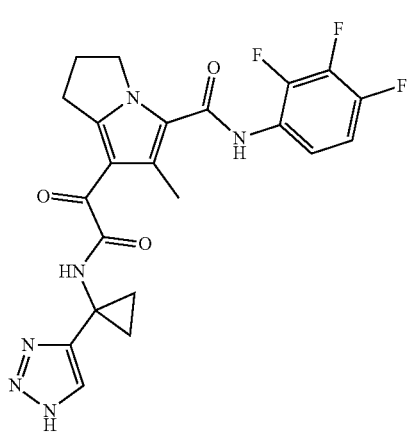

7-(2-((1-(1H-1,2,3-triazol-4-yl)cyclopropyl)amino)-2-oxoacetyl)-6-methyl-N-(2,3,4-trifluorophenyl)-2,3-dihydro-1H-pyrrolizine-5-carboxamide (111) was synthesized in a manner similar to Example 90 using 2,3,4-trifluoroaniline in place of 2,4,5-trifluoroaniline.

Example 112. N-(3-chloro-4-fluorophenyl)-7-(2-((3-cyanobicyclo[1.1.1]pentan-1-yl)amino)-2-oxoacetyl)-6-methyl-2,3-dihydro-1H-pyrrolizine-5-carboxamide

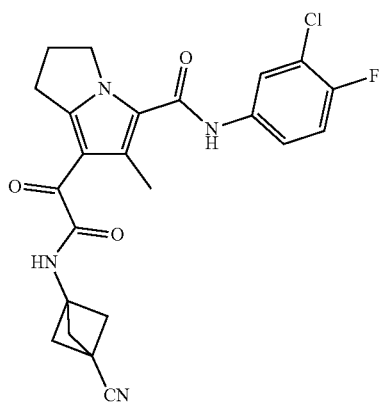

Trifluoroacetic anhydride (28.6 µL, 0.206 mmol) was added via syringe to a stirred mixture of 7-(2-((3-carbamoylbicyclo[1.1.1]pentan-1-yl)amino)-2-oxoacetyl)-N-(3-chloro-4-fluorophenyl)-6-methyl-2,3-dihydro-1H-pyrrolizine-5-carboxamide (32 mg, 0.069 mmol) and 2,6-lutidine (63.8 µL, 0.548 mmol) in tetrahydrofuran (1.5 mL) at ambient temperature. After 10 min, water (0.5 mL) was added, and the resulting biphasic mixture was concentrated under reduced pressure. The residue was purified by was purified by reverse phase preparative HPLC (10-100% acetonitrile in water, 0.1% trifluoroacetic acid) to give N-(3-chloro-4-fluorophenyl)-7-(2-((3-cyanobicyclo[1.1.1]pentan-1-yl)amino)-2-oxoacetyl)-6-methyl-2,3-dihydro-1H-pyrrolizine-5-carboxamide (112).

Example 113. 7-(2-((3-cyanobicyclo[1.1.1]pentan-1-yl)amino)-2-oxoacetyl)-N-(3,4-difluorophenyl)-6-methyl-2,3-dihydro-1H-pyrrolizine-5-carboxamide

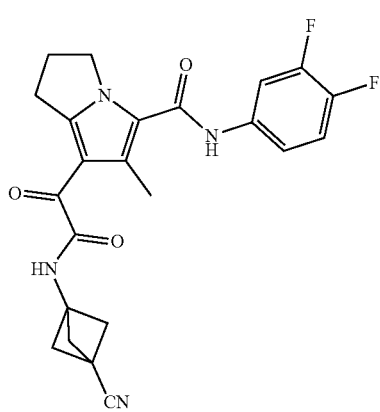

7-(2-((3-Cyanobicyclo[1.1.1]pentan-1-yl)amino)-2-oxoacetyl)-N-(3,4-difluorophenyl)-6-methyl-2,3-dihydro- 1H-pyrrolizine-5-carboxamide (113) was synthesized in a manner similar to Example 112 using 3,4-difluoroaniline in place of 3-chloro-4-fluoroaniline.

Example 114. N-(3-(difluoromethyl)-4-fluorophenyl)-6-methyl-7-(2-((2-methyl-1-(methylamino)-1-oxopropan-2-yl)amino)-2-oxoacetyl)-2,3-dihydro-1H-pyrrolizine-5-carboxamide (114)

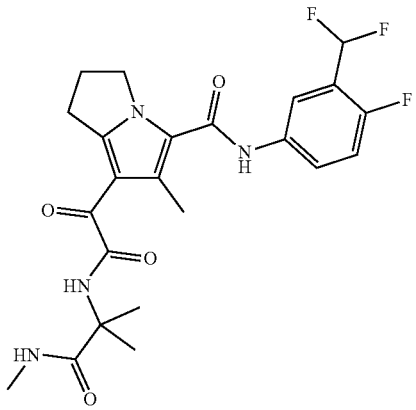

114

N-(3-(difluoromethyl)-4-fluorophenyl)-6-methyl-7-(2-((2-methyl-1-(methylamino)-1-oxopropan-2-yl)amino)-2-oxoacetyl)-2,3-dihydro-1H-pyrrolizine-5-carboxamide (114) was synthesized in a manner similar to Example 82 using 3-(difluoromethyl)-4-fluoroaniline in place of 3-chloro-4-fluoroaniline.

Example 115. 7-(2-((3,3-difluoro-1-(methylcarbamoyl)cyclobutyl)amino)-2-oxoacetyl)-N-(3-(difluoromethyl)phenyl)-6-methyl-2,3-dihydro-1H-pyrrolizine-5-carboxamide

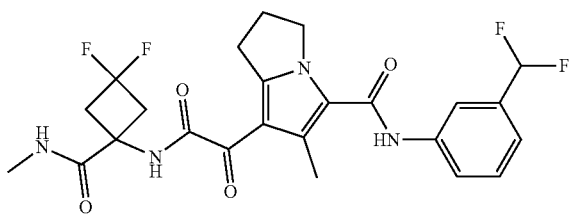

115

7-(2-((3,3-difluoro-1-(methylcarbamoyl)cyclobutyl)amino)-2-oxoacetyl)-N-(3-(difluoromethyl)phenyl)-6-methyl-2,3-dihydro-1H-pyrrolizine-5-carboxamide was synthesized in a manner similar to Example 69 step 2 using 1-amino-3,3-difluoro-N-methylcyclobutane-1-carboxamide hydrochloride in place of 1-ethynylcyclopropan-1-amine 2,2,2-trifluoroacetate and in step 3 using 3-(difluoromethyl) aniline in place of 3-fluoroaniline.

Example 116. 7-(2-((3,3-difluoro-1-(methylcarbamoyl)cyclobutyl)amino)-2-oxoacetyl)-N-(3-(difluoromethyl)-4-fluorophenyl)-6-methyl-2,3-dihydro-1H-pyrrolizine-5-carboxamide

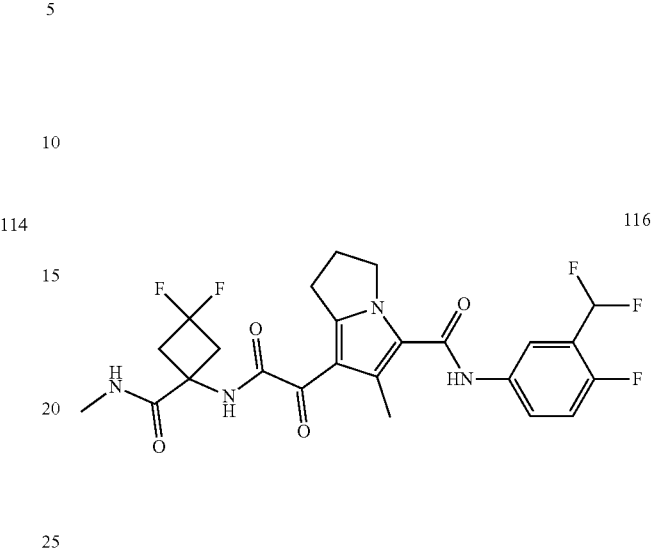

116

7-(2-((3,3-difluoro-1-(methylcarbamoyl)cyclobutyl)amino)-2-oxoacetyl)-N-(3-(difluoromethyl)-4-fluorophenyl)-6-methyl-2,3-dihydro-1H-pyrrolizine-5-carboxamide was synthesized in a manner similar to Example 69 step 2 using 1-amino-3,3-difluoro-N-methylcyclobutane-1-carboxamide hydrochloride in place of 1-ethynylcyclopropan-1-amine 2,2,2-trifluoroacetate and in step 3 using 3-(difluoromethyl)-4-fluoroaniline in place of 3-fluoroaniline.

Example 117. N-(3-chloro-4-fluorophenyl)-7-(2-((3,3-difluoro-1-(hydroxymethyl)cyclobutyl)amino)-2-oxoacetyl)-6-methyl-2,3-dihydro-1H-pyrrolizine-5-carboxamide

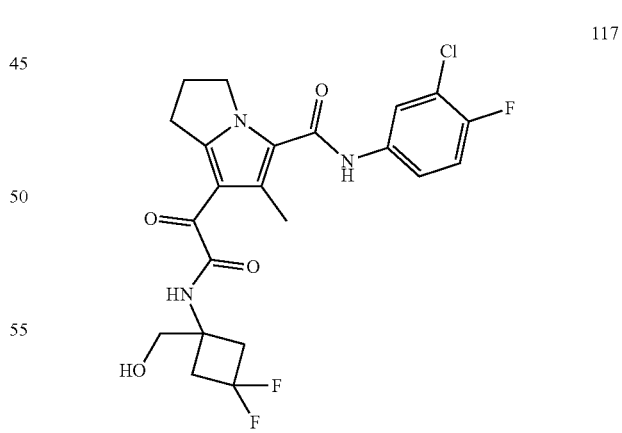

117

N-(3-chloro-4-fluorophenyl)-7-(2-((3,3-difluoro-1-(hydroxymethyl)cyclobutyl)amino)-2-oxoacetyl)-6-methyl-2,3-dihydro-1H-pyrrolizine-5-carboxamide (117) was synthesized in a manner similar to Example 29 using (1-amino-3,3-difluorocyclobutyl)methanol hydrochloride in place of 3,3-difluoro-1-(1H-1,2,3-triazol-4-yl)cyclobutan-1-amine hydrochloride.

Example 118. 7-(2-((3,3-difluoro-1-(hydroxymethyl)cyclobutyl)amino)-2-oxoacetyl)-N-(3,4-difluorophenyl)-6-methyl-2,3-dihydro-1H-pyrrolizine-5-carboxamide

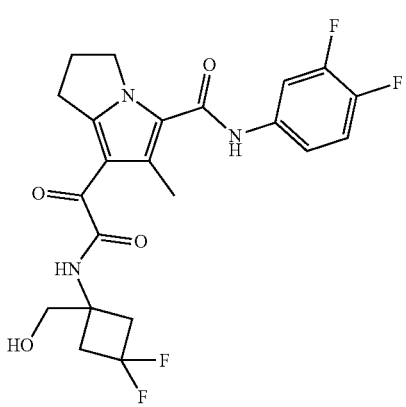

7-(2-((3,3-difluoro-1-(hydroxymethyl)cyclobutyl)amino)-2-oxoacetyl)-N-(3,4-difluorophenyl)-6-methyl-2,3-dihydro-1H-pyrrolizine-5-carboxamide (118) was synthesized in a manner similar to Example 29 using 3,4-difluoroaniline in place of 3-chloro-4-fluoroaniline and using (1-amino-3,3-difluorocyclobutyl)methanol hydrochloride in place of 3,3-difluoro-1-(1H-1,2,3-triazol-4-yl)cyclobutan-1-amine hydrochloride.

Example 119. (1aR,6aR)-N-(2-(difluoromethyl)pyridin-4-yl)-4-methyl-5-(2-oxo-2-((3-(trifluoromethyl)oxetan-3-yl)amino)acetyl)-1,1a,6,6a-tetrahydrocyclopropa[b]pyrrolizine-3-carboxamide

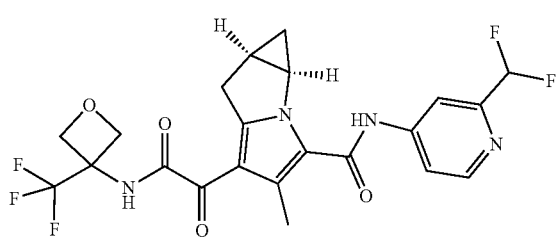

(1aR,6aR)-N-(2-(difluoromethyl)pyridin-4-yl)-4-methyl-5-(2-oxo-2-((3-(trifluoromethyl)oxetan-3-yl)amino)acetyl)-1,1a,6,6a-tetrahydrocyclopropa[b]pyrrolizine-3-carboxamide (119) was synthesized from (1aR,6aR)-5-(carboxycarbonyl)-4-methyl-1,1a,6,6a-tetrahydrocyclopropa[b]pyrrolizine-3-carboxylic acid in a manner similar to Example 80, step 1 and 2 using 3-(trifluoromethyl)oxetan-3-amine hydrochloride and 2-(difluoromethyl)pyridin-4-amine in place of 1-ethynyl-3,3-difluorocyclobutan-1-amine and 2-(difluoromethyl)-3-fluoropyridin-4-amine, respectively.

Example 120. 7-(2-((1-carbamoyl-3,3-difluorocyclobutyl)amino)-2-oxoacetyl)-N-(3-chloro-4-fluorophenyl)-6-methyl-2,3-dihydro-1H-pyrrolizine-5-carboxamide (120)

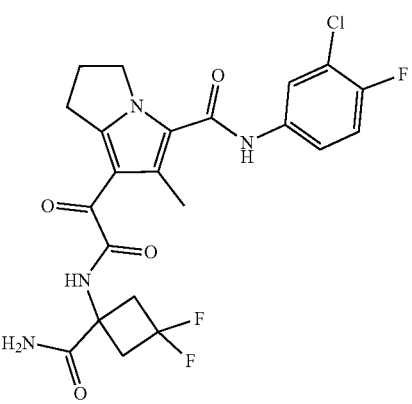

7-(2-((1-carbamoyl-3,3-difluorocyclobutyl)amino)-2-oxoacetyl)-N-(3-chloro-4-fluorophenyl)-6-methyl-2,3-dihydro-1H-pyrrolizine-5-carboxamide (120) was synthesized in a manner similar to Example 3 using 1-amino-3,3-difluorocyclobutane-1-carboxamide hydrochloride in place of 3,3-difluoro-(1-methylaminocarbonyl)-1-cyclobutanamine hydrochloride.

Synthesis of 1-amino-3,3-difluorocyclobutane-1-carboxamide hydrochloride

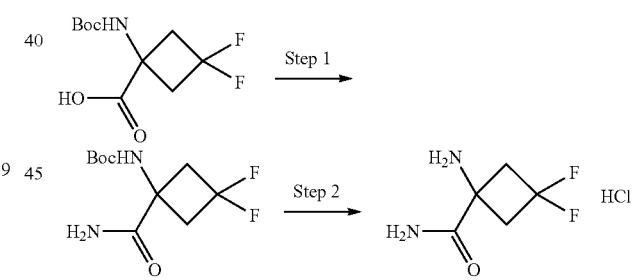

Step 1. To a 0° C. solution of 1-((tert-butoxycarbonyl)amino)-3,3-difluorocyclobutane-1-carboxylic acid (522 mg, 2.1 mmol), ammonium chloride (620 mg, 11.6 mmol), and triethylamine (2.3 mL, 16.5 mmol) in N,N-dimethylformamide (6 mL) was added 1-[Bis(dimethylamino)methylene]-1H-1,2,3-triazolo[4,5-b]pyridinium 3-oxid hexafluorophosphate (1.19 g, 3.12 mmol). The reaction was warmed to ambient temperature and stirred for 5 h, at which point the reaction mixture was diluted with diethyl ether, washed with a saturate aqueous solution of sodium bicarbonate, a 5% aqueous solution of lithium chloride, and brine. The ethereal phase was then dried over sodium sulfate, filtered, and concentrated under reduced pressure to afford tert-butyl (1-carbamoyl-3,3-difluorocyclobutyl)carbamate which was carried forward without further purification.

Step 2. Tert-butyl (1-carbamoyl-3,3-difluorocyclobutyl)carbamate (348 mg, 1.39 mmol) was dissolved in a 4M solution of hydrogen chloride in dioxane (6 mL, 24 mmol) and stirred at room temperature for 60 minutes. Solvent was removed under reduced pressure, twice azeotroping with toluene, and the resultant material dried under high vacuum to afford 1-amino-3,3-difluorocyclobutane-1-carboxamide hydrochloride: $^1$H NMR (400 MHz, DMSO-d6) δ 8.95 (s, 3H), 7.90 (s, 2H), 3.28 (td, J=13.0, 7.2 Hz, 2H), 3.05 (q, J=14.2 Hz, 2H).

Example 121. 7-(2-((1-carbamoyl-3,3-difluorocyclobutyl)amino)-2-oxoacetyl)-N-(3,4-difluorophenyl)-6-methyl-2,3-dihydro-1H-pyrrolizine-5-carboxamide (121)

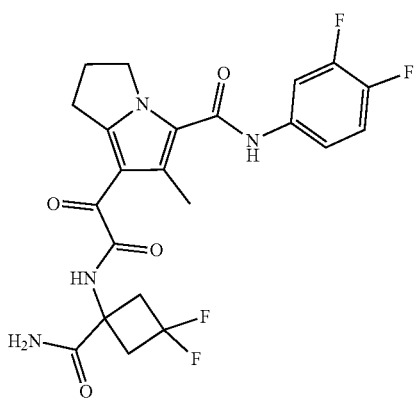

121

7-(2-((1-carbamoyl-3,3-difluorocyclobutyl)amino)-2-oxoacetyl)-N-(3,4-difluorophenyl)-6-methyl-2,3-dihydro-1H-pyrrolizine-5-carboxamide (121) was synthesized in a manner similar to Example 120 using 3,4-difluoroaniline in place of 3-chloro-4-fluoroaniline.

1-amino-3,3-difluoro-N,N-dimethylcyclobutane-1-carboxamide hydrochloride

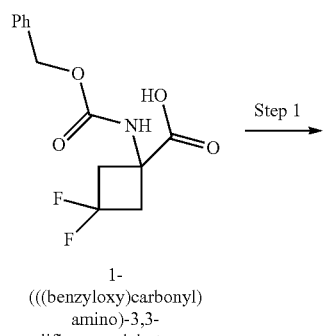

1-(((benzyloxy)carbonyl)amino)-3,3-difluorocyclobutane-1-carboxylic acid

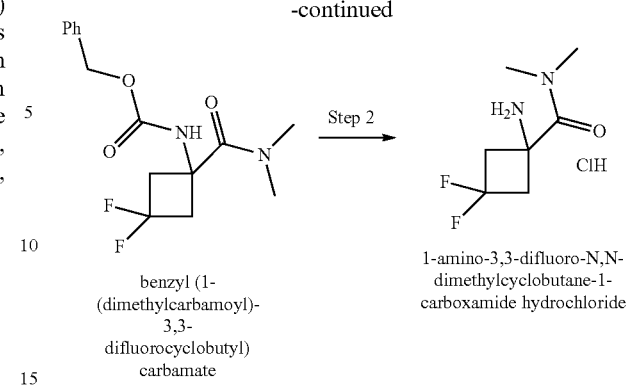

benzyl (1-(dimethylcarbamoyl)-3,3-difluorocyclobutyl)carbamate 1-amino-3,3-difluoro-N,N-dimethylcyclobutane-1-carboxamide hydrochloride Step 1. 1-((dimethylamino)(dimethyliminio)methyl)-1H-[1,2,3]triazolo[4,5-b]pyridine 3-oxide hexafluorophosphate (V) (1.33 g, 3.51 mmol) was added to a stirred mixture of 1-(((benzyloxy)carbonyl)amino)-3,3-difluorocyclobutane-1-carboxylic acid (1.00 g, 3.51 mmol), N,N-diisopropylethylamine (2.44 mL, 14.0 mmol), N,N-dimethylpyridin-4-amine (43 mg, 0.035 mmol), and dimethylamine hydrochloride (715 mg, 8.76 mmol) in N,N-dimethylformamide (10 mL) at ambient temperature. After 90 min, diethyl ether (250 mL) was added. The organic layer was washed sequentially with aqueous hydrogen chloride solution (0.2 M, 2×200 mL), a mixture of saturated aqueous sodium bicarbonate solution and water (1:4 v:v, 200 mL), and water (200 mL), was dried over anhydrous magnesium sulfate, was filtered, and was concentrated under reduced pressure to give benzyl (1-(dimethylcarbamoyl)-3,3-difluorocyclobutyl)carbamate.

Step 2. A heterogeneous mixture of benzyl (1-(dimethylcarbamoyl)-3,3-difluorocyclobutyl)carbamate (645 mg, 2.07 mmol) and palladium on activated carbon (10% wt/wt, 220 mg, 0.207 μmol) in ethanol (10 mL) and ethyl acetate (5.0 mL) at ambient temperature was placed under 1 atm of hydrogen gas and stirred vigorously. After 3.5 h, the reaction mixture was filtered through celite, and the filter cake was extracted with ethyl acetate (80 mL). Hydrogen chloride solution (4 M in 1,4-dioxane, 2.0 mL) was added via syringe to the filtrate, and the resulting mixture was swirled vigorously for 1 min and then concentrated under reduced pressure to give 1-amino-3,3-difluoro-N,N-dimethylcyclobutane-1-carboxamide hydrochloride.

Example 124. N-(3-chloro-4-fluorophenyl)-7-(2-((1-(dimethylcarbamoyl)-3,3-difluorocyclobutyl)amino)-2-oxoacetyl)-6-methyl-2,3-dihydro-1H-pyrrolizine-5-carboxamide

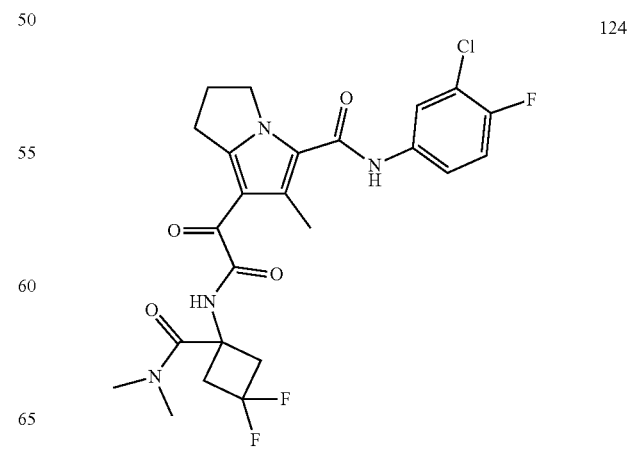

124

N-(3-chloro-4-fluorophenyl)-7-(2-((1-(dimethylcarbamoyl)-3,3-difluorocyclobutyl)amino)-2-oxoacetyl)-6-methyl-2,3-dihydro-1H-pyrrolizine-5-carboxamide (124) was synthesized in a manner similar to Example 29 using 1-amino-3,3-difluoro-N,N-dimethylcyclobutane-1-carboxamide hydrochloride in place of 3,3-difluoro-1-(1H-1,2,3-triazol-4-yl)cyclobutan-1-amine hydrochloride.

Example 125. N-(3,4-difluorophenyl)-7-(2-((1-(dimethylcarbamoyl)-3,3-difluorocyclobutyl)amino)-2-oxoacetyl)-6-methyl-2,3-dihydro-1H-pyrrolizine-5-carboxamide

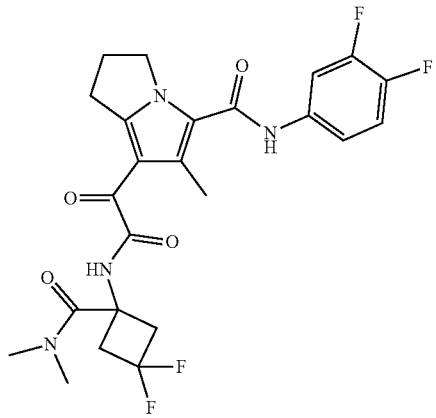

125

N-(3,4-difluorophenyl)-7-(2-((1-(dimethylcarbamoyl)-3,3-difluorocyclobutyl)amino)-2-oxoacetyl)-6-methyl-2,3-dihydro-1H-pyrrolizine-5-carboxamide (125) was synthesized in a manner similar to Example 29 using 3,4-difluoroaniline in place of 3-chloro-4-fluoroaniline and using 1-amino-3,3-difluoro-N,N-dimethylcyclobutane-1-carboxamide hydrochloride in place of 3,3-difluoro-1-(1H-1,2,3-triazol-4-yl)cyclobutan-1-amine hydrochloride.

Example 126. 7-(2-((1-(1H-1,2,3-triazol-4-yl)cyclopropyl)amino)-2-oxoacetyl)-N-(3-cyano-5-fluorophenyl)-6-methyl-2,3-dihydro-1H-pyrrolizine-5-carboxamide

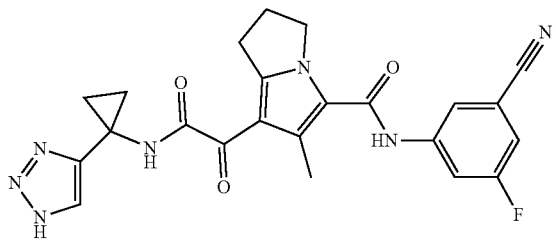

126

7-(2-((1-(1H-1,2,3-triazol-4-yl)cyclopropyl)amino)-2-oxoacetyl)-N-(3-cyano-5-fluorophenyl)-6-methyl-2,3-dihydro-1H-pyrrolizine-5-carboxamide was synthesized in a manner similar to Example 69 using 3-fluoro-5-cyanoaniline in place of 3-fluoroaniline.

Example 127. N-(3-chloro-2,4-difluorophenyl)-7-(2-((3,3-difluoro-1-(methylcarbamoyl)cyclobutyl)amino)-2-oxoacetyl)-6-methyl-2,3-dihydro-1H-pyrrolizine-5-carboxamide (127)

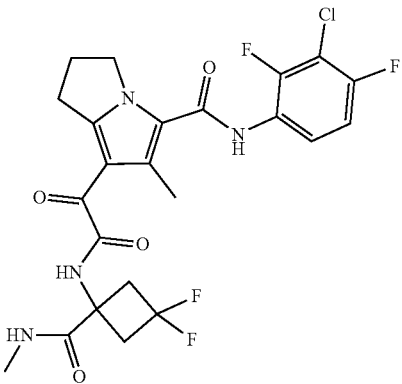

127

N-(3-chloro-2,4-difluorophenyl)-7-(2-((3,3-difluoro-1-(methylcarbamoyl)cyclobutyl)amino)-2-oxoacetyl)-6-methyl-2,3-dihydro-1H-pyrrolizine-5-carboxamide (127) was synthesized in a manner similar to Example 3 using 3-chloro-2,4-difluoroaniline in place of 3-chloro-4-fluoroaniline.

Example 128. (S)—N-(3-chloro-4-fluorophenyl)-6-methyl-7-(2-((3-methyl-1-(methylamino)-1-oxobutan-2-yl)amino)-2-oxoacetyl)-2,3-dihydro-1H-pyrrolizine-5-carboxamide (128)

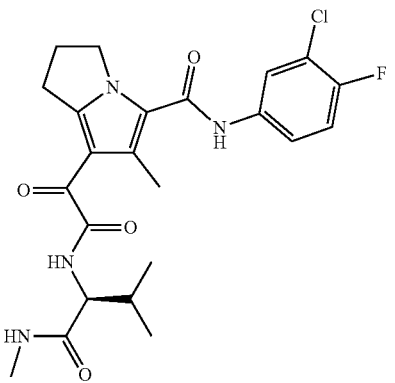

128

(S)—N-(3-chloro-4-fluorophenyl)-6-methyl-7-(2-((3-methyl-1-(methylamino)-1-oxobutan-2-yl)amino)-2-oxoacetyl)-2,3-dihydro-1H-pyrrolizine-5-carboxamide (128) was synthesized in a manner similar to Example 84 using L-valine N-methylamide hydrochloride in place of 1-(1H-1,2,3-triazol-4-yl)cyclopropan-1-amine dihydrochloride and 3-chloro-4-fluoroaniline in place of 3-chloro-2,4-difluoroaniline.

Example 129. N-(3-chloro-4,5-difluorophenyl)-7-(2-((3,3-difluoro-1-(methylcarbamoyl)cyclobutyl)amino)-2-oxoacetyl)-6-methyl-2,3-dihydro-1H-pyrrolizine-5-carboxamide

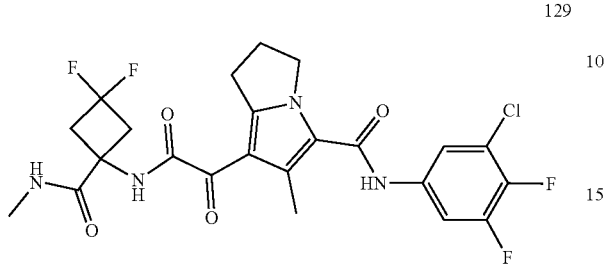

129

N-(3-chloro-4,5-difluorophenyl)-7-(2-((3,3-difluoro-1-(methylcarbamoyl)cyclobutyl)amino)-2-oxoacetyl)-6-methyl-2,3-dihydro-1H-pyrrolizine-5-carboxamide was synthesized in a manner similar to Example 69 step 2 using 1-amino-3,3-difluoro-N-methylcyclobutane-1-carboxamide hydrochloride in place of 1-ethynylcyclopropan-1-amine 2,2,2-trifluoroacetate and in step 3 using 3-chloro-4,5-difluoroaniline in place of 3-fluoroaniline.

Example 130. N-(3-chloro-4-fluorophenyl)-7-(2-((1-cyano-3,3-difluorocyclobutyl)amino)-2-oxoacetyl)-6-methyl-2,3-dihydro-1H-pyrrolizine-5-carboxamide

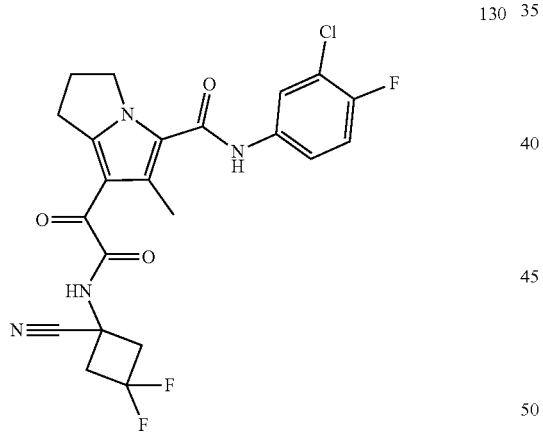

130

Trifluoroacetic anhydride (23 μL, 0.16 mmol) was added via syringe to a stirred mixture of 7-(2-((1-carbamoyl-3,3-difluorocyclobutyl)amino)-2-oxoacetyl)-N-(3-chloro-4-fluorophenyl)-6-methyl-2,3-dihydro-1H-pyrrolizine-5-carboxamide (27 mg, 0.055 mmol) and 2,6-lutidine (51 μL, 0.44 mmol) in tetrahydrofuran (1.0 mL) at ambient temperature. After 10 min, water (0.5 mL) was added, and the resulting biphasic mixture was stirred vigorously. After 5 min, the biphasic mixture was concentrated under reduced pressure. The residue was purified by was purified by reverse phase preparative HPLC (10-100% acetonitrile in water, 0.1% trifluoroacetic acid) to give N-(3-chloro-4-fluorophenyl)-7-(2-((1-cyano-3,3-difluorocyclobutyl)amino)-2-oxoacetyl)-6-methyl-2,3-dihydro-1H-pyrrolizine-5-carboxamide (130).

Example 131. 7-(2-((1-cyano-3,3-difluorocyclobutyl)amino)-2-oxoacetyl)-N-(3,4-difluorophenyl)-6-methyl-2,3-dihydro-1H-pyrrolizine-5-carboxamide

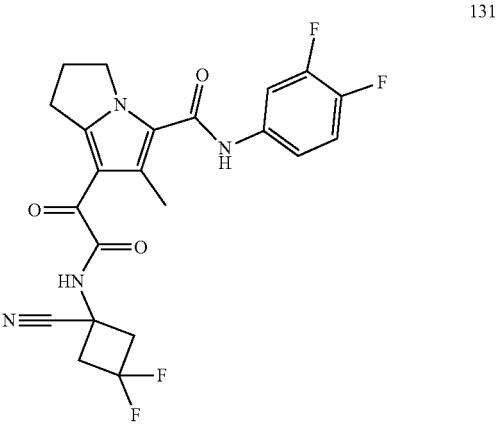 [SMILES: Cc1c(C(=O)C(=O)NC2(C#N)CC(F)(F)C2)c2n(c1C(=O)Nc1ccc(F)c(F)c1)CCC2]

131

7-(2-((1-cyano-3,3-difluorocyclobutyl)amino)-2-oxoacetyl)-N-(3,4-difluorophenyl)-6-methyl-2,3-dihydro-1H-pyrrolizine-5-carboxamide (131) was synthesizes in a manner similar to Example 130 using 7-(2-((1-carbamoyl-3,3-difluorocyclobutyl)amino)-2-oxoacetyl)-N-(3,4-difluorophenyl)-6-methyl-2,3-dihydro-1H-pyrrolizine-5-carboxamide in place of 7-(2-((1-carbamoyl-3,3-difluorocyclobutyl)amino)-2-oxoacetyl)-N-(3-chloro-4-fluorophenyl)-6-methyl-2,3-dihydro-1H-pyrrolizine-5-carboxamide.

Example 132. (R)—N-(3-Chloro-4-fluorophenyl)-6-methyl-7-(2-oxo-2-((1,1,1-trifluoro-3-hydroxy-2-methylpropan-2-yl)amino)acetyl)-2,3-dihydro-1H-pyrrolizine-5-carboxamide

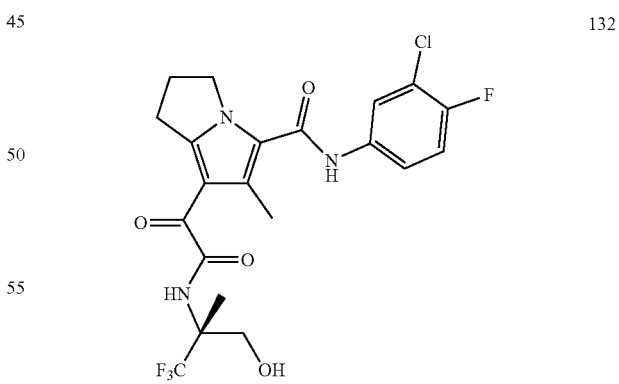

132

(R)—N-(3-chloro-4-fluorophenyl)-6-methyl-7-(2-oxo-2-((1,1,1-trifluoro-3-hydroxy-2-methylpropan-2-yl)amino)acetyl)-2,3-dihydro-1H-pyrrolizine-5-carboxamide (132) was synthesized in a manner similar to Example 29 using (R)-2-amino-3,3,3-trifluoro-2-methylpropan-1-ol hydrochloride in place of 3,3-difluoro-1-(1H-1,2,3-triazol-4-yl)cyclobutan-1-amine hydrochloride.

Example 133. (R)—N-(3,4-difluorophenyl)-6-methyl-7-(2-oxo-2-((1,1,1-trifluoro-3-hydroxy-2-methylpropan-2-yl)amino)acetyl)-2,3-dihydro-1H-pyrrolizine-5-carboxamide

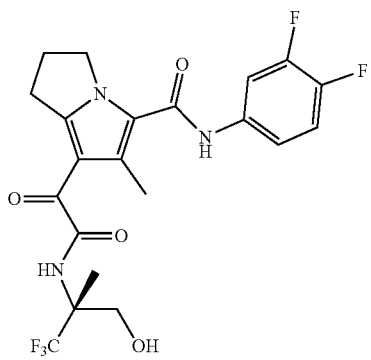

133

(R)—N-(3,4-difluorophenyl)-6-methyl-7-(2-oxo-2-((1,1,1-trifluoro-3-hydroxy-2-methylpropan-2-yl)amino)acetyl)-2,3-dihydro-1H-pyrrolizine-5-carboxamide (133) was synthesized in a manner similar to Example 29 using 3,4-difluoroaniline in place of 3-chloro-4-fluoroaniline and using (R)-2-amino-3,3,3-trifluoro-2-methylpropan-1-ol hydrochloride in place of 3,3-difluoro-1-(1H-1,2,3-triazol-4-yl)cyclobutan-1-amine hydrochloride.

Example 134: (R)-7-(2-((3,3-difluoro-1-(1H-1,2,3-triazol-4-yl)cyclobutyl)amino)-2-oxoacetyl)-N-(2-(difluoromethyl)-3-fluoropyridin-4-yl)-2-fluoro-6-methyl-2,3-dihydro-1H-pyrrolizine-5-carboxamide

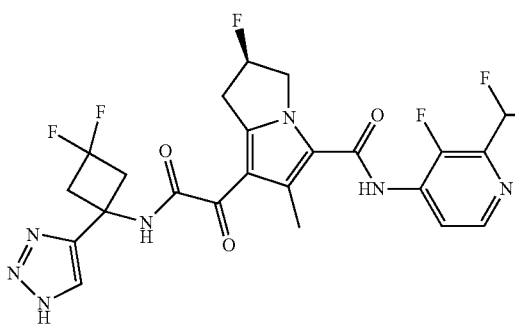

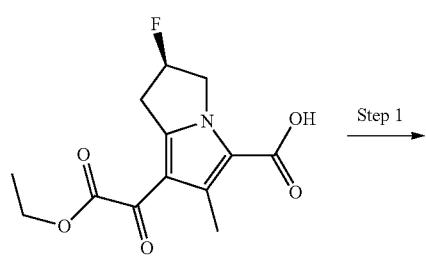

(R)-7-(2-ethoxy-2-oxoacetyl)-2-fluoro-6-methyl-2,3-dihydro-1H-pyrrolizine-5-carboxylic acid

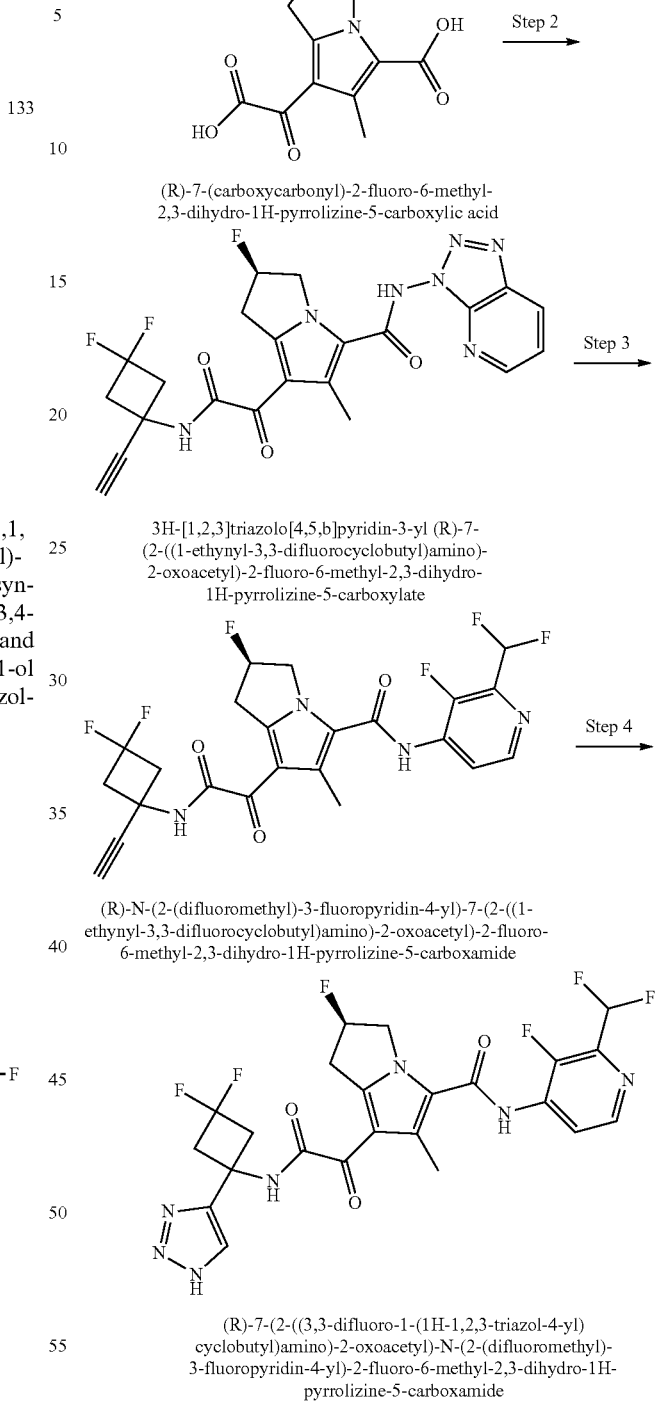

(R)-7-(carboxycarbonyl)-2-fluoro-6-methyl-2,3-dihydro-1H-pyrrolizine-5-carboxylic acid 3H-[1,2,3]triazolo[4,5-b]pyridin-3-yl (R)-7-(2-((1-ethynyl-3,3-difluorocyclobutyl)amino)-2-oxoacetyl)-2-fluoro-6-methyl-2,3-dihydro-1H-pyrrolizine-5-carboxylate (R)-N-(2-(difluoromethyl)-3-fluoropyridin-4-yl)-7-(2-((1-ethynyl-3,3-difluorocyclobutyl)amino)-2-oxoacetyl)-2-fluoro-6-methyl-2,3-dihydro-1H-pyrrolizine-5-carboxamide (R)-7-(2-((3,3-difluoro-1-(1H-1,2,3-triazol-4-yl)cyclobutyl)amino)-2-oxoacetyl)-N-(2-(difluoromethyl)-3-fluoropyridin-4-yl)-2-fluoro-6-methyl-2,3-dihydro-1H-pyrrolizine-5-carboxamide Step 1 (R)-7-(2-ethoxy-2-oxoacetyl)-2-fluoro-6-methyl-2,3-dihydro-1H-pyrrolizine-5-carboxylic acid (0.83 g, 2.9 mmol) was taken up as a homogeneous mixture in THF/MeOH/water (2:2:1, 15 mL) and treated at room temperature with lithium hydroxide monohydrate (0.31 g, 7.3 mmol) in a single portion. The mixture was sonicated to homogeneity. When LC/MS analysis indicated the completion of the reaction, the mixture was diluted with ice (~10 g) and treated dropwise with 20% aqueous sulfuric acid to pH 1. After extraction three three times with ethyl acetate, the combined organics were washed once with saturated aqueous sodium chloride solution, dried over anhydrous magnesium sulfate, filtered, and concentrated to provide (R)-7-(carboxycarbonyl)-2-fluoro-6-methyl-2,3-dihydro-1H-pyrrolizine-5-carboxylic acid. LCMS-ESI+ (m/z): [M+H]+ calculated for C$_{11}$H$_{11}$FNO$_5$: 256.1; found: 255.9.

Step 2 1-[Bis(dimethylamino)methylene]-1H-1,2,3-triazolo[4,5-b]pyridinium 3-oxid hexafluorophosphate (HATU, 2.4 g, 6.3 mmol) was added in a single portion to a mixture of ((R)-7-(carboxycarbonyl)-2-fluoro-6-methyl-2,3-dihydro-1H-pyrrolizine-5-carboxylic acid (0.77 g, 3.0 mmol), 1-ethynyl-3,3-difluorocyclobutan-1-amine bistriflate (1.6 g, 3.8 mmol), and N,N-diisopropylethylamine (5.0 mL, 29 mmol) in N,N-dimethylformamide (15 mL). When LC/MS analysis confirmed the sufficient completion of the reaction, the mixture was partitioned between ethyl acetate and saturated aqueous sodium hydrogen carbonate solution. The aqueous phase was extracted three times with ethyl acetate. The combined extracts were washed with a mixture of saturated aqueous sodium chloride/saturated aqueous sodium hydrogen carbonate solutions (~5:1), dried over anhydrous magnesium sulfate, filtered, and concentrated under reduced pressure.

The residue was purified by flash chromatography (silica gel) to provide 3H-[1,2,3]triazolo[4,5-b]pyridin-3-yl (R)-7-(2-((1-ethynyl-3,3-difluorocyclobutyl)amino)-2-oxoacetyl)-2-fluoro-6-methyl-2,3-dihydro-1H-pyrrolizine-5-carboxylate. LCMS-ESI+ (m/z): [M+H]+ calculated for C$_{22}$H$_{18}$F$_3$N$_6$O$_4$: 487.1; found: 487.9.

Step 3 To a suspension of 3H-[1,2,3]triazolo[4,5-b]pyridin-3-yl (R)-7-(2-((1-ethynyl-3,3-difluorocyclobutyl)amino)-2-oxoacetyl)-2-fluoro-6-methyl-2,3-dihydro-1H-pyrrolizine-5-carboxylate, (0.48 g, 0.99 mmol) and 2-(difluoromethyl)-3-fluoropyridin-4-amine hydrochloride (0.59 g, 3.0 mmol) in dichloromethane (10 mL) was added 2,6-lutidine (0.70 mL, 5.9 mmol). The resulting mixture was concentrated on the rotary evaporator to give a suspension. It was taken up again in dichloromethane (10 mL) and concentrated to a homogeneous residue, which was then heated at 100° C. for seven days.

After cooling, the residue was purified by flash chromatography (silica gel) to provide (R)—N-(2-(difluoromethyl)-3-fluoropyridin-4-yl)-7-(2-((1-ethynyl-3,3-difluorocyclobutyl)amino)-2-oxoacetyl)-2-fluoro-6-methyl-2,3-dihydro-1H-pyrrolizine-5-carboxamide. LCMS-ESI+ (m/z): [M+H]+ calculated for C$_{23}$H$_{19}$F$_6$N$_4$O$_3$: 513.1; found: 513.2.

Step 4 A mixture of (R)—N-(2-(difluoromethyl)-3-fluoropyridin-4-yl)-7-(2-((1-ethynyl-3,3-difluorocyclobutyl)amino)-2-oxoacetyl)-2-fluoro-6-methyl-2,3-dihydro-1H-pyrrolizine-5-carboxamide (0.16 g, 0.31 mmol) in N,N-dimethylformamide/methanol (9:1 mixture, 6 mL) was stirred in an ice-water bath while being degassed with Argon for 10 minutes. To the solution was then added copper(I) thiophene-2-carboxylate (30 mg, 0.16 mmol) and the resulting mixture was further subjected to Argon for 10 minutes. Azidotrimethylsilane (210 μL, 1.6 mmol) was added to the mixture. The vial was sealed and the mixture was stirred overnight at 100° C.

After cooling to room temperature, the reaction mixture was concentrated, and the residue was purified by preparative reverse-phase HPLC (10-80% acetonitrile in water, 0.1% TFA buffer) to provide (R)-7-(2-((3,3-difluoro-1-(1H-1,2,3-triazol-4-yl)cyclobutyl)amino)-2-oxoacetyl)-N-(2-(difluoromethyl)-3-fluoropyridin-4-yl)-2-fluoro-6-methyl-2,3-dihydro-1H-pyrrolizine-5-carboxamide. LCMS-ESI+ (m/z): [M+H]+ calculated for C$_{23}$H$_{20}$F$_6$N$_7$O$_3$: 556.2; found: 556.2.

(R)-2-(2-(5-((3,4-difluorophenyl)carbamoyl)-6-methyl-2,3-dihydro-1H-pyrrolizin-7-yl)-2-oxoacetamido)-3,3,3-trifluoro-2-methylpropanoic acid

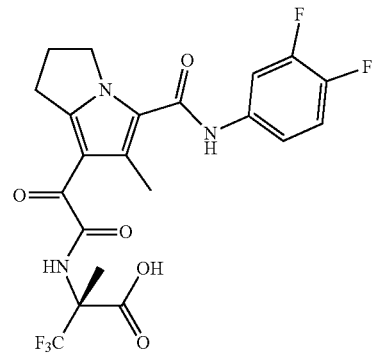 [SMILES: Cc1c(C(=O)C(=O)N[C@](C)(C(=O)O)C(F)(F)F)c2n(c1C(=O)Nc1ccc(F)c(F)c1)CCC2]

(R)-2-(2-(5-((3,4-difluorophenyl)carbamoyl)-6-methyl-2,3-dihydro-1H-pyrrolizin-7-yl)-2-oxoacetamido)-3,3,3-trifluoro-2-methylpropanoic acid was synthesized in a manner similar to Example 29 using 3,4-difluoroaniline in place of 3-chloro-4-fluoroaniline and using (R)-2-amino-3,3,3-trifluoro-2-methylpropanoic acid hydrochloride in place of 3,3-difluoro-1-(1H-1,2,3-triazol-4-yl)cyclobutan-1-amine hydrochloride.

Example 135. (R)—N-(3,4-difluorophenyl)-6-methyl-7-(2-oxo-2-((1,1,1-trifluoro-3-hydroxy-2-methylpropan-2-yl)amino)acetyl)-2,3-dihydro-1H-pyrrolizine-5-carboxamide

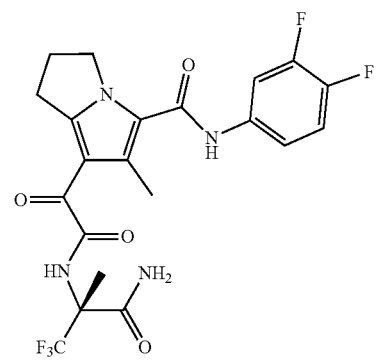

135

1-((Dimethylamino)(dimethyliminio)methyl)-1H-[1,2,3]triazolo[4,5-b]pyridine 3-oxide hexafluorophosphate(V) (35 mg, 0.092 mmol) was added to a stirred mixture of (R)-2-(2-(5-((3,4-difluorophenyl)carbamoyl)-6-methyl-2,3-dihydro-1H-pyrrolizin-7-yl)-2-oxoacetamido)-3,3,3-trifluoro-2-methylpropanoic acid (15 mg, 0.031 mmol), ammonium chloride (8.2 mg, 0.15 mmol), N,N-dimethylpyridin-4-amine (3.8 mg, 0.031 mmol), and 1-methylmorpholine (40.6 μL, 0.369 mmol) in N,N-dimethylformamide (1.5 mL) at ambient temperature. After 120 min, the residue was purified by was purified by reverse phase preparative HPLC (10-100% acetonitrile in water, 0.1% trifluoroacetic acid) to give (R)—N-(3,4-difluorophenyl)-6-methyl-7-(2-oxo-2-((1,1,1-trifluoro-3-hydroxy-2-methylpropan-2-yl)amino)acetyl)-2,3-dihydro-1H-pyrrolizine-5-carboxamide (135).

Example 136. (S)—N-(3,4-difluorophenyl)-6-methyl-7-(2-oxo-2-((1,1,1-trifluoro-3-hydroxy-2-methylpropan-2-yl)amino)acetyl)-2,3-dihydro-1H-pyrrolizine-5-carboxamide

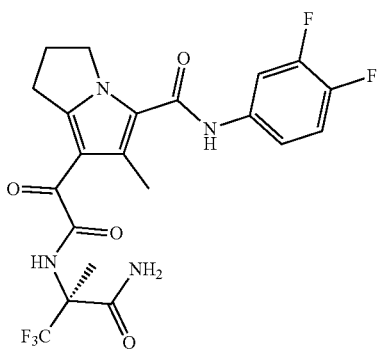

136

(S)-7-(2-((3-amino-1,1,1-trifluoro-2-methyl-3-oxopropan-2-yl)amino)-2-oxoacetyl)-N-(3,4-difluorophenyl)-6-methyl-2,3-dihydro-1H-pyrrolizine-5-carboxamide acid (136) was synthesized in a manner similar to Example 135 using (S)-2-amino-3,3,3-trifluoro-2-methylpropanoic acid hydrochloride in place of (R)-2-amino-3,3,3-trifluoro-2-methylpropanoic acid hydrochloride.

Example 137. (R)—N-(3,4-difluorophenyl)-6-methyl-7-(2-oxo-2-((1,1,1-trifluoro-2-methyl-3-(methylamino)-3-oxopropan-2-yl)amino)acetyl)-2,3-dihydro-1H-pyrrolizine-5-carboxamide

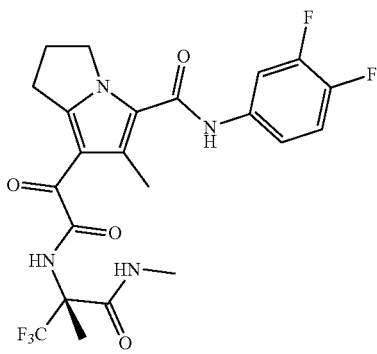

137

(R)—N-(3,4-difluorophenyl)-6-methyl-7-(2-oxo-2-((1,1,1-trifluoro-2-methyl-3-(methylamino)-3-oxopropan-2-yl)amino)acetyl)-2,3-dihydro-1H-pyrrolizine-5-carboxamide (137) was synthesized in a manner similar to Example 135 using methylamine hydrochloride in place of ammonium chloride.

Example 138. (S)—N-(3,4-difluorophenyl)-6-methyl-7-(2-oxo-2-((1,1,1-trifluoro-2-methyl-3-(methylamino)-3-oxopropan-2-yl)amino)acetyl)-2,3-dihydro-1H-pyrrolizine-5-carboxamide

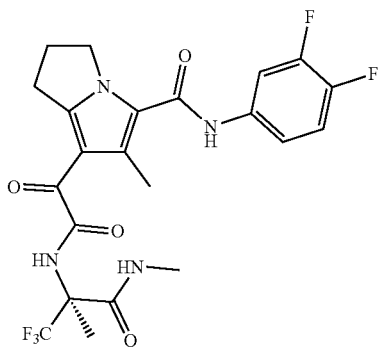

138

(S)—N-(3,4-difluorophenyl)-6-methyl-7-(2-oxo-2-((1,1,1-trifluoro-2-methyl-3-(methylamino)-3-oxopropan-2-yl)amino)acetyl)-2,3-dihydro-1H-pyrrolizine-5-carboxamide (138) was synthesized in a manner similar to Example 135 using methylamine hydrochloride in place of ammonium chloride and using (S)-2-amino-3,3,3-trifluoro-2-methylpropanoic acid hydrochloride in place of (R)-2-amino-3,3,3-trifluoro-2-methylpropanoic acid hydrochloride.

Example 140. 7-(2-((1-carbamoyl-3,3-difluorocyclobutyl)amino)-2-oxoacetyl)-6-methyl-N-(3,4,5-trifluorophenyl)-2,3-dihydro-1H-pyrrolizine-5-carboxamide (140)

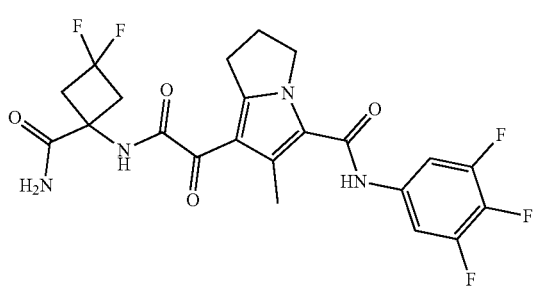

140

7-(2-((1-carbamoyl-3,3-difluorocyclobutyl)amino)-2-oxoacetyl)-6-methyl-N-(3,4,5-trifluorophenyl)-2,3-dihydro-1H-pyrrolizine-5-carboxamide (140) was synthesized in a manner similar to Example 26 Step 4 using 1-amino-3,3-difluorocyclobutane-1-carboxamide in place of 1-(1H-1,2,3-triazol-4-yl)cyclopropan-1-amine dihydrochloric acid.

Example 145. N-(3,4-difluorophenyl)-6-methyl-7-(2-((3-methyl-1-oxidothietan-3-yl)amino)-2-oxoacetyl)-2,3-dihydro-1H-pyrrolizine-5-carboxamide

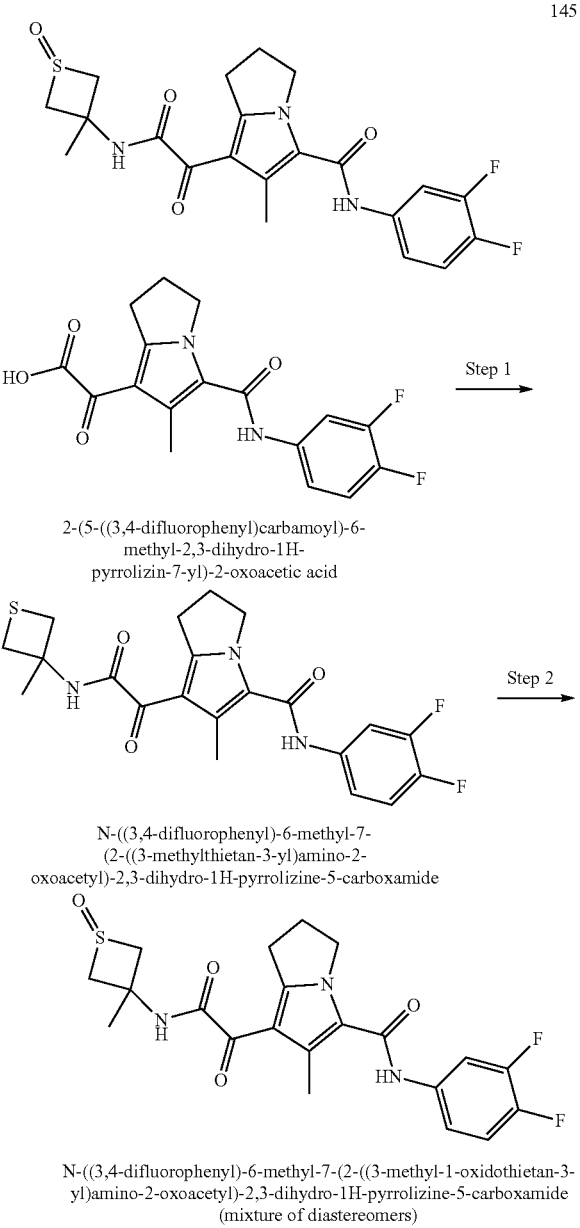

2-(5-((3,4-difluorophenyl)carbamoyl)-6-methyl-2,3-dihydro-1H-pyrrolizin-7-yl)-2-oxoacetic acid N-((3,4-difluorophenyl)-6-methyl-7-(2-((3-methylthietan-3-yl)amino-2-oxoacetyl)-2,3-dihydro-1H-pyrrolizine-5-carboxamide N-((3,4-difluorophenyl)-6-methyl-7-(2-((3-methyl-1-oxidothietan-3-yl)amino-2-oxoacetyl)-2,3-dihydro-1H-pyrrolizine-5-carboxamide (mixture of diastereomers)

Step 1 A mixture of 3-methylthietan-3-amine hydrochloride (93 mg, 0.67 mmol) and 2-(5-((3,4-difluorophenyl)carbamoyl)-6-methyl-2,3-dihydro-1H-pyrrolizin-7-yl)-2-oxoacetic acid (0.20 g, 0.58 mmol) was taken up in N,N-dimethylformamide and treated successively with N,N-diisopropylethylamine (0.51 mL, 2.9 mmol) and 1-[bis(dimethylamino)methylene]-1H-1,2,3-triazolo[4,5-b]pyridinium 3-oxid hexafluorophosphate (HATU, 0.29 g, 0.75 mmol). After 4 hours of stirring, the mixture was partitioned between ethyl acetate and saturated aqueous sodium hydrogen carbonate solution. The aqueous phase was extracted three times with ethyl acetate. The combined organic phases were subsequently washed successively with ~5% aqueous hydrochloric acid, half-saturated aqueous sodium chloride solution, and a 1:1 mixture of saturated aqueous sodium hydrogen carbonate and sodium chloride solutions. The organics were then dried over anhydrous magnesium sulfate, filtered, concentrated, and concentrated to provide N-(3,4-difluorophenyl)-6-methyl-7-(2-((3-methylthietan-3-yl)amino)-2-oxoacetyl)-2,3-dihydro-1H-pyrrolizine-5-carboxamide. LCMS-ESI+ (m/z): [M+H]+ calculated for $C_{21}H_{22}F_2N_3O_3S$: 434.1; found: 434.2.

Step 2 A suspension of N-(3,4-difluorophenyl)-6-methyl-7-(2-((3-methylthietan-3-yl)amino)-2-oxoacetyl)-2,3-dihydro-1H-pyrrolizine-5-carboxamide (0.25 g, 0.58 mmol) was taken up as a suspension in acetonitrile (4 mL) was heated to homogeneity. After cooling, the cloudy mixture was treated with iron(III) chloride (4.7 mg, 0.03 mmol). After five minutes of stirring, periodic acid (hydrated, 0.15 g, 0.64 mmol) was added in a single portion.

After LC/MS analysis confirmed the complete consumption of starting material, the mixture was quenched by the addition of 25% wt/wt aqueous sodium thiosulfate solution (2 mL). The suspension was allowed to stir for 10 minutes, was diluted with water, and then was extracted with ethyl acetate. The combined organic extracts were dried over anhydrous sodium sulfate and filtered. The still biphasic filtrate was poured into separatory funnel. The remaining aqueous layer was removed. The organics were then dried over anhydrous magnesium sulfate, filtered, and concentrated under reduced pressure.

The residue was purified by preparative reverse-phase HPLC (5-60% acetonitrile in water, 0.1% TFA buffer) to provide N-(3,4-difluorophenyl)-6-methyl-7-(2-((3-methyl-1-oxidothietan-3-yl)amino)-2-oxoacetyl)-2,3-dihydro-1H-pyrrolizine-5-carboxamide as an approximately 2:1 mixture of diastereomers. LCMS-ESI+ (m/z): [M+H]+ calculated for $C_{21}H_{22}F_2N_3O_4S$: 450.1; found: 450.2.

Example 147. 7-(2-((3,3-difluoro-1-(methylcarbamoyl)cyclobutyl)amino)-2-oxoacetyl)-N-(2-(difluoromethyl)-3-fluoropyridin-4-yl)-6-methyl-2,3-dihydro-1H-pyrrolizine-5-carboxamide

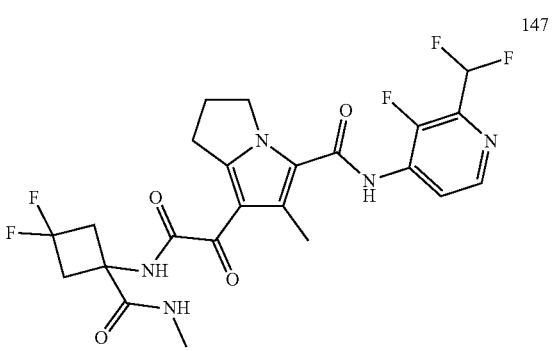 [SMILES: CNC(=O)C1(NC(=O)C(=O)c2c(C)c(C(=O)Nc3ccnc(C(F)F)c3F)n3c2CCC3)CC(F)(F)C1]

7-(2-((3,3-difluoro-1-(methylcarbamoyl)cyclobutyl)amino)-2-oxoacetyl)-N-(2-(difluoromethyl)-3-fluoropyridin-4-yl)-6-methyl-2,3-dihydro-1H-pyrrolizine-5-carboxamide (147) was synthesized in a manner similar to Example 2 using 1-amino-3,3-difluoro-N-methylcyclobutane-1-carboxamide hydrochloride in place of), R-trifluoroisopropylamine, and 2-(difluoromethyl)-3-fluoropyridin-4-amine hydrochloride in place of 3-chloro-4-fluoroaniline Example 150. (R)—N-(2-(difluoromethyl)-3-fluoropyridin-4-yl)-2-fluoro-6-methyl-7-(2-oxo-2-((3-(trifluoromethyl)oxetan-3-yl)amino)acetyl)-2,3-dihydro-1H-pyrrolizine-5-carboxamide

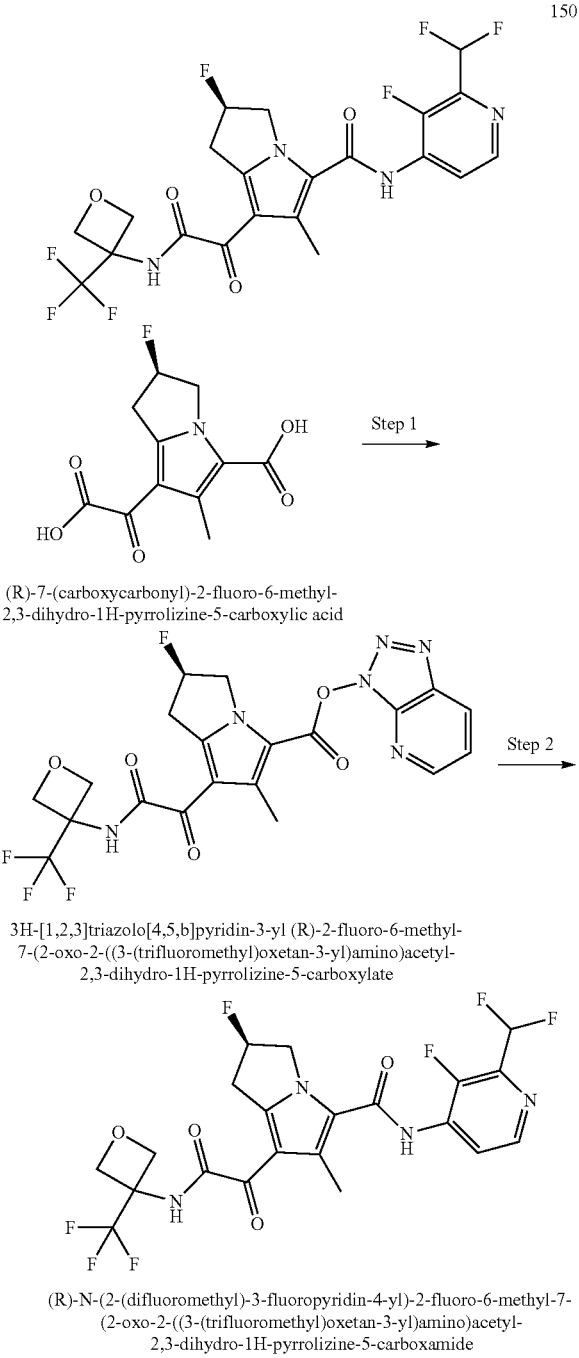

Step 1 3H-[1,2,3]triazolo[4,5-b]pyridin-3-yl (R)-2-fluoro-6-methyl-7-(2-oxo-2-((3-(trifluoromethyl)oxetan-3-yl)amino)acetyl)-2,3-dihydro-1H-pyrrolizine-5-carboxylate was prepared in analogous fashion to 3H-[1,2,3]triazolo[4,5-b]pyridin-3-yl (R)-7-(2-((1-ethynyl-3,3-difluorocyclobutyl)amino)-2-oxoacetyl)-2-fluoro-6-methyl-2,3-dihydro-1H-pyrrolizine-5-carboxylate, using 3-(trifluoromethyl)oxetan-3-amine hydrochloride in place of 1-ethynyl-3,3-difluorocyclobutan-1-amine bistriflate. LCMS-ESI+ (m/z): [M+H]+ calculated for $C_{20}H_{17}F_4N_6O_5$: 497.1; found: 496.9.

Step 2 (R)—N-(2-(difluoromethyl)-3-fluoropyridin-4-yl)-2-fluoro-6-methyl-7-(2-oxo-2-((3-(trifluoromethyl)oxetan-3-yl)amino)acetyl)-2,3-dihydro-1H-pyrrolizine-5-carboxamide was prepared in analogous fashion to (R)—N-(2-(difluoromethyl)-3-fluoropyridin-4-yl)-7-(2-((1-ethynyl-3,3-difluorocyclobutyl)amino)-2-oxoacetyl)-2-fluoro-6-methyl-2,3-dihydro-1H-pyrrolizine-5-carboxamide. LCMS-ESI+ (m/z): [M+H]+ calculated for $C_{21}H_{18}F_7N_4O_4$: 523.1; found: 523.2.

Example 151. N-(3,4-difluorophenyl)-6-methyl-7-(2-(((1r,3r)-3-methyl-1-oxidothietan-3-yl)amino)-2-oxoacetyl)-2,3-dihydro-1H-pyrrolizine-5-carboxamide

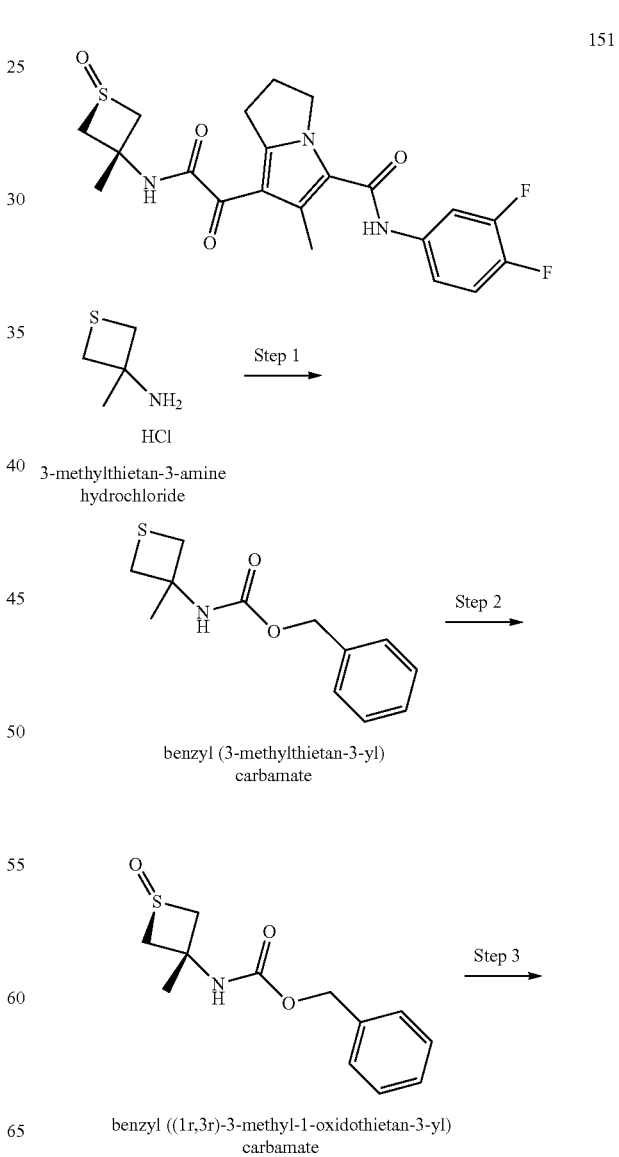

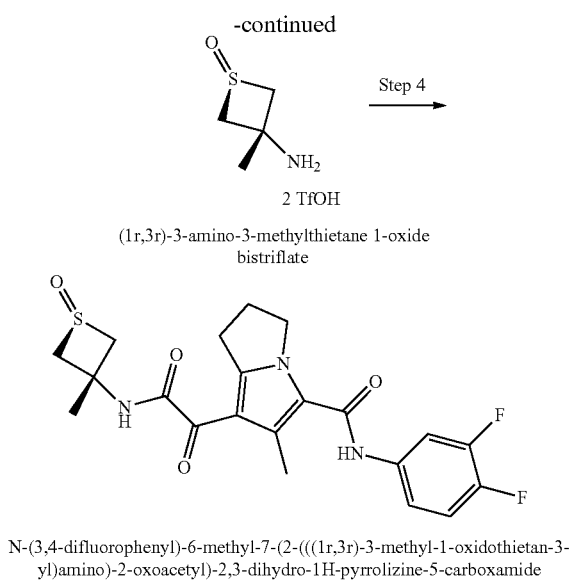

N-(3,4-difluorophenyl)-6-methyl-7-(2-(((1r,3r)-3-methyl-1-oxidothietan-3-yl)amino)-2-oxoacetyl)-2,3-dihydro-1H-pyrrolizine-5-carboxamide Step 1 N,N-diisopropylethylamine (2.0 mL, 11 mmol) and N-Cbz succinimide (1.3 g, 5.2 mmol) were added successively to a solution of 3-methylthietan-3-amine hydrochloride (0.72 g, 5.2 mol) in dichloromethane (15 mL) at room temperature. After remaining overnight at room temperature, the mixture was diluted with diethyl ether (60 mL) and washed successively with 10% aqueous hydrochloric acid (50 mL×2) and saturated aqueous sodium chloride solution. The organic phase was dried over anhydrous magnesium sulfate, filtered, and concentrated to give benzyl (3-methylthietan-3-yl)carbamate. LCMS-ESI+ (m/z): [M+H]+ calculated for $C_{12}H_{16}NO_2S$: 238.1; found: 238.0.

Step 2 A solution of benzyl (3-methylthietan-3-yl)carbamate (1.2 g, 5.2 mmol) in acetonitrile (5 mL) was treated with iron(I) chloride (42 mg, 0.26 mmol), and the resulting mixture was stirred for about 5 minutes at room temperature before the addition of periodic acid (hydrated, 1.3 g, 5.7 mmol). After about 2 hours of stirring, the mixture was quenched by the addition of 25% wt/wt aqueous sodium thiosulfate solution ($Na_2S_2O_3$, ~2 mL). The ensuing suspension was stirred for 10 minutes and then filtered through a pad of Celite diatomaceous earth. The filtrate was concentrated under reduced pressure. The residue was diluted with water and extracted with dichloromethane three times. The aqueous phase was saturated with sodium chloride and subsequently extracted three more times each with dichloromethane and ethyl acetate. The combined organics were dried organics over anhydrous magnesium sulfate, filtered, and concentrated under reduced pressure. The residue was purified by flash chromatography (silica gel) to provide two diastereomers, arbitrarily assigned cis and trans conformations.

Diasteromer 1 (first to elute from silica gel): benzyl ((1r,3r)-3-methyl-1-oxidothietan-3-yl)carbamate Diasteromer 2: benzyl ((1s,3s)-3-methyl-1-oxidothietan-3-yl)carbamate LCMS-ESI+ (m/z): [M+H]+ calculated for $C_{12}H_{16}NO_3S$: 254.1; found: 254.1.

Step 3 A solution benzyl ((1r,3r)-3-methyl-1-oxidothietan-3-yl)carbamate (0.23 g, 0.79 mmol) and anisole (290 μL, 2.7 mmol) in dichloromethane (5 mL) was cooled in an ice-water bath. Trifluoromethanesulfonic acid (160 μL, 1.8 mmol) was added dropwise. The cooling bath was removed, and the mixture was allowed to warm to ambient temperature.

After one hour, the mixture was diluted with water and was extracted once with diethyl ether/hexane (1:3, 20 mL). The aqueous layer was concentrated to provide (1r,3r)-3-amino-3-methylthietane 1-oxide bistriflate. LCMS-ESI+ (m/z): [M+H]+ calculated for $C_4H_{10}NOS$: 120.0; found: 119.8.

Step 4 N-(3,4-difluorophenyl)-6-methyl-7-(2-(((1r,3r)-3-methyl-1-oxidothietan-3-yl)amino)-2-oxoacetyl)-2,3-dihydro-1H-pyrrolizine-5-carboxamide was prepared in analogous fashion to N-(3,4-difluorophenyl)-7-(2-((3-(dimethylphosphoryl)oxetan-3-yl)amino)-2-oxoacetyl)-6-methyl-2,3-dihydro-1H-pyrrolizine-5-carboxamide using (1r,3r)-3-amino-3-methylthietane 1-oxide bistriflate in place of (3-aminooxetan-3-yl)dimethylphosphine oxide hydrochloride and purifying by flash chromatography (silica gel) instead of preparative reverse-phase HPLC. LCMS-ESI+ (m/z): [M+H]+ calculated for $C_{21}H_{22}F_2N_3O_4S$: 450.1; found: 450.2.

Example 152. N-(3,4-difluorophenyl)-6-methyl-7-(2-(((1s,3s)-3-methyl-1-oxidothietan-3-yl)amino)-2-oxoacetyl)-2,3-dihydro-1H-pyrrolizine-5-carboxamide

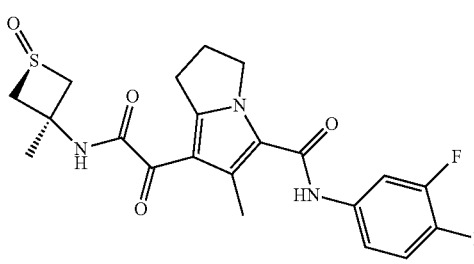

152

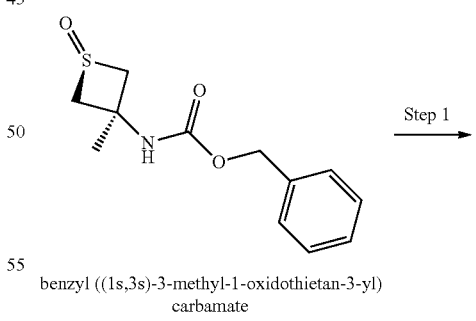

benzyl ((1s,3s)-3-methyl-1-oxidothietan-3-yl)carbamate

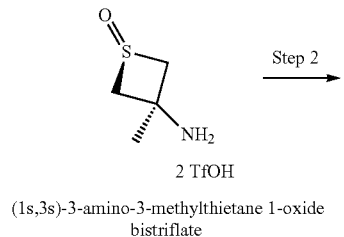

(1s,3s)-3-amino-3-methylthietane 1-oxide bistriflate

-continued

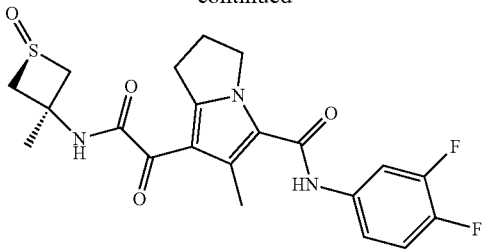

N-(3,4-difluorophenyl)-6-methyl-7-(2-(((1s,3s)-3-methyl-1-oxidothietan-3-yl)amino)-2-oxoacetyl)-2,3-dihydro-1H-pyrrolizine-5-carboxamide Step 1 Benzyl ((1s,3s)-3-methyl-1-oxidothietan-3-yl)carbamate was isolated via the flash chromatography that also provided benzyl ((1r,3r)-3-methyl-1-oxidothietan-3-yl)carbamate LCMS-ESI+ (m/z): [M+H]$^+$ calculated for $C_{12}H_{16}NO_3S$: 254.1; found: 254.1.

Step 2 (1s,3s)-3-amino-3-methylthietane 1-oxide bistriflate was derived from benzyl ((1s,3s)-3-methyl-1-oxidothietan-3-yl)carbamate in a manner similar to that which furnished (1r,3r)-3-amino-3-methylthietane 1-oxide bistriflate Step 3 N-(3,4-difluorophenyl)-6-methyl-7-(2-(((1s,3s)-3-methyl-1-oxidothietan-3-yl)amino)-2-oxoacetyl)-2,3-dihydro-1H-pyrrolizine-5-carboxamide was synthesized in a manner similar to Example 151, using (1s,3s)-3-amino-3-methylthietane 1-oxide bistriflate in place of (1r,3r)-3-amino-3-methylthietane 1-oxide bistriflate and by purifying first via flash chromatography (silica gel) and then by preparative reverse-phase HPLC (10-70% acetonitrile in water, 0.1% TFA buffer). LCMS-ESI+ (m/z): [M+H]$^+$ calculated for $C_{21}H_{22}F_2N_3O_4S$: 450.1; found: 450.2.

Analytical Data for compounds 1 to 49 are set forth in the table below. Additionally, analytical data for compounds 50 to 152 are set forth in the table below.

| Compound # | ES/MS m/z | $^1$H-NMR |
|---|---|---|
| 1 | 430.9 | 1H NMR (400 MHz, Chloroform-d) δ 8.79 (s, 1H), 8.07 (dd, J = 5.5, 2.7 Hz, 1H), 7.71 (ddd, J = 9.1, 4.5, 2.8 Hz, 1H), 7.23-7.15 (m, 1H), 6.83 (s, 1H), 4.54-4.43 (m, 2H), 3.29 (t, J = 7.6 Hz, 2H), 2.48 (p, J = 7.6 Hz, 2H), 1.44 (s, 9H). |
| 2 | 460.2 | 1H NMR (400 MHz, DMSO-d6) δ 9.98 (s, 1H), 9.27 (d, J = 8.8 Hz, 1H), 7.93 (dd, J = 6.9, 2.6 Hz, 1H), 7.58 (ddd, J = 9.0, 4.3, 2.6 Hz, 1H), 7.38 (t, J = 9.1 Hz, 1H), 4.68 (dq, J = 15.3, 7.6 Hz, 1H), 4.13 (t, J = 7.3 Hz, 2H), 2.96-2.78 (m, 2H), 2.42 (s, 5H), 1.30 (d, J = 7.0 Hz, 3H). |
| 3 | 511.4 | 1H NMR (400 MHz, DMSO-d6) δ 9.97 (s, 1H), 9.42 (s, 1H), 7.94 (dd, J = 6.8, 2.6 Hz, 1H), 7.78 (t, J = 4.5 Hz, 1H), 7.58 (ddd, J = 9.0, 4.3, 2.6 Hz, 1H), 7.38 (t, J = 9.1 Hz, 1H), 4.13 (t, J = 7.3 Hz, 2H), 3.20 (td, J = 14.8, 11.7 Hz, 2H), 3.01-2.79 (m, 4H), 2.59 (d, J = 4.6 Hz, 3H), 2.46-2.31 (m, 5H). |
| 4 | 523.0 | 1H NMR (400 MHz, DMSO-d6) δ 10.09 (s, 1H), 9.41 (s, 1H), 7.97 (dd, J = 6.9, 2.6 Hz, 1H), 7.80 (d, J = 4.8 Hz, 1H), 7.61 (ddd, J = 9.1, 4.3, 2.6 Hz, 1H), 7.39 (t, J = 9.1 Hz, 1H), 4.23 (t, J = 5.9 Hz, 1H), 3.32-2.77 (m, 5H), 2.60 (d, J = 4.5 Hz, 3H), 2.40 (s, 3H), 2.10 (t, J = 7.1 Hz, 1H), 1.05 (dd, J = 8.4, 5.7 Hz, 1H), 0.14 (dt, J = 5.9, 3.0 Hz, 1H). |
| 5 | 522.9 | 1H NMR (400 MHz, DMSO-d6) δ 10.09 (s, 1H), 9.41 (s, 1H), 7.97 (dd, J = 6.9, 2.6 Hz, 1H), 7.80 (d, J = 4.8 Hz, 1H), 7.61 (ddd, J = 9.0, 4.3, 2.6 Hz, 1H), 7.39 (t, J = 9.1 Hz, 1H), 4.23 (s, 1H), 3.29-2.76 (m, 2H), 2.60 (d, J = 4.5 Hz, 3H), 2.40 (s, 3H), 1.05 (dd, J = 8.5, 5.7 Hz, 1H), 0.13 (s, 1H). |
| 6 | 471.1 | 1H NMR (400 MHz, Methanol-d4) δ 7.88 (dd, J = 6.7, 2.6 Hz, 1H), 7.72 (s, 1H), 7.51 (ddd, J = 9.0, 4.2, 2.6 Hz, 1H), 7.22 (t, J = 9.0 Hz, 1H), 4.20 (t, J = 7.3 Hz, 2H), 2.97 (t, J = 7.5 Hz, 2H), 2.53 (s, 3H), 2.47 (p, J = 7.4 Hz, 2H), 1.49-1.28 (m, 4H). |
| 7 | 488.0 | 1H NMR (400 MHz, DMSO-d6) δ 10.01 (s, 1H), 9.81 (s, 1H), 7.95 (dd, J = 6.8, 2.6 Hz, 1H), 7.59 (ddd, J = 9.3, 4.3, 2.6 Hz, 1H), 7.40 (t, J = 9.1 Hz, 1H), 4.83 (d, J = 9.1 Hz, 2H), 4.76 (d, J = 8.3 Hz, 2H), 4.22-4.08 (m, 2H), 2.97 (t, J = 7.7 Hz, 2H), 2.45 (d, J = 2.8 Hz, 5H). |
| 8 | 579.1 | 1H NMR (400 MHz, Methanol-d4) δ 7.88 (dd, J = 6.7, 2.6 Hz, 1H), 7.52 (dq, J = 9.0, 3.0 Hz, 1H), 7.23 (t, J = 9.0 Hz, 1H), 4.79 (d, J = 7.0 Hz, 2H), 4.76 (d, J = 7.0 Hz, 2H), 4.54 (s, 2H), 4.22 (t, J = 7.3 Hz, 2H), 4.18 (s, 2H), 3.52-3.33 (m, 2H), 3.02 (t, J = 7.5 Hz, 2H), 2.88 (td, J = 14.3, 6.3 Hz, 2H), 2.55 (s, 3H), 2.54-2.46 (m, 2H). |
| 9 | 656.1 | 1H NMR (400 MHz, DMSO-d6) δ 10.02 (br s, 1H), 9.71 (br s, 1H), 7.95 (dd, J = 6.8, 2.4 Hz, 1H), 7.60 (ddd, J = 9.2, 4.3, 2.4 Hz, 1H), 7.41 (t, J = 9.1 Hz, 1H), 4.30 (s, 2H), 4.16 (t, J = 7.2 Hz, 2H), 4.06 (s, 2H), 4.05-3.95 (m, 4H), 3.44 (t, J = 7.4 Hz, 2H), 2.98 (s, 3H), 2.89 (t, J = 7.4 Hz, 4H), 2.45 (s, 3H), 2.44-2.38 (m, 2H). |
| 10 | 565.1 | 1H NMR (400 MHz, Methanol-d4) δ 7.88 (dd, J = 6.7, 2.6 Hz, 1H), 7.56-7.48 (m, 1H), 7.23 (t, J = 9.0 Hz, 1H), 4.87-4.65 (m, 2H), 4.60-4.35 (s, 2H), 4.23 (t, J = 7.3 Hz, 2H), 3.73 (s, 2H), 3.11 (t, J = 7.6 Hz, 2H), 3.04-2.92 (m, 4H), 2.54 (s, 3H), 2.57-2.45 (m, 2H). |
| 11 | 579.1 | 1H NMR (400 MHz, Methanol-d4) δ 7.88 (dd, J = 5.3, 3.1 Hz, 1H), 7.51 (dd, J = 8.9, 4.5 Hz, 1H), 7.23 (td, J = 9.0, 1.4 Hz, 1H), 5.40 (d, J = 6.8 Hz, 2H), 4.63 (d, J = 6.9 Hz, 2H), 4.19 (dt, J = 26.2, 7.3 Hz, 4H), 3.44 (q, J = 13.9 Hz, 2H), 3.03 (t, J = 7.5 Hz, 2H), 2.88 (td, J = 14.1, 6.6 Hz, 2H), 2.64-2.45 (m, 9H) |
| 12 | 488.1 | 1H NMR (400 MHz, DMSO-d6) δ 10.01 (s, 1H), 9.88 (s, 1H), 9.42 (s, 1H), 7.96 (dd, J = 6.8, 2.4 Hz, 1H), 7.60 (d, J = 8.1 Hz, 1H), 7.40 (t, J = 9.1 Hz, 1H), 4.15 (t, J = 7.3 Hz, 2H), 2.93 (t, J = 7.5 Hz, 2H), 2.45 (s, 3H), 2.38-2.44 (m, 2H), 1.70-1.64 (m, 2H), 1.49-1.43 (m, 2H). |
| 13 | 627.1 | 1H NMR (400 MHz, DMSO-d6) δ 10.03 (br s, 1H), 9.73 (br s, 1H), 7.96 (dd, J = 6.8, 2.5 Hz, 1H), 7.67-7.55 (m, 1H), 7.41 (t, J = 9.1 Hz, 1H), 4.47 (d, J = 13.5 Hz, 2H), 4.40 (s, 2H), 4.38 (d, J = 13.5 Hz, 2H), 4.24-4.05 (m, 4H), 2.90 (quin, J = 7.3 Hz, 4H), 2.45 (s, 3H), 2.42 (d, J = 7.4 Hz, 2H). |
| 14 | 555.1 | 1H NMR (400 MHz, DMSO-d6) δ 10.03 (br s, 1H), 9.74 br (s, 1H), 7.90-7.95 (m, 1H), 7.50-7.65 (m, 1H), 7.30-7.45 (m, 1H), 5.20-5.45 (m, 1H), 4.00-4.60 (m, 6H), 2.83-2.87 (m, 2H), 2.70-2.80 (m, 2H), 2.44 (s, 3H). |
| 15 | 539.0 | 1H NMR (400 MHz, DMSO-d6) δ 10.40 (s, 1H), 9.41 (s, 1H), 7.98 (dd, J = 6.9, 2.6 Hz, 1H), 7.75 (d, J = 4.8 Hz, 1H), 7.60 (ddd, J = 9.1, 4.3, 2.6 Hz, 1H), 7.39 (t, J = 9.1 Hz, 1H), 3.20 (q, J = 14.5 Hz, 2H), 2.91 (dt, J = 23.1, 7.0 Hz, 4H), 2.59 (d, J = 4.6 Hz, 3H), 2.32 (s, 3H), 2.24 (t, J = 7.2 Hz, 2H), 1.50 (s, 6H). |
| 16 | 527.0 | 1H NMR (400 MHz, DMSO-d6) δ 9.94 (s, 1H), 9.41 (s, 1H), 7.93 (dd, J = 6.8, 2.6 Hz, 1H), 7.78 (d, J = 4.8 Hz, 1H), 7.58 (ddd, J = 9.0, 4.2, 2.5 Hz, 1H), 7.38 (t, J = 9.1 Hz, 1H), |

| Compound # | ES/MS m/z | ¹H-NMR |
|---|---|---|
| | | 4.73 (s, 1H), 4.26 (dd, J = 12.4, 5.4 Hz, 1H), 3.96 (dd, J = 12.4, 2.1 Hz, 1H), 3.23-3.12 (m, 3H), 3.01-2.80 (m, 3H), 2.60 (d, J = 4.6 Hz, 3H), 2.45 (s, 3H). |
| 17 | 488.1 | 1H NMR (400 MHz, DMSO-d6) δ 10.43 (s, 1H), 9.25 (d, J = 8.8 Hz, 1H), 7.97 (dd, J = 6.8, 2.6 Hz, 1H), 7.59 (ddd, J = 9.1, 4.3, 2.6 Hz, 1H), 7.39 (t, J = 9.1 Hz, 1H), 4.75-4.60 (m, 1H), 2.89 (td, J = 7.2, 4.7 Hz, 2H), 2.29 (d, J = 10.1 Hz, 5H), 1.50 (d, J = 2.1 Hz, 5H), 1.30 (t, J = 7.0 Hz, 3H). |
| 18 | 525.0 | 1H NMR (400 MHz, Acetone-d6) δ 9.18 (s, 1H), 8.63 (s, 1H), 8.12-8.01 (m, 1H), 7.67 (ddd, J = 9.0, 4.2, 2.7 Hz, 1H), 7.51-7.39 (m, 1H), 7.29 (q, J = 9.2 Hz, 1H), 4.92 (t, J = 6.9 Hz, 1H), 3.31 (s, 6H), 3.17-2.92 (m, 2H), 2.75 (d, J = 4.7 Hz, 3H), 2.52 (s, 3H), 1.30 (d, J = 6.4 Hz, 3H). |
| 19 | 516.0 | 1H NMR (400 MHz, DMSO-d6) δ 10.26 (s, 1H), 9.42 (s, 1H), 8.15 (dd, J = 5.8, 2.7 Hz, 1H), 7.94 (ddd, J = 9.2, 4.8, 2.7 Hz, 1H), 7.78 (d, J = 4.8 Hz, 1H), 7.52 (t, J = 9.1 Hz, 1H), 4.79 (d, J = 6.5 Hz, 1H), 3.27-3.11 (m, 1H), 3.06-2.81 (m, 3H), 2.59 (d, J = 4.5 Hz, 3H), 2.42 (s, 3H), 2.03 (d, J = 7.1 Hz, 1H), 1.19 (d, J = 6.4 Hz, 3H). |
| 20 | 474.2 | 1H NMR (400 MHz, Acetone-d6) δ 8.22-8.00 (m, 1H), 7.67 (dt, J = 9.1, 3.5 Hz, 1H), 7.30 (t, J = 9.0 Hz, 1H), 4.92 (t, J = 6.7 Hz, 1H), 4.79 (p, J = 7.3 Hz, 1H), 4.05 (q, J = 7.1 Hz, 1H), 3.30 (s, 4H), 3.15-2.99 (m, 5H), 2.80 (d, J = 13.3 Hz, 2H), 2.69 (dq, J = 12.8, 8.9 Hz, 1H), 2.51 (d, J = 1.7 Hz, 3H), 2.22-2.09 (m, 1H), 1.96 (s, 2H), 1.46 (d, J = 7.1 Hz, 3H), 1.30 (d, J = 6.4, 2.6 Hz, 3H), 1.20 (t, J = 7.1 Hz, 2H). |
| 21 | 482.1 | 1H NMR (400 MHz, Methanol-d4) δ 7.88 (dd, J = 6.6, 2.6 Hz, 1H), 7.52 (dd, J = 8.4, 3.9 Hz, 1H), 7.23 (t, J = 9.0 Hz, 1H), 4.55 (d, J = 14.4 Hz, 2H), 4.33-4.15 (m, 4H), 3.11 (t, J = 7.6 Hz, 2H), 2.54 (s, 3H), 2.52 (t, J = 7.3 Hz, 2H), 1.81 (s, 3H). |
| 22 | 525.2 | 1H NMR (400 MHz, Chloroform-d) δ 7.78 (dd, J = 6.5, 2.7 Hz, 1H), 7.59 (s, 1H), 7.40-7.33 (m, 2H), 7.13 (t, J = 8.7 Hz, 1H), 6.68 (s, 1H), 5.10-4.98 (m, 1H), 3.52-3.36 (m, 2H), 3.19 (dd, J = 11.8, 5.5 Hz, 2H), 2.95-2.81 (m, 5H), 2.64 (s, 4H), 1.38-1.35 (m, 4H), 1.25 (s, 4H). |
| 23 | 525.2 | 1H NMR (400 MHz, Chloroform-d) δ 7.78 (dd, J = 6.5, 2.6 Hz, 1H), 7.60 (s, 1H), 7.41-7.33 (m, 2H), 7.13 (t, J = 8.7 Hz, 1H), 6.68 (s, 1H), 5.10-4.97 (m, 1H), 3.50-3.35 (m, 2H), 3.26-3.12 (m, 2H), 2.95-2.79 (m, 5H), 2.63 (s, 4H), 1.36 (d, J = 6.4 Hz, 3H), 1.30-1.18 (m, 3H). |
| 24 | 474.3 | 1H NMR (400 MHz, Chloroform-d) δ 7.77 (dd, J = 6.5, 2.6 Hz, 1H), 7.36 (ddd, J = 8.9, 4.0, 2.6 Hz, 2H), 7.13 (t, J = 8.7 Hz, 1H), 7.06 (d, J = 9.7 Hz, 1H), 5.02 (p, J = 6.8 Hz, 1H), 4.68 (dp, J = 9.7, 7.1 Hz, 1H), 3.26 (dt, J = 18.1, 9.3 Hz, 1H), 3.13 (ddd, J = 17.9, 9.3, 2.0 Hz, 1H), 2.65 (s, 4H), 2.19-2.07 (m, 1H), 1.42 (d, J = 7.0 Hz, 3H), 1.37 (d, J = 6.4 Hz, 3H). |
| 25 | 474.3 | 1H NMR (400 MHz, Chloroform-d) δ 7.78 (dd, J = 6.5, 2.6 Hz, 1H), 7.39-7.32 (m, 2H), 7.16-7.06 (m, 2H), 5.03 (t, J = 6.9 Hz, 1H), 4.68 (dt, J = 9.7, 7.0 Hz, 1H), 3.29 (ddd, J = 17.9, 9.6, 2.6 Hz, 1H), 3.16 (dt, J = 17.8, 8.8 Hz, 1H), 2.63 (s, 4H), 2.17-2.07 (m, 1H), 1.42 (d, J = 7.0 Hz, 3H), 1.34 (d, J = 6.4 Hz, 3H). |
| 26 | 473.1 | 1H NMR (400 MHz, Methanol-d4) δ 7.71 (d, J = 1.0 Hz, 1H), 7.48 (dd, J = 10.0, 6.3 Hz, 2H), 4.20 (t, J = 7.3 Hz, 2H), 2.96 (t, J = 7.5 Hz, 2H), 2.51 (d, J = 1.0 Hz, 3H), 2.46 (quin, J = 7.4 Hz, 2H), 1.47-1.30 (m, 4H). |
| 27 | 615.1 | 1H NMR (400 MHz, Methanol-d4) δ 7.88 (dd, J = 6.7, 2.6 Hz, 1H), 7.56-7.48 (m, 1H), 7.23 (t, J = 9.0 Hz, 1H), 4.43 (d, J = 14.1 Hz, 2H), 4.22 (t, J = 7.3 Hz, 2H), 4.15 (d, J = 14.4 Hz, 2H), 3.44-3.32 (m, 2H), 3.09 (t, J = 7.5 Hz, 2H), 2.97-2.79 (m, 2H), 2.55 (s, 3H), 2.54-2.47 (m, 2H), 1.72 (s, 3H). |
| 28 | 601.1 | 1H NMR (400 MHz, Methanol-d4) δ 7.88 (dd, J = 6.7, 2.5 Hz, 1H), 7.51 (ddd, J = 9.0, 4.2, 2.5 Hz, 1H), 7.22 (t, J = 9.0 Hz, 1H), 4.27 (d, J = 14.4 Hz, 2H), 4.22 (t, J = 7.4 Hz, 2H), 4.10 (d, J = 14.6 Hz, 2H), 3.24 (s, 2H), 3.12 (t, J = 7.5 Hz, 2H), 3.07 (s, 2H), 2.96 (t, J = 12.1 Hz, 4H), 2.54 (s, 3H), 2.53-2.47 (m, 2H), 1.69 (s, 3H). |
| 29 | 521.1 | 1H NMR (400 MHz, Acetone-d6) δ 9.03 (s, 1H), 8.68 (s, 1H), 8.05 (dd, J = 6.8, 2.6 Hz, 1H), 7.84 (s, 1H), 7.74-7.56 (m, 1H), 7.29 (t, J = 9.0 Hz, 1H), 4.25 (t, J = 7.3 Hz, 2H), 3.48-3.33 (m, 4H), 3.00 (t, J = 7.5 Hz, 2H), 2.53 (s, 3H), 2.46 (p, J = 7.5 Hz, 2H). |
| 30 | 514.2 | 1H NMR (400 MHz, Acetonitrile-d3) δ 8.39 (s, 1H), 8.09 (dd, J = 5.7, 2.7 Hz, 1H), 8.05 (s, 1H), 7.90 (ddd, J = 9.2, 4.7, 2.8 Hz, 1H), 7.33 (t, J = 9.0 Hz, 1H), 6.77 (s, 1H), 4.29 (ddt, J = 5.9, 3.8, 1.9 Hz, 1H), 3.42-3.19 (m, 3H), 3.11 (dd, J = 18.7, 1.6 Hz, 1H), 2.97-2.79 (m, 2H), 2.69 (d, J = 4.8 Hz, 3H), 2.51 (s, 3H), 2.16-2.03 (m, 1H), 1.07 (dt, J = 8.6, 5.8 Hz, 1H), 0.23 (ddd, J = 7.3, 5.2, 2.1 Hz, 1H). |
| 31 | 505.1 | 1H NMR (400 MHz, acetone-d6) δ 9.03 (s, 1H), 8.65 (s, 1H), 7.90 (ddd, J = 13.2, 7.4, 2.6 Hz, 1H), 7.84 (s, 1H), 7.51-7.41 (m, 1H), 7.29 (dt, J = 10.6, 9.0 Hz, 1H), 4.25 (t, J = 7.3 Hz, 2H), 3.50-3.30 (m, 4H), 3.01 (t, J = 7.5 Hz, 2H), 2.52 (s, 3H), 2.46 (p, J = 7.5 Hz, 2H) |
| 32 | 487.1 | 1H NMR (400 MHz, acetone-d6) δ 8.90 (s, 1H), 8.65 (s, 1H), 7.84 (s, 1H), 7.80-7.72 (m, 2H), 7.11 (t, J = 8.8 Hz, 2H), 4.24 (t, J = 7.2 Hz, 2H), 3.46-3.34 (m, 4H), 3.00 (t, J = 7.5 Hz, 2H), 2.53 (s, 3H), 2.46 (p, J = 7.4 Hz, 2H) |
| 33 | 523.05 | 1H NMR (400 MHz, DMSO-d6) δ 9.89 (s, 1H), 9.45 (s, 1H), 7.91 (dd, J = 6.9, 2.6 Hz, 1H), 7.75 (d, J = 4.9 Hz, 1H), 7.56 (ddd, J = 9.0, 4.3, 2.6 Hz, 1H), 7.38 (t, J = 9.1 Hz, 1H), 4.28 (dd, J = 12.7, 6.0 Hz, 1H), 4.15 (d, J = 12.8 Hz, 1H), 2.95 (td, J = 14.6, 7.8 Hz, 3H), 2.59 (d, J = 4.5 Hz, 5H), 2.40 (s, 3H), 2.33 (d, J = 6.6 Hz, 1H), 1.21 (s, 2H), 0.43 (q, J = 4.3 Hz, 1H). |
| 34 | 523.08 | 1H NMR (400 MHz, DMSO-d6) δ 9.89 (s, 1H), 9.46 (s, 1H), 7.91 (dd, J = 6.8, 2.6 Hz, 1H), 7.75 (d, J = 4.9 Hz, 1H), 7.56 (dt, J = 7.0, 4.3 Hz, 1H), 7.38 (t, J = 9.1 Hz, 1H), 4.28 (dd, J = 12.7, 6.0 Hz, 2H), 4.15 (d, J = 12.8 Hz, 1H), 3.26 (s, 2H), 2.59 (d, J = 4.5 Hz, 5H), 2.40 (s, 3H), 1.21 (d, J = 5.5 Hz, 3H), 0.43 (q, J = 4.4 Hz, 1H). |
| 35 | 502.00 | 1H NMR (400 MHz, DMSO-d6) δ 10.10 (s, 1H), 9.42 (s, 1H), 8.14 (dd, J = 5.8, 2.7 Hz, 1H), 7.94 (ddd, J = 9.2, 5.0, 2.8 Hz, 1H), 7.78 (d, J = 4.9 Hz, 1H), 7.52 (t, J = 9.1 Hz, 1H), 4.14 (t, J = 7.2 Hz, 2H), 3.18 (s, 2H), 2.99-2.85 (m, 4H), 2.59 (d, J = 4.6 Hz, 3H), 2.45 (s, 3H), 2.37 (t, J = 7.4 Hz, 2H). |
| 36 | 512.90 | 1H NMR (400 MHz, DMSO-d6) δ 10.11 (s, 1H), 9.42 (s, 1H), 7.78 (d, J = 4.9 Hz, 1H), 7.58 (dd, J = 10.4, 6.5 Hz, 2H), 4.13 (t, J = 7.3 Hz, 2H), 3.20 (t, J = 12.9 Hz, 2H), 2.93 (t, J = 7.7 Hz, 4H), 2.59 (d, J = 4.5 Hz, 3H), 2.43 (s, 3H), 2.37 (t, J = 7.3 Hz, 2H). |
| 37 | 512.10 | 1H NMR (400 MHz, Acetone-d6) δ 9.17 (s, 1H), 8.67 (s, 1H), 8.23 (dd, J = 5.7, 2.7 Hz, 1H), 8.04 (ddd, J = 9.1, 4.7, 2.8 Hz, 1H), 7.84 (s, 1H), 7.42 |

| Compound # | ES/MS m/z | ¹H-NMR |
|---|---|---|
| | | (t, J = 9.0 Hz, 1H), 4.26 (t, J = 7.3 Hz, 2H), 3.52-3.28 (m, 4H), 3.01 (t, J = 7.5 Hz, 2H), 2.54 (s, 3H), 2.50-2.42 (m, 2H). |
| 38 | 525.09 | 1H NMR (400 MHz, DMSO-d6) δ 10.24 (s, 1H), 9.42 (s, 1H), 7.80 (q, J = 4.6 Hz, 1H), 7.66-7.52 (m, 2H), 4.24-4.17 (m, 1H), 3.23 (d, J = 6.5 Hz, 1H), 3.19 (d, J = 6.6 Hz, 1H), 3.17-3.09 (m, 1H), 3.05 (s, 1H), 3.01 (s, 1H), 2.91-2.78 (m, 1H), 2.60 (d, J = 4.5 Hz, 3H), 2.40 (s, 3H), 2.15-2.05 (m, 1H), 1.05 (dt, J = 8.5, 5.7 Hz, 1H), 0.12 (td, J = 5.3, 2.0 Hz, 1H). |
| 39 | 533.02 | 1H NMR (400 MHz, Acetonitrile-d3) δ 12.77 (s, 1H), 8.25 (s, 1H), 8.04 (s, 1H), 7.89 (dd, J = 6.8, 2.6 Hz, 1H), 7.72 (s, 1H), 7.53 (ddd, J = 8.9, 4.1, 2.6 Hz, 1H), 7.23 (t, J = 9.1 Hz, 1H), 4.28 (s, 1H), 3.32 (m, 4H), 3.23 (dd, J = 18.7, 6.8 Hz, 1H), 3.00 (d, J = 18.7 Hz, 1H), 2.48 (s, 3H), 1.06 (dt, J = 8.5, 5.8 Hz, 1H), 0.28-0.20 (m, 1H). |
| 40 | 535.07 | 1H NMR (400 MHz, Acetonitrile-d3) δ 12.86 (s, 1H), 8.33 (s, 1H), 8.05 (s, 1H), 7.73 (s, 1H), 7.48 (dd, J = 10.2, 6.4 Hz, 2H), 4.26 (td, J = 6.0, 3.0 Hz, 1H), 3.32 (m, 4H), 3.23 (dd, J = 18.7, 6.8 Hz, 1H), 3.06-2.95 (d, J = 18.7 Hz, 1H), 2.47 (s, 3H), 2.06 (p, J = 6.1 Hz, 1H), 1.06 (dt, J = 8.6, 5.8 Hz, 1H), 0.24 (td, J = 5.4, 2.1 Hz, 1H) |
| 41 | 524.13 | 1H NMR (400 MHz, Acetonitrile-d3) δ 8.41-8.31 (m, 1H), 8.07 (dd, J = 5.7, 2.7 Hz, 1H), 8.05 (s, 1H), 7.88 (ddd, J = 9.2, 4.8, 2.8 Hz, 1H), 7.73 (s, 1H), 7.32 (t, J = 9.0 Hz, 1H), 4.28 (tt, J = 5.9, 1.9 Hz, 1H), 3.43-3.27 (m, 4H), 3.23 (d, J = 18.7, 6.8 Hz, 1H), 3.00 (d, J = 18.7 Hz, 1H), 2.49 (s, 3H), 2.11-2.01 (m, 1H), 1.06 (d, J = 8.6, 5.8 Hz, 1H), 0.29-0.18 (m, 1H); |
| 42 | 517.11 | 1H NMR (400 MHz, Acetonitrile-d3) δ 8.27 (s, 1H), 8.03 (s, 1H), 7.77 (ddd, J = 12.9, 7.4, 2.5 Hz, 1H), 7.73 (s, 1H), 7.38-7.29 (m, 1H), 7.25 (dt, J = 10.5, 8.9 Hz, 1H), 4.27 (td, J = 6.1, 3.1 Hz, 1H), 3.42-3.27 (m, 4H), 3.23 (dd, J = 18.6, 6.8 Hz, 1H), 3.00 (dd, J = 18.8, 1.6 Hz, 1H), 2.48 (s, 3H), 2.14-2.00 (m, 1H), 1.06 (dt, J = 8.6, 5.8 Hz, 1H), 0.28-0.20 (m, 1H) |
| 43 | 455.20 | 1H NMR (400 MHz, Acetone-d6) δ 9.02 (s, 1H), 8.45 (s, 1H), 7.95-7.86 (m, 1H), 7.65 (s, 1H), 7.48-7.42 (m, 1H), 7.35-7.25 (m, 1H), 4.25 (t, J = 7.3 Hz, 2H), 3.07 (t, J = 7.5 Hz, 2H), 2.54 (s, 3H), 2.46 (p, J = 7.5 Hz, 2H), 1.44-1.29 (m, 4H). |
| 44 | 495.10 | 1H NMR (400 MHz, DMSO-d6) δ 10.00 (s, 1H), 9.42 (s, 1H), 7.86-7.71 (m, 2H), 7.39 (qd, J = 4.8, 2.5 Hz, 1H), 4.13 (t, J = 7.3 Hz, 2H), 3.28-3.12 (m, 2H), 2.93 (t, J = 7.5 Hz, 3H), 2.59 (d, J = 4.5 Hz, 3H), 2.43 (s, 3H), 2.37 (t, J = 7.3 Hz, 2H). |
| 45 | 489.20 | 1H NMR (400 MHz, DMSO-d6) δ 10.02 (s, 1H), 9.45 (s, 1H), 7.96 (dd, J = 6.8, 2.6 Hz, 1H), 7.60 (m, 2H), 7.41 (t, J = 9.1 Hz, 1H), 5.84-5.60 (m, 1H), 4.46 (m, 1H), 4.38 (m, 1H), 3.34 (ddd, J = 37.1, 18.8, 5.0 Hz, 1H), 3.12 (dd, J = 26.7, 18.9 Hz, 1H), 2.46 (s, 3H), 1.34-1.19 (m, 4H). |
| 46 | 489.20 | 1H NMR (400 MHz, DMSO-d6) δ 10.02 (s, 1H), 9.45 (s, 1H), 7.96 (dd, J = 6.9, 2.6 Hz, 1H), 7.60 (m, 2H), 7.41 (t, J = 9.1 Hz, 1H), 5.72 (m, 1H), 4.48-4.36 (m, 2H), 3.34 (ddd, J = 37.1, 18.8, 5.0 Hz, 1H), 3.12 (dd, J = 26.7, 18.8 Hz, 1H), 2.46 (s, 3H), 1.38-1.18 (m, 4H). |
| 47 | 477.20 | 1H NMR (400 MHz, DMSO-d6) δ 9.84 (s, 1H), 9.41 (s, 1H), 7.77 (d, J = 4.9 Hz, 1H), 7.71-7.58 (m, 2H), 7.16 (t, J = 8.9 Hz, 2H), 4.13 (t, J = 7.2 Hz, 2H), 3.18 (t, J = 13.8 Hz, 2H), 2.92 (t, J = 7.5 Hz, 4H), 2.59 (d, J = 4.6 Hz, 3H), 2.44 (s, 3H), 2.37 (t, J = 7.3 Hz, 2H). |
| 48 | 505.20 | 1H NMR (400 MHz, DMSO-d6) δ 9.91 (s, 1H), 9.73 (s, 1H), 7.82 (s, 1H), 7.72-7.62 (m, 2H), 7.18 (t, J = 8.9 Hz, 2H), 5.83-5.56 (m, 1H), 4.53-4.32 (m, 2H), 3.38-3.14 (m, 1H), 2.98 (dd, J = 26.7, 18.8 Hz, 1H), 2.46 (s, 3H). |
| 49 | 513.10 | 1H NMR (400 MHz, DMSO-d6) δ 10.06 (s, 1H), 9.48 (s, 1H), 7.93 (q, J = 4.5 Hz, 1H), 7.88-7.78 (m, 1H), 7.49-7.36 (m, 2H), 5.86-5.60 (m, 1H), 4.53-4.41 (m, 1H), 4.41-4.34 (m, 1H), 3.40 (td, J = 18.8, 5.0 Hz, 1H), 3.33-3.25 (m, 1H), 3.23 (m, 1H), 3.14 (m, 1H), 3.11-2.94 (m, 1H), 2.95-2.78 (m, 1H), 2.61 (d, J = 4.5 Hz, 3H), 2.48 (s, 3H). |
| 50 | 486.0 | 1H NMR (400 MHz, Acetone-d6) δ 9.02 (s, 1H), 8.54 (s, 1H), 8.09-7.95 (m, 1H), 7.66 (ddd, J = 9.0, 4.2, 2.6 Hz, 1H), 7.29 (t, J = 9.0 Hz, 1H), 4.31 (s, 3H), 4.26 (d, J = 6.7 Hz, 2H), 3.13 (t, J = 7.6 Hz, 2H), 2.56 (s, 3H), 2.54-2.41 (m, 2H), 1.57-1.50 (m, 2H), 1.49-1.41 (m, 2H). |
| 51 | 473.1 | 1H NMR (400 MHz, Methanol-d4) δ 7.87 (dd, J = 6.7, 2.6 Hz, 1H), 7.51 (ddd, J = 8.9, 4.1, 2.6 Hz, 1H), 7.21 (t, J = 9.0 Hz, 1H), 4.20 (t, J = 7.3 Hz, 2H), 3.08 (t, J = 7.3 Hz, 2H), 2.53 (s, 3H), 2.52-2.41 (m, 5H), 1.63-1.39 (m, 4H). |
| 52 | 483.1 | 1H NMR (400 MHz, Chloroform-d) δ 7.81 (dd, J = 6.5, 2.6 Hz, 1H), 7.69 (s, 1H), 7.51 (s, 1H), 7.43 (s, 1H), 7.38 (ddd, J = 8.9, 4.0, 2.8 Hz, 1H), 7.12 (t, J = 8.7 Hz, 1H), 5.56 (s, 2H), 4.53-4.41 (m, 1H), 3.67-3.57 (m, 2H), 3.51 (dd, J = 19.0, 6.9 Hz, 1H), 3.31-3.16 (m, 1H), 2.61 (s, 3H), 2.06 (p, J = 6.0 Hz, 1H), 1.54-1.45 (m, 2H), 1.38-1.30 (m, 2H), 1.25 (s, 1H), 1.10 (t, J = 8.6, 6.0 Hz, 1H), 0.96-0.86 (m, 2H), 0.35-0.26 (m, 1H), −0.03 (s, 9H).; 1H NMR (400 MHz, Acetonitrile-d3) δ 12.58 (s, 1H), 8.26 (s, 1H), 7.94 (s, 1H), 7.89 (dd, J = 6.8, 2.6 Hz, 1H), 7.53 (m, 2H), 7.23 (t, J = 9.1 Hz, 1H), 4.29 (dd, J = 7.0, 5.0 Hz, 1H), 3.30 (dd, J = 18.7, 6.8 Hz, 1H), 3.08 (d, J = 18.9 Hz, 1H), 2.49 (s, 3H), 2.07 (p, J = 6.9, 6.3 Hz, 1H), 1.48-1.17 (m, 5H), 1.06 (dt, J = 8.5, 5.8 Hz, 1H), 0.25 (td, J = 5.5, 2.0 Hz, 1H). |
| 53 | 523.1 | 1H NMR (400 MHz, Acetone-d6) δ 9.13 (s, 1H), 8.66 (s, 1H), 7.83 (s, 1H), 7.63 (dd, J = 10.2, 6.5 Hz, 2H), 4.30-4.22 (m, 2H), 3.49-3.34 (m, 4H), 3.01 (t, J = 7.5 Hz, 2H), 2.52 (s, 3H), 2.47 (q, J = 7.4 Hz, 2H). |
| 54 | 499.1 | 1H NMR (400 MHz, DMSO-d6) δ 10.11 (s, 1H), 9.84 (s, 1H), 9.40 (s, 1H), 7.96 (dd, J = 6.8, 2.7 Hz, 1H), 7.60 (ddd, J = 9.1, 4.3, 2.6 Hz, 1H), 7.39 (t, J = 9.1 Hz, 1H), 4.23 (t, J = 6.0 Hz, 1H), 3.20 (dd, J = 18.5, 6.8 Hz, 1H), 3.05-2.95 (m, 1H), 2.39 (s, 3H), 2.18-2.06 (m, 1H), 1.64 (t, J = 3.9 Hz, 2H), 1.44 (d, J = 2.9 Hz, 2H), 1.07 (dt, J = 8.6, 5.7 Hz, 1H). |
| 55 | 520.1 | 1H NMR (400 MHz, Methanol-d4) δ 8.49 (d, J = 5.7 Hz, 1H), 8.02 (s, 1H), 7.85 (s, 1H), 7.79 (d, J = 5.6 Hz, 1H), 6.69 (t, J = 55.2 Hz, 1H), 4.21 (t, J = 7.2 Hz, 2H), 3.34 (s, 0H), 3.30 (s, 0H), 2.88-2.79 (m, 2H), 2.65-2.38 (m, 4H), 2.26 (t, J = 7.4 Hz, 2H), 1.63-1.54 (m, 2H). |
| 56 | 482.2 | 1H NMR (400 MHz, Acetonitrile-d3) δ 8.61 (s, 1H), 8.54 (d, J = 5.6 Hz, 1H), 7.98 (d, J = 2.3 Hz, 2H), 7.79-7.69 (m, 1H), 7.55 (s, 1H), 6.70 (t, J = 55.4 Hz, 1H), 4.30 (t, J = 6.1 Hz, 1H), 3.31 (dd, J = 18.7, 6.8 Hz, 1H), 3.09 (d, J = 18.7 Hz, 1H), 2.51 (s, 3H), 2.08 (p, J = 6.1 Hz, 1H), 1.35 (d, J = 3.9 Hz, 2H), 1.29 (dd, J = 11.9, 4.9 Hz, 3H), 1.07 (dt, J = 8.5, 5.8 Hz, 1H), 0.33-0.18 (m, 1H). |
| 57 | 502 | 1H NMR (400 MHz, DMSO-d6) δ 10.25 (s, 1H), 9.84 (s, 1H), 9.39 (s, 1H), 7.60 (dd, J = 10.4, 6.4 Hz, 2H), 4.22 (t, J = 6.0 Hz, 1H), 3.21 (dd, J = 18.6, 6.8 Hz, 1H), 3.00 (d, J = 18.6 Hz, 1H), 2.38 (s, 3H), 2.19-2.07 (m, 1H), 1.64 (d, J = 2.9 Hz, 2H), 1.44 (d, J = 2.9 Hz, 2H), 1.07 (dt, J = 8.5, 5.8 Hz, 1H), 0.22-0.13 (m, 1H). |
| 58 | 491.1 | 1H NMR (400 MHz, DMSO-d6) δ 10.25 (s, 1H), 9.84 (s, 1H), 9.40 (s, 1H), 8.17 (dd, J = 5.8, 2.7 Hz, 1H), 7.96 (ddd, J = 9.2, 4.8, 2.7 Hz, 1H), 7.52 (t, J = 9.1 Hz, 1H), 4.24 (t, J = 6.1 Hz, 1H), |

-continued

| Compound # | ES/MS m/z | ¹H-NMR |
|---|---|---|
| | | 3.21 (dd, J = 18.5, 6.7 Hz, 1H), 3.00 (d, J = 18.6 Hz, 1H), 2.40 (s, 3H), 2.13 (q, J = 7.2, 6.7 Hz, 1H), 1.64 (d, J = 2.8 Hz, 2H), 1.45 (t, J = 4.0 Hz, 2H), 1.07 (dt, J = 8.6, 5.8 Hz, 1H), 0.23-0.12 (m, 1H). |
| 59 | 538.1 | 1H NMR (400 MHz, Acetone-d6) δ 8.93 (s, 1H), 8.71 (s, 1H), 8.53 (t, J = 5.7 Hz, 1H), 8.42 (d, J = 5.4 Hz, 1H), 7.85 (s, 1H), 6.94 (t, J = 53.5 Hz, 1H), 4.33 (t, J = 7.3 Hz, 2H), 3.54-3.27 (m, 4H), 3.02 (q, J = 7.0 Hz, 2H), 2.65 (s, 3H), 2.49 (p, J = 7.5 Hz, 2H). |
| 60 | 478.1 | 1H NMR (400 MHz, Acetone-d6) δ 9.00 (s, 1H), 8.50 (s, 1H), 8.05 (dd, J = 6.8, 2.6 Hz, 1H), 7.66 (ddd, J = 8.9, 4.2, 2.6 Hz, 1H), 7.29 (t, J = 9.0 Hz, 1H), 4.31-4.22 (m, 2H), 3.34-3.10 (m, 6H), 3.04 (s, 1H), 2.54 (s, 3H), 2.49 (p, J = 7.5 Hz, 2H). |
| 61 | 484 | 1H NMR (400 MHz, DMSO-d6) δ 10.14 (s, 1H), 9.84 (s, 1H), 9.40 (s, 1H), 7.88-7.76 (m, 1H), 7.44-7.37 (m, 2H), 4.23 (t, J = 5.8 Hz, 1H), 3.20 (dd, J = 18.6, 6.7 Hz, 1H), 3.00 (d, J = 18.6 Hz, 1H), 2.39 (s, 3H), 2.11 (d, J = 7.5 Hz, 1H), 1.64 (d, J = 2.9 Hz, 2H), 1.45 (t, J = 4.0 Hz, 2H), 1.12-1.01 (m, 1H), 0.17 (d, J = 6.9 Hz, 1H). |
| 62 | 499.2 | 1H NMR (400 MHz, Chloroform-d) δ 8.97 (s, 1H), 8.57 (d, J = 5.5 Hz, 1H), 7.93 (s, 1H), 7.81 (d, J = 2.0 Hz, 1H), 7.77-7.67 (m, 2H), 6.62 (t, J = 55.4 Hz, 1H), 4.50 (td, J = 5.8, 2.8 Hz, 1H), 3.54 (dd, J = 19.1, 6.9 Hz, 1H), 3.38-3.19 (m, 1H), 2.65 (s, 3H), 2.16-2.06 (m, 1H), 1.95-1.86 (m, 2H), 1.57-1.51 (m, 2H), 1.14 (dt, J = 8.7, 6.0 Hz, 1H), 0.34 (td, J = 6.6, 5.8, 2.0 Hz, 1H). |
| 63 | 500.2 | 1H NMR (400 MHz, Acetonitrile-d3) δ 8.51 (t, J = 5.7 Hz, 1H), 8.40 (d, J = 5.3 Hz, 2H), 7.96 (s, 1H), 7.53 (s, 1H), 6.90 (t, J = 53.5 Hz, 1H), 4.36 (ddt, J = 5.8, 3.7, 1.9 Hz, 1H), 3.32 (dd, J = 18.8, 6.8 Hz, 1H), 3.11 (d, J = 18.8 Hz, 1H), 2.58 (s, 3H), 2.12-2.05 (m, 1H), 1.42-1.19 (m, 4H), 1.11 (dt, J = 8.6, 5.8 Hz, 1H), 0.32 (td, J = 5.6, 2.1 Hz, 1H). |
| 64 | 486.0 | 1H NMR (400 MHz, Methanol-d4) δ 7.87 (dd, J = 6.8, 2.5 Hz, 1H), 7.57-7.44 (m, 1H), 7.21 (t, J = 9.0 Hz, 1H), 4.21 (t, J = 7.2 Hz, 2H), 3.11 (t, J = 7.5 Hz, 2H), 2.51 (m, 8H), 1.64 (t, J = 4.0 Hz, 2H), 1.48 (t, J = 4.0 Hz, 2H). |
| 65 | 488.0 | 1H NMR (400 MHz, Methanol-d4) δ 7.65-7.32 (m, 2H), 4.21 (t, J = 7.3 Hz, 2H), 3.11 (t, J = 7.4 Hz, 2H), 2.51 (d, J = 13.1 Hz, 8H), 1.73-1.58 (m, 2H), 1.55-1.38 (m, 2H). |
| 66 | 480.0 | 1H NMR (400 MHz, Methanol-d4) δ 7.86 (dd, J = 6.7, 2.6 Hz, 1H), 7.50 (ddd, J = 9.0, 4.2, 2.6 Hz, 1H), 7.37 (dd, J = 8.3, 1.4 Hz, 2H), 7.30 (dd, J = 8.5, 6.8 Hz, 2H), 7.25-7.14 (m, 2H), 4.16 (t, J = 7.2 Hz, 2H), 2.78 (t, J = 7.5 Hz, 2H), 2.51 (s, 3H), 2.45-2.31 (m, 2H), 1.29 (s, 3H). |
| 67 | 481.9 | 1H NMR (400 MHz, Methanol-d4) δ 7.46 (dd, J = 10.0, 6.4 Hz, 2H), 7.41-7.25 (m, 4H), 7.21 (d, J = 7.1 Hz, 1H), 4.16 (t, J = 7.2 Hz, 2H), 2.78 (t, J = 7.6 Hz, 2H), 2.50 (s, 3H), 2.45-2.32 (m, 1H), 1.29 (s, 4H). |
| 68 | 517.2 | (NOTE: suspected mixture of rotamers) 1H NMR (400 MHz, DMSO-d6) δ 11.23 (s, 0H), 10.18 (s, 1H), 9.86 (s, 1H), 9.39 (d, J = 8.2 Hz, 1H), 8.45 (dd, J = 17.8, 5.3 Hz, 1H), 8.24 (t, J = 5.7 Hz, 1H), 7.14 (td, J = 53.1, 4.2 Hz, 1H), 4.26 (d, J = 34.2 Hz, 1H), 3.19 (td, J = 20.5, 19.7, 6.7 Hz, 1H), 3.01 (d, J = 18.3 Hz, 1H), 2.44 (d, J = 20.7 Hz, 3H), 2.21-2.07 (m, 1H), 1.65 (t, J = 4.4 Hz, 2H), 1.47 (d, J = 16.1, 5.3 Hz, 2H), 1.16-1.03 (m, 1H), 0.22 (d, J = 19.8 Hz, 1H). |
| 69 | 436.9 | 1H NMR (400 MHz, DMSO-d6) δ 9.98 (s, 1H), 9.36 (s, 1H), 7.65-7.52 (m, 2H), 7.44-7.30 (m, 2H), 6.89 (td, J = 8.5, 8.1, 2.2 Hz, 1H), 4.12 (t, J = 7.3 Hz, 2H), 2.85 (t, J = 7.3 Hz, 2H), 2.41 (s, 3H), 2.40-2.34 (m, 2H), 1.31-1.23 (m, 2H), 1.20 (t, J = 3.2 Hz, 2H). |
| 70 | 437.0 | 1H NMR (400 MHz, DMSO-d6) δ 9.82 (s, 1H), 9.35 (s, 1H), 7.72-7.59 (m, 2H), 7.55 (d, J = 8.1 Hz, 1H), 7.15 (t, J = 8.9 Hz, 2H), 4.11 (t, J = 7.3 Hz, 2H), 2.85 (t, J = 7.7 Hz, 2H), 2.42 (d, J = 2.2 Hz, 3H), 2.36 (q, J = 7.4 Hz, 1H), 1.26 (d, J = 8.5 Hz, 2H), 1.23-1.15 (m, 1H). |
| 71 | 494.2 | 1H NMR (400 MHz, DMSO-d6) δ 9.38 (s, 1H), 7.96 (dd, J = 6.8, 2.6 Hz, 1H), 7.60 (ddd, J = 9.0, 4.2, 2.6 Hz, 1H), 7.39 (t, J = 9.1 Hz, 1H), 4.52-4.42 (m, 2H), 4.32 (d, J = 3.5 Hz, 1H), 4.29 (d, J = 3.4 Hz, 1H), 4.28-4.19 (m, 1H), 3.27-3.21 (m, 1H), 3.04 (d, J = 18.5 Hz, 1H), 2.39 (s, 3H), 2.15 (q, J = 6.6 Hz, 1H), 1.67 (s, 3H), 1.11-1.03 (m, 1H), 0.17 (t, J = 5.0 Hz, 1H). |
| 72 | 485 | 1H NMR (400 MHz, DMSO-d6) δ 9.39 (s, 2H), 8.17 (dd, J = 5.8, 2.7 Hz, 2H), 7.96 (ddd, J = 9.3, 4.9, 2.7 Hz, 2H), 7.52 (t, J = 9.1 Hz, 2H), 4.52-4.42 (m, 4H), 4.35-4.21 (m, 6H), 3.55 (s, 7H), 3.30-3.20 (m, 2H), 3.05 (d, J = 18.4 Hz, 2H), 2.40 (s, 6H), 2.19-2.10 (m, 2H), 1.67 (s, 6H), 1.08 (dt, J = 8.7, 5.9 Hz, 2H), 0.18 (dd, J = 10.8, 2.0 Hz, 1H), 0.17 (s, 1H). |
| 73 | 496.1 | 1H NMR (400 MHz, DMSO-d6) δ 9.39 (s, 2H), 7.60 (dd, J = 10.3, 6.4 Hz, 4H), 4.52-4.42 (m, 4H), 4.35-4.19 (m, 7H), 3.55 (s, 7H), 3.29-3.20 (m, 2H), 3.05 (d, J = 18.6 Hz, 2H), 2.39 (s, 7H), 2.15 (s, 2H), 2.20-2.09 (m, 1H), 1.66 (s, 6H), 1.08 (dt, J = 8.5, 5.8 Hz, 2H), 0.17 (t, J = 5.7 Hz, 2H). |
| 74 | 452.99 | 1H NMR (400 MHz, DMSO-d6) δ 9.94 (s, 1H), 9.36 (s, 1H), 7.82 (t, J = 2.0 Hz, 1H), 7.55 (d, J = 7.7 Hz, 2H), 7.34 (t, J = 8.1 Hz, 1H), 7.12 (dt, J = 8.1, 1.5 Hz, 1H), 4.12 (t, J = 7.3 Hz, 2H), 2.91-2.80 (m, 2H), 2.42 (s, 3H), 2.40-2.34 (m, 2H), 1.31-1.22 (m, 2H), 1.22-1.14 (m, 2H). |
| 75 | 444.0 | 1H NMR (400 MHz, DMSO-d6) δ 10.08 (s, 1H), 9.37 (s, 1H), 8.10 (q, J = 1.3 Hz, 1H), 7.90 (dt, J = 6.6, 2.5 Hz, 1H), 7.61-7.49 (m, 3H), 4.13 (t, J = 7.2 Hz, 2H), 2.86 (t, J = 7.5 Hz, 2H), 2.43 (s, 3H), 2.38 (t, J = 7.4 Hz, 2H), 1.25 (t, J = 3.2 Hz, 2H), 1.20 (t, J = 3.5 Hz, 2H). |
| 76 | 454.99 | 1H NMR (400 MHz, DMSO-d6) δ 10.13 (s, 1H), 9.37 (s, 1H), 7.56 (s, 1H), 7.38 (dd, J = 9.6, 2.3 Hz, 2H), 6.97-6.86 (m, 1H), 4.12 (t, J = 7.3 Hz, 2H), 2.86 (t, J = 7.4 Hz, 2H), 2.44-2.32 (m, 5H), 1.25 (t, J = 3.1 Hz, 2H), 1.22-1.12 (m, 2H). |
| 77 | 454.99 | 1H NMR (400 MHz, DMSO-d6) δ 10.13 (s, 1H), 9.37 (s, 1H), 7.56 (s, 1H), 7.38 (dd, J = 9.6, 2.3 Hz, 2H), 6.97-6.86 (m, 1H), 4.12 (t, J = 7.3 Hz, 2H), 2.86 (t, J = 7.4 Hz, 2H), 2.44-2.32 (m, 5H), 1.25 (t, J = 3.1 Hz, 2H), 1.22-1.12 (m, 2H). |
| 78 | 532.23 | 1H NMR (400 MHz, Acetonitrile-d3) δ 8.79 (s, 1H), 8.57 (d, J = 5.9 Hz, 1H), 8.09 (d, J = 2.1 Hz, 1H), 8.07 (s, 1H), 7.88 (dd, J = 6.0, 2.1 Hz, 1H), 7.73 (s, 1H), 6.82 (t, J = 54.7 Hz, 1H), 4.35-4.25 (m, 1H), 3.40-3.19 (m, 5H), 3.07-2.96 (m, 1H), 2.51 (s, 3H), 2.08 (dt, J = 13.1, 6.2 Hz, 1H), 1.08 (dt, J = 8.6, 5.9 Hz, 1H), 0.31-0.22 (m, 1H). |
| 79 | 474.14 | 1H NMR (400 MHz, Acetonitrile-d3) δ 8.36 (s, 1H), 8.11-8.04 (m, 1H), 7.93 (s, 1H), 7.92-7.84 (m, 1H), 7.55 (s, 1H), 7.32 (t, J = 9.0 Hz, 1H), 4.29 (m, 1H), 3.31 (dd, J = 18.4, 6.8 Hz, 1H), 3.09 (d, J = 18.5 Hz, 1H), 2.50 (s, 3H), 2.10 (m, 1H), 1.33 (d, J = 19.4 Hz, 4H), 1.06 (q, J = 6.5 Hz, 1H), 0.25 (s, 1H). |
| 80 | 550.17 | 1H NMR (400 MHz, Acetonitrile-d3) δ 8.52 (t, J = 5.7 Hz, 1H), 8.43 (s, 1H), 8.41 (d, J = 5.5 Hz, 1H), 8.09 (s, 1H), 7.75 (s, 1H), 6.92 (t, J = 53.4 Hz, 1H), 4.35 (tt, J = 6.0, 1.9 Hz, 1H), 3.43-3.28 (m, 3H), 3.24 (dd, J = 18.7, 6.8 Hz, 1H), 3.07-2.97 (m, 1H), 2.57 (s, 3H), 2.15-2.04 (m, |

| Compound # | ES/MS m/z | 1H-NMR |
|---|---|---|
| | | 1H), 1.10 (dt, J = 8.6, 5.8 Hz, 1H), 0.31 (td, J = 5.5, 2.1 Hz, 1H). |
| 81 | 467.11 | 1H NMR (400 MHz, Acetonitrile-d3) δ 8.27 (s, 1H), 7.92 (s, 1H), 7.77 (ddd, J = 13.1, 7.4, 2.5 Hz, 1H), 7.55 (s, 1H), 7.37-7.29 (m, 1H), 7.25 (dt, J = 10.5, 8.9 Hz, 1H), 3.31 (dd, J = 18.7, 6.8 Hz, 1H), 3.08 (d, J = 18.6 Hz, 1H), 2.49 (s, 3H), 2.08 (q, J = 7.7 Hz, 1H), 1.39-1.33 (m, 2H), 1.33-1.23 (m, 2H), 1.06 (dt, J = 8.6, 5.8 Hz, 1H), 0.25 (td, J = 5.5, 2.1 Hz, 1H). |
| 82 | 463.1 | 1H NMR (400 MHz, Methanol-d4) δ 7.87 (dd, J = 6.7, 2.6 Hz, 1H), 7.50 (ddd, J = 8.9, 4.2, 2.7 Hz, 1H), 7.21 (t, J = 9.0 Hz, 1H), 4.20 (t, J = 7.3 Hz, 2H), 3.06 (t, J = 7.5 Hz, 2H), 2.74 (s, 3H), 2.51 (m, 5H), 1.54 (s, 6H). |
| 83 | 465.0 | 1H NMR (400 MHz, Methanol-d4) δ 7.47 (dd, J = 10.0, 6.3 Hz, 2H), 4.20 (t, J = 7.3 Hz, 2H), 3.06 (t, J = 7.5 Hz, 2H), 2.74 (s, 3H), 2.50 (m, 5H), 1.54 (s, 6H). |
| 84 | 489.0 | 1H NMR (400 MHz, Methanol-d4) δ 7.83-7.71 (m, 1H), 7.69 (s, 1H), 7.14 (td, J = 9.1, 2.1 Hz, 1H), 4.22 (t, J = 7.3 Hz, 2H), 2.96 (t, J = 7.7 Hz, 2H), 2.58 (s, 3H), 2.54-2.37 (m, 2H), 1.51-1.24 (m, 4H). |
| 85 | 503.0 | 1H NMR (400 MHz, Methanol-d4) δ 7.75 (s, 1H), 7.70 (s, 1H), 7.58-7.48 (m, 1H), 7.41 (t, J = 8.2 Hz, 1H), 7.02 (d, J = 8.2 Hz, 1H), 4.20 (t, J = 7.2 Hz, 2H), 2.96 (t, J = 7.5 Hz, 2H), 2.53 (s, 3H), 2.48 (q, J = 7.2 Hz, 2H), 1.45-1.28 (m, 4H). |
| 86 | 471.0 | 1H NMR (400 MHz, Methanol-d4) δ 8.20-7.99 (m, 1H), 7.69 (s, 1H), 7.28-7.10 (m, 2H), 4.25 (t, J = 7.2 Hz, 2H), 2.96 (t, J = 7.6 Hz, 2H), 2.48 (q, J = 7.4 Hz, 2H), 1.49-1.27 (m, 4H). |
| 87 | 483.12 | 1H NMR (400 MHz, DMSO-d6) δ 11.05 (s, 1H), 10.13 (s, 1H), 9.79 (s, 1H), 7.88-7.75 (m, 2H), 7.45-7.34 (m, 2H), 4.89 (dt, J = 13.0, 6.8 Hz, 4H), 4.21 (t, J = 5.5 Hz, 1H), 3.11 (dd, J = 18.5, 6.7 Hz, 1H), 2.90 (d, J = 18.5 Hz, 1H), 2.38 (s, 3H), 2.13-2.03 (m, 1H), 1.05 (dt, J = 8.1, 5.5 Hz, 1H), 0.19-0.12 (m, 1H). |
| 88 | 487.12 | 1H NMR (400 MHz, DMSO-d6) δ 11.05 (a, 1H), 9.98 (s, 1H), 9.80 (s, 1H), 7.93 (dd, J = 6.9, 2.4 Hz, 1H), 7.78 (s, 1H), 7.61-7.54 (m, 1H), 7.38 (t, J = 9.2 Hz, 1H), 4.94-4.84 (m, 4H), 4.12 (t, J = 7.3 Hz, 2H), 2.82 (t, J = 7.5 Hz, 2H), 2.65 (dt, J = 3.6, 1.6 Hz, 1H), 2.42 (s, 3H), 2.41-2.33 (m, 2H), 2.31 (dt, J = 3.3, 1.5 Hz, 1H). |
| 89 | 537.1 | 1H NMR (400 MHz, Acetone-d6) δ 9.07 (s, 1H), 8.68 (s, 1H), 8.08 (dd, J = 6.3, 2.6 Hz, 1H), 7.95-7.87 (m, 1H), 7.84 (s, 1H), 7.27 (t, J = 9.5 Hz, 1H), 7.10 (t, J = 54.7 Hz, 1H), 4.25 (t, J = 7.3 Hz, 2H), 3.49-3.28 (m, 4H), 3.00 (t, J = 7.5 Hz, 2H), 2.54 (s, 3H), 2.46 (q, J = 7.4 Hz, 2H). |
| 90 | 473.1 | 1H NMR (400 MHz, Acetone-d6) δ 8.47 (s, 1H), 8.29-8.21 (m, 1H), 7.65 (s, 1H), 7.45-7.34 (m, 1H), 4.31 (t, J = 7.3 Hz, 2H), 3.08 (t, J = 7.6 Hz, 2H), 2.63 (s, 3H), 2.48 (t, J = 7.4 Hz, 2H), 1.37 (d, J = 13.0 Hz, 4H). |
| 91 | 489.2 | 1H NMR (400 MHz, Acetone-d6) δ 8.47 (s, 1H), 8.42-8.34 (m, 1H), 7.65 (s, 1H), 7.39 (dd, J = 10.6, 9.1 Hz, 1H), 4.30 (t, J = 7.3 Hz, 2H), 3.08 (t, J = 7.5 Hz, 2H), 2.63 (s, 3H), 2.49 (q, J = 7.4 Hz, 2H), 1.42-1.30 (m, 4H). |
| 92 | 430.1 | 1H NMR (400 MHz, Methanol-d4) 7.48 (dd, J = 10.0, 6.4 Hz, 2H), 4.21 (t, J = 7.5 Hz, 2H), 3.10 (t, J = 7.5 Hz, 2H), 2.58 (s, 1H), 2.50 (s, 3H), 2.50 (d, J = 7.5 Hz, 2H), 1.32-1.22 (m, 2H), 1.17-1.11 (m, 2H). |
| 93 | 455.1 | 1H NMR (400 MHz, Methanol-d4) δ 7.80 (td, J = 8.8, 5.9 Hz, 1H), 7.69 (s, 1H), 7.07 (ddd, J = 10.9, 8.8, 2.8 Hz, 1H), 7.01-6.92 (m, 1H), 4.22 (t, J = 7.3 Hz, 2H), 3.02-2.90 (m, 2H), 2.58 (s, 3H), 2.51-2.41 (m, 2H), 1.48-1.29 (m, 4H). |
| 94 | 428.1 | 1H NMR (400 MHz, Methanol-d4) δ 9.72 (s, 1H), 9.25 (s, 1H), 7.88 (dt, J = 6.7, 2.4 Hz, 1H), 7.51 (ddt, J = 8.9, 4.3, 2.2 Hz, 1H), 7.22 (t, J = 9.0 Hz, 1H), 4.22 (t, J = 7.5 Hz, 3H), 3.10 (t, J = 7.5 Hz, 2H), 2.59 (s, 1H), 2.53 (s, 3H), 4.53 (t, J = 7.5 Hz, 3H), 1.32-1.09 (m, 4H). |
| 95 | 489.2 | 1H NMR (400 MHz, DMSO-d6) δ 9.96 (s, 1H), 9.41 (s, 1H), 7.79 (q, J = 4.6 Hz, 1H), 7.74-7.64 (m, 2H), 7.22-7.11 (m, 2H), 4.22 (s, 1H), 3.30-3.00 (m, 4H), 3.02-2.90 (m, 1H), 2.60 (d, J = 4.6 Hz, 3H), 2.40 (s, 3H), 2.15-2.03 (m, 2H), 1.05 (dt, J = 8.5, 5.7 Hz, 1H), 0.14 (td, J = 5.4, 2.1 Hz, 1H). |
| 96 | 507 | 1H NMR (400 MHz, DMSO-d6) δ 10.12 (s, 1H), 9.41 (s, 1H), 7.88-7.76 (m, 2H), 7.45-7.33 (m, 2H), 4.22 (s, 1H), 3.25 (dd, J = 11.1, 3.8 Hz, 1H), 3.25-3.10 (m, 2H), 3.05 (s, 1H), 2.98 (d, J = 16.1 Hz, 1H), 2.95-2.79 (m, 1H), 2.60 (d, J = 4.6 Hz, 3H), 2.40 (s, 3H), 2.16-2.04 (m, 1H), 1.05 (dt, J = 8.4, 5.7 Hz, 1H), 0.13 (td, J = 5.3, 2.1 Hz, 1H). |
| 98 | 485.1 | 1H NMR (400 MHz, Methanol-d4) δ 7.87 (dd, J = 6.7, 2.7 Hz, 1H), 7.82 (s, 1H), 7.51 (ddd, J = 9.0, 4.1, 2.5 Hz, 1H), 7.22 (t, J = 8.9 Hz, 1H), 4.20 (t, J = 7.3 Hz, 2H), 4.07 (s, 3H), 3.03-2.92 (t, J = 7.3 Hz, 2H), 2.52 (s, 3H), 2.47 (quin, J = 7.4 Hz, 2H), 1.48-1.27 (m, 4H). |
| 99 | 449.2 | 1H NMR (400 MHz, DMSO-d6) δ 9.95 (s, 1H), 9.34 (s, 1H), 7.73-7.65 (m, 2H), 7.22-7.10 (m, 2H), 4.21 (s, 1H), 3.14 (dd, J = 18.5, 6.7 Hz, 2H), 2.93 (d, J = 17.5 Hz, 2H), 2.38 (s, 3H), 2.09 (p, J = 6.1 Hz, 1H), 1.30-1.16 (m, 5H), 1.06 (dt, J = 8.6, 5.8 Hz, 1H), 0.16 (td, J = 5.3, 2.0 Hz, 1H). |
| 100 | 500.00 | 1H NMR (400 MHz, DMSO-d6) δ 9.96 (s, 2H), 9.60 (s, 1H), 7.76-7.64 (m, 4H), 7.16 (t, J = 8.8 Hz, 4H), 4.21 (s, 2H), 3.25 (d, J = 13.6 Hz, 6H), 3.04 (dd, J = 18.5, 6.7 Hz, 2H), 2.89-2.78 (m, 2H), 2.37 (s, 6H), 2.08 (s, 3H), 1.21 (s, 1H), 1.15-1.00 (m, 2H), 0.15 (s, 2H). |
| 101 | 471.1 | 1H NMR (400 MHz, DMSO-d6) δ 10.10 (s, 1H), 9.38 (s, 1H), 7.61-7.58 (m, 1H), 7.57-7.51 (m, 2H), 7.11 (dt, J = 8.6, 2.2 Hz, 1H), 4.12 (t, J = 7.2 Hz, 2H), 2.86 (t, J = 7.5 Hz, 2H), 2.41 (s, 3H), 2.40-2.33 (m, 2H), 1.30-1.22 (m, 2H), 1.22-1.16 (m, 2H). |
| 102 | 487.0 | 1H NMR (400 MHz, DMSO-d6) δ 10.06 (s, 1H), 9.38 (s, 1H), 7.74 (d, J = 1.9 Hz, 2H), 7.56 (s, 1H), 7.29 (t, J = 1.9 Hz, 1H), 4.12 (t, J = 7.3 Hz, 2H), 2.86 (t, J = 7.5 Hz, 2H), 2.42 (s, 3H), 2.37 (q, J = 7.6 Hz, 2H), 1.32-1.22 (m, 2H), 1.22-1.13 (m, 2H). |
| 103 | 469.1 | 1H NMR (400 MHz, DMSO-d6) δ 9.98 (s, 1H), 9.37 (s, 1H), 7.95 (s, 1H), 7.75 (d, J = 8.2 Hz, 1H), 7.56 (s, 1H), 7.46 (t, J = 7.9 Hz, 1H), 7.25 (d, J = 7.6 Hz, 1H), 7.01 (t, J = 55.9 Hz, 1H), 4.13 (t, J = 7.2 Hz, 2H), 2.85 (t, J = 7.5 Hz, 2H), 2.43 (s, 3H), 2.38 (t, J = 7.3 Hz, 2H), 1.32-1.23 (m, 2H), 1.23-1.14 (m, 2H). |
| 104 | 452.1 | 1H NMR (400 MHz, Acetone-d6) δ 9.03 (s, 1H), 8.07 (d, J = 2.7 Hz, 1H), 7.67 (dd, J = 8.7, 3.7 Hz, 1H), 7.46 (s, 1H), 7.29 (t, J = 9.0 Hz, 1H), 4.32-4.22 (m, 2H), 3.82-3.65 (m, 4H), 3.16 (t, J = 7.6 Hz, 2H), 2.53 (s, 3H), 2.49 (q, J = 7.5 Hz, 2H), 1.36 (s, 3H). |
| 105 | 461.02 | 1H NMR (400 MHz, DMSO-d6) δ 9.91 (s, 1H), 8.95 (s, 1H), 7.90 (dd, J = 6.8, 2.6 Hz, 1H), 7.58 (q, J = 4.5 Hz, 1H), 7.53 (ddd, J = 9.0, 4.3, 2.6 Hz, 1H), 7.34 (t, J = 9.1 Hz, 1H), 4.08 (t, J = 7.2 Hz, 2H), 2.94 (t, J = 7.5 Hz, 2H), 2.53 (d, J = 4.6 Hz, 3H), 2.37 (s, 3H), 2.32 (p, J = 7.6 Hz, 2H), 1.23 (q, J = 4.4 Hz, 2H), 0.88 (q, J = 4.4 Hz, 2H). |
| 106 | 473.1 | 1H NMR (400 MHz, Acetone-d6) δ 9.01 (s, 1H), 8.25 (s, 1H), 8.09-8.02 (m, 1H), 7.66 (d, J = 8.8 Hz, 1H), 7.29 (t, J = 9.0 Hz, 1H), 6.76 (s, 1H), 6.26 (s, 1H), 4.26 (t, J = 7.3 Hz, 2H), 3.09 (t, J = 7.5 Hz, 2H), 2.53 (s, 3H), 2.52-2.44 (m, 2H), 2.34 (s, 6H). |

| Compound # | ES/MS m/z | 1H-NMR |
|---|---|---|
| 107 | 471.1 | 1H NMR (400 MHz, DMSO-d6) δ 9.67 (s, 1H), 9.39 (s, 1H), 7.67 (ddd, J = 8.4, 6.8, 1.6 Hz, 1H), 7.56 (s, 1H), 7.39 (ddd, J = 8.3, 6.7, 1.6 Hz, 1H), 7.21 (td, J = 8.1, 1.4 Hz, 1H), 4.14 (t, J = 7.2 Hz, 2H), 2.84 (t, J = 7.5 Hz, 2H), 2.49 (s, 3H), 2.37 (p, J = 7.6 Hz, 2H), 1.30-1.23 (m, 2H), 1.20 (dd, J = 5.9, 2.3 Hz, 2H). |
| 111 | 473.2 | 1H NMR (400 MHz, DMSO-d6) δ 9.71 (s, 1H), 9.39 (s, 1H), 7.56 (s, 1H), 7.51-7.39 (m, 1H), 7.39-7.26 (m, 1H), 4.13 (t, J = 7.2 Hz, 2H), 2.84 (t, J = 7.5 Hz, 2H), 2.46 (s, 3H), 2.38 (q, J = 7.3 Hz, 2H), 1.28-1.23 (m, 2H), 1.22-1.15 (m, 2H). |
| 112 | 455.1 | 1H NMR (400 MHz, Acetone-d6) δ 9.04 (s, 1H), 8.51 (s, 1H), 8.04 (ddd, J = 6.8, 2.7, 1.7 Hz, 1H), 7.65 (dtd, J = 8.8, 2.6, 1.3 Hz, 1H), 7.28 (t, J = 9.0 Hz, 1H), 4.25 (t, J = 7.3 Hz, 2H), 3.08 (t, J = 7.5 Hz, 2H), 2.65 (s, 7H), 2.57-2.41 (m, 2H), 2.51 (s, 3H). |
| 113 | 439.1 | 1H NMR (400 MHz, Acetone-d6) δ 9.06 (s, 1H), 8.49 (s, 1H), 7.91 (ddd, J = 13.1, 7.4, 2.5 Hz, 1H), 7.45 (ddt, J = 8.4, 4.0, 1.7 Hz, 1H), 7.30 (dt, J = 10.5, 9.0 Hz, 1H), 4.25 (t, J = 7.3 Hz, 2H), 3.09 (t, J = 7.5 Hz, 2H), 2.65 (s, 6H), 2.53-2.43 (m, 2H), 2.51 (s, 3H). |
| 114 |  | 1H NMR (400 MHz, Methanol-d4) δ 7.99-7.86 (m, 1H), 7.76 (dd, J = 8.8, 4.3 Hz, 1H), 7.30-7.16 (m, 1H), 6.98 (t, J = 54.8 Hz, 1H), 4.21 (t, J = 7.3 Hz, 2H), 3.06 (t, J = 7.5 Hz, 2H), 2.74 (s, 3H), 2.54 (s, 3H), 2.49 (t, J = 7.3 Hz, 2H), 1.54 (s, 6H). |
| 115 | 509.1 | 1H NMR (400 MHz, DMSO-d6) δ 10.00 (s, 1H), 9.43 (s, 1H), 7.96 (s, 1H), 7.79 (q, J = 4.5 Hz, 1H), 7.75 (dd, J = 7.9, 2.0 Hz, 1H), 7.46 (t, J = 7.9 Hz, 1H), 7.26 (d, J = 7.6 Hz, 1H), 7.02 (t, J = 55.9 Hz, 1H), 4.14 (t, J = 7.2 Hz, 2H), 3.20 (td, J = 14.9, 11.8 Hz, 2H), 3.01-2.84 (m, 4H), 2.59 (d, J = 4.5 Hz, 3H), 2.45 (s, 3H), 2.37 (p, J = 7.5 Hz, 2H). |
| 116 | 527.1 | 1H NMR (400 MHz, DMSO-d6) δ 10.02 (s, 1H), 9.43 (s, 1H), 7.99 (dd, J = 6.6, 2.6 Hz, 1H), 7.79 (q, J = 4.7 Hz, 2H), 7.42-7.01 (m, 2H), 4.14 (t, J = 7.3 Hz, 2H), 3.20 (q, J = 14.6 Hz, 2H), 2.92 (t, J = 7.7 Hz, 4H), 2.59 (d, J = 4.5 Hz, 3H), 2.45 (s, 3H), 2.37 (p, J = 7.4 Hz, 2H). |
| 117 | 484.1 | 1H NMR (400 MHz, Acetone-d6) δ 9.05 (s, 1H), 8.11-7.99 (m, 2H), 7.66 (ddd, J = 9.0, 4.2, 2.6 Hz, 1H), 7.29 (t, J = 9.0 Hz, 1H), 4.49 (s, 1H), 4.26 (t, J = 7.3 Hz, 2H), 3.80 (s, 2H), 3.13 (t, J = 7.5 Hz, 2H), 3.12-2.75 (m, 4H), 2.53 (s, 3H), 2.49 (p, J = 7.4 Hz, 2H). |
| 118 | 468.1 | 1H NMR (400 MHz, Acetone-d6) δ 9.07 (s, 1H), 8.02 (s, 1H), 7.91 (ddd, J = 13.2, 7.4, 2.6 Hz, 1H), 7.50-7.41 (m, 1H), 7.30 (dt, J = 10.5, 9.0 Hz, 1H), 4.26 (t, J = 7.3 Hz, 2H), 3.80 (d, J = 1.1 Hz, 2H), 3.13 (t, J = 7.5 Hz, 2H), 3.10-2.76 (m, 4H), 2.53 (s, 3H), 2.49 (p, J = 7.4 Hz, 2H). |
| 119 | 499.24 | 1H NMR (400 MHz, Acetonitrile-d3) δ 8.93 (s, 1H), 8.60 (d, J = 6.0 Hz, 1H), 8.14 (d, J = 2.1 Hz, 1H), 8.06 (s, 1H), 7.94 (dd, J = 6.2, 2.1 Hz, 1H), 6.94 (s, 4H), 6.88 (t, J = 53.2 Hz, 1H), 4.93 (dd, J = 12.1, 8.3 Hz, 2H), 4.81 (dd, J = 7.9, 3.9 Hz, 2H), 4.31 (tt, J = 6.0, 1.8 Hz, 1H), 3.37 (dd, J = 18.8, 6.8 Hz, 1H), 3.23-3.09 (m, 1H), 2.53 (s, 3H), 2.12 (dq, J = 8.0, 6.1 Hz, 1H), 1.09 (dt, J = 8.6, 5.9 Hz, 1H), 0.33-0.21 (m, 1H). |
| 120 | 497.2 | 1H NMR (400 MHz, DMSO-d6) δ 9.98 (s, 1H), 9.39 (s, 1H), 7.94 (dd, J = 6.8, 2.6 Hz, 1H), 7.58 (ddd, J = 9.0, 4.3, 2.6 Hz, 1H), 7.39 (t, J = 9.1 Hz, 1H), 7.29 (s, 1H), 7.20 (s, 1H), 4.13 (t, J = 7.3 Hz, 2H), 3.20 (q, J = 14.2 Hz, 2H), 2.93 (dt, J = 30.3, 7.1 Hz, 4H), 2.43 (s, 3H), 2.37 (t, J = 7.3 Hz, 2H). |
| 121 | 481.2 | 1H NMR (400 MHz, DMSO-d6) δ 10.01 (s, 1H), 9.39 (s, 1H), 7.84-7.75 (m, 1H), 7.43-7.36 (m, 2H), 7.29 (s, 1H), 7.20 (s, 1H), 4.13 (t, J = 7.2 Hz, 2H), 3.20 (q, J = 14.4 Hz, 2H), 2.93 (dt, J = 30.5, 7.1 Hz, 4H), 2.43 (s, 3H), 2.37 (t, J = 7.3 Hz, 2H). |
| 124 | 524.9 | 1H NMR (400 MHz, Acetone-d6) δ 9.04 (s, 1H), 8.67 (s, 1H), 8.05 (dd, J = 6.8, 2.6 Hz, 1H), 7.66 (ddd, J = 9.0, 4.2, 2.6 Hz, 1H), 7.29 (t, J = 9.0 Hz, 1H), 4.25 (t, J = 7.3 Hz, 2H), 3.53 (ddd, J = 15.3, 13.6, 11.9 Hz, 2H), 3.22-3.00 (m, 7H), 2.91 (s, 3H), 2.53 (s, 3H), 2.49 (p, J = 7.4 Hz, 2H). |
| 125 | 509.0 | 1H NMR (400 MHz, Acetone-d6) δ 9.30 (s, 1H), 8.88 (s, 1H), 7.89 (ddd, J = 13.1, 7.4, 2.5 Hz, 1H), 7.45 (dq, J = 8.4, 2.0 Hz, 1H), 7.29 (dt, J = 10.6, 9.1 Hz, 1H), 4.23 (t, J = 7.3 Hz, 2H), 3.63-3.37 (m, 2H), 3.18-2.97 (m, 7H), 2.90 (s, 3H), 2.51 (s, 3H), 2.50-2.43 (m, 2H). |
| 126 | 462.1 | 1H NMR (400 MHz, DMSO-d6) δ 10.25 (s, 1H), 9.39 (s, 1H), 7.95-7.77 (m, 2H), 7.61-7.49 (m, 2H), 4.13 (t, J = 7.3 Hz, 2H), 2.86 (t, J = 7.5 Hz, 2H), 2.43 (s, 3H), 2.37 (q, J = 7.5 Hz, 2H), 1.32-1.23 (m, 2H), 1.23-1.16 (m, 2H). |
| 127 | 529.0 | 1H NMR (400 MHz, Methanol-d4) δ 7.76 (ddd, J = 9.2, 8.2, 5.7 Hz, 1H), 7.24-7.03 (m, 1H), 4.24 (t, J = 7.3 Hz, 2H), 3.30 (m, 2H), 3.05 (t, J = 7.5 Hz, 2H), 2.90 (td, J = 14.4, 6.7 Hz, 2H), 2.82-2.71 (m, 3H), 2.60 (s, 3H), 2.49 (p, J = 7.5 Hz, 2H). |
| 128 | 477.0 | 1H NMR (400 MHz, Methanol-d4) δ 7.86 (m, 1H), 7.50 (m, 1H), 7.21 (m, 1H), 4.30-4.07 (m, 3H), 3.07-2.92 (m, 2H), 2.76 (m, 3H), 2.53 (s, 3H), 2.51-2.40 (m, 2H), 2.11 (m, 1H), 0.98 (m, 6H). |
| 129 | 528.9 | 1H NMR (400 MHz, DMSO-d6) δ 10.09 (s, 1H), 9.44 (s, 1H), 7.86-7.65 (m, 2H), 4.13 (t, J = 7.3 Hz, 2H), 3.27-3.12 (m, 2H), 2.98-2.84 (m, 4H), 2.59 (d, J = 4.5 Hz, 3H), 2.43 (s, 3H), 2.37 (p, J = 7.6 Hz, 2H). |
| 130 | 497.1 | 1H NMR (400 MHz, Acetone-d6) δ 9.09 (s, 1H), 8.99 (s, 1H), 8.05 (dd, J = 6.8, 2.6 Hz, 1H), 7.66 (ddd, J = 9.0, 4.2, 2.6 Hz, 1H), 7.30 (t, J = 9.0 Hz, 1H), 4.27 (t, J = 7.3 Hz, 2H), 3.53 (tdt, J = 13.8, 8.5, 4.2 Hz, 2H), 3.34 (qd, J = 12.2, 3.4 Hz, 2H), 3.15 (t, J = 7.5 Hz, 2H), 2.54 (s, 3H), 2.50 (p, J = 7.4 Hz, 2H). |
| 131 | 481.1 | 1H NMR (400 MHz, Acetone-d6) δ 9.14 (s, 1H), 9.01 (s, 1H), 7.91 (ddd, J = 13.1, 7.4, 2.6 Hz, 1H), 7.51-7.42 (m, 1H), 7.30 (dt, J = 10.6, 9.0 Hz, 1H), 4.27 (t, J = 7.3 Hz, 2H), 3.63-3.45 (m, 2H), 3.34 (dt, J = 15.2, 12.3 Hz, 2H), 3.15 (t, J = 7.5 Hz, 2H), 2.53 (s, 4H), 2.50 (p, J = 7.5 Hz, 1H). |
| 132 | 490.1 | 1H NMR (400 MHz, Acetone-d6) δ 9.04 (s, 1H), 8.05 (dd, J = 6.8, 2.6 Hz, 1H), 7.75 (s, 1H), 7.66 (ddd, J = 9.0, 4.2, 2.6 Hz, 1H), 7.29 (t, J = 9.0 Hz, 1H), 4.27 (t, J = 7.3 Hz, 2H), 4.15 (d, J = 11.8 Hz, 1H), 3.81 (dd, J = 12.0, 1.7 Hz, 1H), 3.13 (t, J = 7.6 Hz, 2H), 2.54 (s, 3H), 2.49 (p, J = 7.4 Hz, 2H), 1.66 (d, J = 1.0 Hz, 3H). |
| 133 | 474.1 | 1H NMR (400 MHz, Acetone-d6) δ 9.06 (s, 1H), 7.91 (ddd, J = 13.1, 7.4, 2.6 Hz, 1H), 7.74 (s, 1H), 7.46 (dddd, J = 9.0, 4.1, 2.6, 1.6 Hz, 1H), 7.30 (dt, J = 10.5, 9.0 Hz, 1H), 4.76 (s, 1H), 4.31-4.22 (m, 2H), 4.15 (d, J = 12.0 Hz, 1H), 3.81 (d, J = 12.0 Hz, 1H), 3.13 (t, J = 7.5 Hz, 2H), 2.53 (s, 3H), 2.49 (p, J = 7.4 Hz, 2H), 1.66 (d, J = 1.0 Hz, 3H). |
| 134 | 556.2 | 1H NMR (400 MHz, DMSO-d6) δ 10.15 (d, J = 1.6 Hz, 1H), 9.77 (s, 1H), 8.44 (d, J = 5.3 Hz, 1H), 8.21 (t, J = 5.6 Hz, 1H), 7.83 (s, 1H), 7.15 (t, J = 53.1 Hz, 1H), 5.85-5.57 (m, 1H), 4.55-4.40 (m, 3H), 3.37-3.25 (m, 2H), 3.22 (d, J = 18.8, 5.0 Hz, OH), 3.00 (dd, J = 26.6, 18.8 Hz, 1H), 2.52 (s, 3H). |
| 135 | 487.1 | 1H NMR (400 MHz, Acetone-d6) δ 9.07 (s, 1H), 8.32 (s, 1H), 7.97-7.84 (m, 1H), 7.55-7.39 (m, 2H), 7.30 (qd, J = 9.0, 4.5 Hz, 1H), 7.17 (s, 1H), |

| Compound # | ES/MS m/z | $^1$H-NMR |
|---|---|---|
| | | 4.26 (t, J = 7.3 Hz, 2H), 3.14 (t, J = 8.3 Hz, 2H), 2.53 (s, 3H), 2.47 (p, J = 7.2 Hz, 2H), 2.01 (s, 3H). |
| 136 | 487.1 | 1H NMR (400 MHz, Acetone-d6) δ 9.07 (s, 1H), 8.32 (s, 1H), 7.91 (dd, J = 13.1, 7.7 Hz, 1H), 7.55-7.39 (m, 2H), 7.29 (d, J = 9.5 Hz, 1H), 7.17 (s, 1H), 4.26 (t, J = 7.3 Hz, 2H), 3.22-3.06 (m, 2H), 2.53 (s, 3H), 2.47 (p, J = 7.0, 6.6 Hz, 2H), 2.01 (s, 3H). |
| 137 | 501.0 | 1H NMR (400 MHz, Acetone-d6) δ 9.13 (s, 1H), 8.35 (s, 1H), 7.91 (ddt, J = 12.8, 7.7, 2.3 Hz, 1H), 7.73 (s, 1H), 7.53-7.42 (m, 1H), 7.37-7.20 (m, 1H), 4.26 (t, J = 7.4 Hz, 2H), 3.12 (t, J = 7.7 Hz, 2H), 2.82 (d, J = 4.6, 3H), 2.53 (s, 3H), 2.47 (p, J = 7.2 Hz, 2H), 1.95 (s, 3H). |
| 138 | 501.0 | 1H NMR (400 MHz, Acetone-d6) δ 9.07 (s, 1H), 8.32 (s, 1H), 8.00-7.83 (m, 1H), 7.68 (s, 1H), 7.55-7.37 (m, 1H), 7.37-7.21 (m, 1H), 4.26 (t, J = 7.4 Hz, 2H), 3.12 (t, J = 7.6 Hz, 2H), 2.82 (d, J = 2.9 Hz, 3H), 2.53 (s, 3H), 2.47 (p, J = 7.3 Hz, 2H), 1.95 (s, 3H). |
| 140 | 499.1 | 1H NMR (400 MHz, Methanol-d4) δ 7.48 (dd, J = 10.0, 6.3 Hz, 2H), 4.22 (t, J = 7.5 Hz, 2H), 3.41-3.34 (m, 2H), 3.09 (t, J = 7.5 Hz, 2H), 2.91 (td, J = 14.4, 6.9 Hz, 1H), 2.54 (s, 3H), 2.50 (t, J = 7.5 Hz, 2H). |
| 145 | 450.2 | 1H NMR (400 MHz, DMSO-d6) δ 10.02 (s, 1H), 9.15 (s, 0.6H), 9.02 (s, 0.4H), 7.89-7.75 (m, 1H), 7.48-7.32 (m, 2H), 4.15 (m, 2H), 4.09 (m, 0.6H), 3.92 (m, 1.4H), 3.52 (m, 1.4H), 3.19 (m, 0.6H), 2.97 (m, 2H), 2.44 (m, 5H), 1.62 (s, 1H), 1.42 (s, 2H). |
| 147 | 528.19 | 1H NMR (400 MHz, Chloroform-d) δ 8.59 (t, J = 5.6 Hz, 1H), 8.40 (d, J = 5.4 Hz, 1H), 8.05 (s, 1H), 7.57 (s, 1H), 6.64 (d, J = 15.8 Hz, 1H), 5.29 (s, 1H), 4.40 (t, J = 7.4 Hz, 2H), 3.43 (td, J = 14.9, 11.0 Hz, 2H), 3.21 (t, J = 7.6 Hz, 2H), 2.97-2.81 (m, 5H), 2.73 (s, 3H), 2.52 (p, J = 7.6 Hz, 2H). |
| 150 | 523.2 | 1H NMR (400 MHz, DMSO-d6) δ 10.20 (s, 1H), 9.91 (s, 1H), 8.45 (d, J = 5.3 Hz, 1H), 8.22 (t, J = 5.6 Hz, 1H), 7.16 (t, J = 53.1 Hz, 1H), 5.92-5.62 (m, 1H), 4.87 (dd, J = 12.2, 8.4 Hz, 2H), 4.77 (dd, J = 7.9, 2.4 Hz, 2H), 4.56-4.42 (m, 2H), 3.45 (ddd, J = 37.2, 18.9, 5.0 Hz, 1H), 3.22 (dd, J = 26.5, 18.9 Hz, 1H), 2.54 (s, 3H). |
| 151 | 450.2 | 1H NMR (400 MHz, DMSO-d6) δ 10.03 (s, 1H), 9.03 (s, 1H), 7.82 (ddd, J = 14.3, 7.8, 2.2 Hz, 1H), 7.49-7.34 (m, 2H), 4.21-4.04 (m, 4H), 3.23-3.15 (m, 2H), 2.96 (t, J = 7.5 Hz, 2H), 2.47-2.39 (m, 5H), 1.62 (s, 3H). |
| 152 | 450.2 | 1H NMR (400 MHz, DMSO-d6) δ 10.14 (s, 1H), 9.51 (s, 1H), 7.93-7.74 (m, 1H), 7.51-7.34 (m, 2H), 7.30 (s, 1H), 7.26 (s, 1H), 4.84 (dd, J = 25.0, 6.6 Hz, 2H), 4.62 (dd, J = 31.2, 6.6 Hz, 2H), 4.24 (t, J = 6.0 Hz, 1H), 3.30-3.20 (m, 1H), 3.10 (d, J = 18.7 Hz, 1H), 2.42 (s, 3H), 2.11 (t, J = 7.0 Hz, 1H), 1.07 (dt, J = 8.4, 5.7 Hz, 1H), 0.15 (q, J = 3.6, 1.9 Hz, 1H). |

BIOLOGICAL EXAMPLES

HBV DNA Quantification Assay

A HepG2 cell line overexpressing the HBV virus attachment receptor sodium-taurocholate cotransporting polypeptide (NTCP) was grown to confluency in DMEM growth medium, Dulbecco's Modified Eagle Medium without sodium pyruvate (Life Technologies, Rockville, MD) supplemented with 10% FBS (Thermo Scientific, Waltham, MD), 1% penicillin/streptomycin (Life Technologies, Rockville, MD) and 2 mM L-glutamine (Life Technologies, Rockville, MD) in T175 flasks. Cells were infected with HBV AD38 viral particles (Texcell, Frederick, USA) at 4000 genome equivalents per cell. After allowing viral infection to take place for 4 days, the infected cells were harvested from the flasks by trypsinization, washed twice with OptiMEM (Life Technologies, Rockville, MD) and re-suspended in DMEM containing 2% FBS and 1% DMSO at a density of 0.25E6 cells/ml. Infected cells were seeded on 384 well collagen coated plates (Greiner, Austria) at a density of 20,000 cells/well containing serially diluted compounds of the present disclosure or DMSO (0.5%) in a final volume of 80 μl. The assay plates were incubated for a period of 5 days and the antiviral activity of the test compounds were assayed by detecting the presence of HBV DNA in the culture supernatant using the QuantiGene™ 2.0 nucleic acid quantification kit (Affymetrix, Santa Clara, CA).

The culture supernatant was harvested and treated with lysis buffer containing Proteinase K (Affymetrix, Santa Clara, CA). The supernatant was incubated with HBV viral DNA specific probes (Affymetrix, Santa Clara, CA) for 30 minutes at 55° C. This was followed by addition of 0.2M NaOH for 30 minutes at room temperature to denature the DNA, followed by addition of Neutralization buffer (Affymetrix, Santa Clara, CA). The resulting lysed and neutralized supernatant was then added to QuantiGene™ 2.0 384 well plates coated with capture oligonucleotides and incubated overnight at 55° C. The HBV specific probe set consists of Capture Extender oligonucleotides (CE's) and blocking probes. Following the overnight incubation, the wells were incubated for one hour sequentially with a Pre-Amplifier, Amplifier and Labeled probes conjugated to alkaline phosphatase with a wash step between incubations. After the final wash step, the alkaline phosphatase substrate (Luminol APS5) was added and the resulting luminescence signal was read in an EnVision Multilabel Plate Reader (PerkinElmer, Santa Clara, CA). The EC50 values were calculated from the fit of the dose-response curves to a four-parameter equation. All EC50 values represent geometric mean values of a minimum of four determinations. EC50 values for certain compounds of the present disclosure are reported in the table below.

| Compound | EC50-NTCP (nM) |
|---|---|
| 1 | 27.1 |
| 2 | 15.9 |
| 3 | 14.9 |
| 4 | 63.6 |
| 5 | 8.8 |
| 6 | 11.1 |
| 7 | 5.8 |
| 8 | 72.0 |
| 9 | 103.4 |
| 10 | 56.1 |
| 11 | 7.7 |
| 12 | 5.0 |
| 13 | 252.3 |
| 14 | 8.8 |
| 15 | 45.8 |
| 16 | 456.1 |
| 17 | 64.5 |
| 18 | 33.2 |
| 19 | 167.3 |
| 20 | 49.4 |
| 21 | 20.1 |
| 22 | 37.0 |
| 23 | 66.0 |
| 24 | 43.7 |
| 25 | 407.9 |
| 26 | 14.6 |
| 27 | 32.3 |

| Compound | EC50-NTCP (nM) |
|---|---|
| 28 | 112.0 |
| 29 | 3.1 |
| 30 | 58.1 |
| 31 | 3.2 |
| 32 | 8.5 |
| 33 | 27.2 |
| 34 | 202.2 |
| 35 | 109.1 |
| 36 | 24.0 |
| 37 | 5.6 |
| 38 | 13.0 |
| 39 | 2.1 |
| 40 | 1.9 |
| 41 | 7.5 |
| 42 | 2.1 |
| 43 | 23.2 |
| 44 | 31.0 |
| 45 | 9.1 |
| 46 | 263.8 |
| 47 | 56.3 |
| 48 | 6.5 |
| 49 | 69.1 |
| 50 | 53.7 |
| 51 | 75.9 |
| 52 | 7.7 |
| 53 | 3.2 |
| 54 | 7.8 |
| 55 | 54.3 |
| 56 | 87.1 |
| 57 | 9.9 |
| 58 | 27.3 |
| 59 | 23.8 |
| 60 | 1.8 |
| 61 | 12.3 |
| 62 | 78.6 |
| 63 | 71.1 |
| 64 | 30.1 |
| 65 | 36.8 |
| 66 | 6.5 |
| 67 | 6.5 |
| 68 | 110.4 |
| 69 | 49.9 |
| 70 | 63.2 |
| 71 | 15.4 |
| 72 | 69.8 |
| 73 | 15.8 |
| 74 | 42.0 |
| 75 | 106.5 |
| 76 | 31.9 |
| 77 | 19.0 |
| 78 | 16.4 |
| 79 | 47.8 |
| 80 | 8.7 |
| 81 | 17.5 |
| 82 | 133.3 |
| 83 | 198.9 |
| 84 | 31.0 |
| 85 | 293.6 |
| 86 | 184.0 |
| 87 | 12.5 |
| 88 | 8.7 |
| 89 | 2.9 |
| 90 | 182.6 |
| 91 | 91.1 |
| 92 | 6.4 |
| 93 | 253.9 |
| 94 | 5.8 |
| 95 | 33.7 |
| 96 | 16.5 |
| 98 | 30.6 |
| 99 | 51.3 |
| 100 | 3.7 |
| 101 | 29.8 |
| 102 | 111.9 |
| 103 | 40.8 |
| 104 | 96.4 |
| 105 | 170.2 |
| 106 | 123.9 |
| 107 | 145.9 |
| 111 | 153.7 |
| 112 | 29.9 |
| 113 | 45.1 |
| 114 | 156.5 |
| 115 | 49.9 |
| 116 | 24.2 |
| 117 | 13.1 |
| 118 | 26.1 |
| 119 | 25.8 |
| 120 | 12.3 |
| 121 | 14.4 |
| 124 | 11.9 |
| 125 | 23.1 |
| 126 | 165.8 |
| 127 | 32.3 |
| 128 | 169.9 |
| 129 | 20.4 |
| 130 | 10.4 |
| 131 | 10.6 |
| 132 | 8.3 |
| 133 | 16.5 |
| 134 | 23.8 |
| 135 | 79.9 |
| 136 | 70.1 |
| 137 | 158.2 |
| 138 | 159.8 |
| 140 | 12.2 |
| 145 | 46.3 |
| 147 | 102.7 |
| 150 | 74.3 |
| 151 | 30.6 |
| 152 | 65.1 |

Hepatic Stability Assay

The metabolic stability of certain compounds disclosed herein was assessed in vitro in pooled cryopreserved hepatocytes using the in vitro half-life method. Incubations were at 37° C. and final concentrations in the incubations were $1\times10^6$ cells/mL and 1 mM test concentration of the compound. Aliquots were sequentially removed after 0, 1, 3 and 6 hours and analyzed by LC-MS/MS. In vitro half-life was determined by measuring the rate of disappearance of the compound and then scaled to predicted hepatic clearance using the well-stirred model. Data is presented in the table below. This data may be used to compare the relative metabolic stabilities of the compounds. For reference, 39.5 hours is the maximum detectable half life for this assay. As such, compounds having a value of 39.5 may have a half live that exceeds 39.5 hours.

| Compound | t½ (hours) |
|---|---|
| 1 | |
| 2 | 15 |
| 3 | 35.1 |
| 4 | 7.3 |
| 5 | 5.2 |
| 6 | 8.2 |
| 7 | 4.8 |
| 8 | 0.4 |
| 9 | 11.7 |
| 10 | 1 |
| 11 | 0.7 |
| 12 | 6.4 |
| 13 | 16.4 |
| 14 | 2.1 |
| 15 | 0.5 |

289
-continued

| Compound | t½ (hours) |
|---|---|
| 16 | 11.8 |
| 17 | 0.6 |
| 18 | 6 |
| 19 | 18.3 |
| 20 | 14.3 |
| 21 | 17.1 |
| 22 | 2.7 |
| 23 | 9.6 |
| 24 | 5 |
| 25 | 9.1 |
| 26 | 8.2 |
| 27 | 0.9 |
| 28 | 11.8 |
| 29 | 16.1 |
| 30 | 27.2 |
| 31 | 8.6 |
| 32 | 8.8 |
| 33 | 4.3 |
| 34 | 18.1 |
| 35 | 39.5 |
| 36 | 26.5 |
| 37 | 10.9 |
| 38 | 13.8 |
| 39 | 4.2 |
| 40 | 5.2 |
| 41 | 4.9 |
| 42 | 3.5 |
| 43 | 16 |
| 44 | 39.5 |
| 45 | 13.3 |
| 46 | 16 |
| 47 | 39.5 |
| 48 | 7.9 |
| 49 | 39.5 |
| 50 | 15.3 |
| 51 | 9.5 |
| 52 | 4.2 |
| 53 | 10.8 |
| 54 | 6.7 |
| 55 | 15.5 |
| 56 | 39.5 |
| 57 | 8.0 |
| 58 | 38.5 |
| 59 | 22.3 |
| 60 | 3.9 |
| 61 | 5.4 |
| 62 | 5.3 |
| 63 | 11.2 |
| 64 | 13.2 |
| 65 | 14.8 |
| 66 | 1.4 |
| 67 | |
| 68 | 5.2 |
| 69 | 17.0 |
| 70 | 39.5 |
| 71 | 7.3 |
| 72 | 39.5 |
| 73 | 16.1 |
| 74 | 22.2 |
| 75 | 17.3 |
| 76 | 19.5 |
| 77 | 22.1 |
| 78 | 4.8 |
| 79 | 14.9 |
| 80 | 6.3 |
| 81 | 8.0 |
| 82 | |
| 83 | 19.2 |
| 84 | 10.7 |
| 85 | |
| 86 | 9.4 |
| 87 | 6.3 |
| 88 | 9.9 |
| 89 | 10.3 |
| 90 | 31.4 |
| 91 | 19.6 |
| 92 | 2.2 |

290
-continued

| Compound | t½ (hours) |
|---|---|
| 93 | 29.9 |
| 94 | 2.9 |
| 95 | 28.8 |
| 96 | 22.6 |
| 98 | 14.8 |
| 99 | 9.6 |
| 100 | 3.1 |
| 101 | 7.0 |
| 102 | 4.8 |
| 103 | 8.5 |
| 104 | |
| 105 | 24.3 |
| 106 | |
| 107 | 9.8 |
| 111 | 10.1 |
| 112 | |
| 113 | |
| 114 | |
| 115 | 39.5 |
| 116 | 39.5 |
| 117 | 10.5 |
| 118 | 15.2 |
| 119 | 11.0 |
| 120 | 13.5 |
| 121 | 19.8 |
| 124 | 1.0 |
| 125 | 1.9 |
| 126 | 10.7 |
| 127 | 15.2 |
| 128 | |
| 129 | 20.8 |
| 130 | 6.60 |
| 131 | 7.60 |
| 132 | 7.70 |
| 133 | 12.5 |
| 134 | 17.9 |
| 135 | 39.5 |
| 136 | 39.5 |
| 137 | 7.4 |
| 138 | 17.9 |
| 140 | 13.5 |
| 145 | 9.7 |
| 147 | 24.8 |
| 150 | 16.6 |
| 151 | 5.0 |
| 152 | 10.5 |

The invention claimed is:

1. A compound of Formula (I),

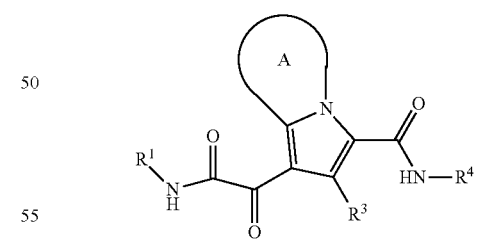

Formula I or a pharmaceutically acceptable salt thereof, wherein:

$R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$;

each $R^{1A}$ is independently halogen, —OH, —CN, $C_{1-2}$ haloalkyl, —C(O)NR$^X$R$^Y$, $C_{6-10}$ aryl optionally substituted with 1 to 3 $R^{1D}$, or a 5 to 8 membered heteroaryl having 1 to 3 heteroatoms selected from N, O, and S, optionally substituted with 1 to 3 $R^{1D}$, provided no more than 1 $R^{1A}$ is $C_{6-10}$ aryl optionally substituted with 1 to 3 $R^{1D}$ or 5 to 8 membered heteroaryl having 1 to 3 heteroatoms selected from N, O, and S;

each $R^{1B}$ is independently —CN, halogen, $C_{1-6}$ alkyl optionally substituted with 1 to 3 —OH or —NR$^a$R$^b$, $C_{2-4}$ alkynyl, $C_{1-4}$ alkoxy, $C_{1-2}$ haloalkyl, $C_{3-6}$ cycloalkyl, —C(O)NR$^X$R$^Y$, or a 5 to 8 membered heteroaryl having 1 to 3 heteroatoms selected from N, O, and S optionally substituted with 1 to 3 $R^{1D}$, provided no more than 1 $R^{1B}$ is $C_{3-6}$ cycloalkyl or 5 to 8 membered heteroaryl having 1 to 3 heteroatoms selected from N, O, and S;

each $R^{1C}$ is independently $C_{1-6}$ alkyl, oxo, $C_{1-4}$ haloalkyl, —C(O)H, —C(O)C$_{1-4}$ alkyl, —C(O)OC$_{1-4}$ alkyl, or a 5 to 12 membered heteroaryl having 1 to 3 heteroatoms selected from N, O, and S optionally substituted with 1 to 3 $R^{1D}$, provided no more than 1 $R^{1C}$ is a 5 to 12 membered heteroaryl having 1 to 3 heteroatoms selected from N, O, and S;

each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$, each $R^Y$ is independently —H or $C_{1-6}$ alkyl optionally substituted with 1 to 3 $R^Z$;

or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$;

wherein each $R^Z$ is independently halogen, methyl, ethyl, oxo, —OH, —S(O)$_2$C$_{1-3}$alkyl, or 3 to 8 membered monocyclic or bicyclic heterocyclyl having 1 to 3 heteroatoms selected from N, O, and S;

each $R^a$ is —H, $C_{1-3}$alkyl, or a 3 to 8 membered monocyclic or bicyclic heterocyclyl having 1 to 3 heteroatoms selected from N, O, and S, optionally substituted with 1 to 3 $R^Z$;

each $R^b$ is —H or $C_{1-3}$alkyl; or $R^a$ and $R^b$ taken together form a 3 to 8 membered monocyclic or bicyclic heterocycle optionally substituted with 1 to 3 $R^Z$;

the moiety

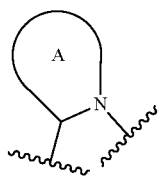

is a pyrrolidine or a 5-7 membered bicyclic heterocycle having one nitrogen, optionally substituted with 1 to 6 $R^2$ groups;

wherein each $R^2$ is independently halogen, $C_{1-3}$alkyl, —OH, or —OC$_{1-3}$ alkyl;

$R^3$ is —H, halogen, or $C_{1-4}$ alkyl;

$R^4$ is phenyl optionally substituted with 1 to 5 $R^{4A}$, or pyridinyl optionally substituted with 1 to 4 $R^{4B}$; and each $R^{1D}$, $R^{4A}$, and $R^{4B}$ are independently —CN, halogen, $C_{1-4}$ alkyl, —OC$_{1-4}$alkyl, —OC$_{1-4}$ haloalkyl, or $C_{1-4}$ haloalkyl.

2. The compound of claim 1, or a pharmaceutically acceptable salt thereof, wherein $R^4$ is phenyl optionally substituted with 1 to 3 $R^{4A}$.

3. The compound of claim 1, or a pharmaceutically acceptable salt thereof, wherein each $R^{4A}$ is independently Cl, F, —CF$_3$, —CHF$_2$, —CH$_3$, —OCF$_3$, —OCF$_2$H, or —CN.

4. The compound of claim 1, or a pharmaceutically acceptable salt thereof, wherein $R^3$ is —Cl or —CH$_3$.

5. The compound of claim 1, or a pharmaceutically acceptable salt thereof, wherein $R^3$ is —CH$_3$.

6. The compound of claim 1, or a pharmaceutically acceptable salt thereof, wherein the compound is a compound of Formula (II)

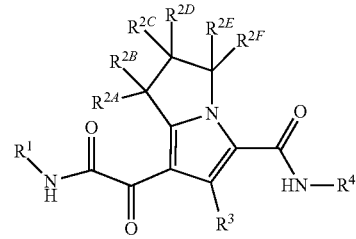

Formula II wherein:

$R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$;

each $R^{1A}$ is independently halogen, —OH, —CN, $C_{1-2}$ haloalkyl, —C(O)NR$^X$R$^Y$, $C_{6-10}$ aryl optionally substituted with 1 to 3 $R^{1D}$, or a 5 to 8 membered heteroaryl having 1 to 3 heteroatoms selected from N, O, and S, optionally substituted with 1 to 3 $R^{1D}$, provided no more than 1 $R^{1A}$ is $C_{6-10}$ aryl optionally substituted with 1 to 3 $R^{1D}$ or 5 to 8 membered heteroaryl having 1 to 3 heteroatoms selected from N, O, and S;

each $R^{1B}$ is independently halogen, $C_{1-6}$ alkyl optionally substituted with 1 to 3-OH or —NR$^a$R$^b$, $C_{1-4}$ alkoxy, $C_{1-2}$ haloalkyl, —C(O)NR$^X$R$^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O;

each $R^{1C}$ is independently $C_{1-6}$ alkyl, oxo, $C_{1-4}$ haloalkyl, —C(O)H, —C(O)C$_{1-4}$ alkyl or —C(O)OC$_{1-4}$ alkyl;

each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;

each $R^Y$ is independently —H or $C_{1-6}$ alkyl optionally substituted with 1 to 3 $R^Z$;

or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$
wherein each $R^Z$ is independently halogen, methyl, ethyl, oxo, —OH, —S(O)$_2$C$_{1-3}$alkyl, or 3 to 8 membered monocyclic or bicyclic heterocyclyl having 1 to 3 heteroatoms selected from N, O, and S;

each $R^a$ is —H, C$_{1-3}$alkyl, or a 3 to 8 membered monocyclic or bicyclic heterocyclyl having 1 to 3 heteroatoms selected from N, O, and S, optionally substituted with 1 to 3 $R^Z$;

each $R^b$ is —H or C$_{1-3}$alkyl; or $R^a$ and $R^b$ taken together form a 3 to 8 membered monocyclic or bicyclic heterocyclyl optionally substituted with 1 to 3 $R^Z$;

each of $R^{2A}$, $R^{2B}$, $R^{2C}$, $R^{2D}$, $R^{2E}$, and $R^{2F}$ are independently —H, halogen, C$_{1-3}$alkyl, —OH, or —OC$_{1-3}$alkyl, or $R^{2C}$ or $R^{2D}$ may be taken together with $R^{2E}$ or $R^{2F}$ to form a cyclopropyl group;

$R^3$ is halogen or methyl;

$R^4$ is phenyl optionally substituted with 1 to 5 $R^{4A}$, or pyridinyl, optionally substituted with 1 to 4 $R^{4B}$; and each $R^{1D}$, $R^{4A}$, and $R^{4B}$ are independently —CN, halogen, C$_{1-4}$ alkyl, —OC$_{1-4}$alkyl, —OC$_{1-4}$ haloalkyl, or C$_{1-4}$ haloalkyl.

7. The compound of claim 1, or a pharmaceutically acceptable salt thereof, wherein the compound is a compound of Formula (IV):

Formula IV

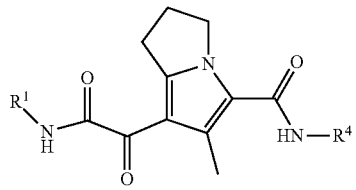

8. The compound of claim 1, or a pharmaceutically acceptable salt thereof, wherein $R^1$ is

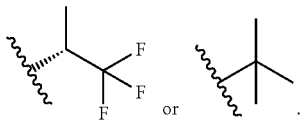

9. The compound of claim 1, or a pharmaceutically acceptable salt thereof, wherein $R^1$ is

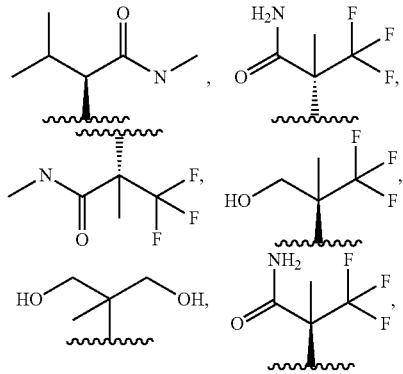

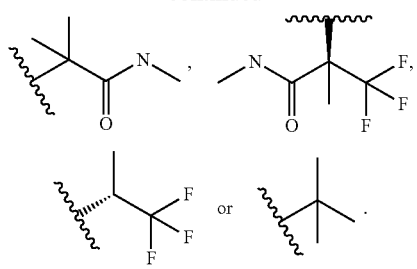

10. The compound of claim 1, or a pharmaceutically acceptable salt thereof, wherein $R^1$ is

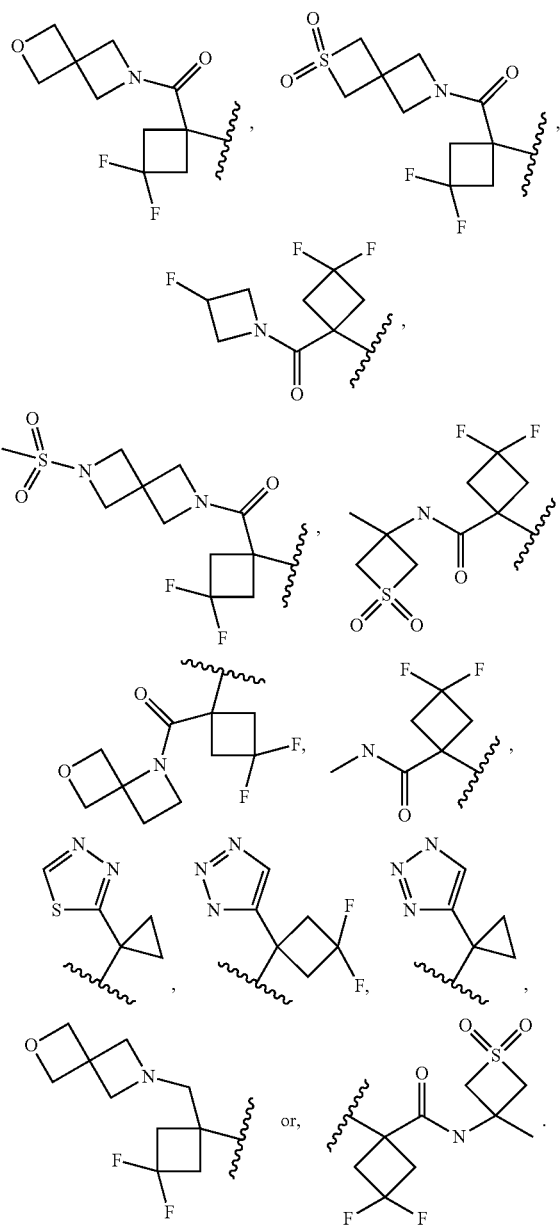

11. The compound of claim 1, or a pharmaceutically acceptable salt thereof, wherein $R^1$ is

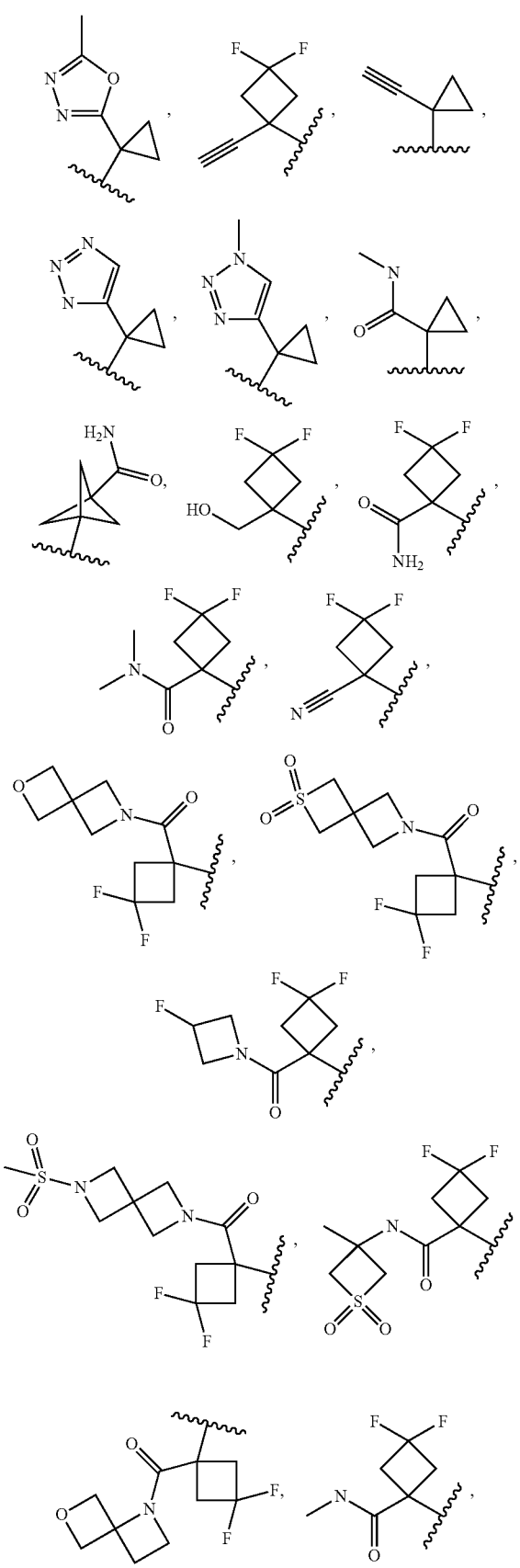

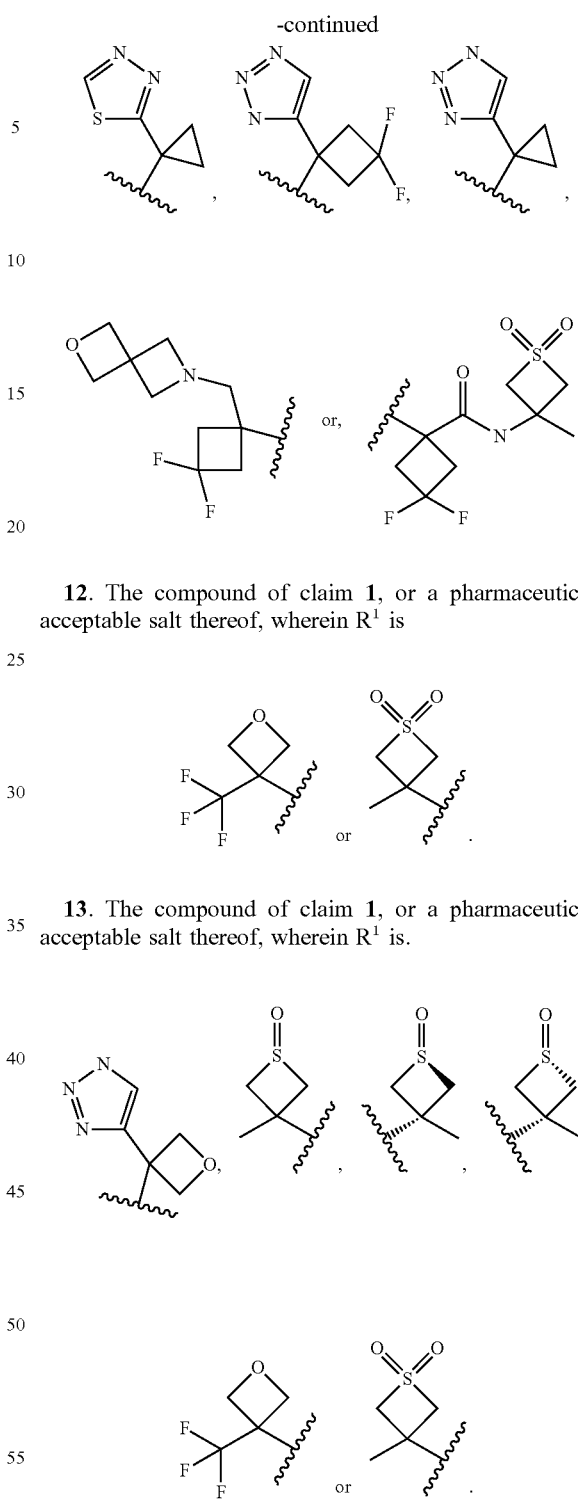

12. The compound of claim 1, or a pharmaceutically acceptable salt thereof, wherein $R^1$ is

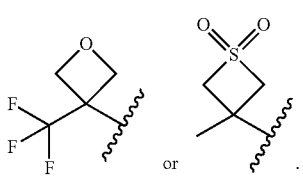

13. The compound of claim 1, or a pharmaceutically acceptable salt thereof, wherein $R^1$ is.

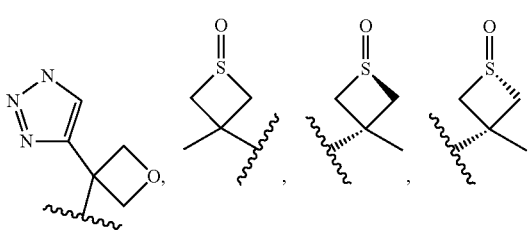

14. The compound of claim 1, or a pharmaceutically acceptable salt thereof, wherein $R^4$ is pyridinyl, optionally substituted with 1 to 4 $R^{4B}$.

15. The compound of claim 14, wherein $R^4$ is pyridin-4-yl, optionally substituted with 1 to 3 groups selected from F, Cl, $CF_3$, and $CHF_2$.

16. The compound of claim 1, or a pharmaceutically acceptable salt thereof, which is

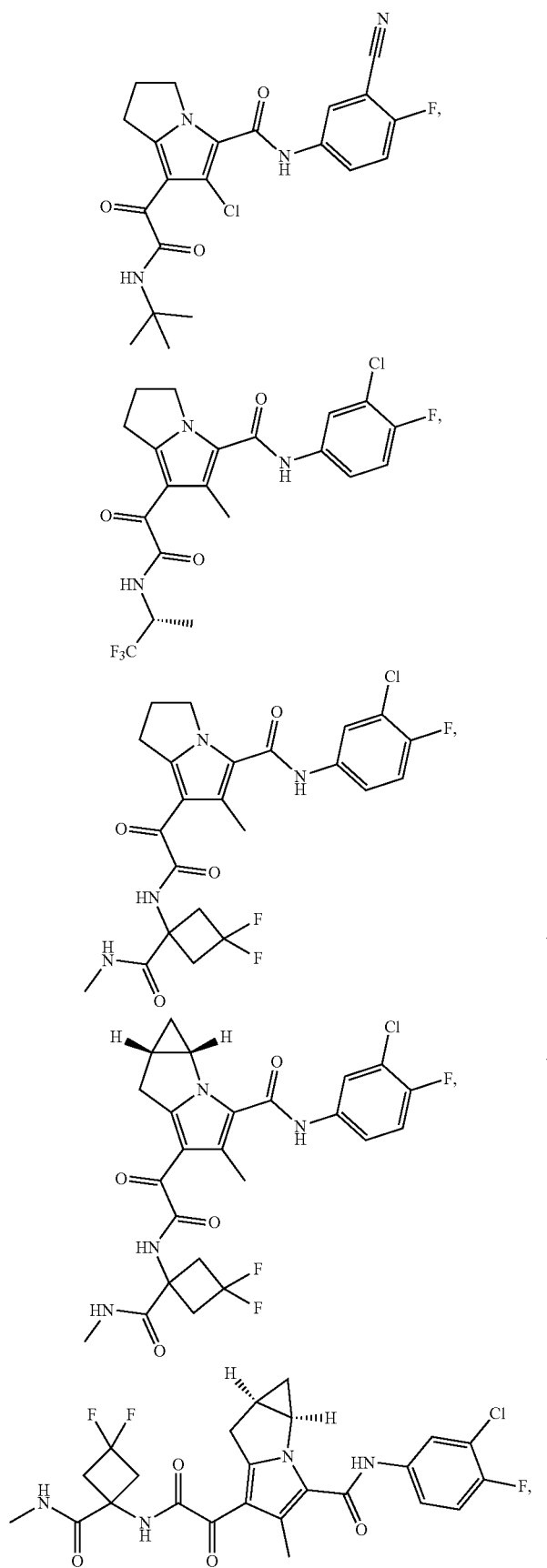
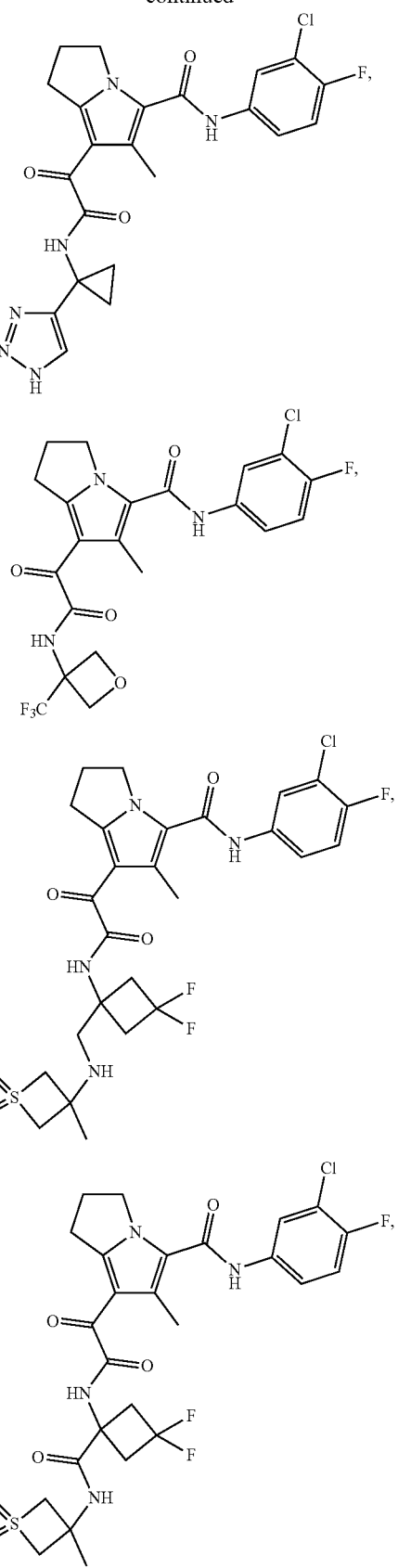

299
-continued
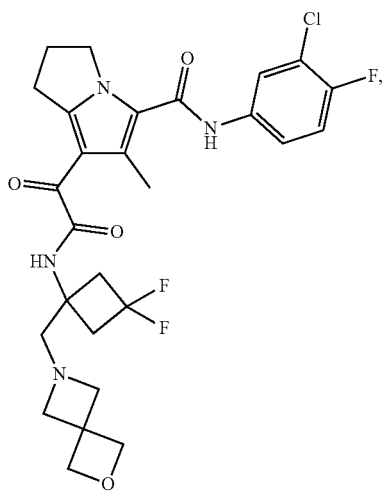
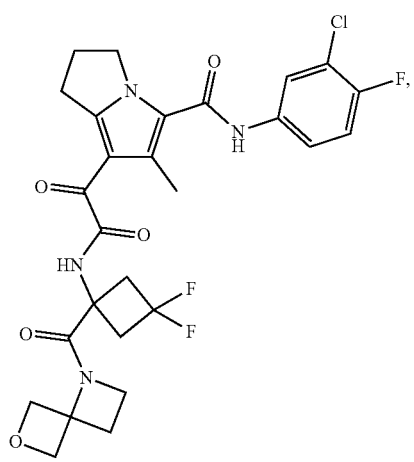
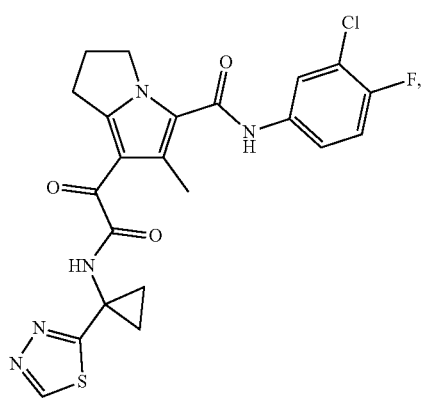
300
-continued
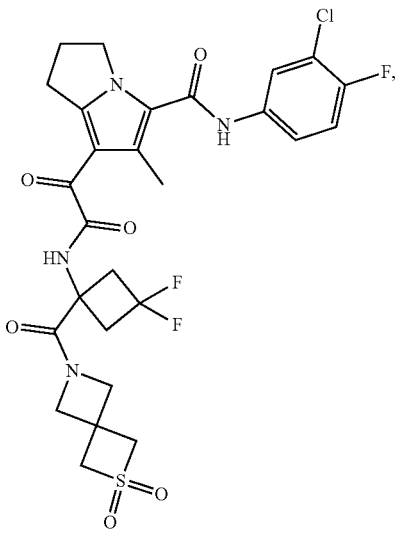
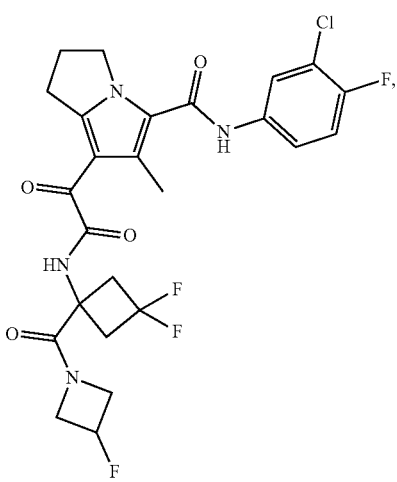
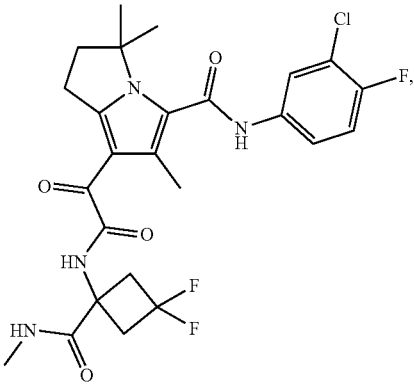

301
-continued
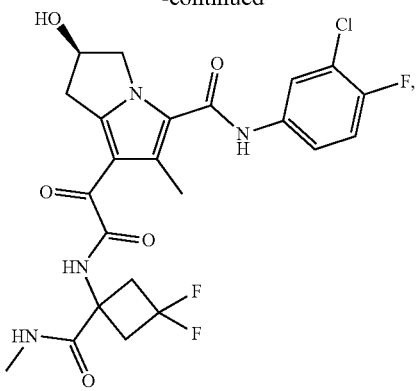
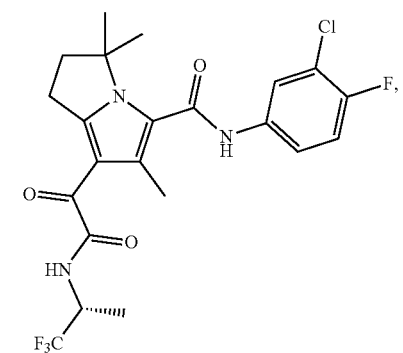
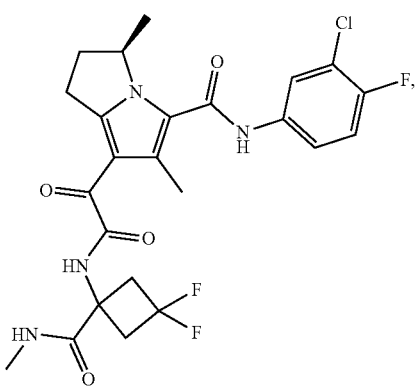
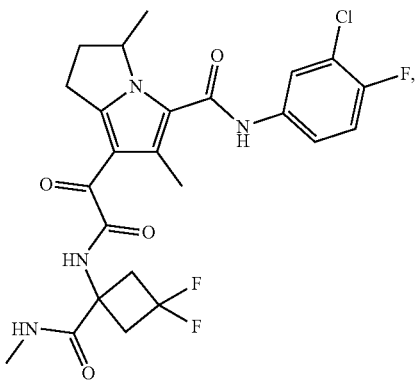
302
-continued
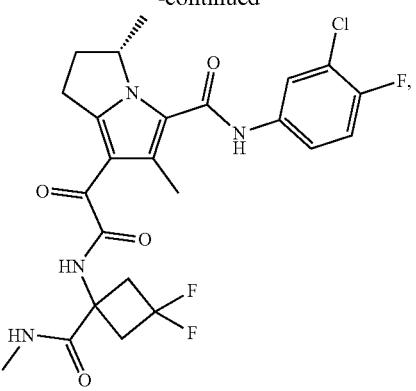
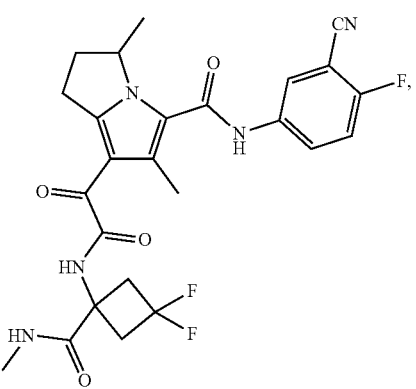
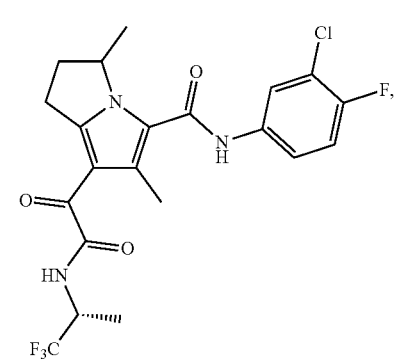
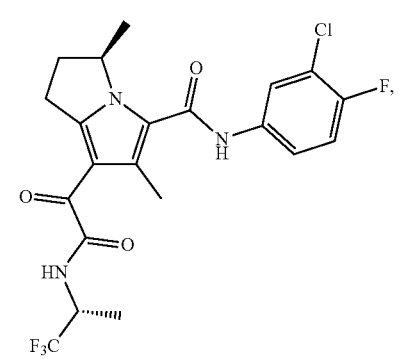

303
-continued
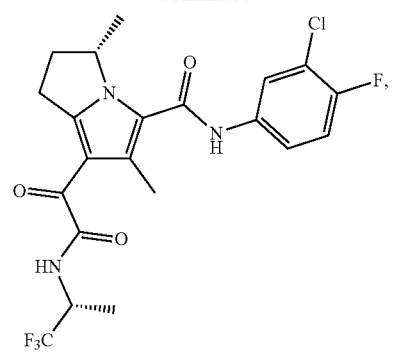
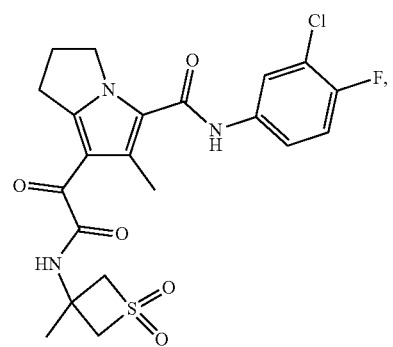
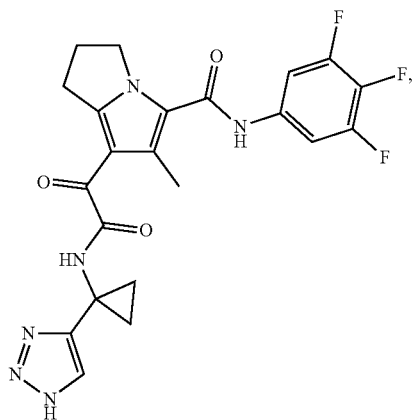
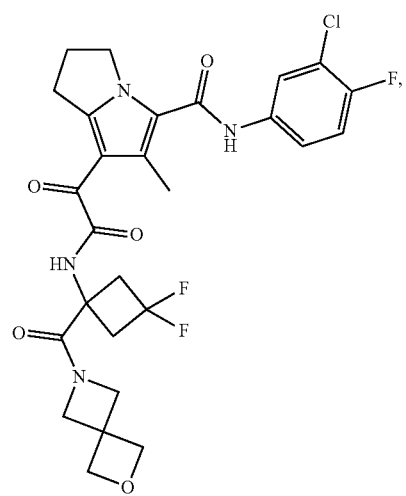
304
-continued
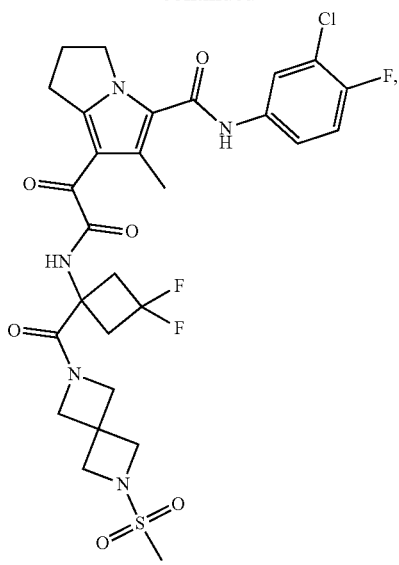
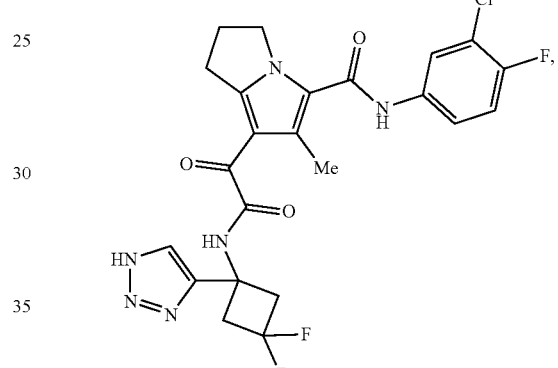
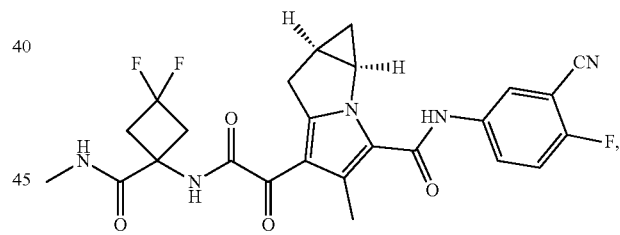
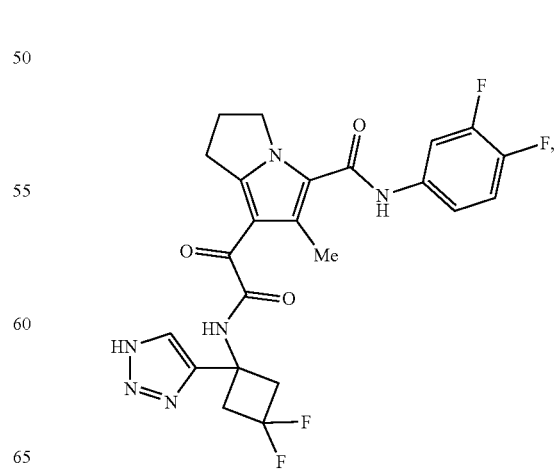

305
-continued
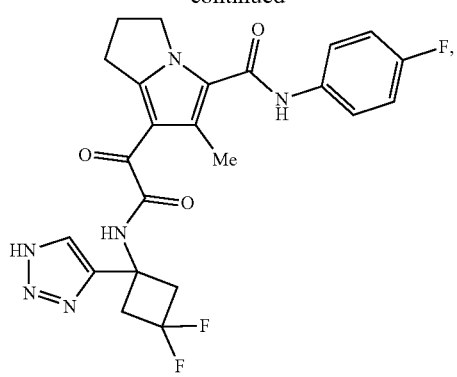
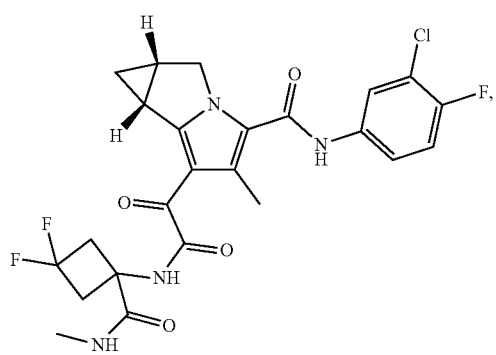
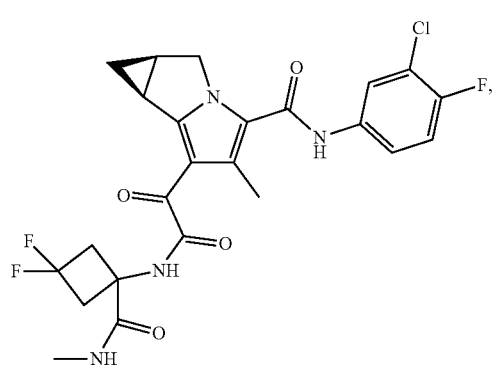
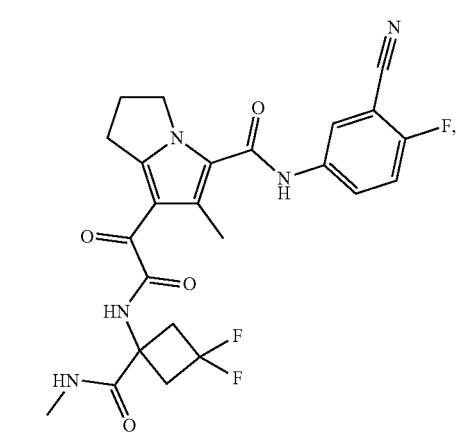
306
-continued
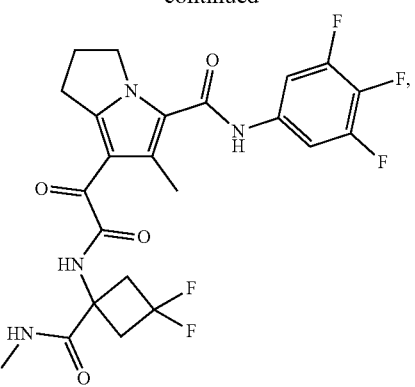
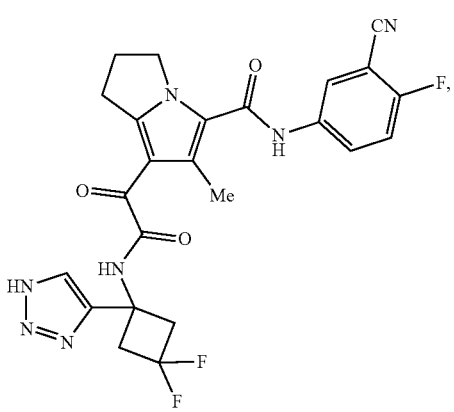
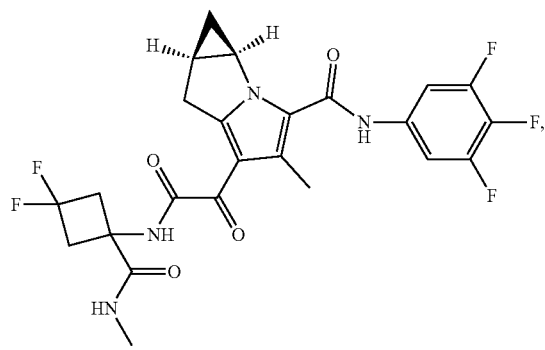
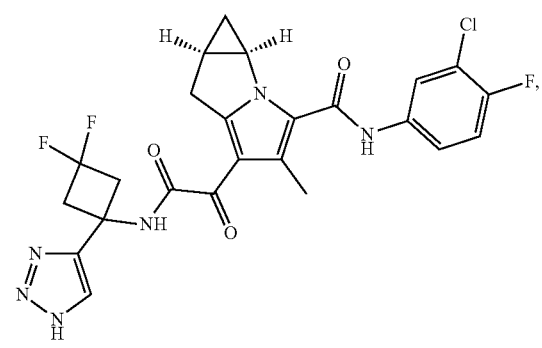

307
-continued
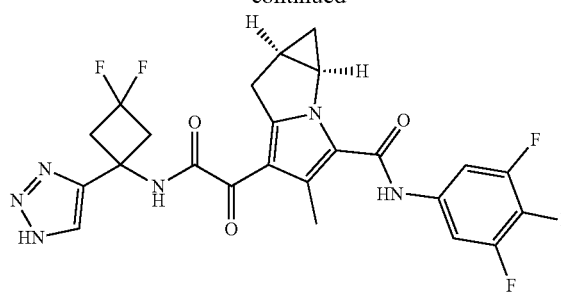
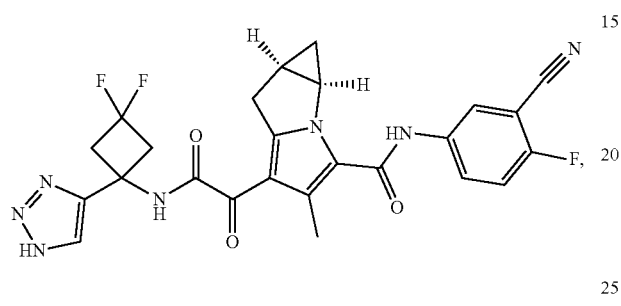
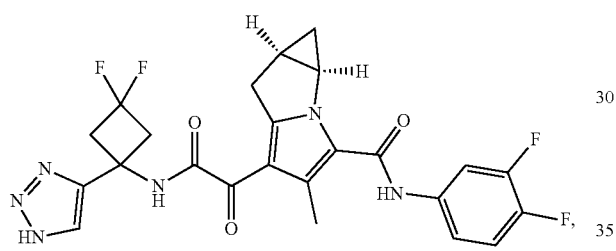
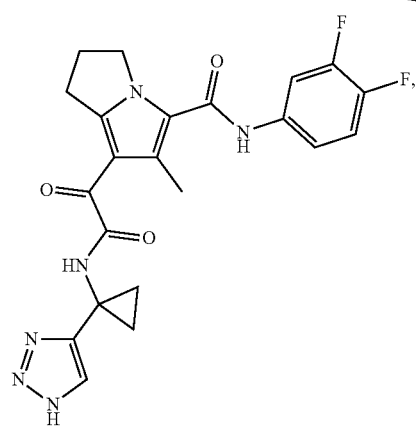
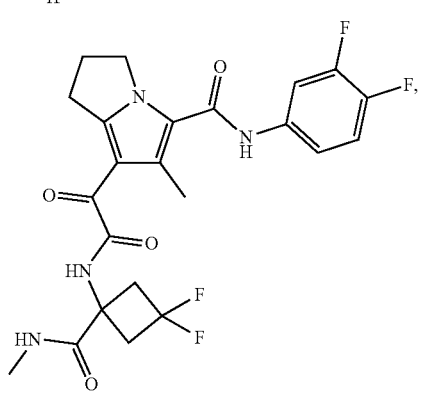
308
-continued
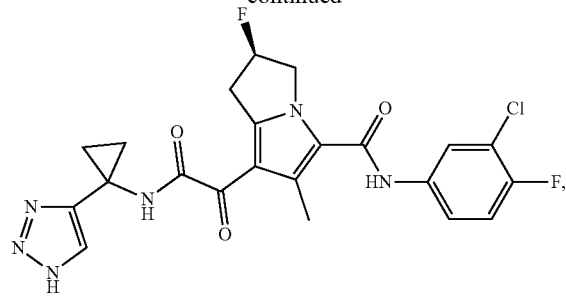
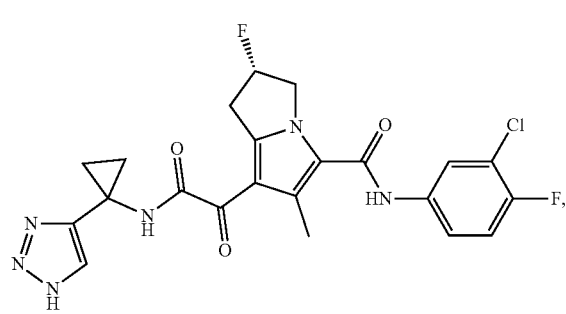
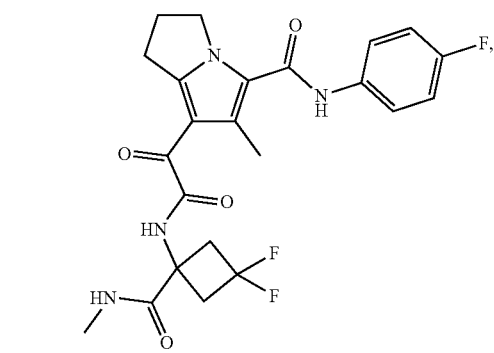
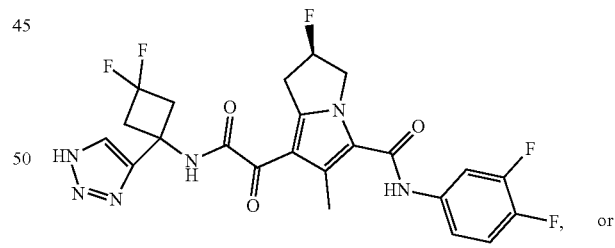, or
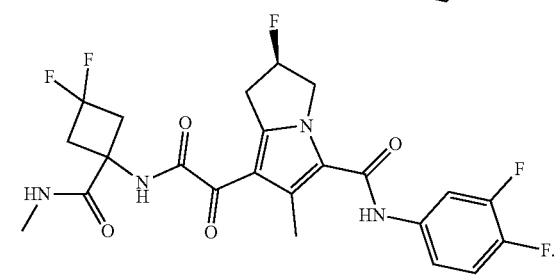.
17. The compound of claim 1, or a pharmaceutically acceptable salt thereof, which is

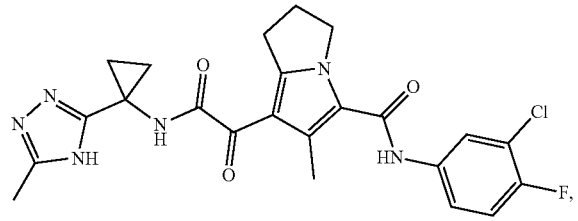
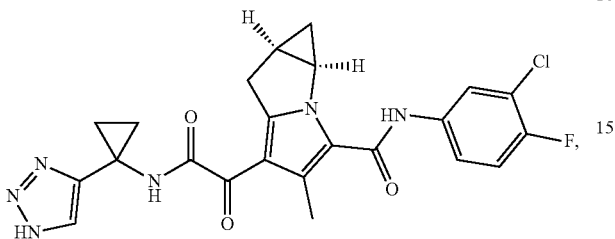
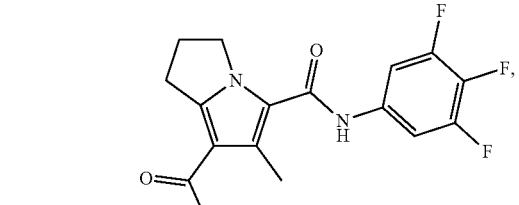
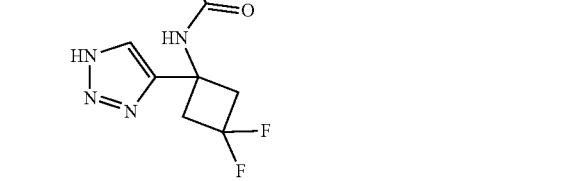
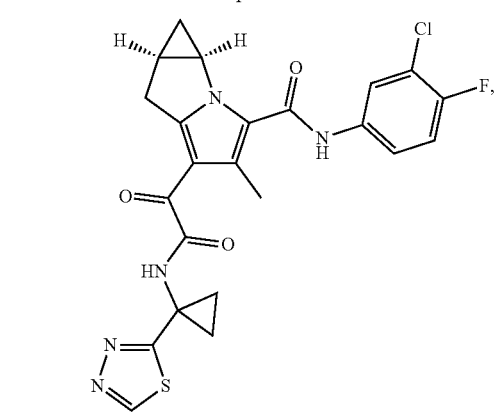
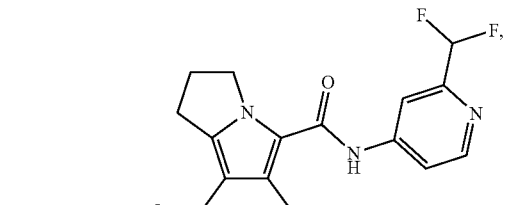
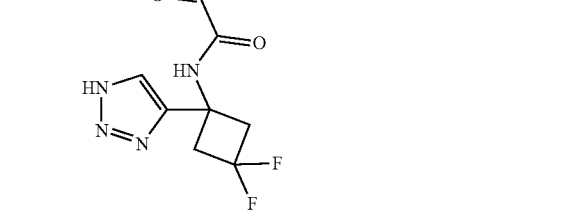
-continued
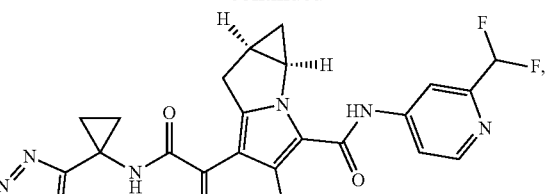
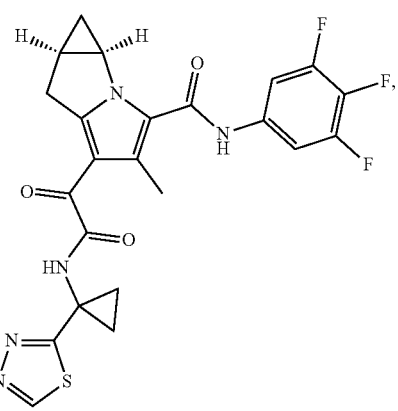
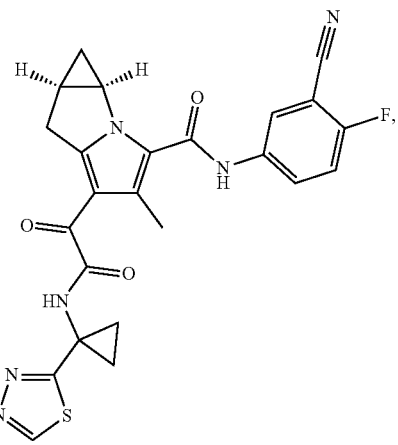
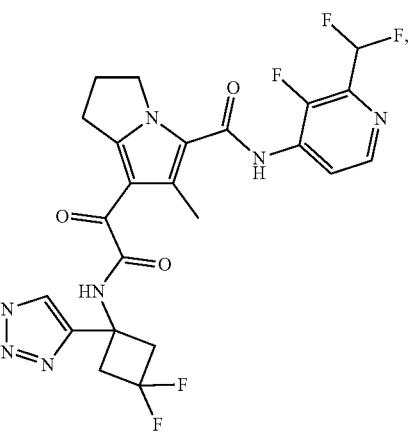

311
-continued
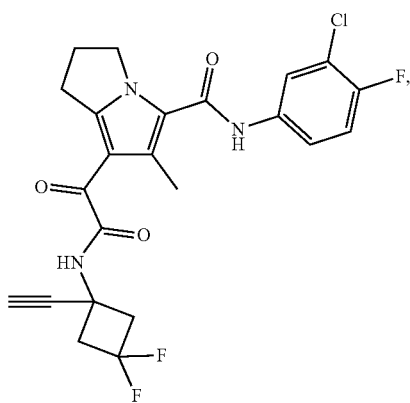
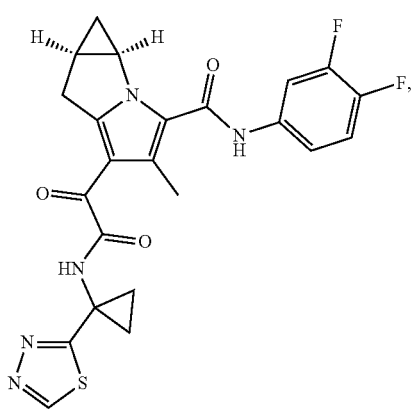
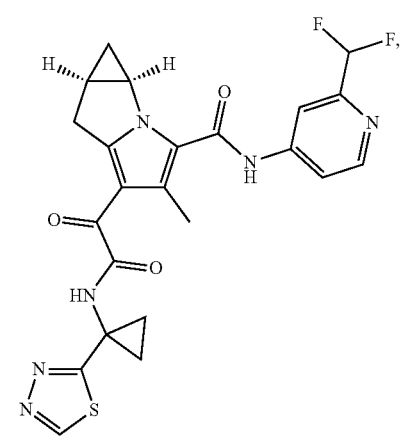
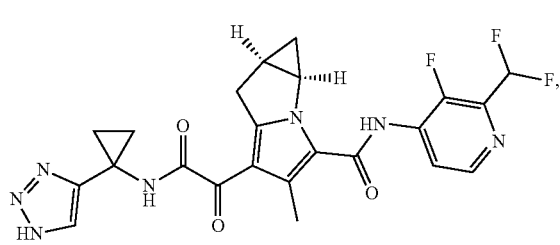
312
-continued
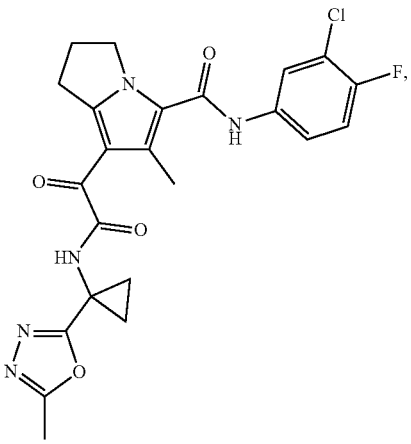
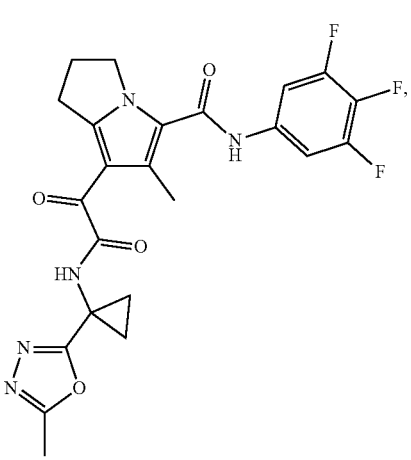
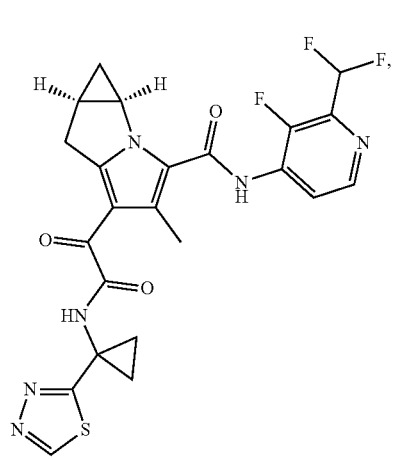
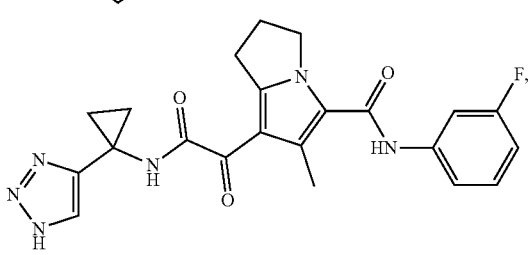

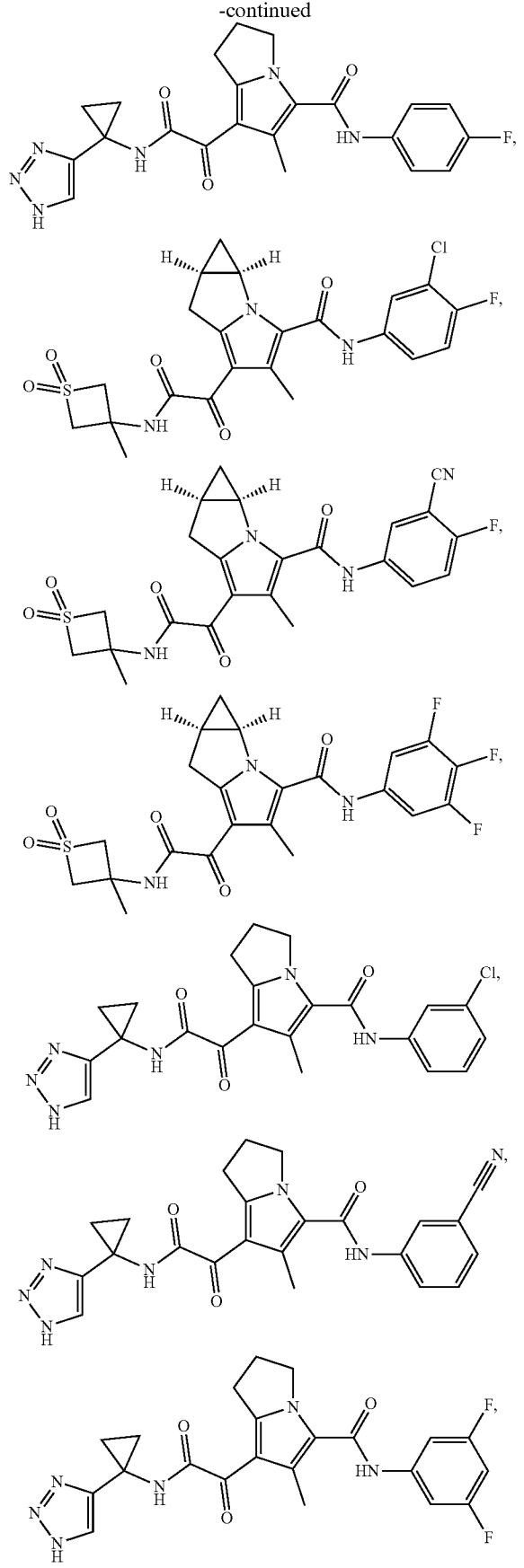
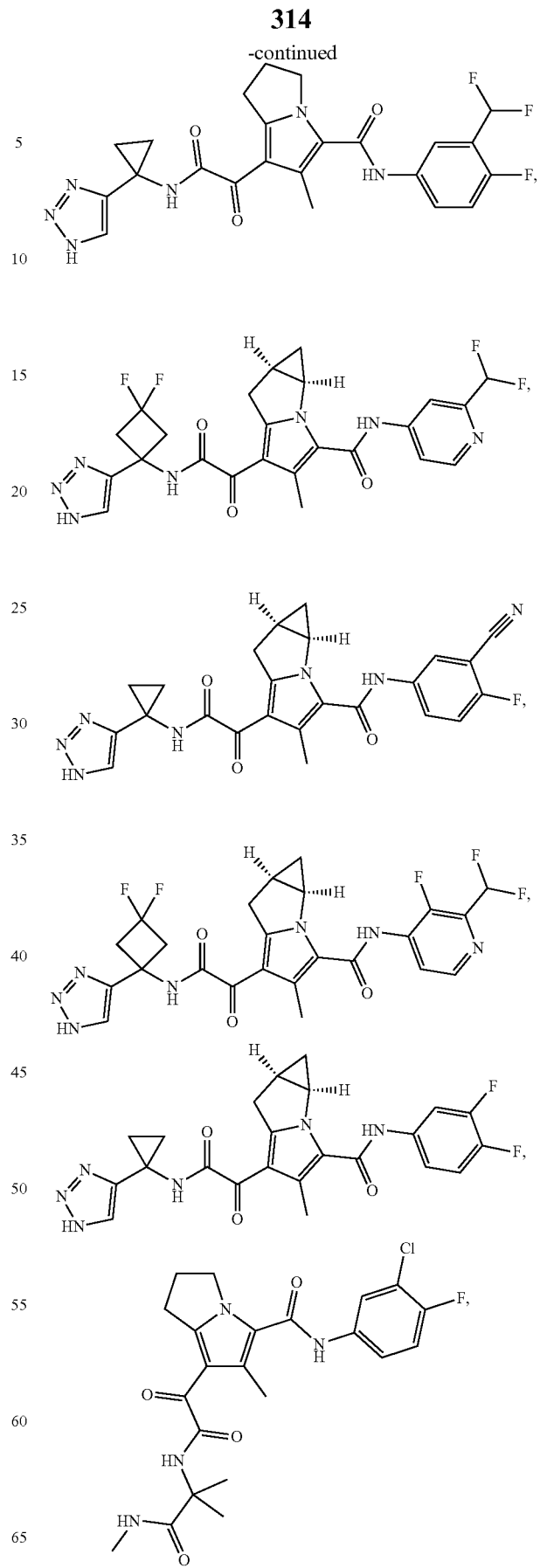

315
-continued
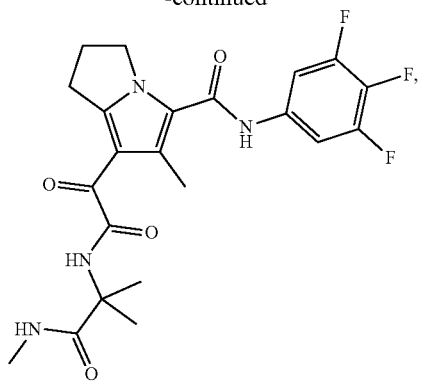
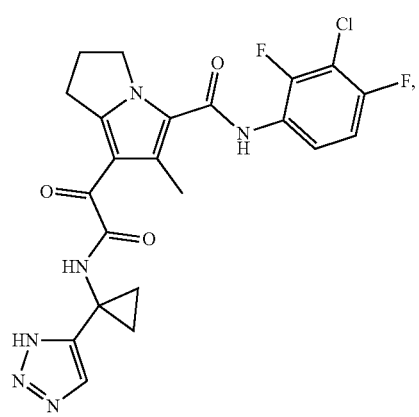
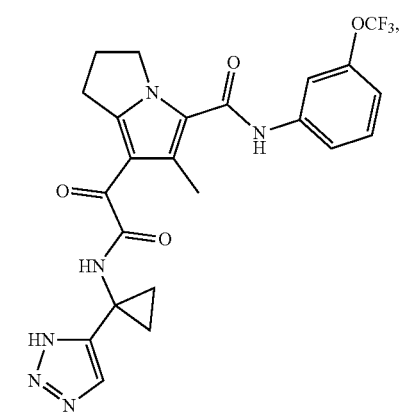
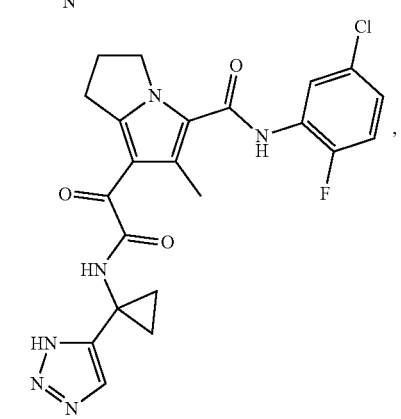
316
-continued
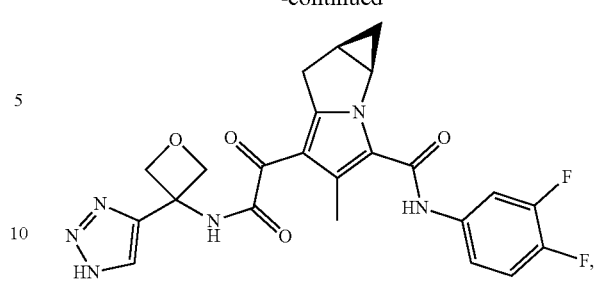
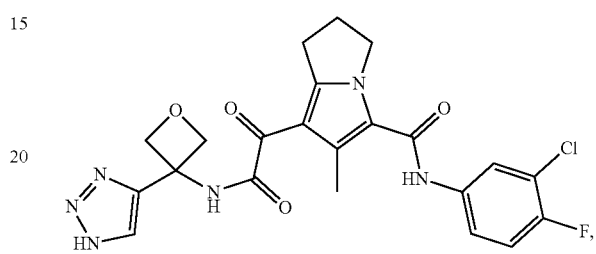
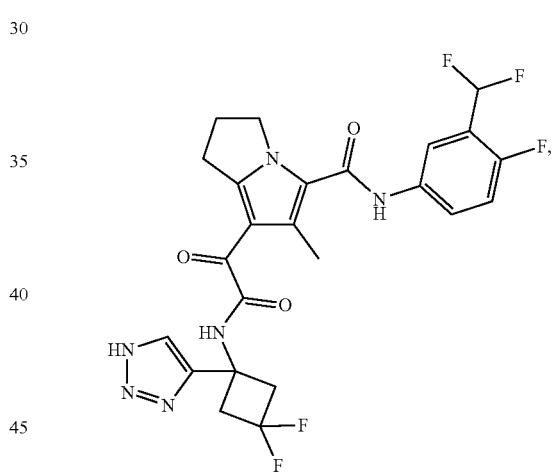
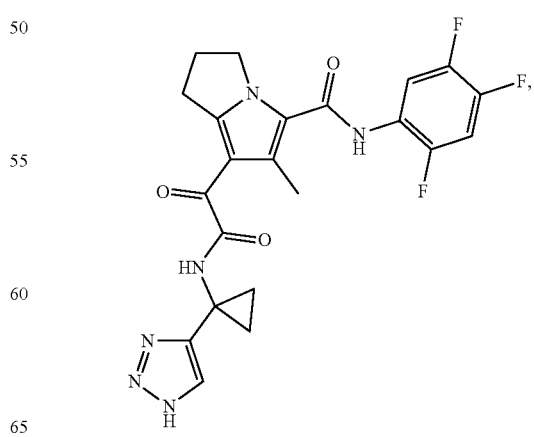

317
-continued
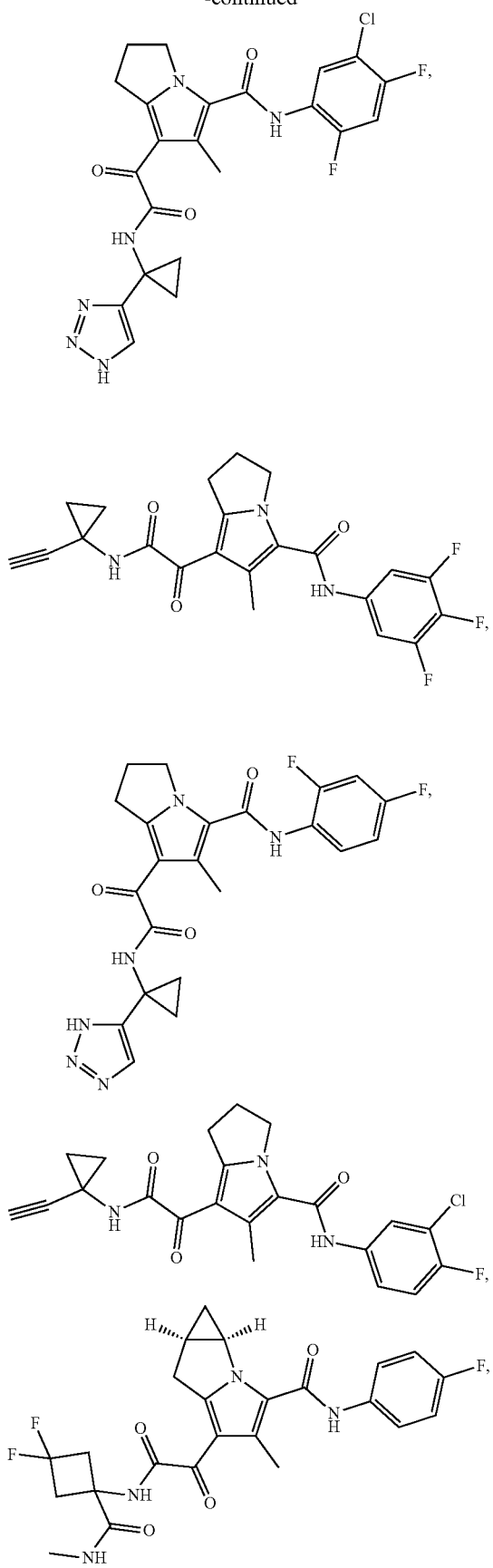
318
-continued
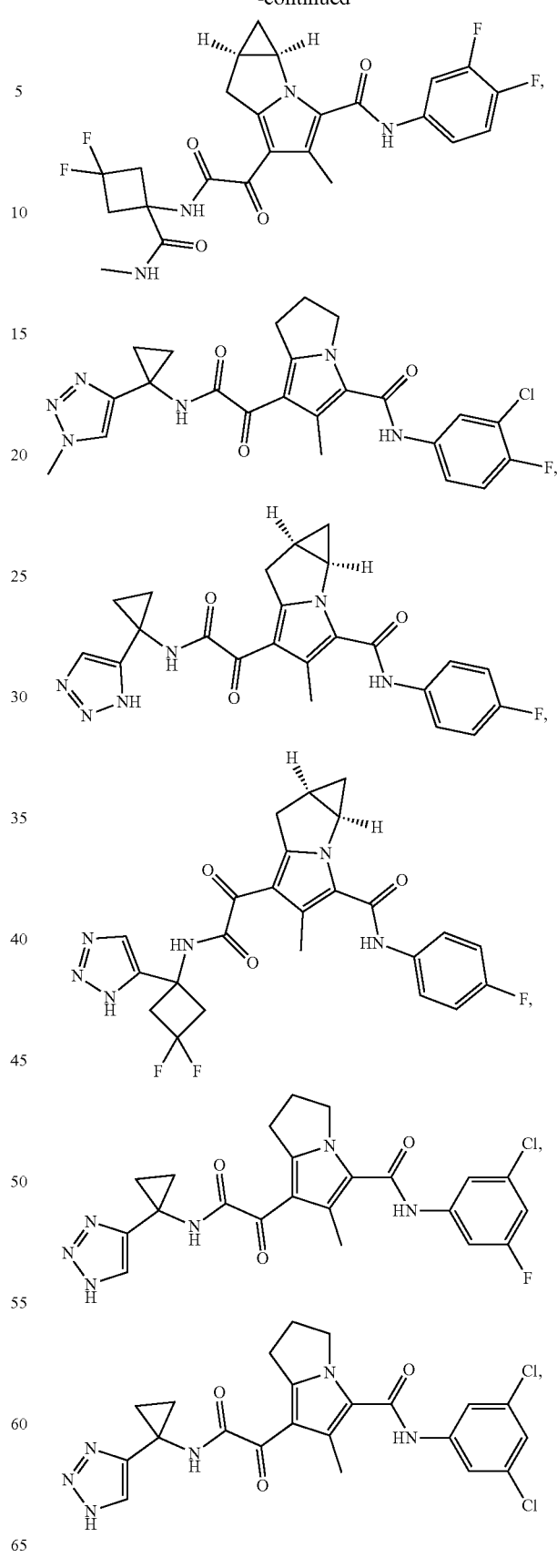

-continued
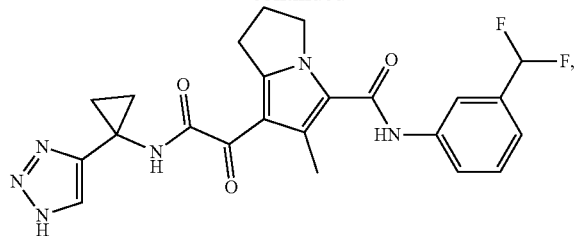
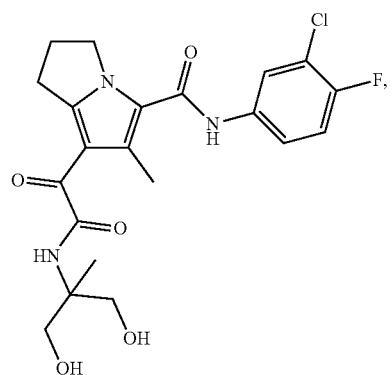
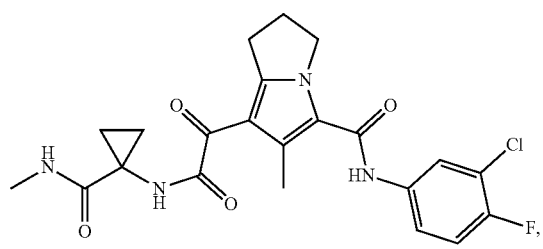
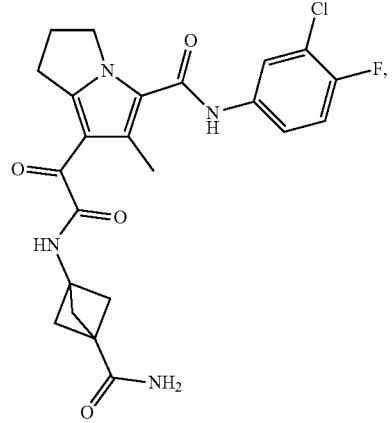
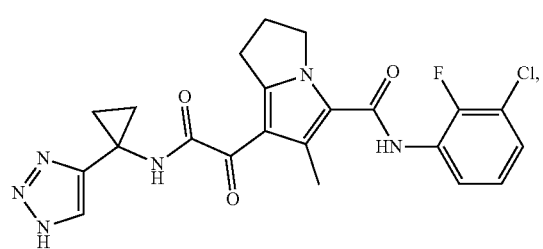
-continued
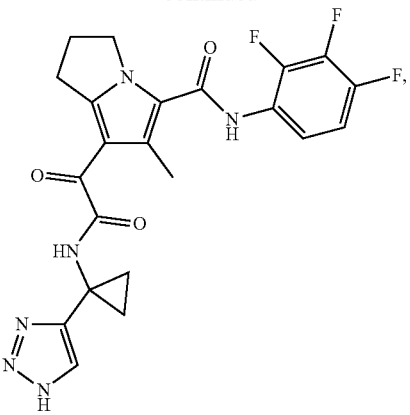
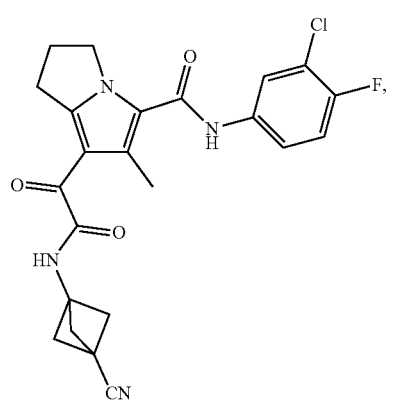
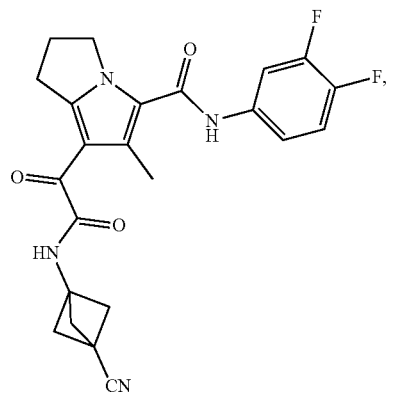
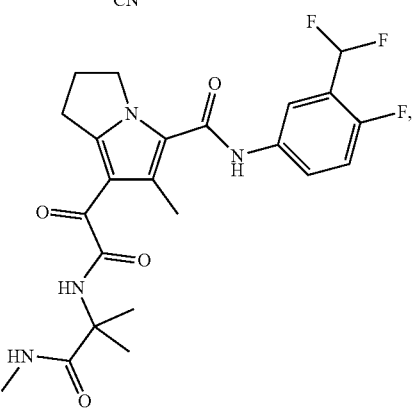

321
-continued
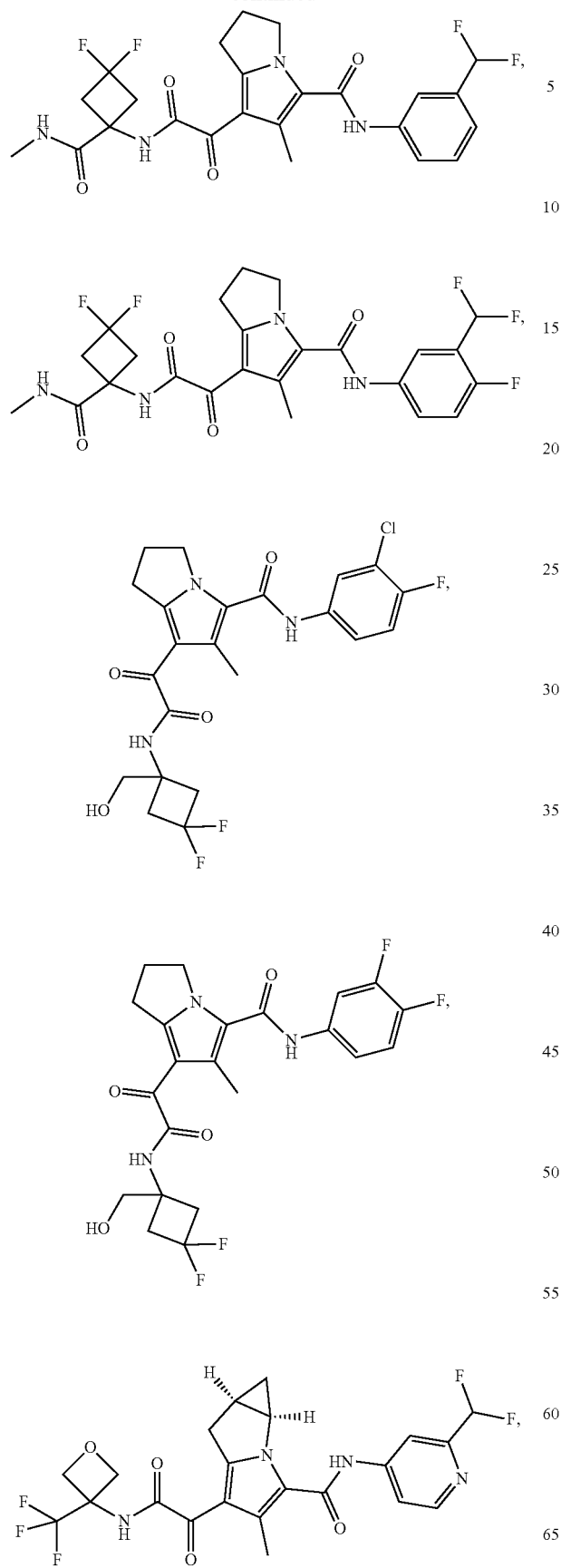
322
-continued
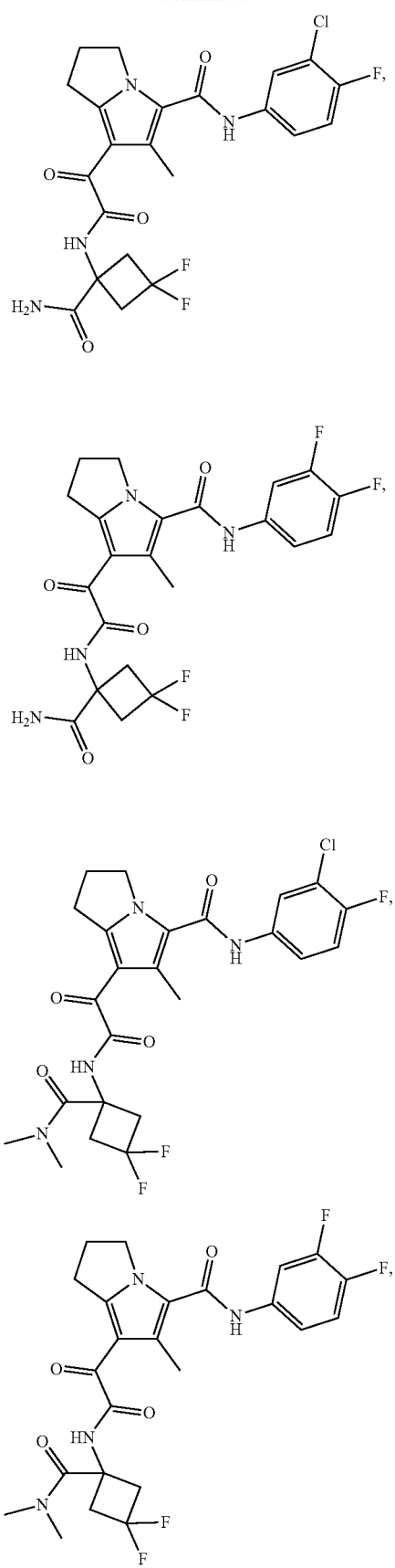

323
-continued
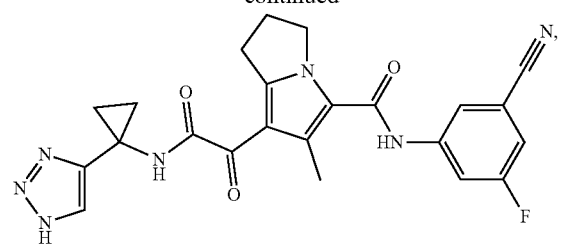
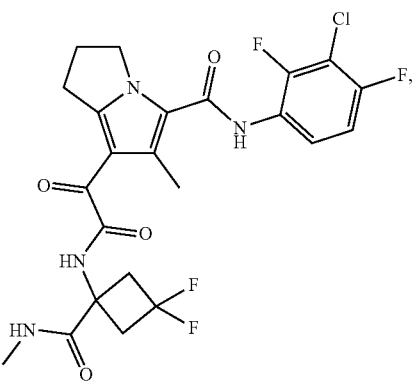
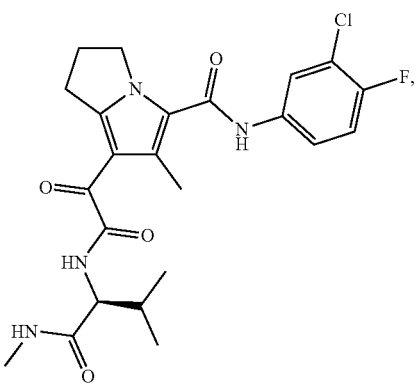
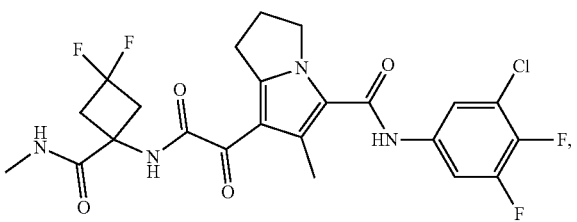
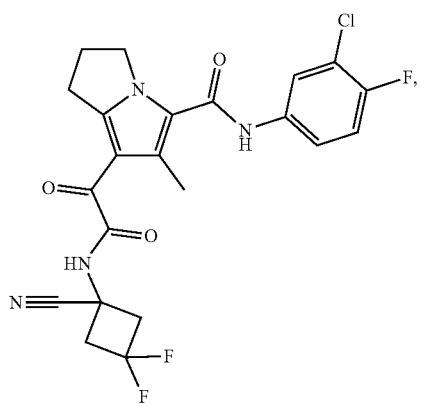
324
-continued
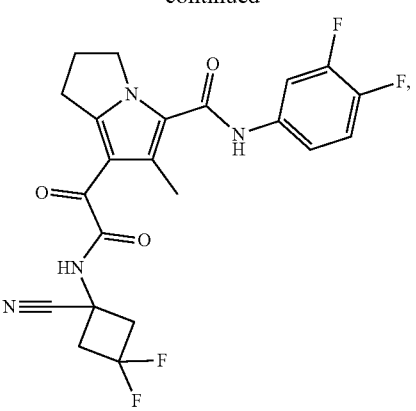
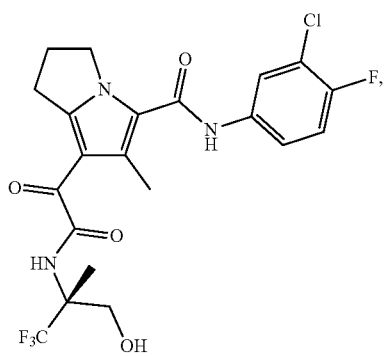
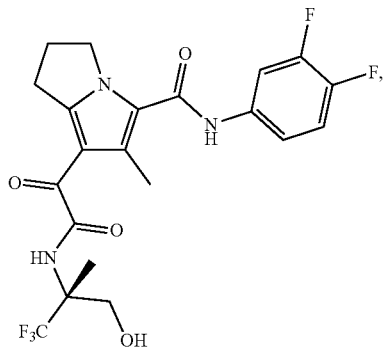
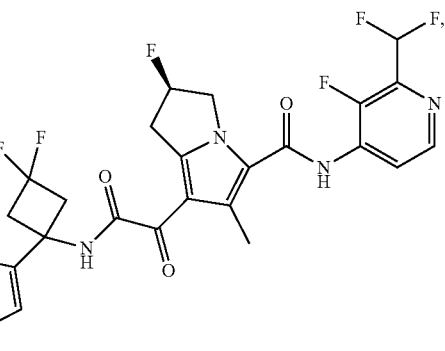

325
-continued
326
-continued
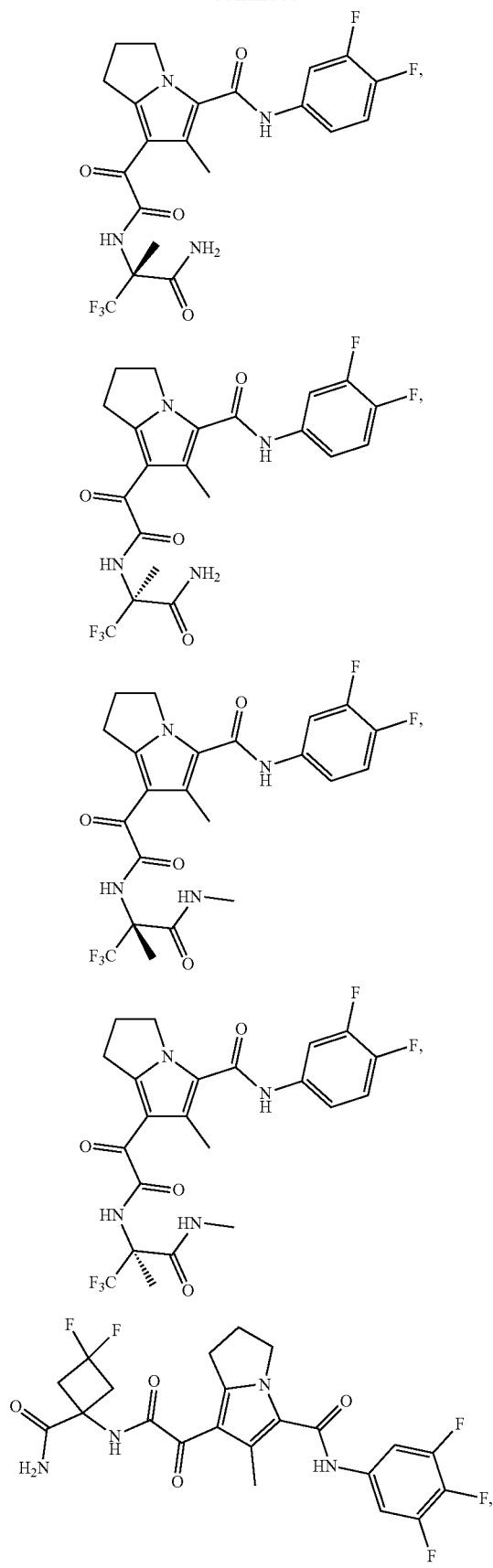
18. The compound of claim 1, or a pharmaceutically acceptable salt thereof, which is 327
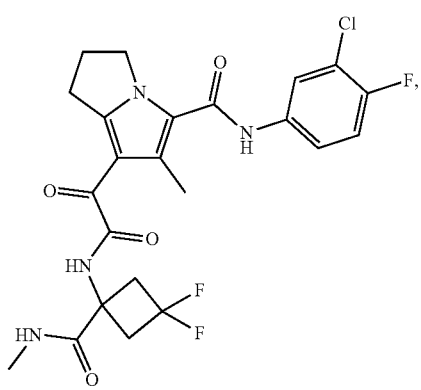
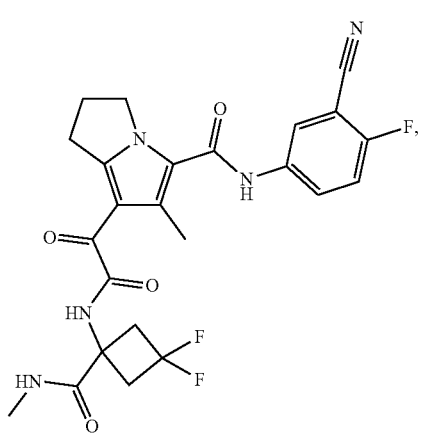
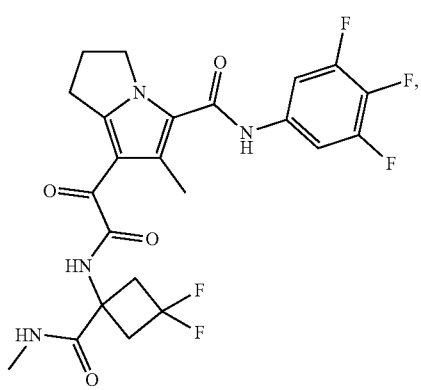
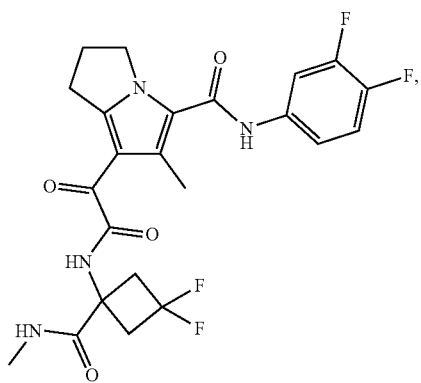
328
-continued
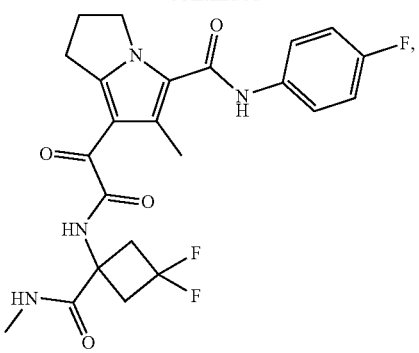
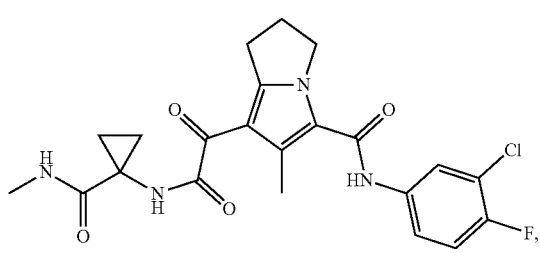
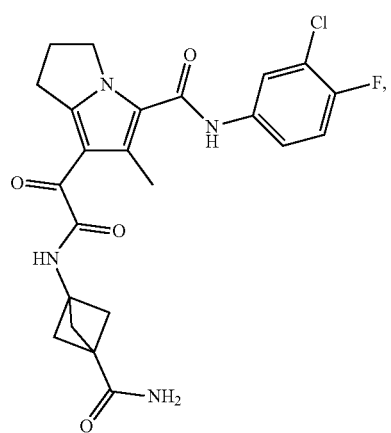
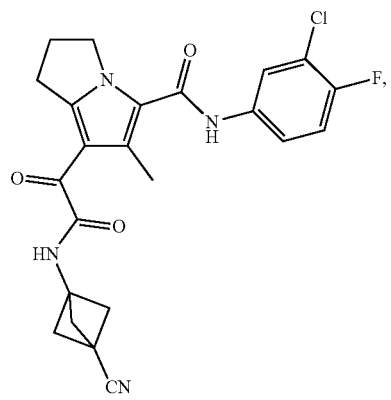

329
-continued
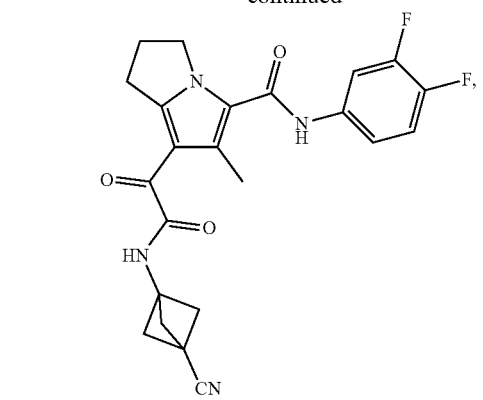
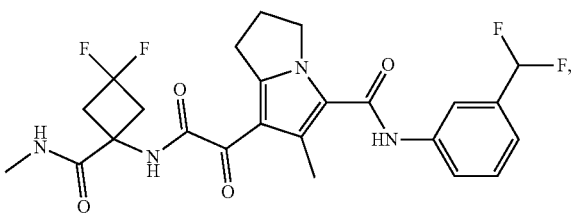
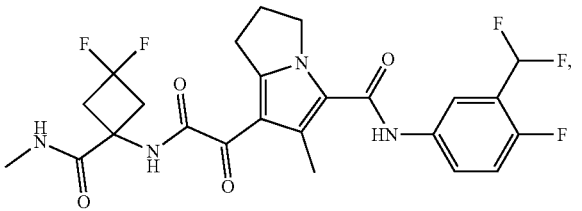 [SMILES: CNC(=O)C1(NC(=O)C(=O)c2c(C)c(C(=O)Nc3ccc(F)c(C(F)F)c3)n3c2CCC3)CC(F)(F)C1]
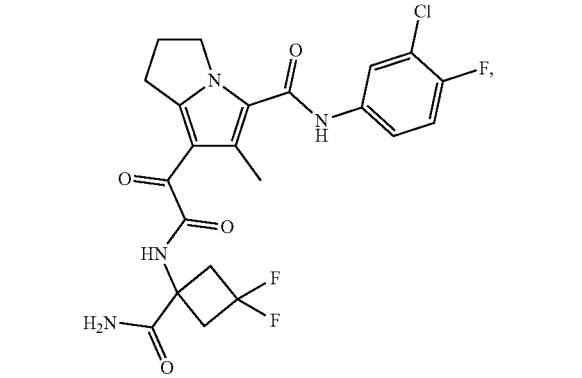
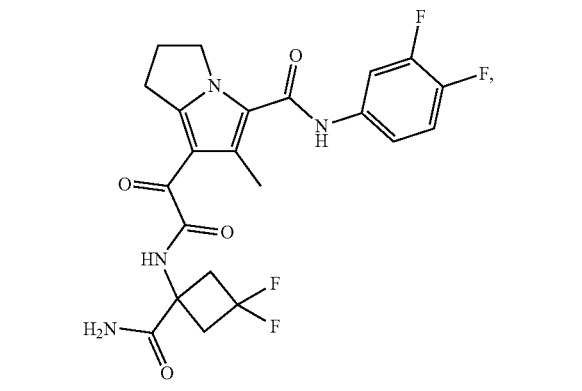
330
-continued
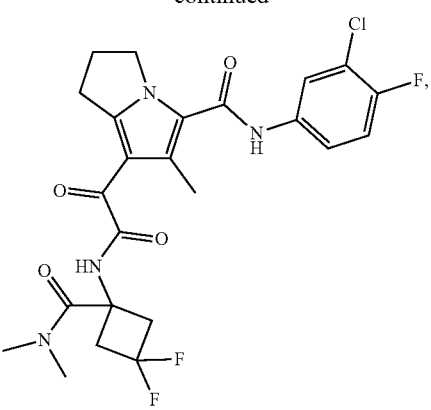
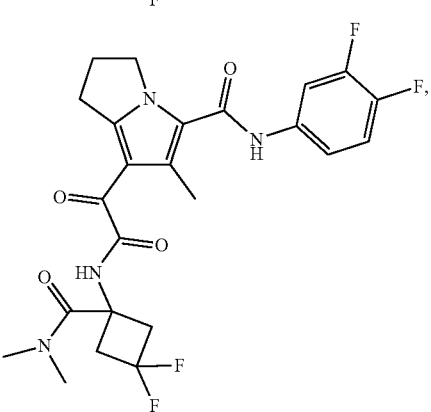
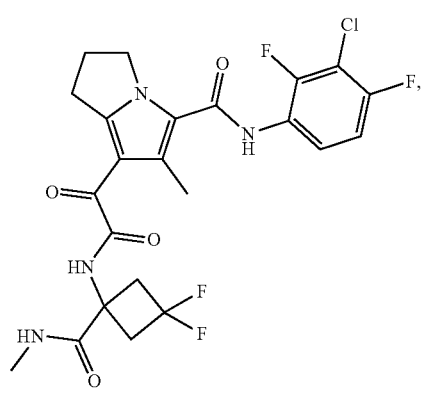
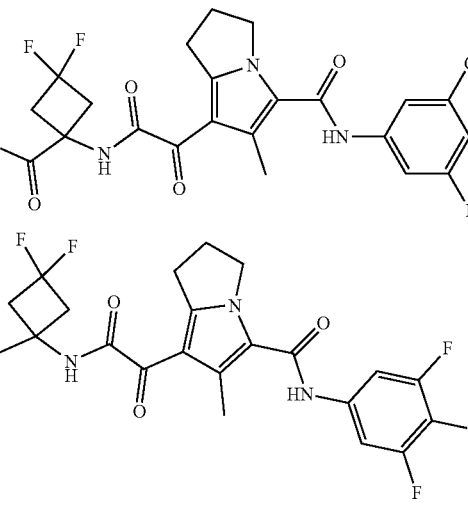
, or 331
-continued
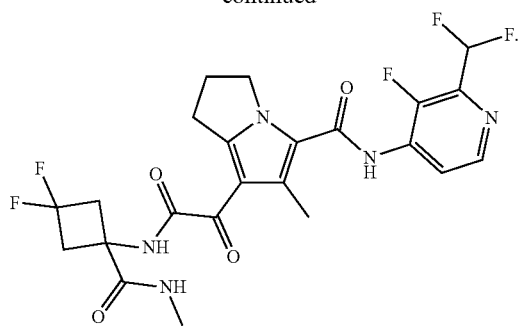
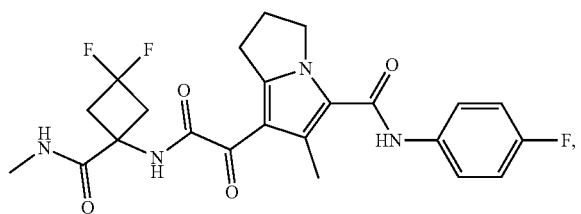
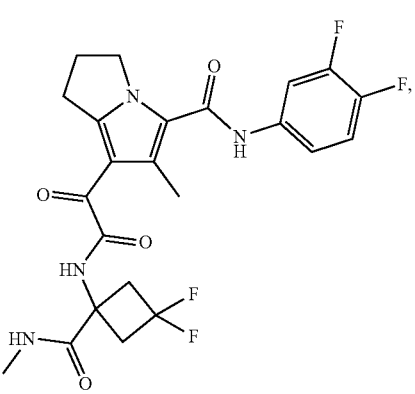
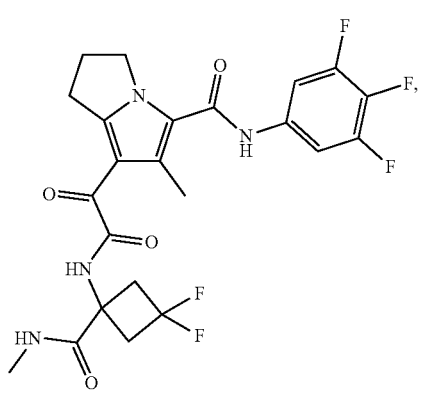
332
-continued
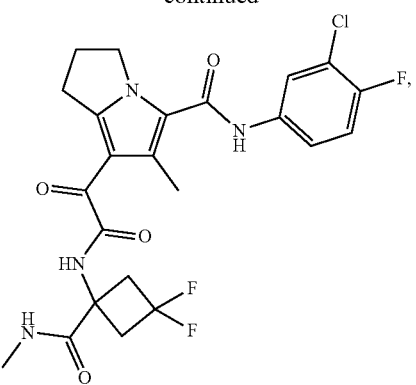
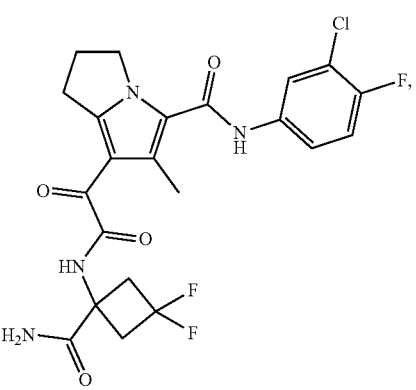
19. The compound of claim 1, which is
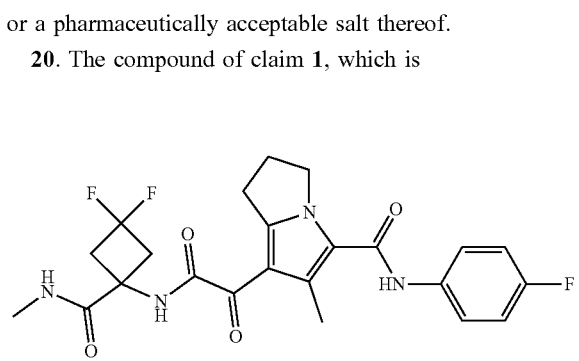
or a pharmaceutically acceptable salt thereof.
20. The compound of claim 1, which is
or a pharmaceutically acceptable salt thereof.

21. A pharmaceutical composition comprising a compound of claim 1, or a pharmaceutically acceptable salt thereof, and a pharmaceutically acceptable excipient.

22. A method of treating or preventing a HBV infection, comprising administering to an individual in need thereof a therapeutically effective amount of a compound of claim 1, or a pharmaceutically acceptable salt thereof.

23. A compound having the structure:

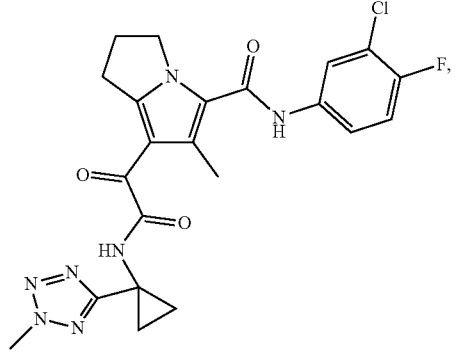

-continued

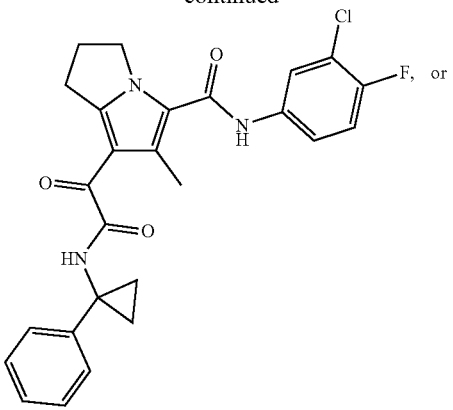

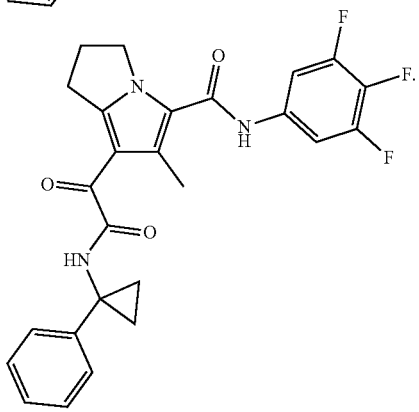

* * * * *